US012807704B2

(12) United States Patent
Zhou

(10) Patent No.: US 12,807,704 B2
(45) Date of Patent: Nov. 24, 2026

(54) PRECURSOR TRI-SPECIFIC ANTIBODY CONSTRUCTS AND METHODS OF USE THEREOF

(71) Applicant: Immunorizon Ltd., Rehovot (IL)

(72) Inventor: Hongxing Zhou, Bedford, MA (US)

(73) Assignee: Immunorizon Ltd., Rehovot (IL)

( * ) Notice: Subject to any disclaimer, the term of this patent is extended or adjusted under 35 U.S.C. 154(b) by 1177 days.

(21) Appl. No.: 17/606,454

(22) PCT Filed: Mar. 26, 2020

(86) PCT No.: PCT/IL2020/050359
§ 371 (c)(1),
(2) Date: Oct. 26, 2021

(87) PCT Pub. No.: WO2020/225805
PCT Pub. Date: Nov. 12, 2020

(65) Prior Publication Data

US 2022/0195041 A1 Jun. 23, 2022

Related U.S. Application Data

(60) Provisional application No. 62/844,303, filed on May 7, 2019.

(51) Int. Cl.
*C07K 16/28* (2006.01)
*A61K 39/00* (2006.01)
*A61P 35/00* (2006.01)
*C07K 16/30* (2006.01)

(52) U.S. Cl.
CPC .......... *C07K 16/2803* (2013.01); *A61P 35/00* (2018.01); *C07K 16/2863* (2013.01); *C07K 16/3069* (2013.01); *A61K 2039/505* (2013.01); *C07K 2317/31* (2013.01); *C07K 2317/33* (2013.01); *C07K 2317/35* (2013.01); *C07K 2317/55* (2013.01); *C07K 2317/622* (2013.01); *C07K 2317/90* (2013.01); *C07K 2319/31* (2013.01); *C07K 2319/50* (2013.01)

(58) Field of Classification Search
None
See application file for complete search history.

(56) References Cited

U.S. PATENT DOCUMENTS

| | | | | |
|---|---|---|---|---|
| 4,237,224 | A | 12/1980 | Cohen et al. | |
| 4,751,180 | A | 6/1988 | Cousens et al. | |
| 4,935,233 | A | 6/1990 | Bell et al. | |
| 5,151,510 | A | 9/1992 | Stec et al. | |
| 5,283,173 | A | 2/1994 | Fields et al. | |
| 5,468,614 | A | 11/1995 | Fields et al. | |
| 5,837,458 | A | 11/1998 | Minshull et al. | |
| 6,005,079 | A | 12/1999 | Casterman et al. | |
| 6,291,158 | B1 | 9/2001 | Winter et al. | |
| 6,291,161 | B1 | 9/2001 | Lerner et al. | |
| 6,423,498 | B1 | 7/2002 | Markland et al. | |
| 9,493,563 | B2 | 11/2016 | Blein et al. | |
| 9,562,073 | B2 | 2/2017 | Moore et al. | |
| 9,587,021 | B2 | 3/2017 | Huang et al. | |
| 9,822,180 | B2 | 11/2017 | Cobbold et al. | |
| 2007/0065431 | A1 | 3/2007 | Coia et al. | |
| 2010/0150918 | A1 | 6/2010 | Kufer et al. | |
| 2011/0091372 | A1 | 4/2011 | Ghayur et al. | |
| 2011/0262439 | A1 | 10/2011 | Kufer et al. | |
| 2012/0135110 | A1 | 5/2012 | Chiba et al. | |
| 2012/0321626 | A1 | 12/2012 | Zhou | |
| 2013/0129729 | A1 | 5/2013 | Kischel et al. | |
| 2014/0161800 | A1* | 6/2014 | Blankenship | A61P 1/04 435/69.6 |
| 2014/0178388 | A1* | 6/2014 | Chou | C07K 16/2809 435/254.2 |
| 2015/0056206 | A1* | 2/2015 | Zhou | A61K 39/39558 435/254.5 |
| 2016/0194399 | A1 | 7/2016 | Irving et al. | |
| 2017/0247476 | A1 | 8/2017 | Yan et al. | |
| 2018/0055944 | A1* | 3/2018 | Lu | A61K 38/07 |
| 2018/0112011 | A1 | 4/2018 | Ollier | |
| 2018/0125972 | A1* | 5/2018 | Igawa | A61K 47/42 |
| 2019/0070248 | A1* | 3/2019 | Sahin | C12N 15/62 |
| 2023/0312753 | A1* | 10/2023 | Bogin | C07K 16/3069 424/136.1 |

FOREIGN PATENT DOCUMENTS

| | | |
|---|---|---|
| EP | 0402226 A1 | 12/1990 |
| EP | 0183070 | 10/1991 |

(Continued)

OTHER PUBLICATIONS

Mertens, Bispecific Antibodies (ed. R. Kontermann), SpringerLink, 2011, 135-149 (Year: 2011).*
Chen, et al., Sci Rep, 2017, 7, 1-12 (Year: 2017).*
Iizasa, et al., Clin Cancer Res, 1999, 5, 149-153 (Year: 1999).*
Orozco, et al., Mabs, 2022, 14, 1-16, (Year: 2022).*
Lescar et al., J Biol Chem, 1995, 270, 18067-18076 (Year: 1995).*
Edwards, et al., J Mol Biol, 2003, 334, 103-118 (Year: 2003).*
Goel, et al., J Immunol, 2004, 173, 7358-7367 (Year: 2004).*
Huang, et al., AACR Annual Meeting, 2017, p. 4608 (Year: 2017).*
Adams RL. "The effect of endogenous pools of thymidylate on the apparent rate of DNA synthesis" Experimental cell research Jul. 1, 1969;56(1):55-8.
Alarcon et al. "The CD3-gamma and CD3-delta subunits of the T cell antigen receptor can be expressed within distinct functional TCR/CD3 complexes" The EMBO Journal. Apr. 1991;10(4):903-12.

(Continued)

*Primary Examiner* — Misook Yu
*Assistant Examiner* — Samantha Lake Hopkins
(74) *Attorney, Agent, or Firm* — Rothwell, Figg, Ernst & Manbeck, P.C.

(57) ABSTRACT

Precursor tri-specific antibody constructs comprising at least one tumor associated antigen binding domain, a T-cell binding domain, and a regulatory domain having enhanced half-life, are described herein. Further, methods of producing the precursor tri-specific antibody constructs are disclosed. Pharmaceutical compositions comprising the precursor constructs and their uses for treating tumors are also disclosed.

7 Claims, 41 Drawing Sheets

Specification includes a Sequence Listing.

(56) References Cited

FOREIGN PATENT DOCUMENTS

| | | | | |
|---|---|---|---|---|
| EP | 0244234 | | 7/1993 | |
| WO | WO 1994/004678 | A1 | 3/1994 | |
| WO | WO 1994/025591 | A1 | 11/1994 | |
| WO | WO 2004/106380 | A2 | 12/2004 | |
| WO | WO 2006/072620 | A1 | 7/2006 | |
| WO | WO 2006/095164 | A1 | 9/2006 | |
| WO | WO 2007/042261 | A2 | 4/2007 | |
| WO | WO 2007/098934 | A1 | 9/2007 | |
| WO | WO 2008/119567 | A2 | 10/2008 | |
| WO | WO 2010/037838 | A2 | 4/2010 | |
| WO | WO 2010/102140 | A1 | 9/2010 | |
| WO | WO 2012/172102 | A1 | 12/2012 | |
| WO | WO 2014/012085 | A2 | 1/2014 | |
| WO | WO 2016/014974 | A2 | 1/2016 | |
| WO | WO 2016/023909 | A1 | 2/2016 | |
| WO | WO 2017/136818 | A2 | 8/2017 | |
| WO | WO 2017/162587 | | 9/2017 | |
| WO | WO-2018004338 | A1 * | 1/2018 | ........... C07D 257/08 |
| WO | 2019164930 | A1 | 8/2019 | |
| WO | WO 2019/160904 | A1 | 8/2019 | |
| WO | 2019219658 | A1 | 11/2019 | |
| WO | WO 2019/222282 | A1 | 11/2019 | |
| WO | WO 2019/231920 | A1 | 12/2019 | |
| WO | WO 2020/033587 | A1 | 2/2020 | |
| WO | WO 2020/084608 | A1 | 4/2020 | |
| WO | 2021224913 | A1 | 11/2021 | |

OTHER PUBLICATIONS

Altschul et al. "Basic local alignment search tool" Journal of molecular biology. Oct. 5, 1990;215(3):403-10.

Anasetti et al. "Induction of specific nonresponsiveness in unprimed human T cells by anti-CD3 antibody and alloantigen" The Journal of experimental medicine. Dec. 1, 1990;172(6):1691-700.

Anton et al. "NK cell proliferation induced by IL-15 transpresentation is negatively regulated by inhibitory receptors" The Journal of Immunology. Nov. 15, 2015;195(10):4810-21.

Beiboer et al. "Guided selection of a pan carcinoma specific antibody reveals similar binding characteristics yet structural divergence between the original murine antibody and its human equivalent" Journal of molecular biology. Feb. 25, 2000;296(3):833-49.

Beverley et al. "Distinctive functional characteristics of human „T lymphocytes defined by E rosetting or a monoclonal anti-T cell antibody" European journal of immunology. 1981;11(4):329-34.

Bird et al. "Single-chain antigen-binding proteins" Science. Oct. 21, 1988;242(4877):423-6.

Borden et al. "Nucleotide sequence of the cDNAs encoding the variable region heavy and light chains of a myeloma protein specific for the terminal nonreducing end of alpha (1----6) dextran" Proceedings of the National Academy of Sciences. Apr. 1, 1987;84(8):2440-3.

Bradley et al. "Toward high-resolution de novo structure prediction for small proteins" Science. Sep. 16, 2005;309(5742):1868-71.

Brooks et al. "Macromolecular energy, minimization and dynamics calculations" J. Comput. Chem . . . 1983;4:187-217.

Burbaum et al. "Understanding structural relationships in proteins of unsolved three-dimensional structure" Proteins. Jan. 1, 1990;7(2):99-111.

Carpenter et al. "A humanized non-FcR-binding anti-CD3 antibody, visilizumab, for treatment of steroid-refractory acute graft-versus-host disease" Blood, The Journal of the American Society of Hematology. Apr. 15, 2002;99(8):2712-9.

Carter et al. "High level *Escherichia coli* expression and production of a bivalent humanized antibody fragment" Bio/technology. Feb. 1992;10(2):163-7.

Chaudhary et al. "A rapid method of cloning functional variable-region antibody genes in *Escherichia coli* as single-chain immunotoxins" Proceedings of the National Academy of Sciences. Feb. 1, 1990;87(3):1066-70.

Chen et al. "Fusion protein linkers: property, design and functionality" Advanced drug delivery reviews. Oct. 15, 2013;65(10):1357-69.

Chester et al. "Natural killer cell immunomodulation: targeting activating, inhibitory, and co-stimulatory receptor signaling for cancer immunotherapy" Frontiers in immunology. Dec. 2, 2015;6:601.

Chothia et al. "Canonical structures for the hypervariable regions of immunoglobulins" Journal of molecular biology. Aug. 20, 1987;196(4):901-17.

Chothia et al. "Conformations of immunoglobulin hypervariable regions" Nature. Dec. 1989;342(6252):877-83.

Clackson et al. "Making antibody fragments using phage display libraries" Nature. Aug. 1991:352(6336):624-8.

Conrad et al. "TCR and CD3 antibody cross-reactivity in 44 species" Cytometry Part A: The Journal of the International Society for Analytical Cytology. Nov. 2007;71(11):925-33.

Davies et al. "Antibody-antigen complexes" Annual review of biochemistry. Jul. 1990;59(1):439-73.

Dietz et al. Protein structure by mechanical triangulation. Proceedings of the National Academy of Sciences. Jan. 31, 2006;103(5):1244-7.

Donate et al. "Molecular evolution and domain structure of plasminogen-related growth factors (HGF/SF and HGF1/MSP)" Protein Science. Dec. 1994;3(12):2378-94.

Duperret et al. "Synthetic DNA-encoded monoclonal antibody delivery of Anti-CTLA-4 antibodies induces tumor shrinkage in vivo" Cancer research. Nov. 15, 2018;78(22):6363-70.

Ehrlich et al. "Isolation of an active heavy-chain variable domain from a homogeneous rabbit antibody by cathepsin B digestion of the aminoethylated heavy chain" Biochemistry. Aug. 1, 1980;19(17):4091-6.

Eisenfeld et al. "Constrained optimization and protein structure determination" American Journal of Physiology—Cell Physiology. Aug. 1, 1991:261(2):C376-86.

Graham et al. "Characteristics of a human cell line transformed by DNA from human adenovirus type 5" Journal of general virology. Jul. 1, 1977;36(1):59-72.

Guss et al. "Structure of the IgG-binding regions of streptococcal protein G" The EMBO journal. Jul. 1986;5(7):1567-75.

Hamers-Casterman et al. "Naturally occurring antibodies devoid of light chains" Nature. Jun. 1993;363(6428):446-8.

Henikoff et al. "Amino acid substitution matrices from protein blocks" Proceedings of the National Academy of Sciences. Nov. 15, 1992;89(22):10915-9.

Herold et al. "Activation of human T cells by FcR nonbinding anti-CD3 mAb, hOKT3γ1 (Ala-Ala)" The Journal of clinical investigation. Feb. 1, 2003;111(3):409-18.

Higgins et al. "Fast and sensitive multiple sequence alignments on a microcomputer" Bioinformatics. Apr. 1, 1989;5(2):151-3.

Hochman et al. "Folding and interaction of subunits at the antibody combining site" Biochemistry. Jun. 1, 1976;15(12):2706-10.

Hofland et al. "Engaging cytotoxic T and NK cells for immunotherapy in chronic lymphocytic leukemia" International journal of molecular sciences. Jan. 2019;20(17):4315.

Holt et al. "Domain antibodies: proteins for therapy" Trends in biotechnology Nov. 1, 2003;21(11):484-90.

Huston et al. "Protein engineering of antibody binding sites: recovery of specific activity in an anti-digoxin single-chain Fv analogue produced in *Escherichia coli*" Proceedings of the National Academy of Sciences. Aug. 1, 1988;85(16):5879-83.

Inbar et al. "Localization of antibody-combining sites within the variable portions of heavy and light chains" Proceedings of the National Academy of Sciences. Sep. 1, 1972;69(9):2659-62.

International Search Report for PCT Application No. PCT/IL2020/050359 dated Jan. 5, 2021.

Jiang et al. "Tumor imaging by means of proteolytic activation of cell-penetrating peptides" Proceedings of the National Academy of Sciences. Dec. 21, 2004;101(51):17867-72.

Kini et al. "Molecular modeling of proteins: a strategy for energy minimization by molecular mechanics in the AMBER force field" Journal of biomolecular structure and dynamics. Dec. 1, 1991;9(3):475-88.

(56) References Cited

OTHER PUBLICATIONS

Klimka et al. "Human anti-CD30 recombinant antibodies by guided phage antibody selection using cell panning" British journal of cancer. Jul. 2000;83(2):252-60.
Koch-Nolte et al. "Single domain antibodies from llama effectively and specifically block T cell ecto-ADP-ribosyltransferase ART2. 2 in vivo" The FASEB Journal. Nov. 2007;21(13):3490-8.
Kwong et al. "Generation, affinity maturation, and characterization of a human anti-human NKG2D monoclonal antibody with dual antagonistic and agonistic activity" Journal of molecular biology. Dec. 31, 2008;384(5):1143-56.
Laplanche et al. "Phosphorothioate-modified oligodeoxyribonucleotides. III. NMR and UV spectroscoptc studies of the R p-R p, S p-S p, and R p-S p duplexes, [d (GGsAATTCC)] 2, derived from diastereomeric O-ethyl phosphorothioates" Nucleic acids research. Nov. 11, 1986;14(22):9081-93.
La Rocca et al. "Zymographic detection and clinical correlations of MMP-2 and MMP-9 in breast cancer sera" British journal of cancer. Apr. 2004;90(7):1414-21.
Lavasani et al. "Monoclonal Antibody against T-Cell Receptor αβ Induces Self-Tolerance in Chronic Experimental Autoimmune Encephalomyelitis" Scandinavian journal of immunology. Jan. 2007;65(1):39-47.
Lavie et al. "Inhibition of the CD8+ T cell-mediated cytotoxicity reaction by hypericin: potential for treatment of T cell-mediated diseases" International immunology. Apr. 1, 2000:12(4):479-86.
Liao et al. "Interleukin-2 at the crossroads of effector responses, tolerance, and immunotherapy" Immunity. Jan. 24, 2013;38(1):13-25.
Lindmark et al. "Binding of immunoglobulins to protein A and immunoglobulin levels in mammalian sera" Journal of immunological methods. Jan. 1, 1983;62(1):1-3.
Liu et al. "SynLinker: an integrated system for designing linkers and synthetic fusion proteins" Bioinformatics. Nov. 15, 2015;31(22):3700-2.
Maloy et al. "Induction of mucosal and systemic immune responses by immunization with ovalbumin entrapped in poly (lactide-co-glycolide) microparticles" Immunology. Apr. 1994;81(4):661.
Maratea et al. "Deletion and fusion analysis of the phage φX174 lysis gene E" Gene. Jan. 1, 1985;40(1):39-46.
Mather JP. "Establishment and characterization of two distinct mouse testicular epithelial cell line" Biology of reproduction. Aug. 1, 1980;23(1):243-52.
Mather et al. "Culture of testicular cells in hormone-supplemented serum-free medium" Annals of the New York Academy of Sciences. Jun. 1982;383(1):44-68.
Miao et al. "Prognostic role of matrix metalloproteinases in bladder carcinoma: a systematic review and meta-analysis" Oncotarget. May 9, 2017;8(19):32309.
Murphy et al. "Genetic construction, expression, and melanoma-selective cytotoxicity of a diphtheria toxin-related alpha-melanocyte-stimulating hormone fusion protein" Proceedings of the National Academy of Sciences. Nov. 1, 1986;83(21):8258-62.
Myers et al. "Optimal alignments in linear space" Bioinformatics. Mar. 1, 1988;4(1):11-7.
Needleman et al. "A general method applicable to the search for similarities in the amino acid sequence of two proteins" Journal of molecular biology. Mar. 28, 1970;48(3):443-53.
Nguyen et al. "Heavy-chain antibodies in Camelidae; a case of evolutionary innovation" Immunogenetics. Apr. 2002;54(1):39-47.
Nguyen et al. "The specific variable domain of camel heavy-chain antibodies is encoded in the germline" Journal of molecular biology. Jan. 23, 1998;275(3):413-8.
Nilson et al. "Protein L from Peptostreptococcus magnus binds to the kappa light chain variable domain" Journal of Biological Chemistry. Feb. 5, 1992;267(4):2234-9.
O'Hare et al. "Cytotoxicity of a recombinant ricin-A-chain fusion protein containing a proteolytically-cleavable spacer sequence" FEBS letters. Oct. 29, 1990;273(1-2):200-4.
Olson et al. "Activatable cell penetrating peptides linked to nanoparticles as dual probes for in vivo fluorescence and MR imaging of proteases" Proceedings of the National Academy of Sciences. Mar. 2, 2010;107(9):4311-6.
Orcutt et al. "A modular IgG-scFv bispecific antibody topology" Protein Engineering, Design & Selection. Apr. 1, 2010;23(4):221-8.
Ortho Multicenter Transplant Study Group "A randomized clinical trial of OKT3 monoclonal antibody for acute rejection of cadaveric renal transplants" New England Journal of Medicine. Aug. 8, 1985;313(6):337-42.
Pearson et al. "Improved tools for biological sequence comparison" Proceedings of the National Academy of Sciences. Apr. 1, 1988,85(8):2444-8.
Pedersen L. "Conformational properties of molecules by ab initio quantum mechanical energy minimization" Environmental health perspectives. Sep. 1985;61:185-90.
Pessano et al. "The T3/T cell receptor complex: antigenic distinction between the two 20-kd T3 (T3-delta and T3-epsilon) subunits" The EMBO journal. Feb. 1985;4(2):337-44.
Pitcher et al. "T-cell receptor signal transmission: who gives an ITAM?" Trends in immunology. Oct. 1, 2003;24(10):554-60.
Plückthun A. "Antibody engineering: advances from the use of *Escherichia coli* expression systems" Bio/technology. Jun. 1991;9(6):545-51.
Qian et al. "High-resolution structure prediction and the crystallographic phase problem" Nature. Nov. 2007;450(7167):259-64.
Rader et al. "A phage display approach for rapid antibody humanization: designed combinatorial V gene libraries" Proceedings of the National Academy of Sciences. Jul. 21, 1998;95(15):8910-5.
Radisky et al. "Matrix metalloproteinases as breast cancer drivers and therapeutic targets" Frontiers in bioscience (Landmark edition). 2015;20:1144.
Raman et al. "NMR structure determination for larger proteins using backbone-only data" Science. Feb. 19, 2010;327(5968):1014-8.
Reff Me. "High-level production of recombinant immunoglobulins in mammalian cells" Current opinion in biotechnology. Oct. 1, 1993;4(5):573-6.
Reinherz et al., editors. "Leukocyte Typing II: vol. 1 Human T Lymphocytes" Springer Science & Business Media; Dec. 6, 2012.
Ridgway et al. "'Knobs-into-holes' engineering of antibody CH3 domains for heavy chain heterodimerization" Protein Engineering, Design and Selection. Jul. 1, 1996:9(7):617-21.
Riechmann et al. "Single domain antibodies: comparison of camel VH and camelised human VH domains" Journal of immunological methods. Dec. 10, 1999;231(1-2):25-38.
Robinson DF. "Comparison of labeled trees with valency three" Journal of combinatorial theory, Series B. Oct. 1, 1971;11(2):105-19.
Roux et al. "Structural analysis of the nurse shark (new) antigen receptor (NAR): molecular convergence of NAR and unusual mammalian immunoglobulins" Proceedings of the National Academy of Sciences. Sep. 29, 1998;95(20):11804-9.
Saitou et al. "The neighbor-joining method: a new method for reconstructing phylogenetic trees" Molecular biology and evolution. Jul. 1, 1987;4(4):406-25.
Scatchard G. "The attractions of proteins for small molecules and ions" Annals of the New York Academy of Sciences. May 1949;51(4):660-72.
Schaefer et al. "Immunoglobulin domain crossover as a generic approach for the production of bispecific IgG antibodies" Proceedings of the National academy of Sciences. Jul. 5, 2011;108(27):11187-92.
Schueler-Furman et al. "Progress in modeling of protein structures and interactions" Science. Oct. 28, 2005;310(5748):638-42.
Segal et al. "The action of norepinephrine in the rat hippocampus. IV. The effects of locus coeruleus stimulation on evoked hippocampal unit activity" Brain research. May 14, 1976;107(3):513-25.
Sivori et al. "Human NK cells: surface receptors, inhibitory checkpoints, and translational applications" Cellular & molecular immunology. May 2019;16(5):430-41.
Smith-Garvin et al. "T cell activation" Annual review of immunology. Apr. 23, 2009;27:591-619.

(56) References Cited

OTHER PUBLICATIONS

Stec et al. "Automated solid-phase synthesis, separation, and stereochemistry of phosphorothioate analogs of oligodeoxyribonucleotides" Journal of the American Chemical Society. Oct. 1984;106(20):6077-9.
Stein et al. "Physicochemical properties of phospborothioate oligodeoxynucleotides" Nucleic acids research. Apr. 25, 1988;16(8):3209-21.
Trill et al. "Production of monoclonal antibodies in COS and CHO cells" Current Opinion in Biotechnology. Jan. 1, 1995;6(5):553-60.
Uhlmann et al. "Antisense oligonucleotides: a new therapeutic principle" Chemical Reviews. Jun. 1, 1990;90(4):543-84.
Urlaub et al. "Isolation of Chinese hamster cell mutants deficient in dihydrofolate reductase activity" Proceedings of the National Academy of Sciences. Jul. 1, 1980;77(7):4216-20.
Vallera et al. "IL15 trispecific killer engagers (TriKE) make natural killer cells specific to CD33+ targets while also inducing persistence, in vivo expansion, and enhanced function" Clinical Cancer Research. Jul. 15, 2016;22(14):3440-50.
Weiner et al. "A new force field for molecular mechanical simulation of nucleic acids and proteins" Journal of the American Chemical Society. Feb. 1984;106(3):765-84.
Weisel et al. "A model for fibrinogen: domains and sequence" Science. Dec. 20, 1985;230(4732):1388-91.
Westby et al. "Preparation and characterization of recombinant proricin containing an alternative protease-sensitive linker sequence" Bioconjugate chemistry. Sep. 1, 1992;3(5):375-81.
Wilbur et al. "Rapid similarity searches of nucleic acid and protein data banks" Proceedings of the National Academy of Sciences. Feb. 1, 1983;80(3):726-30.
Wu et al. "An analysis of the sequences of the variable regions of Bence Jones proteins and myeloma light chains and their implications for antibody complementarity" Journal of Experimental Medicine. Aug. 1, 1970;132(2):211-50.
Yoshino et al. "Upgrading of flow cytometric analysis for absolute counts, cytokines and other antigenic molecules of cynomolgus monkeys (*Macaca fascicularis*) by using anti-human cross-reactive antibodies" Experimental animals. 2000;49(2):97-110.
Zelensky et al. "The C-type lectin-like domain superfamily" The FEBS journal. Dec. 2005;272(24):6179-217.
Zhu et al. "Synergistic innate and adaptive immune response to combination immunotherapy with anti-tumor antigen antibodies and extended serum half-life IL-2" Cancer cell. Apr. 13, 2015;27(4):489-501.
Harper et al., (2017) Preclinical Evaluation of MEDI0641, a Pyrrolobenzodiazepine-Conjugated Antibody-Drug Conjugate Targeting 5T4. Mol Cancer Ther 16(8): 1576-1587.
Wang et al., (2018) A novel 5T4-targeting antibody-drug conjugate H6-DM4 exhibits potent therapeutic efficacy in gastrointestinal tumor xenograft models. Am J Cancer Res 8(4): 610-623.
Altschul et al., (1997) Gapped BLAST and PSI-BLAST: a new generation of protein database search programs. Nucleic Acids Res 25(17): 3389-3402.
Bogin et al., (2002) Insight into Schmid metaphyseal chondrodysplasia from the crystal structure of the collagen X NC1 domain trimer. Structure 10(2): 165-173.
Bogin et al., (2002) Structural basis for the enhanced thermal stability of alcohol dehydrogenase mutants from the mesophilic bacterium *Clostridium beijerinckii*: contribution of salt bridging. Protein Sci 11(11): 2561-2574.
Brinkmann and Kontermann (2017) The making of bispecific antibodies. mAbs 9(2): 182-212.
Darke et al., (1989) Human immunodeficiency virus protease. Bacterial expression and characterization of the purified aspartic protease. Journal of Biological Chemistry 264(4): 2307-2312.
Dassa et al., (2018) The Human Cytomegalovirus Protein UL148A Downregulates the NK Cell-Activating Ligand MICA To Avoid NK Cell Attack. J Virol 92(17): e00162-18, 12 pages.
Dodson (2007) Computational biology: protein predictions. Nature 450(7167): 176-177.
Eckhard et al., (2016) Active site specificity profiling of the matrix metalloproteinase family: Proteomic identification of 4300 cleavage sites by nine MMPs explored with structural and synthetic peptide cleavage analyses. Matrix Biol 49: 37-60.
Froimowitz (1990) The development of computer simulations of the geometries and thermodynamics of biological molecules. Biotechniques 8(6): 640-644, 649-652.
George and Heringa (2003) An analysis of protein domain linkers: their classification and role in protein folding. Protein Eng 15(11): 871-879.
Hecht et al., (2009) A novel peptide agonist of formyl-peptide receptor-like 1 (ALX) displays anti-inflammatory and cardioprotective effects. J Pharmacol Exp Ther 328(2): 426-434.
Hecht et al., (2018) ILDR2 Is a Novel B7-like Protein That Negatively Regulates T Cell Responses. J Immunol 200(6): 2025-2037.
Hein (1990) Unified approach to alignment and phylogenies. Methods Enzymol 183: 626-645.
Hirsch et al., (1988) Effects of in vivo administration of anti-T3 monoclonal antibody on T cell function in mice. I. Immunosuppression of transplantation responses. J Immunol 140(11): 3766-3772.
Kleifeld et al., (2004) Higher metal-ligand coordination in the catalytic site of cobalt-substituted Thermoanaerobacter brockii alcohol dehydrogenase lowers the barrier for enzyme catalysis. Biochemistry 43(22): 7151-7161.
Kvansakul et al., (2003) Crystal structure of the collagen alpha1(VIII) NC1 trimer. Matrix Biol 22(2): 145-152.
Lindmark et al., (1983) Binding of immunoglobulins to protein A and immunoglobulin levels in mammalian sera. J Immunol Methods 62(1): 1-13.
Lybrand (1991) Molecular simulation and drug design. J Pharm Belg 46(1): 49-54. Abstract, 1 page.
Murter et al., (2019) Mouse PVRIG Has CD8+ T Cell-Specific Coinhibitory Functions and Dampens Antitumor Immunity. Cancer Immunol Res 7(2): 244-256.
Owens (2017) Faster, deeper, smaller-the rise of antibody-like scaffolds. Nat Biotechnol 35(7): 602-603.
Pilpel et al., (2003) Polyproline type II conformation in the C-terminal domain of the nuclear pore complex protein gp210. Biochemistry 42(12): 3519-3526.
Portolano et al., (1993) Lack of promiscuity in autoantigen-specific H and L chain combinations as revealed by human H and L chain "roulette". J Immunol 150(3): 880-887.
Reusch et al., (2014) A novel tetravalent bispecific TandAb (CD30/CD16A) efficiently recruits NK cells for the lysis of CD30+ tumor cells. MAbs 6(3): 727-738 with supplemental material.
Salmerón et al., (1991) A conformational epitope expressed upon association of CD3-epsilon with either CD3-delta or CD3-gamma is the main target for recognition by anti-CD3 monoclonal antibodies. J Immunol 147(9): 3047-3052.
Schaeffer and van Hoof (2011) Different nuclease requirements for exosome-mediated degradation of normal and nonstop mRNAs. Proc Natl Acad Sci U S A 108(6): 2366-2371.
Schellenberger et al., (2009) A recombinant polypeptide extends the in vivo half-life of peptides and proteins in a tunable manner. Nat Biotechnol 27(12): 1186-1190.
Shcherbatko et al., (2016) Engineering Highly Potent and Selective Microproteins against Nav1.7 Sodium Channel for Treatment of Pain. J Biol Chem 291(27): 13974-13986.
Smith and Waterman (1981) Comparison of biosequences. Advances in Applied Mathematics 2(4): 482-489.
Stanietsky et al., (2009) The interaction of TIGIT with PVR and PVRL2 inhibits human NK cell cytotoxicity. Proc Natl Acad Sci U S A 106(42): 17858-17863.
Tiran et al., (2008) A novel recombinant soluble splice variant of Met is a potent antagonist of the hepatocyte growth factor/scatter factor-Met pathway. Clin Cancer Res 14(14): 4612-4621.
Turk et al., (2001) Determination of protease cleavage site motifs using mixture-based oriented peptide libraries. Nat Biotechnol 19(7): 661-667.

(56) References Cited

OTHER PUBLICATIONS

Vitenshtein et al., (2016) NK Cell Recognition of Candida glabrata through Binding of NKp46 and NCR1 to Fungal Ligands Epa1, Epa6, and Epa7. Cell Host Microbe 20(4): 527-534 with supplemental information.
Whelan et al., (2019) PVRIG and PVRL2 Are Induced in Cancer and Inhibit CD8+ T-cell Function. Cancer Immunol Res 7(2): 257-268.
Yang et al., (1986) A common pathway for T lymphocyte activation involving both the CD3-Ti complex and CD2 sheep erythrocyte receptor determinants. J Immunol 137(4): 1097-1100.
Yosef et al., (2016) Directed elimination of senescent cells by inhibition of BCL-W and BCL-XL. Nat Commun 7: 11190, 11 pages.
Fournier and Schirrmacher (2013) Bispecific antibodies and trispecific immunocytokines for targeting the immune system against cancer: preparing for the future. BioDrugs 27(1): 35-53.

* cited by examiner

GGSGGSEVQLVESGGGLVQPGGSLRLSCAASGFTFNTYAMNWVRQAPGKGLEWVARIRSKYNNYATYYADSVKDRFTISR
DDSKNTLYLQMNSLRAEDTAVYYCVRHGNFGNSYVSWFAYWGQGTMVTVSSASTKGPSVFPLAPSSKSTSGGTAALGCLV
KDYFPEPVTVSWNSGALTSGVHTFPAVLQSSGLYSLSSVVTVPSSSLGTQTYICNVNHKPSNTKVDKRVEPKSCPPCGGG
GSDIQMTQSPSSLSASVGDRVTITCQASQDISNYLNWYQQKPGKAPKLLIYDASNLETGVPSRFSGSGSGTDFTFTISSL
QPEDIATYFCQHFDHLPLAFGGGTKVEIKGGGGSGGGGSGGGGSQVQLQESGPGLVKPSETLSLTCTVSGGSVSSGDYYW
TWIRQSPGKGLEWIGHIYYSGNTNYNPSLKSRLTISIDTSKTQFSLKLSSVTAADTAIYYCVRDRVTGAFDIWGQGTMVT
VSS (SEQ ID NO: 138)

Figure 4A ggcggcagcggcggctccgaggtgcagctggtggagtccggcggcggcctggtgcagcccggcggcagcctgaggctgtcctgcgccgc
ctctggcttcacctttaacacatacgcaatgaattgggtgcgccaggcaccaggcaagggactggagtgggtggcccggatcagaagca
agtacaacaattatgccacctactatgccgactccgtgaaggatcggtttaccatcagcagagacgattccaagaacacactgtatctg
cagatgaatagcctgcgggccgaggatacagccgtgtactattgcgtgagacacggcaactttggcaattcttacgtgagctggttcgc
ctattggggccagggcaccatggtgacagtgtcctctgcctctaccaagggacctagcgtgttcccactggcacctagctccaagtcta
ccagcggaggcacagccgccctgggatgtctggtgaaggactactttccagagcccgtgacagtgtcctggaactctggcgccctgacc
agcggagtgcacacattccctgccgtgctgcagtctagcggcctgtactccctgtcctctgtggtgaccgtgccaagctcctctctggg
cacccagacatatatctgcaacgtgaatcacaagccctctaatacaaaggtggacaagagggtggagcctaagagctgccccccttgtg
gcggaggcggtagcgatatccagatgacccaaagccccagtagcctgtccgccagtgtaggagatagggtaaccatcacttgccaagcg
agccaagacatcagcaactacctgaattggtatcagcagaagcccggcaaagcacccaagctcctgatctacgacgccagcaatctgga
gaccggcgtgcccagcaggttcagcggatctggtagcggcaccgacttcaccttcaccataagtagtctgcagcccgaggacatcgcca
cctacttctgtcagcacttcgatcacctgcccctggccttcggcggtgggaccaaggtggagatcaagggtgggggtggcagcgggga
ggcggaagcggcggaggtggctctcaggtgcagcttcaagagagcggacccggcctcgtgaagcccagcgagaccttgagcctgacctg
cactgtgagtggcggtagcgtgagcagcggcgactattactggacctggatcaggcagagccctggcaaggggctggagtggatcggcc
acatctactacagcgggaacacgaactacaaccccagcctgaagagcaggctgacgatcagcatcgacacgagcaagacccagttctca
cttaagctcagcagcgtgaccgccgcagacaccgccatatactactgcgtgagggacagggtgacgggcgctttcgacatctggggcca
aggcacaatggtcacggtgagctcc (SEQ ID NO: 150)

Figure 4B

GGSGGSQAVVTQEPSLTVSPGGTVTLTCRSSTGAVTTSNYANWVQQKPGQAPRGLIGGTNKRAPGTPARFSGSLLGGKAA
LTLSGVQPEDEAEYYCALWYSNLWVFGGGTKLTVLGQPKAAPSVTLFPPSSEELQANKATLVCLISDFYPGAVTVAWKAD
SSPVKAGVETTTPSKQSNNKYAASSYLSLTPEQWKSHRSYSCQVTHEGSTVEKTVAPTECPPCSGGGSDIQMTQSPSSLS
ASVGDRVTITCQASQDISNYLNWYQQKPGKAPKLLIYDASNLETGVPSRFSGSGSGTDFTFTISSLQPEDIATYFCQHFD
HLPLAFGGGTKVEIKGGGGSGGGGSGGGGSQVQLQESGPGLVKPSETLSLTCTVSGGSVSSGDYYWTWIRQSPGKGLEWI
GHIYYSGNTNYNPSLKSRLTISIDTSKTQFSLKLSSVTAADTAIYYCVRDRVTGAFDIWGQGTMVTVSS (SEQ ID
NO: 139)

Figure 5A ggcggcagcggcggctcccaagccgtggtaacccaggagcccagtctgacagtgagccctggcggtacagtgaccttgacttgcaggag
cagtaccggagccgtaactacctcaaactacgccaactgggtgcagcagaagcccggtcaggcccccaggggccttattggtgggacta
acaaacgagcacccggaacccccgcaaggttcagcggcagccttctgggcggaaaggccgctctcacattgagcggcgtgcagcccgag
gacgaggccgagtactactgcgccctgtggtacagcaacctgtgggtgttcggcggagggaccaagctgaccgtgctgggccagcccaa
agctgcgccgagcgtgaccctgttcccccgtcaagcgaggagctgcaggctaacaaggccaccctggtgtgcctgattagtgacttct
accccggtgccgtcaccgtggcctggaaggccgacagtagcccagttaaagcgggcgtcgagaccaccactcccagcaagcagagcaac
aacaagtacgccgcgagcagctacctgagtctgacccccgagcagtggaagagccacaggagctacagctgccaggtgacccacgaggg
cagcactgtggagaagactgtggccccgaccgagtgccccccatgtagcggcggagggtccgatatccagatgacccaaagccccagta
gcctgtccgccagtgtaggagatagggtaaccatcacttgccaagcgagccaagacatcagcaactacctgaattggtatcagcagaag
cccggcaaagcacccaagctcctgatctacgacgccagcaatctggagaccggcgtgcccagcaggttcagcggatctggtagcggcac
cgacttcaccttcaccataagtagtctgcagcccgaggacatcgccacctacttctgtcagcacttcgatcacctgcccctggccttcg
gcggtgggaccaaggtggagatcaagggtgggggtggcagcgggggaggcggaagcggcggaggtggctctcaggtgcagcttcaagag
agcggacccggcctcgtgaagcccagcgagaccttgagcctgacctgcactgtgagtggcggtagcgtgagcagcggcgactattactg
gacctggatcaggcagagccctggcaaggggctggagtggatcggccacatctactacagcgggaacacgaactacaaccccagcctga
agagcaggctgacgatcagcatcgacacgagcaagacccagttctcacttaagctcagcagcgtgaccgccgcagacaccgccatatac
tactgcgtgagggacagggtgacgggcgctttcgacatctggggccaaggcacaatggtcacggtgagctcc (SEQ ID NO:
151)

Figure 5B

GGSGGSEVQLVESGGGLVQPGGSLRLSCAASGFTFNTYAMNWVRQAPGKGLEWVARIRSKYNNYATYYADSVKDRFTISR
DDSKNTLYLQMNSLRAEDTAVYYCVRHGNFGNSYVSWFAYWGQGTMVTVSSASTKGPSVFPLAPSSKSTSGGTAALGCLV
KDYFPEPVTVSWNSGALTSGVHTFPAVLQSSGLYSLSSVVTVPSSSLGTQTYICNVNHKPSNTKVDKRVEPKSCPPCGGG
GSQVQLQESGPGLVKPSETLSLTCTVSGGSVSSGDYYWTWIRQSPGKGLEWIGHIYYSGNTNYNPSLKSRLTISIDTSKT
QFSLKLSSVTAADTAIYYCVRDRVTGAFDIWGQGTMVTVSSGGGGSGGGGSGGGGSDIQMTQSPSSLSASVGDRVTITCQ
ASQDISNYLNWYQQKPGKAPKLLIYDASNLETGVPSRFSGSGSGTDFTFTISSLQPEDIATYFCQHFDHLPLAFGGGTKV
EIK (SEQ ID NO: 140)

Figure 6A ggcggcagcggcggctccgaggtgcagctggtggagtccggcggcggcctggtgcagcccggcggcagcctgaggctgtcctgcgccgc
ctctggcttcacctttaacacatacgcaatgaattgggtgcgccaggcaccaggcaagggactggagtgggtggcccggatcagaagca
agtacaacaattatgccacctactatgccgactccgtgaaggatcggtttaccatcagcagagacgattccaagaacacactgtatctg
cagatgaatagcctgcgggccgaggatacagccgtgtactattgcgtgagacacggcaactttggcaattcttacgtgagctggttcgc
ctattggggccagggcaccatggtgacagtgtcctctgcctctaccaagggacctagcgtgttcccactggcacctagctccaagtcta
ccagcggaggcacagccgccctgggatgtctggtgaaggactactttccagagcccgtgacagtgtcctggaactctggcgccctgacc
agcggagtgcacacattccctgccgtgctgcagtctagcggcctgtactccctgtcctctgtggtgaccgtgccaagctcctctctggg
cacccagacatatatctgcaacgtgaatcacaagccctctaatacaaaggtggacaagagggtggagcctaagagctgcccccttgtg
gcggaggcggtagccaggtgcagcttcaagagagcggacccggcctcgtgaagcccagcgagaccttgagcctgacctgcactgtgagt
ggcggtagcgtgagcagcggcgactattactggacctggatcaggcagagccctggcaaggggctggagtggatcggccacatctacta
cagcgggaacacgaactacaaccccagcctgaagagcaggctgacgatcagcatcgacacgagcaagacccagttctcacttaagctca
gcagcgtgaccgccgcagacaccgccatatactactgcgtgagggacagggtgacgggcgctttcgacatctggggccaaggcacaatg
gtcacggtgagctccggtgggggtggcagcgggggaggcggaagcggcggaggtggctctgatatccagatgacccaaagccccagtag
cctgtccgccagtgtaggagatagggtaaccatcacttgccaagcgagccaagacatcagcaactacctgaattggtatcagcagaagc
ccggcaaagcacccaagctcctgatctacgacgccagcaatctggagaccggcgtgcccagcaggttcagcggatctggtagcggcacc
gacttcaccttcaccataagtagtctgcagcccgaggacatcgccacctacttctgtcagcacttcgatcacctgcccctggccttcgg
cggtgggaccaaggtggagatcaag (SEQ ID NO: 152)

Figure 6B

GGSGGSQAVVTQEPSLTVSPGGTVTLTCRSSTGAVTTSNYANWVQQKPGQAPRGLIGGTNKRAPGTPARFSGSLLGGKAA
LTLSGVQPEDEAEYYCALWYSNLWVFGGGTKLTVLGQPKAAPSVTLFPPSSEELQANKATLVCLISDFYPGAVTVAWKAD
SSPVKAGVETTTPSKQSNNKYAASSYLSLTPEQWKSHRSYSCQVTHEGSTVEKTVAPTECPPCSGGGSQVQLQESGPGLV
KPSETLSLTCTVSGGSVSSGDYYWTWIRQSPGKGLEWIGHIYYSGNTNYNPSLKSRLTISIDTSKTQFSLKLSSVTAADT
AIYYCVRDRVTGAFDIWGQGTMVTVSSGGGGSGGGGSGGGGSDIQMTQSPSSLSASVGDRVTITCQASQDISNYLNWYQQ
KPGKAPKLLIYDASNLETGVPSRFSGSGSGTDFTFTISSLQPEDIATYFCQHFDHLPLAFGGGTKVEIK (SEQ ID
NO: 141)

Figure 7A ggcggcagcggcggctcccaagccgtggtaacccaggagcccagtctgacagtgagccctggcggtacagtgaccttgacttgcaggag
cagtaccggagccgtaactacctcaaactacgccaactgggtgcagcagaagcccggtcaggcccccaggggccttattggtgggacta
acaaacgagcacccggaacccccgcaaggttcagcggcagccttctgggcggaaaggccgctctcacattgagcggcgtgcagcccgag
gacgaggccgagtactactgcgccctgtggtacagcaacctgtgggtgttcggcggagggaccaagctgaccgtgctgggccagcccaa
agctgcgccgagcgtgaccctgttcccccccgtcaagcgaggagctgcaggctaacaaggccaccctggtgtgcctgattagtgacttct
accccggtgccgtcaccgtggcctggaaggccgacagtagcccagttaaagcgggcgtcgagaccaccactcccagcaagcagagcaac
aacaagtacgccgcgagcagctacctgagtctgacccccgagcagtggaagagccacaggagctacagctgccaggtgacccacgaggg
cagcactgtggagaagactgtggccccgaccgagtgcccccatgtagcggcggagggtcccaggtgcagcttcaagagagcggacccg
gcctcgtgaagcccagcgagaccttgagcctgacctgcactgtgagtggcggtagcgtgagcagcggcgactattactggacctggatc
aggcagagccctggcaaggggctggagtggatcggccacatctactacagcgggaacacgaactacaaccccagcctgaagagcaggct
gacgatcagcatcgacacgagcaagacccagttctcacttaagctcagcagcgtgaccgccgcagacaccgccatatactactgcgtga
gggacagggtgacgggcgctttcgacatctggggccaaggcacaatggtcacggtgagctccggtgggggtggcagcgggggaggcgga
agcggcggaggtggctctgatatccagatgacccaaagccccagtagcctgtccgccagtgtaggagatagggtaaccatcacttgcca
agcgagccaagacatcagcaactacctgaattggtatcagcagaagcccggcaaagcacccaagctcctgatctacgacgccagcaatc
tggagaccggcgtgcccagcaggttcagcggatctggtagcggcaccgacttcaccttcaccataagtagtctgcagcccgaggacatc
gccacctacttctgtcagcacttcgatcacctgcccctggccttcggcggtgggaccaaggtggagatcaag (SEQ ID NO:
153)

Figure 7B

EVAHRFKDLGEENFKALVLIAFAQYLQQCPFEDHVKLVNEVTEFAKTCVADESAENCDKSLHTLFGDKLCTVA
TLRETYGEMADCCAKQEPERNECFLQHKDDNPNLPRLVRPEVDVMCTAFHDNEETFLKKYLYEIARRHPYFYA
PELLFFAKRYKAAFTECCQAADKAACLLPKLDELRDEGKASSAKQRLKCASLQKFGERAFKAWAVARLSQRFP
KAEFAEVSKLVTDLTKVHTECCHGDLLECADDRADLAKYICENQDSISSKLKECCEKPLLEKSHCIAEVENDE
MPADLPSLAADFVESKDVCKNYAEAKDVFLGMFLYEYARRHPDYSVVLLLRLAKTYETTLEKCCAAADPHECY
AKVFDEFKPLVEEPQNLIKQNCELFEQLGEYKFQNALLVRYTKKVPQVSTPTLVEVSRNLGKVGSKCCKHPEA
KRMPCAEDYLSVVLNQLCVLHEKTPVSDRVTKCCTESLVNRRPCFSALEVDETYVPKEFNAETFTFHADICTL
SEKERQIKKQTALVELVKHKPKATKEQLKAVMDDFAAFVEKCCKADDKETCFAEEGKKLVAASQAAGGSGGSP
LGLAGGGSGGSEVQLVESGGGLVQPGGSLRLSCAASGFTFNTYAMNWVRQAPGKGLEWVARIRSKYNNYATYY
ADSVKDRFTISRDDSKNTLYLQMNSLRAEDTAVYYCVRHGNFGNSYVSWFAYWGQGTMVTVSSASTKGPSVFP
LAPSSKSTSGGTAALGCLVKDYFPEPVTVSWNSGALTSGVHTFPAVLQSSGLYSLSSVVTVPSSSLGTQTYIC
NVNHKPSNTKVDKRVEPKSCPPCGGGGSDIQMTQSPSSLSASVGDRVTITCQASQDISNYLNWYQQKPGKAPK
LLIYDASNLETGVPSRFSGSGSGTDFTFTISSLQPEDIATYFCQHFDHLPLAFGGGTKVEIKGGGGSGGGGSG
GGGSQVQLQESGPGLVKPSETLSLTCTVSGGSVSSGDYYWTWIRQSPGKGLEWIGHIYYSGNTNYNPSLKSRL
TISIDTSKTQFSLKLSSVTAADTAIYYCVRDRVTGAFDIWGQGTMVTVSS (SEQ ID NO: 130)

Figure 8A gaggtggcccacaggttcaaggatctgggcgaggagaacttcaaggccctggtgctgatcgccttcgcccagtatctgcagcagtgccc
ctttgaggaccacgtgaagctggtgaacgaggtgaccgagttcgccaagacatgcgtggccgacgagtccgccgagaattgtgataagt
ctctgcacaccctgtttggcgataagctgtgcaccgtggccacactgagggagacatacggcgagatggccgactgctgtgccaagcag
gagcccgagcgcaacgagtgcttcctgcagcacaaggacgataaccctaatctgccacggctggtgagacctgaggtggacgtgatgtg
caccgccttccacgataatgaggagacatttctgaagaagtacctgtatgagatcgcccggagacacccttacttttatgccccagagc
tgctgttctttgccaagcggtacaaggcagccttcaccgagtgctgtcaggcagcagataaggcagcatgcctgctgccaaagctggac
gagctgagggatgagggcaaggcaagctccgccaagcagcgcctgaagtgtgcaagcctgcagaagttcggagagagggcctttaaggc
atgggcagtggcaaggctgtcccagcggttcccaaaggccgagtttgccgaggtgtctaagctggtgaccgacctgacaaaggtgcaca
ccgagtgctgtcacggcgacctgctggagtgcgcagacgatagagccgatctggccaagtacatctgtgagaaccaggactctatctct
agcaagctgaaggagtgctgtgagaagcccctgctggagaagtcccactgcatcgccgaggtggagaacgacgagatgccagcagatct
gccaagcctggcagcagacttcgtggagtccaaggacgtgtgcaagaattacgccgaggccaaggacgtgttcctgggcatgtttctgt
acgagtatgccaggcgccaccctgactactccgtggtgctgctgctgcggctggccaagacctatgagaccacactggagaagtgctgt
gccgccgccgacccccacgagtgctatgcaaaggtgttcgacgagtttaagcccctggtggaggagcctcagaacctgatcaagcagaa
ttgtgagctgtttgagcagctgggcgagtacaagttccagaacgccctgctggtgagatataccaagaaggtgccacaggtgtctaccc
ccacactggtggaggtgagccggaatctgggcaaggtcggctccaagtgctgtaagcaccctgaggccaagagaatgccatgcgccgag
gattacctgtccgtggtgctgaaccagctgtgcgtgctgcacgagaagacccccgtgagcgacagggtgaccaagtgctgtacagagtc
tctggtgaaccggagaccatgctttagcgccctggaggtggatgagacatatgtgcccaaggagttcaatgccgagaccttcacatttc
acgccgacatctgtaccctgagcgagaaggagcgccagatcaagaagcagacagccctggtggagctggtgaagcacaagccaaaggcc
accaaggagcagctgaaggccgtgatggacgatttcgccgcctttgtggagaagtgctgtaaggccgacgataaggagacatgcttcgc
agaggagggcaagaagctggtggcagcaagccaggcagcaggaggctccggcggctctccactgggcctggccggcggcggcagcggcg
gctccgaggtgcagctggtggagtccggcggcggcctggtgcagcccggcggcagcctgaggctgtcctgcgccgcctctggcttcacc
tttaacacatacgcaatgaattgggtgcgccaggcaccaggcaagggactggagtgggtggcccggatcagaagcaagtacaacaatta
tgccacctactatgccgactccgtgaaggatcggtttaccatcagcagagacgattccaagaacacactgtatctgcagatgaatagcc
tgcgggccgaggatacagccgtgtactattgcgtgagacacggcaactttggcaattcttacgtgagctggttcgcctattggggccag
ggcaccatggtgacagtgtcctctgcctctaccaagggacctagcgtgttcccactggcacctagctccaagtctaccagcggaggcac
agccgccctgggatgtctggtgaaggactactttccagagcccgtgacagtgtcctggaactctggcgccctgaccagcggagtgcaca
cattccctgccgtgctgcagtctagcggcctgtactccctgtcctctgtggtgaccgtgccaagctcctctctgggcacccagacatat
atctgcaacgtgaatcacaagccctctaatacaaaggtggacaagagggtggagcctaagagctgcccccccttgtggcggaggcggtag
cgatatccagatgacccaaagccccagtagcctgtccgccagtgtaggagatagggtaaccatcacttgccaagcgagccaagacatca
gcaactacctgaattggtatcagcagaagcccggcaaagcacccaagctcctgatctacgacgccagcaatctggagaccggcgtgccc
agcaggttcagcggatctggtagcggcaccgacttcaccttcaccataagtagtctgcagcccgaggacatcgccacctacttctgtca
gcacttcgatcacctgcccctggccttcggcggtgggaccaaggtggagatcaagggtgggggtggcagcggggggaggcggaagcggcg
gaggtggctcttgccaggtgcagcttcaagagagcggacccggcctcgtgaagcccagcgagaccttgagcctgacctgcactgtgagt
ggcggtagcgtgagcagcggcgactattactggacctggatcaggcagagccctggcaaggggctggagtggatcggccacatctacta
cagcgggaacacgaactacaaccccagcctgaagagcaggctgacgatcagcatcgacacgagcaagacccagttctcacttaagctca
gcagcgtgaccgccgcagacaccgccatatactactgcgtgagggacagggtgacgggcgctttcgacatctggggccaaggcacaatg
gtcacggtgagctcc (SEQ ID NO: 142)

Figure 8B

QDGNEEMGGITQTPYKVSISGTTVILTGGSGGSPLGLAGGGSGGSQAVVTQEPSLTVSPGGTVTLTCRSSTG
AVTTSNYANWVQQKPGQAPRGLIGGTNKRAPGTPARFSGSLLGGKAALTLSGVQPEDEAEYYCALWYSNLWV
FGGGTKLTVLGQPKAAPSVTLFPPSSEELQANKATLVCLISDFYPGAVTVAWKADSSPVKAGVETTTPSKQS
NNKYAASSYLSLTPEQWKSHRSYSCQVTHEGSTVEKTVAPTECPPCSGGGSDIQMTQSPSSLSASVGDRVTI
TCQASQDISNYLNWYQQKPGKAPKLLIYDASNLETGVPSRFSGSGSGTDFTFTISSLQPEDIATYFCQHFDH
LPLAFGGGTKVEIKGGGGSGGGGSGGGGSQVQLQESGPGLVKPSETLSLTCTVSGGSVSSGDYYWTWIRQSP
GKGLEWIGHIYYSGNTNYNPSLKSRLTISIDTSKTQFSLKLSSVTAADTAIYYCVRDRVTGAFDIWGQGTMV
TVSS (SEQ ID NO: 131)

Figure 9A caggacggcaacgaggagatgggcggcatcacccagacaccatacaaggtgagcatctccggcaccacagtgatcctgaccggaggctc
cggcggctctccactgggcctggccggcggcggcagcggcggctcccaagccgtggtaacccaggagcccagtctgacagtgagccctg
gcggtacagtgaccttgacttgcaggagcagtaccggagccgtaactacctcaaactacgccaactgggtgcagcagaagcccggtcag
gcccccaggggccttattggtgggactaacaaacgagcacccggaacccccgcaaggttcagcggcagccttctgggcggaaaggccgc
tctcacattgagcggcgtgcagcccgaggacgaggccgagtactactgcgccctgtggtacagcaacctgtgggtgttcggcggaggga
ccaagctgaccgtgctgggccagcccaaagctgcgcccgagcgtgaccctgttcccccgtcaagcgaggagctgcaggctaacaaggcc
accctggtgtgcctgattagtgacttctaccccggtgccgtcaccgtggcctggaaggccgacagtagcccagttaaagcgggcgtcga
gaccaccactcccagcaagcagagcaacaacaagtacgccgcgagcagctacctgagtctgacccccgagcagtggaagagccacagga
gctacagctgccaggtgacccacgagggcagcactgtggagaagactgtggccccgaccgagtgcccccatgtagcggcggagggtcc
gatatccagatgacccaaagccccagtagcctgtccgccagtgtaggagatagggtaaccatcacttgccaagcgagccaagacatcag
caactacctgaattggtatcagcagaagcccggcaaagcacccaagctcctgatctacgacgccagcaatctggagaccggcgtgccca
gcaggttcagcggatctggtagcggcaccgacttcaccttcaccataagtagtctgcagcccgaggacatcgccacctacttctgtcag
cacttcgatcacctgcccctggccttcggcggtgggaccaaggtggagatcaagggtgggggtggcagcgggggaggcggaagcggcgg
aggtggctctcaggtgcagcttcaagagagcggacccggcctcgtgaagcccagcgagaccttgagcctgacctgcactgtgagtggcg
gtagcgtgagcagcggcgactattactggacctggatcaggcagagccctggcaaggggctggagtggatcggccacatctactacagc
gggaacacgaactacaaccccagcctgaagagcaggctgacgatcagcatcgacacgagcaagacccagttctcacttaagctcagcag
cgtgaccgccgcagacaccgccatatactactgcgtgagggacagggtgacgggcgctttcgacatctggggccaaggcacaatggtca
cggtgagctcc (SEQ ID NO: 143)

Figure 9B

EVAHRFKDLGEENFKALVLIAFAQYLQQCPFEDHVKLVNEVTEFAKTCVADESAENCDKSLHTLFGDKLCTV
ATLRETYGEMADCCAKQEPERNECFLQHKDDNPNLPRLVRPEVDVMCTAFHDNEETFLKKYLYEIARRHPYF
YAPELLFFAKRYKAAFTECCQAADKAACLLPKLDELRDEGKASSAKQRLKCASLQKFGERAFKAWAVARLSQ
RFPKAEFAEVSKLVTDLTKVHTECCHGDLLECADDRADLAKYICENQDSISSKLKECCEKPLLEKSHCIAEV
ENDEMPADLPSLAADFVESKDVCKNYAEAKDVFLGMFLYEYARRHPDYSVVLLLRLAKTYETTLEKCCAAAD
PHECYAKVFDEFKPLVEEPQNLIKQNCELFEQLGEYKFQNALLVRYTKKVPQVSTPTLVEVSRNLGKVGSKC
CKHPEAKRMPCAEDYLSVVLNQLCVLHEKTPVSDRVTKCCTESLVNRRPCFSALEVDETYVPKEFNAETFTF
HADICTLSEKERQIKKQTALVELVKHKPKATKEQLKAVMDDFAAFVEKCCKADDKETCFAEEGKKLVAASQA
AGGSGGSPLGLAGGGSGGSEVQLVESGGGLVQPGGSLRLSCAASGFTFNTYAMNWVRQAPGKGLEWVARIRS
KYNNYATYYADSVKDRFTISRDDSKNTLYLQMNSLRAEDTAVYYCVRHGNFGNSYVSWFAYWGQGTMVTVSS
ASTKGPSVFPLAPSSKSTSGGTAALGCLVKDYFPEPVTVSWNSGALTSGVHTFPAVLQSSGLYSLSSVVTVP
SSSLGTQTYICNVNHKPSNTKVDKRVEPKSCPPCGGGGSQVQLQESGPGLVKPSETLSLTCTVSGGSVSSGD
YYWTWIRQSPGKGLEWIGHIYYSGNTNYNPSLKSRLTISIDTSKTQFSLKLSSVTAADTAIYYCVRDRVTGA
FDIWGQGTMVTVSSGGGGSGGGGSGGGGSDIQMTQSPSSLSASVGDRVTITCQASQDISNYLNWYQQKPGKA
PKLLIYDASNLETGVPSRFSGSGSGTDFTFTISSLQPEDIATYFCQHFDHLPLAFGGGTKVEIK (SEQ ID
NO: 132)

Figure 10A gaggtggcccacaggttcaaggatctgggcgaggagaacttcaaggccctggtgctgatcgccttcgcccagtatctgcagcagtgccc
ctttgaggaccacgtgaagctggtgaacgaggtgaccgagttcgccaagacatgcgtggccgacgagtccgccgagaattgtgataagt
ctctgcacaccctgtttggcgataagctgtgcaccgtggccacactgagggagacatacggcgagatggccgactgctgtgccaagcag
gagcccgagcgcaacgagtgcttcctgcagcacaaggacgataaccctaatctgccacggctggtgagacctgaggtggacgtgatgtg
caccgccttccacgataatgaggagacatttctgaagaagtacctgtatgagatcgcccggagacacccttacttttatgccccagagc
tgctgttctttgccaagcggtacaaggcagccttcaccgagtgctgtcaggcagcagataaggcagcatgcctgctgccaaagctggac
gagctgagggatgagggcaaggcaagctccgccaagcagcgcctgaagtgtgcaagcctgcagaagttcggagagagggcctttaaggc
atgggcagtggcaaggctgtcccagcggttcccaaaggccgagtttgccgaggtgtctaagctggtgaccgacctgacaaaggtgcaca
ccgagtgctgtcacggcgacctgctggagtgcgcagacgatagagccgatctggccaagtacatctgtgagaaccaggactctatctct
agcaagctgaaggagtgctgtgagaagcccctgctggagaagtcccactgcatcgccgaggtggagaacgacgagatgccagcagatct
gccaagcctggcagcagacttcgtggagtccaaggacgtgtgcaagaattacgccgaggccaaggacgtgttcctgggcatgtttctgt
acgagtatgccaggcgccaccctgactactccgtggtgctgctgctgcggctggccaagacctatgagaccacactggagaagtgctgt
gccgccgccgacccccacgagtgctatgcaaaggtgttcgacgagtttaagcccctggtggaggagcctcagaacctgatcaagcagaa
ttgtgagctgtttgagcagctgggcgagtacaagttccagaacgccctgctggtgagatataccaagaaggtgccacaggtgtctaccc
ccacactggtggaggtgagccggaatctgggcaaggtcggctccaagtgctgtaagcaccctgaggccaagagaatgccatgcgccgag
gattacctgtccgtggtgctgaaccagctgtgcgtgctgcacgagaagacccccgtgagcgacagggtgaccaagtgctgtacagagtc
tctggtgaaccggagaccatgctttagcgccctggaggtggatgagacatatgtgcccaaggagttcaatgccgagaccttcacatttc
acgccgacatctgtaccctgagcgagaaggagcgccagatcaagaagcagacagccctggtggagctggtgaagcacaagccaaaggcc
accaaggagcagctgaaggccgtgatggacgatttcgccgcctttgtggagaagtgctgtaaggccgacgataaggagacatgcttcgc
agaggagggcaagaagctggtggcagcaagccaggcagcaggaggctccggcggctctccactgggcctggccggcggcggcagcggcg
gctccgaggtgcagctggtggagtccggcggcggcctggtgcagcccggcggcagcctgaggctgtcctgcgccgcctctggcttcacc
tttaacacatacgcaatgaattgggtgcgccaggcaccaggcaagggactggagtgggtggcccggatcagaagcaagtacaacaatta
tgccacctactatgccgactccgtgaaggatcggtttaccatcagcagagacgattccaagaacacactgtatctgcagatgaatagcc
tgcgggccgaggatacagccgtgtactattgcgtgagacacggcaactttggcaattcttacgtgagctggttcgcctattggggccag
ggcaccatggtgacagtgtcctctgcctctaccaagggacctagcgtgttcccactggcacctagctccaagtctaccagcggaggcac
agccgccctgggatgtctggtgaaggactactttccagagcccgtgacagtgtcctggaactctggcgccctgaccagcggagtgcaca
cattccctgccgtgctgcagtctagcggcctgtactccctgtcctctgtggtgaccgtgccaagctcctctctgggcacccagacatat
atctgcaacgtgaatcacaagccctctaatacaaaggtggacaagagggtggagcctaagagctgcccccccttgtggcggaggcggtag
ccaggtgcagcttcaagagagcggacccggcctcgtgaagcccagcgagaccttgagcctgacctgcactgtgagtggcggtagcgtga
gcagcggcgactattactggacctggatcaggcagagccctggcaaggggctggagtggatcggccacatctactacagcggaacacg
aactacaaccccagcctgaagagcaggctgacgatcagcatcgacacgagcaagacccagttctcacttaagctcagcagcgtgaccgc
cgcagacaccgccatatactactgcgtgagggacagggtgacgggcgctttcgacatctggggccaaggcacaatggtcacggtgagct
ccggtgggggtggcagcgggggaggcggaagcggcggaggtggctctgatatccagatgacccaaagccccagtagcctgtccgccagt
gtaggagatagggtaaccatcacttgccaagcgagccaagacatcagcaactacctgaattggtatcagcagaagcccggcaaagcacc
caagctcctgatctacgacgccagcaatctggagaccggcgtgcccagcaggttcagcggatctggtagcggcaccgacttcaccttca
ccataagtagtctgcagcccgaggacatcgccacctacttctgtcagcacttcgatcacctgcccctggccttcggcggtgggaccaag
gtggagatcaag (SEQ ID NO: 144)

Figure 10B

QDGNEEMGGITQTPYKVSISGTTVILTGGSGGSPLGLAGGGSGGSQAVVTQEPSLTVSPGGTVTLTCRSSTG
AVTTSNYANWVQQKPGQAPRGLIGGTNKRAPGTPARFSGSLLGGKAALTLSGVQPEDEAEYYCALWYSNLWV
FGGGTKLTVLGQPKAAPSVTLFPPSSEELQANKATLVCLISDFYPGAVTVAWKADSSPVKAGVETTTPSKQS
NNKYAASSYLSLTPEQWKSHRSYSCQVTHEGSTVEKTVAPTECPPCSGGGSQVQLQESGPGLVKPSETLSLT
CTVSGGSVSSGDYYWTWIRQSPGKGLEWIGHIYYSGNTNYNPSLKSRLTISIDTSKTQFSLKLSSVTAADTA
IYYCVRDRVTGAFDIWGQGTMVTVSSGGGGSGGGGSGGGGSDIQMTQSPSSLSASVGDRVTITCQASQDISN
YLNWYQQKPGKAPKLLIYDASNLETGVPSRFSGSGSGTDFTFTISSLQPEDIATYFCQHFDHLPLAFGGGTK
VEIK (SEQ ID NO: 133)

Figure 11A caggacggcaacgaggagatgggcggcatcacccagacaccatacaaggtgagcatctccggcaccacagtgatcctgac
cggaggctccggcggctctccactgggcctggccggcggcggcagcggcggctcccaagccgtggtaacccaggagccca
gtctgacagtgagccctggcggtacagtgaccttgacttgcaggagcagtaccggagccgtaactacctcaaactacgcc
aactgggtgcagcagaagcccggtcaggccccaggggccttattggtgggactaacaaacgagcacccggaacccccgc
aaggttcagcggcagccttctgggcggaaaggccgctctcacattgagcggcgtgcagcccgaggacgaggccgagtact
actgcgccctgtggtacagcaacctgtgggtgttcggcggagggaccaagctgaccgtgctgggccagcccaaagctgcg
ccgagcgtgaccctgttcccccccgtcaagcgaggagctgcaggctaacaaggccaccctggtgtgcctgattagtgactt
ctaccccggtgccgtcaccgtggcctggaaggccgacagtagcccagttaaagcgggcgtcgagaccaccactcccagca
agcagagcaacaacaagtacgccgcgagcagctacctgagtctgacccccgagcagtggaagagccacaggagctacagc
tgccaggtgacccacgagggcagcactgtggagaagactgtggccccgaccgagtgccccccatgtagcggcggagggtc
ccaggtgcagcttcaagagagcggacccggcctcgtgaagcccagcgagaccttgagcctgacctgcactgtgagtggcg
gtagcgtgagcagcggcgactattactggacctggatcaggcagagccctggcaaggggctggagtggatcggccacatc
tactacagcgggaacacgaactacaaccccagcctgaagagcaggctgacgatcagcatcgacacgagcaagacccagtt
ctcacttaagctcagcagcgtgaccgccgcagacaccgccatatactactgcgtgagggacagggtgacgggcgctttcg
acatctggggccaaggcacaatggtcacggtgagctccggtgggggtggcagcgggggaggcggaagcggcggaggtggc
tctgatatccagatgacccaaagccccagtagcctgtccgccagtgtaggagatagggtaaccatcacttgccaagcgag
ccaagacatcagcaactacctgaattggtatcagcagaagcccggcaaagcacccaagctcctgatctacgacgccagca
atctggagaccggcgtgcccagcaggttcagcggatctggtagcggcaccgacttcaccttcaccataagtagtctgcag
cccgaggacatcgccacctacttctgtcagcacttcgatcacctgcccctggccttcggcggtgggaccaaggtggagat
caag (SEQ ID NO: 145)

Figure 11B

EVAHRFKDLGEENFKALVLIAFAQYLQQCPFEDHVKLVNEVTEFAKTCVADESAENCDKSLHTLFGDKLCTV
ATLRETYGEMADCCAKQEPERNECFLQHKDDNPNLPRLVRPEVDVMCTAFHDNEETFLKKYLYEIARRHPYF
YAPELLFFAKRYKAAFTECCQAADKAACLLPKLDELRDEGKASSAKQRLKCASLQKFGERAFKAWAVARLSQ
RFPKAEFAEVSKLVTDLTKVHTECCHGDLLECADDRADLAKYICENQDSISSKLKECCEKPLLEKSHCIAEV
ENDEMPADLPSLAADFVESKDVCKNYAEAKDVFLGMFLYEYARRHPDYSVVLLLRLAKTYETTLEKCCAAAD
PHECYAKVFDEFKPLVEEPQNLIKQNCELFEQLGEYKFQNALLVRYTKKVPQVSTPTLVEVSRNLGKVGSKC
CKHPEAKRMPCAEDYLSVVLNQLCVLHEKTPVSDRVTKCCTESLVNRRPCFSALEVDETYVPKEFNAETFTF
HADICTLSEKERQIKKQTALVELVKHKPKATKEQLKAVMDDFAAFVEKCCKADDKETCFAEEGKKLVAASQA
AGGSGGSGGSGGSGGSGGSEVQLVESGGGLVQPGGSLRLSCAASGFTFNTYAMNWVRQAPGKGLEWVARIRS
KYNNYATYYADSVKDRFTISRDDSKNTLYLQMNSLRAEDTAVYYCVRHGNFGNSYVSWFAYWGQGTMVTVSS
ASTKGPSVFPLAPSSKSTSGGTAALGCLVKDYFPEPVTVSWNSGALTSGVHTFPAVLQSSGLYSLSSVVTVP
SSSLGTQTYICNVNHKPSNTKVDKRVEPKSCPPCGGGGSDIQMTQSPSSLSASVGDRVTITCQASQDISNYL
NWYQQKPGKAPKLLIYDASNLETGVPSRFSGSGSGTDFTFTISSLQPEDIATYFCQHFDHLPLAFGGGTKVE
IKGGGGSGGGGSGGGGSQVQLQESGPGLVKPSETLSLTCTVSGGSVSSGDYYWTWIRQSPGKGLEWIGHIYY
SGNTNYNPSLKSRLTISIDTSKTQFSLKLSSVTAADTAIYYCVRDRVTGAFDIWGQGTMVTVSS (SEQ ID NO: 134)

Figure 12A gaggtggcccacaggttcaaggatctgggcgaggagaacttcaaggccctggtgctgatcgccttcgcccagtatctgcagcagtgccc
ctttgaggaccacgtgaagctggtgaacgaggtgaccgagttcgccaagacatgcgtggccgacgagtccgccgagaattgtgataagt
ctctgcacaccctgtttggcgataagctgtgcaccgtggccacactgagggagacatacggcgagatggccgactgctgtgccaagcag
gagcccgagcgcaacgagtgcttcctgcagcacaaggacgataaccctaatctgccacggctggtgagacctgaggtggacgtgatgtg
caccgccttccacgataatgaggagacatttctgaagaagtacctgtatgagatcgcccggagacacccttacttttatgccccagagc
tgctgttctttgccaagcggtacaaggcagccttcaccgagtgctgtcaggcagcagataaggcagcatgcctgctgccaaagctggac
gagctgagggatgagggcaaggcaagctccgccaagcagcgcctgaagtgtgcaagcctgcagaagttcggagagagggcctttaaggc
atgggcagtggcaaggctgtcccagcggttcccaaaggccgagtttgccgaggtgtctaagctggtgaccgacctgacaaaggtgcaca
ccgagtgctgtcacggcgacctgctggagtgcgcagacgatagagccgatctggccaagtacatctgtgagaaccaggactctatctct
agcaagctgaaggagtgctgtgagaagcccctgctggagaagtcccactgcatcgccgaggtggagaacgacgagatgccagcagatct
gccaagcctggcagcagacttcgtggagtccaaggacgtgtgcaagaattacgccgaggccaaggacgtgttcctgggcatgtttctgt
acgagtatgccaggcgccaccctgactactccgtggtgctgctgctgcggctggccaagacctatgagaccacactggagaagtgctgt
gccgccgccgacccccacgagtgctatgcaaaggtgttcgacgagtttaagcccctggtggaggagcctcagaacctgatcaagcagaa
ttgtgagctgtttgagcagctgggcgagtacaagttccagaacgccctgctggtgagatataccaagaaggtgccacaggtgtctaccc
ccacactggtggaggtgagccggaatctgggcaaggtcggctccaagtgctgtaagcaccctgaggccaagagaatgccatgcgccgag
gattacctgtccgtggtgctgaaccagctgtgcgtgctgcacgagaagacccccgtgagcgacagggtgaccaagtgctgtacagagtc
tctggtgaaccggagaccatgctttagcgccctggaggtggatgagacatatgtgcccaaggagttcaatgccgagaccttcacatttc
acgccgacatctgtaccctgagcgagaaggagcgccagatcaagaagcagacagccctggtggagctggtgaagcacaagccaaaggcc
accaaggagcagctgaaggccgtgatggacgatttcgccgcctttgtggagaagtgctgtaaggccgacgataaggagacatgcttcgc
agaggagggcaagaagctggtggcagcaagccaggcagcaggaggctccggcggctctggggcagcggaggtagtggcggcagcggcg
gctccgaggtgcagctggtggagtccggcggcggcctggtgcagcccggcggcagcctgaggctgtcctgcgccgcctctggcttcacc
tttaacacatacgcaatgaattgggtgcgccaggcaccaggcaagggactggagtgggtggcccggatcagaagcaagtacaacaatta
tgccacctactatgccgactccgtgaaggatcggtttaccatcagcagagacgattccaagaacacactgtatctgcagatgaatagcc
tgcgggccgaggatacagccgtgtactattgcgtgagacacggcaactttggcaattcttacgtgagctggttcgcctattggggccag
ggcaccatggtgacagtgtcctctgcctctaccaaggacctagcgtgttcccactggcacctagctccaagtctaccagcggaggcac
agccgccctgggatgtctggtgaaggactactttccagagcccgtgacagtgtcctggaactctggcgccctgaccagcggagtgcaca
cattccctgccgtgctgcagtctagcggcctgtactccctgtcctctgtggtgaccgtgccaagctcctctctgggcacccagacatat
atctgcaacgtgaatcacaagccctctaatacaaaggtggacaagagggtggagcctaagagc<u>tgc</u>ccccct<u>tgt</u>ggcggaggcggtag
cgatatccagatgacccaaagccccagtagcctgtccgccagtgtaggagatagggtaaccatcacttgccaagcgagccaagacatca
gcaactacctgaattggtatcagcagaagcccggcaaagcacccaagctcctgatctacgacgccagcaatctggagaccggcgtgccc
agcaggttcagcggatctggtagcggcaccgacttcaccttcaccataagtagtctgcagcccgaggacatcgccacctacttctgtca
gcacttcgatcacctgcccctggccttcggcggtgggaccaaggtggagatcaagggtgggggtggcagcgggggaggcggaagcggcg
gaggtggctctcaggtgcagcttcaagagagcggacccggcctcgtgaagcccagcgagaccttgagcctgacctgcactgtgagtggc
ggtagcgtgagcagcggcgactattactggacctggatcaggcagagccctggcaaggggctggagtggatcggccacatctactacag
cgggaacacgaactacaaccccagcctgaagagcaggctgacgatcagcatcgacacgagcaagacccagttctcacttaagctcagca
gcgtgaccgccgcagacaccgccatatactactgcgtgagggacagggtgacgggcgctttcgacatctggggccaaggcacaatggtc
acggtgagctcc (SEQ ID NO: 146)

Figure 12B

QDGNEEMGGITQTPYKVSISGTTVILTGGSGGSGGSGGSGGSGGSQAVVTQEPSLTVSPGGTVTLTCRSSTG
AVTTSNYANWVQQKPGQAPRGLIGGTNKRAPGTPARFSGSLLGGKAALTLSGVQPEDEAEYYCALWYSNLWV
FGGGTKLTVLGQPKAAPSVTLFPPSSEELQANKATLVCLISDFYPGAVTVAWKADSSPVKAGVETTTPSKQS
NNKYAASSYLSLTPEQWKSHRSYSCQVTHEGSTVEKTVAPTE<u>C</u>PP<u>C</u>SGGGSDIQMTQSPSSLSASVGDRVTI
TCQASQDISNYLNWYQQKPGKAPKLLIYDASNLETGVPSRFSGSGSGTDFTFTISSLQPEDIATYFCQHFDH
LPLAFGGGTKVEIKGGGGSGGGGSGGGGSQVQLQESGPGLVKPSETLSLTCTVSGGSVSSGDYYWTWIRQSP
GKGLEWIGHIYYSGNTNYNPSLKSRLTISIDTSKTQFSLKLSSVTAADTAIYYCVRDRVTGAFDIWGQGTMV
TVSS (SEQ ID NO: 135)

Figure 13A caggacggcaacgaggagatgggcggcatcacccagacaccatacaaggtgagcatctccggcaccacagtgatcctgac
cggaggctccggcggctctgggggcagcggaggtagtggcggcagcggcggctcccaagccgtggtaacccaggagccca
gtctgacagtgagccctggcggtacagtgaccttgacttgcaggagcagtaccggagccgtaactacctcaaactacgcc
aactgggtgcagcagaagcccggtcaggccccaggggccttattggtgggactaacaaacgagcacccggaaccccgc
aaggttcagcggcagccttctgggcggaaaggccgctctcacattgagcggcgtgcagcccgaggacgaggccgagtact
actgcgccctgtggtacagcaacctgtgggtgttcggcggagggaccaagctgaccgtgctgggccagcccaaagctgcg
ccgagcgtgaccctgttcccccgtcaagcgaggagctgcaggctaacaaggccaccctggtgtgcctgattagtgactt
ctaccccggtgccgtcaccgtggcctggaaggccgacagtagcccagttaaagcgggcgtcgagaccaccactcccagca
agcagagcaacaacaagtacgccgcgagcagctacctgagtctgacccccgagcagtggaagagccacaggagctacagc
tgccaggtgacccacgagggcagcactgtggagaagactgtggccccgaccgagtgccccccatgtagcggcggagggtc
cgatatccagatgacccaaagccccagtagcctgtccgccagtgtaggagatagggtaaccatcacttgccaagcgagcc
aagacatcagcaactacctgaattggtatcagcagaagcccggcaaagcacccaagctcctgatctacgacgccagcaat
ctggagaccggcgtgcccagcaggttcagcggatctggtagcggcaccgacttcaccttcaccataagtagtctgcagcc
cgaggacatcgccacctacttctgtcagcacttcgatcacctgccccctggccttcggcggtgggaccaaggtggagatca
agggtgggggtggcagcgggggaggcggaagcggcggaggtggctctcaggtgcagcttcaagagagcggacccggcctc
gtgaagcccagcgagaccttgagcctgacctgcactgtgagtggcggtagcgtgagcagcggcgactattactggacctg
gatcaggcagagccctggcaaggggctggagtggatcggccacatctactacagcgggaacacgaactacaaccccagcc
tgaagagcaggctgacgatcagcatcgacacgagcaagacccagttctcacttaagctcagcagcgtgaccgccgcagac
accgccatatactactgcgtgagggacagggtgacgggcgctttcgacatctggggccaaggcacaatggtcacggtgag
ctcc (SEQ ID NO: 147)

Figure 13B

EVAHRFKDLGEENFKALVLIAFAQYLQQCPFEDHVKLVNEVTEFAKTCVADESAENCDKSLHTLFGDKLCTV
ATLRETYGEMADCCAKQEPERNECFLQHKDDNPNLPRLVRPEVDVMCTAFHDNEETFLKKYLYEIARRHPYF
YAPELLFFAKRYKAAFTECCQAADKAACLLPKLDELRDEGKASSAKQRLKCASLQKFGERAFKAWAVARLSQ
RFPKAEFAEVSKLVTDLTKVHTECCHGDLLECADDRADLAKYICENQDSISSKLKECCEKPLLEKSHCIAEV
ENDEMPADLPSLAADFVESKDVCKNYAEAKDVFLGMFLYEYARRHPDYSVVLLLRLAKTYETTLEKCCAAAD
PHECYAKVFDEFKPLVEEPQNLIKQNCELFEQLGEYKFQNALLVRYTKKVPQVSTPTLVEVSRNLGKVGSKC
CKHPEAKRMPCAEDYLSVVLNQLCVLHEKTPVSDRVTKCCTESLVNRRPCFSALEVDETYVPKEFNAETFTF
HADICTLSEKERQIKKQTALVELVKHKPKATKEQLKAVMDDFAAFVEKCCKADDKETCFAEEGKKLVAASQA
AGGSGGSGGSGGSGGSGGSEVQLVESGGGLVQPGGSLRLSCAASGFTFNTYAMNWVRQAPGKGLEWVARIRS
KYNNYATYYADSVKDRFTISRDDSKNTLYLQMNSLRAEDTAVYYCVRHGNFGNSYVSWFAYWGQGTMVTVSS
ASTKGPSVFPLAPSSKSTSGGTAALGCLVKDYFPEPVTVSWNSGALTSGVHTFPAVLQSSGLYSLSSVVTVP
SSSLGTQTYICNVNHKPSNTKVDKRVEPKSCPPCGGGGSQVQLQESGPGLVKPSETLSLTCTVSGGSVSSGD
YYWTWIRQSPGKGLEWIGHIYYSGNTNYNPSLKSRLTISIDTSKTQFSLKLSSVTAADTAIYYCVRDRVTGA
FDIWGQGTMVTVSSGGGGSGGGGSGGGGSDIQMTQSPSSLSASVGDRVTITCQASQDISNYLNWYQQKPGKA
PKLLIYDASNLETGVPSRFSGSGSGTDFTFTISSLQPEDIATYFCQHFDHLPLAFGGGTKVEIK (SEQ ID
NO: 136)

Figure 14A gaggtggcccacaggttcaaggatctgggcgaggagaacttcaaggccctggtgctgatcgccttcgcccagtatctgcagcagtgccc
ctttgaggaccacgtgaagctggtgaacgaggtgaccgagttcgccaagacatgcgtggccgacgagtccgccgagaattgtgataagt
ctctgcacaccctgtttggcgataagctgtgcaccgtggccacactgagggagacatacggcgagatggccgactgctgtgccaagcag
gagcccgagcgcaacgagtgcttcctgcagcacaaggacgataaccctaatctgccacggctggtgagacctgaggtggacgtgatgtg
caccgccttccacgataatgaggagacatttctgaagaagtacctgtatgagatcgcccggagacacccttacttttatgccccagagc
tgctgttctttgccaagcggtacaaggcagccttcaccgagtgctgtcaggcagcagataaggcagcatgcctgctgccaaagctggac
gagctgagggatgagggcaaggcaagctccgccaagcagcgcctgaagtgtgcaagcctgcagaagttcggagagagggcctttaaggc
atgggcagtggcaaggctgtcccagcggttcccaaaggccgagtttgccgaggtgtctaagctggtgaccgacctgacaaaggtgcaca
ccgagtgctgtcacggcgacctgctggagtgcgcagacgatagagccgatctggccaagtacatctgtgagaaccaggactctatctct
agcaagctgaaggagtgctgtgagaagcccctgctggagaagtcccactgcatcgccgaggtggagaacgacgagatgccagcagatct
gccaagcctggcagcagacttcgtggagtccaaggacgtgtgcaagaattacgccgaggccaaggacgtgttcctgggcatgtttctgt
acgagtatgccaggcgccaccctgactactccgtggtgctgctgctgcggctggccaagacctatgagaccacactggagaagtgctgt
gccgccgccgacccccacgagtgctatgcaaaggtgttcgacgagtttaagcccctggtggaggagcctcagaacctgatcaagcagaa
ttgtgagctgtttgagcagctgggcgagtacaagttccagaacgccctgctggtgagatataccaagaaggtgccacaggtgtctaccc
ccacactggtggaggtgagccggaatctgggcaaggtcggctccaagtgctgtaagcaccctgaggccaagagaatgccatgcgccgag
gattacctgtccgtggtgctgaaccagctgtgcgtgctgcacgagaagacccccgtgagcgacagggtgaccaagtgctgtacagagtc
tctggtgaaccggagaccatgctttagcgccctggaggtggatgagacatatgtgcccaaggagttcaatgccgagaccttcacatttc
acgccgacatctgtaccctgagcgagaaggagcgccagatcaagaagcagacagccctggtggagctggtgaagcacaagccaaaggcc
accaaggagcagctgaaggccgtgatggacgatttcgccgcctttgtggagaagtgctgtaaggccgacgataaggagacatgcttcgc
agaggagggcaagaagctggtggcagcaagccaggcagcaggaggctccggcggctctgggggcagcggaggtagtggcggcagcggcg
gctccgaggtgcagctggtggagtccggcggcggcctggtgcagcccggcggcagcctgaggctgtcctgcgccgcctctggcttcacc
tttaacacatacgcaatgaattgggtgcgccaggcaccaggcaagggactggagtgggtggcccggatcagaagcaagtacaacaatta
tgccacctactatgccgactccgtgaaggatcggtttaccatcagcagagacgattccaagaacacactgtatctgcagatgaatagcc
tgcgggccgaggatacagccgtgtactattgcgtgagacacggcaactttggcaattcttacgtgagctggttcgcctattggggccag
ggcaccatggtgacagtgtcctctgcctctaccaaggacctagcgtgttcccactggcacctagctccaagtctaccagcggaggcac
agccgccctgggatgtctggtgaaggactactttccagagcccgtgacagtgtcctggaactctggcgccctgaccagcggagtgcaca
cattccctgccgtgctgcagtctagcggcctgtactccctgtcctctgtggtgaccgtgccaagctcctctctgggcacccagacatat
atctgcaacgtgaatcacaagccctctaatacaaaggtggacaagagggtggagcctaagagctgcccccccttgtggcggaggcggtag
ccaggtgcagcttcaagagagcggacccggcctcgtgaagcccagcgagaccttgagcctgacctgcactgtgagtggcggtagcgtga
gcagcggcgactattactggacctggatcaggcagagccctggcaaggggctggagtggatcggccacatctactacagcgggaacacg
aactacaaccccagcctgaagagcaggctgacgatcagcatcgacacgagcaagacccagttctcacttaagctcagcagcgtgaccgc
cgcagacaccgccatatactactgcgtgagggacagggtgacgggcgctttcgacatctggggccaaggcacaatggtcacggtgagct
ccggtgggggtggcagcgggggaggcggaagcggcggaggtggctctgatatccagatgacccaaagccccagtagcctgtccgccagt
gtaggagatagggtaaccatcacttgccaagcgagccaagacatcagcaactacctgaattggtatcagcagaagcccggcaaagcacc
caagctcctgatctacgacgccagcaatctggagaccggcgtgcccagcaggttcagcggatctggtagcggcaccgacttcaccttca
ccataagtagtctgcagcccgaggacatcgccacctacttctgtcagcacttcgatcacctgcccctggccttcggcggtgggaccaag
gtggagatcaag (SEQ ID NO: 148)

Figure 14B

QDGNEEMGGITQTPYKVSISGTTVILTGGSGGSGGSGGSGGSGGSQAVVTQEPSLTVSPGGTVTLTCRSSTG
AVTTSNYANWVQQKPGQAPRGLIGGTNKRAPGTPARFSGSLLGGKAALTLSGVQPEDEAEYYCALWYSNLWV
FGGGTKLTVLGQPKAAPSVTLFPPSSEELQANKATLVCLISDFYPGAVTVAWKADSSPVKAGVETTTPSKQS
NNKYAASSYLSLTPEQWKSHRSYSCQVTHEGSTVEKTVAPTECPPCSGGGSQVQLQESGPGLVKPSETLSLT
CTVSGGSVSSGDYYWTWIRQSPGKGLEWIGHIYYSGNTNYNPSLKSRLTISIDTSKTQFSLKLSSVTAADTA
IYYCVRDRVTGAFDIWGQGTMVTVSSGGGGSGGGGSGGGGSDIQMTQSPSSLSASVGDRVTITCQASQDISN
YLNWYQQKPGKAPKLLIYDASNLETGVPSRFSGSGSGTDFTFTISSLQPEDIATYFCQHFDHLPLAFGGGTK
VEIK(SEQ ID NO: 137)

Figure 15A caggacggcaacgaggagatgggcggcatcacccagacaccatacaaggtgagcatctccggcaccacagtgatcctgac
cggaggcggctccggaggcggtagcggcggtggatctggcggcagcggcggctcccaagccgtggtaacccaggagccca
gtctgacagtgagccctggcggtacagtgaccttgacttgcaggagcagtaccggagccgtaactacctcaaactacgcc
aactgggtgcagcagaagcccggtcaggcccccaggggccttattggtgggactaacaaacgagcacccggaacccccgc
aaggttcagcggcagccttctgggcggaaaggccgctctcacattgagcggcgtgcagcccgaggacgaggccgagtact
actgcgccctgtggtacagcaacctgtgggtgttcggcggagggaccaagctgaccgtgctgggccagcccaaagctgcg
ccgagcgtgaccctgttcccccgtcaagcgaggagctgcaggctaacaaggccaccctggtgtgcctgattagtgactt
ctaccccggtgccgtcaccgtggcctggaaggccgacagtagcccagttaaagcgggcgtcgagaccaccactcccagca
agcagagcaacaacaagtacgccgcgagcagctacctgagtctgacccccgagcagtggaagagccacaggagctacagc
tgccaggtgacccacgagggcagcactgtggagaagactgtggccccgaccgagtgccccccatgtagcggcggagggtc
ccaggtgcagcttcaagagagcggacccggcctcgtgaagcccagcgagaccttgagcctgacctgcactgtgagtggcg
gtagcgtgagcagcggcgactattactggacctggatcaggcagagccctggcaaggggctggagtggatcggccacatc
tactacagcgggaacacgaactacaaccccagcctgaagagcaggctgacgatcagcatcgacacgagcaagacccagtt
ctcacttaagctcagcagcgtgaccgccgcagacaccgccatatactactgcgtgagggacagggtgacgggcgctttcg
acatctggggccaaggcacaatggtcacggtgagctccggtgggggtggcagcgggggaggcggaagcggcggaggtggc
tctgatatccagatgacccaaagccccagtagcctgtccgccagtgtaggagatagggtaaccatcacttgccaagcgag
ccaagacatcagcaactacctgaattggtatcagcagaagcccggcaaagcacccaagctcctgatctacgacgccagca
atctggagaccggcgtgcccagcaggttcagcggatctggtagcggcaccgacttcaccttcaccataagtagtctgcag
cccgaggacatcgccacctacttctgtcagcacttcgatcacctgcccctggccttcggcggtgggaccaaggtggagat
caag (SEQ ID NO: 149)

Figure 15B

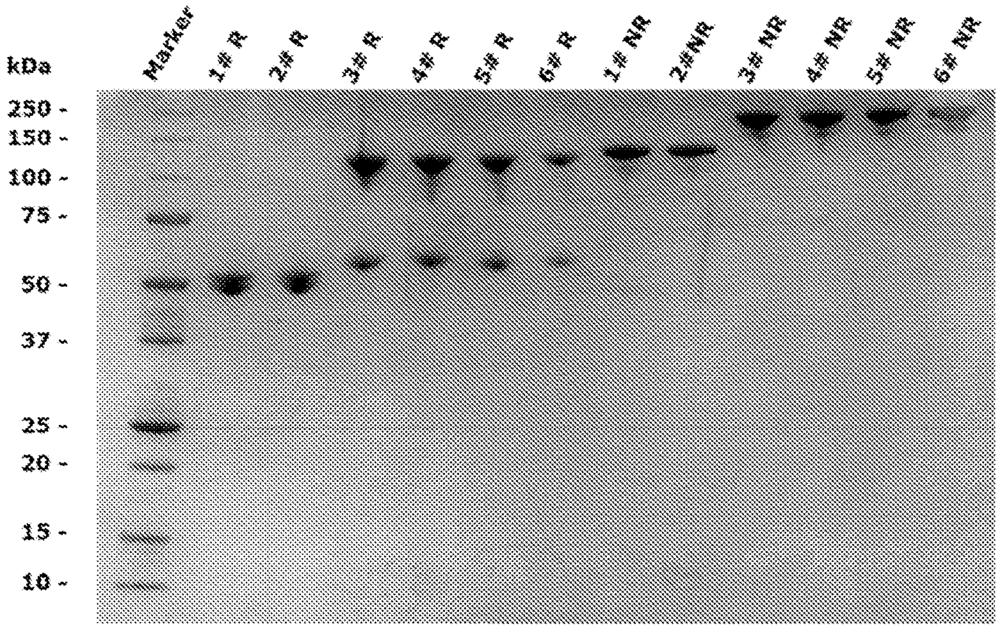

Figure 16

ProTriBody-NC-(VLVH):

ProTriBody-C-(VHVL)

ProTriBody-NC-(VHVL)

ProTriBody-C-(VHVL)

ProTriBody-NC-(VHVL)

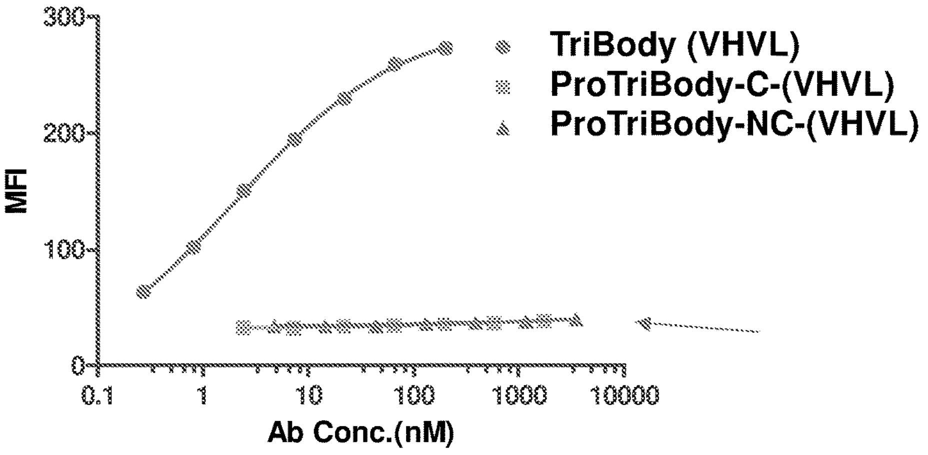

Figure 25

DIQMTQSPSSLSASVGDRVTINCQASQSIDSNLAWYQQKPGKPPKLLIYRASNLASGVPSRFSGSGSGTDFTLTISSLQPEDVATYYCLGG
VGNVSYRTSFGGGTKVEIKGGGGSGGGGSGGGGSGGGGSQSVKESEGDLVTPAGNLTLTCTASGSDINDYPISWVRQAPGKGLEWIG
FINSGGSTWYASWVKGRFTISRTSTTVDLKMTSLTTDDTATYFCARGYSTYYGDFNIWGPGTLVTIS
(SEQ ID NO: 156)

Figure 26A

GACATCCAGATGACTCAGTCCCCCAGTTCCCTGTCCGCCTCCGTGGGCGACAGGGTGACAATCAACTGCCAGGCCTCACAGTCTAT
CGACAGTAACCTTGCCTGGTATCAACAGAAGCCCGGGAAGCCCCCCAAGCTGCTGATCTACAGGGCCTCCAATCTGGCATCCGGC
GTGCCCTCCAGGTTCTCCGGTTCCGGCTCAGGCACCGATTTTACCCTGACCATATCCTCCTTGCAGCCCGAGGACGTGGCTACCTAC
TACTGTCTGGGCGGTGTGGGCAACGTGTCCTACAGGACCTCCTTTGGTGGCGGCACCAAGGTGGAGATCAAGGGCGGAGGAGGG
TCCGGTGGAGGGGGCAGTGGTGGGGGAGGATCAGGAGGTGGTGGCTCCCAGAGTGTGAAGGAGTCCGAGGGCGACCTGGTGA
CCCCTGCTGGCAATCTGACCCTCACCTGCACCGCTTCCGGTAGCGACATCAACGACTACCCCATATCATGGGTGAGACAGGCTCCC
GGCAAGGGCCTGGAGTGGATCGGCTTCATCAATAGCGGTGGGTCCACATGGTACGCAAGTTGGGTGAAGGGCAGGTTCACCATC
TCTCGAACCTCAACTACCGTCGACCTGAAAATGACCTCCCTGACAACCGACGACACCGCAACCTATTTCTGCGCCAGGGGCTACTCC
ACATACTATGGCGACTTCAACATCTGGGGGCCAGGGACCCTGGTCACTATCTCA (SEQ ID NO: 157)

Figure 26B

QSVKESEGDLVTPAGNLTLTCTASGSDINDYPISWVRQAPGKGLEWIGFINSGGSTWYASWVKGRFTISRTSTTVDLKMT
SLTTDDTATYFCARGYSTYYGDFNIWGPGTLVTISGGGGSGGGGSGGGGSGGGGSDIQMTQSPSSLSASVGDRVTINCQA
SQSIDSNLAWYQQKPGKPPKLLIYRASNLASGVPSRFSGSGSGTDFTLTISSLQPEDVATYYCLGGVGNVSYRTSFGGGT
KVEIK (SEQ ID NO: 166)

Figure 27A

CAGAGTGTGAAGGAGTCCGAGGGCGACCTGGTGACCCCTGCTGGCAATCTGACCCTCACCTGCACCGCTTCCGGTAGCGACATCAACGA
CTACCCCATATCATGGGTGAGACAGGCTCCCGGCAAGGGCCTGGAGTGGATCGGCTTCATCAATAGCGGTGGGTCCACATGGTACGCAA
GTTGGGTGAAGGGCAGGTTCACCATCTCTCGAACCTCAACTACCGTCGACCTGAAAATGACCTCCCTGACAACCGACGACACCGCAACC
TATTTCTGCGCCAGGGGCTACTCCACATACTATGGCGACTTCAACATCTGGGGCCCAGGGACCCTGGTCACTATCTCAGGCGGAGGAGG
GTCCGGTGGAGGGGGCAGTGGTGGGGGAGGATCAGGAGGTGGTGGCTCCGACATCCAGATGACTCAGTCCCCCAGTTCCCTGTCCGCCT
CCGTGGGCGACAGGGTGACAATCAACTGCCAGGCCTCACAGTCTATCGACAGTAACCTTGCCTGGTATCAACAGAAGCCCGGGAAGCCC
CCCAAGCTGCTGATCTACAGGGCCTCCAATCTGGCATCCGGCGTGCCCTCCAGGTTCTCCGGTTCCGGCTCAGGCACCGATTTACCCT
GACCATATCCTCCTTGCAGCCCGAGGACGTGGCTACCTACTACTGTCTGGGCGGTGTGGGCAACGTGTCCTACAGGACCTCCTTTGGTG
GCGGCACCAAGGTGGAGATCAAG (SEQ ID NO: 167)

Figure 27B

DVQITQSPSYLAASPGETITINCRASKSISKYLAWYQEKPGKANKLLIHSGSTLQSGIPSRFSGSGSGTDFTLTISSLEP
EDFAMYYCQQHIEYPWTFGGGTKLEIKRAGGGGSGGGGSSGGGGSEIQLQQSGPELVKPGASVKMSCKASGYTFTDYYMH
WVKQNNGESLEWIGYFNPYNDYTRYNQNFNGKATLTVDKSSSTAYMQLNSLTSEDSAFYYCARSDGYYDAMDYWGQGTSV
TVSS (SEQ ID NO: 168)

Figure 28A

GACGTGCAGATCACCCAGTCCCCCTCCTATCTGGCCGCTTCCCCCGGTGAGACCATCACCATCAACTGTAGGGCCTCCAAGTCCATCTC
CAAATACCTGGCCTGGTATCAGGAGAAGCCCGGAAAAGCCAACAAACTGCTGATCCATAGCGGCTCTACCCTGCAGAGTGGCATCCCCT
CCAGGTTCTCAGGCTCCGGTTCTGGAACCGACTTTACTCTTACAATTTCCTCACTCGAACCCGAAGACTTCGCCATGTACTACTGCCAG
CAGCACATCGAGTACCCCTGGACCTTCGGAGGAGGCACTAAGCTGGAGATCAAGAGGGCTGGCGGAGGTGGCAGTGGGGGAGGCGGTTC
CTCCGGCGGTGGCGGGAGCGAGATCCAGCTGCAACAGTCCGGTCCCGAGCTGGTGAAGCCTGGAGCCTCCGTGAAGATGTCCTGTAAGG
CCTCTGGCTACACCTTTACCGACTACTACATGCACTGGGTAAAACAGAACAACGGCGAGTCCCTGGAGTGGATAGGCTACTTCAACCCC
TACAACGACTACACCAGGTACAACCAGAACTTCAATGGCAAGGCCACCCTGACCGTGGACAAGAGCTCCTCCACAGCCTATATGCAGCT
CAACTCCCTGACTTCCGAGGACTCCGCCTTCTACTATTGCGCCAGGTCCGACGGGTACTACGACGCCATGGACTACTGGGGCCAGGGCA
CCTCAGTGACAGTGTCCTCC (SEQ ID NO: 169)

Figure 28B

EIQLQQSGPELVKPGASVKMSCKASGYTFTDYYMHWVKQNNGESLEWIGYFNPYNDYTRYNQNFNGKATLTVDKSSSTAY
MQLNSLTSEDSAFYYCARSDGYYDAMDYWGQGTSVTVSSGGGGSGGGGSSGGGGSDVQITQSPSYLAASPGETITINCRA
SKSISKYLAWYQEKPGKANKLLIHSGSTLQSGIPSRFSGSGSGTDFTLTISSLEPEDFAMYYCQQHIEYPWTFGGGTKLE
IKRA (SEQ ID NO: 170)

Figure 29A

GAGATCCAGCTGCAACAGTCCGGTCCCGAGCTGGTGAAGCCTGGAGCCTCCGTGAAGATGTCCTGTAAGGCCTCTGGCTACACCTTTAC
CGACTACTACATGCACTGGGTAAAACAGAACAACGGCGAGTCCCTGGAGTGGATAGGCTACTTCAACCCCTACAACGACTACACCAGGT
ACAACCAGAACTTCAATGGCAAGGCCACCCTGACCGTGGACAAGAGCTCCTCCACAGCCTATATGCAGCTCAACTCCCTGACTTCCGAG
GACTCCGCCTTCTACTATTGCGCCAGGTCCGACGGGTACTACGACGCCATGGACTACTGGGGCCAGGGCACCTCAGTGACAGTGTCCTC
CGGCGGAGGTGGCAGTGGGGGAGGCGGTTCCTCCGGCGGTGGCGGGAGCGACGTGCAGATCACCCAGTCCCCCTCCTATCTGGCCGCTT
CCCCCGGTGAGACCATCACCATCAACTGTAGGGCCTCCAAGTCCATCTCCAAATACCTGGCCTGGTATCAGGAGAAGCCCGGAAAAGCC
AACAAACTGCTGATCCATAGCGGCTCTACCCTGCAGAGTGGCATCCCCTCCAGGTTCTCAGGCTCCGGTTCTGGAACCGACTTTACTCT
TACAATTTCCTCACTCGAACCCGAAGACTTCGCCATGTACTACTGCCAGCAGCACATCGAGTACCCCTGGACCTTCGGAGGAGGCACTA
AGCTGGAGATCAAGAGGGCT (SEQ ID NO: 171)

Figure 29B

DIQMTQSPSSLSASVGDRVTITCRASQGISNYLAWFQQKPGKAPKSLIYRANRLQSGVPSRFSGSGSGTDFTLTISSLQP
EDVATYYCLQYDDFPWTFGQGTKLEIKGGGGSGGGGSGGGGSGGGGSQVQLVQSGAEVKKPGASVKVSCKASGYTFTSFW
MHWVRQAPGQGLEWMGRIDPNRGGTEYNEKAKSRVTMTADKSTSTAYMELSSLRSEDTAVYYCAGGNPYYPMDYWGQGTT
VTVSS (SEQ ID NO: 172)

Figure 30A

GACATACAGATGACCCAGTCCCCCAGCTCCCTCTCAGCCTCTGTGGGCGACAGGGTGACCATCACCTGCAGAGCTTCCCAAGGCATCTC
CAACTACCTGGCCTGGTTCCAGCAGAAGCCAGGCAAGGCTCCTAAGAGCCTGATCTACAGGGCTAACCGTCTGCAGTCCGGCGTGCCCT
CCAGGTTCTCTGGGTCCGGCAGCGGCACAGACTTCACCCTTACCATCTCCTCCCTGCAGCCCGAGGACGTAGCCACATATTACTGCCTG
CAGTACGATGACTTCCCCTGGACTTTCGGACAGGGCACCAAGCTGGAGATAAAGGGAGGTGGTGGCTCAGGGGGTGGGGGCTCCGGCGG
AGGGGGGTCTGGCGGTGGCGGGTCCCAGGTGCAGCTGGTTCAGTCTGGTGCTGAGGTGAAGAAGCCTGGCGCCTCAGTTAAAGTGTCAT
GCAAGGCCTCCGGCTACACCTTCACCAGTTTCTGGATGCACTGGGTGAGGCAGGCACCCGGTCAGGGCCTGGAGTGGATGGGCCGAATC
GATCCCAACCGTGGCGGCACTGAGTACAACGAGAAGGCCAAGAGCAGGGTCACAATGACCGCCGACAAGTCCACCTCAACTGCTTATAT
GGAGCTGTCCTCCTTGCGTTCTGAGGACACTGCCGTGTACTACTGTGCAGGCGGCAACCCCTACTACCCCATGGACTATTGGGGGCAGG
GTACCACTGTCACCGTGTCATCT (SEQ ID NO: 173)

Figure 30B

QVQLVQSGAEVKKPGASVKVSCKASGYTFTSFWMHWVRQAPGQGLEWMGRIDPNRGGTEYNEKAKSRVTMTADKSTSTAY
MELSSLRSEDTAVYYCAGGNPYYPMDYWGQGTTVTVSSGGGGSGGGGSGGGGSGGGGSDIQMTQSPSSLSASVGDRVTIT
CRASQGISNYLAWFQQKPGKAPKSLIYRANRLQSGVPSRFSGSGSGTDFTLTISSLQPEDVATYYCLQYDDFPWTFGQGT
KLEIK (SEQ ID NO: 174)

Figure 31A

CAGGTGCAGCTGGTTCAGTCTGGTGCTGAGGTGAAGAAGCCTGGCGCCTCAGTTAAAGTGTCATGCAAGGCCTCCGGCTACACCTTCAC
CAGTTTCTGGATGCACTGGGTGAGGCAGGCACCCGGTCAGGGCCTGGAGTGGATGGGCCGAATCGATCCCAACCGTGGCGGCACTGAGT
ACAACGAGAAGGCCAAGAGCAGGGTCACAATGACCGCCGACAAGTCCACCTCAACTGCTTATATGGAGCTGTCCTCCTTGCGTTCTGAG
GACACTGCCGTGTACTACTGTGCAGGCGGCAACCCCTACTACCCCATGGACTATTGGGGGCAGGGTACCACTGTCACCGTGTCATCTGG
AGGTGGTGGCTCAGGGGGTGGGGGCTCCGGCGGAGGGGGGTCTGGCGGTGGCGGGTCCGACATACAGATGACCCAGTCCCCCAGCTCCC
TCTCAGCCTCTGTGGGCGACAGGGTGACCATCACCTGCAGAGCTTCCCAAGGCATCTCCAACTACCTGGCCTGGTTCCAGCAGAAGCCA
GGCAAGGCTCCTAAGAGCCTGATCTACAGGGCTAACCGTCTGCAGTCCGGCGTGCCCTCCAGGTTCTCTGGGTCCGGCAGCGGCACAGA
CTTCACCCTTACCATCTCCTCCCTGCAGCCCGAGGACGTAGCCACATATTACTGCCTGCAGTACGATGACTTCCCCTGGACTTTCGGAC
AGGGCACCAAGCTGGAGATAAAG (SEQ ID NO: 175)

Figure 31B

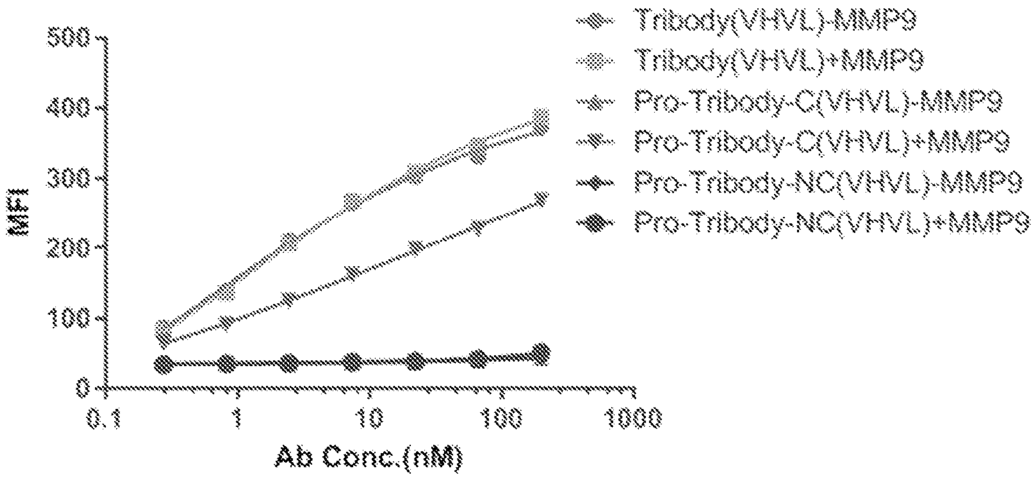

Figure 32

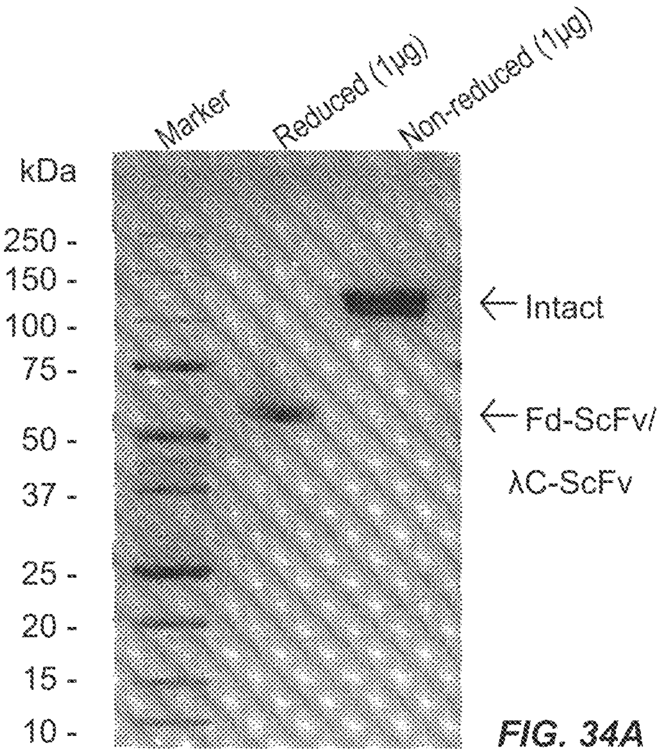
FIG. 34A
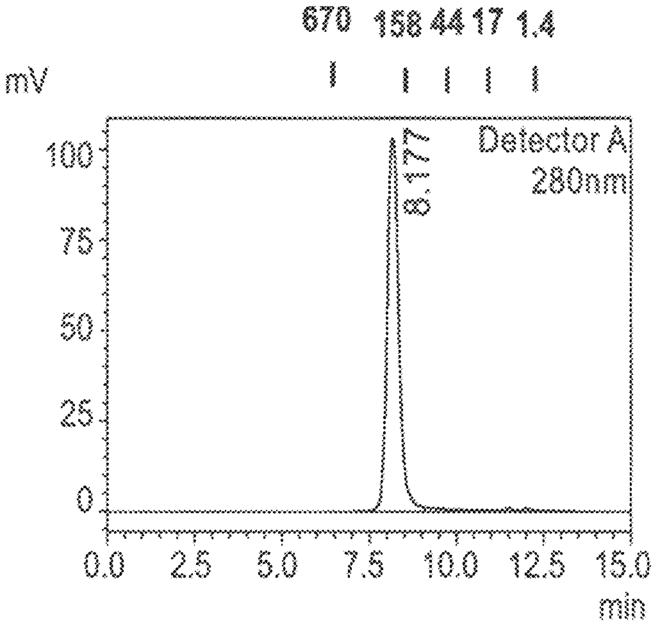
FIG. 34B
<Peak Table>
Detector A 280nm
| Peak# | Ret. Time | Area | Area% | Height | Height% |
|---|---|---|---|---|---|
| 1 | 8.177 | 2144088 | 100.000 | 102961 | 100.000 |
| Total | | 2144088 | 100.000 | 102961 | 100.000 |
FIG. 34C

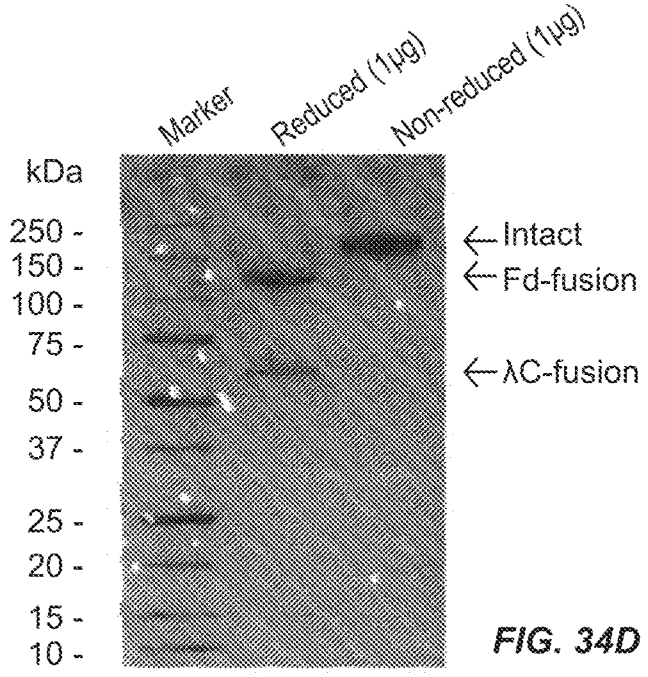
*FIG. 34D*
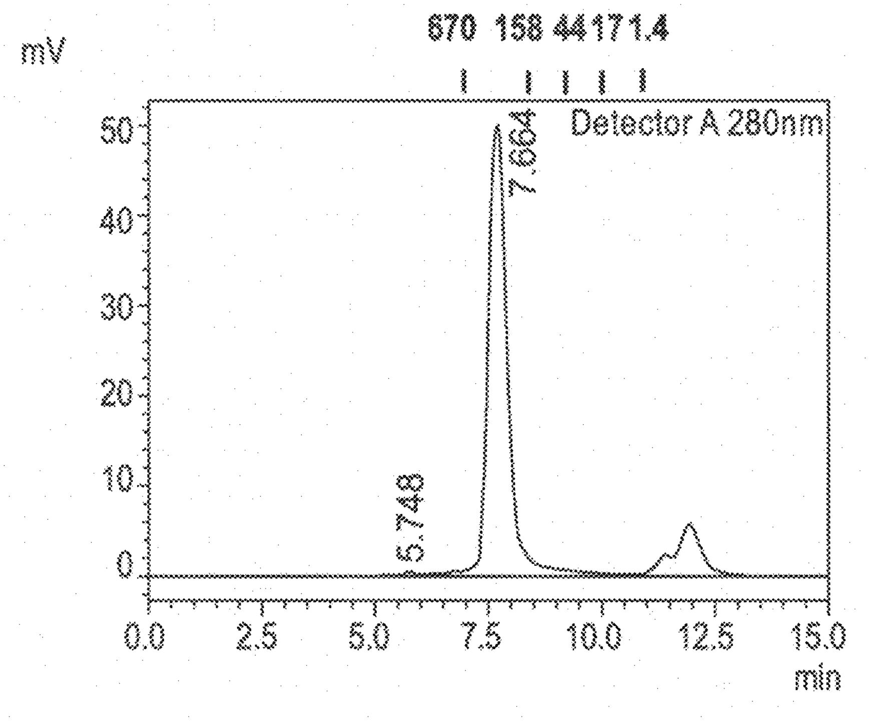
*FIG. 34E*
<Peak Table>
Detector A 280nm
| Peak# | Ret. Time | Area | Area% | Height | Height% |
|---|---|---|---|---|---|
| 1 | 5.748 | 10531 | 0.789 | 485 | 0.965 |
| 2 | 7.664 | 1323738 | 99.211 | 49737 | 99.035 |
| Total | | 1334269 | 100.000 | 50221 | 100.000 |
*FIG. 34F*

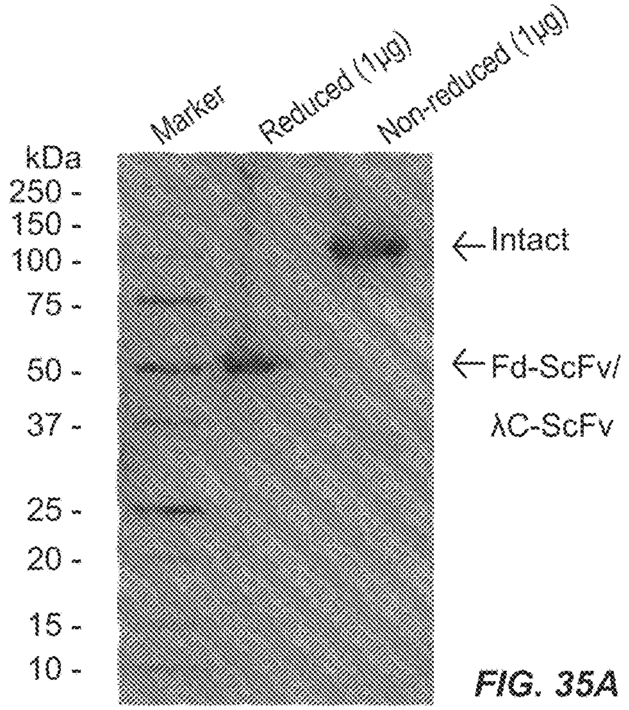
FIG. 35A
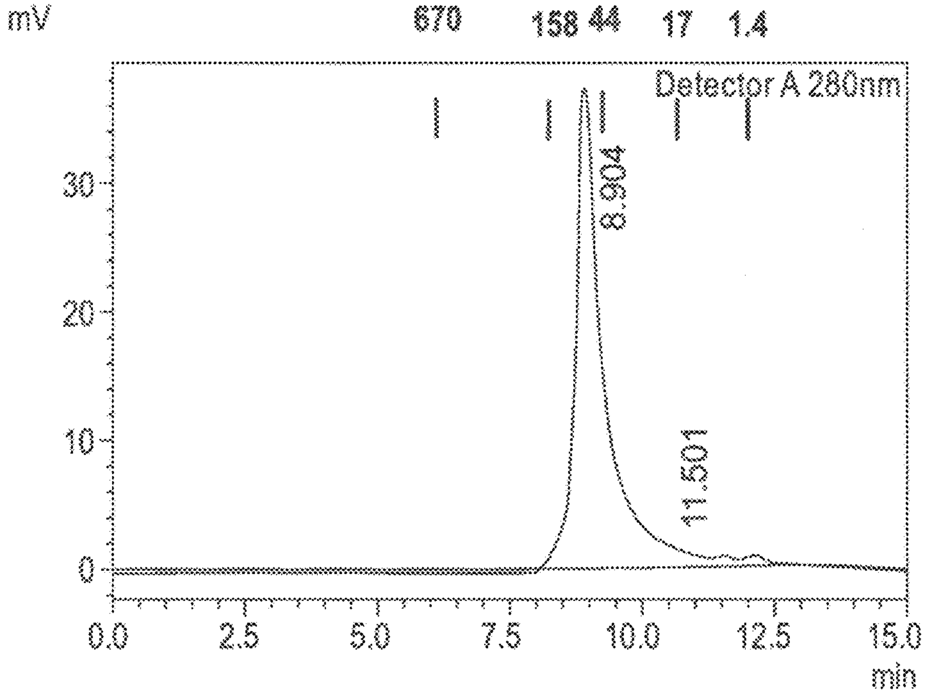
FIG. 35B
<Peak Table>
Detector A 280nm
| Peak# | Ret. Time | Area | Area% | Height | Height% |
|---|---|---|---|---|---|
| 1 | 8.904 | 1520518 | 99.724 | 37534 | 99.225 |
| 2 | 11.501 | 4207 | 0.276 | 293 | 0.775 |
| Total | | 1524725 | 100.000 | 37827 | 100.000 |
FIG. 35C

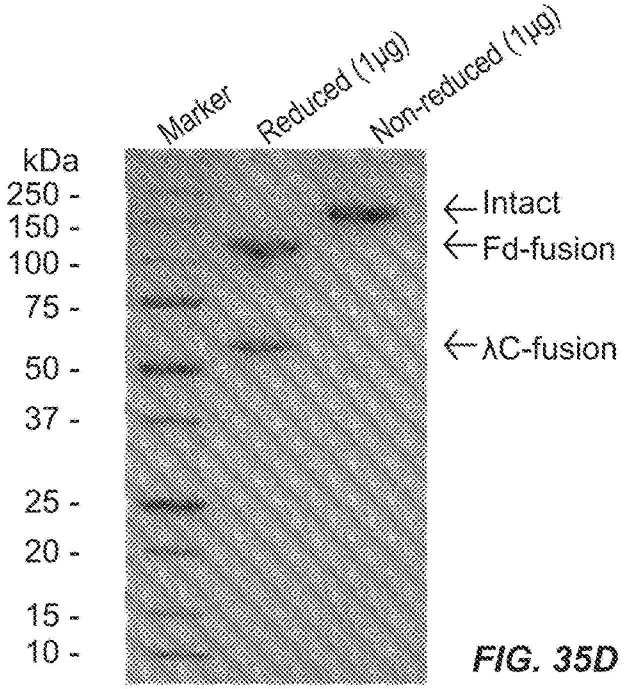
FIG. 35D
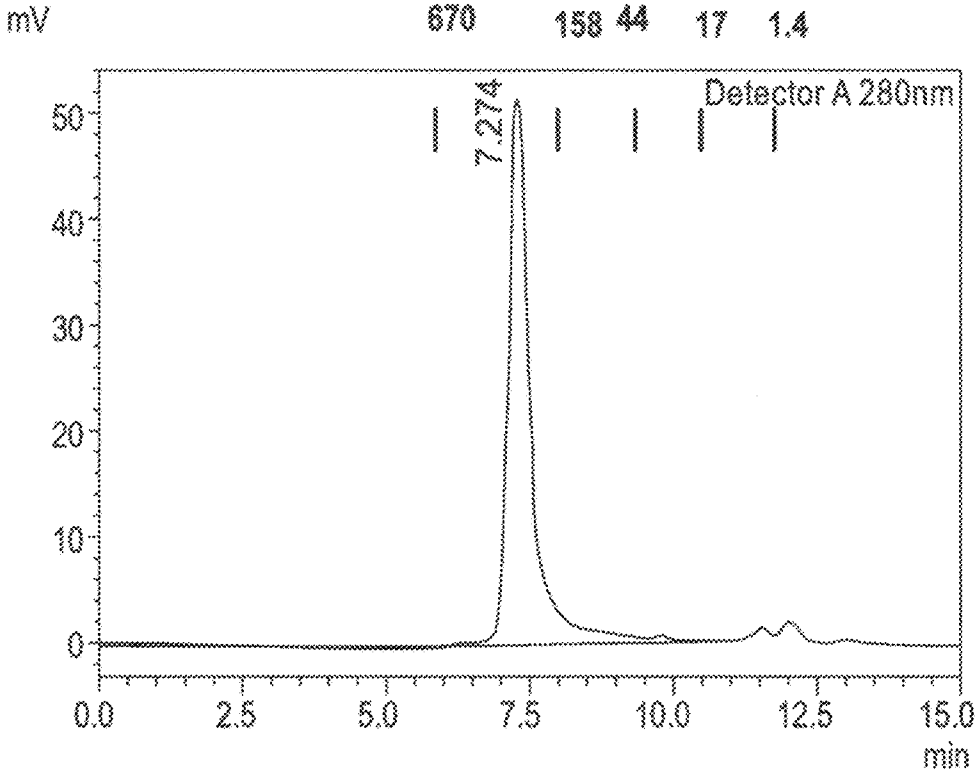
FIG. 35E
<Peak Table>
Detector A 280nm
| Peak# | Ret. Time | Area | Area% | Height | Height% |
|---|---|---|---|---|---|
| 1 | 7.274 | 1457299 | 100.000 | 51378 | 100.000 |
| Total | | 1457299 | 100.000 | 51378 | 100.000 |
FIG. 35F

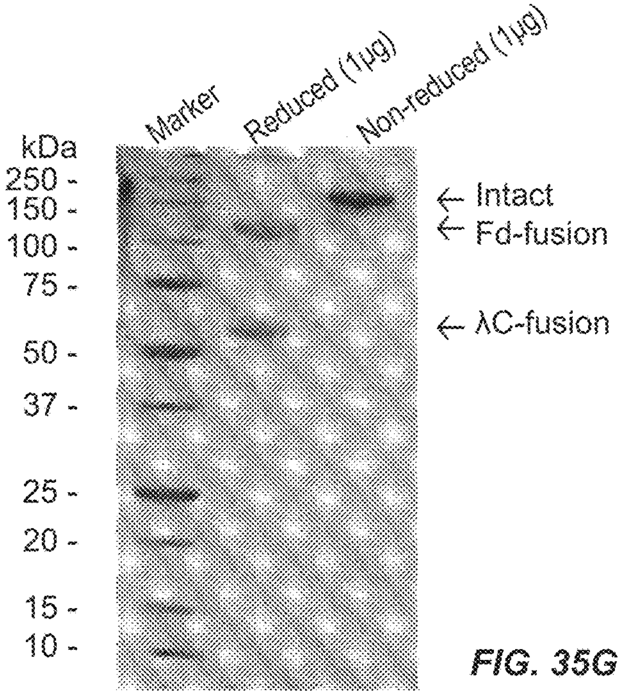
FIG. 35G
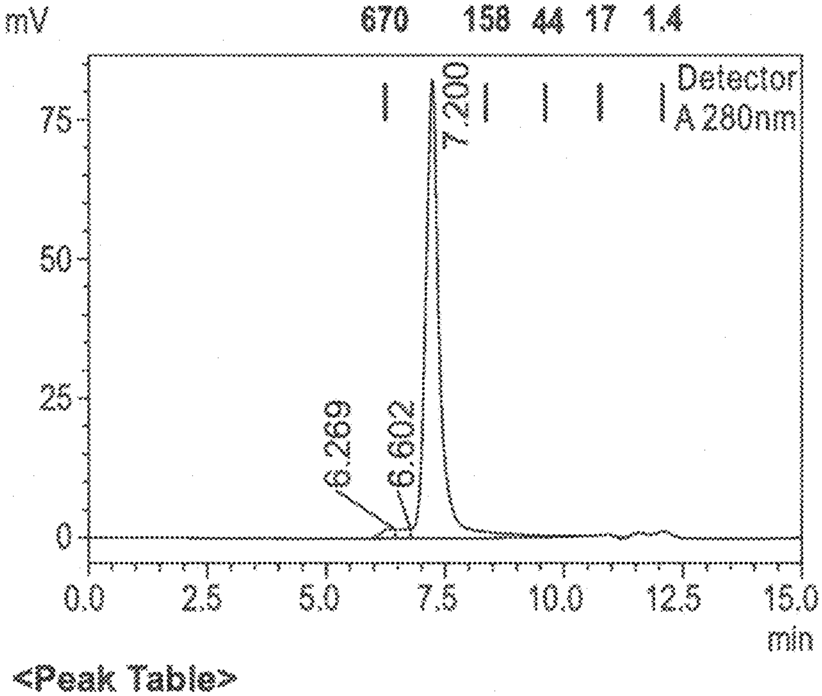
FIG. 35H
<Peak Table>
Detector A 280nm
| Peak# | Ret. Time | Area | Area% | Height | Height% |
|---|---|---|---|---|---|
| 1 | 6.269 | 37202 | 2.052 | 1769 | 2.072 |
| 2 | 6.602 | 34230 | 1.888 | 1826 | 2.138 |
| 3 | 7.200 | 1741654 | 96.060 | 81792 | 95.790 |
| Total | | 1813087 | 100.000 | 85387 | 100.000 |
FIG. 35I T cell Mediated-Cytotoxicity ProTriBody Variants on MCF-7 cells T cell Mediated-Cytotoxicity of ProTriBody Variants on NCI-H226 cells QDGNEEMGGITQTPYKVSISGTTVILTGGGGSGGGGSGGGGSEVAHRFKDLGEENFKALVLIAFAQYL
QQCPFEDHVKLVNEVTEFAKTCVADESAENCDKSLHTLFGDKLCTVATLRETYGEMADCCAKQEPERN
ECFLQHKDDNPNLPRLVRPEVDVMCTAFHDNEETFLKKYLYEIARRHPYFYAPELLFFAKRYKAAFTE
CCQAADKAACLLPKLDELRDEGKASSAKQRLKCASLQKFGERAFKAWAVARLSQRFPKAEFAEVSKLV
TDLTKVHTECCHGDLLECADDRADLAKYICENQDSISSKLKECCEKPLLEKSHCIAEVENDEMPADLP
SLAADFVESKDVCKNYAEAKDVFLGMFLYEYARRHPDYSVVLLLRLAKTYETTLEKCCAAADPHECYA
KVFDEFKPLVEEPQNLIKQNCELFEQLGEYKFQNALLVRYTKKVPQVSTPTLVEVSRNLGKVGSKCCK
HPEAKRMPCAEDYLSVVLNQLCVLHEKTPVSDRVTKCCTESLVNRRPCFSALEVDETYVPKEFNAETF
TFHADICTLSEKERQIKKQTALVELVKHKPKATKEQLKAVMDDFAAFVEKCCKADDKETCFAEEGKKL
VAASQAAGGSGGSPLGLAGGGGSGRSDNHGGSGGSEVQLVESGGGLVQPGGSLRLSCAASGFTFNTYA
MNWVRQAPGKGLEWVARIRSKYNNYATYYADSVKDRFTISRDDSKNTLYLQMNSLRAEDTAVYYCVRH
GNFGNSYVSWFAYWGQGTMVTVSSASTKGPSVFPLAPSSKSTSGGTAALGCLVKDYFPEPVTVSWNSG
ALTSGVHTFPAVLQSSGLYSLSSVVTVPSSSLGTQTYICNVNHKPSNTKVDKRVEPKSCPPCGGGGSD
IQMTQSPSSLSASVGDRVTITCQASQDISNYLNWYQQKPGKAPKLLIYDASNLETGVPSRFSGSGSGT
DFTFTISSLQPEDIATYFCQHFDHLPLAFGGGTKVEIKGGGGSGGGGSGGGGSQVQLQESGPGLVKPS
ETLSLTCTVSGGSVSSGDYYWTWIRQSPGKGLEWIGHIYYSGNTNYNPSLKSRLTISIDTSKTQFSLK
LSSVTAADTAIYYCVRDRVTGAFDIWGQGTMVTVSS (SEQ ID NO: 28)

Figure 45A

QDGNEEMGGITQTPYKVSISGTTVILTGGGGSGGGGSGGGGSEVAHRFKDLGEENFKALVLIAFAQYL
QQCPFEDHVKLVNEVTEFAKTCVADESAENCDKSLHTLFGDKLCTVATLRETYGEMADCCAKQEPERN
ECFLQHKDDNPNLPRLVRPEVDVMCTAFHDNEETFLKKYLYEIARRHPYFYAPELLFFAKRYKAAFTE
CCQAADKAACLLPKLDELRDEGKASSAKQRLKCASLQKFGERAFKAWAVARLSQRFPKAEFAEVSKLV
TDLTKVHTECCHGDLLECADDRADLAKYICENQDSISSKLKECCEKPLLEKSHCIAEVENDEMPADLP
SLAADFVESKDVCKNYAEAKDVFLGMFLYEYARRHPDYSVVLLLRLAKTYETTLEKCCAAADPHECYA
KVFDEFKPLVEEPQNLIKQNCELFEQLGEYKFQNALLVRYTKKVPQVSTPTLVEVSRNLGKVGSKCCK
HPEAKRMPCAEDYLSVVLNQLCVLHEKTPVSDRVTKCCTESLVNRRPCFSALEVDETYVPKEFNAETF
TFHADICTLSEKERQIKKQTALVELVKHKPKATKEQLKAVMDDFAAFVEKCCKADDKETCFAEEGKKL
VAASQAAGGSGGSPLGLAGGSGGSEVQLVESGGGLVQPGGSLRLSCAASGFTFNTYAMNWVRQAPGK
GLEWVARIRSKYNNYATYYADSVKDRFTISRDDSKNTLYLQMNSLRAEDTAVYYCVRHGNFGNSYVSW
FAYWGQGTMVTVSSASTKGPSVFPLAPSSKSTSGGTAALGCLVKDYFPEPVTVSWNSGALTSGVHTFP
AVLQSSGLYSLSSVVTVPSSSLGTQTYICNVNHKPSNTKVDKRVEPKSCPPCGGGGSDIQMTQSPSSL
SASVGDRVTITCQASQDISNYLNWYQQKPGKAPKLLIYDASNLETGVPSRFSGSGSGTDFTFTISSLQ
PEDIATYFCQHFDHLPLAFGGGTKVEIKGGGGSGGGGSGGGGSQVQLQESGPGLVKPSETLSLTCTVS
GGSVSSGDYYWTWIRQSPGKGLEWIGHIYYSGNTNYNPSLKSRLTISIDTSKTQFSLKLSSVTAADTA
IYYCVRDRVTGAFDIWGQGTMVTVSS (SEQ ID NO: 31)

Figure 45B

GGSGGSQAVVTQEPSLTVSPGGTVTLTCRSSTGAVTTSNYANWVQQKPGQAPRGLIGGTNKRAPGTPA
RFSGSLLGGKAALTLSGVQPEDEAEYYCALWYSNLWVFGGGTKLTVLGQPKAAPSVTLFPPSSEELQA
NKATLVCLISDFYPGAVTVAWKADSSPVKAGVETTTPSKQSNNKYAASSYLSLTPEQWKSHRSYSCQV
THEGSTVEKTVAPTECPPCSGGGSDIQMTQSPSSLSASVGDRVTITCQASQDISNYLNWYQQKPGKAP
KLLIYDASNLETGVPSRFSGSGSGTDFTFTISSLQPEDIATYFCQHFDHLPLAFGGGTKVEIKGGGGS
GGGGSGGGGSQVQLQESGPGLVKPSETLSLTCTVSGGSVSSGDYYWTWIRQSPGKGLEWIGHIYYSGN
TNYNPSLKSRLTISIDTSKTQFSLKLSSVTAADTAIYYCVRDRVTGAFDIWGQGTMVTVSS (SEQ ID
NO: 32)

Figure 46

QDGNEEMGGITQTPYKVSISGTTVILTGGGGSGGGGSGGGGSEVAHRFKDLGEENFKALVLIAFAQYL
QQCPFEDHVKLVNEVTEFAKTCVADESAENCDKSLHTLFGDKLCTVATLRETYGEMADCCAKQEPERN
ECFLQHKDDNPNLPRLVRPEVDVMCTAFHDNEETFLKKYLYEIARRHPYFYAPELLFFAKRYKAAFTE
CCQAADKAACLLPKLDELRDEGKASSAKQRLKCASLQKFGERAFKAWAVARLSQRFPKAEFAEVSKLV
TDLTKVHTECCHGDLLECADDRADLAKYICENQDSISSKLKECCEKPLLEKSHCIAEVENDEMPADLP
SLAADFVESKDVCKNYAEAKDVFLGMFLYEYARRHPDYSVVLLLRLAKTYETTLEKCCAAADPHECYA
KVFDEFKPLVEEPQNLIKQNCELFEQLGEYKFQNALLVRYTKKVPQVSTPTLVEVSRNLGKVGSKCCK
HPEAKRMPCAEDYLSVVLNQLCVLHEKTPVSDRVTKCCTESLVNRRPCFSALEVDETYVPKEFNAETF
TFHADICTLSEKERQIKKQTALVELVKHKPKATKEQLKAVMDDFAAFVEKCCKADDKETCFAEEGKKL
VAASQAAGGSGGSPLGLAGGGGSGRSDNHGGSGGSEVQLVESGGGLVQPGGSLRLSCAASGFTFNTYA
MNWVRQAPGKGLEWVARIRSKYNNYATYYADSVKDRFTISRDDSKNTLYLQMNSLRAEDTAVYYCVRH
GNFGNSYVSWFAYWGQGTMVTVSSASTKGPSVFPLAPSSKSTSGGTAALGCLVKDYFPEPVTVSWNSG
ALTSGVHTFPAVLQSSGLYSLSSVVTVPSSSLGTQTYICNVNHKPSNTKVDKRVEPKSCPPCGGGGSD
DIQMTQSPSSLSASVGDRVTITCRASQGISNYLAWFQQKPGKAPKSLIYRANRLQSGVPSRFSGSGSG
TDFTLTISSLQPEDVATYYCLQYDDFPWTFGQGTKLEIKGGGGSGGGGSGGGGSGGGGSQVQLVQSGA
EVKKPGASVKVSCKASGYTFTSFWMHWVRQAPGQGLEWMGRIDPNRGGTEYNEKAKSRVTMTADKSTS
TAYMELSSLRSEDTAVYYCAGGNPYYPMDYWGQGTTVTVSS (SEQ ID NO: 118)

Figure 47A

QDGNEEMGGITQTPYKVSISGTTVILTGGGGSGGGGSGGGGSEVAHRFKDLGEENFKALVLIAFAQYL
QQCPFEDHVKLVNEVTEFAKTCVADESAENCDKSLHTLFGDKLCTVATLRETYGEMADCCAKQEPERN
ECFLQHKDDNPNLPRLVRPEVDVMCTAFHDNEETFLKKYLYEIARRHPYFYAPELLFFAKRYKAAFTE
CCQAADKAACLLPKLDELRDEGKASSAKQRLKCASLQKFGERAFKAWAVARLSQRFPKAEFAEVSKLV
TDLTKVHTECCHGDLLECADDRADLAKYICENQDSISSKLKECCEKPLLEKSHCIAEVENDEMPADLP
SLAADFVESKDVCKNYAEAKDVFLGMFLYEYARRHPDYSVVLLLRLAKTYETTLEKCCAAADPHECYA
KVFDEFKPLVEEPQNLIKQNCELFEQLGEYKFQNALLVRYTKKVPQVSTPTLVEVSRNLGKVGSKCCK
HPEAKRMPCAEDYLSVVLNQLCVLHEKTPVSDRVTKCCTESLVNRRPCFSALEVDETYVPKEFNAETF
TFHADICTLSEKERQIKKQTALVELVKHKPKATKEQLKAVMDDFAAFVEKCCKADDKETCFAEEGKKL
VAASQAAGGSGGSPLGLAGGSGGSEVQLVESGGGLVQPGGSLRLSCAASGFTFNTYAMNWVRQAPGK
GLEWVARIRSKYNNYATYYADSVKDRFTISRDDSKNTLYLQMNSLRAEDTAVYYCVRHGNFGNSYVSW
FAYWGQGTMVTVSSASTKGPSVFPLAPSSKSTSGGTAALGCLVKDYFPEPVTVSWNSGALTSGVHTFP
AVLQSSGLYSLSSVVTVPSSSLGTQTYICNVNHKPSNTKVDKRVEPKSCPPCGGGGSDDIQMTQSPSS
LSASVGDRVTITCRASQGISNYLAWFQQKPGKAPKSLIYRANRLQSGVPSRFSGSGSGTDFTLTISSL
QPEDVATYYCLQYDDFPWTFGQGTKLEIKGGGGSGGGGSGGGGSGGGGSQVQLVQSGAEVKKPGASVK
VSCKASGYTFTSFWMHWVRQAPGQGLEWMGRIDPNRGGTEYNEKAKSRVTMTADKSTSTAYMELSSLR
SEDTAVYYCAGGNPYYPMDYWGQGTTVTVSS (SEQ ID NO: 176)

Figure 47B

GGSGGSQAVVTQEPSLTVSPGGTVTLTCRSSTGAVTTSNYANWVQQKPGQAPRGLIGGTNKRAPGTPA
RFSGSLLGGKAALTLSGVQPEDEAEYYCALWYSNLWVFGGGTKLTVLGQPKAAPSVTLFPPSSEELQA
NKATLVCLISDFYPGAVTVAWKADSSPVKAGVETTTPSKQSNNKYAASSYLSLTPEQWKSHRSYSCQV
THEGSTVEKTVAPTECPPCSGGGSDIQMTQSPSSLSASVGDRVTITCRASQGISNYLAWFQQKPGKAP
KSLIYRANRLQSGVPSRFSGSGSGTDFTLTISSLQPEDVATYYCLQYDDFPWTFGQGTKLEIKGGGGS
GGGGSGGGGSGGGGSQVQLVQSGAEVKKPGASVKVSCKASGYTFTSFWMHWVRQAPGQGLEWMGRIDP
NRGGTEYNEKAKSRVTMTADKSTSTAYMELSSLRSEDTAVYYCAGGNPYYPMDYWGQGTTVTVSS
(SEQ ID NO: 177)

Figure 48

SEQUENCE LISTING

<160> NUMBER OF SEQ ID NOS: 177

<210> SEQ ID NO 1

```
<211> LENGTH: 207
<212> TYPE: PRT
<213> ORGANISM: Homo sapiens

<400> SEQUENCE: 1

Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45

Cys Pro Gln Tyr Pro Gly Ser Glu Ile Leu Trp Gln His Asn Asp Lys
    50                  55                  60

Asn Ile Gly Gly Asp Glu Asp Asp Lys Asn Ile Gly Ser Asp Glu Asp
65                  70                  75                  80

His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
            100                 105                 110

Tyr Leu Arg Ala Arg Val Cys Glu Asn Cys Met Glu Met Asp Val Met
        115                 120                 125

Ser Val Ala Thr Ile Val Ile Val Asp Ile Cys Ile Thr Gly Gly Leu
    130                 135                 140

Leu Leu Leu Val Tyr Tyr Trp Ser Lys Asn Arg Lys Ala Lys Ala Lys
145                 150                 155                 160

Pro Val Thr Arg Gly Ala Gly Ala Gly Gly Arg Gln Arg Gly Gln Asn
                165                 170                 175

Lys Glu Arg Pro Pro Pro Val Pro Asn Pro Asp Tyr Glu Pro Ile Arg
            180                 185                 190

Lys Gly Gln Arg Asp Leu Tyr Ser Gly Leu Asn Gln Arg Arg Ile
        195                 200                 205


<210> SEQ ID NO 2
<211> LENGTH: 186
<212> TYPE: PRT
<213> ORGANISM: Homo sapiens

<400> SEQUENCE: 2

Gln Asp Gly Asn Glu Glu Met Gly Gly Ile Thr Gln Thr Pro Tyr Lys
1               5                   10                  15

Val Ser Ile Ser Gly Thr Thr Val Ile Leu Thr Cys Pro Gln Tyr Pro
            20                  25                  30

Gly Ser Glu Ile Leu Trp Gln His Asn Asp Lys Asn Ile Gly Gly Asp
        35                  40                  45

Glu Asp Asp Lys Asn Ile Gly Ser Asp Glu Asp His Leu Ser Leu Lys
    50                  55                  60

Glu Phe Ser Glu Leu Glu Gln Ser Gly Tyr Tyr Val Cys Tyr Pro Arg
65                  70                  75                  80

Gly Ser Lys Pro Glu Asp Ala Asn Phe Tyr Leu Tyr Leu Arg Ala Arg
                85                  90                  95

Val Cys Glu Asn Cys Met Glu Met Asp Val Met Ser Val Ala Thr Ile
            100                 105                 110

Val Ile Val Asp Ile Cys Ile Thr Gly Gly Leu Leu Leu Leu Val Tyr
        115                 120                 125

Tyr Trp Ser Lys Asn Arg Lys Ala Lys Ala Lys Pro Val Thr Arg Gly
    130                 135                 140
```

```
Ala Gly Ala Gly Gly Arg Gln Arg Gly Gln Asn Lys Glu Arg Pro Pro
145                 150                 155                 160

Pro Val Pro Asn Pro Asp Tyr Glu Pro Ile Arg Lys Gly Gln Arg Asp
                165                 170                 175

Leu Tyr Ser Gly Leu Asn Gln Arg Arg Ile
            180                 185


<210> SEQ ID NO 3
<211> LENGTH: 126
<212> TYPE: PRT
<213> ORGANISM: Artificial Sequence
<220> FEATURE:
<223> OTHER INFORMATION: extracellular CD3 epsilon

<400> SEQUENCE: 3

Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45

Cys Pro Gln Tyr Pro Gly Ser Glu Ile Leu Trp Gln His Asn Asp Lys
    50                  55                  60

Asn Ile Gly Gly Asp Glu Asp Asp Lys Asn Ile Gly Ser Asp Glu Asp
65                  70                  75                  80

His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
            100                 105                 110

Tyr Leu Arg Ala Arg Val Cys Glu Asn Cys Met Glu Met Asp
        115                 120                 125


<210> SEQ ID NO 4
<211> LENGTH: 105
<212> TYPE: PRT
<213> ORGANISM: Artificial Sequence
<220> FEATURE:
<223> OTHER INFORMATION: extracellular CD3 epsilon mature

<400> SEQUENCE: 4

Gln Asp Gly Asn Glu Glu Met Gly Gly Ile Thr Gln Thr Pro Tyr Lys
1               5                   10                  15

Val Ser Ile Ser Gly Thr Thr Val Ile Leu Thr Cys Pro Gln Tyr Pro
            20                  25                  30

Gly Ser Glu Ile Leu Trp Gln His Asn Asp Lys Asn Ile Gly Gly Asp
        35                  40                  45

Glu Asp Asp Lys Asn Ile Gly Ser Asp Glu Asp His Leu Ser Leu Lys
    50                  55                  60

Glu Phe Ser Glu Leu Glu Gln Ser Gly Tyr Tyr Val Cys Tyr Pro Arg
65                  70                  75                  80

Gly Ser Lys Pro Glu Asp Ala Asn Phe Tyr Leu Tyr Leu Arg Ala Arg
                85                  90                  95

Val Cys Glu Asn Cys Met Glu Met Asp
            100                 105


<210> SEQ ID NO 5
<211> LENGTH: 27
<212> TYPE: PRT
```

<213> ORGANISM: Artificial Sequence
<220> FEATURE:
<223> OTHER INFORMATION: CAP

<400> SEQUENCE: 5

```
Gln Asp Gly Asn Glu Glu Met Gly Gly Ile Thr Gln Thr Pro Tyr Lys
1               5                   10                  15

Val Ser Ile Ser Gly Thr Thr Val Ile Leu Thr
            20                  25
```

<210> SEQ ID NO 6
<211> LENGTH: 578
<212> TYPE: PRT
<213> ORGANISM: Homo sapiens

<400> SEQUENCE: 6

```
Ser Glu Val Ala His Arg Phe Lys Asp Leu Gly Glu Glu Asn Phe Lys
1               5                   10                  15

Ala Leu Val Leu Ile Ala Phe Ala Gln Tyr Leu Gln Gln Cys Pro Phe
            20                  25                  30

Glu Asp His Val Lys Leu Val Asn Glu Val Thr Glu Phe Ala Lys Thr
        35                  40                  45

Cys Val Ala Asp Glu Ser Ala Glu Asn Cys Asp Lys Ser Leu His Thr
    50                  55                  60

Leu Phe Gly Asp Lys Leu Cys Thr Val Ala Thr Leu Arg Glu Thr Tyr
65                  70                  75                  80

Gly Glu Met Ala Asp Cys Cys Ala Lys Gln Glu Pro Glu Arg Asn Glu
                85                  90                  95

Cys Phe Leu Gln His Lys Asp Asp Asn Pro Asn Leu Pro Arg Leu Val
            100                 105                 110

Arg Pro Glu Val Asp Val Met Cys Thr Ala Phe His Asp Asn Glu Glu
        115                 120                 125

Thr Phe Leu Lys Lys Tyr Leu Tyr Glu Ile Ala Arg Arg His Pro Tyr
    130                 135                 140

Phe Tyr Ala Pro Glu Leu Leu Phe Phe Ala Lys Arg Tyr Lys Ala Ala
145                 150                 155                 160

Phe Thr Glu Cys Cys Gln Ala Ala Asp Lys Ala Ala Cys Leu Leu Pro
                165                 170                 175

Lys Leu Asp Glu Leu Arg Asp Glu Gly Lys Ala Ser Ser Ala Lys Gln
            180                 185                 190

Arg Leu Lys Cys Ala Ser Leu Gln Lys Phe Gly Glu Arg Ala Phe Lys
        195                 200                 205

Ala Trp Ala Val Ala Arg Leu Ser Gln Arg Phe Pro Lys Ala Glu Phe
    210                 215                 220

Ala Glu Val Ser Lys Leu Val Thr Asp Leu Thr Lys Val His Thr Glu
225                 230                 235                 240

Cys Cys His Gly Asp Leu Leu Glu Cys Ala Asp Asp Arg Ala Asp Leu
                245                 250                 255

Ala Lys Tyr Ile Cys Glu Asn Gln Asp Ser Ile Ser Ser Lys Leu Lys
            260                 265                 270

Glu Cys Cys Glu Lys Pro Leu Leu Glu Lys Ser His Cys Ile Ala Glu
        275                 280                 285

Val Glu Asn Asp Glu Met Pro Ala Asp Leu Pro Ser Leu Ala Ala Asp
    290                 295                 300

Phe Val Glu Ser Lys Asp Val Cys Lys Asn Tyr Ala Glu Ala Lys Asp
305                 310                 315                 320
```

```
Val Phe Leu Gly Met Phe Leu Tyr Glu Tyr Ala Arg Arg His Pro Asp
                325                 330                 335

Tyr Ser Val Val Leu Leu Leu Arg Leu Ala Lys Thr Tyr Glu Thr Thr
            340                 345                 350

Leu Glu Lys Cys Cys Ala Ala Ala Asp Pro His Glu Cys Tyr Ala Lys
        355                 360                 365

Val Phe Asp Glu Phe Lys Pro Leu Val Glu Glu Pro Gln Asn Leu Ile
    370                 375                 380

Lys Gln Asn Cys Glu Leu Phe Glu Gln Leu Gly Glu Tyr Lys Phe Gln
385                 390                 395                 400

Asn Ala Leu Leu Val Arg Tyr Thr Lys Lys Val Pro Gln Val Ser Thr
                405                 410                 415

Pro Thr Leu Val Glu Val Ser Arg Asn Leu Gly Lys Val Gly Ser Lys
            420                 425                 430

Cys Cys Lys His Pro Glu Ala Lys Arg Met Pro Cys Ala Glu Asp Tyr
        435                 440                 445

Leu Ser Val Val Leu Asn Gln Leu Cys Val Leu His Glu Lys Thr Pro
    450                 455                 460

Val Ser Asp Arg Val Thr Lys Cys Cys Thr Glu Ser Leu Val Asn Arg
465                 470                 475                 480

Arg Pro Cys Phe Ser Ala Leu Glu Val Asp Glu Thr Tyr Val Pro Lys
                485                 490                 495

Glu Phe Asn Ala Glu Thr Phe Thr Phe His Ala Asp Ile Cys Thr Leu
            500                 505                 510

Ser Glu Lys Glu Arg Gln Ile Lys Lys Gln Thr Ala Leu Val Glu Leu
        515                 520                 525

Val Lys His Lys Pro Lys Ala Thr Lys Glu Gln Leu Lys Ala Val Met
    530                 535                 540

Asp Asp Phe Ala Ala Phe Val Glu Lys Cys Cys Lys Ala Asp Asp Lys
545                 550                 555                 560

Glu Thr Cys Phe Ala Glu Glu Gly Lys Lys Leu Val Ala Ala Ser Gln
                565                 570                 575

Ala Ala
```

<210> SEQ ID NO 7
<211> LENGTH: 577
<212> TYPE: PRT
<213> ORGANISM: Homo sapiens

<400> SEQUENCE: 7

```
Glu Val Ala His Arg Phe Lys Asp Leu Gly Glu Glu Asn Phe Lys Ala
1               5                   10                  15

Leu Val Leu Ile Ala Phe Ala Gln Tyr Leu Gln Gln Cys Pro Phe Glu
            20                  25                  30

Asp His Val Lys Leu Val Asn Glu Val Thr Glu Phe Ala Lys Thr Cys
        35                  40                  45

Val Ala Asp Glu Ser Ala Glu Asn Cys Asp Lys Ser Leu His Thr Leu
    50                  55                  60

Phe Gly Asp Lys Leu Cys Thr Val Ala Thr Leu Arg Glu Thr Tyr Gly
65                  70                  75                  80

Glu Met Ala Asp Cys Cys Ala Lys Gln Glu Pro Glu Arg Asn Glu Cys
                85                  90                  95

Phe Leu Gln His Lys Asp Asp Asn Pro Asn Leu Pro Arg Leu Val Arg
            100                 105                 110
```

```
Pro Glu Val Asp Val Met Cys Thr Ala Phe His Asp Asn Glu Glu Thr
        115                 120                 125

Phe Leu Lys Lys Tyr Leu Tyr Glu Ile Ala Arg Arg His Pro Tyr Phe
    130                 135                 140

Tyr Ala Pro Glu Leu Leu Phe Phe Ala Lys Arg Tyr Lys Ala Ala Phe
145                 150                 155                 160

Thr Glu Cys Cys Gln Ala Ala Asp Lys Ala Ala Cys Leu Leu Pro Lys
                165                 170                 175

Leu Asp Glu Leu Arg Asp Glu Gly Lys Ala Ser Ser Ala Lys Gln Arg
            180                 185                 190

Leu Lys Cys Ala Ser Leu Gln Lys Phe Gly Glu Arg Ala Phe Lys Ala
        195                 200                 205

Trp Ala Val Ala Arg Leu Ser Gln Arg Phe Pro Lys Ala Glu Phe Ala
    210                 215                 220

Glu Val Ser Lys Leu Val Thr Asp Leu Thr Lys Val His Thr Glu Cys
225                 230                 235                 240

Cys His Gly Asp Leu Leu Glu Cys Ala Asp Asp Arg Ala Asp Leu Ala
                245                 250                 255

Lys Tyr Ile Cys Glu Asn Gln Asp Ser Ile Ser Ser Lys Leu Lys Glu
            260                 265                 270

Cys Cys Glu Lys Pro Leu Leu Glu Lys Ser His Cys Ile Ala Glu Val
        275                 280                 285

Glu Asn Asp Glu Met Pro Ala Asp Leu Pro Ser Leu Ala Ala Asp Phe
    290                 295                 300

Val Glu Ser Lys Asp Val Cys Lys Asn Tyr Ala Glu Ala Lys Asp Val
305                 310                 315                 320

Phe Leu Gly Met Phe Leu Tyr Glu Tyr Ala Arg Arg His Pro Asp Tyr
                325                 330                 335

Ser Val Val Leu Leu Leu Arg Leu Ala Lys Thr Tyr Glu Thr Thr Leu
            340                 345                 350

Glu Lys Cys Cys Ala Ala Ala Asp Pro His Glu Cys Tyr Ala Lys Val
        355                 360                 365

Phe Asp Glu Phe Lys Pro Leu Val Glu Glu Pro Gln Asn Leu Ile Lys
    370                 375                 380

Gln Asn Cys Glu Leu Phe Glu Gln Leu Gly Glu Tyr Lys Phe Gln Asn
385                 390                 395                 400

Ala Leu Leu Val Arg Tyr Thr Lys Lys Val Pro Gln Val Ser Thr Pro
                405                 410                 415

Thr Leu Val Glu Val Ser Arg Asn Leu Gly Lys Val Gly Ser Lys Cys
            420                 425                 430

Cys Lys His Pro Glu Ala Lys Arg Met Pro Cys Ala Glu Asp Tyr Leu
        435                 440                 445

Ser Val Val Leu Asn Gln Leu Cys Val Leu His Glu Lys Thr Pro Val
    450                 455                 460

Ser Asp Arg Val Thr Lys Cys Cys Thr Glu Ser Leu Val Asn Arg Arg
465                 470                 475                 480

Pro Cys Phe Ser Ala Leu Glu Val Asp Glu Thr Tyr Val Pro Lys Glu
                485                 490                 495

Phe Asn Ala Glu Thr Phe Thr Phe His Ala Asp Ile Cys Thr Leu Ser
            500                 505                 510

Glu Lys Glu Arg Gln Ile Lys Lys Gln Thr Ala Leu Val Glu Leu Val
        515                 520                 525
```

```
Lys His Lys Pro Lys Ala Thr Lys Glu Gln Leu Lys Ala Val Met Asp
    530                 535                 540

Asp Phe Ala Ala Phe Val Glu Lys Cys Cys Lys Ala Asp Asp Lys Glu
545                 550                 555                 560

Thr Cys Phe Ala Glu Glu Gly Lys Lys Leu Val Ala Ala Ser Gln Ala
                565                 570                 575

Ala


<210> SEQ ID NO 8
<211> LENGTH: 1731
<212> TYPE: DNA
<213> ORGANISM: Homo sapiens

<400> SEQUENCE: 8

gaggtggccc acaggttcaa ggatctgggc gaggagaact tcaaggccct ggtgctgatc     60

gccttcgccc agtatctgca gcagtgcccc tttgaggacc acgtgaagct ggtgaacgag    120

gtgaccgagt tcgccaagac atgcgtggcc gacgagtccg ccgagaattg tgataagtct    180

ctgcacaccc tgtttggcga taagctgtgc accgtggcca cactgaggga gacatacggc    240

gagatggccg actgctgtgc caagcaggag cccgagcgca acgagtgctt cctgcagcac    300

aaggacgata accctaatct gccacggctg gtgagacctg aggtggacgt gatgtgcacc    360

gccttccacg ataatgagga gacatttctg aagaagtacc tgtatgagat cgcccggaga    420

caccccttact tttatgcccc agagctgctg ttctttgcca agcggtacaa ggcagccttc    480

accgagtgct gtcaggcagc agataaggca gcatgcctgc tgccaaagct ggacgagctg    540

agggatgagg gcaaggcaag ctccgccaag cagcgcctga agtgtgcaag cctgcagaag    600

ttcggagaga gggcctttaa ggcatgggca gtggcaaggc tgtcccagcg gttcccaaag    660

gccgagtttg ccgaggtgtc taagctggtg accgacctga caaaggtgca caccgagtgc    720

tgtcacggcg acctgctgga gtgcgcagac gatagagccg atctggccaa gtacatctgt    780

gagaaccagg actctatctc tagcaagctg aaggagtgct gtgagaagcc cctgctggag    840

aagtcccact gcatcgccga ggtggagaac gacgagatgc cagcagatct gccaagcctg    900

gcagcagact tcgtggagtc caaggacgtg tgcaagaatt acgccgaggc caaggacgtg    960

ttcctgggca tgtttctgta cgagtatgcc aggcgccacc ctgactactc cgtggtgctg   1020

ctgctgcggc tggccaagac ctatgagacc acactggaga agtgctgtgc cgccgccgac   1080

ccccacgagt gctatgcaaa ggtgttcgac gagtttaagc ccctggtgga ggagcctcag   1140

aacctgatca agcagaattg tgagctgttt gagcagctgg gcgagtacaa gttccagaac   1200

gccctgctgg tgagatatac caagaaggtg ccacaggtgt ctacccccac actggtggag   1260

gtgagccgga atctgggcaa ggtcggctcc aagtgctgta agcaccctga ggccaagaga   1320

atgccatgcg ccgaggatta cctgtccgtg gtgctgaacc agctgtgcgt gctgcacgag   1380

aagacccccg tgagcgacag ggtgaccaag tgctgtacag agtctctggt gaaccggaga   1440

ccatgcttta gcgccctgga ggtggatgag acatatgtgc ccaaggagtt caatgccgag   1500

accttcacat ttcacgccga catctgtacc ctgagcgaga aggagcgcca gatcaagaag   1560

cagacagccc tggtggagct ggtgaagcac aagccaaagg ccaccaagga gcagctgaag   1620

gccgtgatgg acgatttcgc cgcctttgtg gagaagtgct gtaaggccga cgataaggag   1680

acatgcttcg cagaggaggg caagaagctg gtggcagcaa gccaggcagc a            1731


<210> SEQ ID NO 9
```

<211> LENGTH: 6
<212> TYPE: PRT
<213> ORGANISM: Artificial Sequence
<220> FEATURE:
<223> OTHER INFORMATION: MPP cleavable

<400> SEQUENCE: 9

Pro Leu Gly Leu Ala Gly
1 5

<210> SEQ ID NO 10
<211> LENGTH: 8
<212> TYPE: PRT
<213> ORGANISM: Artificial Sequence
<220> FEATURE:
<223> OTHER INFORMATION: protease cleavable

<400> SEQUENCE: 10

Gly Pro Leu Gly Met Leu Ser Gln
1 5

<210> SEQ ID NO 11
<211> LENGTH: 8
<212> TYPE: PRT
<213> ORGANISM: Artificial Sequence
<220> FEATURE:
<223> OTHER INFORMATION: protease cleavable

<400> SEQUENCE: 11

Gly Pro Leu Gly Leu Trp Ala Gln
1 5

<210> SEQ ID NO 12
<211> LENGTH: 7
<212> TYPE: PRT
<213> ORGANISM: Artificial Sequence
<220> FEATURE:
<223> OTHER INFORMATION: protease cleavable

<400> SEQUENCE: 12

Gly Pro Leu Gly Leu Ala Gly
1 5

<210> SEQ ID NO 13
<211> LENGTH: 12
<212> TYPE: PRT
<213> ORGANISM: Artificial Sequence
<220> FEATURE:
<223> OTHER INFORMATION: protease cleavable

<400> SEQUENCE: 13

Lys Lys Asn Pro Ala Glu Leu Ile Gly Pro Val Asp
1 5 10

<210> SEQ ID NO 14
<211> LENGTH: 13
<212> TYPE: PRT
<213> ORGANISM: Artificial Sequence
<220> FEATURE:
<223> OTHER INFORMATION: protease cleavable

<400> SEQUENCE: 14

Lys Lys Gln Pro Ala Ala Asn Leu Val Ala Pro Glu Asp
1 5 10

<210> SEQ ID NO 15
<211> LENGTH: 8

<212> TYPE: PRT
<213> ORGANISM: Artificial Sequence
<220> FEATURE:
<223> OTHER INFORMATION: protease cleavable

<400> SEQUENCE: 15

Gly Pro Leu Gly Ile Ala Gly Gln
1               5

<210> SEQ ID NO 16
<211> LENGTH: 6
<212> TYPE: PRT
<213> ORGANISM: Artificial Sequence
<220> FEATURE:
<223> OTHER INFORMATION: protease cleavable

<400> SEQUENCE: 16

Pro Val Gly Leu Ile Gly
1               5

<210> SEQ ID NO 17
<211> LENGTH: 6
<212> TYPE: PRT
<213> ORGANISM: Artificial Sequence
<220> FEATURE:
<223> OTHER INFORMATION: protease cleavable

<400> SEQUENCE: 17

Asn Ser Gly Arg Ala Val
1               5

<210> SEQ ID NO 18
<211> LENGTH: 5
<212> TYPE: PRT
<213> ORGANISM: Artificial Sequence
<220> FEATURE:
<223> OTHER INFORMATION: protease cleavable

<400> SEQUENCE: 18

Ser Gly Arg Ser Ala
1               5

<210> SEQ ID NO 19
<211> LENGTH: 13
<212> TYPE: PRT
<213> ORGANISM: Artificial Sequence
<220> FEATURE:
<223> OTHER INFORMATION: protease cleavable

<400> SEQUENCE: 19

Leu Gly Gly Ser Gly Arg Ser Ala Asn Ala Ile Leu Glu
1               5                   10

<210> SEQ ID NO 20
<211> LENGTH: 4
<212> TYPE: PRT
<213> ORGANISM: Artificial Sequence
<220> FEATURE:
<223> OTHER INFORMATION: protease cleavable

<400> SEQUENCE: 20

Ser Gly Arg Ser
1

<210> SEQ ID NO 21
<211> LENGTH: 9
<212> TYPE: PRT

<213> ORGANISM: Artificial Sequence
<220> FEATURE:
<223> OTHER INFORMATION: protease cleavable

<400> SEQUENCE: 21

Gly Gly Ser Gly Arg Ser Ala Asn Lys
1 5

<210> SEQ ID NO 22
<211> LENGTH: 14
<212> TYPE: PRT
<213> ORGANISM: Artificial Sequence
<220> FEATURE:
<223> OTHER INFORMATION: protease cleavable

<400> SEQUENCE: 22

Leu Gly Gly Ser Gly Arg Ser Ala Asn Ala Ile Leu Glu Cys
1 5 10

<210> SEQ ID NO 23
<211> LENGTH: 5
<212> TYPE: PRT
<213> ORGANISM: Artificial Sequence
<220> FEATURE:
<223> OTHER INFORMATION: protease cleavable

<400> SEQUENCE: 23

Gly Gly Gly Arg Arg
1 5

<210> SEQ ID NO 24
<211> LENGTH: 6
<212> TYPE: PRT
<213> ORGANISM: Artificial Sequence
<220> FEATURE:
<223> OTHER INFORMATION: protease cleavable

<400> SEQUENCE: 24

Thr Gly Arg Gly Pro Ser
1 5

<210> SEQ ID NO 25
<211> LENGTH: 8
<212> TYPE: PRT
<213> ORGANISM: Artificial Sequence
<220> FEATURE:
<223> OTHER INFORMATION: protease cleavable

<400> SEQUENCE: 25

Leu Ser Gly Arg Ser Asp Asn His
1 5

<210> SEQ ID NO 26
<211> LENGTH: 8
<212> TYPE: PRT
<213> ORGANISM: Artificial Sequence
<220> FEATURE:
<223> OTHER INFORMATION: protease cleavable

<400> SEQUENCE: 26

Pro Leu Thr Gly Arg Ser Gly Gly
1 5

<210> SEQ ID NO 27
<211> LENGTH: 7
<212> TYPE: PRT
<213> ORGANISM: Artificial Sequence
<220> FEATURE:
<223> OTHER INFORMATION: protease cleavable

<400> SEQUENCE: 27

Gln Arg Arg Val Val Gly Gly
1               5

<210> SEQ ID NO 28
<211> LENGTH: 1124
<212> TYPE: PRT
<213> ORGANISM: Artificial Sequence
<220> FEATURE:
<223> OTHER INFORMATION: HC EGFR Polypeptide with multiple cleavage
      protease sequence

<400> SEQUENCE: 28

Gln Asp Gly Asn Glu Glu Met Gly Gly Ile Thr Gln Thr Pro Tyr Lys
1               5                   10                  15

Val Ser Ile Ser Gly Thr Thr Val Ile Leu Thr Gly Gly Gly Gly Ser
            20                  25                  30

Gly Gly Gly Gly Ser Gly Gly Gly Gly Ser Glu Val Ala His Arg Phe
        35                  40                  45

Lys Asp Leu Gly Glu Glu Asn Phe Lys Ala Leu Val Leu Ile Ala Phe
    50                  55                  60

Ala Gln Tyr Leu Gln Gln Cys Pro Phe Glu Asp His Val Lys Leu Val
65                  70                  75                  80

Asn Glu Val Thr Glu Phe Ala Lys Thr Cys Val Ala Asp Glu Ser Ala
                85                  90                  95

Glu Asn Cys Asp Lys Ser Leu His Thr Leu Phe Gly Asp Lys Leu Cys
            100                 105                 110

Thr Val Ala Thr Leu Arg Glu Thr Tyr Gly Glu Met Ala Asp Cys Cys
        115                 120                 125

Ala Lys Gln Glu Pro Glu Arg Asn Glu Cys Phe Leu Gln His Lys Asp
    130                 135                 140

Asp Asn Pro Asn Leu Pro Arg Leu Val Arg Pro Glu Val Asp Val Met
145                 150                 155                 160

Cys Thr Ala Phe His Asp Asn Glu Glu Thr Phe Leu Lys Lys Tyr Leu
                165                 170                 175

Tyr Glu Ile Ala Arg Arg His Pro Tyr Phe Tyr Ala Pro Glu Leu Leu
            180                 185                 190

Phe Phe Ala Lys Arg Tyr Lys Ala Ala Phe Thr Glu Cys Cys Gln Ala
        195                 200                 205

Ala Asp Lys Ala Ala Cys Leu Leu Pro Lys Leu Asp Glu Leu Arg Asp
    210                 215                 220

Glu Gly Lys Ala Ser Ser Ala Lys Gln Arg Leu Lys Cys Ala Ser Leu
225                 230                 235                 240

Gln Lys Phe Gly Glu Arg Ala Phe Lys Ala Trp Ala Val Ala Arg Leu
                245                 250                 255

Ser Gln Arg Phe Pro Lys Ala Glu Phe Ala Glu Val Ser Lys Leu Val
            260                 265                 270

Thr Asp Leu Thr Lys Val His Thr Glu Cys Cys His Gly Asp Leu Leu
        275                 280                 285

Glu Cys Ala Asp Asp Arg Ala Asp Leu Ala Lys Tyr Ile Cys Glu Asn
    290                 295                 300

Gln Asp Ser Ile Ser Ser Lys Leu Lys Glu Cys Cys Glu Lys Pro Leu
305                 310                 315                 320

```
Leu Glu Lys Ser His Cys Ile Ala Glu Val Glu Asn Asp Glu Met Pro
                325                 330                 335

Ala Asp Leu Pro Ser Leu Ala Ala Asp Phe Val Glu Ser Lys Asp Val
            340                 345                 350

Cys Lys Asn Tyr Ala Glu Ala Lys Asp Val Phe Leu Gly Met Phe Leu
        355                 360                 365

Tyr Glu Tyr Ala Arg Arg His Pro Asp Tyr Ser Val Val Leu Leu Leu
    370                 375                 380

Arg Leu Ala Lys Thr Tyr Glu Thr Thr Leu Glu Lys Cys Cys Ala Ala
385                 390                 395                 400

Ala Asp Pro His Glu Cys Tyr Ala Lys Val Phe Asp Glu Phe Lys Pro
                405                 410                 415

Leu Val Glu Glu Pro Gln Asn Leu Ile Lys Gln Asn Cys Glu Leu Phe
            420                 425                 430

Glu Gln Leu Gly Glu Tyr Lys Phe Gln Asn Ala Leu Leu Val Arg Tyr
        435                 440                 445

Thr Lys Lys Val Pro Gln Val Ser Thr Pro Thr Leu Val Glu Val Ser
    450                 455                 460

Arg Asn Leu Gly Lys Val Gly Ser Lys Cys Cys Lys His Pro Glu Ala
465                 470                 475                 480

Lys Arg Met Pro Cys Ala Glu Asp Tyr Leu Ser Val Val Leu Asn Gln
                485                 490                 495

Leu Cys Val Leu His Glu Lys Thr Pro Val Ser Asp Arg Val Thr Lys
            500                 505                 510

Cys Cys Thr Glu Ser Leu Val Asn Arg Arg Pro Cys Phe Ser Ala Leu
        515                 520                 525

Glu Val Asp Glu Thr Tyr Val Pro Lys Glu Phe Asn Ala Glu Thr Phe
    530                 535                 540

Thr Phe His Ala Asp Ile Cys Thr Leu Ser Glu Lys Glu Arg Gln Ile
545                 550                 555                 560

Lys Lys Gln Thr Ala Leu Val Glu Leu Val Lys His Lys Pro Lys Ala
                565                 570                 575

Thr Lys Glu Gln Leu Lys Ala Val Met Asp Asp Phe Ala Ala Phe Val
            580                 585                 590

Glu Lys Cys Cys Lys Ala Asp Asp Lys Glu Thr Cys Phe Ala Glu Glu
        595                 600                 605

Gly Lys Lys Leu Val Ala Ala Ser Gln Ala Ala Gly Gly Ser Gly Gly
    610                 615                 620

Ser Pro Leu Gly Leu Ala Gly Gly Gly Gly Ser Gly Arg Ser Asp Asn
625                 630                 635                 640

His Gly Gly Ser Gly Gly Ser Glu Val Gln Leu Val Glu Ser Gly Gly
                645                 650                 655

Gly Leu Val Gln Pro Gly Gly Ser Leu Arg Leu Ser Cys Ala Ala Ser
            660                 665                 670

Gly Phe Thr Phe Asn Thr Tyr Ala Met Asn Trp Val Arg Gln Ala Pro
        675                 680                 685

Gly Lys Gly Leu Glu Trp Val Ala Arg Ile Arg Ser Lys Tyr Asn Asn
    690                 695                 700

Tyr Ala Thr Tyr Tyr Ala Asp Ser Val Lys Asp Arg Phe Thr Ile Ser
705                 710                 715                 720

Arg Asp Asp Ser Lys Asn Thr Leu Tyr Leu Gln Met Asn Ser Leu Arg
                725                 730                 735
```

```
Ala Glu Asp Thr Ala Val Tyr Tyr Cys Val Arg His Gly Asn Phe Gly
            740                 745                 750

Asn Ser Tyr Val Ser Trp Phe Ala Tyr Trp Gly Gln Gly Thr Met Val
        755                 760                 765

Thr Val Ser Ser Ala Ser Thr Lys Gly Pro Ser Val Phe Pro Leu Ala
    770                 775                 780

Pro Ser Ser Lys Ser Thr Ser Gly Gly Thr Ala Ala Leu Gly Cys Leu
785                 790                 795                 800

Val Lys Asp Tyr Phe Pro Glu Pro Val Thr Val Ser Trp Asn Ser Gly
                805                 810                 815

Ala Leu Thr Ser Gly Val His Thr Phe Pro Ala Val Leu Gln Ser Ser
            820                 825                 830

Gly Leu Tyr Ser Leu Ser Ser Val Val Thr Val Pro Ser Ser Ser Leu
        835                 840                 845

Gly Thr Gln Thr Tyr Ile Cys Asn Val Asn His Lys Pro Ser Asn Thr
    850                 855                 860

Lys Val Asp Lys Arg Val Glu Pro Lys Ser Cys Pro Pro Cys Gly Gly
865                 870                 875                 880

Gly Gly Ser Asp Ile Gln Met Thr Gln Ser Pro Ser Ser Leu Ser Ala
                885                 890                 895

Ser Val Gly Asp Arg Val Thr Ile Thr Cys Gln Ala Ser Gln Asp Ile
            900                 905                 910

Ser Asn Tyr Leu Asn Trp Tyr Gln Gln Lys Pro Gly Lys Ala Pro Lys
        915                 920                 925

Leu Leu Ile Tyr Asp Ala Ser Asn Leu Glu Thr Gly Val Pro Ser Arg
    930                 935                 940

Phe Ser Gly Ser Gly Ser Gly Thr Asp Phe Thr Phe Thr Ile Ser Ser
945                 950                 955                 960

Leu Gln Pro Glu Asp Ile Ala Thr Tyr Phe Cys Gln His Phe Asp His
                965                 970                 975

Leu Pro Leu Ala Phe Gly Gly Gly Thr Lys Val Glu Ile Lys Gly Gly
            980                 985                 990

Gly Gly Ser Gly Gly Gly Gly Ser  Gly Gly Gly Gly Ser  Gln Val Gln
        995                 1000                1005

Leu Gln  Glu Ser Gly Pro Gly  Leu Val Lys Pro Ser  Glu Thr Leu
    1010                1015                1020

Ser Leu  Thr Cys Thr Val Ser  Gly Gly Ser Val Ser  Ser Gly Asp
    1025                1030                1035

Tyr Tyr  Trp Thr Trp Ile Arg  Gln Ser Pro Gly Lys  Gly Leu Glu
    1040                1045                1050

Trp Ile  Gly His Ile Tyr Tyr  Ser Gly Asn Thr Asn  Tyr Asn Pro
    1055                1060                1065

Ser Leu  Lys Ser Arg Leu Thr  Ile Ser Ile Asp Thr  Ser Lys Thr
    1070                1075                1080

Gln Phe  Ser Leu Lys Leu Ser  Ser Val Thr Ala Ala  Asp Thr Ala
    1085                1090                1095

Ile Tyr  Tyr Cys Val Arg Asp  Arg Val Thr Gly Ala  Phe Asp Ile
    1100                1105                1110

Trp Gly  Gln Gly Thr Met Val  Thr Val Ser Ser
    1115                1120
```

<210> SEQ ID NO 29
<211> LENGTH: 4

<212> TYPE: PRT
<213> ORGANISM: Artificial Sequence
<220> FEATURE:
<223> OTHER INFORMATION: protease cleavable

<400> SEQUENCE: 29

Ala Ala Asn Leu
1

<210> SEQ ID NO 30
<211> LENGTH: 4
<212> TYPE: PRT
<213> ORGANISM: Artificial Sequence
<220> FEATURE:
<223> OTHER INFORMATION: protease cleavable

<400> SEQUENCE: 30

Pro Thr Asn Leu
1

<210> SEQ ID NO 31
<211> LENGTH: 1114
<212> TYPE: PRT
<213> ORGANISM: Artificial Sequence
<220> FEATURE:
<223> OTHER INFORMATION: HC EGFR Polypeptide with MMP2/9 cleavage protease sequence

<400> SEQUENCE: 31

```
Gln Asp Gly Asn Glu Glu Met Gly Gly Ile Thr Gln Thr Pro Tyr Lys
1               5                   10                  15

Val Ser Ile Ser Gly Thr Thr Val Ile Leu Thr Gly Gly Gly Gly Ser
            20                  25                  30

Gly Gly Gly Gly Ser Gly Gly Gly Gly Ser Glu Val Ala His Arg Phe
        35                  40                  45

Lys Asp Leu Gly Glu Glu Asn Phe Lys Ala Leu Val Leu Ile Ala Phe
    50                  55                  60

Ala Gln Tyr Leu Gln Gln Cys Pro Phe Glu Asp His Val Lys Leu Val
65                  70                  75                  80

Asn Glu Val Thr Glu Phe Ala Lys Thr Cys Val Ala Asp Glu Ser Ala
                85                  90                  95

Glu Asn Cys Asp Lys Ser Leu His Thr Leu Phe Gly Asp Lys Leu Cys
            100                 105                 110

Thr Val Ala Thr Leu Arg Glu Thr Tyr Gly Glu Met Ala Asp Cys Cys
        115                 120                 125

Ala Lys Gln Glu Pro Glu Arg Asn Glu Cys Phe Leu Gln His Lys Asp
    130                 135                 140

Asp Asn Pro Asn Leu Pro Arg Leu Val Arg Pro Glu Val Asp Val Met
145                 150                 155                 160

Cys Thr Ala Phe His Asp Asn Glu Glu Thr Phe Leu Lys Lys Tyr Leu
                165                 170                 175

Tyr Glu Ile Ala Arg Arg His Pro Tyr Phe Tyr Ala Pro Glu Leu Leu
            180                 185                 190

Phe Phe Ala Lys Arg Tyr Lys Ala Ala Phe Thr Glu Cys Cys Gln Ala
        195                 200                 205

Ala Asp Lys Ala Ala Cys Leu Leu Pro Lys Leu Asp Glu Leu Arg Asp
    210                 215                 220

Glu Gly Lys Ala Ser Ser Ala Lys Gln Arg Leu Lys Cys Ala Ser Leu
225                 230                 235                 240
```

-continued

```
Gln Lys Phe Gly Glu Arg Ala Phe Lys Ala Trp Ala Val Ala Arg Leu
                245                 250                 255

Ser Gln Arg Phe Pro Lys Ala Glu Phe Ala Glu Val Ser Lys Leu Val
            260                 265                 270

Thr Asp Leu Thr Lys Val His Thr Glu Cys Cys His Gly Asp Leu Leu
        275                 280                 285

Glu Cys Ala Asp Asp Arg Ala Asp Leu Ala Lys Tyr Ile Cys Glu Asn
    290                 295                 300

Gln Asp Ser Ile Ser Ser Lys Leu Lys Glu Cys Cys Glu Lys Pro Leu
305                 310                 315                 320

Leu Glu Lys Ser His Cys Ile Ala Glu Val Glu Asn Asp Glu Met Pro
                325                 330                 335

Ala Asp Leu Pro Ser Leu Ala Ala Asp Phe Val Glu Ser Lys Asp Val
            340                 345                 350

Cys Lys Asn Tyr Ala Glu Ala Lys Asp Val Phe Leu Gly Met Phe Leu
        355                 360                 365

Tyr Glu Tyr Ala Arg Arg His Pro Asp Tyr Ser Val Val Leu Leu Leu
    370                 375                 380

Arg Leu Ala Lys Thr Tyr Glu Thr Thr Leu Glu Lys Cys Cys Ala Ala
385                 390                 395                 400

Ala Asp Pro His Glu Cys Tyr Ala Lys Val Phe Asp Glu Phe Lys Pro
                405                 410                 415

Leu Val Glu Glu Pro Gln Asn Leu Ile Lys Gln Asn Cys Glu Leu Phe
            420                 425                 430

Glu Gln Leu Gly Glu Tyr Lys Phe Gln Asn Ala Leu Leu Val Arg Tyr
        435                 440                 445

Thr Lys Lys Val Pro Gln Val Ser Thr Pro Thr Leu Val Glu Val Ser
    450                 455                 460

Arg Asn Leu Gly Lys Val Gly Ser Lys Cys Cys Lys His Pro Glu Ala
465                 470                 475                 480

Lys Arg Met Pro Cys Ala Glu Asp Tyr Leu Ser Val Val Leu Asn Gln
                485                 490                 495

Leu Cys Val Leu His Glu Lys Thr Pro Val Ser Asp Arg Val Thr Lys
            500                 505                 510

Cys Cys Thr Glu Ser Leu Val Asn Arg Arg Pro Cys Phe Ser Ala Leu
        515                 520                 525

Glu Val Asp Glu Thr Tyr Val Pro Lys Glu Phe Asn Ala Glu Thr Phe
    530                 535                 540

Thr Phe His Ala Asp Ile Cys Thr Leu Ser Glu Lys Glu Arg Gln Ile
545                 550                 555                 560

Lys Lys Gln Thr Ala Leu Val Glu Leu Val Lys His Lys Pro Lys Ala
                565                 570                 575

Thr Lys Glu Gln Leu Lys Ala Val Met Asp Asp Phe Ala Ala Phe Val
            580                 585                 590

Glu Lys Cys Cys Lys Ala Asp Asp Lys Glu Thr Cys Phe Ala Glu Glu
        595                 600                 605

Gly Lys Lys Leu Val Ala Ala Ser Gln Ala Ala Gly Gly Ser Gly Gly
    610                 615                 620

Ser Pro Leu Gly Leu Ala Gly Gly Gly Ser Gly Gly Ser Glu Val Gln
625                 630                 635                 640

Leu Val Glu Ser Gly Gly Gly Leu Val Gln Pro Gly Gly Ser Leu Arg
                645                 650                 655
```

Leu Ser Cys Ala Ala Ser Gly Phe Thr Phe Asn Thr Tyr Ala Met Asn
660 665 670

Trp Val Arg Gln Ala Pro Gly Lys Gly Leu Glu Trp Val Ala Arg Ile
675 680 685

Arg Ser Lys Tyr Asn Asn Tyr Ala Thr Tyr Tyr Ala Asp Ser Val Lys
690 695 700

Asp Arg Phe Thr Ile Ser Arg Asp Asp Ser Lys Asn Thr Leu Tyr Leu
705 710 715 720

Gln Met Asn Ser Leu Arg Ala Glu Asp Thr Ala Val Tyr Tyr Cys Val
725 730 735

Arg His Gly Asn Phe Gly Asn Ser Tyr Val Ser Trp Phe Ala Tyr Trp
740 745 750

Gly Gln Gly Thr Met Val Thr Val Ser Ser Ala Ser Thr Lys Gly Pro
755 760 765

Ser Val Phe Pro Leu Ala Pro Ser Ser Lys Ser Thr Ser Gly Gly Thr
770 775 780

Ala Ala Leu Gly Cys Leu Val Lys Asp Tyr Phe Pro Glu Pro Val Thr
785 790 795 800

Val Ser Trp Asn Ser Gly Ala Leu Thr Ser Gly Val His Thr Phe Pro
805 810 815

Ala Val Leu Gln Ser Ser Gly Leu Tyr Ser Leu Ser Ser Val Val Thr
820 825 830

Val Pro Ser Ser Ser Leu Gly Thr Gln Thr Tyr Ile Cys Asn Val Asn
835 840 845

His Lys Pro Ser Asn Thr Lys Val Asp Lys Arg Val Glu Pro Lys Ser
850 855 860

Cys Pro Pro Cys Gly Gly Gly Gly Ser Asp Ile Gln Met Thr Gln Ser
865 870 875 880

Pro Ser Ser Leu Ser Ala Ser Val Gly Asp Arg Val Thr Ile Thr Cys
885 890 895

Gln Ala Ser Gln Asp Ile Ser Asn Tyr Leu Asn Trp Tyr Gln Gln Lys
900 905 910

Pro Gly Lys Ala Pro Lys Leu Leu Ile Tyr Asp Ala Ser Asn Leu Glu
915 920 925

Thr Gly Val Pro Ser Arg Phe Ser Gly Ser Gly Ser Gly Thr Asp Phe
930 935 940

Thr Phe Thr Ile Ser Ser Leu Gln Pro Glu Asp Ile Ala Thr Tyr Phe
945 950 955 960

Cys Gln His Phe Asp His Leu Pro Leu Ala Phe Gly Gly Gly Thr Lys
965 970 975

Val Glu Ile Lys Gly Gly Gly Gly Ser Gly Gly Gly Gly Ser Gly Gly
980 985 990

Gly Gly Ser Gln Val Gln Leu Gln Glu Ser Gly Pro Gly Leu Val Lys
995 1000 1005

Pro Ser Glu Thr Leu Ser Leu Thr Cys Thr Val Ser Gly Gly Ser
1010 1015 1020

Val Ser Ser Gly Asp Tyr Tyr Trp Thr Trp Ile Arg Gln Ser Pro
1025 1030 1035

Gly Lys Gly Leu Glu Trp Ile Gly His Ile Tyr Tyr Ser Gly Asn
1040 1045 1050

Thr Asn Tyr Asn Pro Ser Leu Lys Ser Arg Leu Thr Ile Ser Ile
1055 1060 1065

```
Asp Thr  Ser Lys Thr Gln Phe  Ser Leu Lys Leu Ser  Ser Val Thr
    1070                1075                1080

Ala Ala  Asp Thr Ala Ile Tyr  Tyr Cys Val Arg Asp  Arg Val Thr
    1085                1090                1095

Gly Ala  Phe Asp Ile Trp Gly  Gln Gly Thr Met Val  Thr Val Ser
    1100                1105                1110

Ser


<210> SEQ ID NO 32
<211> LENGTH: 469
<212> TYPE: PRT
<213> ORGANISM: Artificial Sequence
<220> FEATURE:
<223> OTHER INFORMATION: LC EGFR Polypeptide

<400> SEQUENCE: 32

Gly Gly Ser Gly Gly Ser Gln Ala Val Val Thr Gln Glu Pro Ser Leu
1               5                   10                  15

Thr Val Ser Pro Gly Gly Thr Val Thr Leu Thr Cys Arg Ser Ser Thr
            20                  25                  30

Gly Ala Val Thr Thr Ser Asn Tyr Ala Asn Trp Val Gln Gln Lys Pro
        35                  40                  45

Gly Gln Ala Pro Arg Gly Leu Ile Gly Gly Thr Asn Lys Arg Ala Pro
    50                  55                  60

Gly Thr Pro Ala Arg Phe Ser Gly Ser Leu Leu Gly Gly Lys Ala Ala
65                  70                  75                  80

Leu Thr Leu Ser Gly Val Gln Pro Glu Asp Glu Ala Glu Tyr Tyr Cys
                85                  90                  95

Ala Leu Trp Tyr Ser Asn Leu Trp Val Phe Gly Gly Gly Thr Lys Leu
            100                 105                 110

Thr Val Leu Gly Gln Pro Lys Ala Ala Pro Ser Val Thr Leu Phe Pro
        115                 120                 125

Pro Ser Ser Glu Glu Leu Gln Ala Asn Lys Ala Thr Leu Val Cys Leu
    130                 135                 140

Ile Ser Asp Phe Tyr Pro Gly Ala Val Thr Val Ala Trp Lys Ala Asp
145                 150                 155                 160

Ser Ser Pro Val Lys Ala Gly Val Glu Thr Thr Thr Pro Ser Lys Gln
                165                 170                 175

Ser Asn Asn Lys Tyr Ala Ala Ser Ser Tyr Leu Ser Leu Thr Pro Glu
            180                 185                 190

Gln Trp Lys Ser His Arg Ser Tyr Ser Cys Gln Val Thr His Glu Gly
        195                 200                 205

Ser Thr Val Glu Lys Thr Val Ala Pro Thr Glu Cys Pro Pro Cys Ser
    210                 215                 220

Gly Gly Gly Ser Asp Ile Gln Met Thr Gln Ser Pro Ser Ser Leu Ser
225                 230                 235                 240

Ala Ser Val Gly Asp Arg Val Thr Ile Thr Cys Gln Ala Ser Gln Asp
                245                 250                 255

Ile Ser Asn Tyr Leu Asn Trp Tyr Gln Gln Lys Pro Gly Lys Ala Pro
            260                 265                 270

Lys Leu Leu Ile Tyr Asp Ala Ser Asn Leu Glu Thr Gly Val Pro Ser
        275                 280                 285

Arg Phe Ser Gly Ser Gly Ser Gly Thr Asp Phe Thr Phe Thr Ile Ser
    290                 295                 300
```

Ser Leu Gln Pro Glu Asp Ile Ala Thr Tyr Phe Cys Gln His Phe Asp
305 310 315 320

His Leu Pro Leu Ala Phe Gly Gly Gly Thr Lys Val Glu Ile Lys Gly
325 330 335

Gly Gly Gly Ser Gly Gly Gly Gly Ser Gly Gly Gly Gly Ser Gln Val
340 345 350

Gln Leu Gln Glu Ser Gly Pro Gly Leu Val Lys Pro Ser Glu Thr Leu
355 360 365

Ser Leu Thr Cys Thr Val Ser Gly Gly Ser Val Ser Ser Gly Asp Tyr
370 375 380

Tyr Trp Thr Trp Ile Arg Gln Ser Pro Gly Lys Gly Leu Glu Trp Ile
385 390 395 400

Gly His Ile Tyr Tyr Ser Gly Asn Thr Asn Tyr Asn Pro Ser Leu Lys
405 410 415

Ser Arg Leu Thr Ile Ser Ile Asp Thr Ser Lys Thr Gln Phe Ser Leu
420 425 430

Lys Leu Ser Ser Val Thr Ala Ala Asp Thr Ala Ile Tyr Tyr Cys Val
435 440 445

Arg Asp Arg Val Thr Gly Ala Phe Asp Ile Trp Gly Gln Gly Thr Met
450 455 460

Val Thr Val Ser Ser
465

<210> SEQ ID NO 33
<211> LENGTH: 18
<212> TYPE: DNA
<213> ORGANISM: Artificial Sequence
<220> FEATURE:
<223> OTHER INFORMATION: protease cleavable

<400> SEQUENCE: 33
ccactgggcc tggccggc 18

<210> SEQ ID NO 34
<211> LENGTH: 107
<212> TYPE: PRT
<213> ORGANISM: Artificial Sequence
<220> FEATURE:
<223> OTHER INFORMATION: anti-EGFR VL

<400> SEQUENCE: 34

Asp Ile Gln Met Thr Gln Ser Pro Ser Ser Leu Ser Ala Ser Val Gly
1 5 10 15

Asp Arg Val Thr Ile Thr Cys Gln Ala Ser Gln Asp Ile Ser Asn Tyr
20 25 30

Leu Asn Trp Tyr Gln Gln Lys Pro Gly Lys Ala Pro Lys Leu Leu Ile
35 40 45

Tyr Asp Ala Ser Asn Leu Glu Thr Gly Val Pro Ser Arg Phe Ser Gly
50 55 60

Ser Gly Ser Gly Thr Asp Phe Thr Phe Thr Ile Ser Ser Leu Gln Pro
65 70 75 80

Glu Asp Ile Ala Thr Tyr Phe Cys Gln His Phe Asp His Leu Pro Leu
85 90 95

Ala Phe Gly Gly Gly Thr Lys Val Glu Ile Lys
100 105

<210> SEQ ID NO 35

<211> LENGTH: 13
<212> TYPE: PRT
<213> ORGANISM: Artificial Sequence
<220> FEATURE:
<223> OTHER INFORMATION: protease cleavable

<400> SEQUENCE: 35

Pro Leu Gly Leu Ala Gly Ser Gly Arg Ser Asp Asn His
1 5 10

<210> SEQ ID NO 36
<211> LENGTH: 321
<212> TYPE: DNA
<213> ORGANISM: Artificial Sequence
<220> FEATURE:
<223> OTHER INFORMATION: anti-EGFR VL

<400> SEQUENCE: 36
gatatccaga tgacccaaag ccccagtagc ctgtccgcca gtgtaggaga tagggtaacc 60
atcacttgcc aagcgagcca agacatcagc aactacctga attggtatca gcagaagccc 120
ggcaaagcac ccaagctcct gatctacgac gccagcaatc tggagaccgg cgtgcccagc 180
aggttcagcg gatctggtag cggcaccgac ttcaccttca ccataagtag tctgcagccc 240
gaggacatcg ccacctactt ctgtcagcac ttcgatcacc tgcccctggc cttcggcggt 300
gggaccaagg tggagatcaa g 321

<210> SEQ ID NO 37
<211> LENGTH: 119
<212> TYPE: PRT
<213> ORGANISM: Artificial Sequence
<220> FEATURE:
<223> OTHER INFORMATION: anti-EGFR-VH

<400> SEQUENCE: 37

Gln Val Gln Leu Gln Glu Ser Gly Pro Gly Leu Val Lys Pro Ser Glu
1 5 10 15

Thr Leu Ser Leu Thr Cys Thr Val Ser Gly Gly Ser Val Ser Ser Gly
20 25 30

Asp Tyr Tyr Trp Thr Trp Ile Arg Gln Ser Pro Gly Lys Gly Leu Glu
35 40 45

Trp Ile Gly His Ile Tyr Tyr Ser Gly Asn Thr Asn Tyr Asn Pro Ser
50 55 60

Leu Lys Ser Arg Leu Thr Ile Ser Ile Asp Thr Ser Lys Thr Gln Phe
65 70 75 80

Ser Leu Lys Leu Ser Ser Val Thr Ala Ala Asp Thr Ala Ile Tyr Tyr
85 90 95

Cys Val Arg Asp Arg Val Thr Gly Ala Phe Asp Ile Trp Gly Gln Gly
100 105 110

Thr Met Val Thr Val Ser Ser
115

<210> SEQ ID NO 38
<211> LENGTH: 357
<212> TYPE: DNA
<213> ORGANISM: Artificial Sequence
<220> FEATURE:
<223> OTHER INFORMATION: anti-EGFR-VH

<400> SEQUENCE: 38

```
caggtgcagc ttcaagagag cggacccggc ctcgtgaagc ccagcgagac cttgagcctg     60

acctgcactg tgagtggcgg tagcgtgagc agcggcgact attactggac ctggatcagg    120

cagagccctg gcaaggggct ggagtggatc ggccacatct actacagcgg gaacacgaac    180

tacaacccca gcctgaagag caggctgacg atcagcatcg acacgagcaa gacccagttc    240

tcacttaagc tcagcagcgt gaccgccgca gacaccgcca tatactactg cgtgagggac    300

agggtgacgg gcgctttcga catctggggc caaggcacaa tggtcacggt gagctcc       357
```

<210> SEQ ID NO 39
<211> LENGTH: 15
<212> TYPE: PRT
<213> ORGANISM: Artificial Sequence
<220> FEATURE:
<223> OTHER INFORMATION: linker

<400> SEQUENCE: 39

```
Gly Gly Gly Gly Ser Gly Gly Gly Gly Ser Gly Gly Gly Gly Ser
1               5                   10                  15
```

<210> SEQ ID NO 40
<211> LENGTH: 45
<212> TYPE: DNA
<213> ORGANISM: Artificial Sequence
<220> FEATURE:
<223> OTHER INFORMATION: linker

<400> SEQUENCE: 40

```
ggtgggggtg gcagcggggg aggcggaagc ggcggaggtg gctct                     45
```

<210> SEQ ID NO 41
<211> LENGTH: 241
<212> TYPE: PRT
<213> ORGANISM: Artificial Sequence
<220> FEATURE:
<223> OTHER INFORMATION: anti-EGFR VL-linker-VH

<400> SEQUENCE: 41

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln His Phe Asp His Leu Pro Leu
                85                  90                  95

Ala Phe Gly Gly Gly Thr Lys Val Glu Ile Lys Gly Gly Gly Gly Ser
            100                 105                 110

Gly Gly Gly Gly Ser Gly Gly Gly Gly Ser Gln Val Gln Leu Gln Glu
        115                 120                 125

Ser Gly Pro Gly Leu Val Lys Pro Ser Glu Thr Leu Ser Leu Thr Cys
    130                 135                 140

Thr Val Ser Gly Gly Ser Val Ser Ser Gly Asp Tyr Tyr Trp Thr Trp
145                 150                 155                 160
```

Ile Arg Gln Ser Pro Gly Lys Gly Leu Glu Trp Ile Gly His Ile Tyr
165 170 175

Tyr Ser Gly Asn Thr Asn Tyr Asn Pro Ser Leu Lys Ser Arg Leu Thr
180 185 190

Ile Ser Ile Asp Thr Ser Lys Thr Gln Phe Ser Leu Lys Leu Ser Ser
195 200 205

Val Thr Ala Ala Asp Thr Ala Ile Tyr Tyr Cys Val Arg Asp Arg Val
210 215 220

Thr Gly Ala Phe Asp Ile Trp Gly Gln Gly Thr Met Val Thr Val Ser
225 230 235 240

Ser

<210> SEQ ID NO 42
<211> LENGTH: 241
<212> TYPE: PRT
<213> ORGANISM: Artificial Sequence
<220> FEATURE:
<223> OTHER INFORMATION: anti-EGFR VH-linker-VL

<400> SEQUENCE: 42

Gln Val Gln Leu Gln Glu Ser Gly Pro Gly Leu Val Lys Pro Ser Glu
1 5 10 15

Thr Leu Ser Leu Thr Cys Thr Val Ser Gly Gly Ser Val Ser Ser Gly
20 25 30

Asp Tyr Tyr Trp Thr Trp Ile Arg Gln Ser Pro Gly Lys Gly Leu Glu
35 40 45

Trp Ile Gly His Ile Tyr Tyr Ser Gly Asn Thr Asn Tyr Asn Pro Ser
50 55 60

Leu Lys Ser Arg Leu Thr Ile Ser Ile Asp Thr Ser Lys Thr Gln Phe
65 70 75 80

Ser Leu Lys Leu Ser Ser Val Thr Ala Ala Asp Thr Ala Ile Tyr Tyr
85 90 95

Cys Val Arg Asp Arg Val Thr Gly Ala Phe Asp Ile Trp Gly Gln Gly
100 105 110

Thr Met Val Thr Val Ser Ser Gly Gly Gly Gly Ser Gly Gly Gly Gly
115 120 125

Ser Gly Gly Gly Gly Ser Asp Ile Gln Met Thr Gln Ser Pro Ser Ser
130 135 140

Leu Ser Ala Ser Val Gly Asp Arg Val Thr Ile Thr Cys Gln Ala Ser
145 150 155 160

Gln Asp Ile Ser Asn Tyr Leu Asn Trp Tyr Gln Gln Lys Pro Gly Lys
165 170 175

Ala Pro Lys Leu Leu Ile Tyr Asp Ala Ser Asn Leu Glu Thr Gly Val
180 185 190

Pro Ser Arg Phe Ser Gly Ser Gly Ser Gly Thr Asp Phe Thr Phe Thr
195 200 205

Ile Ser Ser Leu Gln Pro Glu Asp Ile Ala Thr Tyr Phe Cys Gln His
210 215 220

Phe Asp His Leu Pro Leu Ala Phe Gly Gly Gly Thr Lys Val Glu Ile
225 230 235 240

Lys

<210> SEQ ID NO 43
<211> LENGTH: 726
<212> TYPE: DNA

<213> ORGANISM: Artificial Sequence
<220> FEATURE:
<223> OTHER INFORMATION: anti-EGFR VL-linker-VH

<400> SEQUENCE: 43
gatatccaga tgacccaaag ccccagtagc ctgtccgcca gtgtaggaga tagggtaacc 60
atcacttgcc aagcgagcca agacatcagc aactacctga attggtatca gcagaagccc 120
ggcaaagcac ccaagctcct gatctacgac gccagcaatc tggagaccgg cgtgcccagc 180
aggttcagcg gatctggtag cggcaccgac ttcaccttca ccataagtag tctgcagccc 240
gaggacatcg ccacctactt ctgtcagcac ttcgatcacc tgcccctggc cttcggcggt 300
gggaccaagg tggagatcaa gggtgggggt ggcagcgggg gaggcggaag cggcggaggt 360
ggctcttgcc aggtgcagct tcaagagagc ggacccggcc tcgtgaagcc cagcgagacc 420
ttgagcctga cctgcactgt gagtggcggt agcgtgagca gcggcgacta ttactggacc 480
tggatcaggc agagccctgg caaggggctg gagtggatcg gccacatcta ctacagcggg 540
aacacgaact acaaccccag cctgaagagc aggctgacga tcagcatcga cacgagcaag 600
acccagttct cacttaagct cagcagcgtg accgccgcag acaccgccat atactactgc 660
gtgagggaca gggtgacggg cgctttcgac atctggggcc aaggcacaat ggtcacggtg 720
agctcc 726

<210> SEQ ID NO 44
<211> LENGTH: 723
<212> TYPE: DNA
<213> ORGANISM: Artificial Sequence
<220> FEATURE:
<223> OTHER INFORMATION: anti-EGFR VH-linker-VL

<400> SEQUENCE: 44
caggtgcagc ttcaagagag cggacccggc ctcgtgaagc ccagcgagac cttgagcctg 60
acctgcactg tgagtggcgg tagcgtgagc agcggcgact attactggac ctggatcagg 120
cagagccctg gcaaggggct ggagtggatc ggccacatct actacagcgg gaacacgaac 180
tacaacccca gcctgaagag caggctgacg atcagcatcg acacgagcaa gacccagttc 240
tcacttaagc tcagcagcgt gaccgccgca gacaccgcca tatactactg cgtgagggac 300
agggtgacgg gcgctttcga catctggggc caaggcacaa tggtcacggt gagctccggt 360
gggggtggca gcgggggagg cggaagcggc ggaggtggct ctgatatcca gatgacccaa 420
agccccagta gcctgtccgc cagtgtagga gatagggtaa ccatcacttg ccaagcgagc 480
caagacatca gcaactacct gaattggtat cagcagaagc ccggcaaagc acccaagctc 540
ctgatctacg acgccagcaa tctggagacc ggcgtgccca gcaggttcag cggatctggt 600
agcggcaccg acttcacctt caccataagt agtctgcagc ccgaggacat cgccacctac 660
ttctgtcagc acttcgatca cctgcccctg gccttcggcg gtgggaccaa ggtggagatc 720
aag 723

<210> SEQ ID NO 45
<211> LENGTH: 125
<212> TYPE: PRT
<213> ORGANISM: Mus musculus

<400> SEQUENCE: 45

Glu Val Gln Leu Val Glu Ser Gly Gly Gly Leu Val Gln Pro Lys Gly
1               5                   10                  15

```
Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Gln Ser Ile
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ala
        115                 120                 125
```

<210> SEQ ID NO 46
<211> LENGTH: 125
<212> TYPE: PRT
<213> ORGANISM: Artificial Sequence
<220> FEATURE:
<223> OTHER INFORMATION: anti-CD3 VH chain

<400> SEQUENCE: 46

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125
```

<210> SEQ ID NO 47
<211> LENGTH: 125
<212> TYPE: PRT
<213> ORGANISM: Artificial Sequence
<220> FEATURE:
<223> OTHER INFORMATION: anti-CD3 VH chain

<400> SEQUENCE: 47

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80
```

```
Leu Tyr Leu Gln Met Asn Ser Leu Arg Ala Glu Asp Thr Ala Val Tyr
                85                  90                  95

Tyr Cys Ala Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125


<210> SEQ ID NO 48
<211> LENGTH: 125
<212> TYPE: PRT
<213> ORGANISM: Artificial Sequence
<220> FEATURE:
<223> OTHER INFORMATION: anti-CD3 VH chain

<400> SEQUENCE: 48

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125


<210> SEQ ID NO 49
<211> LENGTH: 125
<212> TYPE: PRT
<213> ORGANISM: Artificial Sequence
<220> FEATURE:
<223> OTHER INFORMATION: anti-CD3 VH chain

<400> SEQUENCE: 49

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125
```

<210> SEQ ID NO 50
<211> LENGTH: 125
<212> TYPE: PRT
<213> ORGANISM: Artificial Sequence
<220> FEATURE:
<223> OTHER INFORMATION: anti-CD3 VH chain

<400> SEQUENCE: 50

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 51
<211> LENGTH: 125
<212> TYPE: PRT
<213> ORGANISM: Artificial Sequence
<220> FEATURE:
<223> OTHER INFORMATION: anti-CD3 VH chain

<400> SEQUENCE: 51

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg His Gly Asn Phe Gly Asn Ser Tyr Val Ser Trp Phe
            100                 105                 110

Ala Tyr Trp Gly Gln Gly Thr Met Val Thr Val Ser Ser
        115                 120                 125

<210> SEQ ID NO 52
<211> LENGTH: 125
<212> TYPE: PRT
<213> ORGANISM: Artificial Sequence
<220> FEATURE:
<223> OTHER INFORMATION: anti-CD3 VH chain

<400> SEQUENCE: 52

Glu Val Gln Leu Val Glu Ser Gly Gly Gly Leu Val Gln Pro Gly Gly
1               5                   10                  15

```
Ser Leu Lys Leu Ser Cys Ala Ala Ser Gly Phe Thr Phe Asn Lys Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Ile Ser Tyr Trp
            100                 105                 110

Ala Tyr Trp Gly Gln Gly Thr Leu Val Thr Val Ser Ser
        115                 120                 125


<210> SEQ ID NO 53
<211> LENGTH: 125
<212> TYPE: PRT
<213> ORGANISM: Artificial Sequence
<220> FEATURE:
<223> OTHER INFORMATION: anti-CD3 VH chain

<400> SEQUENCE: 53

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Ile Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Ser Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Val Ser Phe Phe
            100                 105                 110

Ala Tyr Trp Gly Gln Gly Thr Leu Val Thr Val Ser Ser
        115                 120                 125


<210> SEQ ID NO 54
<211> LENGTH: 125
<212> TYPE: PRT
<213> ORGANISM: Artificial Sequence
<220> FEATURE:
<223> OTHER INFORMATION: anti-CD3 VH chain

<400> SEQUENCE: 54

Glu Val Gln Leu Leu Glu Ser Gly Gly Gly Leu Val Gln Pro Gly Gly
1               5                   10                  15

Ser Leu Lys Leu Ser Cys Ala Ala Ser Gly Phe Thr Phe Asn Ile Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60
```

```
Ser Val Lys Ser Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Val Ser Phe Phe
            100                 105                 110

Ala Tyr Trp Gly Gln Gly Thr Leu Val Thr Val Ser Ser
        115                 120                 125


<210> SEQ ID NO 55
<211> LENGTH: 125
<212> TYPE: PRT
<213> ORGANISM: Artificial Sequence
<220> FEATURE:
<223> OTHER INFORMATION: anti-CD3 VH chain

<400> SEQUENCE: 55

Glu Val Gln Leu Leu Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Ile Ser Tyr Trp
            100                 105                 110

Ala Tyr Trp Gly Gln Gly Thr Leu Val Thr Val Ser Ser
        115                 120                 125


<210> SEQ ID NO 56
<211> LENGTH: 125
<212> TYPE: PRT
<213> ORGANISM: Artificial Sequence
<220> FEATURE:
<223> OTHER INFORMATION: anti-CD3 VH chain

<400> SEQUENCE: 56

Glu Val Gln Leu Val Glu Ser Gly Gly Gly Leu Glu Gln Pro Gly Gly
1               5                   10                  15

Ser Leu Lys Leu Ser Cys Ala Ala Ser Gly Phe Thr Phe Asn Ser Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Leu Ser Phe Trp
            100                 105                 110
```

```
Ala Tyr Trp Gly Gln Gly Thr Leu Val Thr Val Ser Ser
        115                 120                 125
```

<210> SEQ ID NO 57
<211> LENGTH: 125
<212> TYPE: PRT
<213> ORGANISM: Artificial Sequence
<220> FEATURE:
<223> OTHER INFORMATION: anti-CD3 VH chain

<400> SEQUENCE: 57

```
Glu Val Gln Leu Leu Glu Ser Gly Gly Gly Leu Glu Gln Pro Gly Gly
1               5                   10                  15

Ser Leu Lys Leu Ser Cys Ala Ala Ser Gly Phe Thr Phe Asn Ser Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Leu Ser Phe Trp
            100                 105                 110

Ala Tyr Trp Gly Gln Gly Thr Leu Val Thr Val Ser Ser
        115                 120                 125
```

<210> SEQ ID NO 58
<211> LENGTH: 125
<212> TYPE: PRT
<213> ORGANISM: Artificial Sequence
<220> FEATURE:
<223> OTHER INFORMATION: anti-CD3 VH chain

<400> SEQUENCE: 58

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Arg Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Leu Ser Tyr Phe
            100                 105                 110

Ala Tyr Trp Gly Gln Gly Thr Leu Val Thr Val Ser Ser
        115                 120                 125
```

<210> SEQ ID NO 59
<211> LENGTH: 125
<212> TYPE: PRT
<213> ORGANISM: Artificial Sequence
<220> FEATURE:
<223> OTHER INFORMATION: anti-CD3 VH chain

<400> SEQUENCE: 59

Glu Val Gln Leu Leu Glu Ser Gly Gly Gly Leu Val Gln Pro Gly Gly
1               5                   10                  15

Ser Leu Lys Leu Ser Cys Ala Ala Ser Gly Phe Thr Phe Asn Arg Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Leu Ser Tyr Phe
            100                 105                 110

Ala Tyr Trp Gly Gln Gly Thr Leu Val Thr Val Ser Ser
        115                 120                 125

<210> SEQ ID NO 60
<211> LENGTH: 125
<212> TYPE: PRT
<213> ORGANISM: Artificial Sequence
<220> FEATURE:
<223> OTHER INFORMATION: anti-CD3 VH chain

<400> SEQUENCE: 60

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Val Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Lys Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Leu Ser Trp Trp
            100                 105                 110

Ala Tyr Trp Gly Gln Gly Thr Leu Val Thr Val Ser Ser
        115                 120                 125

<210> SEQ ID NO 61
<211> LENGTH: 125
<212> TYPE: PRT
<213> ORGANISM: Artificial Sequence
<220> FEATURE:
<223> OTHER INFORMATION: anti-CD3 VH chain

<400> SEQUENCE: 61

Glu Val Gln Leu Leu Glu Ser Gly Gly Gly Leu Val Gln Pro Gly Gly
1               5                   10                  15

Ser Leu Lys Leu Ser Cys Ala Ala Ser Gly Phe Thr Phe Asn Val Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Lys Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Leu Ser Trp Trp
            100                 105                 110

Ala Tyr Trp Gly Gln Gly Thr Leu Val Thr Val Ser Ser
        115                 120                 125

<210> SEQ ID NO 62
<211> LENGTH: 125
<212> TYPE: PRT
<213> ORGANISM: Artificial Sequence
<220> FEATURE:
<223> OTHER INFORMATION: anti-CD3 VH chain

<400> SEQUENCE: 62

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Ser Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Thr Ser Tyr Tyr
            100                 105                 110

Ala Tyr Trp Gly Gln Gly Thr Leu Val Thr Val Ser Ser
        115                 120                 125

<210> SEQ ID NO 63
<211> LENGTH: 125
<212> TYPE: PRT
<213> ORGANISM: Artificial Sequence
<220> FEATURE:
<223> OTHER INFORMATION: anti-CD3 VH chain

<400> SEQUENCE: 63

Glu Val Gln Leu Leu Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Ser Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Thr Ser Tyr Tyr
100 105 110

Ala Tyr Trp Gly Gln Gly Thr Leu Val Thr Val Ser Ser
115 120 125

<210> SEQ ID NO 64
<211> LENGTH: 125
<212> TYPE: PRT
<213> ORGANISM: Artificial Sequence
<220> FEATURE:
<223> OTHER INFORMATION: anti-CD3 VH chain

<400> SEQUENCE: 64

Glu Val Gln Leu Val Glu Ser Gly Gly Gly Leu Val Gln Pro Gly Gly
1 5 10 15

Ser Leu Lys Leu Ser Cys Ala Ala Ser Gly Phe Thr Phe Asn Gly Tyr
20 25 30

Ala Met Asn Trp Val Arg Gln Ala Pro Gly Lys Gly Leu Glu Trp Val
35 40 45

Ala Arg Ile Arg Ser Lys Tyr Asn Asn Tyr Ala Thr Tyr Tyr Ala Asp
50 55 60

Ser Val Lys Glu Arg Phe Thr Ile Ser Arg Asp Asp Ser Lys Asn Thr
65 70 75 80

Ala Tyr Leu Gln Met Asn Asn Leu Lys Thr Glu Asp Thr Ala Val Tyr
85 90 95

Tyr Cys Val Arg His Arg Asn Phe Gly Asn Ser Tyr Leu Ser Trp Phe
100 105 110

Ala Tyr Trp Gly Gln Gly Thr Leu Val Thr Val Ser Ser
115 120 125

<210> SEQ ID NO 65
<211> LENGTH: 125
<212> TYPE: PRT
<213> ORGANISM: Artificial Sequence
<220> FEATURE:
<223> OTHER INFORMATION: anti-CD3 VH chain

<400> SEQUENCE: 65

Glu Val Gln Leu Leu Glu Ser Gly Gly Gly Leu Val Gln Pro Gly Gly
1 5 10 15

Ser Leu Lys Leu Ser Cys Ala Ala Ser Gly Phe Thr Phe Asn Gly Tyr
20 25 30

Ala Met Asn Trp Val Arg Gln Ala Pro Gly Lys Gly Leu Glu Trp Val
35 40 45

Ala Arg Ile Arg Ser Lys Tyr Asn Asn Tyr Ala Thr Tyr Tyr Ala Asp
50 55 60

Ser Val Lys Glu Arg Phe Thr Ile Ser Arg Asp Asp Ser Lys Asn Thr
65 70 75 80

Ala Tyr Leu Gln Met Asn Asn Leu Lys Thr Glu Asp Thr Ala Val Tyr
85 90 95

Tyr Cys Val Arg His Arg Asn Phe Gly Asn Ser Tyr Leu Ser Trp Phe
100 105 110

Ala Tyr Trp Gly Gln Gly Thr Leu Val Thr Val Ser Ser
115 120 125

<210> SEQ ID NO 66
<211> LENGTH: 125
<212> TYPE: PRT

```
<213> ORGANISM: Artificial Sequence
<220> FEATURE:
<223> OTHER INFORMATION: anti-CD3 VH chain

<400> SEQUENCE: 66

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Val Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Lys Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Ile Ser Trp Trp
            100                 105                 110

Ala Tyr Trp Gly Gln Gly Thr Leu Val Thr Val Ser Ser
        115                 120                 125


<210> SEQ ID NO 67
<211> LENGTH: 125
<212> TYPE: PRT
<213> ORGANISM: Artificial Sequence
<220> FEATURE:
<223> OTHER INFORMATION: anti-CD3 VH chain

<400> SEQUENCE: 67

Glu Val Gln Leu Leu Glu Ser Gly Gly Gly Leu Val Gln Pro Gly Gly
1               5                   10                  15

Ser Leu Lys Leu Ser Cys Ala Ala Ser Gly Phe Thr Phe Asn Val Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Lys Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Ile Ser Trp Trp
            100                 105                 110

Ala Tyr Trp Gly Gln Gly Thr Leu Val Thr Val Ser Ser
        115                 120                 125


<210> SEQ ID NO 68
<211> LENGTH: 125
<212> TYPE: PRT
<213> ORGANISM: Artificial Sequence
<220> FEATURE:
<223> OTHER INFORMATION: anti-CD3 VH chain

<400> SEQUENCE: 68

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Ser Tyr
            20                  25                  30
```

Ala Met Asn Trp Val Arg Gln Ala Pro Gly Lys Gly Leu Glu Trp Val
35 40 45

Ala Arg Ile Arg Ser Lys Tyr Asn Asn Tyr Ala Thr Tyr Tyr Ala Asp
50 55 60

Ser Val Lys Gly Arg Phe Thr Ile Ser Arg Asp Asp Ser Lys Asn Thr
65 70 75 80

Ala Tyr Leu Gln Met Asn Asn Leu Lys Thr Glu Asp Thr Ala Val Tyr
85 90 95

Tyr Cys Val Arg His Gly Asn Phe Gly Asn Ser Tyr Val Ser Trp Trp
100 105 110

Ala Tyr Trp Gly Gln Gly Thr Leu Val Thr Val Ser Ser
115 120 125

<210> SEQ ID NO 69
<211> LENGTH: 125
<212> TYPE: PRT
<213> ORGANISM: Artificial Sequence
<220> FEATURE:
<223> OTHER INFORMATION: anti-CD3 VH chain

<400> SEQUENCE: 69

Glu Val Gln Leu Leu Glu Ser Gly Gly Gly Leu Val Gln Pro Gly Gly
1 5 10 15

Ser Leu Lys Leu Ser Cys Ala Ala Ser Gly Phe Thr Phe Asn Ser Tyr
20 25 30

Ala Met Asn Trp Val Arg Gln Ala Pro Gly Lys Gly Leu Glu Trp Val
35 40 45

Ala Arg Ile Arg Ser Lys Tyr Asn Asn Tyr Ala Thr Tyr Tyr Ala Asp
50 55 60

Ser Val Lys Gly Arg Phe Thr Ile Ser Arg Asp Asp Ser Lys Asn Thr
65 70 75 80

Ala Tyr Leu Gln Met Asn Asn Leu Lys Thr Glu Asp Thr Ala Val Tyr
85 90 95

Tyr Cys Val Arg His Gly Asn Phe Gly Asn Ser Tyr Val Ser Trp Trp
100 105 110

Ala Tyr Trp Gly Gln Gly Thr Leu Val Thr Val Ser Ser
115 120 125

<210> SEQ ID NO 70
<211> LENGTH: 125
<212> TYPE: PRT
<213> ORGANISM: Artificial Sequence
<220> FEATURE:
<223> OTHER INFORMATION: anti-CD3 VH chain

<400> SEQUENCE: 70

Glu Val Gln Leu Leu Glu Ser Gly Gly Gly Leu Val Gln Pro Gly Gly
1 5 10 15

Ser Leu Lys Leu Ser Cys Ala Ala Ser Gly Phe Thr Phe Asn Lys Tyr
20 25 30

Ala Met Asn Trp Val Arg Gln Ala Pro Gly Lys Gly Leu Glu Trp Val
35 40 45

Ala Arg Ile Arg Ser Lys Tyr Asn Asn Tyr Ala Thr Tyr Tyr Ala Asp
50 55 60

Ser Val Lys Asp Arg Phe Thr Ile Ser Arg Asp Asp Ser Lys Asn Thr
65 70 75 80

Ala Tyr Leu Gln Met Asn Asn Leu Lys Thr Glu Asp Thr Ala Val Tyr
85 90 95

Tyr Cys Val Arg His Gly Asn Phe Gly Asn Ser Tyr Ile Ser Tyr Trp
100 105 110

Ala Tyr Trp Gly Gln Gly Thr Leu Val Thr Val Ser Ser
115 120 125

<210> SEQ ID NO 71
<211> LENGTH: 125
<212> TYPE: PRT
<213> ORGANISM: Artificial Sequence
<220> FEATURE:
<223> OTHER INFORMATION: anti-CD3 VH chain

<400> SEQUENCE: 71

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Asn Thr Tyr
20 25 30

Ala Met Asn Trp Val Arg Gln Ala Pro Gly Lys Gly Leu Glu Trp Val
35 40 45

Ala Arg Ile Arg Ser Lys Tyr Asn Asn Tyr Ala Thr Tyr Tyr Ala Asp
50 55 60

Ser Val Lys Asp Arg Phe Thr Ile Ser Arg Asp Asp Ser Lys Asn Ser
65 70 75 80

Leu Tyr Leu Gln Met Asn Ser Leu Lys Thr Glu Asp Thr Ala Val Tyr
85 90 95

Tyr Cys Val Arg His Gly Asn Phe Gly Asn Ser Tyr Val Ser Trp Phe
100 105 110

Ala Tyr Trp Gly Gln Gly Thr Leu Val Thr Val Ser Ser
115 120 125

<210> SEQ ID NO 72
<211> LENGTH: 125
<212> TYPE: PRT
<213> ORGANISM: Artificial Sequence
<220> FEATURE:
<223> OTHER INFORMATION: anti-CD3 VH chain

<400> SEQUENCE: 72

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Thr Tyr
20 25 30

Ala Met Asn Trp Val Arg Gln Ala Pro Gly Lys Gly Leu Glu Trp Val
35 40 45

Gly Arg Ile Arg Ser Lys Tyr Asn Asn Tyr Ala Thr Tyr Tyr Ala Asp
50 55 60

Ser Val Lys Gly Arg Phe Thr Ile Ser Arg Asp Asp Ser Lys Asn Thr
65 70 75 80

Leu Tyr Leu Gln Met Asn Ser Leu Arg Ala Glu Asp Thr Ala Val Tyr
85 90 95

Tyr Cys Val Arg His Gly Asn Phe Gly Asp Ser Tyr Val Ser Trp Phe
100 105 110

Ala Tyr Trp Gly Gln Gly Thr Leu Val Thr Val Ser Ser
115 120 125

<210> SEQ ID NO 73
<211> LENGTH: 109
<212> TYPE: PRT
<213> ORGANISM: Mus musculus

<400> SEQUENCE: 73

Gln Ala Val Val Thr Gln Glu Ser Ala Leu Thr Thr Ser Pro Gly Glu
1 5 10 15

Thr Val Thr Leu Thr Cys Arg Ser Ser Thr Gly Ala Val Thr Thr Ser
20 25 30

Asn Tyr Ala Asn Trp Val Gln Glu Lys Pro Asp His Leu Phe Thr Gly
35 40 45

Leu Ile Gly Gly Thr Asn Lys Arg Ala Pro Gly Val Pro Ala Arg Phe
50 55 60

Ser Gly Ser Leu Ile Gly Asp Lys Ala Ala Leu Thr Ile Thr Gly Ala
65 70 75 80

Gln Thr Glu Asp Glu Ala Ile Tyr Phe Cys Ala Leu Trp Tyr Ser Asn
85 90 95

Leu Trp Val Phe Gly Gly Gly Thr Lys Leu Thr Val Leu
100 105

<210> SEQ ID NO 74
<211> LENGTH: 213
<212> TYPE: PRT
<213> ORGANISM: Artificial Sequence
<220> FEATURE:
<223> OTHER INFORMATION: anti-CD3 epsilon Variable Light chain and Constant Light Chain

<400> SEQUENCE: 74

Gln Ala Val Val Thr Gln Glu Pro Ser Leu Thr Val Ser Pro Gly Gly
1 5 10 15

Thr Val Thr Leu Thr Cys Arg Ser Ser Thr Gly Ala Val Thr Thr Ser
20 25 30

Asn Tyr Ala Asn Trp Val Gln Gln Lys Pro Gly Gln Ala Pro Arg Gly
35 40 45

Leu Ile Gly Gly Thr Asn Lys Arg Ala Pro Gly Thr Pro Ala Arg Phe
50 55 60

Ser Gly Ser Leu Leu Gly Gly Lys Ala Ala Leu Thr Leu Ser Gly Val
65 70 75 80

Gln Pro Glu Asp Glu Ala Glu Tyr Tyr Cys Ala Leu Trp Tyr Ser Asn
85 90 95

Leu Trp Val Phe Gly Gly Gly Thr Lys Leu Thr Val Leu Gly Gln Pro
100 105 110

Lys Ala Ala Pro Ser Val Thr Leu Phe Pro Pro Ser Ser Glu Glu Leu
115 120 125

Gln Ala Asn Lys Ala Thr Leu Val Cys Leu Ile Ser Asp Phe Tyr Pro
130 135 140

Gly Ala Val Thr Val Ala Trp Lys Ala Asp Ser Ser Pro Val Lys Ala
145 150 155 160

Gly Val Glu Thr Thr Thr Pro Ser Lys Gln Ser Asn Asn Lys Tyr Ala
165 170 175

Ala Ser Ser Tyr Leu Ser Leu Thr Pro Glu Gln Trp Lys Ser His Arg
180 185 190

```
Ser Tyr Ser Cys Gln Val Thr His Glu Gly Ser Thr Val Glu Lys Thr
        195                 200                 205

Val Ala Pro Thr Glu
    210


<210> SEQ ID NO 75
<211> LENGTH: 99
<212> TYPE: PRT
<213> ORGANISM: Artificial Sequence
<220> FEATURE:
<223> OTHER INFORMATION: anti-CD3 epsilon VL

<400> SEQUENCE: 75

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Leu Trp Val


<210> SEQ ID NO 76
<211> LENGTH: 99
<212> TYPE: PRT
<213> ORGANISM: Artificial Sequence
<220> FEATURE:
<223> OTHER INFORMATION: anti-CD3 epsilon VL

<400> SEQUENCE: 76

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Leu Trp Val


<210> SEQ ID NO 77
<211> LENGTH: 99
<212> TYPE: PRT
<213> ORGANISM: Artificial Sequence
<220> FEATURE:
<223> OTHER INFORMATION: anti-CD3 epsilon VL

<400> SEQUENCE: 77

Gln Thr Val Val Thr Gln Glu Pro Ser Leu Thr Val Ser Pro Gly Gly
1               5                   10                  15
```

```
Thr Val Thr Leu Thr Cys Ala Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Leu Trp Val


<210> SEQ ID NO 78
<211> LENGTH: 99
<212> TYPE: PRT
<213> ORGANISM: Artificial Sequence
<220> FEATURE:
<223> OTHER INFORMATION: anti-CD3 epsilon VL

<400> SEQUENCE: 78

Gln Thr Val Val Thr Gln Glu Pro Ser Leu Thr Val Ser Pro Gly Gly
1               5                   10                  15

Thr Val Thr Leu Thr Cys Ala Ser Ser Thr Gly Ala Val Thr Ser Gly
            20                  25                  30

Tyr Tyr Pro Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Leu Trp Val


<210> SEQ ID NO 79
<211> LENGTH: 99
<212> TYPE: PRT
<213> ORGANISM: Artificial Sequence
<220> FEATURE:
<223> OTHER INFORMATION: anti-CD3 epsilon VL

<400> SEQUENCE: 79

Gln Thr Val Val Thr Gln Glu Pro Ser Leu Thr Val Ser Pro Gly Gly
1               5                   10                  15

Thr Val Thr Leu Thr Cys Ala Ser Ser Thr Gly Ala Val Thr Ser Gly
            20                  25                  30

Tyr Tyr Pro Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Leu Leu Trp Tyr Ser Asn
                85                  90                  95

Leu Trp Val
```

<210> SEQ ID NO 80
<211> LENGTH: 109
<212> TYPE: PRT
<213> ORGANISM: Artificial Sequence
<220> FEATURE:
<223> OTHER INFORMATION: anti-CD3 epsilon VL

<400> SEQUENCE: 80

```
Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Thr
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
            100                 105
```

<210> SEQ ID NO 81
<211> LENGTH: 109
<212> TYPE: PRT
<213> ORGANISM: Artificial Sequence
<220> FEATURE:
<223> OTHER INFORMATION: anti-CD3 epsilon VL

<400> SEQUENCE: 81

```
Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Leu Ser Trp Thr
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
            100                 105
```

<210> SEQ ID NO 82
<211> LENGTH: 109
<212> TYPE: PRT
<213> ORGANISM: Artificial Sequence
<220> FEATURE:
<223> OTHER INFORMATION: anti-CD3 epsilon VL

<400> SEQUENCE: 82

```
Gln Thr Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

Tyr Tyr Pro Asn Trp Val Gln Gln Lys Pro Gly Gln Ala Pro Arg Gly
        35                  40                  45
```

Leu Ile Gly Gly Thr Lys Phe Leu Ala Pro Gly Thr Pro Ala Arg Phe
50 55 60

Ser Gly Ser Leu Leu Gly Gly Lys Ala Ala Leu Thr Leu Ser Gly Val
65 70 75 80

Gln Pro Glu Asp Glu Ala Glu Tyr Tyr Cys Ala Leu Trp Tyr Ser Asn
85 90 95

Arg Trp Val Phe Gly Gly Gly Thr Lys Leu Thr Val Leu
100 105

<210> SEQ ID NO 83
<211> LENGTH: 109
<212> TYPE: PRT
<213> ORGANISM: Artificial Sequence
<220> FEATURE:
<223> OTHER INFORMATION: anti-CD3 epsilon VL

<400> SEQUENCE: 83

Gln Thr Val Val Thr Gln Glu Pro Ser Leu Thr Val Ser Pro Gly Gly
1 5 10 15

Thr Val Thr Leu Thr Cys Gly Ser Ser Thr Gly Ala Val Thr Ser Gly
20 25 30

Asn Tyr Pro Asn Trp Val Gln Gln Lys Pro Gly Gln Ala Pro Arg Gly
35 40 45

Leu Ile Gly Gly Thr Lys Phe Leu Ala Pro Gly Thr Pro Ala Arg Phe
50 55 60

Ser Gly Ser Leu Leu Gly Gly Lys Ala Ala Leu Thr Leu Ser Gly Val
65 70 75 80

Gln Pro Glu Asp Glu Ala Glu Tyr Tyr Cys Val Leu Trp Tyr Ser Asn
85 90 95

Arg Trp Val Phe Gly Gly Gly Thr Lys Leu Thr Val Leu
100 105

<210> SEQ ID NO 84
<211> LENGTH: 109
<212> TYPE: PRT
<213> ORGANISM: Artificial Sequence
<220> FEATURE:
<223> OTHER INFORMATION: anti-CD3 epsilon VL

<400> SEQUENCE: 84

Gln Thr Val Val Thr Gln Glu Pro Ser Leu Thr Val Ser Pro Gly Gly
1 5 10 15

Thr Val Thr Leu Thr Cys Gly Ser Ser Thr Gly Ala Val Thr Ser Gly
20 25 30

Tyr Tyr Pro Asn Trp Val Gln Gln Lys Pro Gly Gln Ala Pro Arg Gly
35 40 45

Leu Ile Gly Gly Thr Lys Phe Leu Ala Pro Gly Thr Pro Ala Arg Phe
50 55 60

Ser Gly Ser Leu Leu Gly Gly Lys Ala Ala Leu Thr Leu Ser Gly Val
65 70 75 80

Gln Pro Glu Asp Glu Ala Glu Tyr Tyr Cys Ala Leu Trp Tyr Ser Asn
85 90 95

Arg Trp Val Phe Gly Gly Gly Thr Lys Leu Thr Val Leu
100 105

<210> SEQ ID NO 85
<211> LENGTH: 109
<212> TYPE: PRT

<213> ORGANISM: Artificial Sequence
<220> FEATURE:
<223> OTHER INFORMATION: anti-CD3 epsilon VL

<400> SEQUENCE: 85

```
Glu Leu Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

Tyr Tyr Pro Asn Trp Val Gln Gln Lys Pro Gly Gln Ala Pro Arg Gly
        35                  40                  45

Leu Ile Gly Gly Thr Lys Phe Leu Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Arg Trp Val Phe Gly Gly Gly Thr Lys Leu Thr Val Leu
            100                 105
```

<210> SEQ ID NO 86
<211> LENGTH: 109
<212> TYPE: PRT
<213> ORGANISM: Artificial Sequence
<220> FEATURE:
<223> OTHER INFORMATION: anti-CD3 epsilon VL

<400> SEQUENCE: 86

```
Glu Leu Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

Tyr Tyr Pro Asn Trp Val Gln Gln Lys Pro Gly Gln Ala Pro Arg Gly
        35                  40                  45

Leu Ile Gly Gly Thr Lys Phe Leu Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Arg Trp Val Phe Gly Gly Gly Thr Lys Leu Thr Val Leu
            100                 105
```

<210> SEQ ID NO 87
<211> LENGTH: 109
<212> TYPE: PRT
<213> ORGANISM: Artificial Sequence
<220> FEATURE:
<223> OTHER INFORMATION: anti-CD3 epsilon VL

<400> SEQUENCE: 87

```
Gln Thr Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

Tyr Tyr Pro Asn Trp Val Gln Gln Lys Pro Gly Gln Ala Pro Arg Gly
        35                  40                  45

Leu Ile Gly Gly Thr Lys Phe Leu Ala Pro Gly Thr Pro Ala Arg Phe
    50                  55                  60
```

Ser Gly Ser Leu Leu Gly Gly Lys Ala Ala Leu Thr Leu Ser Gly Val
65 70 75 80

Gln Pro Glu Asp Glu Ala Glu Tyr Tyr Cys Ala Leu Trp Tyr Ser Asn
85 90 95

Arg Trp Val Phe Gly Gly Gly Thr Lys Leu Thr Val Leu
100 105

<210> SEQ ID NO 88
<211> LENGTH: 109
<212> TYPE: PRT
<213> ORGANISM: Artificial Sequence
<220> FEATURE:
<223> OTHER INFORMATION: anti-CD3 epsilon VL

<400> SEQUENCE: 88

Glu Leu Val Val Thr Gln Glu Pro Ser Leu Thr Val Ser Pro Gly Gly
1 5 10 15

Thr Val Thr Leu Thr Cys Gly Ser Ser Thr Gly Ala Val Thr Ser Gly
20 25 30

Tyr Tyr Pro Asn Trp Val Gln Gln Lys Pro Gly Gln Ala Pro Arg Gly
35 40 45

Leu Ile Gly Gly Thr Lys Phe Leu Ala Pro Gly Thr Pro Ala Arg Phe
50 55 60

Ser Gly Ser Leu Leu Gly Gly Lys Ala Ala Leu Thr Leu Ser Gly Val
65 70 75 80

Gln Pro Glu Asp Glu Ala Glu Tyr Tyr Cys Ala Leu Trp Tyr Ser Asn
85 90 95

Arg Trp Val Phe Gly Gly Gly Thr Lys Leu Thr Val Leu
100 105

<210> SEQ ID NO 89
<211> LENGTH: 109
<212> TYPE: PRT
<213> ORGANISM: Artificial Sequence
<220> FEATURE:
<223> OTHER INFORMATION: anti-CD3 epsilon VL

<400> SEQUENCE: 89

Gln Thr Val Val Thr Gln Glu Pro Ser Leu Thr Val Ser Pro Gly Gly
1 5 10 15

Thr Val Thr Leu Thr Cys Gly Ser Ser Thr Gly Ala Val Thr Ser Gly
20 25 30

Tyr Tyr Pro Asn Trp Val Gln Gln Lys Pro Gly Gln Ala Pro Arg Gly
35 40 45

Leu Ile Gly Gly Thr Lys Phe Leu Ala Pro Gly Thr Pro Ala Arg Phe
50 55 60

Ser Gly Ser Leu Leu Gly Gly Lys Ala Ala Leu Thr Leu Ser Gly Val
65 70 75 80

Gln Pro Glu Asp Glu Ala Glu Tyr Tyr Cys Ala Leu Trp Tyr Ser Asn
85 90 95

Arg Trp Val Phe Gly Gly Gly Thr Lys Leu Thr Val Leu
100 105

<210> SEQ ID NO 90
<211> LENGTH: 109
<212> TYPE: PRT
<213> ORGANISM: Artificial Sequence
<220> FEATURE:
<223> OTHER INFORMATION: anti-CD3 epsilon VL

<400> SEQUENCE: 90

Glu Leu Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

Tyr Tyr Pro Asn Trp Val Gln Gln Lys Pro Gly Gln Ala Pro Arg Gly
        35                  40                  45

Leu Ile Gly Gly Thr Lys Phe Leu Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Arg Trp Val Phe Gly Gly Gly Thr Lys Leu Thr Val Leu
            100                 105

<210> SEQ ID NO 91
<211> LENGTH: 109
<212> TYPE: PRT
<213> ORGANISM: Artificial Sequence
<220> FEATURE:
<223> OTHER INFORMATION: anti-CD3 epsilon VL

<400> SEQUENCE: 91

Gln Thr Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Ser Gly
            20                  25                  30

Tyr Tyr Pro Asn Trp Val Gln Gln Lys Pro Gly Gln Ala Pro Arg Gly
        35                  40                  45

Leu Ile Gly Ala Thr Asp Met Arg Pro Ser Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Arg Trp Val Phe Gly Gly Gly Thr Lys Leu Thr Val Leu
            100                 105

<210> SEQ ID NO 92
<211> LENGTH: 109
<212> TYPE: PRT
<213> ORGANISM: Artificial Sequence
<220> FEATURE:
<223> OTHER INFORMATION: anti-CD3 epsilon VL

<400> SEQUENCE: 92

Glu Leu Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Ser Gly
            20                  25                  30

Tyr Tyr Pro Asn Trp Val Gln Gln Lys Pro Gly Gln Ala Pro Arg Gly
        35                  40                  45

Leu Ile Gly Ala Thr Asp Met Arg Pro Ser Gly Thr Pro Ala Arg Phe
    50                  55                  60

Ser Gly Ser Leu Leu Gly Gly Lys Ala Ala Leu Thr Leu Ser Gly Val
65                  70                  75                  80

```
Gln Pro Glu Asp Glu Ala Glu Tyr Tyr Cys Ala Leu Trp Tyr Ser Asn
                85                  90                  95

Arg Trp Val Phe Gly Gly Gly Thr Lys Leu Thr Val Leu
            100                 105


<210> SEQ ID NO 93
<211> LENGTH: 109
<212> TYPE: PRT
<213> ORGANISM: Artificial Sequence
<220> FEATURE:
<223> OTHER INFORMATION: anti-CD3 epsilon VL

<400> SEQUENCE: 93

Gln Thr Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

Tyr Tyr Pro Asn Trp Val Gln Gln Lys Pro Gly Gln Ala Pro Arg Gly
        35                  40                  45

Leu Ile Gly Gly Thr Lys Phe Leu Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Arg Trp Val Phe Gly Gly Gly Thr Lys Leu Thr Val Leu
            100                 105


<210> SEQ ID NO 94
<211> LENGTH: 109
<212> TYPE: PRT
<213> ORGANISM: Artificial Sequence
<220> FEATURE:
<223> OTHER INFORMATION: anti-CD3 epsilon VL

<400> SEQUENCE: 94

Glu Leu Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

Tyr Tyr Pro Asn Trp Val Gln Gln Lys Pro Gly Gln Ala Pro Arg Gly
        35                  40                  45

Leu Ile Gly Gly Thr Lys Phe Leu Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Arg Trp Val Phe Gly Gly Gly Thr Lys Leu Thr Val Leu
            100                 105


<210> SEQ ID NO 95
<211> LENGTH: 109
<212> TYPE: PRT
<213> ORGANISM: Artificial Sequence
<220> FEATURE:
<223> OTHER INFORMATION: anti-CD3 epsilon VL
```

<400> SEQUENCE: 95

Gln Thr Val Val Thr Gln Glu Pro Ser Leu Thr Val Ser Pro Gly Gly
1 5 10 15

Thr Val Thr Leu Thr Cys Arg Ser Ser Thr Gly Ala Val Thr Ser Gly
20 25 30

Tyr Tyr Pro Asn Trp Val Gln Gln Lys Pro Gly Gln Ala Pro Arg Gly
35 40 45

Leu Ile Gly Ala Thr Asp Met Arg Pro Ser Gly Thr Pro Ala Arg Phe
50 55 60

Ser Gly Ser Leu Leu Gly Gly Lys Ala Ala Leu Thr Leu Ser Gly Val
65 70 75 80

Gln Pro Glu Asp Glu Ala Glu Tyr Tyr Cys Ala Leu Trp Tyr Ser Asn
85 90 95

Arg Trp Val Phe Gly Gly Gly Thr Lys Leu Thr Val Leu
100 105

<210> SEQ ID NO 96
<211> LENGTH: 109
<212> TYPE: PRT
<213> ORGANISM: Artificial Sequence
<220> FEATURE:
<223> OTHER INFORMATION: anti-CD3 epsilon VL

<400> SEQUENCE: 96

Glu Leu Val Val Thr Gln Glu Pro Ser Leu Thr Val Ser Pro Gly Gly
1 5 10 15

Thr Val Thr Leu Thr Cys Arg Ser Ser Thr Gly Ala Val Thr Ser Gly
20 25 30

Tyr Tyr Pro Asn Trp Val Gln Gln Lys Pro Gly Gln Ala Pro Arg Gly
35 40 45

Leu Ile Gly Ala Thr Asp Met Arg Pro Ser Gly Thr Pro Ala Arg Phe
50 55 60

Ser Gly Ser Leu Leu Gly Gly Lys Ala Ala Leu Thr Leu Ser Gly Val
65 70 75 80

Gln Pro Glu Asp Glu Ala Glu Tyr Tyr Cys Ala Leu Trp Tyr Ser Asn
85 90 95

Arg Trp Val Phe Gly Gly Gly Thr Lys Leu Thr Val Leu
100 105

<210> SEQ ID NO 97
<211> LENGTH: 109
<212> TYPE: PRT
<213> ORGANISM: Artificial Sequence
<220> FEATURE:
<223> OTHER INFORMATION: anti-CD3 epsilon VL

<400> SEQUENCE: 97

Gln Thr Val Val Thr Gln Glu Pro Ser Leu Thr Val Ser Pro Gly Gly
1 5 10 15

Thr Val Thr Leu Thr Cys Gly Ser Ser Thr Gly Ala Val Thr Ser Gly
20 25 30

Tyr Tyr Pro Asn Trp Val Gln Gln Lys Pro Gly Gln Ala Pro Arg Gly
35 40 45

Leu Ile Gly Gly Thr Lys Phe Leu Ala Pro Gly Thr Pro Ala Arg Phe
50 55 60

Ser Gly Ser Leu Leu Gly Gly Lys Ala Ala Leu Thr Leu Ser Gly Val
65 70 75 80

```
Gln Pro Glu Asp Glu Ala Glu Tyr Tyr Cys Ala Leu Trp Tyr Ser Asn
                85                  90                  95

Arg Trp Val Phe Gly Gly Gly Thr Lys Leu Thr Val Leu
            100                 105


<210> SEQ ID NO 98
<211> LENGTH: 109
<212> TYPE: PRT
<213> ORGANISM: Artificial Sequence
<220> FEATURE:
<223> OTHER INFORMATION: anti-CD3 epsilon VL

<400> SEQUENCE: 98

Glu Leu Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

Tyr Tyr Pro Asn Trp Val Gln Gln Lys Pro Gly Gln Ala Pro Arg Gly
        35                  40                  45

Leu Ile Gly Gly Thr Lys Phe Leu Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Arg Trp Val Phe Gly Gly Gly Thr Lys Leu Thr Val Leu
            100                 105


<210> SEQ ID NO 99
<211> LENGTH: 109
<212> TYPE: PRT
<213> ORGANISM: Artificial Sequence
<220> FEATURE:
<223> OTHER INFORMATION: anti-CD3 epsilon VL

<400> SEQUENCE: 99

Gln Thr Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

Asn Tyr Pro Asn Trp Val Gln Gln Lys Pro Gly Gln Ala Pro Arg Gly
        35                  40                  45

Leu Ile Gly Gly Thr Lys Phe Leu Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Val Leu Trp Tyr Ser Asn
                85                  90                  95

Arg Trp Val Phe Gly Gly Gly Thr Lys Leu Thr Val Leu
            100                 105


<210> SEQ ID NO 100
<211> LENGTH: 109
<212> TYPE: PRT
<213> ORGANISM: Artificial Sequence
<220> FEATURE:
<223> OTHER INFORMATION: anti-CD3 epsilon VL
```

<400> SEQUENCE: 100

Glu Leu Val Val Thr Gln Glu Pro Ser Leu Thr Val Ser Pro Gly Gly
1 5 10 15

Thr Val Thr Leu Thr Cys Gly Ser Ser Thr Gly Ala Val Thr Ser Gly
20 25 30

Asn Tyr Pro Asn Trp Val Gln Gln Lys Pro Gly Gln Ala Pro Arg Gly
35 40 45

Leu Ile Gly Gly Thr Lys Phe Leu Ala Pro Gly Thr Pro Ala Arg Phe
50 55 60

Ser Gly Ser Leu Leu Gly Gly Lys Ala Ala Leu Thr Leu Ser Gly Val
65 70 75 80

Gln Pro Glu Asp Glu Ala Glu Tyr Tyr Cys Val Leu Trp Tyr Ser Asn
85 90 95

Arg Trp Val Phe Gly Gly Gly Thr Lys Leu Thr Val Leu
100 105

<210> SEQ ID NO 101
<211> LENGTH: 109
<212> TYPE: PRT
<213> ORGANISM: Artificial Sequence
<220> FEATURE:
<223> OTHER INFORMATION: anti-CD3 epsilon VL

<400> SEQUENCE: 101

Glu Leu Val Val Thr Gln Glu Pro Ser Leu Thr Val Ser Pro Gly Gly
1 5 10 15

Thr Val Thr Leu Thr Cys Gly Ser Ser Thr Gly Ala Val Thr Ser Gly
20 25 30

Asn Tyr Pro Asn Trp Val Gln Gln Lys Pro Gly Gln Ala Pro Arg Gly
35 40 45

Leu Ile Gly Gly Thr Lys Phe Leu Ala Pro Gly Thr Pro Ala Arg Phe
50 55 60

Ser Gly Ser Leu Leu Gly Gly Lys Ala Ala Leu Thr Leu Ser Gly Val
65 70 75 80

Gln Pro Glu Asp Glu Ala Glu Tyr Tyr Cys Val Leu Trp Tyr Ser Asn
85 90 95

Arg Trp Val Phe Gly Gly Gly Thr Lys Leu Thr Val Leu
100 105

<210> SEQ ID NO 102
<211> LENGTH: 109
<212> TYPE: PRT
<213> ORGANISM: Artificial Sequence
<220> FEATURE:
<223> OTHER INFORMATION: anti-CD3 epsilon VL

<400> SEQUENCE: 102

Gln Ala Val Val Thr Gln Glu Pro Ser Leu Thr Val Ser Pro Gly Gly
1 5 10 15

Thr Val Thr Leu Thr Cys Arg Ser Ser Thr Gly Ala Val Thr Thr Ser
20 25 30

Asn Tyr Ala Asn Trp Val Gln Gln Lys Pro Gly Gln Ala Pro Arg Gly
35 40 45

Leu Ile Gly Gly Thr Asn Lys Arg Ala Pro Trp Thr Pro Ala Arg Phe
50 55 60

Ser Gly Ser Leu Leu Gly Gly Lys Ala Ala Leu Thr Ile Thr Gly Ala
65 70 75 80

Gln Ala Glu Asp Glu Ala Asp Tyr Tyr Cys Ala Leu Trp Tyr Ser Asn
85 90 95

Leu Trp Val Phe Gly Gly Gly Thr Lys Leu Thr Val Leu
100 105

<210> SEQ ID NO 103
<211> LENGTH: 109
<212> TYPE: PRT
<213> ORGANISM: Artificial Sequence
<220> FEATURE:
<223> OTHER INFORMATION: anti-CD3 epsilon VL

<400> SEQUENCE: 103

Gln Ala Val Val Thr Gln Glu Pro Ser Leu Thr Val Ser Pro Gly Gly
1 5 10 15

Thr Val Thr Leu Thr Cys Gly Ser Ser Thr Gly Ala Val Thr Thr Ser
20 25 30

Asn Tyr Ala Asn Trp Val Gln Gln Lys Pro Gly Lys Ser Pro Arg Gly
35 40 45

Leu Ile Gly Gly Thr Asn Lys Arg Ala Pro Gly Val Pro Ala Arg Phe
50 55 60

Ser Gly Ser Leu Leu Gly Gly Lys Ala Ala Leu Thr Ile Ser Gly Ala
65 70 75 80

Gln Pro Glu Asp Glu Ala Asp Tyr Tyr Cys Ala Leu Trp Tyr Ser Asn
85 90 95

His Trp Val Phe Gly Gly Gly Thr Lys Leu Thr Val Leu
100 105

<210> SEQ ID NO 104
<211> LENGTH: 7
<212> TYPE: PRT
<213> ORGANISM: Artificial Sequence
<220> FEATURE:
<223> OTHER INFORMATION: CDR1of Heavy Chain (CDR-H1)
<220> FEATURE:
<221> NAME/KEY: misc_feature
<222> LOCATION: (2)..(3)
<223> OTHER INFORMATION: Xaa can be any naturally occurring amino acid

<400> SEQUENCE: 104

Thr Xaa Xaa Tyr Ala Met Asn
1 5

<210> SEQ ID NO 105
<211> LENGTH: 19
<212> TYPE: PRT
<213> ORGANISM: Artificial Sequence
<220> FEATURE:
<223> OTHER INFORMATION: CDR2 of Heavy Chain (CDR-H2)

<400> SEQUENCE: 105

Arg Ile Arg Ser Lys Tyr Asn Asn Tyr Ala Thr Tyr Tyr Ala Asp Ser
1 5 10 15

Val Lys Asp

<210> SEQ ID NO 106
<211> LENGTH: 14
<212> TYPE: PRT
<213> ORGANISM: Artificial Sequence
<220> FEATURE:
<223> OTHER INFORMATION: CDR3 of Heavy Chain (CDR-H3)

<400> SEQUENCE: 106

His Gly Asn Phe Gly Asn Ser Tyr Val Ser Trp Phe Ala Tyr
1 5 10

<210> SEQ ID NO 107
<211> LENGTH: 14
<212> TYPE: PRT
<213> ORGANISM: Artificial Sequence
<220> FEATURE:
<223> OTHER INFORMATION: CDR1 of Light Chain (CDR-L1)

<400> SEQUENCE: 107

Arg Ser Ser Thr Gly Ala Val Thr Thr Ser Asn Tyr Ala Asn
1 5 10

<210> SEQ ID NO 108
<211> LENGTH: 14
<212> TYPE: PRT
<213> ORGANISM: Artificial Sequence
<220> FEATURE:
<223> OTHER INFORMATION: CDR1 of Light Chain (CDR-L1)

<400> SEQUENCE: 108

Ala Ser Ser Thr Gly Ala Val Thr Thr Ser Asn Tyr Ala Asn
1 5 10

<210> SEQ ID NO 109
<211> LENGTH: 14
<212> TYPE: PRT
<213> ORGANISM: Artificial Sequence
<220> FEATURE:
<223> OTHER INFORMATION: CDR1 of Light Chain (CDR-L1)

<400> SEQUENCE: 109

Ala Ser Ser Thr Gly Ala Val Thr Ser Gly Tyr Tyr Pro Asn
1 5 10

<210> SEQ ID NO 110
<211> LENGTH: 7
<212> TYPE: PRT
<213> ORGANISM: Artificial Sequence
<220> FEATURE:
<223> OTHER INFORMATION: CDR2 of Light Chain (CDR-L2)

<400> SEQUENCE: 110

Gly Thr Asn Lys Arg Ala Pro
1 5

<210> SEQ ID NO 111
<211> LENGTH: 9
<212> TYPE: PRT
<213> ORGANISM: Artificial Sequence
<220> FEATURE:
<223> OTHER INFORMATION: CDR3 of Light Chain (CDR-L3)

<400> SEQUENCE: 111

Ala Leu Trp Tyr Ser Asn Leu Trp Val
1 5

<210> SEQ ID NO 112
<211> LENGTH: 9
<212> TYPE: PRT
<213> ORGANISM: Artificial Sequence
<220> FEATURE:
<223> OTHER INFORMATION: CDR3 of Light Chain (CDR-L3)

<400> SEQUENCE: 112

Leu Leu Trp Tyr Ser Asn Leu Trp Val
1               5

<210> SEQ ID NO 113
<211> LENGTH: 223
<212> TYPE: PRT
<213> ORGANISM: Artificial Sequence
<220> FEATURE:
<223> OTHER INFORMATION: anti-CD3 Variable Heavy chain?and heavy constant region 1

<400> SEQUENCE: 113

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Met Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Arg Val
    210                 215                 220

<210> SEQ ID NO 114
<211> LENGTH: 125
<212> TYPE: PRT
<213> ORGANISM: Artificial Sequence
<220> FEATURE:
<223> OTHER INFORMATION: anti-CD3 epsilon VH

<400> SEQUENCE: 114

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65 70 75 80

Leu Tyr Leu Gln Met Asn Ser Leu Arg Ala Glu Asp Thr Ala Val Tyr
85 90 95

Tyr Cys Val Arg His Gly Asn Phe Gly Asn Ser Tyr Val Ser Trp Phe
100 105 110

Ala Tyr Trp Gly Gln Gly Thr Met Val Thr Val Ser Ser
115 120 125

<210> SEQ ID NO 115
<211> LENGTH: 98
<212> TYPE: PRT
<213> ORGANISM: Artificial Sequence
<220> FEATURE:
<223> OTHER INFORMATION: anti-CD3 epsilon Constant Heavy Chain

<400> SEQUENCE: 115

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Arg Val

<210> SEQ ID NO 116
<211> LENGTH: 109
<212> TYPE: PRT
<213> ORGANISM: Artificial Sequence
<220> FEATURE:
<223> OTHER INFORMATION: anti-CD3 epsilon VL

<400> SEQUENCE: 116

Gln Ala Val Val Thr Gln Glu Pro Ser Leu Thr Val Ser Pro Gly Gly
1 5 10 15

Thr Val Thr Leu Thr Cys Arg Ser Ser Thr Gly Ala Val Thr Thr Ser
20 25 30

Asn Tyr Ala Asn Trp Val Gln Gln Lys Pro Gly Gln Ala Pro Arg Gly
35 40 45

Leu Ile Gly Gly Thr Asn Lys Arg Ala Pro Gly Thr Pro Ala Arg Phe
50 55 60

Ser Gly Ser Leu Leu Gly Gly Lys Ala Ala Leu Thr Leu Ser Gly Val
65 70 75 80

Gln Pro Glu Asp Glu Ala Glu Tyr Tyr Cys Ala Leu Trp Tyr Ser Asn
85 90 95

Leu Trp Val Phe Gly Gly Gly Thr Lys Leu Thr Val Leu
100 105

<210> SEQ ID NO 117
<211> LENGTH: 109
<212> TYPE: PRT
<213> ORGANISM: Artificial Sequence
<220> FEATURE:
<223> OTHER INFORMATION: anti-CD3 epsilon Constant Light Chain

<400> SEQUENCE: 117

Gly Gln Pro Lys Ala Ala Pro Ser Val Thr Leu Phe Pro Pro Ser Ser
1 5 10 15

Glu Glu Leu Gln Ala Asn Lys Ala Thr Leu Val Cys Leu Ile Ser Asp
20 25 30

Phe Tyr Pro Gly Ala Val Thr Val Ala Trp Lys Ala Asp Ser Ser Pro
35 40 45

Val Lys Ala Gly Val Glu Thr Thr Thr Pro Ser Lys Gln Ser Asn Asn
50 55 60

Lys Tyr Ala Ala Ser Ser Tyr Leu Ser Leu Thr Pro Glu Gln Trp Lys
65 70 75 80

Ser His Arg Ser Tyr Ser Cys Gln Val Thr His Glu Gly Ser Thr Val
85 90 95

Glu Lys Thr Val Ala Pro Thr Glu Cys Pro Pro Cys Ser
100 105

<210> SEQ ID NO 118
<211> LENGTH: 1129
<212> TYPE: PRT
<213> ORGANISM: Artificial Sequence
<220> FEATURE:
<223> OTHER INFORMATION: HC 5T4 Polypeptide with multiple cleavage protease sequence

<400> SEQUENCE: 118

Gln Asp Gly Asn Glu Glu Met Gly Gly Ile Thr Gln Thr Pro Tyr Lys
1 5 10 15

Val Ser Ile Ser Gly Thr Thr Val Ile Leu Thr Gly Gly Gly Gly Ser
20 25 30

Gly Gly Gly Gly Ser Gly Gly Gly Gly Ser Glu Val Ala His Arg Phe
35 40 45

Lys Asp Leu Gly Glu Glu Asn Phe Lys Ala Leu Val Leu Ile Ala Phe
50 55 60

Ala Gln Tyr Leu Gln Gln Cys Pro Phe Glu Asp His Val Lys Leu Val
65 70 75 80

Asn Glu Val Thr Glu Phe Ala Lys Thr Cys Val Ala Asp Glu Ser Ala
85 90 95

Glu Asn Cys Asp Lys Ser Leu His Thr Leu Phe Gly Asp Lys Leu Cys
100 105 110

Thr Val Ala Thr Leu Arg Glu Thr Tyr Gly Glu Met Ala Asp Cys Cys
115 120 125

Ala Lys Gln Glu Pro Glu Arg Asn Glu Cys Phe Leu Gln His Lys Asp
130 135 140

Asp Asn Pro Asn Leu Pro Arg Leu Val Arg Pro Glu Val Asp Val Met
145 150 155 160

Cys Thr Ala Phe His Asp Asn Glu Glu Thr Phe Leu Lys Lys Tyr Leu
165 170 175

Tyr Glu Ile Ala Arg Arg His Pro Tyr Phe Tyr Ala Pro Glu Leu Leu
180 185 190

Phe Phe Ala Lys Arg Tyr Lys Ala Ala Phe Thr Glu Cys Cys Gln Ala
195 200 205

Ala Asp Lys Ala Ala Cys Leu Leu Pro Lys Leu Asp Glu Leu Arg Asp
210 215 220

```
Glu Gly Lys Ala Ser Ser Ala Lys Gln Arg Leu Lys Cys Ala Ser Leu
225                 230                 235                 240

Gln Lys Phe Gly Glu Arg Ala Phe Lys Ala Trp Ala Val Ala Arg Leu
                245                 250                 255

Ser Gln Arg Phe Pro Lys Ala Glu Phe Ala Glu Val Ser Lys Leu Val
            260                 265                 270

Thr Asp Leu Thr Lys Val His Thr Glu Cys Cys His Gly Asp Leu Leu
        275                 280                 285

Glu Cys Ala Asp Asp Arg Ala Asp Leu Ala Lys Tyr Ile Cys Glu Asn
    290                 295                 300

Gln Asp Ser Ile Ser Ser Lys Leu Lys Glu Cys Cys Glu Lys Pro Leu
305                 310                 315                 320

Leu Glu Lys Ser His Cys Ile Ala Glu Val Glu Asn Asp Glu Met Pro
                325                 330                 335

Ala Asp Leu Pro Ser Leu Ala Ala Asp Phe Val Glu Ser Lys Asp Val
            340                 345                 350

Cys Lys Asn Tyr Ala Glu Ala Lys Asp Val Phe Leu Gly Met Phe Leu
        355                 360                 365

Tyr Glu Tyr Ala Arg Arg His Pro Asp Tyr Ser Val Val Leu Leu Leu
    370                 375                 380

Arg Leu Ala Lys Thr Tyr Glu Thr Thr Leu Glu Lys Cys Cys Ala Ala
385                 390                 395                 400

Ala Asp Pro His Glu Cys Tyr Ala Lys Val Phe Asp Glu Phe Lys Pro
                405                 410                 415

Leu Val Glu Glu Pro Gln Asn Leu Ile Lys Gln Asn Cys Glu Leu Phe
            420                 425                 430

Glu Gln Leu Gly Glu Tyr Lys Phe Gln Asn Ala Leu Leu Val Arg Tyr
        435                 440                 445

Thr Lys Lys Val Pro Gln Val Ser Thr Pro Thr Leu Val Glu Val Ser
    450                 455                 460

Arg Asn Leu Gly Lys Val Gly Ser Lys Cys Cys Lys His Pro Glu Ala
465                 470                 475                 480

Lys Arg Met Pro Cys Ala Glu Asp Tyr Leu Ser Val Val Leu Asn Gln
                485                 490                 495

Leu Cys Val Leu His Glu Lys Thr Pro Val Ser Asp Arg Val Thr Lys
            500                 505                 510

Cys Cys Thr Glu Ser Leu Val Asn Arg Arg Pro Cys Phe Ser Ala Leu
        515                 520                 525

Glu Val Asp Glu Thr Tyr Val Pro Lys Glu Phe Asn Ala Glu Thr Phe
    530                 535                 540

Thr Phe His Ala Asp Ile Cys Thr Leu Ser Glu Lys Glu Arg Gln Ile
545                 550                 555                 560

Lys Lys Gln Thr Ala Leu Val Glu Leu Val Lys His Lys Pro Lys Ala
                565                 570                 575

Thr Lys Glu Gln Leu Lys Ala Val Met Asp Asp Phe Ala Ala Phe Val
            580                 585                 590

Glu Lys Cys Cys Lys Ala Asp Asp Lys Glu Thr Cys Phe Ala Glu Glu
        595                 600                 605

Gly Lys Lys Leu Val Ala Ala Ser Gln Ala Ala Gly Gly Ser Gly Gly
    610                 615                 620

Ser Pro Leu Gly Leu Ala Gly Gly Gly Gly Ser Gly Arg Ser Asp Asn
625                 630                 635                 640
```

```
His Gly Gly Ser Gly Gly Ser Glu Val Gln Leu Val Glu Ser Gly Gly
                645                 650                 655

Gly Leu Val Gln Pro Gly Gly Ser Leu Arg Leu Ser Cys Ala Ala Ser
            660                 665                 670

Gly Phe Thr Phe Asn Thr Tyr Ala Met Asn Trp Val Arg Gln Ala Pro
        675                 680                 685

Gly Lys Gly Leu Glu Trp Val Ala Arg Ile Arg Ser Lys Tyr Asn Asn
    690                 695                 700

Tyr Ala Thr Tyr Tyr Ala Asp Ser Val Lys Asp Arg Phe Thr Ile Ser
705                 710                 715                 720

Arg Asp Asp Ser Lys Asn Thr Leu Tyr Leu Gln Met Asn Ser Leu Arg
                725                 730                 735

Ala Glu Asp Thr Ala Val Tyr Tyr Cys Val Arg His Gly Asn Phe Gly
            740                 745                 750

Asn Ser Tyr Val Ser Trp Phe Ala Tyr Trp Gly Gln Gly Thr Met Val
        755                 760                 765

Thr Val Ser Ser Ala Ser Thr Lys Gly Pro Ser Val Phe Pro Leu Ala
    770                 775                 780

Pro Ser Ser Lys Ser Thr Ser Gly Gly Thr Ala Ala Leu Gly Cys Leu
785                 790                 795                 800

Val Lys Asp Tyr Phe Pro Glu Pro Val Thr Val Ser Trp Asn Ser Gly
                805                 810                 815

Ala Leu Thr Ser Gly Val His Thr Phe Pro Ala Val Leu Gln Ser Ser
            820                 825                 830

Gly Leu Tyr Ser Leu Ser Ser Val Val Thr Val Pro Ser Ser Ser Leu
        835                 840                 845

Gly Thr Gln Thr Tyr Ile Cys Asn Val Asn His Lys Pro Ser Asn Thr
    850                 855                 860

Lys Val Asp Lys Arg Val Glu Pro Lys Ser Cys Pro Pro Cys Gly Gly
865                 870                 875                 880

Gly Gly Ser Asp Asp Ile Gln Met Thr Gln Ser Pro Ser Ser Leu Ser
                885                 890                 895

Ala Ser Val Gly Asp Arg Val Thr Ile Thr Cys Arg Ala Ser Gln Gly
            900                 905                 910

Ile Ser Asn Tyr Leu Ala Trp Phe Gln Gln Lys Pro Gly Lys Ala Pro
        915                 920                 925

Lys Ser Leu Ile Tyr Arg Ala Asn Arg Leu Gln Ser Gly Val Pro Ser
    930                 935                 940

Arg Phe Ser Gly Ser Gly Ser Gly Thr Asp Phe Thr Leu Thr Ile Ser
945                 950                 955                 960

Ser Leu Gln Pro Glu Asp Val Ala Thr Tyr Tyr Cys Leu Gln Tyr Asp
                965                 970                 975

Asp Phe Pro Trp Thr Phe Gly Gln Gly Thr Lys Leu Glu Ile Lys Gly
            980                 985                 990

Gly Gly Gly Ser Gly Gly Gly Gly  Ser Gly Gly Gly Gly  Ser Gly Gly
        995                 1000                1005

Gly Gly  Ser Gln Val Gln Leu  Val Gln Ser Gly Ala  Glu Val Lys
    1010                1015                1020

Lys Pro  Gly Ala Ser Val Lys  Val Ser Cys Lys Ala  Ser Gly Tyr
    1025                1030                1035

Thr Phe  Thr Ser Phe Trp Met  His Trp Val Arg Gln  Ala Pro Gly
    1040                1045                1050
```

Gln Gly Leu Glu Trp Met Gly Arg Ile Asp Pro Asn Arg Gly Gly
1055 1060 1065

Thr Glu Tyr Asn Glu Lys Ala Lys Ser Arg Val Thr Met Thr Ala
1070 1075 1080

Asp Lys Ser Thr Ser Thr Ala Tyr Met Glu Leu Ser Ser Leu Arg
1085 1090 1095

Ser Glu Asp Thr Ala Val Tyr Tyr Cys Ala Gly Gly Asn Pro Tyr
1100 1105 1110

Tyr Pro Met Asp Tyr Trp Gly Gln Gly Thr Thr Val Thr Val Ser
1115 1120 1125

Ser

<210> SEQ ID NO 119
<211> LENGTH: 6
<212> TYPE: PRT
<213> ORGANISM: Artificial Sequence
<220> FEATURE:
<223> OTHER INFORMATION: linker

<400> SEQUENCE: 119

Gly Ser Gly Gly Ser Asn
1 5

<210> SEQ ID NO 120
<211> LENGTH: 5
<212> TYPE: PRT
<213> ORGANISM: Artificial Sequence
<220> FEATURE:
<223> OTHER INFORMATION: linker

<400> SEQUENCE: 120

Gly Gly Gly Ser Asn
1 5

<210> SEQ ID NO 121
<211> LENGTH: 4
<212> TYPE: PRT
<213> ORGANISM: Artificial Sequence
<220> FEATURE:
<223> OTHER INFORMATION: linker

<400> SEQUENCE: 121

Gly Gly Ser Gly
1

<210> SEQ ID NO 122
<211> LENGTH: 5
<212> TYPE: PRT
<213> ORGANISM: Artificial Sequence
<220> FEATURE:
<223> OTHER INFORMATION: linker

<400> SEQUENCE: 122

Gly Gly Ser Gly Gly
1 5

<210> SEQ ID NO 123
<211> LENGTH: 5
<212> TYPE: PRT
<213> ORGANISM: Artificial Sequence
<220> FEATURE:
<223> OTHER INFORMATION: linker

<400> SEQUENCE: 123

Gly Ser Gly Ser Gly
1 5

<210> SEQ ID NO 124
<211> LENGTH: 5
<212> TYPE: PRT
<213> ORGANISM: Artificial Sequence
<220> FEATURE:
<223> OTHER INFORMATION: linker

<400> SEQUENCE: 124

Gly Ser Gly Gly Gly
1 5

<210> SEQ ID NO 125
<211> LENGTH: 5
<212> TYPE: PRT
<213> ORGANISM: Artificial Sequence
<220> FEATURE:
<223> OTHER INFORMATION: linker

<400> SEQUENCE: 125

Gly Gly Gly Ser Gly
1 5

<210> SEQ ID NO 126
<211> LENGTH: 5
<212> TYPE: PRT
<213> ORGANISM: Artificial Sequence
<220> FEATURE:
<223> OTHER INFORMATION: linker

<400> SEQUENCE: 126

Gly Ser Ser Ser Gly
1 5

<210> SEQ ID NO 127
<211> LENGTH: 14
<212> TYPE: PRT
<213> ORGANISM: Artificial Sequence
<220> FEATURE:
<223> OTHER INFORMATION: linker

<400> SEQUENCE: 127

Glu Gly Lys Ser Ser Gly Ser Gly Ser Glu Ser Lys Val Asp
1 5 10

<210> SEQ ID NO 128
<211> LENGTH: 18
<212> TYPE: PRT
<213> ORGANISM: Artificial Sequence
<220> FEATURE:
<223> OTHER INFORMATION: linker

<400> SEQUENCE: 128

Lys Glu Ser Gly Ser Val Ser Ser Glu Gln Leu Ala Gln Phe Arg Ser
1 5 10 15

Leu Asp

<210> SEQ ID NO 129
<211> LENGTH: 5
<212> TYPE: PRT
<213> ORGANISM: Artificial Sequence
<220> FEATURE:

<223> OTHER INFORMATION: linker

<400> SEQUENCE: 129

Gly Gly Gly Gly Ser
1 5

<210> SEQ ID NO 130
<211> LENGTH: 1072
<212> TYPE: PRT
<213> ORGANISM: Artificial Sequence
<220> FEATURE:
<223> OTHER INFORMATION: HC polypeptide

<400> SEQUENCE: 130

Glu Val Ala His Arg Phe Lys Asp Leu Gly Glu Glu Asn Phe Lys Ala
1 5 10 15

Leu Val Leu Ile Ala Phe Ala Gln Tyr Leu Gln Gln Cys Pro Phe Glu
20 25 30

Asp His Val Lys Leu Val Asn Glu Val Thr Glu Phe Ala Lys Thr Cys
35 40 45

Val Ala Asp Glu Ser Ala Glu Asn Cys Asp Lys Ser Leu His Thr Leu
50 55 60

Phe Gly Asp Lys Leu Cys Thr Val Ala Thr Leu Arg Glu Thr Tyr Gly
65 70 75 80

Glu Met Ala Asp Cys Cys Ala Lys Gln Glu Pro Glu Arg Asn Glu Cys
85 90 95

Phe Leu Gln His Lys Asp Asp Asn Pro Asn Leu Pro Arg Leu Val Arg
100 105 110

Pro Glu Val Asp Val Met Cys Thr Ala Phe His Asp Asn Glu Glu Thr
115 120 125

Phe Leu Lys Lys Tyr Leu Tyr Glu Ile Ala Arg Arg His Pro Tyr Phe
130 135 140

Tyr Ala Pro Glu Leu Leu Phe Phe Ala Lys Arg Tyr Lys Ala Ala Phe
145 150 155 160

Thr Glu Cys Cys Gln Ala Ala Asp Lys Ala Ala Cys Leu Leu Pro Lys
165 170 175

Leu Asp Glu Leu Arg Asp Glu Gly Lys Ala Ser Ser Ala Lys Gln Arg
180 185 190

Leu Lys Cys Ala Ser Leu Gln Lys Phe Gly Glu Arg Ala Phe Lys Ala
195 200 205

Trp Ala Val Ala Arg Leu Ser Gln Arg Phe Pro Lys Ala Glu Phe Ala
210 215 220

Glu Val Ser Lys Leu Val Thr Asp Leu Thr Lys Val His Thr Glu Cys
225 230 235 240

Cys His Gly Asp Leu Leu Glu Cys Ala Asp Asp Arg Ala Asp Leu Ala
245 250 255

Lys Tyr Ile Cys Glu Asn Gln Asp Ser Ile Ser Ser Lys Leu Lys Glu
260 265 270

Cys Cys Glu Lys Pro Leu Leu Glu Lys Ser His Cys Ile Ala Glu Val
275 280 285

Glu Asn Asp Glu Met Pro Ala Asp Leu Pro Ser Leu Ala Ala Asp Phe
290 295 300

Val Glu Ser Lys Asp Val Cys Lys Asn Tyr Ala Glu Ala Lys Asp Val
305 310 315 320

Phe Leu Gly Met Phe Leu Tyr Glu Tyr Ala Arg Arg His Pro Asp Tyr
325 330 335

```
Ser Val Val Leu Leu Leu Arg Leu Ala Lys Thr Tyr Glu Thr Thr Leu
            340                 345                 350

Glu Lys Cys Cys Ala Ala Ala Asp Pro His Glu Cys Tyr Ala Lys Val
        355                 360                 365

Phe Asp Glu Phe Lys Pro Leu Val Glu Glu Pro Gln Asn Leu Ile Lys
    370                 375                 380

Gln Asn Cys Glu Leu Phe Glu Gln Leu Gly Glu Tyr Lys Phe Gln Asn
385                 390                 395                 400

Ala Leu Leu Val Arg Tyr Thr Lys Lys Val Pro Gln Val Ser Thr Pro
                405                 410                 415

Thr Leu Val Glu Val Ser Arg Asn Leu Gly Lys Val Gly Ser Lys Cys
            420                 425                 430

Cys Lys His Pro Glu Ala Lys Arg Met Pro Cys Ala Glu Asp Tyr Leu
        435                 440                 445

Ser Val Val Leu Asn Gln Leu Cys Val Leu His Glu Lys Thr Pro Val
    450                 455                 460

Ser Asp Arg Val Thr Lys Cys Cys Thr Glu Ser Leu Val Asn Arg Arg
465                 470                 475                 480

Pro Cys Phe Ser Ala Leu Glu Val Asp Glu Thr Tyr Val Pro Lys Glu
                485                 490                 495

Phe Asn Ala Glu Thr Phe Thr Phe His Ala Asp Ile Cys Thr Leu Ser
            500                 505                 510

Glu Lys Glu Arg Gln Ile Lys Lys Gln Thr Ala Leu Val Glu Leu Val
        515                 520                 525

Lys His Lys Pro Lys Ala Thr Lys Glu Gln Leu Lys Ala Val Met Asp
    530                 535                 540

Asp Phe Ala Ala Phe Val Glu Lys Cys Cys Lys Ala Asp Asp Lys Glu
545                 550                 555                 560

Thr Cys Phe Ala Glu Glu Gly Lys Lys Leu Val Ala Ala Ser Gln Ala
                565                 570                 575

Ala Gly Gly Ser Gly Gly Ser Pro Leu Gly Leu Ala Gly Gly Gly Ser
            580                 585                 590

Gly Gly Ser Glu Val Gln Leu Val Glu Ser Gly Gly Gly Leu Val Gln
        595                 600                 605

Pro Gly Gly Ser Leu Arg Leu Ser Cys Ala Ala Ser Gly Phe Thr Phe
    610                 615                 620

Asn Thr Tyr Ala Met Asn Trp Val Arg Gln Ala Pro Gly Lys Gly Leu
625                 630                 635                 640

Glu Trp Val Ala Arg Ile Arg Ser Lys Tyr Asn Asn Tyr Ala Thr Tyr
                645                 650                 655

Tyr Ala Asp Ser Val Lys Asp Arg Phe Thr Ile Ser Arg Asp Asp Ser
            660                 665                 670

Lys Asn Thr Leu Tyr Leu Gln Met Asn Ser Leu Arg Ala Glu Asp Thr
        675                 680                 685

Ala Val Tyr Tyr Cys Val Arg His Gly Asn Phe Gly Asn Ser Tyr Val
    690                 695                 700

Ser Trp Phe Ala Tyr Trp Gly Gln Gly Thr Met Val Thr Val Ser Ser
705                 710                 715                 720

Ala Ser Thr Lys Gly Pro Ser Val Phe Pro Leu Ala Pro Ser Ser Lys
                725                 730                 735

Ser Thr Ser Gly Gly Thr Ala Ala Leu Gly Cys Leu Val Lys Asp Tyr
            740                 745                 750
```

Phe Pro Glu Pro Val Thr Val Ser Trp Asn Ser Gly Ala Leu Thr Ser
755 760 765

Gly Val His Thr Phe Pro Ala Val Leu Gln Ser Ser Gly Leu Tyr Ser
770 775 780

Leu Ser Ser Val Val Thr Val Pro Ser Ser Ser Leu Gly Thr Gln Thr
785 790 795 800

Tyr Ile Cys Asn Val Asn His Lys Pro Ser Asn Thr Lys Val Asp Lys
805 810 815

Arg Val Glu Pro Lys Ser Cys Pro Pro Cys Gly Gly Gly Gly Ser Asp
820 825 830

Ile Gln Met Thr Gln Ser Pro Ser Ser Leu Ser Ala Ser Val Gly Asp
835 840 845

Arg Val Thr Ile Thr Cys Gln Ala Ser Gln Asp Ile Ser Asn Tyr Leu
850 855 860

Asn Trp Tyr Gln Gln Lys Pro Gly Lys Ala Pro Lys Leu Leu Ile Tyr
865 870 875 880

Asp Ala Ser Asn Leu Glu Thr Gly Val Pro Ser Arg Phe Ser Gly Ser
885 890 895

Gly Ser Gly Thr Asp Phe Thr Phe Thr Ile Ser Ser Leu Gln Pro Glu
900 905 910

Asp Ile Ala Thr Tyr Phe Cys Gln His Phe Asp His Leu Pro Leu Ala
915 920 925

Phe Gly Gly Gly Thr Lys Val Glu Ile Lys Gly Gly Gly Gly Ser Gly
930 935 940

Gly Gly Gly Ser Gly Gly Gly Gly Ser Gln Val Gln Leu Gln Glu Ser
945 950 955 960

Gly Pro Gly Leu Val Lys Pro Ser Glu Thr Leu Ser Leu Thr Cys Thr
965 970 975

Val Ser Gly Gly Ser Val Ser Ser Gly Asp Tyr Tyr Trp Thr Trp Ile
980 985 990

Arg Gln Ser Pro Gly Lys Gly Leu Glu Trp Ile Gly His Ile Tyr Tyr
995 1000 1005

Ser Gly Asn Thr Asn Tyr Asn Pro Ser Leu Lys Ser Arg Leu Thr
1010 1015 1020

Ile Ser Ile Asp Thr Ser Lys Thr Gln Phe Ser Leu Lys Leu Ser
1025 1030 1035

Ser Val Thr Ala Ala Asp Thr Ala Ile Tyr Tyr Cys Val Arg Asp
1040 1045 1050

Arg Val Thr Gly Ala Phe Asp Ile Trp Gly Gln Gly Thr Met Val
1055 1060 1065

Thr Val Ser Ser
1070

<210> SEQ ID NO 131
<211> LENGTH: 508
<212> TYPE: PRT
<213> ORGANISM: Artificial Sequence
<220> FEATURE:
<223> OTHER INFORMATION: LC polypeptide

<400> SEQUENCE: 131

Gln Asp Gly Asn Glu Glu Met Gly Gly Ile Thr Gln Thr Pro Tyr Lys
1 5 10 15

Val Ser Ile Ser Gly Thr Thr Val Ile Leu Thr Gly Gly Ser Gly Gly
20 25 30

```
Ser Pro Leu Gly Leu Ala Gly Gly Gly Ser Gly Gly Ser Gln Ala Val
        35                  40                  45

Val Thr Gln Glu Pro Ser Leu Thr Val Ser Pro Gly Gly Thr Val Thr
    50                  55                  60

Leu Thr Cys Arg Ser Ser Thr Gly Ala Val Thr Thr Ser Asn Tyr Ala
65                  70                  75                  80

Asn Trp Val Gln Gln Lys Pro Gly Gln Ala Pro Arg Gly Leu Ile Gly
                85                  90                  95

Gly Thr Asn Lys Arg Ala Pro Gly Thr Pro Ala Arg Phe Ser Gly Ser
            100                 105                 110

Leu Leu Gly Gly Lys Ala Ala Leu Thr Leu Ser Gly Val Gln Pro Glu
        115                 120                 125

Asp Glu Ala Glu Tyr Tyr Cys Ala Leu Trp Tyr Ser Asn Leu Trp Val
    130                 135                 140

Phe Gly Gly Gly Thr Lys Leu Thr Val Leu Gly Gln Pro Lys Ala Ala
145                 150                 155                 160

Pro Ser Val Thr Leu Phe Pro Pro Ser Ser Glu Glu Leu Gln Ala Asn
                165                 170                 175

Lys Ala Thr Leu Val Cys Leu Ile Ser Asp Phe Tyr Pro Gly Ala Val
            180                 185                 190

Thr Val Ala Trp Lys Ala Asp Ser Ser Pro Val Lys Ala Gly Val Glu
        195                 200                 205

Thr Thr Thr Pro Ser Lys Gln Ser Asn Asn Lys Tyr Ala Ala Ser Ser
    210                 215                 220

Tyr Leu Ser Leu Thr Pro Glu Gln Trp Lys Ser His Arg Ser Tyr Ser
225                 230                 235                 240

Cys Gln Val Thr His Glu Gly Ser Thr Val Glu Lys Thr Val Ala Pro
                245                 250                 255

Thr Glu Cys Pro Pro Cys Ser Gly Gly Gly Ser Asp Ile Gln Met Thr
            260                 265                 270

Gln Ser Pro Ser Ser Leu Ser Ala Ser Val Gly Asp Arg Val Thr Ile
        275                 280                 285

Thr Cys Gln Ala Ser Gln Asp Ile Ser Asn Tyr Leu Asn Trp Tyr Gln
    290                 295                 300

Gln Lys Pro Gly Lys Ala Pro Lys Leu Leu Ile Tyr Asp Ala Ser Asn
305                 310                 315                 320

Leu Glu Thr Gly Val Pro Ser Arg Phe Ser Gly Ser Gly Ser Gly Thr
                325                 330                 335

Asp Phe Thr Phe Thr Ile Ser Ser Leu Gln Pro Glu Asp Ile Ala Thr
            340                 345                 350

Tyr Phe Cys Gln His Phe Asp His Leu Pro Leu Ala Phe Gly Gly Gly
        355                 360                 365

Thr Lys Val Glu Ile Lys Gly Gly Gly Gly Ser Gly Gly Gly Gly Ser
    370                 375                 380

Gly Gly Gly Gly Ser Gln Val Gln Leu Gln Glu Ser Gly Pro Gly Leu
385                 390                 395                 400

Val Lys Pro Ser Glu Thr Leu Ser Leu Thr Cys Thr Val Ser Gly Gly
                405                 410                 415

Ser Val Ser Ser Gly Asp Tyr Tyr Trp Thr Trp Ile Arg Gln Ser Pro
            420                 425                 430

Gly Lys Gly Leu Glu Trp Ile Gly His Ile Tyr Tyr Ser Gly Asn Thr
        435                 440                 445
```

Asn Tyr Asn Pro Ser Leu Lys Ser Arg Leu Thr Ile Ser Ile Asp Thr
450 455 460

Ser Lys Thr Gln Phe Ser Leu Lys Leu Ser Ser Val Thr Ala Ala Asp
465 470 475 480

Thr Ala Ile Tyr Tyr Cys Val Arg Asp Arg Val Thr Gly Ala Phe Asp
485 490 495

Ile Trp Gly Gln Gly Thr Met Val Thr Val Ser Ser
500 505

<210> SEQ ID NO 132
<211> LENGTH: 1072
<212> TYPE: PRT
<213> ORGANISM: Artificial Sequence
<220> FEATURE:
<223> OTHER INFORMATION: HC polypeptide

<400> SEQUENCE: 132

Glu Val Ala His Arg Phe Lys Asp Leu Gly Glu Glu Asn Phe Lys Ala
1 5 10 15

Leu Val Leu Ile Ala Phe Ala Gln Tyr Leu Gln Gln Cys Pro Phe Glu
20 25 30

Asp His Val Lys Leu Val Asn Glu Val Thr Glu Phe Ala Lys Thr Cys
35 40 45

Val Ala Asp Glu Ser Ala Glu Asn Cys Asp Lys Ser Leu His Thr Leu
50 55 60

Phe Gly Asp Lys Leu Cys Thr Val Ala Thr Leu Arg Glu Thr Tyr Gly
65 70 75 80

Glu Met Ala Asp Cys Cys Ala Lys Gln Glu Pro Glu Arg Asn Glu Cys
85 90 95

Phe Leu Gln His Lys Asp Asp Asn Pro Asn Leu Pro Arg Leu Val Arg
100 105 110

Pro Glu Val Asp Val Met Cys Thr Ala Phe His Asp Asn Glu Glu Thr
115 120 125

Phe Leu Lys Lys Tyr Leu Tyr Glu Ile Ala Arg Arg His Pro Tyr Phe
130 135 140

Tyr Ala Pro Glu Leu Leu Phe Phe Ala Lys Arg Tyr Lys Ala Ala Phe
145 150 155 160

Thr Glu Cys Cys Gln Ala Ala Asp Lys Ala Ala Cys Leu Leu Pro Lys
165 170 175

Leu Asp Glu Leu Arg Asp Glu Gly Lys Ala Ser Ser Ala Lys Gln Arg
180 185 190

Leu Lys Cys Ala Ser Leu Gln Lys Phe Gly Glu Arg Ala Phe Lys Ala
195 200 205

Trp Ala Val Ala Arg Leu Ser Gln Arg Phe Pro Lys Ala Glu Phe Ala
210 215 220

Glu Val Ser Lys Leu Val Thr Asp Leu Thr Lys Val His Thr Glu Cys
225 230 235 240

Cys His Gly Asp Leu Leu Glu Cys Ala Asp Asp Arg Ala Asp Leu Ala
245 250 255

Lys Tyr Ile Cys Glu Asn Gln Asp Ser Ile Ser Ser Lys Leu Lys Glu
260 265 270

Cys Cys Glu Lys Pro Leu Leu Glu Lys Ser His Cys Ile Ala Glu Val
275 280 285

Glu Asn Asp Glu Met Pro Ala Asp Leu Pro Ser Leu Ala Ala Asp Phe
290 295 300

```
Val Glu Ser Lys Asp Val Cys Lys Asn Tyr Ala Glu Ala Lys Asp Val
305                 310                 315                 320

Phe Leu Gly Met Phe Leu Tyr Glu Tyr Ala Arg Arg His Pro Asp Tyr
                325                 330                 335

Ser Val Val Leu Leu Leu Arg Leu Ala Lys Thr Tyr Glu Thr Thr Leu
            340                 345                 350

Glu Lys Cys Cys Ala Ala Ala Asp Pro His Glu Cys Tyr Ala Lys Val
        355                 360                 365

Phe Asp Glu Phe Lys Pro Leu Val Glu Glu Pro Gln Asn Leu Ile Lys
    370                 375                 380

Gln Asn Cys Glu Leu Phe Glu Gln Leu Gly Glu Tyr Lys Phe Gln Asn
385                 390                 395                 400

Ala Leu Leu Val Arg Tyr Thr Lys Lys Val Pro Gln Val Ser Thr Pro
                405                 410                 415

Thr Leu Val Glu Val Ser Arg Asn Leu Gly Lys Val Gly Ser Lys Cys
            420                 425                 430

Cys Lys His Pro Glu Ala Lys Arg Met Pro Cys Ala Glu Asp Tyr Leu
        435                 440                 445

Ser Val Val Leu Asn Gln Leu Cys Val Leu His Glu Lys Thr Pro Val
    450                 455                 460

Ser Asp Arg Val Thr Lys Cys Cys Thr Glu Ser Leu Val Asn Arg Arg
465                 470                 475                 480

Pro Cys Phe Ser Ala Leu Glu Val Asp Glu Thr Tyr Val Pro Lys Glu
                485                 490                 495

Phe Asn Ala Glu Thr Phe Thr Phe His Ala Asp Ile Cys Thr Leu Ser
            500                 505                 510

Glu Lys Glu Arg Gln Ile Lys Lys Gln Thr Ala Leu Val Glu Leu Val
        515                 520                 525

Lys His Lys Pro Lys Ala Thr Lys Glu Gln Leu Lys Ala Val Met Asp
    530                 535                 540

Asp Phe Ala Ala Phe Val Glu Lys Cys Cys Lys Ala Asp Asp Lys Glu
545                 550                 555                 560

Thr Cys Phe Ala Glu Glu Gly Lys Lys Leu Val Ala Ala Ser Gln Ala
                565                 570                 575

Ala Gly Gly Ser Gly Gly Ser Pro Leu Gly Leu Ala Gly Gly Gly Ser
            580                 585                 590

Gly Gly Ser Glu Val Gln Leu Val Glu Ser Gly Gly Gly Leu Val Gln
        595                 600                 605

Pro Gly Gly Ser Leu Arg Leu Ser Cys Ala Ala Ser Gly Phe Thr Phe
    610                 615                 620

Asn Thr Tyr Ala Met Asn Trp Val Arg Gln Ala Pro Gly Lys Gly Leu
625                 630                 635                 640

Glu Trp Val Ala Arg Ile Arg Ser Lys Tyr Asn Asn Tyr Ala Thr Tyr
                645                 650                 655

Tyr Ala Asp Ser Val Lys Asp Arg Phe Thr Ile Ser Arg Asp Asp Ser
            660                 665                 670

Lys Asn Thr Leu Tyr Leu Gln Met Asn Ser Leu Arg Ala Glu Asp Thr
        675                 680                 685

Ala Val Tyr Tyr Cys Val Arg His Gly Asn Phe Gly Asn Ser Tyr Val
    690                 695                 700

Ser Trp Phe Ala Tyr Trp Gly Gln Gly Thr Met Val Thr Val Ser Ser
705                 710                 715                 720
```

```
Ala Ser Thr Lys Gly Pro Ser Val Phe Pro Leu Ala Pro Ser Ser Lys
                725                 730                 735

Ser Thr Ser Gly Gly Thr Ala Ala Leu Gly Cys Leu Val Lys Asp Tyr
            740                 745                 750

Phe Pro Glu Pro Val Thr Val Ser Trp Asn Ser Gly Ala Leu Thr Ser
        755                 760                 765

Gly Val His Thr Phe Pro Ala Val Leu Gln Ser Ser Gly Leu Tyr Ser
    770                 775                 780

Leu Ser Ser Val Val Thr Val Pro Ser Ser Ser Leu Gly Thr Gln Thr
785                 790                 795                 800

Tyr Ile Cys Asn Val Asn His Lys Pro Ser Asn Thr Lys Val Asp Lys
                805                 810                 815

Arg Val Glu Pro Lys Ser Cys Pro Pro Cys Gly Gly Gly Gly Ser Gln
            820                 825                 830

Val Gln Leu Gln Glu Ser Gly Pro Gly Leu Val Lys Pro Ser Glu Thr
        835                 840                 845

Leu Ser Leu Thr Cys Thr Val Ser Gly Gly Ser Val Ser Ser Gly Asp
    850                 855                 860

Tyr Tyr Trp Thr Trp Ile Arg Gln Ser Pro Gly Lys Gly Leu Glu Trp
865                 870                 875                 880

Ile Gly His Ile Tyr Tyr Ser Gly Asn Thr Asn Tyr Asn Pro Ser Leu
                885                 890                 895

Lys Ser Arg Leu Thr Ile Ser Ile Asp Thr Ser Lys Thr Gln Phe Ser
            900                 905                 910

Leu Lys Leu Ser Ser Val Thr Ala Ala Asp Thr Ala Ile Tyr Tyr Cys
        915                 920                 925

Val Arg Asp Arg Val Thr Gly Ala Phe Asp Ile Trp Gly Gln Gly Thr
    930                 935                 940

Met Val Thr Val Ser Ser Gly Gly Gly Gly Ser Gly Gly Gly Gly Ser
945                 950                 955                 960

Gly Gly Gly Gly Ser Asp Ile Gln Met Thr Gln Ser Pro Ser Ser Leu
                965                 970                 975

Ser Ala Ser Val Gly Asp Arg Val Thr Ile Thr Cys Gln Ala Ser Gln
            980                 985                 990

Asp Ile Ser Asn Tyr Leu Asn Trp  Tyr Gln Gln Lys Pro  Gly Lys Ala
        995                 1000                1005

Pro Lys  Leu Leu Ile Tyr Asp  Ala Ser Asn Leu Glu  Thr Gly Val
    1010                1015                1020

Pro Ser  Arg Phe Ser Gly Ser  Gly Ser Gly Thr Asp  Phe Thr Phe
    1025                1030                1035

Thr Ile  Ser Ser Leu Gln Pro  Glu Asp Ile Ala Thr  Tyr Phe Cys
    1040                1045                1050

Gln His  Phe Asp His Leu Pro  Leu Ala Phe Gly Gly  Gly Thr Lys
    1055                1060                1065

Val Glu  Ile Lys
    1070
```

<210> SEQ ID NO 133
<211> LENGTH: 508
<212> TYPE: PRT
<213> ORGANISM: Artificial Sequence
<220> FEATURE:
<223> OTHER INFORMATION: LC polypeptide

<400> SEQUENCE: 133

Gln Asp Gly Asn Glu Glu Met Gly Gly Ile Thr Gln Thr Pro Tyr Lys
1 5 10 15

Val Ser Ile Ser Gly Thr Thr Val Ile Leu Thr Gly Gly Ser Gly Gly
20 25 30

Ser Pro Leu Gly Leu Ala Gly Gly Gly Ser Gly Gly Ser Gln Ala Val
35 40 45

Val Thr Gln Glu Pro Ser Leu Thr Val Ser Pro Gly Gly Thr Val Thr
50 55 60

Leu Thr Cys Arg Ser Ser Thr Gly Ala Val Thr Thr Ser Asn Tyr Ala
65 70 75 80

Asn Trp Val Gln Gln Lys Pro Gly Gln Ala Pro Arg Gly Leu Ile Gly
85 90 95

Gly Thr Asn Lys Arg Ala Pro Gly Thr Pro Ala Arg Phe Ser Gly Ser
100 105 110

Leu Leu Gly Gly Lys Ala Ala Leu Thr Leu Ser Gly Val Gln Pro Glu
115 120 125

Asp Glu Ala Glu Tyr Tyr Cys Ala Leu Trp Tyr Ser Asn Leu Trp Val
130 135 140

Phe Gly Gly Gly Thr Lys Leu Thr Val Leu Gly Gln Pro Lys Ala Ala
145 150 155 160

Pro Ser Val Thr Leu Phe Pro Pro Ser Ser Glu Glu Leu Gln Ala Asn
165 170 175

Lys Ala Thr Leu Val Cys Leu Ile Ser Asp Phe Tyr Pro Gly Ala Val
180 185 190

Thr Val Ala Trp Lys Ala Asp Ser Ser Pro Val Lys Ala Gly Val Glu
195 200 205

Thr Thr Thr Pro Ser Lys Gln Ser Asn Asn Lys Tyr Ala Ala Ser Ser
210 215 220

Tyr Leu Ser Leu Thr Pro Glu Gln Trp Lys Ser His Arg Ser Tyr Ser
225 230 235 240

Cys Gln Val Thr His Glu Gly Ser Thr Val Glu Lys Thr Val Ala Pro
245 250 255

Thr Glu Cys Pro Pro Cys Ser Gly Gly Gly Ser Gln Val Gln Leu Gln
260 265 270

Glu Ser Gly Pro Gly Leu Val Lys Pro Ser Glu Thr Leu Ser Leu Thr
275 280 285

Cys Thr Val Ser Gly Gly Ser Val Ser Ser Gly Asp Tyr Tyr Trp Thr
290 295 300

Trp Ile Arg Gln Ser Pro Gly Lys Gly Leu Glu Trp Ile Gly His Ile
305 310 315 320

Tyr Tyr Ser Gly Asn Thr Asn Tyr Asn Pro Ser Leu Lys Ser Arg Leu
325 330 335

Thr Ile Ser Ile Asp Thr Ser Lys Thr Gln Phe Ser Leu Lys Leu Ser
340 345 350

Ser Val Thr Ala Ala Asp Thr Ala Ile Tyr Tyr Cys Val Arg Asp Arg
355 360 365

Val Thr Gly Ala Phe Asp Ile Trp Gly Gln Gly Thr Met Val Thr Val
370 375 380

Ser Ser Gly Gly Gly Gly Ser Gly Gly Gly Gly Ser Gly Gly Gly Gly
385 390 395 400

Ser Asp Ile Gln Met Thr Gln Ser Pro Ser Ser Leu Ser Ala Ser Val
405 410 415

Gly Asp Arg Val Thr Ile Thr Cys Gln Ala Ser Gln Asp Ile Ser Asn
420 425 430

Tyr Leu Asn Trp Tyr Gln Gln Lys Pro Gly Lys Ala Pro Lys Leu Leu
435 440 445

Ile Tyr Asp Ala Ser Asn Leu Glu Thr Gly Val Pro Ser Arg Phe Ser
450 455 460

Gly Ser Gly Ser Gly Thr Asp Phe Thr Phe Thr Ile Ser Ser Leu Gln
465 470 475 480

Pro Glu Asp Ile Ala Thr Tyr Phe Cys Gln His Phe Asp His Leu Pro
485 490 495

Leu Ala Phe Gly Gly Gly Thr Lys Val Glu Ile Lys
500 505

<210> SEQ ID NO 134
<211> LENGTH: 1072
<212> TYPE: PRT
<213> ORGANISM: Artificial Sequence
<220> FEATURE:
<223> OTHER INFORMATION: HC polypeptide

<400> SEQUENCE: 134

Glu Val Ala His Arg Phe Lys Asp Leu Gly Glu Glu Asn Phe Lys Ala
1 5 10 15

Leu Val Leu Ile Ala Phe Ala Gln Tyr Leu Gln Gln Cys Pro Phe Glu
20 25 30

Asp His Val Lys Leu Val Asn Glu Val Thr Glu Phe Ala Lys Thr Cys
35 40 45

Val Ala Asp Glu Ser Ala Glu Asn Cys Asp Lys Ser Leu His Thr Leu
50 55 60

Phe Gly Asp Lys Leu Cys Thr Val Ala Thr Leu Arg Glu Thr Tyr Gly
65 70 75 80

Glu Met Ala Asp Cys Cys Ala Lys Gln Glu Pro Glu Arg Asn Glu Cys
85 90 95

Phe Leu Gln His Lys Asp Asp Asn Pro Asn Leu Pro Arg Leu Val Arg
100 105 110

Pro Glu Val Asp Val Met Cys Thr Ala Phe His Asp Asn Glu Glu Thr
115 120 125

Phe Leu Lys Lys Tyr Leu Tyr Glu Ile Ala Arg Arg His Pro Tyr Phe
130 135 140

Tyr Ala Pro Glu Leu Leu Phe Phe Ala Lys Arg Tyr Lys Ala Ala Phe
145 150 155 160

Thr Glu Cys Cys Gln Ala Ala Asp Lys Ala Ala Cys Leu Leu Pro Lys
165 170 175

Leu Asp Glu Leu Arg Asp Glu Gly Lys Ala Ser Ser Ala Lys Gln Arg
180 185 190

Leu Lys Cys Ala Ser Leu Gln Lys Phe Gly Glu Arg Ala Phe Lys Ala
195 200 205

Trp Ala Val Ala Arg Leu Ser Gln Arg Phe Pro Lys Ala Glu Phe Ala
210 215 220

Glu Val Ser Lys Leu Val Thr Asp Leu Thr Lys Val His Thr Glu Cys
225 230 235 240

Cys His Gly Asp Leu Leu Glu Cys Ala Asp Asp Arg Ala Asp Leu Ala
245 250 255

```
Lys Tyr Ile Cys Glu Asn Gln Asp Ser Ile Ser Ser Lys Leu Lys Glu
            260                 265                 270

Cys Cys Glu Lys Pro Leu Leu Glu Lys Ser His Cys Ile Ala Glu Val
        275                 280                 285

Glu Asn Asp Glu Met Pro Ala Asp Leu Pro Ser Leu Ala Ala Asp Phe
    290                 295                 300

Val Glu Ser Lys Asp Val Cys Lys Asn Tyr Ala Glu Ala Lys Asp Val
305                 310                 315                 320

Phe Leu Gly Met Phe Leu Tyr Glu Tyr Ala Arg Arg His Pro Asp Tyr
                325                 330                 335

Ser Val Val Leu Leu Leu Arg Leu Ala Lys Thr Tyr Glu Thr Thr Leu
            340                 345                 350

Glu Lys Cys Cys Ala Ala Ala Asp Pro His Glu Cys Tyr Ala Lys Val
        355                 360                 365

Phe Asp Glu Phe Lys Pro Leu Val Glu Glu Pro Gln Asn Leu Ile Lys
    370                 375                 380

Gln Asn Cys Glu Leu Phe Glu Gln Leu Gly Glu Tyr Lys Phe Gln Asn
385                 390                 395                 400

Ala Leu Leu Val Arg Tyr Thr Lys Lys Val Pro Gln Val Ser Thr Pro
                405                 410                 415

Thr Leu Val Glu Val Ser Arg Asn Leu Gly Lys Val Gly Ser Lys Cys
            420                 425                 430

Cys Lys His Pro Glu Ala Lys Arg Met Pro Cys Ala Glu Asp Tyr Leu
        435                 440                 445

Ser Val Val Leu Asn Gln Leu Cys Val Leu His Glu Lys Thr Pro Val
    450                 455                 460

Ser Asp Arg Val Thr Lys Cys Cys Thr Glu Ser Leu Val Asn Arg Arg
465                 470                 475                 480

Pro Cys Phe Ser Ala Leu Glu Val Asp Glu Thr Tyr Val Pro Lys Glu
                485                 490                 495

Phe Asn Ala Glu Thr Phe Thr Phe His Ala Asp Ile Cys Thr Leu Ser
            500                 505                 510

Glu Lys Glu Arg Gln Ile Lys Lys Gln Thr Ala Leu Val Glu Leu Val
        515                 520                 525

Lys His Lys Pro Lys Ala Thr Lys Glu Gln Leu Lys Ala Val Met Asp
    530                 535                 540

Asp Phe Ala Ala Phe Val Glu Lys Cys Cys Lys Ala Asp Asp Lys Glu
545                 550                 555                 560

Thr Cys Phe Ala Glu Glu Gly Lys Lys Leu Val Ala Ala Ser Gln Ala
                565                 570                 575

Ala Gly Gly Ser Gly Gly Ser Gly Gly Ser Gly Gly Ser Gly Gly Ser
            580                 585                 590

Gly Gly Ser Glu Val Gln Leu Val Glu Ser Gly Gly Gly Leu Val Gln
        595                 600                 605

Pro Gly Gly Ser Leu Arg Leu Ser Cys Ala Ala Ser Gly Phe Thr Phe
    610                 615                 620

Asn Thr Tyr Ala Met Asn Trp Val Arg Gln Ala Pro Gly Lys Gly Leu
625                 630                 635                 640

Glu Trp Val Ala Arg Ile Arg Ser Lys Tyr Asn Asn Tyr Ala Thr Tyr
                645                 650                 655

Tyr Ala Asp Ser Val Lys Asp Arg Phe Thr Ile Ser Arg Asp Asp Ser
            660                 665                 670
```

```
Lys Asn Thr Leu Tyr Leu Gln Met Asn Ser Leu Arg Ala Glu Asp Thr
        675                 680                 685

Ala Val Tyr Tyr Cys Val Arg His Gly Asn Phe Gly Asn Ser Tyr Val
    690                 695                 700

Ser Trp Phe Ala Tyr Trp Gly Gln Gly Thr Met Val Thr Val Ser Ser
705                 710                 715                 720

Ala Ser Thr Lys Gly Pro Ser Val Phe Pro Leu Ala Pro Ser Ser Lys
                725                 730                 735

Ser Thr Ser Gly Gly Thr Ala Ala Leu Gly Cys Leu Val Lys Asp Tyr
            740                 745                 750

Phe Pro Glu Pro Val Thr Val Ser Trp Asn Ser Gly Ala Leu Thr Ser
        755                 760                 765

Gly Val His Thr Phe Pro Ala Val Leu Gln Ser Ser Gly Leu Tyr Ser
    770                 775                 780

Leu Ser Ser Val Val Thr Val Pro Ser Ser Ser Leu Gly Thr Gln Thr
785                 790                 795                 800

Tyr Ile Cys Asn Val Asn His Lys Pro Ser Asn Thr Lys Val Asp Lys
                805                 810                 815

Arg Val Glu Pro Lys Ser Cys Pro Pro Cys Gly Gly Gly Gly Ser Asp
            820                 825                 830

Ile Gln Met Thr Gln Ser Pro Ser Ser Leu Ser Ala Ser Val Gly Asp
        835                 840                 845

Arg Val Thr Ile Thr Cys Gln Ala Ser Gln Asp Ile Ser Asn Tyr Leu
    850                 855                 860

Asn Trp Tyr Gln Gln Lys Pro Gly Lys Ala Pro Lys Leu Leu Ile Tyr
865                 870                 875                 880

Asp Ala Ser Asn Leu Glu Thr Gly Val Pro Ser Arg Phe Ser Gly Ser
                885                 890                 895

Gly Ser Gly Thr Asp Phe Thr Phe Thr Ile Ser Ser Leu Gln Pro Glu
            900                 905                 910

Asp Ile Ala Thr Tyr Phe Cys Gln His Phe Asp His Leu Pro Leu Ala
        915                 920                 925

Phe Gly Gly Gly Thr Lys Val Glu Ile Lys Gly Gly Gly Gly Ser Gly
    930                 935                 940

Gly Gly Gly Ser Gly Gly Gly Gly Ser Gln Val Gln Leu Gln Glu Ser
945                 950                 955                 960

Gly Pro Gly Leu Val Lys Pro Ser Glu Thr Leu Ser Leu Thr Cys Thr
                965                 970                 975

Val Ser Gly Gly Ser Val Ser Ser Gly Asp Tyr Tyr Trp Thr Trp Ile
            980                 985                 990

Arg Gln Ser Pro Gly Lys Gly Leu  Glu Trp Ile Gly His  Ile Tyr Tyr
        995                 1000                1005

Ser Gly  Asn Thr Asn Tyr Asn  Pro Ser Leu Lys Ser  Arg Leu Thr
    1010                1015                1020

Ile Ser  Ile Asp Thr Ser Lys  Thr Gln Phe Ser Leu  Lys Leu Ser
    1025                1030                1035

Ser Val  Thr Ala Ala Asp Thr  Ala Ile Tyr Tyr Cys  Val Arg Asp
    1040                1045                1050

Arg Val  Thr Gly Ala Phe Asp  Ile Trp Gly Gln Gly  Thr Met Val
    1055                1060                1065

Thr Val  Ser Ser
    1070
```

<210> SEQ ID NO 135
<211> LENGTH: 508
<212> TYPE: PRT
<213> ORGANISM: Artificial Sequence
<220> FEATURE:
<223> OTHER INFORMATION: LC polypeptide

<400> SEQUENCE: 135

Gln Asp Gly Asn Glu Glu Met Gly Gly Ile Thr Gln Thr Pro Tyr Lys
1               5                   10                  15

Val Ser Ile Ser Gly Thr Thr Val Ile Leu Thr Gly Gly Ser Gly Gly
            20                  25                  30

Ser Gly Gly Ser Gly Gly Ser Gly Gly Ser Gly Gly Ser Gln Ala Val
        35                  40                  45

Val Thr Gln Glu Pro Ser Leu Thr Val Ser Pro Gly Gly Thr Val Thr
    50                  55                  60

Leu Thr Cys Arg Ser Ser Thr Gly Ala Val Thr Thr Ser Asn Tyr Ala
65                  70                  75                  80

Asn Trp Val Gln Gln Lys Pro Gly Gln Ala Pro Arg Gly Leu Ile Gly
                85                  90                  95

Gly Thr Asn Lys Arg Ala Pro Gly Thr Pro Ala Arg Phe Ser Gly Ser
            100                 105                 110

Leu Leu Gly Gly Lys Ala Ala Leu Thr Leu Ser Gly Val Gln Pro Glu
        115                 120                 125

Asp Glu Ala Glu Tyr Tyr Cys Ala Leu Trp Tyr Ser Asn Leu Trp Val
    130                 135                 140

Phe Gly Gly Gly Thr Lys Leu Thr Val Leu Gly Gln Pro Lys Ala Ala
145                 150                 155                 160

Pro Ser Val Thr Leu Phe Pro Pro Ser Ser Glu Glu Leu Gln Ala Asn
                165                 170                 175

Lys Ala Thr Leu Val Cys Leu Ile Ser Asp Phe Tyr Pro Gly Ala Val
            180                 185                 190

Thr Val Ala Trp Lys Ala Asp Ser Ser Pro Val Lys Ala Gly Val Glu
        195                 200                 205

Thr Thr Thr Pro Ser Lys Gln Ser Asn Asn Lys Tyr Ala Ala Ser Ser
    210                 215                 220

Tyr Leu Ser Leu Thr Pro Glu Gln Trp Lys Ser His Arg Ser Tyr Ser
225                 230                 235                 240

Cys Gln Val Thr His Glu Gly Ser Thr Val Glu Lys Thr Val Ala Pro
                245                 250                 255

Thr Glu Cys Pro Pro Cys Ser Gly Gly Gly Ser Asp Ile Gln Met Thr
            260                 265                 270

Gln Ser Pro Ser Ser Leu Ser Ala Ser Val Gly Asp Arg Val Thr Ile
        275                 280                 285

Thr Cys Gln Ala Ser Gln Asp Ile Ser Asn Tyr Leu Asn Trp Tyr Gln
    290                 295                 300

Gln Lys Pro Gly Lys Ala Pro Lys Leu Leu Ile Tyr Asp Ala Ser Asn
305                 310                 315                 320

Leu Glu Thr Gly Val Pro Ser Arg Phe Ser Gly Ser Gly Ser Gly Thr
                325                 330                 335

Asp Phe Thr Phe Thr Ile Ser Ser Leu Gln Pro Glu Asp Ile Ala Thr
            340                 345                 350

Tyr Phe Cys Gln His Phe Asp His Leu Pro Leu Ala Phe Gly Gly Gly
        355                 360                 365

Thr Lys Val Glu Ile Lys Gly Gly Gly Gly Ser Gly Gly Gly Gly Ser
370 375 380

Gly Gly Gly Gly Ser Gln Val Gln Leu Gln Glu Ser Gly Pro Gly Leu
385 390 395 400

Val Lys Pro Ser Glu Thr Leu Ser Leu Thr Cys Thr Val Ser Gly Gly
405 410 415

Ser Val Ser Ser Gly Asp Tyr Tyr Trp Thr Trp Ile Arg Gln Ser Pro
420 425 430

Gly Lys Gly Leu Glu Trp Ile Gly His Ile Tyr Tyr Ser Gly Asn Thr
435 440 445

Asn Tyr Asn Pro Ser Leu Lys Ser Arg Leu Thr Ile Ser Ile Asp Thr
450 455 460

Ser Lys Thr Gln Phe Ser Leu Lys Leu Ser Ser Val Thr Ala Ala Asp
465 470 475 480

Thr Ala Ile Tyr Tyr Cys Val Arg Asp Arg Val Thr Gly Ala Phe Asp
485 490 495

Ile Trp Gly Gln Gly Thr Met Val Thr Val Ser Ser
500 505

<210> SEQ ID NO 136
<211> LENGTH: 1072
<212> TYPE: PRT
<213> ORGANISM: Artificial Sequence
<220> FEATURE:
<223> OTHER INFORMATION: HC polypeptide

<400> SEQUENCE: 136

Glu Val Ala His Arg Phe Lys Asp Leu Gly Glu Glu Asn Phe Lys Ala
1 5 10 15

Leu Val Leu Ile Ala Phe Ala Gln Tyr Leu Gln Gln Cys Pro Phe Glu
20 25 30

Asp His Val Lys Leu Val Asn Glu Val Thr Glu Phe Ala Lys Thr Cys
35 40 45

Val Ala Asp Glu Ser Ala Glu Asn Cys Asp Lys Ser Leu His Thr Leu
50 55 60

Phe Gly Asp Lys Leu Cys Thr Val Ala Thr Leu Arg Glu Thr Tyr Gly
65 70 75 80

Glu Met Ala Asp Cys Cys Ala Lys Gln Glu Pro Glu Arg Asn Glu Cys
85 90 95

Phe Leu Gln His Lys Asp Asp Asn Pro Asn Leu Pro Arg Leu Val Arg
100 105 110

Pro Glu Val Asp Val Met Cys Thr Ala Phe His Asp Asn Glu Glu Thr
115 120 125

Phe Leu Lys Lys Tyr Leu Tyr Glu Ile Ala Arg Arg His Pro Tyr Phe
130 135 140

Tyr Ala Pro Glu Leu Leu Phe Phe Ala Lys Arg Tyr Lys Ala Ala Phe
145 150 155 160

Thr Glu Cys Cys Gln Ala Ala Asp Lys Ala Ala Cys Leu Leu Pro Lys
165 170 175

Leu Asp Glu Leu Arg Asp Glu Gly Lys Ala Ser Ser Ala Lys Gln Arg
180 185 190

Leu Lys Cys Ala Ser Leu Gln Lys Phe Gly Glu Arg Ala Phe Lys Ala
195 200 205

Trp Ala Val Ala Arg Leu Ser Gln Arg Phe Pro Lys Ala Glu Phe Ala
210 215 220

```
Glu Val Ser Lys Leu Val Thr Asp Leu Thr Lys Val His Thr Glu Cys
225                 230                 235                 240

Cys His Gly Asp Leu Leu Glu Cys Ala Asp Asp Arg Ala Asp Leu Ala
                245                 250                 255

Lys Tyr Ile Cys Glu Asn Gln Asp Ser Ile Ser Ser Lys Leu Lys Glu
            260                 265                 270

Cys Cys Glu Lys Pro Leu Leu Glu Lys Ser His Cys Ile Ala Glu Val
        275                 280                 285

Glu Asn Asp Glu Met Pro Ala Asp Leu Pro Ser Leu Ala Ala Asp Phe
    290                 295                 300

Val Glu Ser Lys Asp Val Cys Lys Asn Tyr Ala Glu Ala Lys Asp Val
305                 310                 315                 320

Phe Leu Gly Met Phe Leu Tyr Glu Tyr Ala Arg Arg His Pro Asp Tyr
                325                 330                 335

Ser Val Val Leu Leu Leu Arg Leu Ala Lys Thr Tyr Glu Thr Thr Leu
            340                 345                 350

Glu Lys Cys Cys Ala Ala Ala Asp Pro His Glu Cys Tyr Ala Lys Val
        355                 360                 365

Phe Asp Glu Phe Lys Pro Leu Val Glu Glu Pro Gln Asn Leu Ile Lys
    370                 375                 380

Gln Asn Cys Glu Leu Phe Glu Gln Leu Gly Glu Tyr Lys Phe Gln Asn
385                 390                 395                 400

Ala Leu Leu Val Arg Tyr Thr Lys Lys Val Pro Gln Val Ser Thr Pro
                405                 410                 415

Thr Leu Val Glu Val Ser Arg Asn Leu Gly Lys Val Gly Ser Lys Cys
            420                 425                 430

Cys Lys His Pro Glu Ala Lys Arg Met Pro Cys Ala Glu Asp Tyr Leu
        435                 440                 445

Ser Val Val Leu Asn Gln Leu Cys Val Leu His Glu Lys Thr Pro Val
    450                 455                 460

Ser Asp Arg Val Thr Lys Cys Cys Thr Glu Ser Leu Val Asn Arg Arg
465                 470                 475                 480

Pro Cys Phe Ser Ala Leu Glu Val Asp Glu Thr Tyr Val Pro Lys Glu
                485                 490                 495

Phe Asn Ala Glu Thr Phe Thr Phe His Ala Asp Ile Cys Thr Leu Ser
            500                 505                 510

Glu Lys Glu Arg Gln Ile Lys Lys Gln Thr Ala Leu Val Glu Leu Val
        515                 520                 525

Lys His Lys Pro Lys Ala Thr Lys Glu Gln Leu Lys Ala Val Met Asp
    530                 535                 540

Asp Phe Ala Ala Phe Val Glu Lys Cys Cys Lys Ala Asp Asp Lys Glu
545                 550                 555                 560

Thr Cys Phe Ala Glu Glu Gly Lys Lys Leu Val Ala Ala Ser Gln Ala
                565                 570                 575

Ala Gly Gly Ser Gly Gly Ser Gly Gly Ser Gly Gly Ser Gly Gly Ser
            580                 585                 590

Gly Gly Ser Glu Val Gln Leu Val Glu Ser Gly Gly Gly Leu Val Gln
        595                 600                 605

Pro Gly Gly Ser Leu Arg Leu Ser Cys Ala Ala Ser Gly Phe Thr Phe
    610                 615                 620

Asn Thr Tyr Ala Met Asn Trp Val Arg Gln Ala Pro Gly Lys Gly Leu
625                 630                 635                 640
```

```
Glu Trp Val Ala Arg Ile Arg Ser Lys Tyr Asn Asn Tyr Ala Thr Tyr
                645                 650                 655

Tyr Ala Asp Ser Val Lys Asp Arg Phe Thr Ile Ser Arg Asp Asp Ser
            660                 665                 670

Lys Asn Thr Leu Tyr Leu Gln Met Asn Ser Leu Arg Ala Glu Asp Thr
        675                 680                 685

Ala Val Tyr Tyr Cys Val Arg His Gly Asn Phe Gly Asn Ser Tyr Val
    690                 695                 700

Ser Trp Phe Ala Tyr Trp Gly Gln Gly Thr Met Val Thr Val Ser Ser
705                 710                 715                 720

Ala Ser Thr Lys Gly Pro Ser Val Phe Pro Leu Ala Pro Ser Ser Lys
                725                 730                 735

Ser Thr Ser Gly Gly Thr Ala Ala Leu Gly Cys Leu Val Lys Asp Tyr
            740                 745                 750

Phe Pro Glu Pro Val Thr Val Ser Trp Asn Ser Gly Ala Leu Thr Ser
        755                 760                 765

Gly Val His Thr Phe Pro Ala Val Leu Gln Ser Ser Gly Leu Tyr Ser
    770                 775                 780

Leu Ser Ser Val Val Thr Val Pro Ser Ser Ser Leu Gly Thr Gln Thr
785                 790                 795                 800

Tyr Ile Cys Asn Val Asn His Lys Pro Ser Asn Thr Lys Val Asp Lys
                805                 810                 815

Arg Val Glu Pro Lys Ser Cys Pro Pro Cys Gly Gly Gly Gly Ser Gln
            820                 825                 830

Val Gln Leu Gln Glu Ser Gly Pro Gly Leu Val Lys Pro Ser Glu Thr
        835                 840                 845

Leu Ser Leu Thr Cys Thr Val Ser Gly Gly Ser Val Ser Ser Gly Asp
    850                 855                 860

Tyr Tyr Trp Thr Trp Ile Arg Gln Ser Pro Gly Lys Gly Leu Glu Trp
865                 870                 875                 880

Ile Gly His Ile Tyr Tyr Ser Gly Asn Thr Asn Tyr Asn Pro Ser Leu
                885                 890                 895

Lys Ser Arg Leu Thr Ile Ser Ile Asp Thr Ser Lys Thr Gln Phe Ser
            900                 905                 910

Leu Lys Leu Ser Ser Val Thr Ala Ala Asp Thr Ala Ile Tyr Tyr Cys
        915                 920                 925

Val Arg Asp Arg Val Thr Gly Ala Phe Asp Ile Trp Gly Gln Gly Thr
    930                 935                 940

Met Val Thr Val Ser Ser Gly Gly Gly Gly Ser Gly Gly Gly Gly Ser
945                 950                 955                 960

Gly Gly Gly Gly Ser Asp Ile Gln Met Thr Gln Ser Pro Ser Ser Leu
                965                 970                 975

Ser Ala Ser Val Gly Asp Arg Val Thr Ile Thr Cys Gln Ala Ser Gln
            980                 985                 990

Asp Ile Ser Asn Tyr Leu Asn Trp  Tyr Gln Gln Lys Pro  Gly Lys Ala
        995                 1000                1005

Pro Lys  Leu Leu Ile Tyr Asp  Ala Ser Asn Leu Glu  Thr Gly Val
    1010                1015                1020

Pro Ser  Arg Phe Ser Gly Ser  Gly Ser Gly Thr Asp  Phe Thr Phe
    1025                1030                1035

Thr Ile  Ser Ser Leu Gln Pro  Glu Asp Ile Ala Thr  Tyr Phe Cys
    1040                1045                1050
```

```
Gln His  Phe Asp His Leu Pro  Leu Ala Phe Gly Gly  Gly Thr Lys
    1055                1060                1065

Val Glu  Ile Lys
    1070


<210> SEQ ID NO 137
<211> LENGTH: 508
<212> TYPE: PRT
<213> ORGANISM: Artificial Sequence
<220> FEATURE:
<223> OTHER INFORMATION: LC polypeptide

<400> SEQUENCE: 137

Gln Asp Gly Asn Glu Glu Met Gly Gly Ile Thr Gln Thr Pro Tyr Lys
1               5                   10                  15

Val Ser Ile Ser Gly Thr Thr Val Ile Leu Thr Gly Gly Ser Gly Gly
            20                  25                  30

Ser Gly Gly Ser Gly Gly Ser Gly Gly Ser Gly Gly Ser Gln Ala Val
        35                  40                  45

Val Thr Gln Glu Pro Ser Leu Thr Val Ser Pro Gly Gly Thr Val Thr
    50                  55                  60

Leu Thr Cys Arg Ser Ser Thr Gly Ala Val Thr Thr Ser Asn Tyr Ala
65                  70                  75                  80

Asn Trp Val Gln Gln Lys Pro Gly Gln Ala Pro Arg Gly Leu Ile Gly
                85                  90                  95

Gly Thr Asn Lys Arg Ala Pro Gly Thr Pro Ala Arg Phe Ser Gly Ser
            100                 105                 110

Leu Leu Gly Gly Lys Ala Ala Leu Thr Leu Ser Gly Val Gln Pro Glu
        115                 120                 125

Asp Glu Ala Glu Tyr Tyr Cys Ala Leu Trp Tyr Ser Asn Leu Trp Val
    130                 135                 140

Phe Gly Gly Gly Thr Lys Leu Thr Val Leu Gly Gln Pro Lys Ala Ala
145                 150                 155                 160

Pro Ser Val Thr Leu Phe Pro Pro Ser Ser Glu Glu Leu Gln Ala Asn
                165                 170                 175

Lys Ala Thr Leu Val Cys Leu Ile Ser Asp Phe Tyr Pro Gly Ala Val
            180                 185                 190

Thr Val Ala Trp Lys Ala Asp Ser Ser Pro Val Lys Ala Gly Val Glu
        195                 200                 205

Thr Thr Thr Pro Ser Lys Gln Ser Asn Asn Lys Tyr Ala Ala Ser Ser
    210                 215                 220

Tyr Leu Ser Leu Thr Pro Glu Gln Trp Lys Ser His Arg Ser Tyr Ser
225                 230                 235                 240

Cys Gln Val Thr His Glu Gly Ser Thr Val Glu Lys Thr Val Ala Pro
                245                 250                 255

Thr Glu Cys Pro Pro Cys Ser Gly Gly Gly Ser Gln Val Gln Leu Gln
            260                 265                 270

Glu Ser Gly Pro Gly Leu Val Lys Pro Ser Glu Thr Leu Ser Leu Thr
        275                 280                 285

Cys Thr Val Ser Gly Gly Ser Val Ser Ser Gly Asp Tyr Tyr Trp Thr
    290                 295                 300

Trp Ile Arg Gln Ser Pro Gly Lys Gly Leu Glu Trp Ile Gly His Ile
305                 310                 315                 320

Tyr Tyr Ser Gly Asn Thr Asn Tyr Asn Pro Ser Leu Lys Ser Arg Leu
                325                 330                 335
```

Thr Ile Ser Ile Asp Thr Ser Lys Thr Gln Phe Ser Leu Lys Leu Ser
340 345 350

Ser Val Thr Ala Ala Asp Thr Ala Ile Tyr Tyr Cys Val Arg Asp Arg
355 360 365

Val Thr Gly Ala Phe Asp Ile Trp Gly Gln Gly Thr Met Val Thr Val
370 375 380

Ser Ser Gly Gly Gly Gly Ser Gly Gly Gly Gly Ser Gly Gly Gly Gly
385 390 395 400

Ser Asp Ile Gln Met Thr Gln Ser Pro Ser Ser Leu Ser Ala Ser Val
405 410 415

Gly Asp Arg Val Thr Ile Thr Cys Gln Ala Ser Gln Asp Ile Ser Asn
420 425 430

Tyr Leu Asn Trp Tyr Gln Gln Lys Pro Gly Lys Ala Pro Lys Leu Leu
435 440 445

Ile Tyr Asp Ala Ser Asn Leu Glu Thr Gly Val Pro Ser Arg Phe Ser
450 455 460

Gly Ser Gly Ser Gly Thr Asp Phe Thr Phe Thr Ile Ser Ser Leu Gln
465 470 475 480

Pro Glu Asp Ile Ala Thr Tyr Phe Cys Gln His Phe Asp His Leu Pro
485 490 495

Leu Ala Phe Gly Gly Gly Thr Lys Val Glu Ile Lys
500 505

<210> SEQ ID NO 138
<211> LENGTH: 483
<212> TYPE: PRT
<213> ORGANISM: Artificial Sequence
<220> FEATURE:
<223> OTHER INFORMATION: HC polypeptide

<400> SEQUENCE: 138

Gly Gly Ser Gly Gly Ser Glu Val Gln Leu Val Glu Ser Gly Gly Gly
1 5 10 15

Leu Val Gln Pro Gly Gly Ser Leu Arg Leu Ser Cys Ala Ala Ser Gly
20 25 30

Phe Thr Phe Asn Thr Tyr Ala Met Asn Trp Val Arg Gln Ala Pro Gly
35 40 45

Lys Gly Leu Glu Trp Val Ala Arg Ile Arg Ser Lys Tyr Asn Asn Tyr
50 55 60

Ala Thr Tyr Tyr Ala Asp Ser Val Lys Asp Arg Phe Thr Ile Ser Arg
65 70 75 80

Asp Asp Ser Lys Asn Thr Leu Tyr Leu Gln Met Asn Ser Leu Arg Ala
85 90 95

Glu Asp Thr Ala Val Tyr Tyr Cys Val Arg His Gly Asn Phe Gly Asn
100 105 110

Ser Tyr Val Ser Trp Phe Ala Tyr Trp Gly Gln Gly Thr Met Val Thr
115 120 125

Val Ser Ser Ala Ser Thr Lys Gly Pro Ser Val Phe Pro Leu Ala Pro
130 135 140

Ser Ser Lys Ser Thr Ser Gly Gly Thr Ala Ala Leu Gly Cys Leu Val
145 150 155 160

Lys Asp Tyr Phe Pro Glu Pro Val Thr Val Ser Trp Asn Ser Gly Ala
165 170 175

Leu Thr Ser Gly Val His Thr Phe Pro Ala Val Leu Gln Ser Ser Gly
180 185 190

Leu Tyr Ser Leu Ser Ser Val Val Thr Val Pro Ser Ser Ser Leu Gly
195 200 205

Thr Gln Thr Tyr Ile Cys Asn Val Asn His Lys Pro Ser Asn Thr Lys
210 215 220

Val Asp Lys Arg Val Glu Pro Lys Ser Cys Pro Pro Cys Gly Gly Gly
225 230 235 240

Gly Ser Asp Ile Gln Met Thr Gln Ser Pro Ser Ser Leu Ser Ala Ser
245 250 255

Val Gly Asp Arg Val Thr Ile Thr Cys Gln Ala Ser Gln Asp Ile Ser
260 265 270

Asn Tyr Leu Asn Trp Tyr Gln Gln Lys Pro Gly Lys Ala Pro Lys Leu
275 280 285

Leu Ile Tyr Asp Ala Ser Asn Leu Glu Thr Gly Val Pro Ser Arg Phe
290 295 300

Ser Gly Ser Gly Ser Gly Thr Asp Phe Thr Phe Thr Ile Ser Ser Leu
305 310 315 320

Gln Pro Glu Asp Ile Ala Thr Tyr Phe Cys Gln His Phe Asp His Leu
325 330 335

Pro Leu Ala Phe Gly Gly Gly Thr Lys Val Glu Ile Lys Gly Gly Gly
340 345 350

Gly Ser Gly Gly Gly Gly Ser Gly Gly Gly Gly Ser Gln Val Gln Leu
355 360 365

Gln Glu Ser Gly Pro Gly Leu Val Lys Pro Ser Glu Thr Leu Ser Leu
370 375 380

Thr Cys Thr Val Ser Gly Gly Ser Val Ser Ser Gly Asp Tyr Tyr Trp
385 390 395 400

Thr Trp Ile Arg Gln Ser Pro Gly Lys Gly Leu Glu Trp Ile Gly His
405 410 415

Ile Tyr Tyr Ser Gly Asn Thr Asn Tyr Asn Pro Ser Leu Lys Ser Arg
420 425 430

Leu Thr Ile Ser Ile Asp Thr Ser Lys Thr Gln Phe Ser Leu Lys Leu
435 440 445

Ser Ser Val Thr Ala Ala Asp Thr Ala Ile Tyr Tyr Cys Val Arg Asp
450 455 460

Arg Val Thr Gly Ala Phe Asp Ile Trp Gly Gln Gly Thr Met Val Thr
465 470 475 480

Val Ser Ser

<210> SEQ ID NO 139
<211> LENGTH: 469
<212> TYPE: PRT
<213> ORGANISM: Artificial Sequence
<220> FEATURE:
<223> OTHER INFORMATION: LC polypeptide

<400> SEQUENCE: 139

Gly Gly Ser Gly Gly Ser Gln Ala Val Val Thr Gln Glu Pro Ser Leu
1 5 10 15

Thr Val Ser Pro Gly Gly Thr Val Thr Leu Thr Cys Arg Ser Ser Thr
20 25 30

Gly Ala Val Thr Thr Ser Asn Tyr Ala Asn Trp Val Gln Gln Lys Pro
35 40 45

Gly Gln Ala Pro Arg Gly Leu Ile Gly Gly Thr Asn Lys Arg Ala Pro
50 55 60

-continued

```
Gly Thr Pro Ala Arg Phe Ser Gly Ser Leu Leu Gly Gly Lys Ala Ala
65                  70                  75                  80

Leu Thr Leu Ser Gly Val Gln Pro Glu Asp Glu Ala Glu Tyr Tyr Cys
                85                  90                  95

Ala Leu Trp Tyr Ser Asn Leu Trp Val Phe Gly Gly Gly Thr Lys Leu
            100                 105                 110

Thr Val Leu Gly Gln Pro Lys Ala Ala Pro Ser Val Thr Leu Phe Pro
        115                 120                 125

Pro Ser Ser Glu Glu Leu Gln Ala Asn Lys Ala Thr Leu Val Cys Leu
    130                 135                 140

Ile Ser Asp Phe Tyr Pro Gly Ala Val Thr Val Ala Trp Lys Ala Asp
145                 150                 155                 160

Ser Ser Pro Val Lys Ala Gly Val Glu Thr Thr Thr Pro Ser Lys Gln
                165                 170                 175

Ser Asn Asn Lys Tyr Ala Ala Ser Ser Tyr Leu Ser Leu Thr Pro Glu
            180                 185                 190

Gln Trp Lys Ser His Arg Ser Tyr Ser Cys Gln Val Thr His Glu Gly
        195                 200                 205

Ser Thr Val Glu Lys Thr Val Ala Pro Thr Glu Cys Pro Pro Cys Ser
    210                 215                 220

Gly Gly Gly Ser Asp Ile Gln Met Thr Gln Ser Pro Ser Ser Leu Ser
225                 230                 235                 240

Ala Ser Val Gly Asp Arg Val Thr Ile Thr Cys Gln Ala Ser Gln Asp
                245                 250                 255

Ile Ser Asn Tyr Leu Asn Trp Tyr Gln Gln Lys Pro Gly Lys Ala Pro
            260                 265                 270

Lys Leu Leu Ile Tyr Asp Ala Ser Asn Leu Glu Thr Gly Val Pro Ser
        275                 280                 285

Arg Phe Ser Gly Ser Gly Ser Gly Thr Asp Phe Thr Phe Thr Ile Ser
    290                 295                 300

Ser Leu Gln Pro Glu Asp Ile Ala Thr Tyr Phe Cys Gln His Phe Asp
305                 310                 315                 320

His Leu Pro Leu Ala Phe Gly Gly Gly Thr Lys Val Glu Ile Lys Gly
                325                 330                 335

Gly Gly Gly Ser Gly Gly Gly Gly Ser Gly Gly Gly Gly Ser Gln Val
            340                 345                 350

Gln Leu Gln Glu Ser Gly Pro Gly Leu Val Lys Pro Ser Glu Thr Leu
        355                 360                 365

Ser Leu Thr Cys Thr Val Ser Gly Gly Ser Val Ser Ser Gly Asp Tyr
    370                 375                 380

Tyr Trp Thr Trp Ile Arg Gln Ser Pro Gly Lys Gly Leu Glu Trp Ile
385                 390                 395                 400

Gly His Ile Tyr Tyr Ser Gly Asn Thr Asn Tyr Asn Pro Ser Leu Lys
                405                 410                 415

Ser Arg Leu Thr Ile Ser Ile Asp Thr Ser Lys Thr Gln Phe Ser Leu
            420                 425                 430

Lys Leu Ser Ser Val Thr Ala Ala Asp Thr Ala Ile Tyr Tyr Cys Val
        435                 440                 445

Arg Asp Arg Val Thr Gly Ala Phe Asp Ile Trp Gly Gln Gly Thr Met
    450                 455                 460

Val Thr Val Ser Ser
465
```

<210> SEQ ID NO 140
<211> LENGTH: 483
<212> TYPE: PRT
<213> ORGANISM: Artificial Sequence
<220> FEATURE:
<223> OTHER INFORMATION: HC polypeptide

<400> SEQUENCE: 140

Gly Gly Ser Gly Gly Ser Glu Val Gln Leu Val Glu Ser Gly Gly Gly
1 5 10 15

Leu Val Gln Pro Gly Gly Ser Leu Arg Leu Ser Cys Ala Ala Ser Gly
20 25 30

Phe Thr Phe Asn Thr Tyr Ala Met Asn Trp Val Arg Gln Ala Pro Gly
35 40 45

Lys Gly Leu Glu Trp Val Ala Arg Ile Arg Ser Lys Tyr Asn Asn Tyr
50 55 60

Ala Thr Tyr Tyr Ala Asp Ser Val Lys Asp Arg Phe Thr Ile Ser Arg
65 70 75 80

Asp Asp Ser Lys Asn Thr Leu Tyr Leu Gln Met Asn Ser Leu Arg Ala
85 90 95

Glu Asp Thr Ala Val Tyr Tyr Cys Val Arg His Gly Asn Phe Gly Asn
100 105 110

Ser Tyr Val Ser Trp Phe Ala Tyr Trp Gly Gln Gly Thr Met Val Thr
115 120 125

Val Ser Ser Ala Ser Thr Lys Gly Pro Ser Val Phe Pro Leu Ala Pro
130 135 140

Ser Ser Lys Ser Thr Ser Gly Gly Thr Ala Ala Leu Gly Cys Leu Val
145 150 155 160

Lys Asp Tyr Phe Pro Glu Pro Val Thr Val Ser Trp Asn Ser Gly Ala
165 170 175

Leu Thr Ser Gly Val His Thr Phe Pro Ala Val Leu Gln Ser Ser Gly
180 185 190

Leu Tyr Ser Leu Ser Ser Val Val Thr Val Pro Ser Ser Ser Leu Gly
195 200 205

Thr Gln Thr Tyr Ile Cys Asn Val Asn His Lys Pro Ser Asn Thr Lys
210 215 220

Val Asp Lys Arg Val Glu Pro Lys Ser Cys Pro Pro Cys Gly Gly Gly
225 230 235 240

Gly Ser Gln Val Gln Leu Gln Glu Ser Gly Pro Gly Leu Val Lys Pro
245 250 255

Ser Glu Thr Leu Ser Leu Thr Cys Thr Val Ser Gly Gly Ser Val Ser
260 265 270

Ser Gly Asp Tyr Tyr Trp Thr Trp Ile Arg Gln Ser Pro Gly Lys Gly
275 280 285

Leu Glu Trp Ile Gly His Ile Tyr Tyr Ser Gly Asn Thr Asn Tyr Asn
290 295 300

Pro Ser Leu Lys Ser Arg Leu Thr Ile Ser Ile Asp Thr Ser Lys Thr
305 310 315 320

Gln Phe Ser Leu Lys Leu Ser Ser Val Thr Ala Ala Asp Thr Ala Ile
325 330 335

Tyr Tyr Cys Val Arg Asp Arg Val Thr Gly Ala Phe Asp Ile Trp Gly
340 345 350

Gln Gly Thr Met Val Thr Val Ser Ser Gly Gly Gly Gly Ser Gly Gly
355 360 365

Gly Gly Ser Gly Gly Gly Gly Ser Asp Ile Gln Met Thr Gln Ser Pro
370 375 380

Ser Ser Leu Ser Ala Ser Val Gly Asp Arg Val Thr Ile Thr Cys Gln
385 390 395 400

Ala Ser Gln Asp Ile Ser Asn Tyr Leu Asn Trp Tyr Gln Gln Lys Pro
405 410 415

Gly Lys Ala Pro Lys Leu Leu Ile Tyr Asp Ala Ser Asn Leu Glu Thr
420 425 430

Gly Val Pro Ser Arg Phe Ser Gly Ser Gly Ser Gly Thr Asp Phe Thr
435 440 445

Phe Thr Ile Ser Ser Leu Gln Pro Glu Asp Ile Ala Thr Tyr Phe Cys
450 455 460

Gln His Phe Asp His Leu Pro Leu Ala Phe Gly Gly Gly Thr Lys Val
465 470 475 480

Glu Ile Lys

<210> SEQ ID NO 141
<211> LENGTH: 469
<212> TYPE: PRT
<213> ORGANISM: Artificial Sequence
<220> FEATURE:
<223> OTHER INFORMATION: LC polypeptide

<400> SEQUENCE: 141

Gly Gly Ser Gly Gly Ser Gln Ala Val Val Thr Gln Glu Pro Ser Leu
1 5 10 15

Thr Val Ser Pro Gly Gly Thr Val Thr Leu Thr Cys Arg Ser Ser Thr
20 25 30

Gly Ala Val Thr Thr Ser Asn Tyr Ala Asn Trp Val Gln Gln Lys Pro
35 40 45

Gly Gln Ala Pro Arg Gly Leu Ile Gly Gly Thr Asn Lys Arg Ala Pro
50 55 60

Gly Thr Pro Ala Arg Phe Ser Gly Ser Leu Leu Gly Gly Lys Ala Ala
65 70 75 80

Leu Thr Leu Ser Gly Val Gln Pro Glu Asp Glu Ala Glu Tyr Tyr Cys
85 90 95

Ala Leu Trp Tyr Ser Asn Leu Trp Val Phe Gly Gly Gly Thr Lys Leu
100 105 110

Thr Val Leu Gly Gln Pro Lys Ala Ala Pro Ser Val Thr Leu Phe Pro
115 120 125

Pro Ser Ser Glu Glu Leu Gln Ala Asn Lys Ala Thr Leu Val Cys Leu
130 135 140

Ile Ser Asp Phe Tyr Pro Gly Ala Val Thr Val Ala Trp Lys Ala Asp
145 150 155 160

Ser Ser Pro Val Lys Ala Gly Val Glu Thr Thr Thr Pro Ser Lys Gln
165 170 175

Ser Asn Asn Lys Tyr Ala Ala Ser Ser Tyr Leu Ser Leu Thr Pro Glu
180 185 190

Gln Trp Lys Ser His Arg Ser Tyr Ser Cys Gln Val Thr His Glu Gly
195 200 205

Ser Thr Val Glu Lys Thr Val Ala Pro Thr Glu Cys Pro Pro Cys Ser
210 215 220

Gly Gly Gly Ser Gln Val Gln Leu Gln Glu Ser Gly Pro Gly Leu Val
225 230 235 240

```
Lys Pro Ser Glu Thr Leu Ser Leu Thr Cys Thr Val Ser Gly Gly Ser
                245                 250                 255

Val Ser Ser Gly Asp Tyr Tyr Trp Thr Trp Ile Arg Gln Ser Pro Gly
            260                 265                 270

Lys Gly Leu Glu Trp Ile Gly His Ile Tyr Tyr Ser Gly Asn Thr Asn
        275                 280                 285

Tyr Asn Pro Ser Leu Lys Ser Arg Leu Thr Ile Ser Ile Asp Thr Ser
    290                 295                 300

Lys Thr Gln Phe Ser Leu Lys Leu Ser Ser Val Thr Ala Ala Asp Thr
305                 310                 315                 320

Ala Ile Tyr Tyr Cys Val Arg Asp Arg Val Thr Gly Ala Phe Asp Ile
                325                 330                 335

Trp Gly Gln Gly Thr Met Val Thr Val Ser Ser Gly Gly Gly Gly Ser
            340                 345                 350

Gly Gly Gly Gly Ser Gly Gly Gly Gly Ser Asp Ile Gln Met Thr Gln
        355                 360                 365

Ser Pro Ser Ser Leu Ser Ala Ser Val Gly Asp Arg Val Thr Ile Thr
    370                 375                 380

Cys Gln Ala Ser Gln Asp Ile Ser Asn Tyr Leu Asn Trp Tyr Gln Gln
385                 390                 395                 400

Lys Pro Gly Lys Ala Pro Lys Leu Leu Ile Tyr Asp Ala Ser Asn Leu
                405                 410                 415

Glu Thr Gly Val Pro Ser Arg Phe Ser Gly Ser Gly Ser Gly Thr Asp
            420                 425                 430

Phe Thr Phe Thr Ile Ser Ser Leu Gln Pro Glu Asp Ile Ala Thr Tyr
        435                 440                 445

Phe Cys Gln His Phe Asp His Leu Pro Leu Ala Phe Gly Gly Gly Thr
    450                 455                 460

Lys Val Glu Ile Lys
465
```

<210> SEQ ID NO 142
<211> LENGTH: 3219
<212> TYPE: DNA
<213> ORGANISM: Artificial Sequence
<220> FEATURE:
<223> OTHER INFORMATION: HC polypeptide

<400> SEQUENCE: 142

```
gaggtggccc acaggttcaa ggatctgggc gaggagaact tcaaggccct ggtgctgatc      60

gccttcgccc agtatctgca gcagtgcccc tttgaggacc acgtgaagct ggtgaacgag     120

gtgaccgagt tcgccaagac atgcgtggcc gacgagtccg ccgagaattg tgataagtct     180

ctgcacaccc tgtttggcga taagctgtgc accgtggcca cactgaggga gacatacggc     240

gagatggccg actgctgtgc caagcaggag cccgagcgca acgagtgctt cctgcagcac     300

aaggacgata accctaatct gccacggctg gtgagacctg aggtggacgt gatgtgcacc     360

gccttccacg ataatgagga gacatttctg aagaagtacc tgtatgagat cgcccggaga     420

cacccttact tttatgcccc agagctgctg ttctttgcca agcggtacaa ggcagccttc     480

accgagtgct gtcaggcagc agataaggca gcatgcctgc tgccaaagct ggacgagctg     540

agggatgagg gcaaggcaag ctccgccaag cagcgcctga agtgtgcaag cctgcagaag     600

ttcggagaga gggcctttaa ggcatgggca gtggcaaggc tgtcccagcg gttcccaaag     660

gccgagtttg ccgaggtgtc taagctggtg accgacctga caaaggtgca caccgagtgc     720
```

-continued

```
tgtcacggcg acctgctgga gtgcgcagac gatagagccg atctggccaa gtacatctgt    780
gagaaccagg actctatctc tagcaagctg aaggagtgct gtgagaagcc cctgctggag    840
aagtcccact gcatcgccga ggtggagaac gacgagatgc cagcagatct gccaagcctg    900
gcagcagact tcgtggagtc caaggacgtg tgcaagaatt acgccgaggc caaggacgtg    960
ttcctgggca tgtttctgta cgagtatgcc aggcgccacc ctgactactc cgtggtgctg   1020
ctgctgcggc tggccaagac ctatgagacc acactggaga agtgctgtgc cgccgccgac   1080
ccccacgagt gctatgcaaa ggtgttcgac gagtttaagc ccctggtgga ggagcctcag   1140
aacctgatca agcagaattg tgagctgttt gagcagctgg gcgagtacaa gttccagaac   1200
gccctgctgg tgagatatac caagaaggtg ccacaggtgt ctacccccac actggtggag   1260
gtgagccgga atctgggcaa ggtcggctcc aagtgctgta agcaccctga ggccaagaga   1320
atgccatgcg ccgaggatta cctgtccgtg gtgctgaacc agctgtgcgt gctgcacgag   1380
aagacccccg tgagcgacag ggtgaccaag tgctgtacag agtctctggt gaaccggaga   1440
ccatgcttta gcgccctgga ggtggatgag acatatgtgc ccaaggagtt caatgccgag   1500
accttcacat ttcacgccga catctgtacc ctgagcgaga aggagcgcca gatcaagaag   1560
cagacagccc tggtggagct ggtgaagcac aagccaaagg ccaccaagga gcagctgaag   1620
gccgtgatgg acgatttcgc cgcctttgtg gagaagtgct gtaaggccga cgataaggag   1680
acatgcttcg cagaggaggg caagaagctg gtggcagcaa gccaggcagc aggaggctcc   1740
ggcggctctc cactgggcct ggccggcggc ggcagcggcg gctccgaggt gcagctggtg   1800
gagtccggcg gcggcctggt gcagcccggc ggcagcctga ggctgtcctg cgccgcctct   1860
ggcttcacct ttaacacata cgcaatgaat tgggtgcgcc aggcaccagg caagggactg   1920
gagtgggtgg cccggatcag aagcaagtac aacaattatg ccacctacta tgccgactcc   1980
gtgaaggatc ggtttaccat cagcagagac gattccaaga acacactgta tctgcagatg   2040
aatagcctgc gggccgagga tacagccgtg tactattgcg tgagacacgg caactttggc   2100
aattcttacg tgagctggtt cgcctattgg ggccagggca ccatggtgac agtgtcctct   2160
gcctctacca agggacctag cgtgttccca ctggcaccta gctccaagtc taccagcgga   2220
ggcacagccg ccctgggatg tctggtgaag gactactttc cagagcccgt gacagtgtcc   2280
tggaactctg gcgccctgac cagcggagtg cacacattcc ctgccgtgct gcagtctagc   2340
ggcctgtact ccctgtcctc tgtggtgacc gtgccaagct cctctctggg cacccagaca   2400
tatatctgca acgtgaatca caagccctct aatacaaagg tggacaagag ggtggagcct   2460
aagagctgcc ccccttgtgg cggaggcggt agcgatatcc agatgaccca aagccccagt   2520
agcctgtccg ccagtgtagg agatagggta accatcactt gccaagcgag ccaagacatc   2580
agcaactacc tgaattggta tcagcagaag cccggcaaag cacccaagct cctgatctac   2640
gacgccagca atctggagac cggcgtgccc agcaggttca gcggatctgg tagcggcacc   2700
gacttcacct tcaccataag tagtctgcag cccgaggaca tcgccaccta cttctgtcag   2760
cacttcgatc acctgcccct ggccttcggc ggtgggacca aggtggagat caagggtggg   2820
ggtggcagcg ggggaggcgg aagcggcgga ggtggctctt gccaggtgca gcttcaagag   2880
agcggacccg gcctcgtgaa gcccagcgag accttgagcc tgacctgcac tgtgagtggc   2940
ggtagcgtga gcagcggcga ctattactgg acctggatca ggcagagccc tggcaagggg   3000
ctggagtgga tcggccacat ctactacagc gggaacacga actacaaccc cagcctgaag   3060
agcaggctga cgatcagcat cgacacgagc aagacccagt tctcacttaa gctcagcagc   3120
```

gtgaccgccg cagacaccgc catatactac tgcgtgaggg acagggtgac gggcgctttc 3180
gacatctggg gccaaggcac aatggtcacg gtgagctcc 3219

<210> SEQ ID NO 143
<211> LENGTH: 1524
<212> TYPE: DNA
<213> ORGANISM: Artificial Sequence
<220> FEATURE:
<223> OTHER INFORMATION: LC polypeptide

<400> SEQUENCE: 143
caggacggca acgaggagat gggcggcatc acccagacac catacaaggt gagcatctcc 60
ggcaccacag tgatcctgac cggaggctcc ggcggctctc cactgggcct ggccggcggc 120
ggcagcggcg gctcccaagc cgtggtaacc caggagccca gtctgacagt gagccctggc 180
ggtacagtga ccttgacttg caggagcagt accggagccg taactacctc aaactacgcc 240
aactgggtgc agcagaagcc cggtcaggcc cccaggggcc ttattggtgg gactaacaaa 300
cgagcacccg gaaccccgc aaggttcagc ggcagccttc tgggcggaaa ggccgctctc 360
acattgagcg gcgtgcagcc cgaggacgag gccgagtact actgcgccct gtggtacagc 420
aacctgtggg tgttcggcgg agggaccaag ctgaccgtgc tgggccagcc caaagctgcg 480
ccgagcgtga ccctgttccc cccgtcaagc gaggagctgc aggctaacaa ggccaccctg 540
gtgtgcctga ttagtgactt ctaccccggt gccgtcaccg tggcctggaa ggccgacagt 600
agcccagtta aagcgggcgt cgagaccacc actcccagca agcagagcaa caacaagtac 660
gccgcgagca gctacctgag tctgaccccc gagcagtgga agagccacag gagctacagc 720
tgccaggtga cccacgaggg cagcactgtg gagaagactg tggccccgac cgagtgcccc 780
ccatgtagcg gcggagggtc cgatatccag atgacccaaa gccccagtag cctgtccgcc 840
agtgtaggag atagggtaac catcacttgc caagcgagcc aagacatcag caactacctg 900
aattggtatc agcagaagcc cggcaaagca cccaagctcc tgatctacga cgccagcaat 960
ctggagaccg gcgtgcccag caggttcagc ggatctggta gcggcaccga cttcaccttc 1020
accataagta gtctgcagcc cgaggacatc gccacctact tctgtcagca cttcgatcac 1080
ctgcccctgg ccttcggcgg tgggaccaag gtggagatca agggtggggg tggcagcggg 1140
ggaggcggaa gcggcggagg tggctctcag gtgcagcttc aagagagcgg acccggcctc 1200
gtgaagccca gcgagacctt gagcctgacc tgcactgtga gtggcggtag cgtgagcagc 1260
ggcgactatt actggacctg gatcaggcag agccctggca aggggctgga gtggatcggc 1320
cacatctact acagcgggaa cacgaactac aaccccagcc tgaagagcag gctgacgatc 1380
agcatcgaca cgagcaagac ccagttctca cttaagctca gcagcgtgac cgccgcagac 1440
accgccatat actactgcgt gagggacagg gtgacgggcg ctttcgacat ctggggccaa 1500
ggcacaatgg tcacggtgag ctcc 1524

<210> SEQ ID NO 144
<211> LENGTH: 3216
<212> TYPE: DNA
<213> ORGANISM: Artificial Sequence
<220> FEATURE:
<223> OTHER INFORMATION: HC polypeptide

<400> SEQUENCE: 144
gaggtggccc acaggttcaa ggatctgggc gaggagaact tcaaggccct ggtgctgatc 60
gccttcgccc agtatctgca gcagtgcccc tttgaggacc acgtgaagct ggtgaacgag 120
gtgaccgagt tcgccaagac atgcgtggcc gacgagtccg ccgagaattg tgataagtct 180
ctgcacaccc tgtttggcga taagctgtgc accgtggcca cactgaggga gacatacggc 240
gagatggccg actgctgtgc caagcaggag cccgagcgca acgagtgctt cctgcagcac 300
aaggacgata accctaatct gccacggctg gtgagacctg aggtggacgt gatgtgcacc 360
gccttccacg ataatgagga gacatttctg aagaagtacc tgtatgagat cgcccggaga 420
cacccttact tttatgcccc agagctgctg ttctttgcca agcggtacaa ggcagccttc 480
accgagtgct gtcaggcagc agataaggca gcatgcctgc tgccaaagct ggacgagctg 540
agggatgagg gcaaggcaag ctccgccaag cagcgcctga agtgtgcaag cctgcagaag 600
ttcggagaga gggcctttaa ggcatgggca gtggcaaggc tgtcccagcg gttcccaaag 660
gccgagtttg ccgaggtgtc taagctggtg accgacctga caaaggtgca caccgagtgc 720
tgtcacggcg acctgctgga gtgcgcagac gatagagccg atctggccaa gtacatctgt 780
gagaaccagg actctatctc tagcaagctg aaggagtgct gtgagaagcc cctgctggag 840
aagtcccact gcatcgccga ggtggagaac gacgagatgc cagcagatct gccaagcctg 900
gcagcagact tcgtggagtc caaggacgtg tgcaagaatt acgccgaggc caaggacgtg 960
ttcctgggca tgtttctgta cgagtatgcc aggcgccacc ctgactactc cgtggtgctg 1020
ctgctgcggc tggccaagac ctatgagacc acactggaga agtgctgtgc cgccgccgac 1080
ccccacgagt gctatgcaaa ggtgttcgac gagtttaagc ccctggtgga ggagcctcag 1140
aacctgatca agcagaattg tgagctgttt gagcagctgg gcgagtacaa gttccagaac 1200
gccctgctgg tgagatatac caagaaggtg ccacaggtgt ctacccccac actggtggag 1260
gtgagccgga atctgggcaa ggtcggctcc aagtgctgta agcaccctga ggccaagaga 1320
atgccatgcg ccgaggatta cctgtccgtg gtgctgaacc agctgtgcgt gctgcacgag 1380
aagacccccg tgagcgacag ggtgaccaag tgctgtacag agtctctggt gaaccggaga 1440
ccatgcttta gcgccctgga ggtggatgag acatatgtgc ccaaggagtt caatgccgag 1500
accttcacat ttcacgccga catctgtacc ctgagcgaga aggagcgcca gatcaagaag 1560
cagacagccc tggtggagct ggtgaagcac aagccaaagg ccaccaagga gcagctgaag 1620
gccgtgatgg acgatttcgc cgcctttgtg gagaagtgct gtaaggccga cgataaggag 1680
acatgcttcg cagaggaggg caagaagctg gtggcagcaa gccaggcagc aggaggctcc 1740
ggcggctctc cactgggcct ggccggcggc ggcagcggcg gctccgaggt gcagctggtg 1800
gagtccggcg gcggcctggt gcagcccggc ggcagcctga ggctgtcctg cgccgcctct 1860
ggcttcacct ttaacacata cgcaatgaat tgggtgcgcc aggcaccagg caagggactg 1920
gagtgggtgg cccggatcag aagcaagtac aacaattatg ccacctacta tgccgactcc 1980
gtgaaggatc ggtttaccat cagcagagac gattccaaga acacactgta tctgcagatg 2040
aatagcctgc gggccgagga tacagccgtg tactattgcg tgagacacgg caactttggc 2100
aattcttacg tgagctggtt cgcctattgg ggccagggca ccatggtgac agtgtcctct 2160
gcctctacca agggacctag cgtgttccca ctggcaccta gctccaagtc taccagcgga 2220
ggcacagccg ccctgggatg tctggtgaag gactactttc cagagcccgt gacagtgtcc 2280
tggaactctg gcgccctgac cagcggagtg cacacattcc ctgccgtgct gcagtctagc 2340
ggcctgtact ccctgtcctc tgtggtgacc gtgccaagct cctctctggg cacccagaca 2400
tatatctgca acgtgaatca caagccctct aatacaaagg tggacaagag ggtggagcct 2460
aagagctgcc ccccttgtgg cggaggcggt agccaggtgc agcttcaaga gagcggaccc 2520
ggcctcgtga agcccagcga gaccttgagc ctgacctgca ctgtgagtgg cggtagcgtg 2580
agcagcggcg actattactg gacctggatc aggcagagcc ctggcaaggg gctggagtgg 2640
atcggccaca tctactacag cgggaacacg aactacaacc ccagcctgaa gagcaggctg 2700
acgatcagca tcgacacgag caagacccag ttctcactta agctcagcag cgtgaccgcc 2760
gcagacaccg ccatatacta ctgcgtgagg gacagggtga cgggcgcttt cgacatctgg 2820
ggccaaggca caatggtcac ggtgagctcc ggtgggggtg gcagcggggg aggcggaagc 2880
ggcggaggtg gctctgatat ccagatgacc caaagcccca gtagcctgtc cgccagtgta 2940
ggagataggg taaccatcac ttgccaagcg agccaagaca tcagcaacta cctgaattgg 3000
tatcagcaga agcccggcaa agcacccaag ctcctgatct acgacgccag caatctggag 3060
accggcgtgc ccagcaggtt cagcggatct ggtagcggca ccgacttcac cttcaccata 3120
agtagtctgc agcccgagga catcgccacc tacttctgtc agcacttcga tcacctgccc 3180
ctggccttcg gcggtgggac caaggtggag atcaag 3216

<210> SEQ ID NO 145
<211> LENGTH: 1524
<212> TYPE: DNA
<213> ORGANISM: Artificial Sequence
<220> FEATURE:
<223> OTHER INFORMATION: LC polypeptide

<400> SEQUENCE: 145
caggacggca acgaggagat gggcggcatc acccagacac catacaaggt gagcatctcc 60
ggcaccacag tgatcctgac cggaggctcc ggcggctctc cactgggcct ggccggcggc 120
ggcagcggcg gctcccaagc cgtggtaacc caggagccca gtctgacagt gagccctggc 180
ggtacagtga ccttgacttg caggagcagt accggagccg taactacctc aaactacgcc 240
aactgggtgc agcagaagcc cggtcaggcc cccaggggcc ttattggtgg gactaacaaa 300
cgagcacccg gaaccccccgc aaggttcagc ggcagccttc tgggcggaaa ggccgctctc 360
acattgagcg gcgtgcagcc cgaggacgag gccgagtact actgcgccct gtggtacagc 420
aacctgtggg tgttcggcgg agggaccaag ctgaccgtgc tgggccagcc caaagctgcg 480
ccgagcgtga ccctgttccc cccgtcaagc gaggagctgc aggctaacaa ggccaccctg 540
gtgtgcctga ttagtgactt ctaccccggt gccgtcaccg tggcctggaa ggccgacagt 600
agcccagtta aagcgggcgt cgagaccacc actcccagca agcagagcaa caacaagtac 660
gccgcgagca gctacctgag tctgaccccc gagcagtgga agagccacag gagctacagc 720
tgccaggtga cccacgaggg cagcactgtg gagaagactg tggcccccgac cgagtgcccc 780
ccatgtagcg gcggagggtc ccaggtgcag cttcaagaga gcggacccgg cctcgtgaag 840
cccagcgaga ccttgagcct gacctgcact gtgagtggcg gtagcgtgag cagcggcgac 900
tattactgga cctggatcag gcagagccct ggcaaggggc tggagtggat cggccacatc 960
tactacagcg ggaacacgaa ctacaacccc agcctgaaga gcaggctgac gatcagcatc 1020
gacacgagca agacccagtt ctcacttaag ctcagcagcg tgaccgccgc agacaccgcc 1080
atatactact gcgtgaggga cagggtgacg ggcgctttcg acatctgggg ccaaggcaca 1140
atggtcacgg tgagctccgg tgggggtggc agcgggggag gcggaagcgg cggaggtggc 1200
tctgatatcc agatgaccca aagccccagt agcctgtccg ccagtgtagg agatagggta 1260
accatcactt gccaagcgag ccaagacatc agcaactacc tgaattggta tcagcagaag 1320
cccggcaaag cacccaagct cctgatctac gacgccagca atctggagac cggcgtgccc 1380
agcaggttca gcggatctgg tagcggcacc gacttcacct tcaccataag tagtctgcag 1440
cccgaggaca tcgccaccta cttctgtcag cacttcgatc acctgcccct ggccttcggc 1500
ggtgggacca aggtggagat caag 1524

<210> SEQ ID NO 146
<211> LENGTH: 3216
<212> TYPE: DNA
<213> ORGANISM: Artificial Sequence
<220> FEATURE:
<223> OTHER INFORMATION: HC polypeptide

<400> SEQUENCE: 146
gaggtggccc acaggttcaa ggatctgggc gaggagaact tcaaggccct ggtgctgatc 60
gccttcgccc agtatctgca gcagtgcccc tttgaggacc acgtgaagct ggtgaacgag 120
gtgaccgagt tcgccaagac atgcgtggcc gacgagtccg ccgagaattg tgataagtct 180
ctgcacaccc tgtttggcga taagctgtgc accgtggcca cactgaggga gacatacggc 240
gagatggccg actgctgtgc caagcaggag cccgagcgca acgagtgctt cctgcagcac 300
aaggacgata accctaatct gccacggctg gtgagacctg aggtggacgt gatgtgcacc 360
gccttccacg ataatgagga gacatttctg aagaagtacc tgtatgagat cgcccggaga 420 caccccttact tttatgcccc agagctgctg ttctttgcca agcggtacaa ggcagccttc 480
accgagtgct gtcaggcagc agataaggca gcatgcctgc tgccaaagct ggacgagctg 540
agggatgagg gcaaggcaag ctccgccaag cagcgcctga agtgtgcaag cctgcagaag 600
ttcggagaga gggcctttaa ggcatgggca gtggcaaggc tgtcccagcg gttcccaaag 660
gccgagtttg ccgaggtgtc taagctggtg accgacctga caaaggtgca caccgagtgc 720
tgtcacggcg acctgctgga gtgcgcagac gatagagccg atctggccaa gtacatctgt 780
gagaaccagg actctatctc tagcaagctg aaggagtgct gtgagaagcc cctgctggag 840
aagtcccact gcatcgccga ggtggagaac gacgagatgc cagcagatct gccaagcctg 900
gcagcagact tcgtggagtc caaggacgtg tgcaagaatt acgccgaggc caaggacgtg 960
ttcctgggca tgtttctgta cgagtatgcc aggcgccacc ctgactactc cgtggtgctg 1020
ctgctgcggc tggccaagac ctatgagacc acactggaga agtgctgtgc cgccgccgac 1080
ccccacgagt gctatgcaaa ggtgttcgac gagtttaagc ccctggtgga ggagcctcag 1140
aacctgatca agcagaattg tgagctgttt gagcagctgg gcgagtacaa gttccagaac 1200
gccctgctgg tgagatatac caagaaggtg ccacaggtgt ctaccccccac actggtggag 1260 gtgagccgga atctgggcaa ggtcggctcc aagtgctgta agcaccctga ggccaagaga 1320
atgccatgcg ccgaggatta cctgtccgtg gtgctgaacc agctgtgcgt gctgcacgag 1380
aagacccccg tgagcgacag ggtgaccaag tgctgtacag agtctctggt gaaccggaga 1440
ccatgcttta gcgccctgga ggtggatgag acatatgtgc ccaaggagtt caatgccgag 1500
accttcacat ttcacgccga catctgtacc ctgagcgaga aggagcgcca gatcaagaag 1560
cagacagccc tggtggagct ggtgaagcac aagccaaagg ccaccaagga gcagctgaag 1620
gccgtgatgg acgatttcgc cgcctttgtg gagaagtgct gtaaggccga cgataaggag 1680
acatgcttcg cagaggaggg caagaagctg gtggcagcaa gccaggcagc aggaggctcc 1740
ggcggctctg gggcagcgg aggtagtggc ggcagcggcg gctccgaggt gcagctggtg 1800
gagtccggcg gcggcctggt gcagcccggc ggcagcctga ggctgtcctg cgccgcctct 1860
ggcttcacct ttaacacata cgcaatgaat tgggtgcgcc aggcaccagg caagggactg 1920
gagtgggtgg cccggatcag aagcaagtac aacaattatg ccacctacta tgccgactcc 1980
gtgaaggatc ggtttaccat cagcagagac gattccaaga acacactgta tctgcagatg 2040
aatagcctgc gggccgagga tacagccgtg tactattgcg tgagacacgg caactttggc 2100
aattcttacg tgagctggtt cgcctattgg ggccagggca ccatggtgac agtgtcctct 2160
gcctctacca agggacctag cgtgttccca ctggcaccta gctccaagtc taccagcgga 2220
ggcacagccg ccctgggatg tctggtgaag gactactttc cagagcccgt gacagtgtcc 2280
tggaactctg gcgccctgac cagcggagtg cacacattcc ctgccgtgct gcagtctagc 2340
ggcctgtact ccctgtcctc tgtggtgacc gtgccaagct cctctctggg cacccagaca 2400
tatatctgca acgtgaatca caagccctct aatacaaagg tggacaagag ggtggagcct 2460
aagagctgcc ccccttgtgg cggaggcggt agcgatatcc agatgaccca aagccccagt 2520
agcctgtccg ccagtgtagg agatagggta accatcactt gccaagcgag ccaagacatc 2580
agcaactacc tgaattggta tcagcagaag cccggcaaag cacccaagct cctgatctac 2640
gacgccagca atctggagac cggcgtgccc agcaggttca gcggatctgg tagcggcacc 2700
gacttcacct tcaccataag tagtctgcag cccgaggaca tcgccaccta cttctgtcag 2760
cacttcgatc acctgcccct ggccttcggc ggtgggacca aggtggagat caagggtggg 2820
ggtggcagcg gggaggcgg aagcggcgga ggtggctctc aggtgcagct tcaagagagc 2880
ggacccggcc tcgtgaagcc cagcgagacc ttgagcctga cctgcactgt gagtggcggt 2940
agcgtgagca gcggcgacta ttactggacc tggatcaggc agagccctgg caaggggctg 3000
gagtggatcg gccacatcta ctacagcggg aacacgaact acaaccccag cctgaagagc 3060
aggctgacga tcagcatcga cacgagcaag acccagttct cacttaagct cagcagcgtg 3120
accgccgcag acaccgccat atactactgc gtgagggaca gggtgacggg cgctttcgac 3180
atctggggcc aaggcacaat ggtcacggtg agctcc 3216

<210> SEQ ID NO 147
<211> LENGTH: 1524
<212> TYPE: DNA
<213> ORGANISM: Artificial Sequence
<220> FEATURE:
<223> OTHER INFORMATION: LC polypeptide

<400> SEQUENCE: 147
caggacggca acgaggagat gggcggcatc acccagacac catacaaggt gagcatctcc 60
ggcaccacag tgatcctgac cggaggctcc ggcggctctg ggggcagcgg aggtagtggc 120
ggcagcggcg gctcccaagc cgtggtaacc caggagccca gtctgacagt gagccctggc 180
ggtacagtga ccttgacttg caggagcagt accggagccg taactacctc aaactacgcc 240
aactgggtgc agcagaagcc cggtcaggcc cccaggggcc ttattggtgg gactaacaaa 300
cgagcacccg gaaccccgc aaggttcagc ggcagccttc tgggcggaaa ggccgctctc 360
acattgagcg gcgtgcagcc cgaggacgag gccgagtact actgcgccct gtggtacagc 420
aacctgtggg tgttcggcgg agggaccaag ctgaccgtgc tgggccagcc caaagctgcg 480

```
ccgagcgtga ccctgttccc cccgtcaagc gaggagctgc aggctaacaa ggccaccctg    540

gtgtgcctga ttagtgactt ctaccccggt gccgtcaccg tggcctggaa ggccgacagt    600

agcccagtta aagcgggcgt cgagaccacc actcccagca agcagagcaa caacaagtac    660

gccgcgagca gctacctgag tctgaccccc gagcagtgga agagccacag gagctacagc    720

tgccaggtga cccacgaggg cagcactgtg gagaagactg tggcccccgac cgagtgcccc   780

ccatgtagcg gcggagggtc cgatatccag atgacccaaa gccccagtag cctgtccgcc    840

agtgtaggag atagggtaac catcacttgc caagcgagcc aagacatcag caactacctg    900

aattggtatc agcagaagcc cggcaaagca cccaagctcc tgatctacga cgccagcaat    960

ctggagaccg gcgtgcccag caggttcagc ggatctggta gcggcaccga cttcaccttc   1020

accataagta gtctgcagcc cgaggacatc gccacctact tctgtcagca cttcgatcac   1080

ctgcccctgg ccttcggcgg tgggaccaag gtggagatca agggtggggg tggcagcggg   1140

ggaggcggaa gcggcggagg tggctctcag gtgcagcttc aagagagcgg acccggcctc   1200

gtgaagccca gcgagacctt gagcctgacc tgcactgtga gtggcggtag cgtgagcagc   1260

ggcgactatt actggacctg gatcaggcag agccctggca aggggctgga gtggatcggc   1320

cacatctact acagcgggaa cacgaactac aaccccagcc tgaagagcag gctgacgatc   1380

agcatcgaca cgagcaagac ccagttctca cttaagctca gcagcgtgac cgccgcagac   1440

accgccatat actactgcgt gagggacagg gtgacgggcg ctttcgacat ctggggccaa   1500

ggcacaatgg tcacggtgag ctcc                                          1524
```

<210> SEQ ID NO 148
<211> LENGTH: 3216
<212> TYPE: DNA
<213> ORGANISM: Artificial Sequence
<220> FEATURE:
<223> OTHER INFORMATION: HC polypeptide

<400> SEQUENCE: 148

```
gaggtggccc acaggttcaa ggatctgggc gaggagaact tcaaggccct ggtgctgatc     60

gccttcgccc agtatctgca gcagtgcccc tttgaggacc acgtgaagct ggtgaacgag    120

gtgaccgagt tcgccaagac atgcgtggcc gacgagtccg ccgagaattg tgataagtct    180

ctgcacaccc tgtttggcga taagctgtgc accgtggcca cactgaggga gacatacggc    240

gagatggccg actgctgtgc caagcaggag cccgagcgca acgagtgctt cctgcagcac    300

aaggacgata accctaatct gccacggctg gtgagacctg aggtggacgt gatgtgcacc    360

gccttccacg ataatgagga gacatttctg aagaagtacc tgtatgagat cgcccggaga    420

caccccttact tttatgcccc agagctgctg ttctttgcca agcggtacaa ggcagccttc   480

accgagtgct gtcaggcagc agataaggca gcatgcctgc tgccaaagct ggacgagctg    540

agggatgagg gcaaggcaag ctccgccaag cagcgcctga agtgtgcaag cctgcagaag    600

ttcggagaga gggcctttaa ggcatgggca gtggcaaggc tgtcccagcg gttcccaaag    660

gccgagtttg ccgaggtgtc taagctggtg accgacctga caaaggtgca caccgagtgc    720

tgtcacggcg acctgctgga gtgcgcagac gatagagccg atctggccaa gtacatctgt    780

gagaaccagg actctatctc tagcaagctg aaggagtgct gtgagaagcc cctgctggag    840

aagtcccact gcatcgccga ggtggagaac gacgagatgc cagcagatct gccaagcctg    900

gcagcagact tcgtggagtc caaggacgtg tgcaagaatt acgccgaggc caaggacgtg    960
```

-continued

```
ttcctgggca tgtttctgta cgagtatgcc aggcgccacc ctgactactc cgtggtgctg   1020
ctgctgcggc tggccaagac ctatgagacc acactggaga agtgctgtgc cgccgccgac   1080
ccccacgagt gctatgcaaa ggtgttcgac gagtttaagc ccctggtgga ggagcctcag   1140
aacctgatca agcagaattg tgagctgttt gagcagctgg gcgagtacaa gttccagaac   1200
gccctgctgg tgagatatac caagaaggtg ccacaggtgt ctacccccac actggtggag   1260
gtgagccgga atctgggcaa ggtcggctcc aagtgctgta agcaccctga ggccaagaga   1320
atgccatgcg ccgaggatta cctgtccgtg gtgctgaacc agctgtgcgt gctgcacgag   1380
aagacccccg tgagcgacag ggtgaccaag tgctgtacag agtctctggt gaaccggaga   1440
ccatgcttta gcgccctgga ggtggatgag acatatgtgc ccaaggagtt caatgccgag   1500
accttcacat ttcacgccga catctgtacc ctgagcgaga aggagcgcca gatcaagaag   1560
cagacagccc tggtggagct ggtgaagcac aagccaaagg ccaccaagga gcagctgaag   1620
gccgtgatgg acgatttcgc cgcctttgtg gagaagtgct gtaaggccga cgataaggag   1680
acatgcttcg cagaggaggg caagaagctg gtggcagcaa gccaggcagc aggaggctcc   1740
ggcggctctg gggcagcgg aggtagtggc ggcagcggcg gctccgaggt gcagctggtg   1800
gagtccggcg gcggcctggt gcagcccggc ggcagcctga ggctgtcctg cgccgcctct   1860
ggcttcacct ttaacacata cgcaatgaat tgggtgcgcc aggcaccagg caagggactg   1920
gagtgggtgg cccggatcag aagcaagtac aacaattatg ccacctacta tgccgactcc   1980
gtgaaggatc ggtttaccat cagcagagac gattccaaga acacactgta tctgcagatg   2040
aatagcctgc gggccgagga tacagccgtg tactattgcg tgagacacgg caactttggc   2100
aattcttacg tgagctggtt cgcctattgg ggccagggca ccatggtgac agtgtcctct   2160
gcctctacca agggacctag cgtgttccca ctggcaccta gctccaagtc taccagcgga   2220
ggcacagccg ccctgggatg tctggtgaag gactactttc cagagcccgt gacagtgtcc   2280
tggaactctg gcgccctgac cagcggagtg cacacattcc ctgccgtgct gcagtctagc   2340
ggcctgtact ccctgtcctc tgtggtgacc gtgccaagct cctctctggg cacccagaca   2400
tatatctgca acgtgaatca caagccctct aatacaaagg tggacaagag ggtggagcct   2460
aagagctgcc ccccttgtgg cggaggcggt agccaggtgc agcttcaaga gagcggaccc   2520
ggcctcgtga agcccagcga gaccttgagc ctgacctgca ctgtgagtgg cggtagcgtg   2580
agcagcggcg actattactg gacctggatc aggcagagcc ctggcaaggg gctggagtgg   2640
atcggccaca tctactacag cgggaacacg aactacaacc ccagcctgaa gagcaggctg   2700
acgatcagca tcgacacgag caagacccag ttctcactta agctcagcag cgtgaccgcc   2760
gcagacaccg ccatatacta ctgcgtgagg gacagggtga cgggcgcttt cgacatctgg   2820
ggccaaggca caatggtcac ggtgagctcc ggtgggggtg gcagcggggg aggcggaagc   2880
ggcggaggtg gctctgatat ccagatgacc caaagcccca gtagcctgtc cgccagtgta   2940
ggagataggg taaccatcac ttgccaagcg agccaagaca tcagcaacta cctgaattgg   3000
tatcagcaga agcccggcaa agcacccaag ctcctgatct acgacgccag caatctggag   3060
accggcgtgc ccagcaggtt cagcggatct ggtagcggca ccgacttcac cttcaccata   3120
agtagtctgc agcccgagga catcgccacc tacttctgtc agcacttcga tcacctgccc   3180
ctggccttcg gcggtgggac caaggtggag atcaag                             3216
```

<210> SEQ ID NO 149
<211> LENGTH: 1524

<212> TYPE: DNA
<213> ORGANISM: Artificial Sequence
<220> FEATURE:
<223> OTHER INFORMATION: LC polypeptide

<400> SEQUENCE: 149
caggacggca acgaggagat gggcggcatc acccagacac catacaaggt gagcatctcc 60
ggcaccacag tgatcctgac cggaggcggc tccggaggcg gtagcggcgg tggatctggc 120
ggcagcggcg gctcccaagc cgtggtaacc caggagccca gtctgacagt gagccctggc 180
ggtacagtga ccttgacttg caggagcagt accggagccg taactacctc aaactacgcc 240
aactgggtgc agcagaagcc cggtcaggcc cccaggggcc ttattggtgg gactaacaaa 300
cgagcacccg gaaccccccgc aaggttcagc ggcagccttc tgggcggaaa ggccgctctc 360
acattgagcg gcgtgcagcc cgaggacgag gccgagtact actgcgccct gtggtacagc 420
aacctgtggg tgttcggcgg agggaccaag ctgaccgtgc tgggccagcc caaagctgcg 480
ccgagcgtga ccctgttccc cccgtcaagc gaggagctgc aggctaacaa ggccaccctg 540
gtgtgcctga ttagtgactt ctaccccggt gccgtcaccg tggcctggaa ggccgacagt 600
agcccagtta aagcgggcgt cgagaccacc actcccagca agcagagcaa caacaagtac 660
gccgcgagca gctacctgag tctgaccccc gagcagtgga agagccacag gagctacagc 720
tgccaggtga cccacgaggg cagcactgtg gagaagactg tggccccgac cgagtgcccc 780
ccatgtagcg gcggagggtc ccaggtgcag cttcaagaga gcggacccgg cctcgtgaag 840
cccagcgaga ccttgagcct gacctgcact gtgagtggcg gtagcgtgag cagcggcgac 900
tattactgga cctggatcag gcagagccct ggcaaggggc tggagtggat cggccacatc 960
tactacagcg ggaacacgaa ctacaacccc agcctgaaga gcaggctgac gatcagcatc 1020
gacacgagca agacccagtt ctcacttaag ctcagcagcg tgaccgccgc agacaccgcc 1080
atatactact gcgtgaggga cagggtgacg ggcgctttcg acatctgggg ccaaggcaca 1140
atggtcacgg tgagctccgg tgggggtggc agcgggggag gcggaagcgg cggaggtggc 1200
tctgatatcc agatgaccca aagccccagt agcctgtccg ccagtgtagg agatagggta 1260
accatcactt gccaagcgag ccaagacatc agcaactacc tgaattggta tcagcagaag 1320
cccggcaaag cacccaagct cctgatctac gacgccagca atctggagac cggcgtgccc 1380
agcaggttca gcggatctgg tagcggcacc gacttcacct tcaccataag tagtctgcag 1440
cccgaggaca tcgccaccta cttctgtcag cacttcgatc acctgcccct ggccttcggc 1500
ggtgggacca aggtggagat caag 1524

<210> SEQ ID NO 150
<211> LENGTH: 1449
<212> TYPE: DNA
<213> ORGANISM: Artificial Sequence
<220> FEATURE:
<223> OTHER INFORMATION: HC polypeptide

<400> SEQUENCE: 150
ggcggcagcg gcggctccga ggtgcagctg gtggagtccg gcggcggcct ggtgcagccc 60
ggcggcagcc tgaggctgtc ctgcgccgcc tctggcttca cctttaacac atacgcaatg 120
aattgggtgc gccaggcacc aggcaaggga ctggagtggg tggcccggat cagaagcaag 180
tacaacaatt atgccaccta ctatgccgac tccgtgaagg atcggtttac catcagcaga 240
gacgattcca agaacacact gtatctgcag atgaatagcc tgcgggccga ggatacagcc 300
gtgtactatt gcgtgagaca cggcaacttt ggcaattctt acgtgagctg gttcgcctat 360
tggggccagg gcaccatggt gacagtgtcc tctgcctcta ccaagggacc tagcgtgttc 420
ccactggcac ctagctccaa gtctaccagc ggaggcacag ccgccctggg atgtctggtg 480
aaggactact ttccagagcc cgtgacagtg tcctggaact ctggcgccct gaccagcgga 540
gtgcacacat tccctgccgt gctgcagtct agcggcctgt actccctgtc ctctgtggtg 600
accgtgccaa gctcctctct gggcacccag acatatatct gcaacgtgaa tcacaagccc 660
tctaatacaa aggtggacaa gagggtggag cctaagagct gcccccccttg tggcggaggc 720 ggtagcgata tccagatgac ccaaagcccc agtagcctgt ccgccagtgt aggagatagg 780
gtaaccatca cttgccaagc gagccaagac atcagcaact acctgaattg gtatcagcag 840
aagcccggca aagcacccaa gctcctgatc tacgacgcca gcaatctgga gaccggcgtg 900
cccagcaggt tcagcggatc tggtagcggc accgacttca ccttcaccat aagtagtctg 960
cagcccgagg acatcgccac ctacttctgt cagcacttcg atcacctgcc cctggccttc 1020
ggcggtggga ccaaggtgga gatcaagggt gggggtggca gcgggggagg cggaagcggc 1080
ggaggtggct ctcaggtgca gcttcaagag agcggacccg gcctcgtgaa gcccagcgag 1140
accttgagcc tgacctgcac tgtgagtggc ggtagcgtga gcagcggcga ctattactgg 1200
acctggatca ggcagagccc tggcaagggg ctggagtgga tcggccacat ctactacagc 1260
gggaacacga actacaaccc cagcctgaag agcaggctga cgatcagcat cgacacgagc 1320
aagacccagt tctcacttaa gctcagcagc gtgaccgccg cagacaccgc catatactac 1380
tgcgtgaggg acagggtgac gggcgctttc gacatctggg gccaaggcac aatggtcacg 1440
gtgagctcc 1449

<210> SEQ ID NO 151
<211> LENGTH: 1407
<212> TYPE: DNA
<213> ORGANISM: Artificial Sequence
<220> FEATURE:
<223> OTHER INFORMATION: LC polypeptide

<400> SEQUENCE: 151
ggcggcagcg gcggctccca agccgtggta acccaggagc ccagtctgac agtgagccct 60
ggcggtacag tgaccttgac ttgcaggagc agtaccggag ccgtaactac ctcaaactac 120
gccaactggg tgcagcagaa gcccggtcag gcccccaggg gccttattgg tgggactaac 180
aaacgagcac ccggaacccc cgcaaggttc agcggcagcc ttctgggcgg aaaggccgct 240
ctcacattga gcggcgtgca gcccgaggac gaggccgagt actactgcgc cctgtggtac 300
agcaacctgt gggtgttcgg cggagggacc aagctgaccg tgctgggcca gcccaaagct 360
gcgccgagcg tgaccctgtt ccccccgtca agcgaggagc tgcaggctaa caaggccacc 420
ctggtgtgcc tgattagtga cttctacccc ggtgccgtca ccgtggcctg gaaggccgac 480
agtagcccag ttaaagcggg cgtcgagacc accactccca gcaagcagag caacaacaag 540
tacgccgcga gcagctacct gagtctgacc cccgagcagt ggaagagcca caggagctac 600
agctgccagg tgacccacga gggcagcact gtggagaaga ctgtggcccc gaccgagtgc 660
cccccatgta gcggcggagg gtccgatatc cagatgaccc aaagccccag tagcctgtcc 720
gccagtgtag gagataggg t aaccatcact tgccaagcga gccaagacat cagcaactac 780
ctgaattggt atcagcagaa gcccggcaaa gcacccaagc tcctgatcta cgacgccagc 840
aatctggaga ccggcgtgcc cagcaggttc agcggatctg gtagcggcac cgacttcacc 900
ttcaccataa gtagtctgca gcccgaggac atcgccacct acttctgtca gcacttcgat 960
cacctgcccc tggccttcgg cggtgggacc aaggtggaga tcaagggtgg gggtggcagc 1020
gggggaggcg gaagcggcgg aggtggctct caggtgcagc ttcaagagag cggacccggc 1080
ctcgtgaagc ccagcgagac cttgagcctg acctgcactg tgagtggcgg tagcgtgagc 1140
agcggcgact attactggac ctggatcagg cagagccctg gcaaggggct ggagtggatc 1200
ggccacatct actacagcgg gaacacgaac tacaacccca gcctgaagag caggctgacg 1260
atcagcatcg acacgagcaa gacccagttc tcacttaagc tcagcagcgt gaccgccgca 1320
gacaccgcca tatactactg cgtgagggac agggtgacgg gcgctttcga catctggggc 1380
caaggcacaa tggtcacggt gagctcc 1407

<210> SEQ ID NO 152
<211> LENGTH: 1449
<212> TYPE: DNA
<213> ORGANISM: Artificial Sequence
<220> FEATURE:
<223> OTHER INFORMATION: HC polypeptide

<400> SEQUENCE: 152
ggcggcagcg gcggctccga ggtgcagctg gtggagtccg gcggcggcct ggtgcagccc 60
ggcggcagcc tgaggctgtc ctgcgccgcc tctggcttca cctttaacac atacgcaatg 120
aattgggtgc gccaggcacc aggcaaggga ctggagtggg tggcccggat cagaagcaag 180
tacaacaatt atgccaccta ctatgccgac tccgtgaagg atcggtttac catcagcaga 240
gacgattcca agaacacact gtatctgcag atgaatagcc tgcgggccga ggatacagcc 300
gtgtactatt gcgtgagaca cggcaacttt ggcaattctt acgtgagctg gttcgcctat 360
tggggccagg gcaccatggt gacagtgtcc tctgcctcta ccaagggacc tagcgtgttc 420
ccactggcac ctagctccaa gtctaccagc ggaggcacag ccgccctggg atgtctggtg 480
aaggactact ttccagagcc cgtgacagtg tcctggaact ctggcgccct gaccagcgga 540
gtgcacacat tccctgccgt gctgcagtct agcggcctgt actccctgtc ctctgtggtg 600
accgtgccaa gctcctctct gggcacccag acatatatct gcaacgtgaa tcacaagccc 660
tctaatacaa aggtggacaa gagggtggag cctaagagct gcccccccttg tggcggaggc 720 ggtagccagg tgcagcttca agagagcgga cccggcctcg tgaagcccag cgagaccttg 780
agcctgacct gcactgtgag tggcggtagc gtgagcagcg gcgactatta ctggacctgg 840
atcaggcaga gccctggcaa ggggctggag tggatcggcc acatctacta cagcgggaac 900
acgaactaca accccagcct gaagagcagg ctgacgatca gcatcgacac gagcaagacc 960
cagttctcac ttaagctcag cagcgtgacc gccgcagaca ccgccatata ctactgcgtg 1020
agggacaggg tgacgggcgc tttcgacatc tggggccaag gcacaatggt cacggtgagc 1080
tccggtgggg gtggcagcgg gggaggcgga agcggcggag gtggctctga tatccagatg 1140
acccaaagcc ccagtagcct gtccgccagt gtaggagata gggtaaccat cacttgccaa 1200
gcgagccaag acatcagcaa ctacctgaat tggtatcagc agaagcccgg caaagcaccc 1260
aagctcctga tctacgacgc cagcaatctg gagaccggcg tgcccagcag gttcagcgga 1320
tctggtagcg gcaccgactt caccttcacc ataagtagtc tgcagcccga ggacatcgcc 1380
acctacttct gtcagcactt cgatcacctg cccctggcct tcggcggtgg gaccaaggtg 1440
gagatcaag 1449

<210> SEQ ID NO 153
<211> LENGTH: 1407
<212> TYPE: DNA
<213> ORGANISM: Artificial Sequence
<220> FEATURE:
<223> OTHER INFORMATION: LC polypeptide

<400> SEQUENCE: 153
ggcggcagcg gcggctccca agccgtggta acccaggagc ccagtctgac agtgagccct 60
ggcggtacag tgaccttgac ttgcaggagc agtaccggag ccgtaactac ctcaaactac 120
gccaactggg tgcagcagaa gcccggtcag gcccccaggg gccttattgg tgggactaac 180
aaacgagcac ccggaacccc cgcaaggttc agcggcagcc ttctgggcgg aaaggccgct 240
ctcacattga gcggcgtgca gcccgaggac gaggccgagt actactgcgc cctgtggtac 300
agcaacctgt gggtgttcgg cggagggacc aagctgaccg tgctgggcca gcccaaagct 360
gcgccgagcg tgaccctgtt ccccccgtca agcgaggagc tgcaggctaa caaggccacc 420
ctggtgtgcc tgattagtga cttctacccc ggtgccgtca ccgtggcctg gaaggccgac 480
agtagcccag ttaaagcggg cgtcgagacc accactccca gcaagcagag caacaacaag 540
tacgccgcga gcagctacct gagtctgacc cccgagcagt ggaagagcca caggagctac 600
agctgccagg tgacccacga gggcagcact gtggagaaga ctgtggcccc gaccgagtgc 660
cccccatgta gcggcggagg gtcccaggtg cagcttcaag agagcggacc cggcctcgtg 720
aagcccagcg agaccttgag cctgacctgc actgtgagtg gcggtagcgt gagcagcggc 780
gactattact ggacctggat caggcagagc cctggcaagg ggctggagtg gatcggccac 840
atctactaca gcgggaacac gaactacaac cccagcctga agagcaggct gacgatcagc 900
atcgacacga gcaagaccca gttctcactt aagctcagca gcgtgaccgc cgcagacacc 960
gccatatact actgcgtgag ggacagggtg acgggcgctt tcgacatctg gggccaaggc 1020
acaatggtca cggtgagctc cggtgggggt ggcagcgggg gaggcggaag cggcggaggt 1080
ggctctgata tccagatgac ccaaagcccc agtagcctgt ccgccagtgt aggagatagg 1140
gtaaccatca cttgccaagc gagccaagac atcagcaact acctgaattg gtatcagcag 1200
aagcccggca aagcacccaa gctcctgatc tacgacgcca gcaatctgga gaccggcgtg 1260
cccagcaggt tcagcggatc tggtagcggc accgacttca ccttcaccat aagtagtctg 1320
cagcccgagg acatcgccac ctacttctgt cagcacttcg atcacctgcc cctggccttc 1380
ggcggtggga ccaaggtgga gatcaag 1407

<210> SEQ ID NO 154
<211> LENGTH: 18
<212> TYPE: DNA
<213> ORGANISM: Artificial Sequence
<220> FEATURE:
<223> OTHER INFORMATION: linker

<400> SEQUENCE: 154
ggcggcagcg gcggctcc 18

<210> SEQ ID NO 155
<211> LENGTH: 669
<212> TYPE: DNA
<213> ORGANISM: Artificial Sequence
<220> FEATURE:
<223> OTHER INFORMATION: anti-CD3VH-CH1

<400> SEQUENCE: 155
gaggtgcagc tggtggagtc cggcggcggc ctggtgcagc ccggcggcag cctgaggctg 60
tcctgcgccg cctctggctt caccttttaac acatacgcaa tgaattgggt gcgccaggca 120
ccaggcaagg gactggagtg ggtggcccgg atcagaagca agtacaacaa ttatgccacc 180
tactatgccg actccgtgaa ggatcggttt accatcagca gagacgattc caagaacaca 240
ctgtatctgc agatgaatag cctgcgggcc gaggatacag ccgtgtacta ttgcgtgaga 300
cacggcaact ttggcaattc ttacgtgagc tggttcgcct attggggcca gggcaccatg 360
gtgacagtgt cctctgcctc taccaaggga cctagcgtgt tcccactggc acctagctcc 420
aagtctacca gcggaggcac agccgccctg ggatgtctgg tgaaggacta ctttccagag 480
cccgtgacag tgtcctggaa ctctggcgcc ctgaccagcg gagtgcacac attccctgcc 540
gtgctgcagt ctagcggcct gtactccctg tcctctgtgg tgaccgtgcc aagctcctct 600
ctgggcaccc agacatatat ctgcaacgtg aatcacaagc cctctaatac aaaggtggac 660
aagagggtg 669

<210> SEQ ID NO 156
<211> LENGTH: 245
<212> TYPE: PRT
<213> ORGANISM: Artificial Sequence
<220> FEATURE:
<223> OTHER INFORMATION: anti-ROR1 (VL-VH)

<400> SEQUENCE: 156

Asp Ile Gln Met Thr Gln Ser Pro Ser Ser Leu Ser Ala Ser Val Gly
1 5 10 15

Asp Arg Val Thr Ile Asn Cys Gln Ala Ser Gln Ser Ile Asp Ser Asn
20 25 30

Leu Ala Trp Tyr Gln Gln Lys Pro Gly Lys Pro Pro Lys Leu Leu Ile
35 40 45

Tyr Arg Ala Ser Asn Leu Ala Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Val Ala Thr Tyr Tyr Cys Leu Gly Gly Val Gly Asn Val Ser
85 90 95

Tyr Arg Thr Ser Phe Gly Gly Gly Thr Lys Val Glu Ile Lys Gly Gly
100 105 110

Gly Gly Ser Gly Gly Gly Gly Ser Gly Gly Gly Gly Ser Gly Gly Gly
115 120 125

Gly Ser Gln Ser Val Lys Glu Ser Glu Gly Asp Leu Val Thr Pro Ala
130 135 140

Gly Asn Leu Thr Leu Thr Cys Thr Ala Ser Gly Ser Asp Ile Asn Asp
145 150 155 160

Tyr Pro Ile Ser Trp Val Arg Gln Ala Pro Gly Lys Gly Leu Glu Trp
165 170 175

Ile Gly Phe Ile Asn Ser Gly Gly Ser Thr Trp Tyr Ala Ser Trp Val
180 185 190

Lys Gly Arg Phe Thr Ile Ser Arg Thr Ser Thr Thr Val Asp Leu Lys
195 200 205

Met Thr Ser Leu Thr Thr Asp Asp Thr Ala Thr Tyr Phe Cys Ala Arg
210 215 220

Gly Tyr Ser Thr Tyr Tyr Gly Asp Phe Asn Ile Trp Gly Pro Gly Thr
225 230 235 240

Leu Val Thr Ile Ser
245

<210> SEQ ID NO 157
<211> LENGTH: 735
<212> TYPE: DNA
<213> ORGANISM: Artificial Sequence
<220> FEATURE:
<223> OTHER INFORMATION: anti-ROR1 (VL-VH)

<400> SEQUENCE: 157
gacatccaga tgactcagtc ccccagttcc ctgtccgcct ccgtgggcga cagggtgaca 60
atcaactgcc aggcctcaca gtctatcgac agtaaccttg cctggtatca acagaagccc 120
gggaagcccc ccaagctgct gatctacagg gcctccaatc tggcatccgg cgtgccctcc 180
aggttctccg gttccggctc aggcaccgat tttaccctga ccatatcctc cttgcagccc 240
gaggacgtgg ctacctacta ctgtctgggc ggtgtgggca acgtgtccta caggacctcc 300
tttggtggcg gcaccaaggt ggagatcaag ggcggaggag ggtccggtgg agggggcagt 360
ggtgggggag gatcaggagg tggtggctcc cagagtgtga aggagtccga gggcgacctg 420
gtgacccctg ctggcaatct gaccctcacc tgcaccgctt ccggtagcga catcaacgac 480
taccccatat catgggtgag acaggctccc ggcaagggcc tggagtggat cggcttcatc 540
aatagcggtg ggtccacatg gtacgcaagt tgggtgaagg gcaggttcac catctctcga 600
acctcaacta ccgtcgacct gaaaatgacc tccctgacaa ccgacgacac cgcaacctat 660
ttctgcgcca ggggctactc cacatactat ggcgacttca acatctgggg gccagggacc 720
ctggtcacta tctca 735

<210> SEQ ID NO 158
<211> LENGTH: 6
<212> TYPE: PRT
<213> ORGANISM: Artificial Sequence
<220> FEATURE:
<223> OTHER INFORMATION: linker

<400> SEQUENCE: 158

Gly Gly Ser Gly Gly Ser
1 5

<210> SEQ ID NO 159
<211> LENGTH: 639
<212> TYPE: DNA
<213> ORGANISM: Artificial Sequence
<220> FEATURE:
<223> OTHER INFORMATION: anti CD3 epsilon VL-CL

<400> SEQUENCE: 159
caagccgtgg taacccagga gcccagtctg acagtgagcc ctggcggtac agtgaccttg 60
acttgcagga gcagtaccgg agccgtaact acctcaaact acgccaactg ggtgcagcag 120
aagcccggtc aggcccccag gggccttatt ggtgggacta acaaacgagc acccggaacc 180
cccgcaaggt tcagcggcag ccttctgggc ggaaaggccg ctctcacatt gagcggcgtg 240
cagcccgagg acgaggccga gtactactgc gccctgtggt acagcaacct gtgggtgttc 300
ggcggaggga ccaagctgac cgtgctgggc cagcccaaag ctgcgccgag cgtgaccctg 360
ttccccccgt caagcgagga gctgcaggct aacaaggcca ccctggtgtg cctgattagt 420
gacttctacc ccggtgccgt caccgtggcc tggaaggccg acagtagccc agttaaagcg 480
ggcgtcgaga ccaccactcc cagcaagcag agcaacaaca agtacgccgc gagcagctac 540
ctgagtctga cccccgagca gtggaagagc cacaggagct acagctgcca ggtgacccac 600
gagggcagca ctgtggagaa gactgtggcc ccgaccgag 639

<210> SEQ ID NO 160
<211> LENGTH: 18
<212> TYPE: PRT
<213> ORGANISM: Artificial Sequence
<220> FEATURE:
<223> OTHER INFORMATION: linker with cleavable sequence

<400> SEQUENCE: 160

Gly Gly Ser Gly Gly Ser Pro Leu Gly Leu Ala Gly Gly Gly Ser Gly
1 5 10 15

Gly Ser

<210> SEQ ID NO 161
<211> LENGTH: 54
<212> TYPE: DNA
<213> ORGANISM: Artificial Sequence
<220> FEATURE:
<223> OTHER INFORMATION: linker with cleavable sequence

<400> SEQUENCE: 161
ggaggctccg gcggctctcc actgggcctg gccggcggcg gcagcggcgg ctcc 54

<210> SEQ ID NO 162
<211> LENGTH: 18
<212> TYPE: PRT
<213> ORGANISM: Artificial Sequence
<220> FEATURE:
<223> OTHER INFORMATION: linker with non-cleavable sequence

<400> SEQUENCE: 162

Gly Gly Ser Gly Gly Ser Gly Gly Ser Gly Gly Ser Gly Gly Ser Gly
1 5 10 15

Gly Ser

<210> SEQ ID NO 163
<211> LENGTH: 54
<212> TYPE: DNA
<213> ORGANISM: Artificial Sequence
<220> FEATURE:
<223> OTHER INFORMATION: linker with non-cleavable sequence

<400> SEQUENCE: 163
ggaggctccg gcggctctgg gggcagcgga ggtagtggcg gcagcggcgg ctcc 54

<210> SEQ ID NO 164
<211> LENGTH: 81
<212> TYPE: DNA
<213> ORGANISM: Artificial Sequence
<220> FEATURE:
<223> OTHER INFORMATION: CAP

<400> SEQUENCE: 164
caggacggca acgaggagat gggcggcatc acccagacac catacaaggt gagcatctcc 60
ggcaccacag tgatcctgac c 81

<210> SEQ ID NO 165
<211> LENGTH: 6

<212> TYPE: PRT
<213> ORGANISM: Artificial Sequence
<220> FEATURE:
<223> OTHER INFORMATION: linker

<400> SEQUENCE: 165

Gly Gly Ser Gly Gly Ser
1 5

<210> SEQ ID NO 166
<211> LENGTH: 245
<212> TYPE: PRT
<213> ORGANISM: Artificial Sequence
<220> FEATURE:
<223> OTHER INFORMATION: anti-ROR1 (VH-VL)

<400> SEQUENCE: 166

Gln Ser Val Lys Glu Ser Glu Gly Asp Leu Val Thr Pro Ala Gly Asn
1 5 10 15

Leu Thr Leu Thr Cys Thr Ala Ser Gly Ser Asp Ile Asn Asp Tyr Pro
20 25 30

Ile Ser Trp Val Arg Gln Ala Pro Gly Lys Gly Leu Glu Trp Ile Gly
35 40 45

Phe Ile Asn Ser Gly Gly Ser Thr Trp Tyr Ala Ser Trp Val Lys Gly
50 55 60

Arg Phe Thr Ile Ser Arg Thr Ser Thr Thr Val Asp Leu Lys Met Thr
65 70 75 80

Ser Leu Thr Thr Asp Asp Thr Ala Thr Tyr Phe Cys Ala Arg Gly Tyr
85 90 95

Ser Thr Tyr Tyr Gly Asp Phe Asn Ile Trp Gly Pro Gly Thr Leu Val
100 105 110

Thr Ile Ser Gly Gly Gly Gly Ser Gly Gly Gly Gly Ser Gly Gly Gly
115 120 125

Gly Ser Gly Gly Gly Gly Ser Asp Ile Gln Met Thr Gln Ser Pro Ser
130 135 140

Ser Leu Ser Ala Ser Val Gly Asp Arg Val Thr Ile Asn Cys Gln Ala
145 150 155 160

Ser Gln Ser Ile Asp Ser Asn Leu Ala Trp Tyr Gln Gln Lys Pro Gly
165 170 175

Lys Pro Pro Lys Leu Leu Ile Tyr Arg Ala Ser Asn Leu Ala Ser Gly
180 185 190

Val Pro Ser Arg Phe Ser Gly Ser Gly Ser Gly Thr Asp Phe Thr Leu
195 200 205

Thr Ile Ser Ser Leu Gln Pro Glu Asp Val Ala Thr Tyr Tyr Cys Leu
210 215 220

Gly Gly Val Gly Asn Val Ser Tyr Arg Thr Ser Phe Gly Gly Gly Thr
225 230 235 240

Lys Val Glu Ile Lys
245

<210> SEQ ID NO 167
<211> LENGTH: 735
<212> TYPE: DNA
<213> ORGANISM: Artificial Sequence
<220> FEATURE:
<223> OTHER INFORMATION: anti-ROR1 (VH-VL)

<400> SEQUENCE: 167

```
cagagtgtga aggagtccga gggcgacctg gtgacccctg ctggcaatct gaccctcacc     60
tgcaccgctt ccggtagcga catcaacgac taccccatat catgggtgag acaggctccc    120
ggcaagggcc tggagtggat cggcttcatc aatagcggtg ggtccacatg gtacgcaagt    180
tgggtgaagg gcaggttcac catctctcga acctcaacta ccgtcgacct gaaaatgacc    240
tccctgacaa ccgacgacac cgcaacctat ttctgcgcca ggggctactc cacatactat    300
ggcgacttca acatctgggg gccagggacc ctggtcacta tctcaggcgg aggagggtcc    360
ggtggagggg gcagtggtgg gggaggatca ggaggtggtg gctccgacat ccagatgact    420
cagtccccca gttccctgtc cgcctccgtg ggcgacaggg tgacaatcaa ctgccaggcc    480
tcacagtcta tcgacagtaa ccttgcctgg tatcaacaga agcccgggaa gccccccaag    540
ctgctgatct acagggcctc caatctggca tccggcgtgc cctccaggtt ctccggttcc    600
ggctcaggca ccgattttac cctgaccata tcctccttgc agcccgagga cgtggctacc    660
tactactgtc tgggcggtgt gggcaacgtg tcctacagga cctcctttgg tggcggcacc    720
aaggtggaga tcaag                                                     735
```

<210> SEQ ID NO 168
<211> LENGTH: 244
<212> TYPE: PRT
<213> ORGANISM: Artificial Sequence
<220> FEATURE:
<223> OTHER INFORMATION: anti-PSMA (VL-VH)

<400> SEQUENCE: 168

```
Asp Val Gln Ile Thr Gln Ser Pro Ser Tyr Leu Ala Ala Ser Pro Gly
1               5                   10                  15

Glu Thr Ile Thr Ile Asn Cys Arg Ala Ser Lys Ser Ile Ser Lys Tyr
            20                  25                  30

Leu Ala Trp Tyr Gln Glu Lys Pro Gly Lys Ala Asn Lys Leu Leu Ile
        35                  40                  45

His Ser Gly Ser Thr Leu Gln Ser Gly Ile Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Ile Glu Tyr Pro Trp
                85                  90                  95

Thr Phe Gly Gly Gly Thr Lys Leu Glu Ile Lys Arg Ala Gly Gly Gly
            100                 105                 110

Gly Ser Gly Gly Gly Gly Ser Ser Gly Gly Gly Gly Ser Glu Ile Gln
        115                 120                 125

Leu Gln Gln Ser Gly Pro Glu Leu Val Lys Pro Gly Ala Ser Val Lys
    130                 135                 140

Met Ser Cys Lys Ala Ser Gly Tyr Thr Phe Thr Asp Tyr Tyr Met His
145                 150                 155                 160

Trp Val Lys Gln Asn Asn Gly Glu Ser Leu Glu Trp Ile Gly Tyr Phe
                165                 170                 175

Asn Pro Tyr Asn Asp Tyr Thr Arg Tyr Asn Gln Asn Phe Asn Gly Lys
            180                 185                 190

Ala Thr Leu Thr Val Asp Lys Ser Ser Ser Thr Ala Tyr Met Gln Leu
        195                 200                 205
```

Asn Ser Leu Thr Ser Glu Asp Ser Ala Phe Tyr Tyr Cys Ala Arg Ser
    210                 215                 220

Asp Gly Tyr Tyr Asp Ala Met Asp Tyr Trp Gly Gln Gly Thr Ser Val
225                 230                 235                 240

Thr Val Ser Ser

<210> SEQ ID NO 169
<211> LENGTH: 732
<212> TYPE: DNA
<213> ORGANISM: Artificial Sequence
<220> FEATURE:
<223> OTHER INFORMATION: anti-PSMA (VL-VH)

<400> SEQUENCE: 169
gacgtgcaga tcacccagtc cccctcctat ctggccgctt cccccggtga gaccatcacc 60
atcaactgta gggcctccaa gtccatctcc aaatacctgg cctggtatca ggagaagccc 120
ggaaaagcca acaaactgct gatccatagc ggctctaccc tgcagagtgg catcccctcc 180
aggttctcag gctccggttc tggaaccgac tttactctta caatttcctc actcgaaccc 240
gaagacttcg ccatgtacta ctgccagcag cacatcgagt acccctggac cttcggagga 300
ggcactaagc tggagatcaa gagggctggc ggaggtggca gtgggggagg cggttcctcc 360
ggcggtggcg ggagcgagat ccagctgcaa cagtccggtc ccgagctggt gaagcctgga 420
gcctccgtga agatgtcctg taaggcctct ggctacacct ttaccgacta ctacatgcac 480
tgggtaaaac agaacaacgg cgagtccctg gagtggatag gctacttcaa cccctacaac 540
gactacacca ggtacaacca gaacttcaat ggcaaggcca ccctgaccgt ggacaagagc 600
tcctccacag cctatatgca gctcaactcc ctgacttccg aggactccgc cttctactat 660
tgcgccaggt ccgacgggta ctacgacgcc atggactact ggggccaggg cacctcagtg 720
acagtgtcct cc 732

<210> SEQ ID NO 170
<211> LENGTH: 244
<212> TYPE: PRT
<213> ORGANISM: Artificial Sequence
<220> FEATURE:
<223> OTHER INFORMATION: anti-PSMA (VH-VL)

<400> SEQUENCE: 170

Glu Ile Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Met His Trp Val Lys Gln Asn Asn Gly Glu Ser Leu Glu Trp Ile
        35                  40                  45

Gly Tyr Phe Asn Pro Tyr Asn Asp Tyr Thr Arg Tyr Asn Gln Asn Phe
    50                  55                  60

Asn Gly Lys Ala Thr Leu Thr Val Asp Lys Ser Ser Ser Thr Ala Tyr
65                  70                  75                  80

Met Gln Leu Asn Ser Leu Thr Ser Glu Asp Ser Ala Phe Tyr Tyr Cys
                85                  90                  95

Ala Arg Ser Asp Gly Tyr Tyr Asp Ala Met Asp Tyr Trp Gly Gln Gly
            100                 105                 110

Thr Ser Val Thr Val Ser Ser Gly Gly Gly Gly Ser Gly Gly Gly Gly
        115                 120                 125

Ser Ser Gly Gly Gly Gly Ser Asp Val Gln Ile Thr Gln Ser Pro Ser
130 135 140

Tyr Leu Ala Ala Ser Pro Gly Glu Thr Ile Thr Ile Asn Cys Arg Ala
145 150 155 160

Ser Lys Ser Ile Ser Lys Tyr Leu Ala Trp Tyr Gln Glu Lys Pro Gly
165 170 175

Lys Ala Asn Lys Leu Leu Ile His Ser Gly Ser Thr Leu Gln Ser Gly
180 185 190

Ile Pro Ser Arg Phe Ser Gly Ser Gly Ser Gly Thr Asp Phe Thr Leu
195 200 205

Thr Ile Ser Ser Leu Glu Pro Glu Asp Phe Ala Met Tyr Tyr Cys Gln
210 215 220

Gln His Ile Glu Tyr Pro Trp Thr Phe Gly Gly Gly Thr Lys Leu Glu
225 230 235 240

Ile Lys Arg Ala

<210> SEQ ID NO 171
<211> LENGTH: 732
<212> TYPE: DNA
<213> ORGANISM: Artificial Sequence
<220> FEATURE:
<223> OTHER INFORMATION: anti-PSMA (VH-VL)

<400> SEQUENCE: 171
gagatccagc tgcaacagtc cggtcccgag ctggtgaagc ctggagcctc cgtgaagatg 60
tcctgtaagg cctctggcta cacctttacc gactactaca tgcactgggt aaaacagaac 120
aacggcgagt ccctggagtg gataggctac ttcaacccct acaacgacta caccaggtac 180
aaccagaact tcaatggcaa ggccaccctg accgtggaca agagctcctc cacagcctat 240
atgcagctca actccctgac ttccgaggac tccgccttct actattgcgc caggtccgac 300
gggtactacg acgccatgga ctactggggc cagggcacct cagtgacagt gtcctccggc 360
ggaggtggca gtgggggagg cggttcctcc ggcggtggcg ggagcgacgt gcagatcacc 420 cagtcccccct cctatctggc cgcttccccc ggtgagacca tcaccatcaa ctgtagggcc 480
tccaagtcca tctccaaata cctggcctgg tatcaggaga agcccggaaa agccaacaaa 540
ctgctgatcc atagcggctc taccctgcag agtggcatcc cctccaggtt ctcaggctcc 600
ggttctggaa ccgactttac tcttacaatt tcctcactcg aacccgaaga cttcgccatg 660
tactactgcc agcagcacat cgagtacccc tggaccttcg gaggaggcac taagctggag 720
atcaagaggg ct 732

<210> SEQ ID NO 172
<211> LENGTH: 245
<212> TYPE: PRT
<213> ORGANISM: Artificial Sequence
<220> FEATURE:
<223> OTHER INFORMATION: anti-5T4 (VL-VH)

<400> SEQUENCE: 172

Asp Ile Gln Met Thr Gln Ser Pro Ser Ser Leu Ser Ala Ser Val Gly
1 5 10 15

Asp Arg Val Thr Ile Thr Cys Arg Ala Ser Gln Gly Ile Ser Asn Tyr
20 25 30

Leu Ala Trp Phe Gln Gln Lys Pro Gly Lys Ala Pro Lys Ser Leu Ile
35 40 45

```
Tyr Arg Ala Asn Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Leu Gln Tyr Asp Asp Phe Pro Trp
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Gly Ser Gly Gly Gly Gly Ser Gln
        115                 120                 125

Val Gln Leu Val Gln Ser Gly Ala Glu Val Lys Lys Pro Gly Ala Ser
    130                 135                 140

Val Lys Val Ser Cys Lys Ala Ser Gly Tyr Thr Phe Thr Ser Phe Trp
145                 150                 155                 160

Met His Trp Val Arg Gln Ala Pro Gly Gln Gly Leu Glu Trp Met Gly
                165                 170                 175

Arg Ile Asp Pro Asn Arg Gly Gly Thr Glu Tyr Asn Glu Lys Ala Lys
            180                 185                 190

Ser Arg Val Thr Met Thr Ala Asp Lys Ser Thr Ser Thr Ala Tyr Met
        195                 200                 205

Glu Leu Ser Ser Leu Arg Ser Glu Asp Thr Ala Val Tyr Tyr Cys Ala
    210                 215                 220

Gly Gly Asn Pro Tyr Tyr Pro Met Asp Tyr Trp Gly Gln Gly Thr Thr
225                 230                 235                 240

Val Thr Val Ser Ser
                245
```

```
<210> SEQ ID NO 173
<211> LENGTH: 735
<212> TYPE: DNA
<213> ORGANISM: Artificial Sequence
<220> FEATURE:
<223> OTHER INFORMATION: anti-5T4 (VL-VH)

<400> SEQUENCE: 173

gacatacaga tgacccagtc ccccagctcc ctctcagcct ctgtgggcga cagggtgacc     60

atcacctgca gagcttccca aggcatctcc aactacctgg cctggttcca gcagaagcca    120

ggcaaggctc ctaagagcct gatctacagg gctaaccgtc tgcagtccgg cgtgccctcc    180

aggttctctg ggtccggcag cggcacagac ttcacctta ccatctcctc cctgcagccc    240

gaggacgtag ccacatatta ctgcctgcag tacgatgact tcccctggac tttcggacag    300

ggcaccaagc tggagataaa gggaggtggt ggctcagggg gtgggggctc cggcggaggg    360

gggtctggcg gtggcgggtc ccaggtgcag ctggttcagt ctggtgctga ggtgaagaag    420

cctggcgcct cagttaaagt gtcatgcaag gcctccggct acaccttcac cagtttctgg    480

atgcactggg tgaggcaggc acccggtcag ggcctggagt ggatgggccg aatcgatccc    540

aaccgtggcg gcactgagta caacgagaag gccaagagca gggtcacaat gaccgccgac    600

aagtccacct caactgctta tatggagctg tcctccttgc gttctgagga cactgccgtg    660

tactactgtg caggcggcaa cccctactac cccatggact attgggggca gggtaccact    720

gtcaccgtgt catct                                                     735

<210> SEQ ID NO 174
<211> LENGTH: 245
```

<212> TYPE: PRT
<213> ORGANISM: Artificial Sequence
<220> FEATURE:
<223> OTHER INFORMATION: anti-5T4 (VH-VL)

<400> SEQUENCE: 174

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Phe
            20                  25                  30

Trp Met His Trp Val Arg Gln Ala Pro Gly Gln Gly Leu Glu Trp Met
        35                  40                  45

Gly Arg Ile Asp Pro Asn Arg Gly Gly Thr Glu Tyr Asn Glu Lys Ala
    50                  55                  60

Lys Ser Arg Val Thr Met Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Gly Gly Asn Pro Tyr Tyr Pro Met Asp Tyr Trp Gly Gln Gly Thr
            100                 105                 110

Thr Val Thr Val Ser Ser Gly Gly Gly Gly Ser Gly Gly Gly Gly Ser
        115                 120                 125

Gly Gly Gly Gly Ser Gly Gly Gly Gly Ser Asp Ile Gln Met Thr Gln
    130                 135                 140

Ser Pro Ser Ser Leu Ser Ala Ser Val Gly Asp Arg Val Thr Ile Thr
145                 150                 155                 160

Cys Arg Ala Ser Gln Gly Ile Ser Asn Tyr Leu Ala Trp Phe Gln Gln
                165                 170                 175

Lys Pro Gly Lys Ala Pro Lys Ser Leu Ile Tyr Arg Ala Asn Arg Leu
            180                 185                 190

Gln Ser Gly Val Pro Ser Arg Phe Ser Gly Ser Gly Ser Gly Thr Asp
        195                 200                 205

Phe Thr Leu Thr Ile Ser Ser Leu Gln Pro Glu Asp Val Ala Thr Tyr
    210                 215                 220

Tyr Cys Leu Gln Tyr Asp Asp Phe Pro Trp Thr Phe Gly Gln Gly Thr
225                 230                 235                 240

Lys Leu Glu Ile Lys
                245
```

<210> SEQ ID NO 175
<211> LENGTH: 735
<212> TYPE: DNA
<213> ORGANISM: Artificial Sequence
<220> FEATURE:
<223> OTHER INFORMATION: anti-5T4 (VH-VL)

<400> SEQUENCE: 175

```
caggtgcagc tggttcagtc tggtgctgag gtgaagaagc ctggcgcctc agttaaagtg      60

tcatgcaagg cctccggcta caccttcacc agtttctgga tgcactgggt gaggcaggca     120

cccggtcagg gcctggagtg gatgggccga atcgatccca accgtggcgg cactgagtac     180

aacgagaagg ccaagagcag ggtcacaatg accgccgaca agtccacctc aactgcttat     240

atggagctgt cctccttgcg ttctgaggac actgccgtgt actactgtgc aggcggcaac     300

ccctactacc ccatggacta ttgggggcag ggtaccactg tcaccgtgtc atctggaggt     360

ggtggctcag gggtgggggg ctccggcgga ggggggtctg gcggtggcgg gtccgacata     420
```

```
cagatgaccc agtcccccag ctccctctca gcctctgtgg gcgacagggt gaccatcacc    480

tgcagagctt cccaaggcat ctccaactac ctggcctggt tccagcagaa gccaggcaag    540

gctcctaaga gcctgatcta cagggctaac cgtctgcagt ccggcgtgcc ctccaggttc    600

tctgggtccg gcagcggcac agacttcacc cttaccatct cctccctgca gcccgaggac    660

gtagccacat attactgcct gcagtacgat gacttcccct ggactttcgg acagggcacc    720

aagctggaga taaag                                                     735


<210> SEQ ID NO 176
<211> LENGTH: 1119
<212> TYPE: PRT
<213> ORGANISM: Artificial Sequence
<220> FEATURE:
<223> OTHER INFORMATION: HC 5T4 Polypeptide with MMP 2/9 cleavage
      protease sequence

<400> SEQUENCE: 176

Gln Asp Gly Asn Glu Glu Met Gly Gly Ile Thr Gln Thr Pro Tyr Lys
1               5                   10                  15

Val Ser Ile Ser Gly Thr Thr Val Ile Leu Thr Gly Gly Gly Gly Ser
            20                  25                  30

Gly Gly Gly Gly Ser Gly Gly Gly Gly Ser Glu Val Ala His Arg Phe
        35                  40                  45

Lys Asp Leu Gly Glu Glu Asn Phe Lys Ala Leu Val Leu Ile Ala Phe
    50                  55                  60

Ala Gln Tyr Leu Gln Gln Cys Pro Phe Glu Asp His Val Lys Leu Val
65                  70                  75                  80

Asn Glu Val Thr Glu Phe Ala Lys Thr Cys Val Ala Asp Glu Ser Ala
                85                  90                  95

Glu Asn Cys Asp Lys Ser Leu His Thr Leu Phe Gly Asp Lys Leu Cys
            100                 105                 110

Thr Val Ala Thr Leu Arg Glu Thr Tyr Gly Glu Met Ala Asp Cys Cys
        115                 120                 125

Ala Lys Gln Glu Pro Glu Arg Asn Glu Cys Phe Leu Gln His Lys Asp
    130                 135                 140

Asp Asn Pro Asn Leu Pro Arg Leu Val Arg Pro Glu Val Asp Val Met
145                 150                 155                 160

Cys Thr Ala Phe His Asp Asn Glu Glu Thr Phe Leu Lys Lys Tyr Leu
                165                 170                 175

Tyr Glu Ile Ala Arg Arg His Pro Tyr Phe Tyr Ala Pro Glu Leu Leu
            180                 185                 190

Phe Phe Ala Lys Arg Tyr Lys Ala Ala Phe Thr Glu Cys Cys Gln Ala
        195                 200                 205

Ala Asp Lys Ala Ala Cys Leu Leu Pro Lys Leu Asp Glu Leu Arg Asp
    210                 215                 220

Glu Gly Lys Ala Ser Ser Ala Lys Gln Arg Leu Lys Cys Ala Ser Leu
225                 230                 235                 240

Gln Lys Phe Gly Glu Arg Ala Phe Lys Ala Trp Ala Val Ala Arg Leu
                245                 250                 255

Ser Gln Arg Phe Pro Lys Ala Glu Phe Ala Glu Val Ser Lys Leu Val
            260                 265                 270

Thr Asp Leu Thr Lys Val His Thr Glu Cys Cys His Gly Asp Leu Leu
        275                 280                 285

Glu Cys Ala Asp Asp Arg Ala Asp Leu Ala Lys Tyr Ile Cys Glu Asn
    290                 295                 300
```

Gln Asp Ser Ile Ser Ser Lys Leu Lys Glu Cys Cys Glu Lys Pro Leu
305 310 315 320

Leu Glu Lys Ser His Cys Ile Ala Glu Val Glu Asn Asp Glu Met Pro
325 330 335

Ala Asp Leu Pro Ser Leu Ala Ala Asp Phe Val Glu Ser Lys Asp Val
340 345 350

Cys Lys Asn Tyr Ala Glu Ala Lys Asp Val Phe Leu Gly Met Phe Leu
355 360 365

Tyr Glu Tyr Ala Arg Arg His Pro Asp Tyr Ser Val Val Leu Leu Leu
370 375 380

Arg Leu Ala Lys Thr Tyr Glu Thr Thr Leu Glu Lys Cys Cys Ala Ala
385 390 395 400

Ala Asp Pro His Glu Cys Tyr Ala Lys Val Phe Asp Glu Phe Lys Pro
405 410 415

Leu Val Glu Glu Pro Gln Asn Leu Ile Lys Gln Asn Cys Glu Leu Phe
420 425 430

Glu Gln Leu Gly Glu Tyr Lys Phe Gln Asn Ala Leu Leu Val Arg Tyr
435 440 445

Thr Lys Lys Val Pro Gln Val Ser Thr Pro Thr Leu Val Glu Val Ser
450 455 460

Arg Asn Leu Gly Lys Val Gly Ser Lys Cys Cys Lys His Pro Glu Ala
465 470 475 480

Lys Arg Met Pro Cys Ala Glu Asp Tyr Leu Ser Val Val Leu Asn Gln
485 490 495

Leu Cys Val Leu His Glu Lys Thr Pro Val Ser Asp Arg Val Thr Lys
500 505 510

Cys Cys Thr Glu Ser Leu Val Asn Arg Arg Pro Cys Phe Ser Ala Leu
515 520 525

Glu Val Asp Glu Thr Tyr Val Pro Lys Glu Phe Asn Ala Glu Thr Phe
530 535 540

Thr Phe His Ala Asp Ile Cys Thr Leu Ser Glu Lys Glu Arg Gln Ile
545 550 555 560

Lys Lys Gln Thr Ala Leu Val Glu Leu Val Lys His Lys Pro Lys Ala
565 570 575

Thr Lys Glu Gln Leu Lys Ala Val Met Asp Asp Phe Ala Ala Phe Val
580 585 590

Glu Lys Cys Cys Lys Ala Asp Asp Lys Glu Thr Cys Phe Ala Glu Glu
595 600 605

Gly Lys Lys Leu Val Ala Ala Ser Gln Ala Ala Gly Gly Ser Gly Gly
610 615 620

Ser Pro Leu Gly Leu Ala Gly Gly Gly Ser Gly Gly Ser Glu Val Gln
625 630 635 640

Leu Val Glu Ser Gly Gly Gly Leu Val Gln Pro Gly Gly Ser Leu Arg
645 650 655

Leu Ser Cys Ala Ala Ser Gly Phe Thr Phe Asn Thr Tyr Ala Met Asn
660 665 670

Trp Val Arg Gln Ala Pro Gly Lys Gly Leu Glu Trp Val Ala Arg Ile
675 680 685

Arg Ser Lys Tyr Asn Asn Tyr Ala Thr Tyr Tyr Ala Asp Ser Val Lys
690 695 700

Asp Arg Phe Thr Ile Ser Arg Asp Asp Ser Lys Asn Thr Leu Tyr Leu
705 710 715 720

-continued

```
Gln Met Asn Ser Leu Arg Ala Glu Asp Thr Ala Val Tyr Tyr Cys Val
                725                 730                 735

Arg His Gly Asn Phe Gly Asn Ser Tyr Val Ser Trp Phe Ala Tyr Trp
            740                 745                 750

Gly Gln Gly Thr Met Val Thr Val Ser Ser Ala Ser Thr Lys Gly Pro
        755                 760                 765

Ser Val Phe Pro Leu Ala Pro Ser Ser Lys Ser Thr Ser Gly Gly Thr
    770                 775                 780

Ala Ala Leu Gly Cys Leu Val Lys Asp Tyr Phe Pro Glu Pro Val Thr
785                 790                 795                 800

Val Ser Trp Asn Ser Gly Ala Leu Thr Ser Gly Val His Thr Phe Pro
                805                 810                 815

Ala Val Leu Gln Ser Ser Gly Leu Tyr Ser Leu Ser Ser Val Val Thr
            820                 825                 830

Val Pro Ser Ser Ser Leu Gly Thr Gln Thr Tyr Ile Cys Asn Val Asn
        835                 840                 845

His Lys Pro Ser Asn Thr Lys Val Asp Lys Arg Val Glu Pro Lys Ser
    850                 855                 860

Cys Pro Pro Cys Gly Gly Gly Gly Ser Asp Asp Ile Gln Met Thr Gln
865                 870                 875                 880

Ser Pro Ser Ser Leu Ser Ala Ser Val Gly Asp Arg Val Thr Ile Thr
                885                 890                 895

Cys Arg Ala Ser Gln Gly Ile Ser Asn Tyr Leu Ala Trp Phe Gln Gln
            900                 905                 910

Lys Pro Gly Lys Ala Pro Lys Ser Leu Ile Tyr Arg Ala Asn Arg Leu
        915                 920                 925

Gln Ser Gly Val Pro Ser Arg Phe Ser Gly Ser Gly Ser Gly Thr Asp
    930                 935                 940

Phe Thr Leu Thr Ile Ser Ser Leu Gln Pro Glu Asp Val Ala Thr Tyr
945                 950                 955                 960

Tyr Cys Leu Gln Tyr Asp Asp Phe Pro Trp Thr Phe Gly Gln Gly Thr
                965                 970                 975

Lys Leu Glu Ile Lys Gly Gly Gly Gly Ser Gly Gly Gly Gly Ser Gly
            980                 985                 990

Gly Gly Gly Ser Gly Gly Gly Gly  Ser Gln Val Gln Leu  Val Gln Ser
        995                 1000                1005

Gly Ala  Glu Val Lys Lys Pro  Gly Ala Ser Val Lys  Val Ser Cys
    1010                 1015                1020

Lys Ala  Ser Gly Tyr Thr Phe  Thr Ser Phe Trp Met  His Trp Val
    1025                 1030                1035

Arg Gln  Ala Pro Gly Gln Gly  Leu Glu Trp Met Gly  Arg Ile Asp
    1040                 1045                1050

Pro Asn  Arg Gly Gly Thr Glu  Tyr Asn Glu Lys Ala  Lys Ser Arg
    1055                 1060                1065

Val Thr  Met Thr Ala Asp Lys  Ser Thr Ser Thr Ala  Tyr Met Glu
    1070                 1075                1080

Leu Ser  Ser Leu Arg Ser Glu  Asp Thr Ala Val Tyr  Tyr Cys Ala
    1085                 1090                1095

Gly Gly  Asn Pro Tyr Tyr Pro  Met Asp Tyr Trp Gly  Gln Gly Thr
    1100                 1105                1110

Thr Val  Thr Val Ser Ser
    1115
```

<210> SEQ ID NO 177
<211> LENGTH: 473
<212> TYPE: PRT
<213> ORGANISM: Artificial Sequence
<220> FEATURE:
<223> OTHER INFORMATION: LC 5T4 Polypeptide

<400> SEQUENCE: 177

Gly Gly Ser Gly Gly Ser Gln Ala Val Val Thr Gln Glu Pro Ser Leu
1 5 10 15

Thr Val Ser Pro Gly Gly Thr Val Thr Leu Thr Cys Arg Ser Ser Thr
20 25 30

Gly Ala Val Thr Thr Ser Asn Tyr Ala Asn Trp Val Gln Gln Lys Pro
35 40 45

Gly Gln Ala Pro Arg Gly Leu Ile Gly Gly Thr Asn Lys Arg Ala Pro
50 55 60

Gly Thr Pro Ala Arg Phe Ser Gly Ser Leu Leu Gly Gly Lys Ala Ala
65 70 75 80

Leu Thr Leu Ser Gly Val Gln Pro Glu Asp Glu Ala Glu Tyr Tyr Cys
85 90 95

Ala Leu Trp Tyr Ser Asn Leu Trp Val Phe Gly Gly Gly Thr Lys Leu
100 105 110

Thr Val Leu Gly Gln Pro Lys Ala Ala Pro Ser Val Thr Leu Phe Pro
115 120 125

Pro Ser Ser Glu Glu Leu Gln Ala Asn Lys Ala Thr Leu Val Cys Leu
130 135 140

Ile Ser Asp Phe Tyr Pro Gly Ala Val Thr Val Ala Trp Lys Ala Asp
145 150 155 160

Ser Ser Pro Val Lys Ala Gly Val Glu Thr Thr Thr Pro Ser Lys Gln
165 170 175

Ser Asn Asn Lys Tyr Ala Ala Ser Ser Tyr Leu Ser Leu Thr Pro Glu
180 185 190

Gln Trp Lys Ser His Arg Ser Tyr Ser Cys Gln Val Thr His Glu Gly
195 200 205

Ser Thr Val Glu Lys Thr Val Ala Pro Thr Glu Cys Pro Pro Cys Ser
210 215 220

Gly Gly Gly Ser Asp Ile Gln Met Thr Gln Ser Pro Ser Ser Leu Ser
225 230 235 240

Ala Ser Val Gly Asp Arg Val Thr Ile Thr Cys Arg Ala Ser Gln Gly
245 250 255

Ile Ser Asn Tyr Leu Ala Trp Phe Gln Gln Lys Pro Gly Lys Ala Pro
260 265 270

Lys Ser Leu Ile Tyr Arg Ala Asn Arg Leu Gln Ser Gly Val Pro Ser
275 280 285

Arg Phe Ser Gly Ser Gly Ser Gly Thr Asp Phe Thr Leu Thr Ile Ser
290 295 300

Ser Leu Gln Pro Glu Asp Val Ala Thr Tyr Tyr Cys Leu Gln Tyr Asp
305 310 315 320

Asp Phe Pro Trp Thr Phe Gly Gln Gly Thr Lys Leu Glu Ile Lys Gly
325 330 335

Gly Gly Gly Ser Gly Gly Gly Gly Ser Gly Gly Gly Gly Ser Gly Gly
340 345 350

Gly Gly Ser Gln Val Gln Leu Val Gln Ser Gly Ala Glu Val Lys Lys
355 360 365

-continued

```
Pro Gly Ala Ser Val Lys Val Ser Cys Lys Ala Ser Gly Tyr Thr Phe
    370                 375                 380

Thr Ser Phe Trp Met His Trp Val Arg Gln Ala Pro Gly Gln Gly Leu
385                 390                 395                 400

Glu Trp Met Gly Arg Ile Asp Pro Asn Arg Gly Gly Thr Glu Tyr Asn
                405                 410                 415

Glu Lys Ala Lys Ser Arg Val Thr Met Thr Ala Asp Lys Ser Thr Ser
            420                 425                 430

Thr Ala Tyr Met Glu Leu Ser Ser Leu Arg Ser Glu Asp Thr Ala Val
        435                 440                 445

Tyr Tyr Cys Ala Gly Gly Asn Pro Tyr Tyr Pro Met Asp Tyr Trp Gly
    450                 455                 460

Gln Gly Thr Thr Val Thr Val Ser Ser
465                 470
```

PRECURSOR TRI-SPECIFIC ANTIBODY CONSTRUCTS AND METHODS OF USE THEREOF

CROSS-REFERENCE TO RELATED APPLICATIONS

This application is a National Phase Application of PCT International Application No. PCT/IL2020/050359, International Filing Date Mar. 26, 2020, claiming the benefit of U.S. Patent Application Ser. No. 62/844,303, filed May 7, 2019. The entire content and disclosure of the preceding applications is incorporated by reference in its entirety into this application.

SEQUENCE LISTING STATEMENT

The instant application contains a Sequence Listing which has been submitted electronically in ASCII format and is hereby incorporated by reference in its entirety. The ASCII copy, created on Oct. 27, 2021, is named P-586968-PC-CORRECTED-27OCT21.txt and is 279 kilobytes in size.

FIELD OF THE DISCLOSURE

Disclosed herein are precursor tri-specific antibody constructs and methods of use thereof for these precursor constructs. Methods of use include for treatment of cancer, wherein the precursor constructs comprise prodrugs having tumor restricted activation and multiple antigen binding sites.

BACKGROUND

The functionality of monoclonal antibodies (non conjugated or naked antibody) currently approved by drug regulatory agencies worldwide for clinical use in oncology setting are known to use one or a combination of the following mechanisms: 1) blocking cell growth signaling, 2) blocking the blood supply to cancer cells, 3) directly mediating cell apoptosis, 4) eliciting immunological effector functions such as antibody dependent cellular cytoxicity (ADCC), antibody dependent cellular phagocytosis (ADCP) and complement dependent cytotoxicity (CDC), and 5) promoting adaptive immunity towards tumors.

Monoclonal antibody therapies have demonstrated survival benefits in the clinic. However, the overall response rates in cancer patients are low, and the survival benefits are marginal (several months) compared to chemotherapy. Although the underlying reasons for the lack of robust clinical anti-cancer activities are not fully understood, research has suggested that cancer cells often quickly develop compensating signaling pathways to escape cell death. Also, cancer stem cells (CSC), which are considered as potent cancer initiating cells, are less active at cell proliferation therefore they tend to sustain the lack of growth signal better.

In an attempt to improve anti-tumor activity of monoclonal antibodies, multi-specific antibodies are being developed. In contrast to classical monoclonal antibodies, which are the standard first-line therapy in several tumor entities, these multi-specific antibodies may bring together a tumor cell and the means to destroy the tumor cell, thereby increasing the efficiency of treatment. These multi-specific antibodies provide for new treatment options for cancer patients.

Another anti-cancer therapeutic approach is to utilize T-cells. T-cells provide defense against cancer throughout life by patrolling the body in search for newly arisen cancer cells and eliminating them effectively and promptly. Therapeutic approaches utilizing T-cells have proved successful in cancer treatment of at least metastatic melanoma, metastatic kidney cancer, asymptomatic metastatic hormone refractory prostate cancer, and advanced melanoma.

Another consideration in tumor cytotoxicity is the tumor microenvironment (TME). The TME includes novel targets that can help direct and improve the actions of antibody therapies by potentiating host antitumor immune responses. For example, T-cells play an unexpectedly critical role in anti-tumor antigen antibody therapy, although their importance is often not observed due to studies being performed in immunodeficient mice.

A pitfall of antibody therapeutics used in cancer treatment is the "off-target" binding of the antibody to non-cancer tumor-associated-antigen-expressing cells, especially if such binding leads to cytotoxicity. Thus, "off-target" binding by multi-specific and bispecific antibodies presents a potential challenge to controlling their "off-target" activity against normal tissues that also express antigen, even at extremely low levels. These "off-target" effects are a serious limitation to multi-specific and bispecific antibody therapeutics. Another drawback of many bispecific or multi-specific antibodies is their short half-life.

There remains a need to provide multi-specific trivalent antibodies with qualities that specifically target cytotoxicity to tumor cells while reducing the toxic side effects and preserving the antibodies effectiveness. Reducing the non-specific toxic side effects of multi-specific antibodies and concurrently enhancing these antibodies effectiveness, requires an antibody having a precursor form that (1) engages a target associated with a tumor cell, a tumor-associated cell, or a tumor cell environment, and (2) activates cytotoxic cells, for example T cells, once localized to the tumor microenvironment. Further, it is essential that such multi-specific antibodies do not reduce significantly the immunogenicity to a tumor or tumor-associated target. The precursor tri-specific antibody constructs described herein addresses this need by attaching a regulatable half-life enhancing component and a blocking component that inhibits the antibody from engaging a toxicity providing cell prior to binding to a tumor or tumor-associated target.

SUMMARY

In one aspect, disclosed herein is a precursor tri-specific antibody construct, comprising:

- a first binding domain that binds to a first tumor associated antigen (TAA); a second binding domain that binds to a second TAA; a third binding domain that binds to an extracellular epitope of human T-cell surface glycoprotein CD3 (CD3ε); a first regulatory domain, comprising a protease cleavage domain and a half-life prolonging (HLP) domain; and a second regulatory domain, comprising a protease cleavage domain and a CAP component that reduces the ability of the third binding domain to bind the extracellular epitope of human CD3ε.

In one aspect, disclosed herein is a precursor tri-specific antibody construct, comprising: a first binding domain that binds to a first tumor associated antigen (TAA); a second binding domain that binds to a second TAA; a third binding domain that binds to an extracellular epitope of human CD3ε; and a regulatory domain, said regulatory domain comprising either a first and a second sub-regulatory domain, said first sub-regulatory domain comprising a first protease cleavage domain and a half-life prolonging (HLP) domain, and said second sub-regulatory domain comprising a second protease cleavage domain and a CAP component that reduces the ability of the third binding domain to bind the extracellular epitope of human CD3ε; or a single regulatory domain comprising a protease cleavage domain, a half-life prolonging (HLP) domain, and a CAP component that reduces the ability of the third binding domain to bind the extracellular epitope of human CD3ε.

In one aspect, disclosed herein is a precursor tri-specific antibody construct, comprising: a first binding domain that binds to a first tumor associated antigen (TAA); a second binding domain that binds to a second TAA; a third binding domain that binds to an extracellular epitope of human CD3ε; and a regulatory domain comprising a protease cleavage domain, a half-life prolonging (HLP) domain, and a CAP component that reduces the ability of the third binding domain to bind the extracellular epitope of human CD3ε.

In a related aspect, the first binding domain and said second binding domain bind to the same TAA. In another related aspect, the first binding domain and said second binding domain bind to different TAAs.

In a related aspect, the first TAA, or said second TAA, or both said first TAA and said second TAA can be an extracellular epitope of a tumor-cell-surface antigen, a tumor micro-environment antigen, a stromal antigen in the tumor micro-environment (TME), an angiogenic antigen in the TME, an antigen on a blood vessel in a TME, or a cytokine antigen in a TME, or any combination thereof. In another related aspect, the TAA can be one of the following: epidermal growth factor receptor (EGFR), FcγRI, FcγRIIa FcγRIIb, FcγRIIIb, CD28, CD137, CTLA-4, FAS, fibroblast growth factor receptor 1 (FGFR1), FGFR2, FGFR3, FGFR4, glucocorticoid-induced TNFR-related (GITR) protein, lymphotoxin-beta receptor (LTβR), toll-like receptors (TLR), tumor necrosis factor-related apoptosis-inducing ligand-receptor 1 (TRAIL receptor 1), TRAIL receptor 2, prostate-specific membrane antigen (PSMA) protein, prostate stem cell antigen (PSCA) protein, tumor-associated protein carbonic anhydrase IX (CAIX), epidermal growth factor receptor 1 (EGFR1), EGFRvIII, human epidermal growth factor receptor 2 (Her2/neu; Erb2), ErbB3 (HER3), Folate receptor, ephrin receptors, PDGFRa, ErbB-2, CD20, CD22, CD30, CD33, CD40, CD37, CD3ε, CD70, CD74, CD40), CD80, CD86, CD2, p53, cMet (tyrosine-protein kinase Met) (hepatocyte growth factor receptor) (HGFR), MAGE-A1, MAGE-A2, MAGE-A3, MAGE-A4, MAGE-A6, MAGE-A10, MAGE-A12, BAGE, DAM−6, DAM−10, GAGE-1, GAGE-2, GAGE-8, GAGE-3, GAGE-4, GAGE-5, GAGE-6, GAGE-7B, NA88-A, NY-ESO-1, BRCA1, BRCA2, MART-1, MC1R, Gp100, PSA, PSM, Tyrosinase, Wilms' tumor antigen (WT1), TRP-1, TRP-2, ART-4, CAMEL, Cyp-B, hTERT, hTRT, iCE, MUC1, MUC2, P-cadherin, Myostatin (GDF8), Cripto (TDGF1), MUC5AC, PRAME, P15, RU1, RU2, SART-1, SART-3, WT1, AFP, B-catenin/m, Caspase-8/m, CDK-4/m, ELF2M, GnT-V, G250, HSP70-2M, HST-2, KIAA0205, MUM−1, MUM−2, MUM−3, Myosin/m, RAGE, SART-2, TRP-2/INT2, 707-AP, Annexin II, CDC27/m, TPI/mbcr-abl, ETV6/AML, LDLR/FUT, Pml/RARa, TEL/AML1, CD28, CD137, CanAg, Mesothelin, DR5, PD-1, PDIL, IGF-1R, CXCR4, Neuropilin 1, Glypicans, EphA2, CD138, B7-H3, B7-H4, gpA33, GPC3, SSTR2, Tyrosine-protein kinase transmembrane receptor ROR1 (ROR1), Trophoblast glycoprotein-TPBG (5T4), and Vascular endothelial growth factor (VEGF-R2), or any combination thereof. In a further related aspect, the TAA bound by said first binding domain or said second binding domain or both is selected from the group consisting of EGFR, ROR1, PSMA, and 5T4. In another related aspect, when the TAA antigen is EGFR, the amino acid sequence of the first binding domain or the second binding domain or both comprise the amino acid sequence set forth in any one of SEQ ID NOs: 34, 37, or a combination thereof. In another related aspect, when the TAA antigen is ROR1, the amino acid sequence of the first binding domain or the second binding domain or both comprise the amino acid sequence set forth in any one of SEQ ID NOs: 156 and 166, or a combination thereof. In another related aspect, when the TAA antigen is PSMA, the amino acid sequence of the first binding domain or the second binding domain or both comprise the amino acid sequence set forth in any one of SEQ ID NOs: 168 and 170, or a combination thereof. In another related aspect, when the TAA antigen is 5T4, the amino acid sequence of the first binding domain or the second binding domain or both comprise the amino acid sequence set forth in any one of SEQ ID NOs: 172 and 174, or a combination thereof.

In another related aspect, a tumor micro-environment antigen can be a KIR, a LILR, or a TIGIT antigen. In another related aspect, a stromal antigen in the tumor micro-environment can be a fibroblast activation protein (FAP), alpha smooth muscle actin (aSMA), Platelet-derived growth factor receptor A (PDGFRa), Integrin a11ß1 (ITGA11) VEGF, Tenascin-C, periostin, fibroblast specific protein 1 (S10A4, FSP1), desmin, vimentin, paladin, urokinase-type plasminogen activator receptor associated protein (UPARAP), galectin-3, podoplanin, platelet, CCL2, or CXCL12. In another related aspect, an angiogenic antigen in the tumor micro-environment can be a bFGF, Interferon (INF), or a VEGF. In a further related aspect, an antigen on the surface of a blood vessel in the tumor micro-environment comprises an endothelial cell surface antigen selected from CD31, CD105, CD146, and CD144. In yet another related aspect, a cytokine antigen can be Tumor necrosis factor alpha (TNF-alpha), Interleukin (IL)-6, Transforming Growth Factor beta (TGF-beta), IL-10, IL-8, IL-17, IL-21, INF, or Vascular Endothelial Growth Factor (VEGF).

In a related aspect, the HLP domain comprises a human serum albumin (HSA) polypeptide.

In a related aspect, the CAP component of said second sub-regulatory domain comprises an amino acid sequence of the extracellular epitope of human CD3ε. In another related aspect, the amino acid sequence of the CAP component is set forth in SEQ ID NO: 5, or a homolog thereof.

In a related aspect, the first binding domain, the second binding domain, or both, each comprises a single chain variable fragment (scFv). In another related aspect, the third binding domain comprises a Fab antigen binding fragment.

In a related aspect, the protease cleavage domain in the first and second sub-regulatory domains are cleaved by the same protease. In another related aspect, the protease cleavage domain in the first and second sub-regulatory domain are cleaved by different proteases. In another related aspect, the first, and or second protease cleavage domain comprises a protease-cleavable amino acid sequence cleavable by a serine protease, a cysteine protease, an aspartate protease, or a matrix metalloprotease (MMP), or is a combination substrate cleaved by one or more of MMP2/9, uPA, matriptase and legumain, or any combination thereof. In another related aspect, the MMP can be a matrix metalloprotease 1 (MMP- 1), a matrix metalloprotease 2 (MMP-2), a matrix metalloprotease 9 (MMP-9), or a matrix metalloprotease 14 (MMP-14). In another related aspect, the serine protease can be a urokinase-type plasminogen activator (uPA) protease or a membrane-type serine protease (MT-SP1). In another related aspect, the amino acid sequence of the combination substrate cleaved by one or more of MMP2/9, uPA, matriptase and legumain is set forth in SEQ ID NO: 35. In a further related aspect, the first, and or second protease cleavage domain comprises the sequence set forth in SEQ ID NO: 9 (PLGLAG), SEQ ID NO: 10 (GPLGMLSQ), SEQ ID NO: 11 (GPLGLWAQ), SEQ ID NO: 12 (GPLGLAG), SEQ ID NO: 13 (KKNPAELIGPVD), or SEQ ID NO: 14 (KKQPAANLVAPED), or SEQ ID NO: 35. In yet another related aspect, the first, and or second protease cleavage domain comprises a sequence set forth in SEQ ID NO: 9. In still another aspect, the first, and or second protease cleavage domain comprises a sequence set forth in SEQ ID NO: 35.

In a related aspect, the third binding domain comprises a variable heavy chain (VH3-CH1) region and a variable light chain (VL3-CL) region; wherein said first binding domain is located C-terminally to said VL3-CL or said VH3-CH1 region of the third binding domain; wherein when said first binding domain is located C-terminally to said VL3-CL region, said second sub-regulatory domain is located C-terminally to said VH3-CH1 region, and when said first binding domain is located C-terminally to said VH3-CH1 region, said second sub-regulatory domain is located C-terminally to said VL3-CL region. In another related aspect, third binding domain comprises a variable heavy chain (VH3) region and a variable light chain (VL3) region; wherein said first sub-regulatory domain, comprising said HLP domain located N-terminally to said protease cleavage domain, is located N-terminally to said VH3 region or to said VL3 region of said third binding domain; wherein when said first sub-regulatory domain is located N-terminally to said VL3 region, said second sub-regulatory domain, comprising said CAP component located N-terminally to said protease cleavage domain, is located N-terminally to said VH3 region, and when said first sub-regulatory domain is located N-terminally to said VH3 region, said second sub-regulatory domain comprising said CAP component located N-terminally to said protease cleavage domain, is located N-terminally to said VL3 region.

In another aspect, the precursor tri-specific antibody construct comprises two polypeptides, polypeptide A and polypeptide B, wherein polypeptide A comprises components having an order N-terminal to C-terminal: HLP domain, protease cleavage domain, third binding domain (VH3 region), first binding domain (VL-VH); and polypeptide B comprises components having an order N-terminal to C-terminal: CAP component, protease cleavage domain, third binding domain (VL region), second binding domain (VL-VH); or polypeptide A comprises components having an order N-terminal to C-terminal: HLP domain, protease cleavage domain, third binding domain (VH3 region), first binding domain (VH-VL); and polypeptide B comprises components having an order N-terminal to C-terminal: CAP component, protease cleavage domain, third binding domain (VL region), second binding domain (VH-VL); or polypeptide A comprises components having an order N-terminal to C-terminal: HLP domain, protease cleavage domain, third binding domain (VL3 region), first binding domain (VL-VH); and polypeptide B comprises components having an order N-terminal to C-terminal: CAP component, protease cleavage domain, third binding domain (VH3 region), second binding domain (VL-VH); or polypeptide A comprises components having an order N-terminal to C-terminal: HLP domain, protease cleavage domain, third binding domain (VL3 region), first binding domain (VH-VL); and polypeptide B comprises components having an order N-terminal to C-terminal: CAP component, protease cleavage domain, third binding domain (VH region), second binding domain (VH-VL); or polypeptide A comprises components having an order N-terminal to C-terminal: HLP domain, protease cleavage domain, third binding domain (VL3 region), first binding domain (VL-VH); and polypeptide B comprises components having an order N-terminal to C-terminal: CAP component, protease cleavage domain, third binding domain (VH region), second binding domain (VL-VH); or polypeptide A comprises components having an order N-terminal to C-terminal: HLP domain, protease cleavage domain, third binding domain (VL3 region), first binding domain (VH-VL); and polypeptide B comprises components having an order N-terminal to C-terminal: CAP component, protease cleavage domain, third binding domain (VH3 region), second binding domain (VH-VL); or polypeptide A comprises components having an order N-terminal to C-terminal: HLP domain, protease cleavage domain, third binding domain (VH3 region), first binding domain (VL-VH); and polypeptide B comprises components having an order N-terminal to C-terminal: CAP component, protease cleavage domain, third binding domain (VL3 region), second binding domain (VL-VH); or polypeptide A comprises components having an order N-terminal to C-terminal: HLP domain, protease cleavage domain, third binding domain (VH3 region), first binding domain (VH-VL); and polypeptide B comprises components having an order N-terminal to C-terminal: CAP component, protease cleavage domain, third binding domain (VL3 region), second binding domain (VH-VL).

In a related aspect, a third binding domain comprises a VL3 region and a VH3 region, wherein said VL3 region comprises CDR-L1 (selected from SEQ ID NOs: 107-109), CDR-L2 (SEQ ID NO: 110), and CDR-L3 (selected from SEQ ID NOs: 111-112), and said VH3 region comprises CDR-H1 (SEQ ID NO: 104), CDR-H2 (SEQ ID NO: 105), and CDR-H3 (SEQ ID NO: 106). In another related aspect, the VL3 region comprises an amino acid sequence selected from the group set forth in any of SEQ ID NO: 75-103 and 116, or an amino acid sequence having at least 80% homology thereto. In another related aspect, the VH3 region comprises the amino acid sequence set forth in any of SEQ ID NO: 46-72 and 114, or an amino acid sequence having at least 80% homology thereto.

In one aspect, disclosed herein is a pharmaceutical composition, comprising a precursor tri-specific antibody construct and a pharmaceutically acceptable carrier, the precursor tri-specific antibody construct comprising: a first binding domain, binding to a first tumor associated antigen (TAA); a second binding domain, binding to a second tumor associated antigen (TAA); a third binding domain, binding to an extracellular epitope of human CD3; a first sub-regulatory domain, comprising a protease cleavage domain and a half-life prolonging (HLP) domain; and a second sub-regulatory domain, comprising a protease cleavage domain and a CAP component that reduces the ability of the third binding domain to bind the extracellular epitope of human CD3ε.

In one aspect, disclosed herein is a nucleic acid construct, comprising a nucleic acid sequence, or a plurality of nucleic acid sequences, encoding a precursor tri-specific antibody construct comprising: a first binding domain, binding to a first tumor associated antigen (TAA); a second binding domain, binding to a second tumor associated antigen (TAA); a third binding domain, binding to an extracellular epitope of human CD3ε; a first sub-regulatory domain, comprising a protease cleavage domain and a half-life prolonging (HLP) domain; and a second sub-regulatory domain, comprising a protease cleavage domain and a CAP component that reduces the ability of the third binding domain to bind the extracellular epitope of human CD3ε.

In one aspect, disclosed herein is an expression vector, comprising the nucleic acid construct or constructs encoding a polypeptide or polypeptides of a precursor tri-specific antibody construct disclosed herein.

In one aspect, disclosed herein is an isolated host cell, comprising a nucleic acid sequence, or a plurality of nucleic acid sequences, encoding a precursor tri-specific antibody construct comprising: a first binding domain, binding to a first tumor associated antigen (TAA); a second binding domain, binding to a second tumor associated antigen (TAA); a third binding domain, binding to an extracellular epitope of human CD3ε; a first sub-regulatory domain, comprising a protease cleavage domain and a half-life prolonging (HLP) domain; and a second sub-regulatory domain, comprising a protease cleavage domain and a CAP component that reduces the ability of the third binding domain to bind the extracellular epitope of human CD3ε.

In one aspect, disclosed herein is a method of treating, preventing, inhibiting the growth of, delaying disease progression, reducing tumor load, or reducing the incidence of a cancer or a tumor, or any combination thereof, in a subject in need of such treatment, comprising a step of administering to the subject a pharmaceutical composition comprising a precursor tri-specific antibody construct comprising: a first binding domain, binding to a first tumor associated antigen (TAA); a second binding domain, binding to a second tumor associated antigen (TAA); a third binding domain, binding to an extracellular epitope of human CD3ε; a first sub-regulatory domain, comprising a protease cleavage domain and a half-life prolonging (HLP) domain; and a second sub-regulatory domain, comprising a protease cleavage domain and a CAP component that reduces the ability of the third binding domain to bind the extracellular epitope of human CD3ε; wherein the method treats, prevents, inhibits the growth of, delays the disease progression, reduces the tumor load, or reduces the incidence of the cancer or a tumor in the subject.

In a related aspect, use of methods disclosed herein for treating a subject in need reduces the minimal residual disease, increases remission, increases remission duration, reduces tumor relapse rate, prevents metastasis of the tumor or the cancer, or reduces the rate of metastasis of the tumor or the cancer, or any combination thereof, compared with a subject not administered with the pharmaceutical composition disclosed herein. In another related aspect, the cancer or tumor comprises a solid tumor or non-solid tumor, or wherein the cancer or tumor comprises a metastasis of a cancer or tumor. In a further related aspect, the non-solid cancer or tumor can be a hematopoietic malignancy, a blood cell cancer, a leukemia, a myelodysplastic syndrome, a lymphoma, a multiple myeloma (a plasma cell myeloma), an acute lymphoblastic leukemia, an acute myelogenous leukemia, a chronic myelogenous leukemia, a Hodgkin lymphoma, a non-Hodgkin lymphoma, or plasma cell leukemia; or wherein the solid tumor can be a sarcoma or a carcinoma, a fibrosarcoma, a myxosarcoma, a liposarcoma, a chondrosarcoma, an osteogenic sarcoma, a chordoma, an angiosarcoma, an endotheliosarcoma, a lymphangiosarcoma, a lymphangioendotheliosarcoma, a synovioma, a mesothelioma, an Ewing's tumor, a leiomyosarcoma, a rhabdomyosarcoma, a colon carcinoma, a pancreatic cancer or tumor, a breast cancer or tumor, an ovarian cancer or tumor, a prostate cancer or tumor, a squamous cell carcinoma, a basal cell carcinoma, an adenocarcinoma, a sweat gland carcinoma, a sebaceous gland carcinoma, a papillary carcinoma, a papillary adenocarcinomas, a cystadenocarcinoma, a medullary carcinoma, a bronchogenic carcinoma, a renal cell carcinoma, a hepatoma, a bile duct carcinoma, a choriocarcinoma, a seminoma, an embryonal carcinoma, a Wilm's tumor, a cervical cancer or tumor, a uterine cancer or tumor, a testicular cancer or tumor, a lung carcinoma, a small cell lung carcinoma, a bladder carcinoma, an epithelial carcinoma, a glioma, an astrocytoma, a medulloblastoma, a craniopharyngioma, an ependymoma, a pinealoma, a hemangioblastoma, an acoustic neuroma, an oligodenroglioma, a schwannoma, a meningioma, a melanoma, a neuroblastoma, or a retinoblastoma.

In one aspect, disclosed herein is a method of treating, preventing, inhibiting the growth of, delaying disease progression, reducing tumor load, or reducing the incidence of a cancer or a tumor, or any combination thereof, in a subject in need of such treatment, comprising a step of administering a pharmaceutical composition to the subject, said composition comprising a nucleic acid construct or a plurality of nucleic acid constructs comprising a nucleic acid sequence, or a plurality of nucleic acid sequences, encoding a precursor tri-specific antibody construct comprising: a first binding domain, binding to a first tumor associated antigen (TAA); a second binding domain, binding to a second tumor associated antigen (TAA); a third binding domain, binding to an extracellular epitope of human CD3ε; a first sub-regulatory domain, comprising a protease cleavage domain and a half-life prolonging (HLP) domain; and a second sub-regulatory domain, comprising a protease cleavage domain and a CAP component that reduces the ability of the third binding domain to bind the extracellular epitope of human CD3ε; wherein the method treats, prevents, inhibits the growth of, delays the disease progression, reduces the tumor load, or reduces the incidence of the cancer or a tumor in the subject.

In a related aspect, use of a method disclosed herein for treating a subject in need, reduces the minimal residual disease, increases remission, increases remission duration, reduces tumor relapse rate, prevents metastasis of the tumor or the cancer, or reduces the rate of metastasis of the tumor or the cancer, or any combination thereof, compared with a subject not administered with the pharmaceutical composition.

In one aspect, disclosed herein is a method of producing a precursor tri-specific antibody construct, comprising: a first binding domain, binding to a first tumor associated antigen (TAA); a second binding domain, binding to a second tumor associated antigen (TAA); a third binding domain, binding to an extracellular epitope of human CD3ε; a first sub-regulatory domain, comprising a protease cleavage domain and a half-life prolonging (HLP) domain; and a second sub-regulatory domain, comprising a protease cleavage domain and a CAP component that reduces the ability of the third binding domain to bind the extracellular epitope of human CD3ε; said method comprising the steps of: culturing a host cell comprising a nucleic acid sequence encoding precursor tri-specific antibody construct polypeptides A and B, expressing said polypeptides A and B, isolating said expressed precursor bispecific antibody construct polypeptides A and B, and dimerizing said polypeptides A and B.

In a related aspect, in a method of producing a precursor tri-specific antibody construct, expression comprises expression from a same host cell or comprises two host cells each expressing a different polypeptide, polypeptide A and polypeptide B, respectively.

BRIEF DESCRIPTION OF THE DRAWINGS

The subject matter regarded as the precursor tri-specific (tri-body) antibody constructs disclosed herein, is particularly pointed out and distinctly claimed in the concluding portion of the specification. The precursor tri-specific (tri-body) antibody constructs, however, both as to organization and method of use, together with objects, features, and advantages thereof, may best be understood by reference to the following detailed description when read with the accompanying drawings in which:

FIGS. 2A and 2B present schematic embodiments of a precursor tri-specific antibody construct comprising two anti-tumor associated antigen binding domain wherein the tumor associated antigen is EGFR, in which the N-terminal to C-terminal order of one of the variable regions is VL2-L4-VH2 and the other is VH3-L9-VL3 (FIG. 2A) or one scFv is VH2-L4-VL2 and the other isVL3-L9-VH3 (FIG. 2B). The precursor tri-specific antibody construct further includes an anti-CD3ε Fab domain N-terminal to the scFv binding domains, and two sub-regulatory domains comprising protease cleavable linkers, and either a human serum albumin (HSA) polypeptide sequence or a CD3 CAP, wherein is some embodiments the amino acids of the CAP are amino acids 1-27 of the mature CD3ε polypeptide (SEQ ID NO: 4)N-terminal to the Fab domain. The order of components in the regulatory domains is N-terminus to C-terminus is CAP or HSA-linker-protease cleavable linker. L1, L2, etc represent possible linkers between the different domains or domain components. Linkers may or may not be present. FIG. 2C presents a schematic of a precursor tri-specific antibody construct as in FIG. 2B but lacking the regulatory domain comprising the half-life extending component (HSA). FIG. 2D presents a schematic of a precursor tri-specific antibody construct as in FIG. 2B but lacking the sub-regulatory domain comprising the CD3 CAP domain. FIG. 2E presents a schematic of an active tri-specific (tribody) antibody construct, wherein the precursor construct of FIG. 2B is in the active form and lacks both sub-regulatory domains. FIG. 2F presents a schematic of a precursor tri-specific antibody construct, wherein the regulatory domain comprises a single regulatory domain comprising a CAP domain, a HSA sequence, and a protease cleavable linker on the same polypeptide.

FIG. 3A shows the influence of a cancer (tumor) microenvironment on a precursor tri-specific antibody construct. The precursor tri-specific antibody construct comprises two protease cleavable domains, wherein one is C-terminal to an HSA half-life extendable polypeptide and the other is C-terminal to a CAP component that may specifically be bound by the third (anti-CD3 Fab) binding domain. Entry into a cancer microenvironment, that are known to be rich in cancer-cell secreted proteases, results in protease cleavage and removable of the HSA and CAP regulatory component, wherein in some embodiments the CAP comprises an extracellular CD3ε epitope. In some embodiments, the protease cleavable domains may be cleavable by the same or difference proteases. The resultant activated antibody (activated tri-specific antibody construct) may now bind and activate a T-cell. Were the precursor construct to bind to a TAA not in a tumor microenvironment, protease cleavage would not occur, and neither would T-cell activation. The design of the precursor tri-specific antibody construct provides for improved protease-activated controlled release of CAP and HSA regulatory domains with tri-specific binding epitopes. FIG. 3B shows the protease specific cleavage of HSA and CD3 CAP within the cancer microenvironment followed by T-cell activation and the binding of the activated tri-body construct to both a T-cell and a tumor cell. The precursor tri-specific antibody construct remains intact with an extended in vivo half-life when in circulation or present in normal tissue. Upon binding to a TAA target antigen, in this case EGFR, wherein that target antigen is present on the surface of a tumor (in a tumor microenvironment), protease specific activation may occur, leading to cleavage of both sub-regulatory domains and exposure of the anti-CD3 binding site. The activated tri-specific antibody construct antibody has a reduced limited half-life of hours compared with days to weeks for the precursor tri-specific antibody construct. (Data not shown). Furthermore, in some embodiments, a cleaved and activated tri-specific antibody comprises a smaller size than the precursor construct, which may improve activated tri-specific antibody tumor penetration.

FIGS. 4A and 4B present embodiments of an amino acid sequence of a Heavy Chain (HC) polypeptide of an activated tri-specific (tri-body) antibody construct (Construct 1; VLVH) and an optimized nucleotide sequences encoding the Heavy Chain (HC) activated construct, Amino acid sequences are presented N-terminal to C-terminal, and nucleic acid sequences are presented 5' to 3'. FIG. 4A presents one embodiment of an amino acid sequence of a Heavy Chain (HC) polypeptide of an activated construct, having the N-terminal to C-terminal order and components as follows: h1F3.5-G1Fd anti-EGFR VL-linker-VH (SEQ ID NO: 138). The amino acid sequences of the component parts of the HC polypeptide shown in FIG. 4A include: Linker (SEQ ID NO: 158), anti-CD3epsilon variable heavy chain and constant heavy chain region 1 (SEQ ID NO: 113), followed by two marked cysteine residues (marked bold and underlined), which may participate in disulfide double bond, followed by an anti-EGFR scFv VL (SEQ ID NO: 34)-linker (SEQ ID NO: 39)-VH (SEQ ID NO: 37) chain. FIG. 4B presents one embodiment of an optimized nucleic acid sequence (DNA) encoding a Heavy Chain (HC) polypeptide of an activated tri-specific (tri-body) construct, having the 5' to 3' order and components as follows (SEQ ID NO: 150). The nucleic acid sequences encoding the component parts of the HC polypeptide shown in FIG. 4A include: Linker (e.g., L7 of FIG. 2E) (SEQ ID NO: 154), anti-CD3epsilon variable heavy chain and constant heavy chain region 1 (SEQ ID NO: 155), followed by two marked cysteine residues (marked bold and underlined), which may participate in disulfide double bond, followed by an anti-EGFR scFv VL (SEQ ID NO: 36)-linker (SEQ ID NO: 40)-VH (SEQ ID NO: 38) chain.

FIGS. 5A and 5B present embodiments of an amino acid sequence of a Light Chain (LC) polypeptide of an activated tri-specific (tri-body) antibody construct (Construct 1; VLVH) and an optimized nucleotide sequences encoding the Light Chain (LC) activated construct, Amino acid sequences are presented N-terminal to C-terminal, and nucleic acid sequences are presented 5' to 3'. FIG. 5A presents one embodiment of an amino acid sequence of a Light Chain (LC) polypeptide of an activated construct, having the N-terminal to C-terminal order and components as follows: h1F3.1-ALC anti-EGFR VL-linker-VH (SEQ ID NO: 139;). The amino acid sequences of the component parts of the LC polypeptide shown in FIG. 5A include: Linker (e.g., L2 of FIG. 2E) (SEQ ID NO: 158), anti-CD3epsilon variable light chain and lambda light chain (SEQ ID NO: 74), followed by marked cysteine residues (marked bold and underlined), which may participate in a disulfide double bond, followed by an anti-EGFR scFv VL (SEQ ID NO: 34)-linker (SEQ ID NO: 40)-VH (SEQ ID NO: 37) chain. FIG. 5B presents one embodiment of an optimized nucleic acid sequence (DNA) encoding a Light Chain (LC) polypeptide of an activated tri-specific (tri-body) construct, having the 5' to 3' order and components as follows (SEQ ID NO: 151). The nucleic acid sequences encoding the component parts of the LC polypeptide shown in FIG. 5A include: Linker (e.g., L2 of FIG. 2E) (SEQ ID NO: 154), anti-CD3epsilon variable light chain and lambda light chain region (SEQ ID NO: 159), followed by marked cysteine residues (marked bold and underlined), which may participate in a disulfide double bond, followed by an anti-EGFR scFv VL (SEQ ID NO: 34)-linker (SEQ ID NO: 40)-VH (SEQ ID NO: 37) chain.

FIGS. 6A and 6B present embodiments of an amino acid sequence of a Heavy Chain (HC) polypeptide of an activated tri-specific (tri-body) antibody construct (Construct 2; VHVL) and an optimized nucleotide sequences encoding the Heavy Chain (HC) activated construct. Amino acid sequences are presented N-terminal to C-terminal, and nucleic acid sequences are presented 5' to 3'. FIG. 6A presents one embodiment of an amino acid sequence of a Heavy Chain (HC) polypeptide of an activated construct, having the N-terminal to C-terminal order and components as follows: h1F3.5-G1Fd-(VH-linker-VL) (SEQ ID NO: 140). The amino acid sequences of the component parts of the HC polypeptide shown in FIG. 6A include: Linker (SEQ ID NO: 158), anti-CD3epsilon variable heavy chain and constant heavy chain region 1 (SEQ ID NO: 113), followed by two marked cysteine residues (marked bold and underlined), which may participate in disulfide double bond, followed by an anti-EGFR scFv VH (SEQ ID NO: 37)-linker (SEQ ID NO: 40)-VL (SEQ ID NO: 34) chain. FIG. 6B presents one embodiment of an optimized nucleic acid sequence (DNA) encoding a Heavy Chain (HC) polypeptide of an activated tri-specific (tri-body) construct, having the 5' to 3' order and components as follows (SEQ ID NO: 152). The nucleic acid sequences encoding the component parts of the HC polypeptide shown in FIG. 6A include: Linker (SEQ ID NO: 154), anti-CD3epsilon variable heavy chain and constant heavy chain region 1 (SEQ ID NO: 155), followed by two marked cysteine residues (marked bold and underlined), which may participate in disulfide double bonds, followed by an anti-EGFR scFv VH (SEQ ID NO: 38)-linker (SEQ ID NO: 40)-VH (SEQ ID NO: 36) chain.

FIGS. 7A and 7B present embodiments of an amino acid sequence of a Light Chain (LC) polypeptide of an activated tri-specific (tri-body) antibody construct (Construct 2; VHVL) and an optimized nucleotide sequences encoding the Light Chain (LC) activated construct. Amino acid sequences are presented N-terminal to C-terminal, and nucleic acid sequences are presented 5' to 3'. FIG. 7A presents one embodiment of an amino acid sequence of a Light Chain (LC) polypeptide of an activated construct, having the N-terminal to C-terminal order and components as follows: h1F3.1-ALC-Anti-EGFR (VH-linker-VL) (SEQ ID NO: 141). The amino acid sequences of the component parts of the LC polypeptide shown in FIG. 7A include: Linker (SEQ ID NO: 158), anti-CD3epsilon variable light chain and lambda light chain (SEQ ID NO: 74), followed by marked cysteine residues (marked bold and underlined), which may participate in a disulfide double bond, followed by an anti-EGFR scFv VH (SEQ ID NO: 37)-linker (SEQ ID NO: 40)-VL (SEQ ID NO: 34) chain. FIG. 7B presents one embodiment of an optimized nucleic acid sequence (DNA) encoding a Light Chain (LC) polypeptide of an activated tri-specific (tri-body) construct, having the 5' to 3' order and components as follows (SEQ ID NO: 153). The nucleic acid sequences encoding the component parts of the LC polypeptide shown in FIG. 7A include: Linker (SEQ ID NO: 154), anti-CD3epsilon variable light chain and lambda light chain region (SEQ ID NO: 159), followed by marked cysteine residues (marked bold and underlined), which may participate in a disulfide double bond, followed by an anti-EGFR scFv VH (SEQ ID NO: 38)-linker (SEQ ID NO: 40)-VL (SEQ ID NO: 36) chain.

FIGS. 8A and 8B present embodiments of an amino acid sequence of a Heavy Chain (HC) polypeptide of precursor tri-specific (tri-body) antibody construct (Construct 3; VLVH) and an optimized nucleotide sequences encoding the Heavy Chain (HC) precursor construct, Amino acid sequences are presented N-terminal to C-terminal, and nucleic acid sequences are presented 5' to 3'. FIG. 8A presents one embodiment of an amino acid sequence of a Heavy Chain (HC) polypeptide of a precursor construct, having the N-terminal to C-terminal order and components as follows: hALB-G-PLGLAG (MMP2/9)-(cloning)-h1F3.5-G1Fd anti-EGFR VL-linker-VH (SEQ ID NO: 130). The amino acid sequences of the component parts of the HC polypeptide shown in FIG. 8A include: human serum albumin (HSA) (SEQ ID NO: 7), MMP2/9 protease cleavable Linker (SEQ ID NO: 160 (linker with cleavable sequence) and SEQ ID NO: 9 (cleavable sequence)), anti-CD3epsilon variable heavy chain and constant heavy chain region 1 (SEQ ID NO: 113), followed by two marked cysteine residues (marked bold and underlined), which may participate in disulfide double bonds, followed by an anti-EGFR scFv VL (SEQ ID NO: 34)-linker (SEQ ID NO: 40)-VH (SEQ ID NO: 37) chain. FIG. 8B presents one embodiment of an optimized nucleic acid sequence (DNA) encoding a Heavy Chain (HC) polypeptide of the precursor tri-specific (tri-body) antibody construct, having the 5' to 3' order and components as follows (SEQ ID NO: 142). The nucleic acid sequences encoding the component parts of the HC polypeptide shown in FIG. 8A include: human serum albumin (HSA) (SEQ ID NO: 8), MMP2/9 protease cleavable Linker (SEQ ID NO: 161 (linker with cleavable sequence and SEQ ID NO: 33 (cleavable sequence)), anti-CD3epsilon variable heavy chain and constant heavy chain region 1 (SEQ ID NO: 155), followed by two marked cysteine residues (marked bold and underlined), which may participate in disulfide double bond, followed by an anti-EGFR scFv VL (SEQ ID NO: 36)-linker (SEQ ID NO: 40)-VH (SEQ ID NO: 38) chain.

FIGS. 9A and 9B present embodiments of an amino acid sequence of a Light Chain (LC) polypeptide of a precursor tri-specific (tri-body) antibody construct (Construct 3; VLVH) and an optimized nucleotide sequences encoding the Light Chain (LC) precursor construct, Amino acid sequences are presented N-terminal to C-terminal, and nucleic acid sequences are presented 5' to 3'. FIG. 9A presents one embodiment of an amino acid sequence of a Light Chain (LC) polypeptide of a precursor construct, having the N-terminal to C-terminal order and components as follows: Cap-h1F3.1-ALC anti-EGFR VL-linker-VH MM2/9 cleavage; SEQ ID NO: 131). The amino acid sequences of the component parts of the LC polypeptide shown in FIG. 9A include: CAP (SEQ ID NO: 5), MMP2/9 protease cleavable Linker (SEQ ID NO: 160 and SEQ ID NO: 9 (cleavable sequence)), anti-CD3epsilon variable light chain and lambda light chain (SEQ ID NO: 74), followed by marked cysteine residues (marked bold and underlined), which may participate in a disulfide double bond, followed by an anti-EGFR scFv VL (SEQ ID NO: 34)-linker (SEQ ID NO: 40)-VH (SEQ ID NO: 37) chain. FIG. 9B presents one embodiment of an optimized nucleic acid sequence (DNA) encoding the Light Chain (LC) polypeptide of the precursor tri-specific (tri-body) antibody construct, having the 5' to 3' order and components as follows (SEQ ID NO: 143). The nucleic acid sequences encoding the component parts of the LC polypeptide shown in FIG. 9A include: CAP (SEQ ID NO: 164), MMP2/9 protease cleavable Linker (SEQ ID NO: 161 and SEQ ID NO: 33 (cleavable sequence), anti-CD3epsilon variable light chain and lambda light chain region (SEQ ID NO: 159), followed by marked cysteine residues (marked bold and underlined), which may participate in a disulfide double bond, followed by an anti-EGFR scFv VL (SEQ ID NO: 36)-linker (SEQ ID NO: 40)-VH (SEQ ID NO: 38) chain.

FIGS. 10A and 10B present embodiments of an amino acid sequence of a Heavy Chain (HC) polypeptide of precursor tri-specific (tri-body) antibody construct (Construct 4; VHVL) and an optimized nucleotide sequences encoding the Heavy Chain (HC) precursor construct. Amino acid sequences are presented N-terminal to C-terminal, and nucleic acid sequences are presented 5' to 3'. FIG. 10A presents one embodiment of an amino acid sequence of a Heavy Chain (HC) polypeptide of a precursor construct, having the N-terminal to C-terminal order and components as follows: hALB-G-PLGLAG (MMP2/9)-(cloning)-h1F3.5-G1Fd Anti-EGFR (VH-linker-VL) (SEQ ID NO: 132). The amino acid sequences of the component parts of the HC polypeptide shown in FIG. 10A include: human serum albumin (HSA) (SEQ ID NO: 7), MMP2/9 protease cleavable Linker (SEQ ID NO: 160 and SEQ ID NO: 9 (cleavable portion)), anti-CD3epsilon variable heavy chain and constant heavy chain region 1 (SEQ ID NO: 113), followed by two marked cysteine residues (marked bold and underlined), which may participate in disulfide double bonds, followed by an anti-EGFR scFv VH (SEQ ID NO: 37)-linker (SEQ ID NO: 40)-VL (SEQ ID NO: 34) chain. FIG. 10B presents one embodiment of an optimized nucleic acid sequence (DNA) encoding the Heavy Chain (HC) polypeptide of the precursor tri-specific (tri-body) antibody construct, having the 5' to 3' order and components as follows (SEQ ID NO: 144). The nucleic acid sequences encoding the component parts of the HC polypeptide shown in FIG. 10A include: human serum albumin (HSA) (SEQ ID NO: 8), MMP2/9 protease cleavable Linker (SEQ ID NO: 161 and SEQ ID NO: 33 (cleavable linker)), anti-CD3epsilon variable heavy chain and constant heavy chain region 1 (SEQ ID NO: 155), followed by two marked cysteine residues (marked bold and underlined), which may participate in disulfide double bond, followed by an anti-EGFR scFv VH (SEQ ID NO: 38)-linker (SEQ ID NO: 40)-VL (SEQ ID NO: 36) chain.

FIGS. 11A and 11B present embodiments of an amino acid sequence of a Light Chain (LC) polypeptide of a precursor tri-specific (tri-body) antibody construct (Construct 4; VLVH) and an optimized nucleotide sequences encoding the Light Chain (LC) precursor construct. Amino acid sequences are presented N-terminal to C-terminal, and nucleic acid sequences are presented 5' to 3'. FIG. 11A presents one embodiment of an amino acid sequence of a Light Chain (LC) polypeptide of a precursor construct, having the N-terminal to C-terminal order and components as follows: Cap-MMP2/9 cleavage-h1F3.1-ALC-Anti-EGFR (VH-linker-VL) (SEQ ID NO: 133; plasmid 7). The amino acid sequences of the component parts of the LC polypeptide shown in FIG. 11A include: CAP (SEQ ID NO: 5), MMP2/9 protease cleavable Linker (SEQ ID NO: 160 and SEQ ID NO: 9 (cleavable linker), anti-CD3epsilon variable light chain and lambda light chain (SEQ ID NO: 74), followed by marked cysteine residues (marked bold and underlined), which may participate in a disulfide double bond, followed by an anti-EGFR scFv VH (SEQ ID NO: 37)-linker (SEQ ID NO: 40)-VL (SEQ ID NO: 34) chain. FIG. 11B presents one embodiment of an optimized nucleic acid sequence (DNA) encoding the Light Chain (LC) polypeptide of the precursor tri-specific (tri-body) antibody construct, having the 5' to 3' order and components as follows (SEQ ID NO: 145). The nucleic acid sequences encoding the component parts of the LC polypeptide shown in FIG. 11A include: CAP (SEQ ID NO: 164), MMP2/9 protease cleavable Linker (SEQ ID NO: 161 and SEQ ID NO: 33 (cleavable sequence)), anti-CD3epsilon variable light chain and lambda light chain region (SEQ ID NO: 159), followed by marked cysteine residues (marked bold and underlined), which may participate in a disulfide double bond, followed by an anti-EGFR scFv VH (SEQ ID NO: 38)-linker (SEQ ID NO: 40)-VL (SEQ ID NO: 36) chain.

FIGS. 12A and 12B present embodiments of an amino acid sequence of a Heavy Chain (HC) polypeptide of non-cleavable (non-activatable) precursor tri-specific (tri-body) antibody construct (Construct 5; VLVH) and an optimized nucleotide sequences encoding the Heavy Chain (HC) non-cleavable precursor construct. Amino acid sequences are presented N-terminal to C-terminal, and nucleic acid sequences are presented 5' to 3'. FIG. 12A presents one embodiment of an amino acid sequence of a Heavy Chain (HC) polypeptide of a non-cleavable precursor construct, having the N-terminal to C-terminal order and components as follows: hALB-G-PLGLAG NC-h1F3.5-G1Fd anti-EGFR VL-linker-VH (SEQ ID NO: 134). The amino acid sequences of the component parts of the HC polypeptide shown in FIG. 12A include: human serum albumin (HSA) (SEQ ID NO: 7), non-cleavable Linker (SEQ ID NO: 162), anti-CD3epsilon variable heavy chain and constant heavy chain region 1 (SEQ ID NO: 113), followed by two marked cysteine residues (marked bold and underlined), which may participate in disulfide double bonds, followed by an anti-EGFR scFv VL (SEQ ID NO: 34)-linker (SEQ ID NO: 40)-VH (SEQ ID NO: 37) chain. FIG. 12B presents one embodiment of an optimized nucleic acid sequence (DNA) encoding a Heavy Chain (HC) polypeptide of the non-cleavable precursor tri-specific (tri-body) antibody construct, having the 5' to 3' order and components as follows (SEQ ID NO: 146). The nucleic acid sequences encoding the component parts of the HC polypeptide shown in FIG. 12A include: human serum albumin (HSA) (SEQ ID NO: 8), non-cleavable Linker (SEQ ID NO: 163), anti-CD3epsilon variable heavy chain and constant heavy chain region 1 (SEQ ID NO: 155), followed by two marked cysteine residues (marked bold and underlined), which may participate in disulfide double bond, followed by an anti-EGFR scFv VL (SEQ ID NO: 36)-linker (SEQ ID NO: 40)-VH (SEQ ID NO: 38) chain.

FIGS. 13A and 13B present embodiments of an amino acid sequence of a Light Chain (LC) polypeptide of a non-cleavable precursor tri-specific (tri-body) antibody construct (Construct 5; VLVH) and an optimized nucleotide sequences encoding the Light Chain (LC) non-cleavable precursor construct. Amino acid sequences are presented N-terminal to C-terminal, and nucleic acid sequences are presented 5' to 3'. FIG. 13A presents one embodiment of an amino acid sequence of a Light Chain (LC) polypeptide of a non-cleavable precursor construct, having the N-terminal to C-terminal order and components as follows: Cap-(h1F3.1-2LC anti-EGFR VL-linker-VH Non-Cleavable (SEQ ID NO: 135). The amino acid sequences of the component parts of the LC polypeptide shown in FIG. 13A include: CAP (SEQ ID NO: 5), non-cleavable Linker (SEQ ID NO: 162), anti-CD3epsilon variable light chain and lambda light chain (SEQ ID NO: 74), followed by marked cysteine residues (marked bold and underlined), which may participate in a disulfide double bond, followed by an anti-EGFR scFv VL (SEQ ID NO: 34)-linker (SEQ ID NO: 40)-VH (SEQ ID NO: 37) chain. FIG. 13B presents one embodiment of an optimized nucleic acid sequence (DNA) encoding the Light Chain (LC) polypeptide of the non-cleavable precursor tri-specific (tri-body) antibody construct, having the 5' to 3' order and components as follows (SEQ ID NO: 147). The nucleic acid sequences encoding the component parts of the LC polypeptide shown in FIG. 13A include: CAP (SEQ ID NO: 164), non-cleavable Linker (SEQ ID NO: 163),anti-CD3epsilon variable light chain and lambda light chain region (SEQ ID NO: 159), followed by marked cysteine residues (marked bold and underlined), which may participate in a disulfide double bond, followed by an anti-EGFR scFv VL (SEQ ID NO: 36)-linker (SEQ ID NO: 40)-VH (SEQ ID NO: 38) chain.

FIGS. 14A and 14B present embodiments of an amino acid sequence of a Heavy Chain (HC) polypeptide of a non-cleavable precursor tri-specific (tri-body) antibody construct (Construct 6; VHVL) and an optimized nucleotide sequences encoding the Heavy Chain (HC) non-cleavable precursor construct. Amino acid sequences are presented N-terminal to C-terminal, and nucleic acid sequences are presented 5' to 3'. FIG. 14A presents one embodiment of an amino acid sequence of a Heavy Chain (HC) polypeptide of a non-cleavable precursor construct, having the N-terminal to C-terminal order and components as follows: hALB-G-PLGLAG (NC)-(cloning)-h1F3.5-G1Fd-(VH-linker-VL) (SEQ ID NO: 136). The amino acid sequences of the component parts of the HC polypeptide shown in FIG. 14A include: human serum albumin (HSA) (SEQ ID NO: 7), non-cleavable Linker (SEQ ID NO: 162), anti-CD3epsilon variable heavy chain and constant heavy chain region 1 (SEQ ID NO: 113), followed by two marked cysteine residues (marked bold and underlined), which may participate in disulfide double bonds, followed by an anti-EGFR scFv VH (SEQ ID NO: 37)-linker (SEQ ID NO: 40)-VL (SEQ ID NO: 34) chain. FIG. 14B presents one embodiment of an optimized nucleic acid sequence (DNA) encoding the Heavy Chain (HC) polypeptide of the non-cleavable precursor tri-specific (tri-body) antibody construct, having the 5' to 3' order and components as follows (SEQ ID NO: 148). The nucleic acid sequences encoding the component parts of the HC polypeptide shown in FIG. 14A include: human serum albumin (HSA) (SEQ ID NO: 8), non-cleavable Linker (SEQ ID NO: 163), anti-CD3epsilon variable heavy chain and constant heavy chain region 1 (SEQ ID NO: 155), followed by two marked cysteine residues (marked bold and underlined), which may participate in disulfide double bond, followed by an anti-EGFR scFv VH (SEQ ID NO: 38)-linker (SEQ ID NO: 40)-VL (SEQ ID NO: 36) chain.

FIGS. 15A and 15B present embodiments of an amino acid sequence of a Light Chain (LC) polypeptide of a non-cleavable precursor tri-specific (tri-body) antibody construct (Construct 6; VLVH) and an optimized nucleotide sequences encoding the Light Chain (LC) non-cleavable precursor construct. Amino acid sequences are presented N-terminal to C-terminal, and nucleic acid sequences are presented 5' to 3'. FIG. 15A presents one embodiment of an amino acid sequence of a Light Chain (LC) polypeptide of a precursor construct, having the N-terminal to C-terminal order and components as follows: Cap (NC)-h1F3.1-ALC-Anti-EGFR (VH-linker-V) (SEQ ID NO: 137). The amino acid sequences of the component parts of the LC polypeptide shown in FIG. 15A include: CAP (SEQ ID NO: 5), non-cleavable Linker (SEQ ID NO: 162), anti-CD3epsilon variable light chain and lambda light chain (SEQ ID NO: 74), followed by marked cysteine residues (marked bold and underlined), which may participate in a disulfide double bond, followed by an anti-EGFR scFv VH (SEQ ID NO: 37)-linker (SEQ ID NO: 40)-VL (SEQ ID NO: 34) chain. FIG. 15B presents one embodiment of an optimized nucleic acid sequence (DNA) encoding the Light Chain (LC) polypeptide of the non-cleavable precursor tri-specific (tri-body) antibody construct, having the 5' to 3' order and components as follows (SEQ ID NO: 149). The nucleic acid sequences encoding the component parts of the LC polypeptide shown in FIG. 15A include: CAP (SEQ ID NO: 164), non-cleavable Linker (SEQ ID NO: 163), anti-CD3epsilon variable light chain and lambda light chain region (SEQ ID NO: 159), followed by marked cysteine residues (marked bold and underlined), which may participate in a disulfide double bond, followed by an anti-EGFR scFv VH (SEQ ID NO: 38)-linker (SEQ ID NO: 40)-VL (SEQ ID NO: 36) chain.

FIG. 16 presents SDS-PAGE of Activated Tri-Body and Precursor Tri-body Antibody Constructs. In FIG. 16 all Tri-Body and Precursor Tri-Body constructs were analyzed by SDS-PAGE, either in reduced (R) and non-reduced (NR) form. Number 1 is construct 1: activated Tri-body construct (VL-VH); Number 2 is construct 2: activated Tri-body construct (VH-VL); Number 3 is construct 3: Precursor Tri-body construct (VL-VH); Number 4 is construct 4: Precursor Tri-body construct (VH-VL); Number 5 is construct 5: Non-Cleavable Precursor Tri-body construct (VL-VH); and Number 6 is construct 6: Non-Cleavable Precursor Tri-body construct (VH-VL). Lanes are marked with the construct number and the reduced (R) or non-reduced (NR) form. The Tribody Molecular Weight is 100112 Da, composed of the Fd and the AC fusion, having the MW of 51105 and 49029, respectively.

Figure 1:
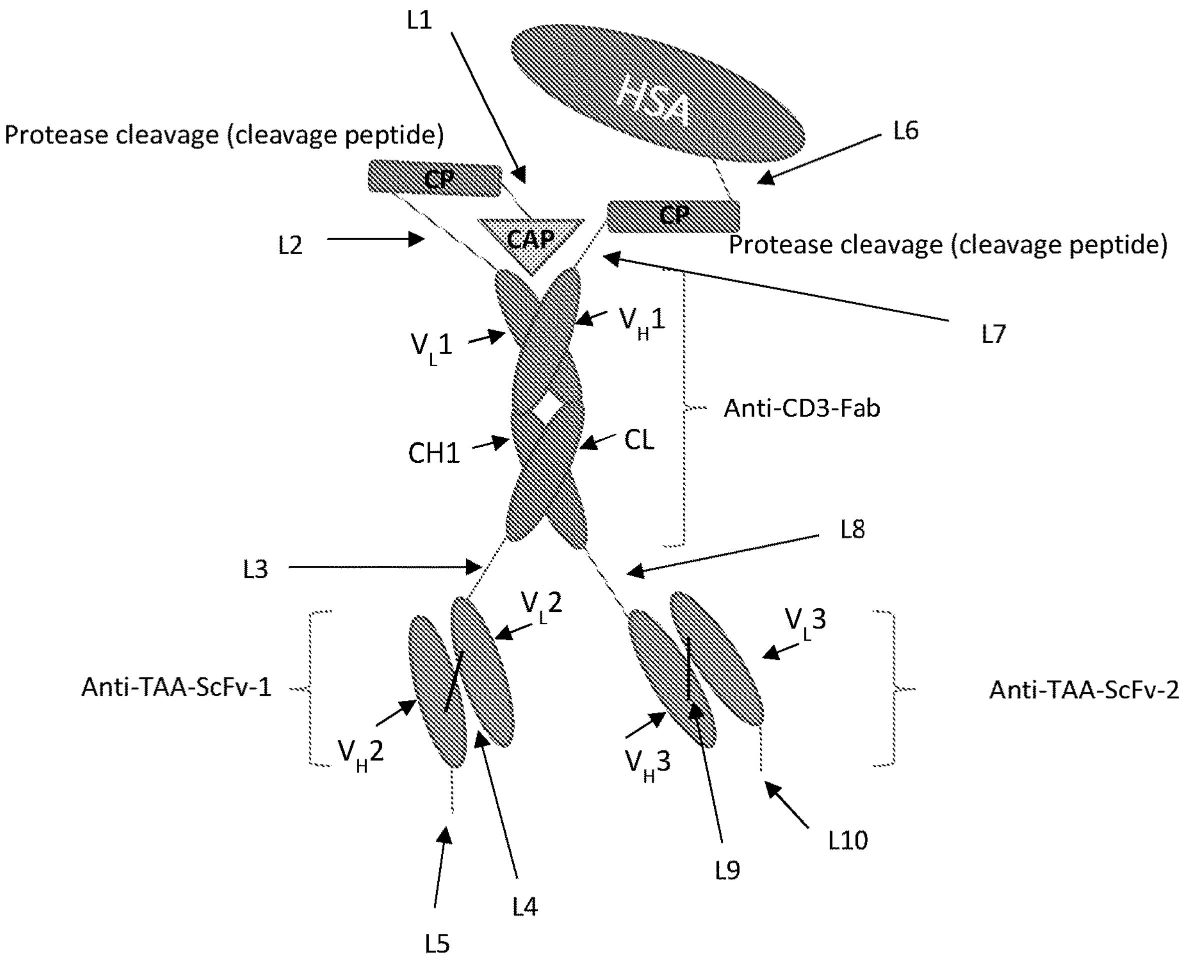
FIG. 1 present a schematic embodiment of a precursor tri-specific (tri-body) antibody construct having modular components, for example but not limited to: (1) modular regulatory domains including in certain embodiments, modular functional components and modular protease cleavage peptides, and (2) modular binding domains including in certain embodiments modular anti-tumor associated antigen binding domains. The embodiment of a precursor tri-specific (tri-body) antibody construct of FIG. 1 has three antibody binding domains, wherein the Fab portion recognizes a CD3 surface antigen, wherein the components and regions of the different domains are identified. In the embodiment shown here, the precursor tri-specific (tri-body) antibody construct is formed by two polypeptides, wherein each of the polypeptides includes an anti-tumor associated antigen (TAA) binding domain (first and second binding domains) that is C-terminal to the anti-CD3 Fab binding domains on each polypeptide (third binding domain). Further, each polypeptide includes a regulatory domain N-terminal to the anti-CD3 Fab binding domain (first and second sub-regulatory domains), wherein a first sub-regulatory domain comprises a protease cleavage domain and a half-life prolonging domain (in this embodiment, a human serum albumin), and a second sub-regulatory domain comprising a protease cleavage domain and a CAP component that reduces the ability of the third binding domain to bind the surface antigen of human CD3. As shown here, each of the anti-TAA binding domains are single chain variable fragments (ScFv). As shown here, the N-terminal to C-terminal order of one of the ScFv is a Variable Light chain region (VL2) followed by a linker (L4) followed by a Variable Heavy chain region (VH2) followed by a linker (L5) while the N-terminal to C-terminal order of the other ScFv is a Variable Heavy chain region (VH3) followed by a linker (L9) followed by a Variable Light chain region (VL3) followed by a linker (L10). In embodiments not shown, the N-terminal to C-terminal order of the scFv may be reversed, may both be the same for both scFv binding domains or different. In embodiments not shown, the two sub-regulatory domains could be linked to the other polypeptide chain from their current linkage, for example the HSA regulatory domain could be linked N-terminal to the Variable Light chain (VL1) of the Fab fragment and the CAP regulatory domain could be linked N-terminal to the Variable Heavy chain (VH1) of the Fab fragment. The linkers between components and between domains are identified by an "L" followed by a numeral, e.g., L1, L2, L3, L4, L5, L6, L7, L8, L9, L10. Linkers may or may not be present. VL1 is a variable light-chain region of binding site three, VH1 is a variable heavy-chain region of binding site three. The oval shape indicated as HSA is the human serum albumin component. The shape indicated as CP is the cleavage peptide. The triangle shape is the CAP component.

As can be seen in FIG. 16, all proteins are pure, and migrated in the appropriate MW as expected, both in their reduced and non-reduced forms. The Precursor TriBody Molecular Weight is 170390 Da, composed of the Fd and the AC fusion, having the MW of 117649 and 52762, respectively. As can be seen in FIG. 16, all proteins are pure, and migrate in the appropriate MW as expected, both in their reduced and non-reduced forms.

FIGS. 17A-17F present Analytical HPLC-Size Exclusion Chromatography of Active TriBody and Precursor Tribody Antibody Constructs. In FIGS. 17A-17F all TriBody and Precursor TriBody were analyzed by Analytical HPLC-Size Exclusion Chromatography (SEC), in their native form. The Tribody Molecular Weight is 100,112 Da, migrating as monomer at its expected size, as compared to known MW markers. The Precursor TriBody Molecular Weight is 170, 390 Da, migrating as monomer at its expected size, as compared to known MW markers. 17A presents the results of construct 1, 17B presents the results of construct 2, 17C presents the results of construct 3, 17D presents the results of construct 4, 17E presents the results of construct 5, and 17F presents the results of construct 6.

Figure 18A:
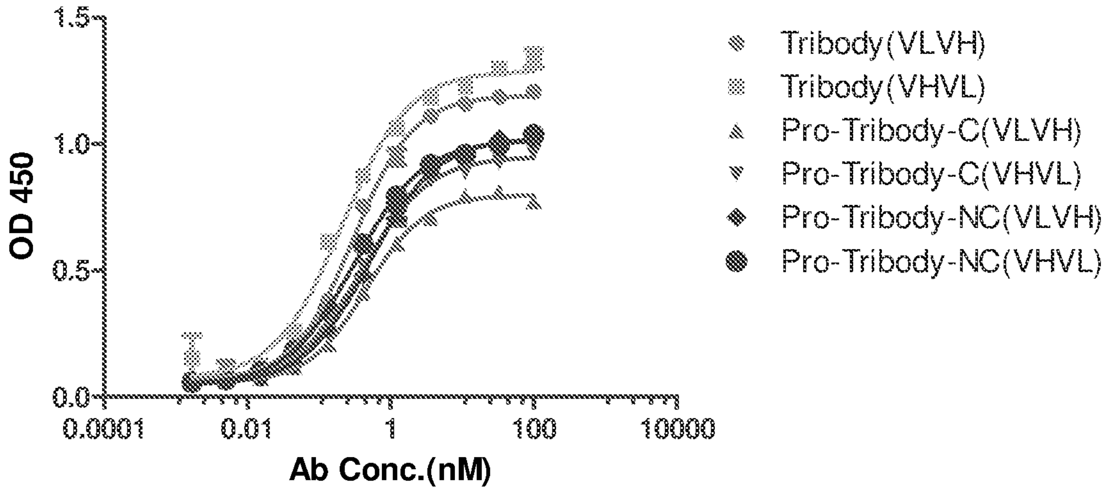
Figure 18B:
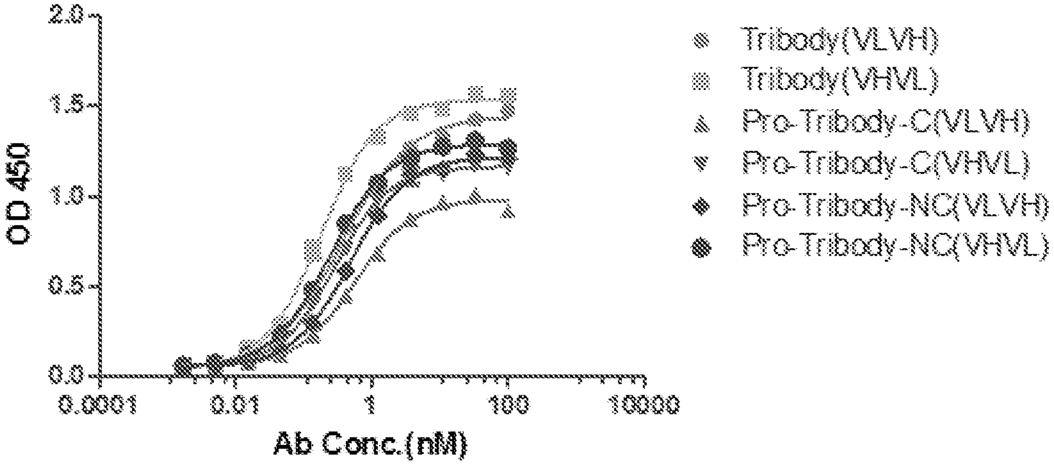

FIGS. 18A and 18B show ELISA Binding studies. FIG. 18A shows ELISA binding studies of TriBody and Precursor TriBody Antibody Constructs Towards human EGFR Antigen. TriBody and Precursor TriBody antibodies, both in their VL-VH or VH-VL formats, were tested for their binding to EGFR extracellular fusion antigen (hEGFR-Fc) using an ELISA method. As can be seen in FIG. 18A, all TriBody and Precursor TriBody forms bound the extracellular domain of hEGFR with similar affinities. Furthermore, there were no major differences between VL-VH and VH-VL forms of the anti-EGFR scFv. FIG. 18B presents ELISA Binding of TriBody and Precursor TriBody Antibodies Towards rhesus EGFR Antigen TriBody and Precursor TriBody antibodies, both in their VL-VH or VH-VL formats, were tested for their binding to rhesus EGFR extracellular fusion antigen (rhesus EGFR-Fc) using ELISA method. As can be seen in FIG. 18B, all TriBody and Precursor TriBody forms bound the extracellular domain of rhesus EGFR with similar affinities. There were no major differences between VL-VH and VH-VL forms of the anti-EGFR scFv. Furthermore, the binding affinities of all TriBody and Precursor TriBody were comparable towards the human and rhesus EGFR. In the graphs of FIGS. 18A and 18B: Construct 1 is represented by small circle, Construct 2 is represented by a small square, Construct 3 is represented by a upward triangle, Construct 4 is represented by a upside-down triangle, Construct 5 is represented by a diamond, and Construct 6 is represented by a large circle.

Figure 19A:
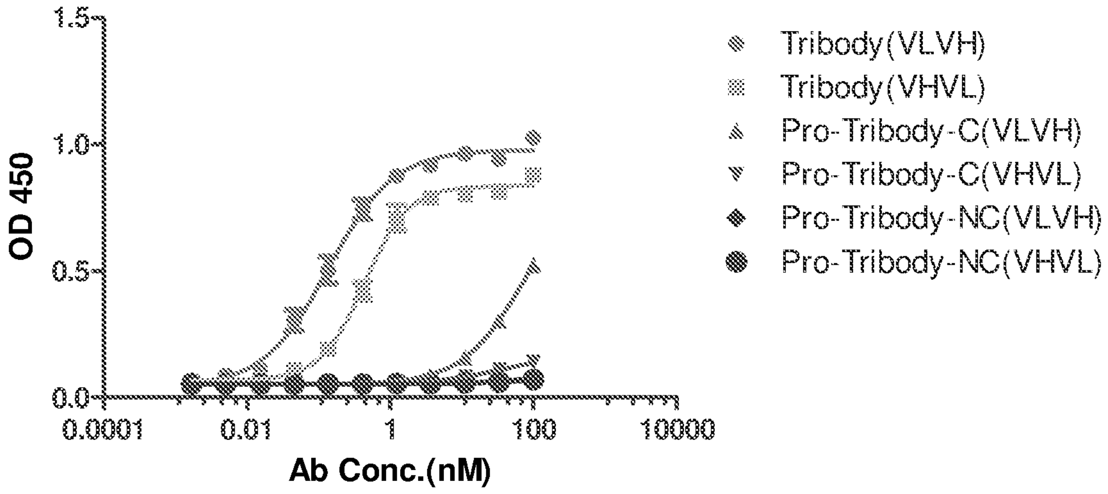
Figure 19B:
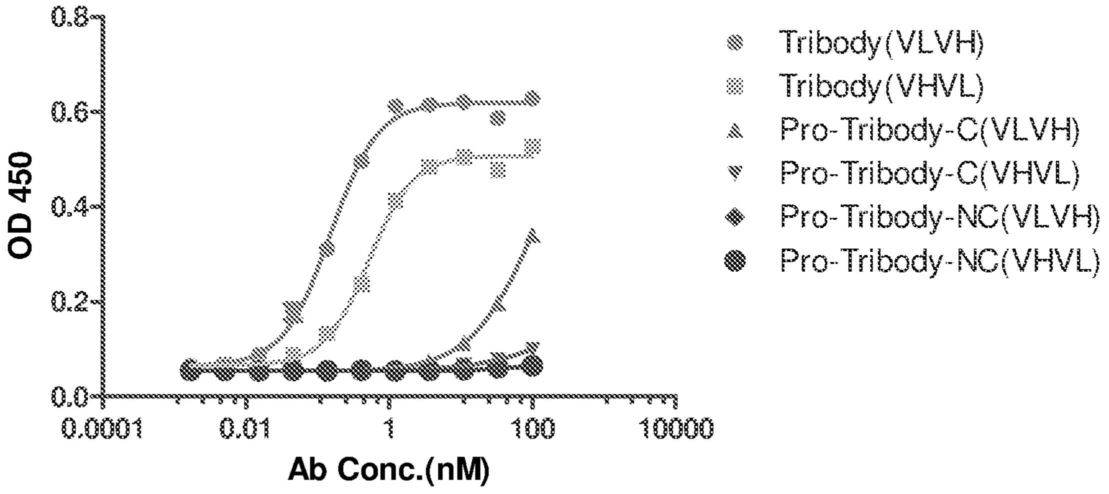

FIGS. 19A and 19B present ELISA Binding Studies towards human and cyno CD38 antigen. FIG. 19A shows ELISA Binding of TriBody and ProTriBody Antibodies Towards human CD3epsilon Antigen. TriBody and ProTriBody antibodies, both in their VL-VH or VH-VL formats, were tested for their binding to human CD3epsilon extracellular fusion antigen (human CD3epsilon-His) using ELISA method. As can be seen in FIG. 19A, TriBody antibodies bound hCD3espilon with sub-nM affinities, while ProTriBody forms (both Cleaved (C) and Non-Cleaved (NC)) bound the extracellular domain of hCD3espilon with much higher EC50s, suggesting hindrance of the CD3epsilon binding towards its antigen. There were no major differences between VL-VH and VH-VL forms of the anti-CD3epsilon. FIG. 19B shows ELISA Binding of TriBody and ProTriBody Antibodies Towards cyno CD3epsilon Antigen. TriBody and ProTriBody antibodies, both in their VL-VH or VH-VL formats, were tested for their binding to human CD3epsilon extracellular fusion antigen (cyno CD3epsilon-His) using ELISA method. As can be seen in FIG. 19B, TriBody antibodies bound cynoCD3espilon with sub-nM affinities, while ProTriBody forms (both Cleaved (C) and Non-Cleaved (NC)) bound the extracellular domain of hCD3espilon with much higher EC50s, suggesting hindrance of the CD3epsilon binding towards its antigen. There were no major differences between VLVH and VHVL forms of the anti-CD3epsilon. Furthermore, the binding affinities of all TriBody and ProTriBody were comparable towards the human and rhesus CD3epsilon.

Figure 20:
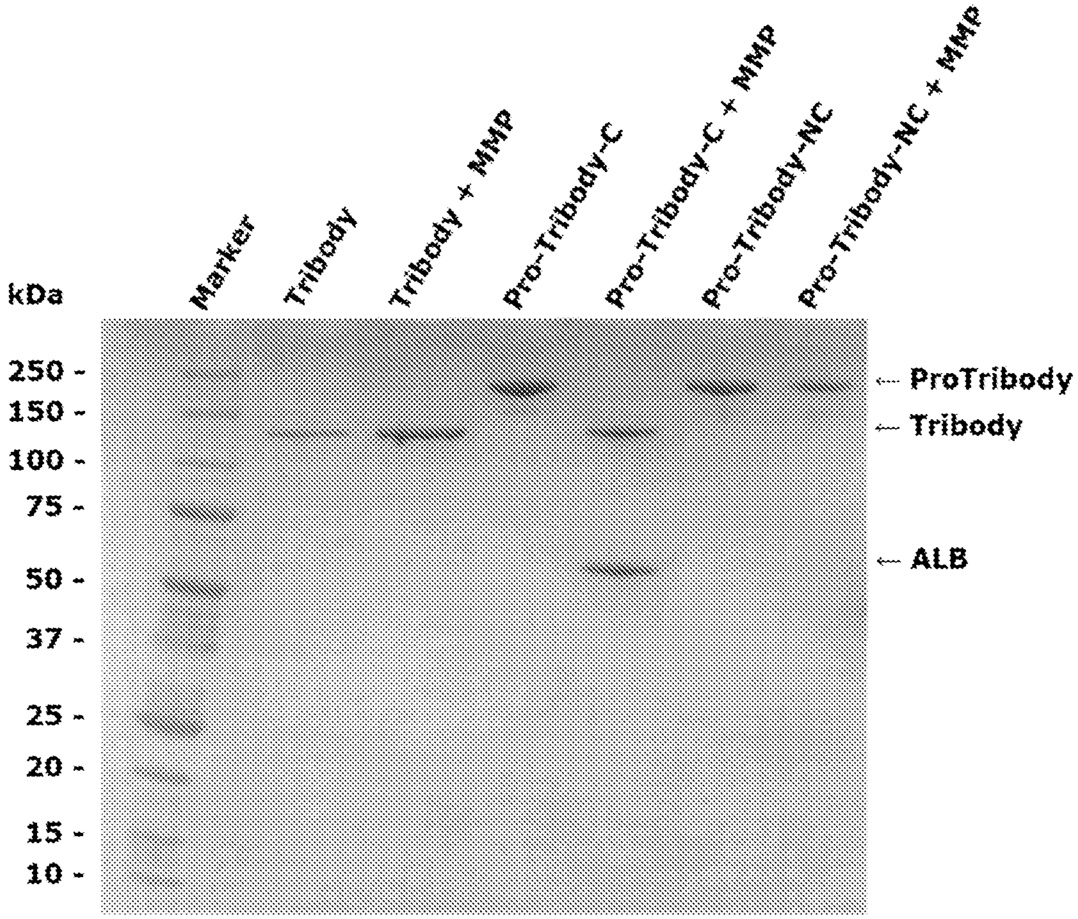

FIG. 20 presents SDS-PAGE of TriBody and ProTribody (VHVL) digested by MMP9. In FIG. 20 all TriBody and ProTriBody are digested by MMP9 and their cleavage products analyzed by SDS-PAGE, either in non-reduced (NR) conditions. The Tribody Molecular Weight is 100112 Da, composed of the Fd and the AC fusion. MMP9 cleavage had no apparent activity on the TriBody, as it does not have any MMP9 cleavage sequence. The ProTriBody Molecular Weight is 170390 Da. The ProTriBody-C represents the ProTriBody having an MMP9 cleavage sequence at the C-terminal end of the half-life extending moiety (Human Serum Albumin) and at the C-terminal end of the CD3epsilon CAP masking moiety. The ProTriBody-NC represents the ProTriBody lacking the MMP9 cleavage sequences, and therefore, should not be cleaved by MMP9. As can be seen, only ProTriBody-C was cleaved by MMP9, resulting with two bands, the TriBody and the half-life extending moiety (Human Serum Albumin (HSA)).

Figure 21A:
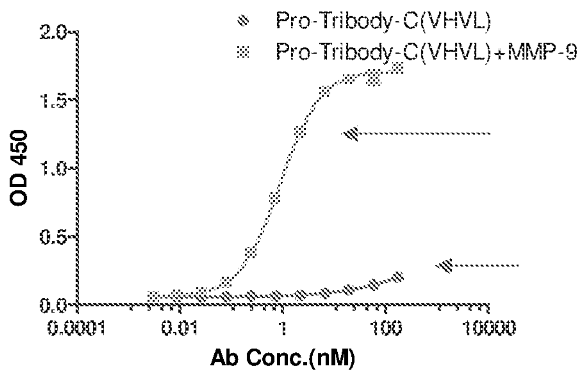
Figure 21B:
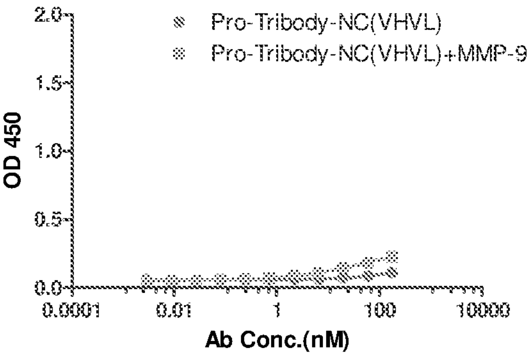
Figure 22A:
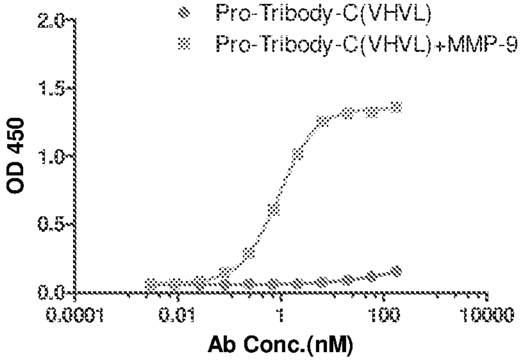
Figure 22B:
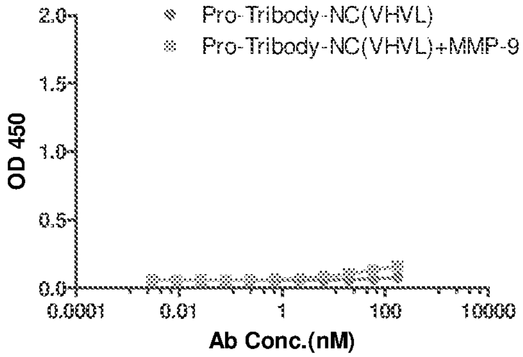

FIGS. 21A and 21B present ELISA Binding of ProTriBody-C(VHVL) and ProTriBody-NC (VHVL) to human CD3e Antigen: cleavage by MMP-9. ProTriBody VH-VL format antibodies, were tested for their binding to human CD3epsilon extracellular fusion antigen (human CD3epsilon-His) using ELISA method before, and after MMP9 cleavage. As can be seen in FIG. 21A, ProTriBody-C antibody did not bind CD3epsilon before cleavage by MMP9, while following cleavage by MMP9, ProTriBody-C bound hCD3espilon with sub-nM affinites. ProTriBody-NC antibody did not bind CD3epsilon either in the presence or absence of MMP9 cleavage (FIGS. 21B). The data suggests that hindrance by the CAP and HSA in the precursor form, results in very little binding of the precursor towards CD3epsilon antigen. Once ProTriBody-C is cleaved by MMP9, thus liberating the HSA and CAP hindrance of the CD3epsilon, the binding EC50 towards human CD3epsilon is markedly improved towards nM biding affinities. ProTriBody-NC antibody was not cleaved, and therefore had little binding towards CD3epsilon FIGS. 22A and 22B present ELISA Binding of ProTriBody-C(VHVL) and ProTriBody-NC (VHVL) to cyno CD3e Antigen, with and without cleavage by MMP-9.

ProTriBody VH-VL antibodies, were tested for their binding to cyno CD3epsilon extracellular fusion antigen (cyno CD3epsilon-His) using ELISA method before, and after MMP9 cleavage. As can be seen in FIG. 22A, ProTriBody-C antibodies did not bind CD3epsilon before cleavage by MMP9, while after cleavage by MMP9 ProTriBody-C bound hCD3espilon with sub-nM affinites. ProTriBody-NC antibody did not bind cynoCD3epsilon either in the presence or absence of MMP9 cleavage (FIG. 22B). The data suggests that hindrance by the CAP and HSA in the precursor resulted in very little binding towards CD3epsilon antigen. Once ProTriBody-C is cleaved by MMP9, thus liberating the HSA and CAP hindrance of the cynoCD3epsilon, the binding EC50 towards human CD3epsilon is markedly improved towards nM biding affinities. ProTriBody-NC antibody was not cleaved, and therefore had little binding towards CD3epsilon.

Figure 23:
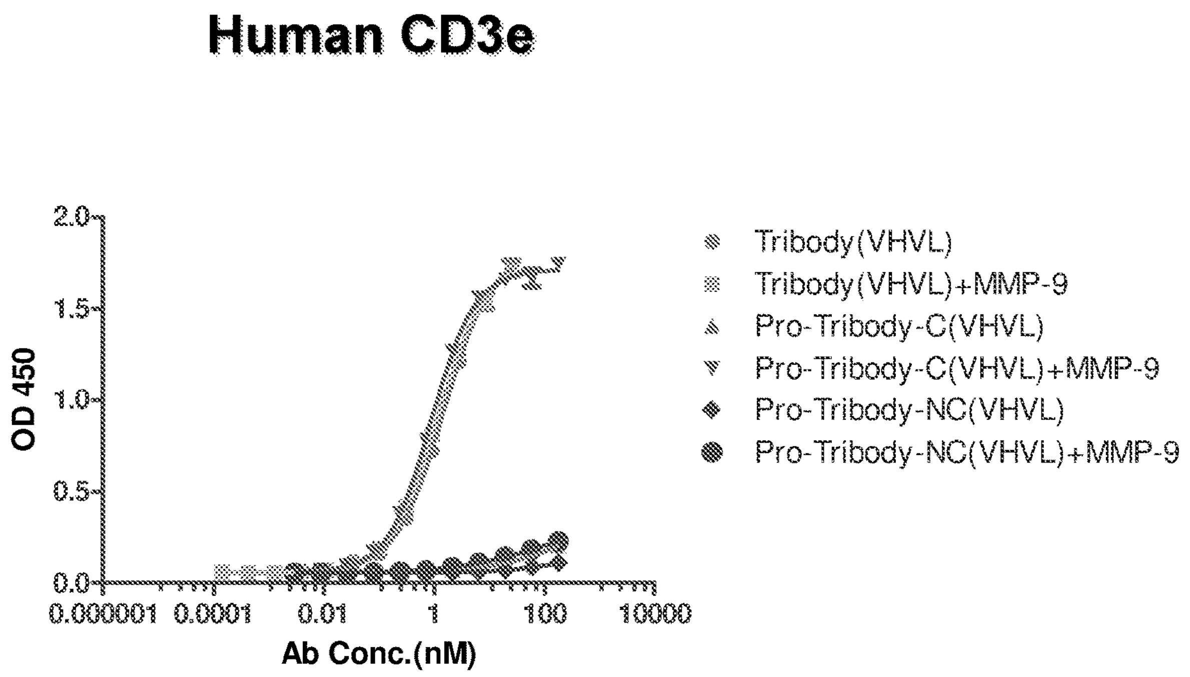

FIG. 23 presents ELISA Binding of TriBody (VHVL), ProTriBody-C(VHVL) and ProTriBody-NC (VHVL) to human CD3e Antigen: cleavage by MMP-9. TriBody VHVL and ProTriBody VHVL format antibodies, were tested for their binding to human CD3epsilon extracellular fusion antigen (human CD3epsilon-His) using ELISA method before, and after MMP9 cleavage. As can be seen in FIG. 23, ProTriBody-C antibodies did not bind CD3epsilon before cleavage by MMP9, while after cleavage by MMP9 ProTriBody-C bound hCD3espilon with sub-nM affinities, similar to the TriBody. ProTriBody-NC antibody did not bind CD3epsilon either in the presence or absence of MMP9 cleavage.

Figure 24:
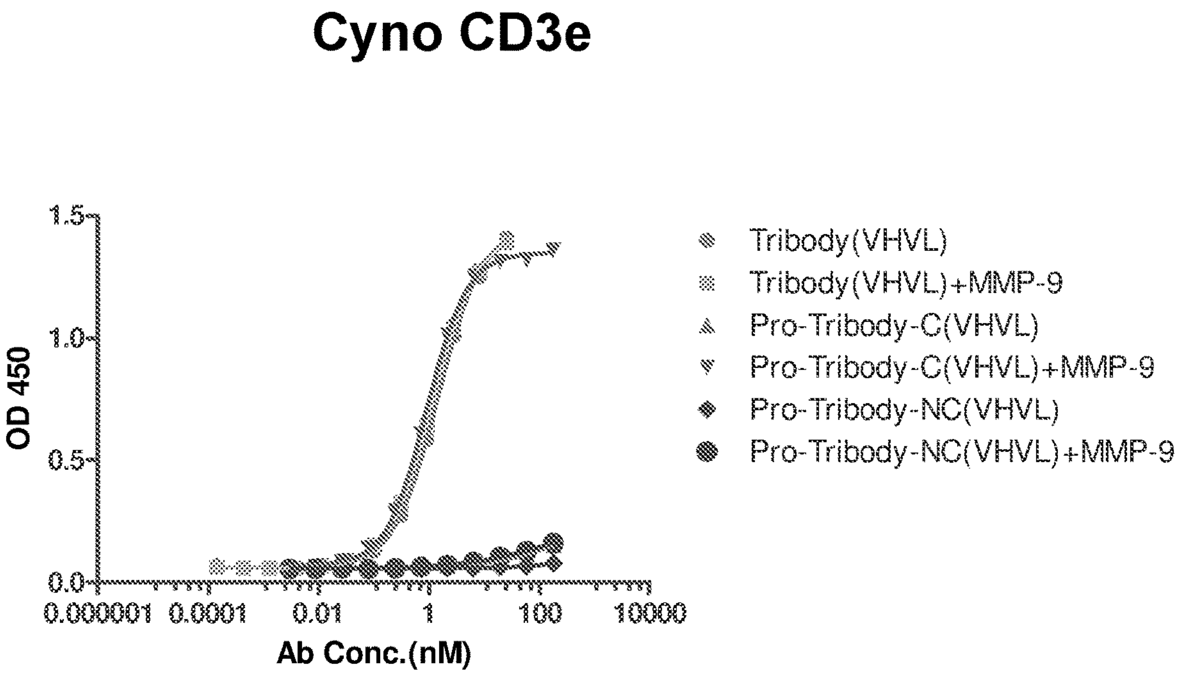

The data suggests that hindrance by the CAP and HSA in the precursor antibody resulted in very little binding towards CD3epsilon antigen. Once ProTriBody-C is cleaved by MMP9, thus liberating the HSA and CAP hindrance of the CD3epsilon, the binding EC50 towards human CD3epsilon is markly improved towards nM biding affinities. ProTriBody-NC antibody was not cleaved, and therefore had little binding towards CD3epsilon FIG. 24 presents ELISA Binding of TriBody (VHVL), ProTriBody-C(VHVL) and ProTriBody-NC (VHVL) to cyno CD3e Antigen: cleavage by MMP-9. TriBody VHVL and ProTriBody VHVL format antibodies, were tested for their binding to cyno CD3epsilon extracellular fusion antigen (cyno CD3epsilon-His) using ELISA method before, and after MMP9 cleavage. As can be seen in FIG. 24, ProTriBody-C antibodies did not bind CD3epsilon before cleavage by MMP9, while after cleavage by MMP9 ProTriBody-C bound hCD3espilon with sub-nM affinities, similar to the TriBody. ProTriBody-NC antibody did not bind CD3epsilon either in the presence or absence of MMP9 cleavage.

The data suggests that hindrance by the CAP and HSA in the precursor antibody resulted in very little binding towards CD3epsilon antigen. Once ProTriBody-C is cleaved by MMP9, thus liberating the HSA and CAP hindrance of the CD3epsilon, the binding EC50 towards human CD3epsilon is markedly improved towards low nM biding affinities. ProTriBody-NC antibody was not cleaved, and therefore had little binding towards CD3epsilon.

FIG. 25 presents FACS Binding of TriBody (VHVL), ProTriBody-C(VHVL) and ProTriBody-NC (VHVL) to Jurkat Cells (Human CD3e). TriBody VHVL and ProTriBody VHVL format antibodies, were tested for their binding to Jurkat Cells (Human CD3e) using the FACS method. As can be seen in FIG. 25, ProTriBody-C and ProTriBody-NC antibodies did not bind to Jurkat Cells while TriBody bound with low nM affinities. The data suggests that hindrance by the CAP and HSA of the precursor structures resulted in very little binding towards Jurkat cells, expressing human CD3epsilon. Once the HSA and CAP hindrance of the CD3epsilon is absent (Tribody (VHVL), the binding EC50 towards human CD3epsilon is markedly improved towards low-nM biding affinities.

FIGS. 26A-26B present embodiments of amino acid and nucleic acid sequences of scFv anti-ROR1 VL-VH. FIG. 26A presents one embodiment of an amino acid sequence of an scFv anti-ROR1 having the N-terminal to C-terminal order: VL-VH, and components as follows: anti-ROR1 VL, linker, and anti-ROR1 VH (SEQ ID NO: 156). FIG. 26B presents one embodiment of an optimized nucleic acid sequence encoding an scFv anti-ROR1 having the N-terminal to C-terminal order: VL-VH (SEQ ID NO: 157).

FIGS. 27A-27B present embodiments of amino acid and nucleic acid sequences of scFv anti-ROR1 VH-VL. FIG. 27A presents one embodiment of an amino acid sequence of an scFv anti-ROR1 having the N-terminal to C-terminal order: VH-VL, and components as follows: anti-ROR1 VH, linker, and anti-ROR1 VL (SEQ ID NO: 166). FIG. 27B presents one embodiment of an optimized nucleic acid sequence encoding an scFv anti-ROR1 having the N-terminal to C-terminal order: VH-VL (SEQ ID NO: 167).

FIGS. 28A-28B present embodiments of amino acid and nucleic acid sequences of scFv anti-PSMA VL-VH. FIG. 28A presents one embodiment of an amino acid sequence of an scFv anti-PSMA having the N-terminal to C-terminal order: VL-VH, and components as follows: anti-PSMA VL, linker, and anti-PSMA VH (SEQ ID NO: 168). FIG. 28B presents one embodiment of an optimized nucleic acid sequence encoding an scFv anti-PSMA having the N-terminal to C-terminal order: VL-VH (SEQ ID NO: 169).

FIGS. 29A-29B present embodiments of amino acid and nucleic acid sequences of scFv anti-PSMA VH-VL. FIG. 29A presents one embodiment of an amino acid sequence of an scFv anti-PSMA having the N-terminal to C-terminal order: VH-VL, and components as follows: anti-PSMA VH, linker, and anti-PSMA VL (SEQ ID NO: 170). FIG. 29B presents one embodiment of an optimized nucleic acid sequence encoding an scFv anti-PSMA having the N-terminal to C-terminal order: VH-VL (SEQ ID NO: 171).

FIGS. 30A-30B present embodiments of amino acid and nucleic acid sequences of scFv anti-5T4 VL-VH. FIG. 30A presents one embodiment of an amino acid sequence of an scFv anti-5T4 having the N-terminal to C-terminal order: VL-VH, and components as follows: anti-5T4 VL, linker, and anti-5T4 VH (SEQ ID NO: 172). FIG. 30B presents one embodiment of an optimized nucleic acid sequence encoding an scFv anti-5T4 having the N-terminal to C-terminal order: VL-VH (SEQ ID NO: 173).

FIGS. 31A-31B present embodiments of amino acid and nucleic acid sequences of scFv anti-5T4 VH-VL. FIG. 31A presents one embodiment of an amino acid sequence of an scFv anti-5T4 having the N-terminal to C-terminal order: VH-VL, and components as follows: anti-5T4 VH, linker, and anti-5T4 VL (SEQ ID NO: 174). FIG. 31B presents one embodiment of an optimized nucleic acid sequence encoding an scFv anti-5T4 having the N-terminal to C-terminal order: VH-VL (SEQ ID NO: 175).

FIG. 32 presents FACS binding data of EGFR binding Tribody and precursor Tribody antibody constructs to Jurkat cells cleaved by MMP9. MFI (mean fluorescent intensity) provides a relative scale of antibody binding. Constructs analyzed: Tribody (VHVL) is Construct 2 of Example 1 (small circles, squares); Pro-Tribody-C(VHVL) is Construct 4 of Example 1 (upward and downward triangles); and Pro-Tribody-NC (VHVL) is Construct 6 of Example 1 (diamonds and large circles).-MMP9 and +MMP9 indicates the absence (−) or presence (+) of an MMP9 protease.

Figure 33A:
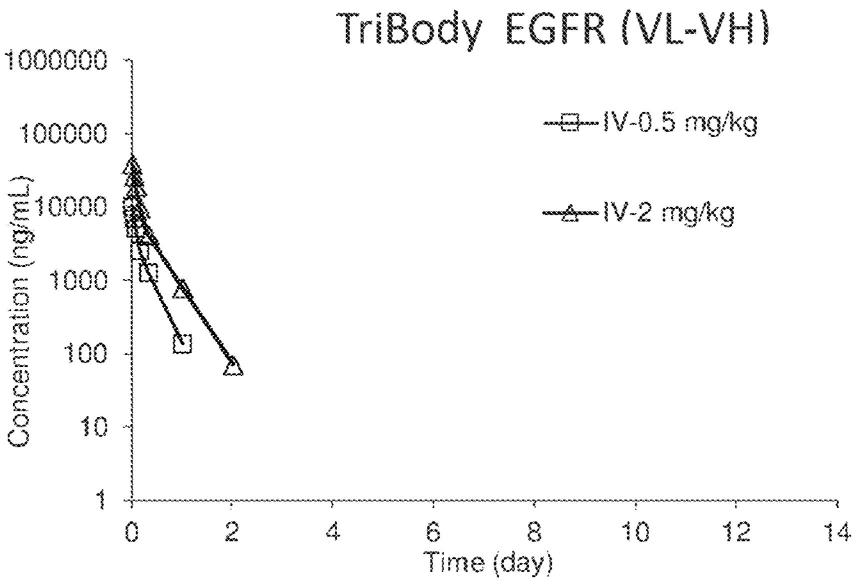
Figure 33B:
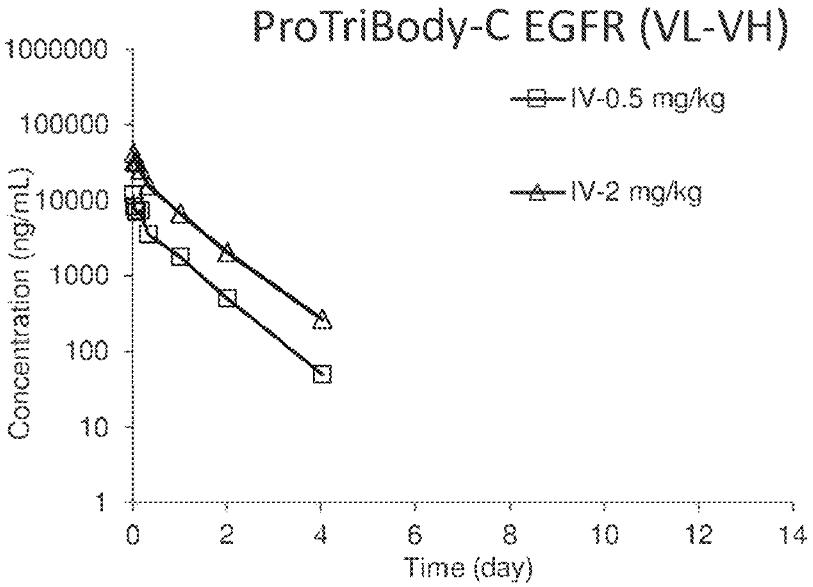

FIGS. 33A-33B present in vivo pharmacokinetics values (PK values) of EGFR activated (FIG. 33A) and precursor (FIG. 33B) Tribody constructs administered to mice. Antibody constructs: Tribody EGFR (VL-VH) is Construct 1 of Example 1 (FIG. 33A); ProTriBody-C EGFR (VL-VH) is Construct 3 of Example 1 (FIG. 33B). Constructs were administered intravenously at two concentrations: 0.5 mg/kg and 2 mg/kg. Results provide half-life information for each construct.

FIGS. 34A-34F present SDS-PAGE results (34A and 34D) and analytical HPLC-Size Exclusion Chromatography results (34B Graph, 34C Table, 34E Graph, and 34F Table). FIGS. 34A-34C show results of a Tribody-ROR1 (VL-VH) construct, wherein both the 1st and 2nd binding sites bind ROR1 and the 3rd binding site is a CD3ε binding site. No regulatory arms are present. (Construct 7 of Example 8). FIGS. 34D-34F show the results of a Protribody-ROR1 (VL-VH) construct, wherein both the 1st and 2nd binding sites bind ROR1 and the 3rd binding site is a CD3ε binding site, wherein the construct includes a CAP regulatory domain masking CD38 binding and an HLP regulatory domain comprising an HSA, wherein both regulatory domains are linked N-terminal to the CD3ε binding site by non-cleavable linkers (Construct 11 of Example 8).

FIGS. 35A-35I present SDS-PAGE results under reducing and non-reducing conditions (35A and 35D and 35G), and analytical HPLC-Size Exclusion Chromatography results (35B Graph, 35C Table, 35E Graph, 35F Table, 35H Graph, and 35I Table). FIGS. 35A-35C show results of a Tribody-5T4 (VL-VH) construct, wherein both the 1st and 2nd binding sites bind 5T4 and the 3rd binding site is a CD3ε binding site (Construct 13 of Example 8). FIGS. 35D-35F show the results of a Protribody-5T4 (VL-VH) construct, wherein both the 1st and 2nd binding sites bind 5T4 and the 3$^{rd}$ binding site is a CD3ε binding site, wherein the construct includes a CAP regulatory domain masking CD3ε binding and an HLP regulatory domain comprising an HSA, wherein both regulatory domains are linked N-terminal to the CD3ε binding site by cleavable linkers (Construct 15 of Example 8). FIGS. 35G-35I show the results of a Protribody -5T4 (VL-VH) construct, wherein both the 1$^{st}$ and 2$^{nd}$ binding sites bind 5T4 and the 3$^{rd}$ binding site is a CD3ε binding site, wherein the construct includes a CAP regulatory domain masking CD3ε binding and an HLP regulatory domain comprising an HSA, wherein both regulatory domains are linked N-terminal to the CD3ε binding site by non-cleavable linkers (Construct 17 of Example 8).

Figure 36:
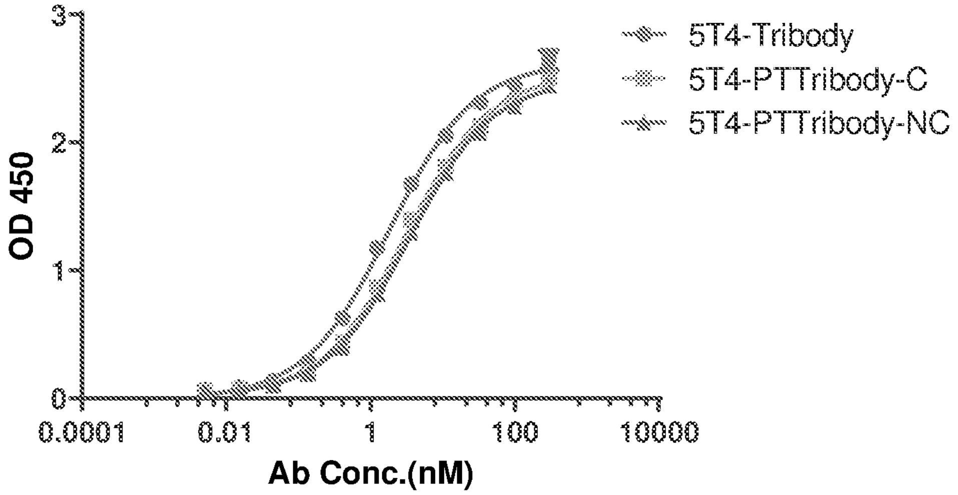

FIG. 36 presents binding curves showing the binding of Tribody and ProTribody antibodies to CD3ε. 5T4-Tribody is an activated Tribody construct wherein the 1$^{st}$ and 2$^{nd}$ binding domains bind 5T4, the 3$^{rd}$ domain binds CD3ε, and there are no regulatory domains. 5T4-PTTribody-C is a Precursor Tribody construct wherein the 1$^{st}$ and 2$^{nd}$ binding domains bind 5T4, the 3$^{rd}$ domain binds CD3ε, and there was a first and second sub-regulatory domain, one each linked N-terminal to the Fab of the CD3ε binding domain, wherein the linkers within the regulatory domains were MMP9 cleavable. 5T4-PTTribody-NC is a Precursor Tribody construct wherein the 1$^{st}$ and 2$^{nd}$ binding domains bind 5T4, the 3$^{rd}$ domain binds CD3ε, and there was a first and second sub-regulatory domain, one each linked N-terminal to the Fab of the CD3ε binding domain, wherein the linkers within the regulatory domains were non-cleavable.

Figure 37:
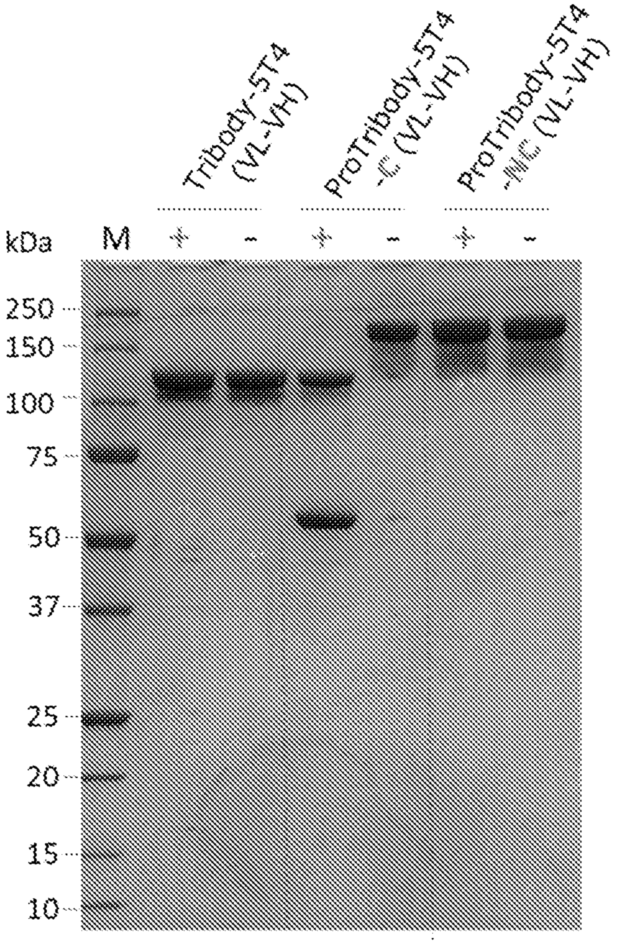

FIG. 37 presents SDS-PAGE results of MMP9 protease cleavage of 5T4 ProTribody Antibody constructs. Tribody-5T4 (VL-VH) is an activated Tribody construct wherein the 1$^{st}$ and 2$^{nd}$ binding domains bind 5T4, the 3$^{rd}$ domain binds CD3ε, and there are no regulatory domains (Construct 13 of Example 8). ProTribody-5T4-C-(VL-VH) is a Precursor Tribody construct wherein the 1$^{st}$ and 2$^{nd}$ binding domains bind 5T4, the 3$^{rd}$ domain binds CD3ε, and there was a first and second sub-regulatory domain, one each linked N-terminal to the Fab of the CD38 binding domain, wherein the linkers within the regulatory domains were MMP9 cleavable (Construct 15 of Example 8). ProTribody-5T4-NC-(VL-VH) is a Precursor Tribody construct wherein the 1$^{st}$ and 2$^{nd}$ binding domains bind 5T4, the 3$^{rd}$ domain binds CD3ε, and there was a first and second sub-regulatory domain, one each linked N-terminal to the Fab of the CD38 binding domain, wherein the linkers within the regulatory domains were non-cleavable (Construct 17 of Example 8).

Figure 38:
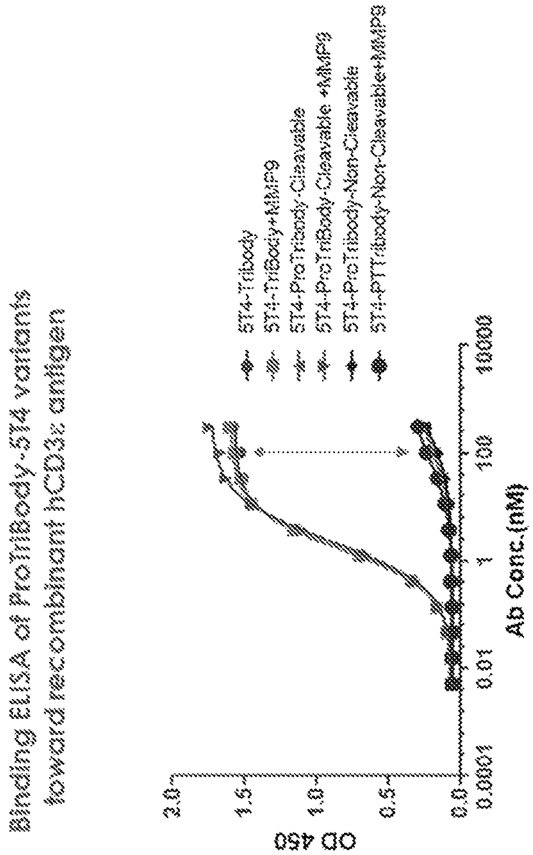

FIG. 38 presents binding curves showing the binding of Tribody and ProTribody antibody constructs to human CD3ε antigen in the present or absence of an MMP9 protease (+MMP9) or (-MMP9), respectively. 5T4-Tribody is an activated Tribody construct wherein the 1$^{st}$ and 2$^{nd}$ binding domains bind 5T4, the 3$^{rd}$ domain binds CD3ε, and there are no regulatory domains. 5T4-PTTribody-C is a Precursor Tribody construct wherein the 1$^{st}$ and 2$^{nd}$ binding domains bind 5T4, the 3$^{rd}$ domain binds CD3ε, and there was a first and second sub-regulatory domain, one each linked N-terminal to the Fab of the CD3ε binding domain, wherein the linkers within the regulatory domains were MMP9 cleavable. 5T4-PTTribody-NC is a Precursor Tribody construct wherein the 1$^{st}$ and 2$^{nd}$ binding domains bind 5T4, the 3$^{rd}$ domain binds CD3ε, and there was a first and second sub-regulatory domain, one each linked N-terminal to the Fab of the CD38 binding domain, wherein the linkers within the regulatory domains were non-cleavable.

Figure 39:
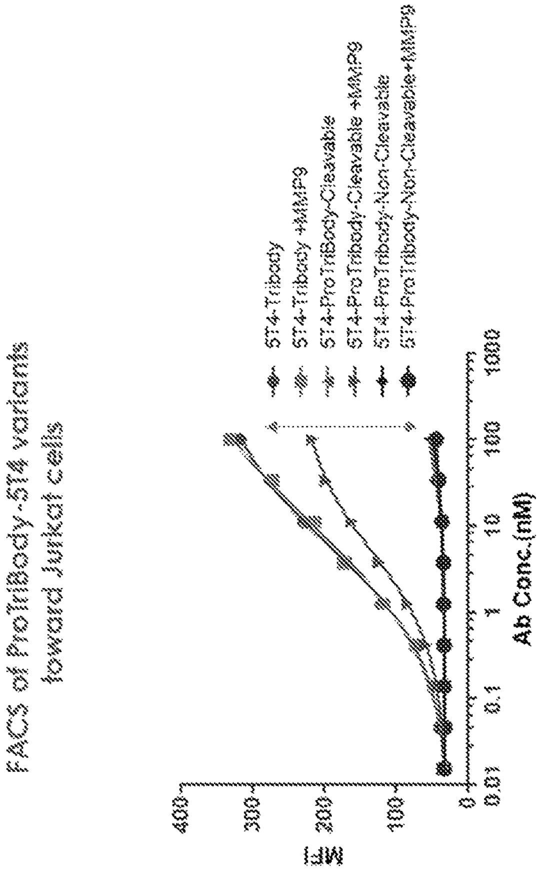

FIG. 39 presents FACS binding of TriBody-5T4, ProTriBody-5T4-C and ProTriBody-5T4-NC to Jurkat Cells (human CD3e) in the presence and absence of MMP9 protease . . .

Figure 40:
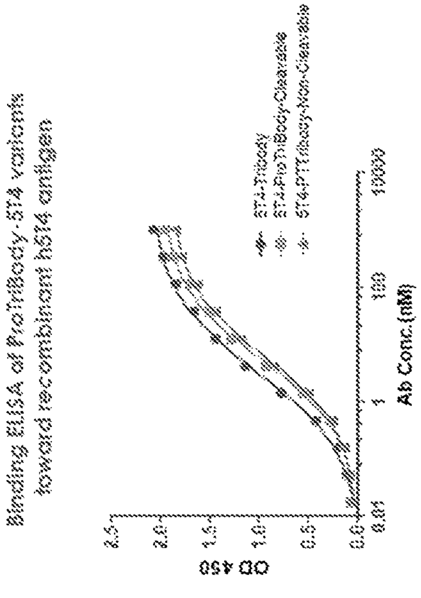

FIGS. 40 show ELISA binding studies of TriBody and precursor TriBody antibody constructs towards human 5T4 antigen.

Figure 41:
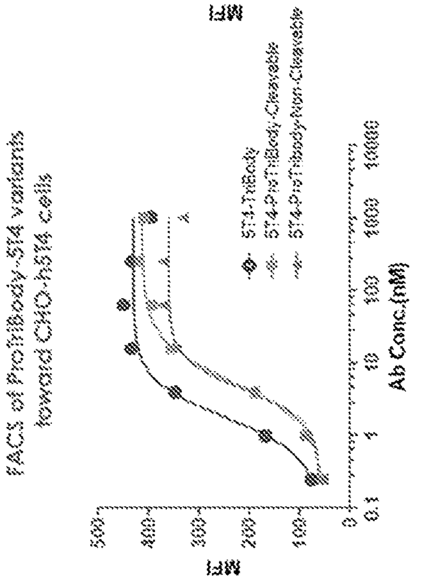

FIG. 41 presents FACS binding data of 5T4 binding Tribody and precursor Tribody antibody constructs to CHO cells expressing human 5T4. MFI (mean fluorescent intensity) provides a relative scale of antibody binding.

Figure 42:
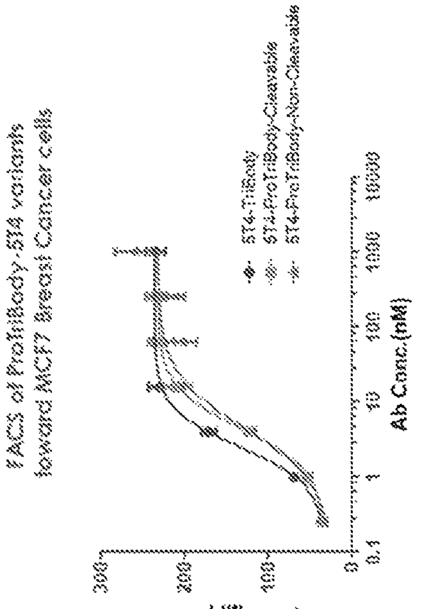

FIG. 42 presents FACS binding data of 5T4 binding Tribody and precursor Tribody antibody constructs to MCF7 breast cancer cell line, known to highly express human 5T4. MFI (mean fluorescent intensity) provides a relative scale of antibody binding.

Figure 43:
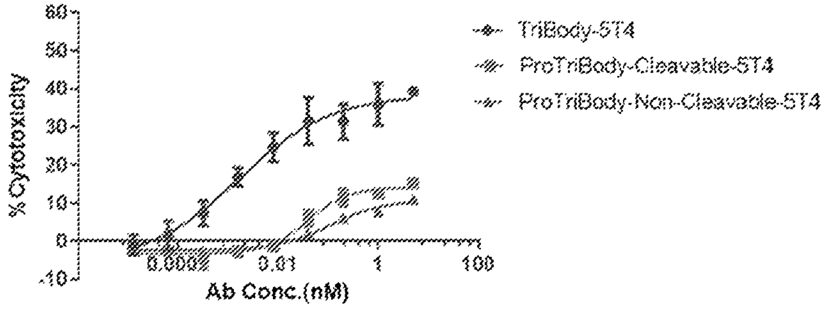
Figure 44:
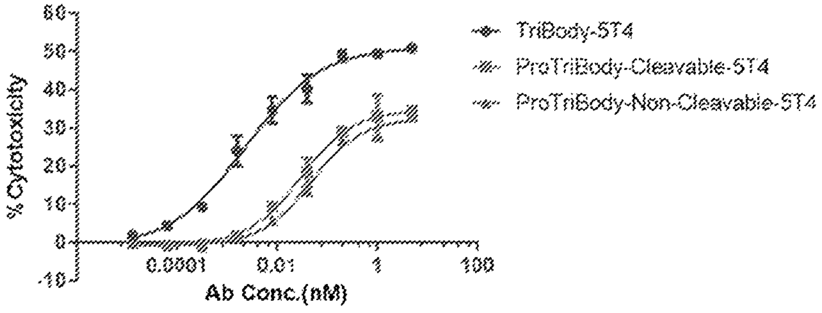

FIGS. 43 and 44 presents cell cytotoxicy assay of 5T4 binding Tribody and precursor Tribody antibody constructs to MCF7 breast cancer cell line (FIG. 43) and NCI-H226 lung cancer cell line (FIG. 44), known to highly express human 5T4.

Figure 2A:
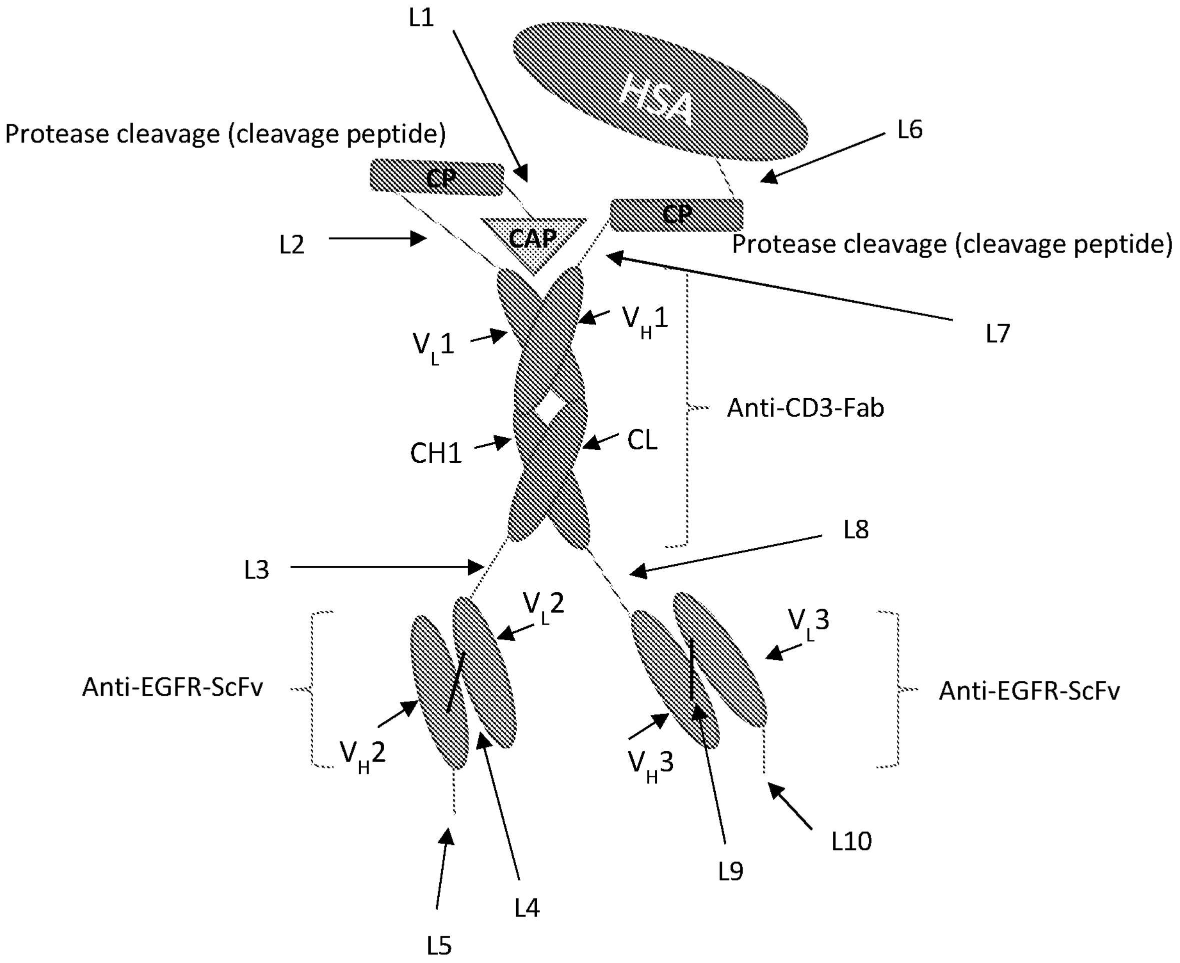
FIGS. 2A to 2F present various embodiments of precursor and active tri-specific (tri-body) antibody constructs described herein.
Figure 2B:
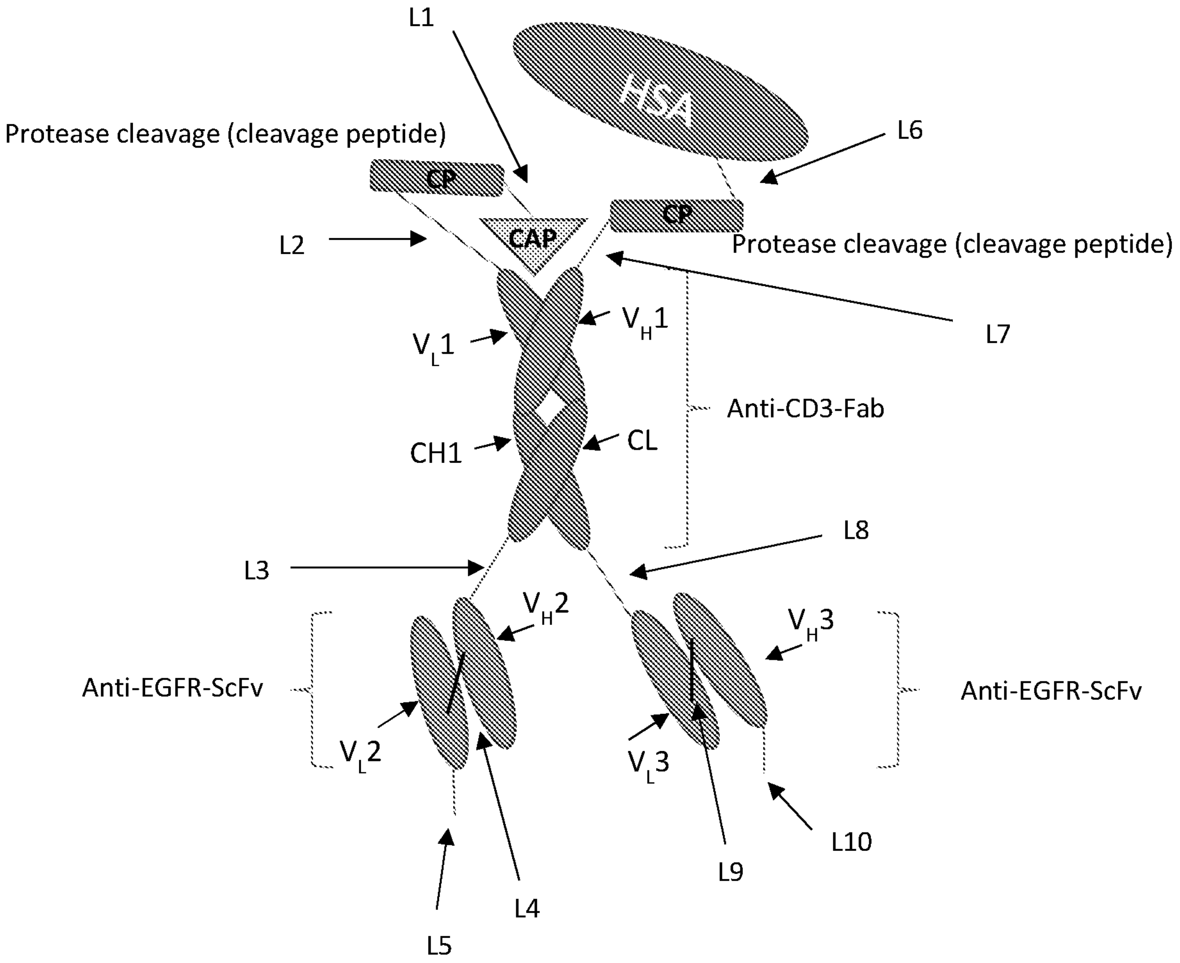
Figure 2C:
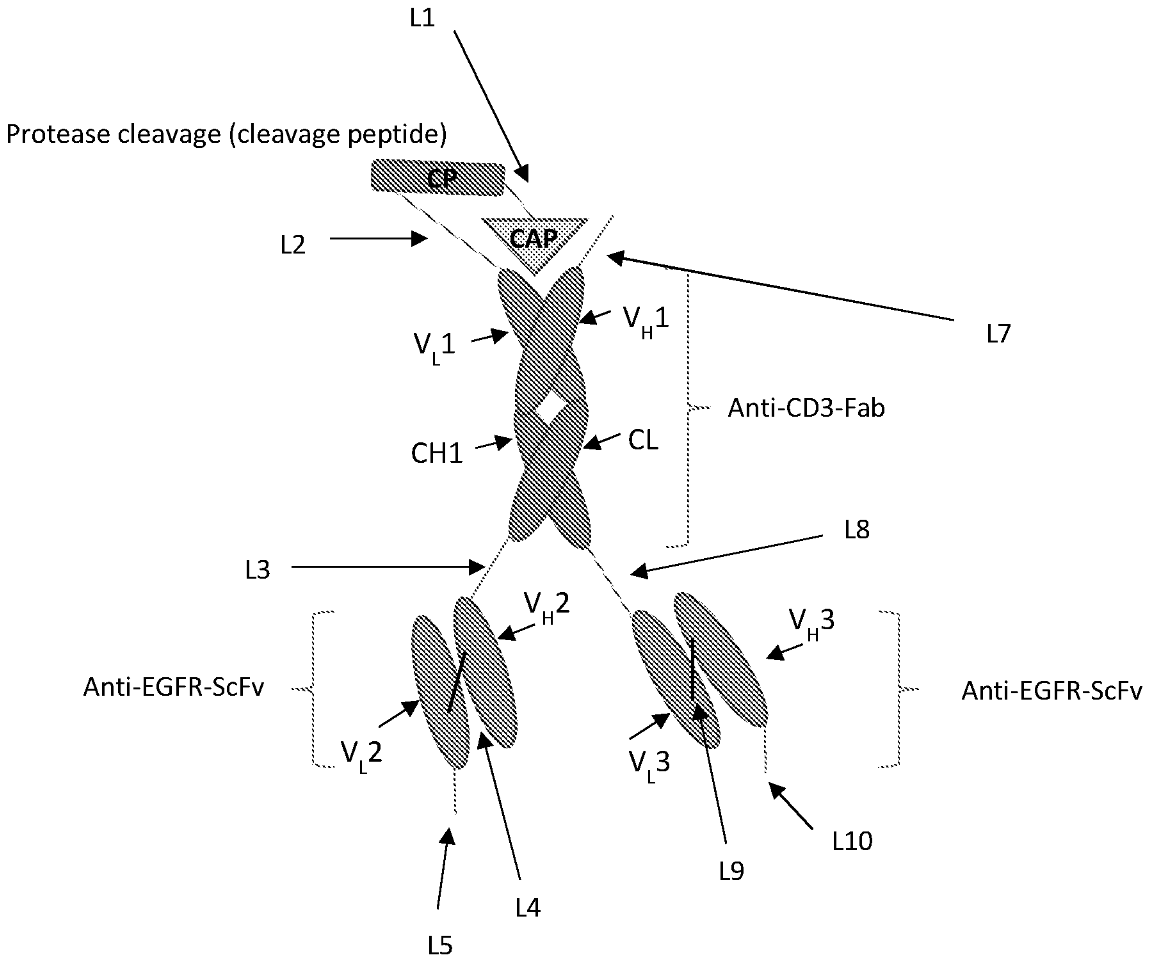
Figure 2D:
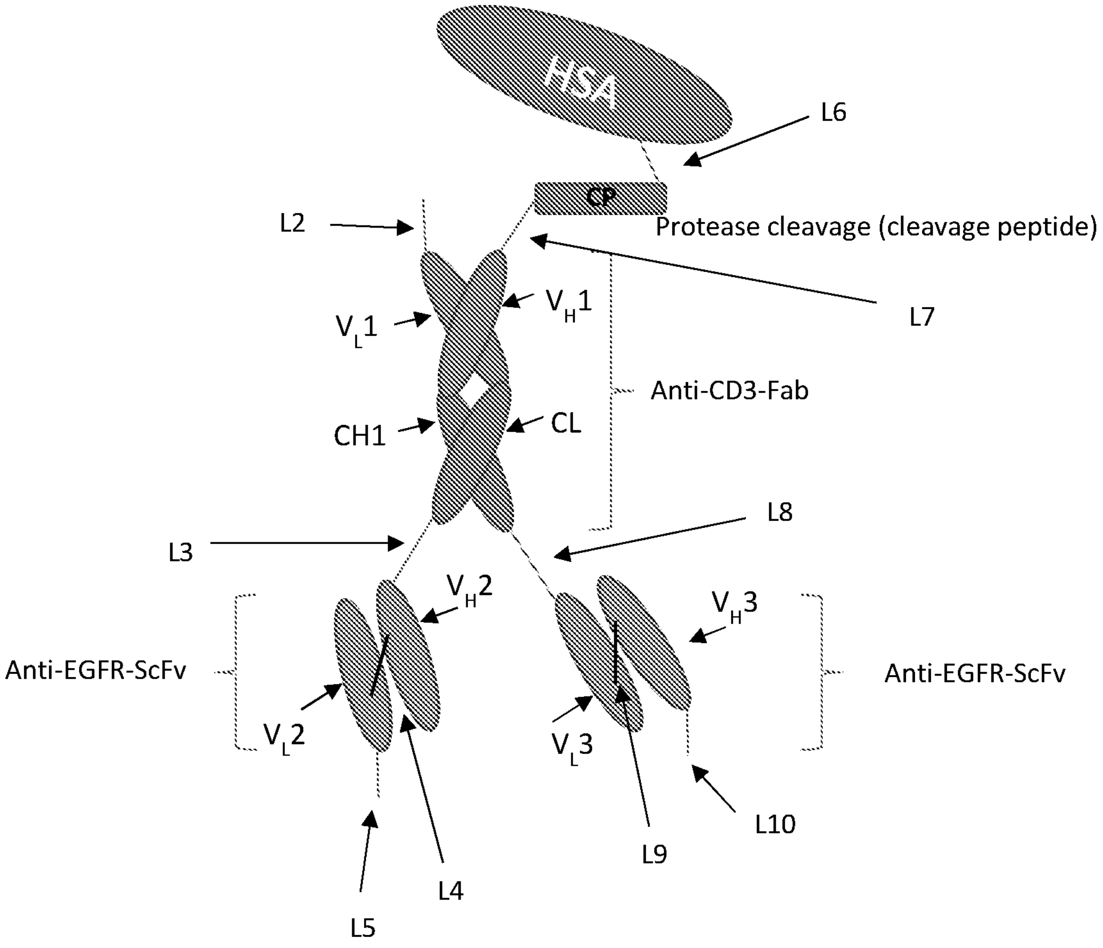
Figure 2E:
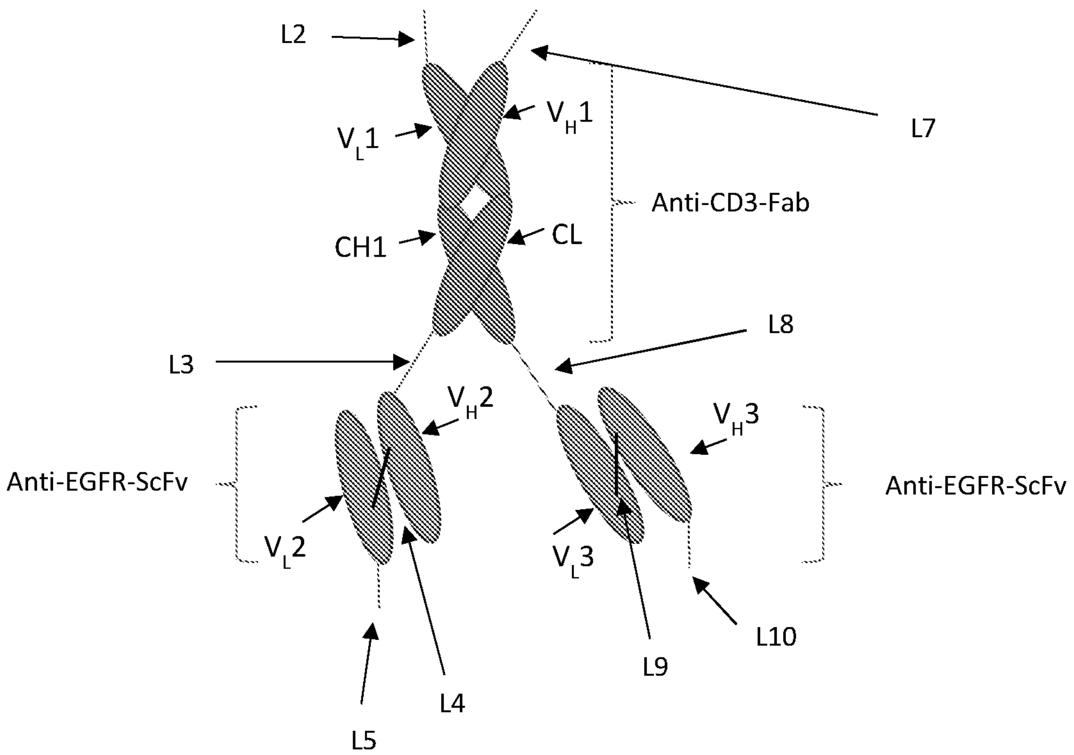
Figure 2F:
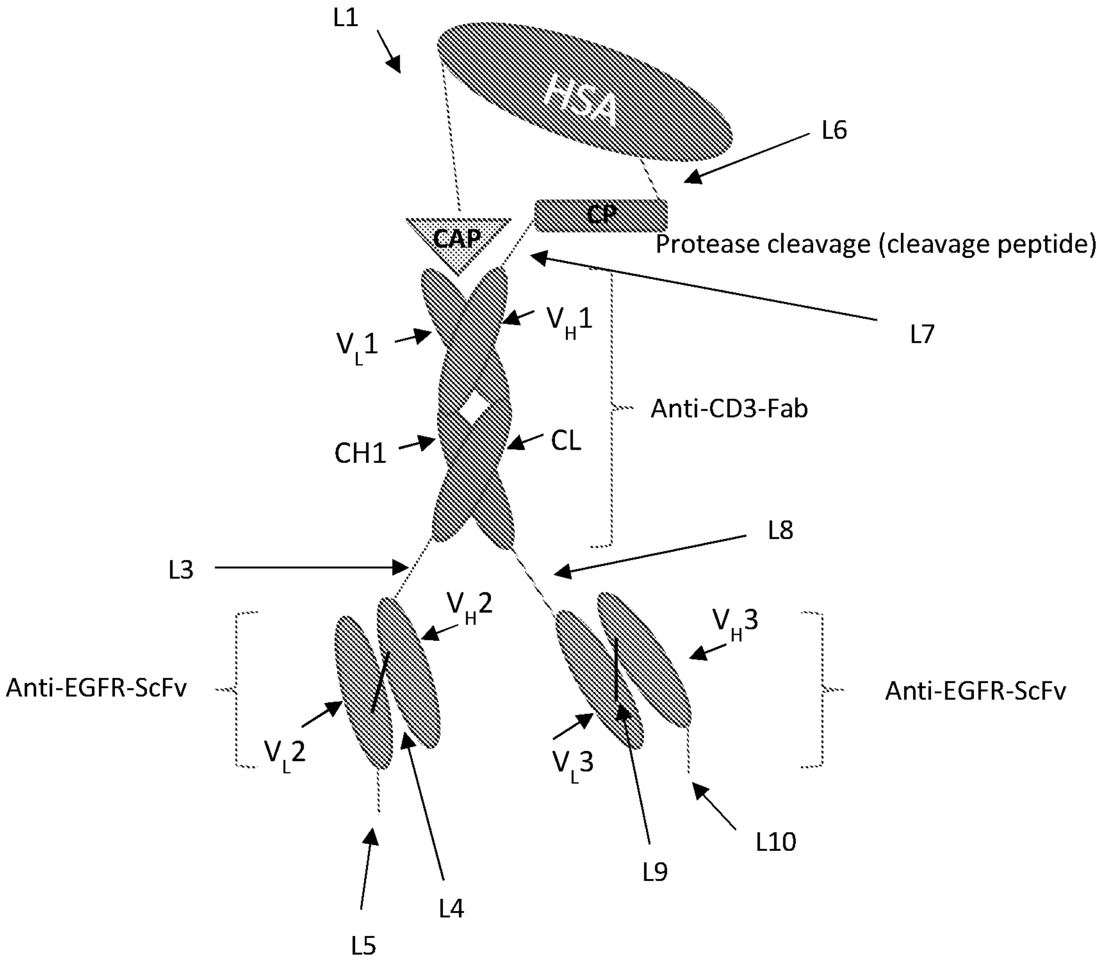

FIGS. 45A-45B present two embodiments of an amino acid sequence of a Heavy Chain (HC) polypeptide of precursor tri-specific (tri-body) antibody construct (for example embodiments of HC of FIG. 2F wherein both scFv bind EGFR). Amino acid sequences are presented N-terminal to C-terminal. FIGS. 45A and 45B presents embodiments of an amino acid sequence of a Heavy Chain (HC) polypeptide of a precursor construct, having the N-terminal to C-terminal order and components as follows: CAP (Bold), linker (italicized), human serum albumin (underlined); protease cleavage sequence (bold and italicized); VH1/CH1 of anti-CD3e Fab (Bold and underlined), VL (italicized and underlined) VH (italicized, bold, and underlined) (EGFR scFv). The two marked cysteine residues (double underline), may participate in disulfide double bonds. The protease cleavage sequence in FIG. 45A is a multiple, protease cleavage sequence. The protease cleavage sequence in FIG. 45B is a MMP2/9 protease cleavage sequence. The amino acid sequence of FIG. 45A is set forth in SEQ ID NO: 28. The amino acid sequence of FIG. 45B is set forth in SEQ ID NO: 31. Embodiments of sequences of the component parts are described throughout this application.

FIG. 46 presents an embodiment of an amino acid sequence of a Light Chain (LC) polypeptide of a precursor tri-specific (tri-body) antibody construct (for example an embodiment of a LC of FIG. 2F wherein both scFv bind EGFR). Amino acid sequences are presented N-terminal to C-terminal. FIG. 46 presents one embodiment of an amino acid sequence of a Light Chain (LC) polypeptide of a precursor construct, having the N-terminal to C-terminal order and components as follows: Linker (italicized), VL1-CL of anti-CD3e Fab (double underline and bold), VL (italicized and underlined), and VH (italicized bold and underlined) wherein the VH is an EGFR scFv). The two marked cysteine residues (double underline), may participate in disulfide double bonds. The amine acid sequence of the LC shown in FIG. 46 is set forth in SEQ ID NO: 32. Embodiments of amino acid sequences of the component parts of the LC polypeptide are described throughout the application.

FIGS. 47A-47B present two embodiments of an amino acid sequence of a Heavy Chain (HC) polypeptide of precursor tri-specific (tri-body) antibody construct (for example embodiments of HC of FIG. 2F wherein both scFv bind 5T4). Amino acid sequences are presented N-terminal to C-terminal. FIGS. 47A and 47B presents embodiments of an amino acid sequence of a Heavy Chain (HC) polypeptide of a precursor construct, having the N-terminal to C-terminal order and components as follows: CAP (Bold), linker (italicized), human serum albumin (underlined); protease cleavage sequence (bold and italicized); VH1/CH1 of anti-CD3e Fab (Bold and underlined), VL (italicized and underlined) VH (italicized, bold, and underlined) (5T4 scFv). The two marked cysteine residues (double underline), may participate in disulfide double bonds. The protease cleavage sequence in FIG. 47A is a multiple, protease cleavage sequence. The protease cleavage sequence in FIG. 47B is a MMP2/9 protease cleavage sequence. The amino acid sequence of FIG. 47A is set forth in SEQ ID NO: 118. The amino acid sequence of FIG. 47B is set forth in SEQ ID NO: 176. Embodiments of sequences of the component parts are described throughout this application.

FIG. 48 presents an embodiment of an amino acid sequence of a Light Chain (LC) polypeptide of a precursor tri-specific (tri-body) antibody construct (for example an embodiment of a LC of FIG. 2F wherein both scFv bind 5T4). Amino acid sequences are presented N-terminal to C-terminal. FIG. 48 presents one embodiment of an amino acid sequence of a Light Chain (LC) polypeptide of a precursor construct, having the N-terminal to C-terminal order and components as follows: Linker (italicized), VL1-CL of anti-CD3e Fab (double underline and bold), VL (italicized and underlined), and VH (italicized bold and underlined) wherein the VH is an 5T4 scFv) The two marked cysteine residues (double underline), may participate in disulfide double bonds. The amine acid sequence of the LC shown in FIG. 48 is set forth in SEQ ID NO: 177. Embodiments of amino acid sequences of the component parts of the LC polypeptide are described throughout the application.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION

In the following detailed description, numerous specific details are set forth in order to provide a thorough understanding of precursor tri-specific antibody constructs. However, it will be understood by those skilled in the art that the precursor constructs presented herein, the production of, and the use thereof may be practiced without these specific details. In other instances, well-known methods, procedures, and components have not been described in detail so as not to obscure the disclosure.

Described herein are precursor tri-specific antibody constructs comprising separate cleavable masking and half-life prolonging domains, wherein these cleavable regulatory domains provide reduced binding to T-cells by the precursor tri-specific constructs when outside the tumor micro-environment (TME) and provide extended half-life. Half-life extension may be limited to the time a precursor tri-specific construct is outside the cancer microenvironment or it may extend to the time a precursor tri-specific construct resides within a cancer microenvironment. An advantage of the precursor tri-specific antibody constructs described herein, have a protease cleavable masking domain and a protease cleavable half-life prolonging (HLP) domain may be the improved protease-activated controlled release of the masking CAP and the HLP domain.

Reduction in T-cell binding may lead to a reduction in T-cell activation. In some embodiments, the precursor tri-specific antibody constructs described herein are regulatable precursor constructs. The regulatable precursor tri-specific antibody constructs describe herein may have an extended half-life, or reduced T-cell binding, or reduced T-cell activation, or any combination thereof.

In some embodiments, the precursor tri-specific antibody constructs described herein provide for a regulatable T-cell activation, wherein the precursor construct provides that T-cell activation is restricted to a tumor microenvironment. In some embodiments, the precursor tri-specific antibody construct described herein have an increased half-life and provide that T-cell activation is restricted to a tumor microenvironment, compared with non-precursor always active multi-valent antibodies. In some embodiments, the precursor tri-specific antibody constructs described herein have reduced T-cell activation in non-tumor microenvironments, compared with non-precursor always active multi-valent antibodies.

In some embodiments, the precursor tri-specific antibody constructs described herein have an extended half-life in non-tumor microenvironments, compared with non-precursor tri-specific antibodies. In some embodiments, the precursor tri-specific antibody constructs described herein have reduced T-cell binding and/or activation in non-tumor microenvironments and an extended half-life in a non-tumor microenvironment, compared with non-precursor always active multi-valent antibodies.

In some embodiments, the precursor tri-specific antibody constructs described herein may bind to T-cells. In some embodiments, the precursor tri-specific antibody constructs described herein may bind to T-cells within a tumor microenvironment (TME). In some embodiments, the precursor tri-specific antibody constructs described herein may bind to T-cells and to two different TAAs. In some embodiments, the precursor tri-specific antibody constructs described herein may bind to a T-cell and to two different TAAs, wherein the TAAs comprise different extracellular epitopes of a tumor-cell-surface antigen. In some embodiments, the precursor tri-specific antibody constructs described herein may bind to a T-cell and to two different TAAs, wherein the TAAs comprise extracellular epitopes of a tumor-cell-surface antigen. In some embodiments, the precursor tri-specific antibody constructs described herein may bind to a T-cell and to two different TAAs, wherein the TAAs comprise an extracellular epitope of a tumor-cell-surface antigen and a TME antigen. In some embodiments, the precursor tri-specific antibody constructs described herein may bind to a T-cell and to two different TAAs, wherein the TAAs comprise an extracellular epitope of a tumor-cell-surface antigen and a stromal antigen in the TME. In some embodiments, the precursor tri-specific antibody constructs described herein may bind to a T-cell and to two different TAAs, wherein the TAAs comprise an extracellular epitope of a tumor-cell-surface antigen and an angiogenic antigen in the TME. In some embodiments, the precursor tri-specific antibody constructs described herein may bind to a T-cell and to two different TAAs, wherein the TAAs comprise an extracellular epitope of a tumor-cell-surface antigen and an antigen on the surface of a blood vessel in the TME. In some embodiments, an antigen on the surface of a blood vessel is an endothelial cell surface antigen. In some embodiments, an antigen on the surface of a blood vessel is an endothelial cell surface antigen selected from CD31, CD105, CD146, and CD144. In some embodiments, the precursor tri-specific antibody constructs described herein may bind to a T-cell and to two different TAAs, wherein the TAAs comprise an extracellular epitope of a tumor-cell-surface antigen and a cytokine in the TME.

In some embodiments, a stromal antigen in the TME comprises a fibroblast activation protein (FAP). In some embodiments, a stromal antigen in the TME comprises an alpha smooth muscle actin (aSMA). In some embodiments, a stromal antigen in the TME comprises a PDGFRa. In some embodiments, a stromal antigen in the TME comprises an integrin a11ß1 (ITGA11). In some embodiments, a stromal antigen in the TME comprises a VEGF. In some embodiments, a stromal antigen in the TME comprises a Tenascin-C, periostin. In some embodiments, a stromal antigen in the TME comprises a fibroblast specific protein 1 (S10A4, FSP1). In some embodiments, a stromal antigen in the TME comprises a desmin. In some embodiments, a stromal antigen in the TME comprises a vimentin. In some embodiments, a stromal antigen in the TME comprises a paladin. In some embodiments, a stromal antigen in the TME comprises a urokinase-type plasminogen activator receptor associated protein (UPARAP). In some embodiments, a stromal antigen in the TME comprises a galectin-3. In some embodiments, a stromal antigen in the TME comprises a podoplanin. In some embodiments, a stromal antigen in the TME comprises a platelet. In some embodiments, a stromal antigen in the TME comprises a CCL2. In some embodiments, a stromal antigen in the TME comprises a CXCL12. In some embodiments, a stromal antigen in the TME is selected from any of fibroblast activation protein (FAP), alpha smooth muscle actin (aSMA), PDGFRa, Integrin a11ß1 (ITGA11) VEGF, Tenascin-C, periostin, fibroblast specific protein 1 (S10A4, FSP1), desmin, vimentin, paladin, urokinase-type plasminogen activator receptor associated protein (UPARAP), galectin-3, podoplanin, platelet, CCL2, or CXCL12.

In some embodiments, described herein are pharmaceutical compositions comprising a precursor tri-specific antibody construct that provides a regulatable T-cell activation in non-tumor microenvironments. In some embodiments, described herein are pharmaceutical compositions comprising a precursor tri-specific antibody construct having an increased half-life and providing that T-cell activation is restricted to a tumor microenvironment. In some embodiments, described herein are pharmaceutical compositions comprising a precursor tri-specific antibody construct comprising an extended half-life in non-tumor microenvironments. In some embodiments, described herein are pharmaceutical compositions comprising a precursor tri-specific antibody construct comprising an extended half-life in non-tumor microenvironments, wherein the half-life is reduced in a tumor microenvironment compared with the half-life in a non-tumor microenvironment. In some embodiments, the pharmaceutical compositions comprising a precursor construct comprises a construct that recognizes a T-cell, and a TAA. In some embodiments, the pharmaceutical compositions comprising a precursor construct comprises a construct that recognizes a T-cell, and two TAAs, wherein each TAA is a different antigen. In some embodiments, the pharmaceutical compositions comprising a precursor construct comprises a construct that recognizes a T-cell, and two TAAs, wherein the TAAs recognize the same antigen.

In some embodiment, described herein are methods of use of a precursor tri-specific antibody construct, as disclosed herein, for use treating, preventing, inhibiting the growth of, delaying disease progression, reducing the tumor load, or reducing the incidence of a cancer or tumor in a subject, or any combination thereof. In some embodiments, the method of treating disclosed herein reduces the minimal residual disease, increases remission, increases remission duration, reduces tumor relapse rate, prevents metastasis of the tumor or the cancer, or reduces the rate of metastasis of the tumor or the cancer, or any combination thereof, in the treated subject compared with a subject not administered with the pharmaceutical composition.

Precursor Tri-specific Antibody Constructs

In some embodiments, a precursor tri-specific antibody construct comprises a first binding domain, binding to a first tumor associated antigen (TAA); a second binding domain, binding to a second TAA; a third binding domain, binding to an extracellular epitope of human CD3ε; a first sub-regulatory domain, comprising a protease cleavage domain and a half-life prolonging (HLP) domain; and a second sub-regulatory domain, comprising a protease cleavage domain and a CAP component that reduces the ability of the third binding domain to bind the extracellular epitope of human CD3ε.

In some embodiments, disclosed herein is a precursor tri-specific antibody construct, comprising:

a first binding domain that binds to a first tumor associated antigen (TAA); a second binding domain that binds to a second TAA; a third binding domain that binds to an extracellular epitope of human CD3ε; and a regulatory domain, said regulatory domain comprising either a first and a second sub-regulatory domain, said first sub-regulatory domain comprising a first protease cleavage domain and a half-life prolonging (HLP) domain, and said second sub-regulatory domain comprising a second protease cleavage domain and a CAP component that reduces the ability of the third binding domain to bind the extracellular epitope of human CD3ε; or a single regulatory domain comprising a protease cleavage domain, a half-life prolonging (HLP) domain, and a CAP component that reduces the ability of the third binding domain to bind the extracellular epitope of human CD3ε.

In some embodiments, disclosed herein is a precursor tri-specific antibody construct, comprising:

a first binding domain that binds to a first tumor associated antigen (TAA); a second binding domain that binds to a second TAA; a third binding domain that binds to an extracellular epitope of human CD3ε; and a regulatory domain comprising a protease cleavage domain, a half-life prolonging (HLP) domain, and a CAP component that reduces the ability of the third binding domain to bind the extracellular epitope of human CD3ε.

In some embodiments, a precursor tri-specific antibody construct comprises a first binding domain, binding to a first tumor associated antigen (TAA); a second binding domain, binding to a second TAA; a third binding domain, binding to an extracellular epitope of human CD3ε; a first sub-regulatory domain, comprising a protease cleavage domain and a half-life prolonging (HLP) domain; and a second sub-regulatory domain, comprising a protease cleavage domain and a CAP component that reduces the ability of the third binding domain to bind the extracellular epitope of human CD3ε.

In some embodiments, a precursor tri-specific antibody construct comprises a first binding domain, binding to a first tumor associated antigen (TAA); a second binding domain, binding to a second TAA; a third binding domain, binding to an extracellular epitope of human CD3ε; a first sub-regulatory domain, comprising a protease cleavage domain and a half-life prolonging (HLP) domain; and a second sub-regulatory domain, comprising a protease cleavage domain and a CAP component that reduces the ability of the third binding domain to bind the extracellular epitope of human CD3ε.

For the precursor constructs described throughout, the skilled artisan will appreciate that the modular structure of said constructs allows for different binding partners based on the amino acid sequences comprised in the first and second binding sites.

A skilled artisan would recognize that a precursor antibody construct is a precursor form or "Pro" form of the active antibody protein. In some embodiments, the term "Pro" is used interchangeably with the term "Precursor" having all the same meanings and qualities.

A skilled artisan would appreciate that as used throughout, in some embodiments the terms "precursor tri-specific antibody construct", "precursor tri-specific antibody construct", "precursor antibody", "precursor construct", "precursor antibody construct", "precursor tri-specific antibody", "tri-specific antibody", "antibody", "tri-specific antibody construct", and "tri-specific construct" may be used interchangeably having all the same qualities and meanings. Additionally, in some embodiments the term "tri-specific" may be replaced with the term "tri-body" with the recognition that the antibody constructs disclosed herein have three antibody binding regions, wherein each region may bind a different antigen (tri-body or tri-specific) or two of the three binding regions may bind the same antigen (tri-body or tri-specific wherein two of the specific binding antigens are the same). Thus, terms as listed above, for example "precursor tri-specific antibody construct" in some embodiments may be used interchangeably with the term "precursor tri-body construct", having all the same meanings and qualities.

In some embodiments, a precursor tri-specific antibody construct comprises a first binding domain, binding to a first tumor associated antigen (TAA); a second binding domain, binding to a second TAA; a third binding domain, binding to an extracellular epitope of human CD3ε; a first sub-regulatory domain, comprising a protease cleavage domain and a half-life prolonging (HLP) domain; and a second sub-regulatory domain, comprising a protease cleavage domain and a CAP component that reduces the ability of the third binding domain to bind the extracellular epitope of human CD3ε, wherein said first TAA or said second TAA or both said first TAA and said second TAA comprise an extracellular epitope of a tumor-cell surface antigen.

In some embodiments, a precursor tri-specific antibody construct comprises a first binding domain, binding to a first tumor associated antigen (TAA); a second binding domain, binding to a second TAA; a third binding domain, binding to an extracellular epitope of human CD3ε; a first sub-regulatory domain, comprising a protease cleavage domain and a half-life prolonging (HLP) domain; and a second sub-regulatory domain, comprising a protease cleavage domain and a CAP component that reduces the ability of the third binding domain to bind the extracellular epitope of human CD3ε, wherein said first TAA or said second TAA or both said first TAA and said second TAA comprise an a TME.

In some embodiments, a precursor tri-specific antibody construct comprises a first binding domain, binding to a first tumor associated antigen (TAA); a second binding domain, binding to a second TAA; a third binding domain, binding to an extracellular epitope of human CD3ε; a first sub-regulatory domain, comprising a protease cleavage domain and a half-life prolonging (HLP) domain; and a second sub-regulatory domain, comprising a protease cleavage domain and a CAP component that reduces the ability of the third binding domain to bind the extracellular epitope of human CD3ε, wherein said first TAA or said second TAA or both said first TAA and said second TAA comprise a stromal antigen in the TME.

In some embodiments, a precursor tri-specific antibody construct comprises a first binding domain, binding to a first tumor associated antigen (TAA); a second binding domain, binding to a second TAA; a third binding domain, binding to an extracellular epitope of human CD3ε; a first sub-regulatory domain, comprising a protease cleavage domain and a half-life prolonging (HLP) domain; and a second sub-regulatory domain, comprising a protease cleavage domain and a CAP component that reduces the ability of the third binding domain to bind the extracellular epitope of human CD3ε, wherein said first TAA or said second TAA or both said first TAA and said second TAA comprise an angiogenic antigen in the TME.

In some embodiments, a precursor tri-specific antibody construct comprises a first binding domain, binding to a first tumor associated antigen (TAA); a second binding domain, binding to a second TAA; a third binding domain, binding to an extracellular epitope of human CD3ε; a first sub-regulatory domain, comprising a protease cleavage domain and a half-life prolonging (HLP) domain; and a second sub-regulatory domain, comprising a protease cleavage domain and a CAP component that reduces the ability of the third binding domain to bind the extracellular epitope of human CD3ε, wherein said first TAA or said second TAA or both said first TAA and said second TAA comprise an antigen on the surface of a blood vessel in the TME.

In some embodiments, a precursor tri-specific antibody construct comprises a first binding domain, binding to a first tumor associated antigen (TAA); a second binding domain, binding to a second TAA; a third binding domain, binding to an extracellular epitope of human CD3ε; a first sub-regulatory domain, comprising a protease cleavage domain and a half-life prolonging (HLP) domain; and a second sub-regulatory domain, comprising a protease cleavage domain and a CAP component that reduces the ability of the third binding domain to bind the extracellular epitope of human CD3ε, wherein said first TAA or said second TAA or both said first TAA and said second TAA comprise a cytokine antigen in a TME.

In some embodiments, a precursor tri-specific antibody construct comprises a first binding domain, binding to a first tumor associated antigen (TAA); a second binding domain, binding to a second TAA; a third binding domain, binding to an extracellular epitope of human CD3ε; a first sub-regulatory domain, comprising a protease cleavage domain and a half-life prolonging (HLP) domain; and a second sub-regulatory domain, comprising a protease cleavage domain and a CAP component that reduces the ability of the third binding domain to bind the extracellular epitope of human CD3ε, wherein said first TAA or said second TAA or both said first TAA and said second TAA comprise an extracellular epitope of a tumor-cell surface antigen or a TME, or a stromal antigen in the TME, or an angiogenic antigen in the TME, or an antigen on the surface of a blood vessel in the TME, or a cytokine antigen in the TME, or any combination thereof.

A skilled artisan would appreciate that in some embodiments, the term "tumor associated antigen" (TAA) may encompass a molecule or a portion thereof, which is displayed on the surface of a cell or a molecule which is present within the milieu of a tumor, that is within the tumor micro-environment. In some embodiments, a TAA encompasses a cell surface tumor associated antigen (TAA). In some embodiments, the cell is a tumor cell. In some embodiments, the cell is a non-tumor cell present in the milieu of a tumor, for example but not limited to a cell present within vasculature tissue associated with a tumor or cancer. In some embodiments, a TAA is an angiogenic antigen in a tumor micro-environment. In some embodiments, a TAA is an antigen on a blood vessel in a tumor micro-environment. In some embodiments, the cells is a stromal cells present in the milieu of a tumor. In some embodiments, a TAA is a stromal cell antigen within a tumor micro-environment. In some embodiments, a TAA encompasses an extracellular epitope of a tumor-cell-surface antigen. In some embodiments, a TAA encompasses an extracellular matrix antigen.

In some embodiments, an angiogenic antigen comprises a bFGF. In some embodiments, an angiogenic antigen comprises a INF. In some embodiments, an angiogenic antigen comprises a VEGF. In some embodiments, an angiogenic antigen comprises a bFGF, an INF, or a VEGF.

In some embodiments, a TAA comprises an antigen present in a TME. In some embodiments, a TAA comprises a cytokine antigen in a TME. In some embodiments, a TAA comprises a molecule secreted by a tumor cell into the TME. In some embodiments, a TAA comprises an effector molecule secreted by a tumor cell into the TME. In some embodiments, the effector molecule comprises a cytokine antigen. In some embodiments, the effector molecule comprises a cytokine antigen in the TME.

In some embodiments, a cytokine antigen in the TME comprises a TNF-alpha, an IL-6, a TGF-beta, an IL-10, an IL-8, an IL-17, an IL-21, an INF, or a VEGF. In some embodiments, a TAA is selected from a TNF-alpha, an IL-6, a TGF-beta, an IL-10, an IL-8, an IL-17, an IL-21, an INF, or an VEGF. In some embodiments, a cytokine antigen for use as a TAA comprises a cytokine antigen known in the art.

In some embodiments, first TAA, or said second TAA, or both said first TAA and said second TAA, comprise an extracellular epitope of a tumor-cell-surface antigen, a tumor micro-environment antigen, a stromal antigen in the tumor micro-environment (TME), an angiogenic antigen in the TME, an antigen on a blood vessel in a TME, or a cytokine antigen in a TME, or any combination thereof.

A skilled artisan would appreciate that the terms "tumor micro-environment" (TME), "cancer microenvironment" and "tumor milieu" may be used interchangeably having the same qualities and meanings and encompassing the microenvironment to tumor development. While the normal cellular microenvironment can inhibit malignant cell growth, the modifications that occur in the tumor microenvironment may synergistically support cell proliferation.

In some embodiments, the first binding domain and the second binding domain of a precursor construct disclosed herein, bind to the same TAA. In some embodiments, the first binding domain and the second binding domain of a precursor construct disclosed herein, bind to different TAAs. In some embodiments, the first binding domain and the second binding domain of a precursor construct disclosed herein, bind to different TAAs on the same cell. In some embodiments, the first binding domain and the second binding domain of a precursor construct disclosed herein, bind to different TAAs on the different cells. In some embodiments, a TAA comprises a cell surface antigen on a tumor cell. In some embodiments, a TAA comprises a cell surface antigen on a cell in a TME.

In some embodiments, a first binding domain and a second binding domain binds to different TAAs. The different TAA may be for example, but not limited to an extracellular epitope of a tumor-cell surface antigen, a TME antigen, a stomal antigen in a TME, an angiogenic antigen in a TME, an antigen on a blood vessel in a TME, or a cytokine in a TME.

A skilled artisan would appreciate that the terms "antigen" or "immunogen" encompass a peptide, protein, or a polypeptide, or any fragment thereof, which is immunogenic. In some embodiments, an antigen is capable of eliciting an immune response in a mammal, and therefore contains at least one and may contain multiple epitopes. An "antigen" molecule or a portion of a molecule is capable of being bound by a selective binding agent, such as an antigen-binding portion of a Fab fragment or an antigen-binding portion of a single chain variable fragment (scFv). Additionally, an "antigen" is capable of being used in an animal to produce antibodies capable of binding to an epitope of that antigen. In some embodiments, a CAP component comprises the portion of an antigen to which the third binding domain binds.

The term "epitope" includes any determinant, in certain embodiments, a polypeptide determinant, capable of specific binding to an anti-TAA binding domain or an anti-T-cell receptor binding domain. An epitope is a region of an antigen that is bound by an antibody or an antigen-binding fragment thereof. In some embodiments, a CAP component comprises the epitope to which the third binding domain binds.

In certain embodiments, epitope determinants include chemically active surface groupings of molecules such as amino acids, sugar side chains, phosphoryl or sulfonyl, and may in certain embodiments have specific three-dimensional structural characteristics, and/or specific charge characteristics. In certain embodiments, a precursor tri-specific antibody construct is said to specifically bind an antigen when it preferentially recognizes its target antigen in a complex mixture of proteins and/or macromolecules. A precursor tri-specific antibody construct is said to specifically bind an antigen when the equilibrium dissociation constant is ≤10-5, 10-6 or 10-7 M. In some embodiments, the equilibrium dissociation constant may be≤10-8 M or 10-9 M. In some further embodiments, the equilibrium dissociation constant may be≤10-10 M or 10-11 M. Antigens disclosed herein included but are not limited to TAA, CAP components, and immuno-effector molecules such as a human CD3 epsilon polypeptide.

In some embodiments, the tumor associated antigen (TAA) is a tumor antigen. In some embodiments, tumor antigens comprise those antigens are presented on tumor cells. In some embodiments, the tumor antigen is present on a cell of solid tumor. In some embodiments, the tumor antigen is a cancer antigen, present on a cell of a non-solid tumor.

In some embodiments, when the TAA is a tumor cell antigen, the tumor cell comprises a cell from a solid tumor. Solid tumors may be benign (not cancer), or malignant (cancer). Different types of solid tumors are named for the type of cells that form them. Examples of solid tumors are sarcomas, carcinomas, and lymphomas. In some embodiments, solid tumors are neoplasms (new growth of cells) or lesions (damage of anatomic structures or disturbance of physiological functions) formed by an abnormal growth of body tissue cells other than blood, bone marrow or lymphatic cells. In some embodiments, a solid tumor consists of an abnormal mass of cells which may stem from different tissue types such as liver, colon, breast, or lung, and which initially grows in the organ of its cellular origin. However, such cancers may spread to other organs through metastatic tumor growth in advanced stages of the disease.

In some embodiments, the solid tumor comprises a sarcoma or a carcinoma, a fibrosarcoma, a myxosarcoma, a liposarcoma, a chondrosarcoma, an osteogenic sarcoma, a chordoma, an angiosarcoma, an endotheliosarcoma, a lymphangiosarcoma, a lymphangioendotheliosarcoma, a synovioma, a mesothelioma, an Ewing's tumor, a leiomyosarcoma, a rhabdomyosarcoma, a colon carcinoma, a pancreatic cancer or tumor, a breast cancer or tumor, an ovarian cancer or tumor, a prostate cancer or tumor, a squamous cell carcinoma, a basal cell carcinoma, an adenocarcinoma, a sweat gland carcinoma, a sebaceous gland carcinoma, a papillary carcinoma, a papillary adenocarcinomas, a cystadenocarcinoma, a medullary carcinoma, a bronchogenic carcinoma, a renal cell carcinoma, a hepatoma, a bile duct carcinoma, a choriocarcinoma, a seminoma, an embryonal carcinoma, a Wilm's tumor, a cervical cancer or tumor, a uterine cancer or tumor, a testicular cancer or tumor, a lung carcinoma, a small cell lung carcinoma, a bladder carcinoma, an epithelial carcinoma, a glioma, an astrocytoma, a medulloblastoma, a craniopharyngioma, an ependymoma, a pinealoma, a hemangioblastoma, an acoustic neuroma, an oligodenroglioma, a schwannoma, a meningioma, a melanoma, a neuroblastoma, or a retinoblastoma. In some embodiments, the solid tumor comprises an Adrenocortical Tumor (Adenoma and Carcinoma), a Carcinoma, a Colorectal Carcinoma, a Desmoid Tumor, a Desmoplastic Small Round Cell Tumor, an Endocrine Tumor, an Ewing Sarcoma, a Germ Cell Tumor, a Hepatoblastoma a Hepatocellular Carcinoma, a Melanoma, a Neuroblastoma, an Osteosarcoma, a Retinoblastoma, a Rhabdomyosarcoma, a Soft Tissue Sarcoma Other Than Rhabdomyosarcoma, and a Wilms Tumor. In some embodiments, the solid tumor is a breast tumor. In another embodiment, the solid tumor is a prostate cancer. In another embodiment, the solid tumor is a colon cancer. In some embodiments, the tumor is a brain tumor. In another embodiment, the tumor is a pancreatic tumor. In another embodiment, the tumor is a colorectal tumor.

In some embodiments, the tumor cell comprises a cell from a non-solid tumor, that is a non-solid cancer. In some embodiments, a cancer may be a diffuse cancer, wherein the cancer is widely spread; not localized or confined. In some embodiments, a diffuse cancer may comprise a non-solid tumor. Examples of diffuse cancers include leukemias. Leukemias comprise a cancer that starts in blood-forming tissue, such as the bone marrow, and causes large numbers of abnormal blood cells to be produced and enter the bloodstream.

In some embodiments, a diffuse cancer comprises a B-cell malignancy. In some embodiments, the diffuse cancer comprises leukemia. In some embodiments, the cancer is lymphoma. In some embodiments, the lymphoma is large B-cell lymphoma.

In some embodiments, the diffuse cancer or tumor comprises a hematological tumor. In some embodiments, hematological tumors are cancer types affecting blood, bone marrow, and lymph nodes. Hematological tumors may derive from either of the two major blood cell lineages: myeloid and lymphoid cell lines. The myeloid cell line normally produces granulocytes, erythrocytes, thrombocytes, macrophages, and masT-cells, whereas the lymphoid cell line produces B, T, and plasma cells. Lymphomas (e.g. Hodgkin's Lymphoma), lymphocytic leukemias, and myeloma are derived from the lymphoid line, while acute and chronic myelogenous leukemia (AML, CML), myelodysplastic syndromes and myeloproliferative diseases are myeloid in origin.

In some embodiments, a non-solid (diffuse) cancer or tumor comprises a hematopoietic malignancy, a blood cell cancer, a leukemia, a myelodysplastic syndrome, a lymphoma, a multiple myeloma (a plasma cell myeloma), an acute lymphoblastic leukemia, an acute myelogenous leukemia, a chronic myelogenous leukemia, a Hodgkin lymphoma, a non-Hodgkin lymphoma, or plasma cell leukemia.

In some embodiments, the tumor or cancer comprises a metastasis of a tumor or cancer.

In some embodiments a cell surface TAA is located in or on the plasma membrane of the cell, such that at least part of this molecule remains accessible from outside the cell in tertiary form. In some embodiments, a cell surface TAA that is located in the plasma membrane is a transmembrane protein comprising, in its tertiary conformation, regions of hydrophilicity and hydrophobicity.

These antigens can be presented on the cell surface with an extracellular part which is often combined with a transmembrane and cytoplasmic part of the molecule. These antigens can sometimes be presented only by tumor cells and never by the normal ones. Tumor antigens can be exclusively expressed on tumor cells or might represent a tumor specific mutation compared to normal cells. In this case, they are called tumor-specific antigens. More common are antigens that are presented by tumor cells and normal cells. In some embodiments, TAA include antigens exclusively expressed on a tumor cell. In some embodiments, TAA include antigens expressed on both tumor and normal cells.

In some embodiments, TAA can be overexpressed on tumor cells compared to normal cells or are accessible for antibody binding in tumor cells due to the less compact structure of the tumor tissue compared to normal tissue.

In some embodiments, a precursor tri-specific antibody constructs described herein comprises (a) an scFv fragment comprising a first binding domain, binding to a TAA (TAA binding domain); (b) an scFv fragment comprising a second binding domain, binding to a TAA (TAA binding domain); (c) an Fab fragment comprising a third binding domain, binding to an extracellular epitope of human CD3ε (CD3 binding domain); (d) a first sub-regulatory domain comprising a protease cleavage domain and a half-life prolonging (HLP) domain; and (e) a second sub-regulatory domain comprising a protease cleaving domain and a CAP component that reduces the ability of the third binding domain to bind the extracellular epitope of CD3ε. In some embodiments, a precursor tri-specific antibody constructs described herein comprises (a) an scFv fragment comprising a first binding domain, binding to a TAA (TAA binding domain); (b) an scFv fragment comprising a second binding domain, binding to a TAA (TAA binding domain); (c) an Fab fragment comprising a third binding domain, binding to an extracellular epitope of human CD3ε (CD3 binding domain); (d) a first sub-regulatory domain comprising a protease cleavage domain and a half-life prolonging (HLP) domain comprising a human serum albumin (HSA) polypeptide; and (e) a second sub-regulatory domain comprising a protease cleaving domain and a CAP component that reduces the ability of the third binding domain to bind the extracellular epitope of CD3ε.

A skilled artisan would appreciate that in some embodiments, a precursor antibody construct encompasses a precursor or derivative form of a pharmaceutically active antibody. In some embodiments, a medicinal preparation comprises a precursor antibody construct. In some embodiments, a formulation comprises a precursor antibody construct. In some embodiments, a precursor antibody construct has reduced adverse effects compared to the activated antibody. In some embodiments, a precursor antibody construct has reduced adverse effects compared to the activated antibody, wherein the precursor antibody may be enzymatically activated or converted into the active form of the antibody.

In some embodiments, precursor tri-specific antibody construct antibodies described herein are precursor tri-specific antibody constructs.

In certain embodiments, a precursor antibody construct has a prolonged half-life compared to the activated antibody. In certain embodiments, a precursor antibody construct has a prolonged half-life compared to the activated antibody, wherein the precursor antibody may be enzymatically activated or converted into the active form of the antibody and the active form has a decreased half-life compared with the precursor antibody construct.

In some embodiments, a precursor antibody construct has reduced ability to bind a T-cell. In certain embodiments, a precursor antibody construct has a reduced ability to activate T-cells compared to the activated antibody. In some embodiments, a precursor antibody construct has reduced ability to bind a T-cell. In certain embodiments, a precursor antibody construct has a reduced ability to activate T-cells compared to the activated antibody, wherein the precursor antibody may be enzymatically activated or converted into the active form of the antibody.

In certain embodiments, a precursor antibody construct has both a prolonged half-life and a reduced ability to activate T-cells compared to the activated antibody. In certain embodiments, a precursor antibody construct has both a prolonged half-life and a reduced ability to bind T-cells compared to the activated antibody. In certain embodiments, a precursor antibody construct has both a prolonged half-life and a reduced ability to activate T-cells compared to the activated antibody, wherein the precursor antibody may be enzymatically activated or converted into the active form of the antibody. In certain embodiments, a precursor antibody construct has both a prolonged half-life and a reduced ability to bind T-cells compared to the activated antibody, wherein the precursor antibody may be enzymatically activated or converted into the active form of the antibody.

In some embodiments, a precursor antibody has reduced ability to bind a T-cell, wherein the regulatory domain comprising the CAP component is cleaved but the regulatory domain comprising the HLP has not been cleaved, wherein the "partially" activated antibody may bind to a T-cell and retain an extended half-life. In some embodiments, binding of a partially activated precursor antibody to a T-cell is reduced compared to a fully activated antibody, wherein both regulatory arms have been proteolytically cleaved. In some embodiments, a precursor antibody has reduced ability to activate a T-cell, wherein the regulatory domain comprising the CAP component is cleaved but the regulatory domain comprising the HLP has not been cleaved, wherein the "partially" activated antibody may activate a T-cell and retain an extended half-life. In some embodiments, activation of a T-cell is reduced following binding of a partially activated precursor construct, compared to a fully activated antibody, wherein both regulatory arms have been proteolytically cleaved.

In some embodiments, a precursor antibody construct is synthesized in vitro. In some embodiments, a precursor antibody construct is not converted to an active form of the antibody, when the precursor is present in vivo (e.g., in circulation) in a non-tumor microenvironment.

In some embodiments, a precursor antibody construct comprises multiple regulatory domains, in addition to antigen binding domains. In some embodiments, a precursor antibody construct comprises two regulatory domains, in addition to antigen binding domains. In some embodiments, a precursor antibody construct comprises enzymatically cleavable regulatory domains, in addition to antigen binding domains. In some embodiments, a precursor antibody construct comprises multiple regulatory domain in addition to antigen binding domains, wherein a portion of said regulatory domains is enzymatically cleavable. In some embodiments, a precursor antibody construct comprises two regulatory domains in addition to antigen binding domains, wherein a portion of said regulatory domains is enzymatically cleavable. In some embodiments, a precursor antibody construct comprises two regulatory domains in addition to three antigen binding domains, wherein said regulatory domains are enzymatically cleavable.

In some embodiments, a precursor tri-specific antibody described herein comprises enhanced selectivity at targeting tumor cells over normal cells prior to cytotoxic activation of T-cells.

Immunological binding generally refers to the non-covalent interactions of the type which occur between an immunoglobulin molecule and an antigen for which the immunoglobulin is specific, for example by way of illustration and not limitation, as a result of electrostatic, ionic, hydrophilic and/or hydrophobic attractions or repulsion, steric forces, hydrogen bonding, van der Waals forces, and other interactions. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and on geometric parameters that equally influence the rate in both directions. Thus, both the "on rate constant" ($k_{on}$) can be determined by calculation of the concentrations and the actual rates of association and the "off rate constant" ($k_{off}$) and can be determined by the actual rates of dissociation. The ratio of $k_{off}/k_{on}$ is thus equal to the dissociation constant $K_D$. See, generally, Davies et al. (1990) Annual Rev. Biochem. 59:439-473.

A skilled artisan would appreciate that a "binding domain" or related expressions such as a domain that "binds" or has "reactivity with/to" a specific target encompasses the ability of the domain to discriminate between the respective antigens and to specifically associate with a target antigen. A "binding domain" or "binding region" according to the present disclosure may be, for example, any protein, polypeptide, oligopeptide, or peptide that possesses the ability to specifically recognize and bind to a biological molecule (e.g., a cell surface receptor or tumor protein, or a component thereof, e.g., an extracellular component thereof). A binding domain includes any naturally occurring, synthetic, semi-synthetic, or recombinantly produced binding partner for a biological molecule of interest. For example, and as further described herein, a binding domain may be antibody light chain and heavy chain variable region regions, or the light and heavy chain variable region regions can be joined together in a single chain and in either orientation (e.g., VL-VH or VH-VL). A variety of assays are known for identifying binding domains of the present disclosure that specifically bind with a particular target, including Western blot, ELISA, flow cytometry, or surface plasmon resonance analysis (e.g., using BIACORE™ analysis).

In some embodiments, binding domain or a portion thereof "specifically binds" to a target molecule if it binds to or associates with a target molecule with an affinity or $K_d$ (i.e., an equilibrium association constant of a particular binding interaction with units of 1/M) of, for example, greater than or equal to about $10^5 M^{-1}$. In certain embodiments, a binding domain or a portion thereof binds to a target with a $K_d$ greater than or equal to about $10^6$ $M^{-1}$, $10^7$ $M^{-1}$, $10^8$ M−1, $10^9$ M−1, $10^{10}$ M−1, $10^{11}$ M−1, $10^{12}$ M−1, or $10^{13}$ M−1, "High affinity" binding domains may encompass those binding domains with a $K_d$ of at least $10^7$ M−1, at least $10^8$ M−1, at least $10^9$ M−1, at least $10^{10}$ M−1, at least 1011 M−1, at least 1012 M−1, at least 1013 M−1, or greater. Alternatively, affinity may be defined as an equilibrium dissociation constant ($K_d$) of a particular binding interaction with units of M (e.g., 105 M to 10-13 M, or less). Affinities of binding domain polypeptides and portions thereof, as described herein can be readily determined using conventional techniques (see, e.g., Scatchard et al. (1949) Ann. N.Y. Acad. Sci. 51:660; and U.S. Pat. Nos. 5,283,173; 5,468,614, or the equivalent, which are incorporated herein in full).

Illustrative binding domains are described herein. In certain embodiments, the target molecule may be a cell surface expressed protein, such as a receptor or a tumor antigen. In some embodiments, the target molecule is a tumor associated antigen (TAA). Illustrative binding domains include immunoglobulin antigen-binding domains such as scFv, scTCR, extracellular domains of receptors, ligands for cell surface molecules/receptors, or receptor binding domains thereof, and tumor binding proteins. In certain embodiments, the antigen binding domains can be an scFv, a VH, a VL, a domain antibody variant (dAb), a camelid antibody (VHH), a fibronectin 3 domain variant, an ankyrin repeat variant and other antigen-specific binding domain derived from other protein scaffolds (Owen, B. (2017) Nat Biotechnol July 12: 35 (7): 602-603).

Thus, in certain embodiments, a binding domain comprises an antibody-derived binding domain but can be a non-antibody derived binding domain. An antibody-derived binding domain can be a fragment of an antibody or a genetically engineered product of one or more fragments of the antibody, which fragment is involved in binding with the antigen. Examples include, without limitation, a complementarity determining region (CDR), a variable region (Fv), a heavy chain variable region (VH), a light chain variable region (VL), a heavy chain, a light chain, a single chain variable region (scFv), a Fab, a single domain camel antibody (camelid VHH), and single domain antibodies (dAb).

The present disclosure provides precursor tri-specific antibody constructs comprising a first binding domain binding to a cell surface tumor associated antigen (TAA), for example but not limited to a TAA being an epidermal growth factor receptor (EGFR) antigen; and a second binding domain binding to a cell surface tumor associated antigen (TAA), for example but not limited to a second TAA being an epidermal growth factor receptor (EGFR) antigen; a third binding domain binding to an immune effector molecule, for example but not limited to a CD3 epsilon chain (CD3ε) extracellular epitope; and two regulatory domains, for example but not limited to a one regulatory domain comprising a cleavable half-life prolonging domain and one regulatory domain comprising a cleavable CAP (masking) domain (FIGS. 1 and 2A-2B). In some embodiments, the precursor tri-specific antibody construct comprises a first binding domain binding to a cell surface tumor associated antigen (TAA), for example but not limited to a TAA being an epidermal growth factor receptor (EGFR) antigen; and a second binding domain binding to a cell surface tumor associated antigen (TAA), for example but not limited to a second TAA being an epidermal growth factor receptor (EGFR) antigen; a third binding domain binding to an immune effector molecule, for example but not limited to a CD3 epsilon chain (CD3ε) extracellular epitope; and a single regulatory domain comprising a protease cleavage domain, a half-life prolonging (HLP) domain, and a CAP component that reduces the ability of the third binding domain to bind, for example but not limited to when the third domain binds the extracellular epitope of human CD3ε (FIG. 2F).

In some embodiments, a precursor tri-specific antibody constructs comprises a first binding domain binding to a cell surface tumor associated antigen (TAA), for example but not limited to a TAA being an epidermal growth factor receptor (EGFR) antigen; and a second binding domain binding to a cell surface tumor associated antigen (TAA), for example but not limited to a second TAA being an epidermal growth factor receptor (EGFR) antigen; a third binding domain binding to an immune effector molecule, for example but not limited to a CD3 epsilon chain (CD3ε) extracellular epitope; and a regulatory domain comprising a cleavable CAP (masking) domain (FIG. 2C). In some embodiments, a precursor tri-specific antibody constructs comprises a first binding domain binding to a cell surface tumor associated antigen (TAA), for example but not limited to a TAA being an epidermal growth factor receptor (EGFR) antigen; and a second binding domain binding to a cell surface tumor associated antigen (TAA), for example but not limited to a second TAA being an epidermal growth factor receptor (EGFR) antigen; a third binding domain binding to an immune effector molecule, for example but not limited to a CD3 epsilon chain (CD3ε) extracellular epitope; and a regulatory domain comprising a cleavable half-life prolonging domain (FIG. 2D).

In some embodiments, the first and second binding domains each comprise a single chain variable fragment (ScFv). A skilled artisan would appreciate that a ScFv is not actually a fragment of an antibody, but instead is a fusion polypeptide comprising the variable heavy chain (VH) and variable light chain (VL) regions of an immunoglobulin, connected by a short linker peptide of ten to about 25 amino acids (FIGS. 1 and FIGS. 2A-2D and 2F).

In some embodiments, the third binding domain comprises a Fab fragment, wherein the first binding domain is attached to the C-terminal end of the CL chain and the second domain is attached at the C-terminal end of the CH1 chain. Alternatively, the third binding domain comprises a Fab fragment, wherein the second binding domain is attached to the C-terminal end of the CH1 chain and the first domain is attached at the C-terminal end of the CL chain.

In some embodiments, the third binding domain comprises a Fab fragment, wherein a first regulatory domain, for example a CAP masking domain, is attached to the N-terminal end of the VL chain and a second regulatory domain, for example an HSA HLP domain, is attached at the N-terminal end of the VH chain. (FIGS. 1, 2A, and 2B). In some embodiments, the third binding domain comprises a Fab fragment, wherein a first regulatory domain, for example a CAP masking domain, is attached to the N-terminal end of the VL chain and a second regulatory domain, for example an HSA HLP domain, is attached at the N-terminal end of the VH chain.

In some embodiments, the third binding domain comprises a Fab fragment, wherein a regulatory domain, comprising for example a CAP masking domain, an HSA HLP domain, and a protease linker is attached to the N-terminal end of the VH chain. (FIG. 2F). In some embodiments, the third binding domain comprises a Fab fragment, wherein a regulatory domain, comprising for example a CAP masking domain, an HSA HLP domain, and a protease linker is attached to the N-terminal end of the VL chain.

In some embodiments, between the scFv of the first binding domain and the CL of the third binding domain there may be a linker sequence. In some embodiments, between the scFv of the first binding domain and the CH1 of the third binding domain there may be a linker sequence. In some embodiments, between the scFv of the second binding domain and the CL of the third binding domain there may be a linker sequence. In some embodiments, between the scFv of the second binding domain and the CH1 of the third binding domain there may be a linker sequence. In some embodiments, between the scFv of the first and second binding domains, and the CL and CH1 of the third binding domains, respectively, there may be linker sequences.

In some embodiments, between the first sub-regulatory domain and the VH chain of the third binding domain, there may be a linker sequence which is cleavable. In some embodiments, between the first sub-regulatory domain and the VL chain of the third binding domain, there may be a linker sequence which is cleavable. In some embodiments, between the second sub-regulatory domain and the VH chain of the third binding domain, there may be a linker sequence which is cleavable. In some embodiments, between the second sub-regulatory domain and the VL chain of the third binding domain, there may be a linker sequence which is cleavable. In some embodiments, between the first and second sub-regulatory domains, and the VH and VL chains of the third binding domains, respectively, there may be linker sequences which are cleavable.

In some embodiments, between a single regulatory domain and the VH chain of the third binding domain, there may be a linker sequence which is cleavable. In some embodiments, between a single regulatory domain and the VL chain of the third binding domain, there may be a linker sequence which is cleavable.

These general formats are the basic structure that can be built upon to construct the precursor tri-specific (tribody) antibody constructs described herein (FIG. 1 and FIGS. 2A, 2B, and 2F).

In some embodiments, a regulatory domain comprises a protease cleavable linker component and a human serum albumin polypeptide (HSA) sequence component (FIGS. 1, 2A, 2B, and 2D). In some embodiments, there is only a single regulatory domain comprising a protease cleavable linker component and a human serum albumin polypeptide (HSA) sequence component (FIG. 2D). In some embodiments, there is only a single regulatory domain comprising a protease cleavable linker component, a human serum albumin polypeptide (HSA) sequence component, and a CAP component (FIG. 2F). In some embodiments, regulatory domains comprise protease cleavable linker components, and one of a human serum albumin polypeptide sequence component, and at least one CAP amino acid component (FIGS. 1, and 2A-2B). In some embodiments, there are two regulatory domains, one consisting essentially of a protease cleavable linker component and a human serum albumin polypeptide sequence component, and the other consisting essentially of protease cleavable linker and a CAP amino acid (masking) component (FIGS. 1 and 2A-2B). In some embodiments, there is only a single regulatory domain that comprises a protease cleavable linker component and a CAP amino acid (masking) component (FIG. 2C). In some embodiments, the is a single regulatory domain that comprises a CAP amino acid (masking) component, a protease cleavable linker component, and a human serum albumin polypeptide (HSA) sequence component (FIG. 2F). The skilled artisan would appreciate that the presence of linkers, for example anyone of the linkers displayed in the constructs shown in FIGS. 1 and 2A-F, provide flexibility to a polypeptide while not necessarily providing essential regulatory feature to the regulatory domain, such as is provided by a CAP (a masking activity) or by an HSA component (increased half-life). In some embodiments, wherein the linker comprises a protease cleavage linker the linker too provides a regulatory function, wherein cleavage of the protease cleavable linker may remove a CAP (masking) component, remove a half-life prolonging component, or may remove both a CAP (masking) component and a half-life prolonging component.

Figure 3A:
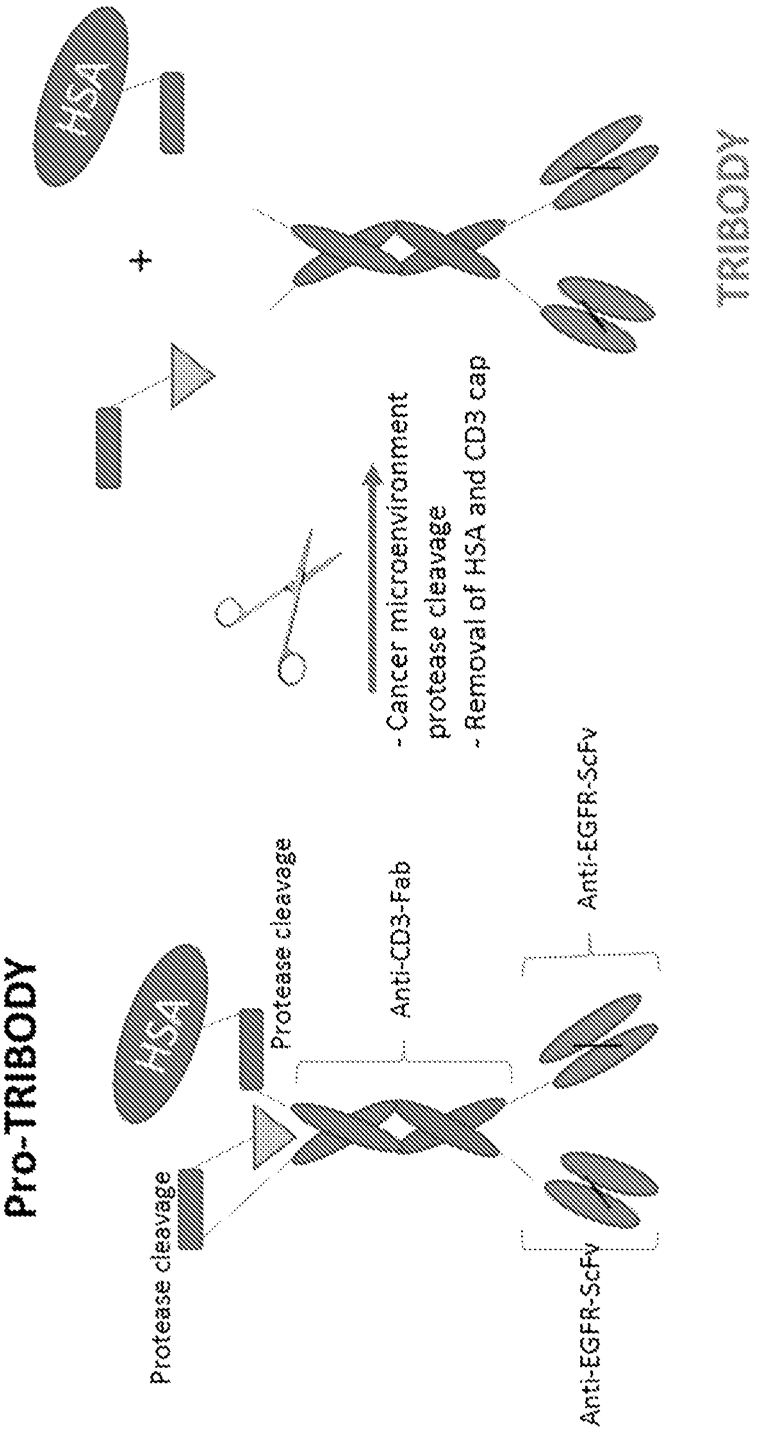
FIGS. 3A and 3B show flow diagrams of protease specific activation within tumor tissue or within a tumor environment of precursor tri-specific antibody constructs, wherein T-cell engagement and activation is limited to tumor sites.
Figure 3B:
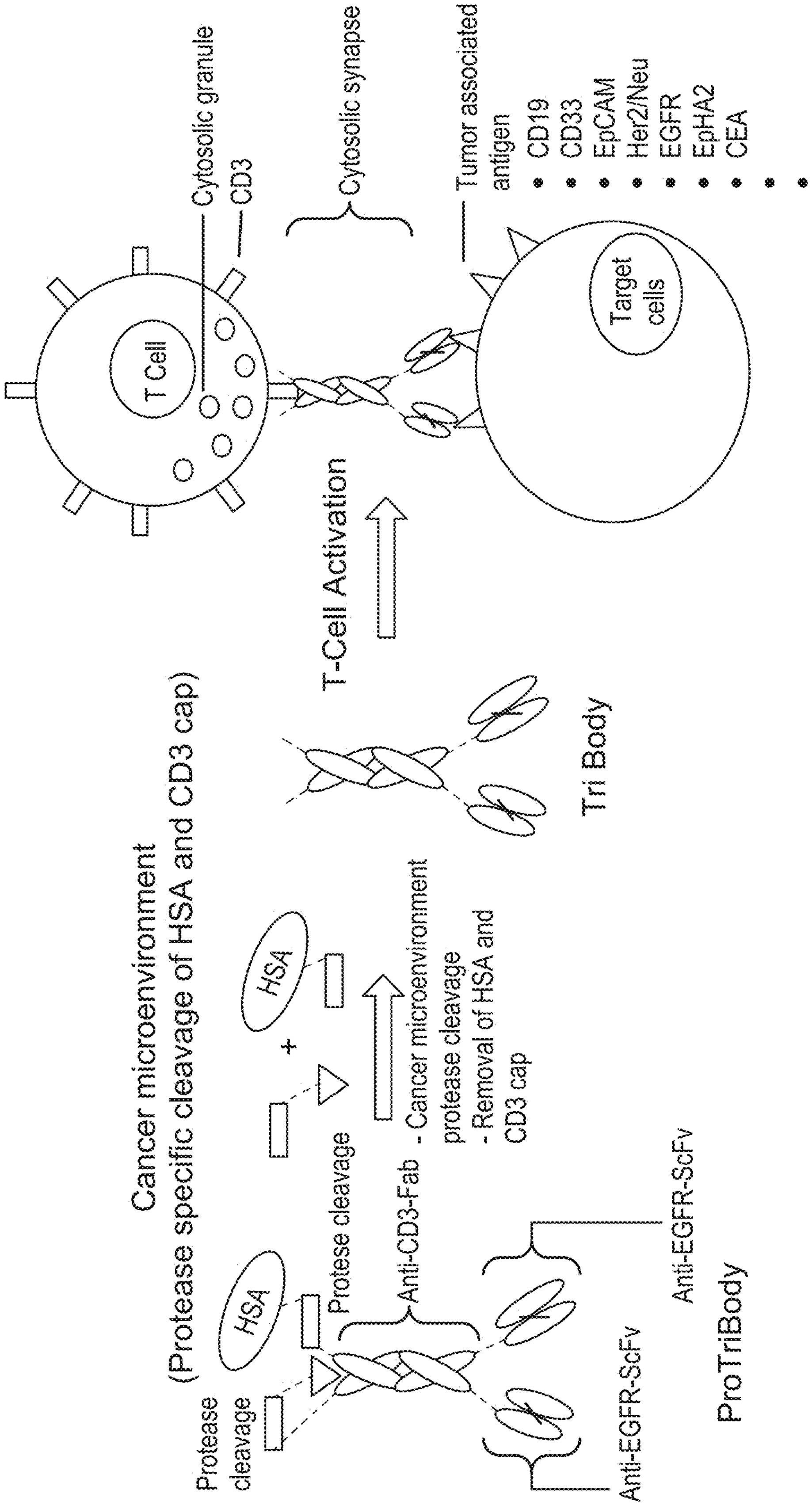

In some embodiments, the third binding domain anti-immune effector molecule, for example but not limited to an anti-CD3 epsilon chain (CD3ε) extracellular epitope, binds specifically to the CAP amino acid component. In some embodiments, the CAP component effectively blocks binding of the precursor tri-specific antibody construct with an immune effector target molecule, for example a T-cell. In some embodiments, activation of cytotoxicity to a target is specifically masked by the CAP component. In some embodiments, wherein the regulatory domain comprises a cleavable CAP component activation of cytotoxicity is limited to a tumor milieu (FIGS. 3A-3B). Some embodiments, the origin of a first or second binding domain target (for example a TAA) comprise those presented in FIG. 3B (righthand-side).

In some embodiments, the CAP component comprises an amino acid sequence present within the human CD3 epsilon polypeptide chain. In some embodiments, the CAP component comprises an amino acid sequence present as part of the extracellular portion of the human CD3 epsilon chain. In some embodiments, the CAP component comprises an amino acid sequence selected from the amino acid sequence of the N-terminal end of human CD3 epsilon precursor polypeptide. In some embodiments, the CAP component comprises an amino acid sequence selected from the amino acid sequence of the N-terminal end of human CD3 epsilon mature polypeptide.

The amino acid sequence of the precursor human CD3 epsilon is set for in SEQ ID NO: 1. Human CD3 epsilon is expressed in a precursor form, wherein amino acids 1-21 form the signal peptide. The amino acid sequence of the mature human CD3 epsilon is set forth in amino acids 22-207 of SEQ ID NO: 1, as set forth herein in SEQ ID NO: 2. In some embodiments, the extracellular epitope of human CD3 epsilon is located within the precursor sequence, as set forth in SEQ ID NO: 3. In some embodiments, the extracellular epitope of a mature human CD3 epsilon is located within amino acids 1-27 of the precursor sequence, which is set forth in SEQ ID NO: 4. In some embodiments, the extracellular epitope of human CD3 epsilon is located within amino acids QDGNEEMGGITQTPYKVSISGTTVILT (SEQ ID NO: 5; AA1-27).

In some embodiments, the amino acid sequence of a CAP component is set forth in SEQ ID NO: 5, or a homolog thereof. In some embodiments, the amino acid sequence of a CAP component is a selected contiguous sequence within SEQ ID NO: 4, or a homolog thereof.

In some embodiments, homologues of SEQ ID NO: 5 or of a CAP sequence selected from SEQ ID NO: 4, comprise polypeptides which are at least 50%, at least 55%, at least 60%, at least 65%, at least 70%, at least 75%, at least 80%, at least 85%, at least 87%, at least 89%, at least 91%, at least 93%, at least 95%, at least 96%, at least 97%, at least 98%, or at least 99% homologous to the amino acid sequence.

In some embodiments, homologues comprise polypeptides which are at least 50%, at least 55%, at least 60%, at least 65%, at least 70%, at least 75%, at least 80%, at least 85%, at least 87%, at least 89%, at least 91%, at least 93%, at least 95%, at least 96%, at least 97%, at least 98%, or at least 99% homologous to a human CD3 epsilon polypeptide or a portion thereof, as determined using BlastP software of the National Center of Biotechnology Information (NCBI) using default parameters.

A skilled artisan would appreciate that the term "homology", and grammatical forms thereof, encompasses the degree of similarity between two or more structures. The term "homologous sequences" refers to regions in macromolecules that have a similar order of monomers. When used in relation to nucleic acid sequences, the term "homology" refers to the degree of similarity between two or more nucleic acid sequences (e.g., genes) or fragments thereof. Typically, the degree of similarity between two or more nucleic acid sequences refers to the degree of similarity of the composition, order, or arrangement of two or more nucleotide bases (or other genotypic feature) of the two or more nucleic acid sequences. The term "homologous nucleic acids" generally refers to nucleic acids comprising nucleotide sequences having a degree of similarity in nucleotide base composition, arrangement, or order. The two or more nucleic acids may be of the same or different species or group. The term "percent homology" when used in relation to nucleic acid sequences, refers generally to a percent degree of similarity between the nucleotide sequences of two or more nucleic acids.

When used in relation to polypeptide (or protein) sequences, the term "homology" refers to the degree of similarity between two or more polypeptide (or protein) sequences (e.g., genes) or fragments thereof. Typically, the degree of similarity between two or more polypeptide (or protein) sequences refers to the degree of similarity of the composition, order, or arrangement of two or more amino acid of the two or more polypeptides (or proteins). The two or more polypeptides (or proteins) may be of the same or different species or group. The term "percent homology" when used in relation to polypeptide (or protein) sequences, refers generally to a percent degree of similarity between the amino acid sequences of two or more polypeptide (or protein) sequences. The term "homologous polypeptides" or "homologous proteins" generally refers to polypeptides or proteins, respectively, that have amino acid sequences and functions that are similar. Such homologous polypeptides or proteins may be related by having amino acid sequences and functions that are similar but are derived or evolved from different or the same species using the techniques described herein.

In some embodiments, homologues comprise polypeptides which are at least 50%, at least 55%, at least 60%, at least 65%, at least 70%, at least 75%, at least 80%, at least 85%, at least 87%, at least 89%, at least 91%, at least 93%, at least 95%, at least 96%, at least 97%, at least 98%, or at least 99% homologous to a polypeptide or a portion thereof disclosed herein, as determined using BlastP software of the National Center of Biotechnology Information (NCBI) using default parameters. In some embodiments, homologues comprise a nucleotide sequences which is at least 50%, at least 55%, at least 60%, at least 65%, at least 70%, at least 75%, at least 80%, at least 85%, at least 87%, at least 89%, at least 91%, at least 93%, at least 95%, at least 96%, at least 97%, at least 98%, or at least 99% homologous to a nucleotide sequence or a portion thereof disclosed herein, as determined using BlastN software of the National Center of Biotechnology Information (NCBI) using default parameters.

In some embodiments, homology also encompasses deletion, insertion, or substitution variants, including an amino acid substitution, thereof and biologically active polypeptide fragments thereof. In one embodiment, the variant comprises conservative substitutions, or deletions, insertions, or substitutions that do not significantly alter the three-dimensional structure of the polypeptide component of interest described herein. In some embodiments, the deletion, insertion, or substitution does not alter the function of interest of the polypeptide component of interest disclosed herein.

In some embodiments, homology also encompasses deletion, insertion, or substitution variants, including an amino acid substitution, thereof and biologically active polypeptide fragments thereof. In one embodiment, the variant comprises conservative substitutions, or deletions, insertions, or substitutions that do not significantly alter the three-dimensional structure of the CAP component, e.g., the portion of a human CD3 epsilon polypeptide present in the CAP component, particularly in the areas of the epitope recognized and bound by the third binding domain. In some embodiments, the deletion, insertion, or substitution does not alter the function of interest of the CAP component, which in some embodiment, is binding to the third binding domain, or reducing T-cell binding, or reducing T-cell activation, or any combination thereof.

In some embodiments, a CAP component is 6-110 amino acids long. In some embodiments, a CAP component is between about 6-10 amino acids long. In some embodiments, a CAP component is between about 10-20 amino acids long. In some embodiments, a CAP component is between about 20-30 amino acids long. In some embodiments, a CAP component is between about 20-40 amino acids long. In some embodiments, a CAP component is between about 30-40 amino acids long. In some embodiments, a CAP component is between about 40-60 amino acids long. In some embodiments, a CAP component is between about 60-80 amino acids long. In some embodiments, a CAP component is between about 80-100 amino acids long. In some embodiments, a CAP component is between about 80-110 amino acids long.

In some embodiments, a CAP component is 6 amino acids long. In some embodiments, a CAP component is 7 amino acids long. In some embodiments, a CAP component is 8 amino acids long. In some embodiments, a CAP component is 9 amino acids long. In some embodiments, a CAP component is 10 amino acids long. In some embodiments, a CAP component is 11 amino acids long. In some embodiments, a CAP component is 12 amino acids long. In some embodiments, a CAP component is 13 amino acids long. In some embodiments, a CAP component is 14 amino acids long.

In some embodiments, a CAP component is 15 amino acids long. In some embodiments, a CAP component is 16 amino acids long. In some embodiments, a CAP component is 17 amino acids long. In some embodiments, a CAP component is 18 amino acids long. In some embodiments, a CAP component is 19 amino acids long. In some embodiments, a CAP component is 20 amino acids long. In some embodiments, a CAP component is 21 amino acids long. In some embodiments, a CAP component is 22 amino acids long. In some embodiments, a CAP component is 23 amino acids long. In some embodiments, a CAP component is 24 amino acids long. In some embodiments, a CAP component is 25 amino acids long. In some embodiments, a CAP component is 26 amino acids long. In some embodiments, a CAP component is 27 amino acids long. In some embodiments, a CAP component is 28 amino acids long. In some embodiments, a CAP component is 29 amino acids long. In some embodiments, a CAP component is 30 amino acids long. In some embodiments, a CAP component is 31, 32, 33, 34, 35, 36, 37, 38, 39, or 40 amino acids long.

In some embodiments, the CAP component specifically binds to the third binding region, thereby reducing T-cell binding of the precursor construct. In some embodiments, the CAP component specifically binds to the third binding region, thereby inhibiting T-cell binding of the precursor construct. In some embodiments, the CAP component specifically binds to the third binding region, thereby reducing T-cell activation the precursor construct. In some embodiments, the CAP component specifically binds to the third binding region, thereby inhibiting T-cell activation by the precursor construct.

In some embodiments, a regulatory domain comprises a cleavable half-life prolonging domain. In some embodiments, a cleavable half-life prolonging domain comprises an HSA polypeptide.

In some embodiments, there is a linker between the components of the regulatory domains. In some embodiments, there is a linker between a regulatory domain and the N-terminus of the VH chain of the Fab fragment. In some embodiments, there is a linker between a regulatory domain and the N-terminus of the VL chain of the Fab fragment. In some embodiments, there is a linker between a regulatory domain and the N-terminus of the VH chain of the Fab fragment and a linker between a regulatory domain and the N-terminus of the VL chain of the Fab fragment. In some embodiments, a linker between components of the regulatory domain and the N-terminus of an Fab fragment polypeptide is a cleavable linker. In some embodiments, any of the linkers between components of the regulatory domain and the Fab polypeptide is a cleavable linker. In some embodiments, a linker between components of the regulatory domain and the Fab polypeptide is not cleavable. (FIGS. 1, 2A-2D, and 3A-3B).

In some embodiments, a regulatory domain comprises a cleavable half-life prolonging domain comprising a protease cleavable domain and a human serum albumin polypeptide (HSA). In some embodiments, the order of components in the regulatory domain is (N-terminal to C-terminal) HSA-L-protease cleavable domain, wherein L is a possible linker amino acid sequence (FIGS. 1, 2A, 2B, and 2D). In some embodiments, a regulatory domain comprises a cleavage regulatory domain comprising a CAP amino acid (masking) component, a protease cleavable domain, and a human serum albumin polypeptide (HSA). In some embodiments, the order of components in the regulatory domain is (N-terminal to C-terminal) CAP-L-HSA-L-protease cleavable domain, wherein L is a possible linker amino acid sequence (FIG. 2F). In some embodiments, wherein the protease cleavable domain is C-terminal to an HSA polypeptide sequence, the precursor construct has a regulatable enhanced half-life wherein the precursor construct has an enhanced half-life in circulation in vivo and in the absence of a tumor microenvironment.

In some embodiments, a regulatory domain comprises a cleavable half-life prolonging domain comprising a protease cleavable domain and a CAP masking domain. In some embodiments, the order of components in the regulatory domain is (N-terminal to C-terminal) CAP-L-protease cleavable domain, wherein L is a possible linker amino acid sequence (FIGS. 1, 2A, 2B, and 2C). In some embodiments, the order of components in the regulatory domain is (N-terminal to C-terminal) CAP-L-HSA-L-protease cleavable domain, wherein L is a possible linker amino acid sequence Prior to entry of the precursor antibody into a tumor microenvironment, the tri-specific precursor construct is effectively blocked from binding with an immune effector target molecule In some embodiments, there is one regulatory domain comprising a cleavable half-life prolonging domain and CAP masking domain. In some embodiments, there are two regulatory domains: one comprising a cleavable half-life prolonging domain and one comprising a cleavable CAP masking domain. In some embodiments, there are three regulatory domains: one comprising a cleavable half-life prolonging domain and two comprising a cleavable CAP masking domain. A precursor tri-specific construct with HSA regulatory domain and at least one CAP regulatory domain, has a regulatable enhances half-life wherein the precursor tri-specific antibody construct has an enhanced half-life and is effectively blocked from binding with at least one immune effector target molecule. Half-life may be enhanced in circulation in vivo and in the absence of a tumor milieu. In some embodiments, activation of cytotoxicity by a precursor tri-specific antibody construct is limited to the tumor milieu. In some embodiments, the precursor construct maintains an enhanced half-life in circulation in vivo and is effectively blocked from binding with an immune effector target molecule in circulation in vivo within a non-tumor milieu (FIGS. 3A-3B). In some embodiments, activation of cytotoxicity to target is specifically masked by a CAP component of the precursor construct in circulation and in the absence of a tumor milieu, and the precursor construct comprises an enhance half-life in circulation in vivo and in the absence or presence of a tumor milieu. In some embodiments, activation of cytotoxicity is limited to the tumor milieu.

In some embodiments, activation of cytotoxicity to target is specifically masked by the CAP component in circulation and in a non-tumor milieu. In some embodiments, activation of cytotoxicity is limited to the tumor milieu. In some embodiments, activation of a T-cell is specifically masked by a CAP component.

In some embodiments, the amino acid sequence of the HSA component is set forth in SEQ ID NO: 6. In some embodiments, the amino acid sequence of the HSA component is set forth in SEQ ID NO: 7.

In some embodiments, the amino acid sequence of the HSA components is any HSA polypeptide sequence known in the art or a portion thereof, or a homolog thereof. In some embodiments, the HSA component of a precursor tri-specific antibody construct comprises, for example but not limited to, any human albumin protein sequence disclosed in a known database such as the protein data base the is part of National Center of Biotechnology Information (NCBI) or Swiss-Prot, wherein the sequence might be identified specifically as human or may be identified as a synthetic construct.

In some embodiments, the HSA component is encoded by the nucleotide sequence set forth in SEQ ID NO: 8.

In some embodiments, the nucleic acid sequence of the HSA components is any HSA nucleotide sequence known in the art or a portion thereof, or a homolog thereof. In some embodiments, the HSA component of a precursor tri-specific antibody construct comprises a nucleic acid sequence that encodes, for example but not limited to, any human albumin protein sequence disclosed in a known database such as the protein data base the is part of National Center of Biotechnology Information (NCBI) or Swiss-Prot, wherein the sequence might be identified specifically as human or may be identified as a synthetic construct.

In some embodiments, homologues of an HSA component comprise polypeptides which are at least 50%, at least 55%, at least 60%, at least 65%, at least 70%, at least 75%, at least 80%, at least 85%, at least 87%, at least 89%, at least 91%, at least 93%, at least 95%, at least 96%, at least 97%, at least 98%, or at least 99% homologous to the amino acid sequence. In some embodiments, homologues comprise polypeptides which are at least 50%, at least 55%, at least 60%, at least 65%, at least 70%, at least 75%, at least 80%, at least 85%, at least 87%, at least 89%, at least 91%, at least 93%, at least 95%, at least 96%, at least 97%, at least 98%, or at least 99% homologous to an HSA polypeptide or a portion thereof, as determined using BlastP software of the National Center of Biotechnology Information (NCBI) using default parameters. In some embodiments, homologues encoding an HSA component comprise nucleotides which are at least 50%, at least 55%, at least 60%, at least 65%, at least 70%, at least 75%, at least 80%, at least 85%, at least 87%, at least 89%, at least 91%, at least 93%, at least 95%, at least 96%, at least 97%, at least 98%, or at least 99% homologous to the nucleic acid sequence. In some embodiments, homologues encode polypeptides which are at least 50%, at least 55%, at least 60%, at least 65%, at least 70%, at least 75%, at least 80%, at least 85%, at least 87%, at least 89%, at least 91%, at least 93%, at least 95%, at least 96%, at least 97%, at least 98%, or at least 99% homologous to an HSA polypeptide or a portion thereof, as determined using BlastP software of the National Center of Biotechnology Information (NCBI) using default parameters.

In some embodiments, homology also encompasses deletion, insertion, or substitution variants, including an amino acid substitution, thereof and biologically active polypeptide fragments thereof. In one embodiment, the variant comprises conservative substitutions, or deletions, insertions, or substitutions that do not significantly alter the three-dimensional structure of the HSA component. In some embodiments, the deletion, insertion, or substitution does not alter the function of interest of the HSA component, which in some embodiment, is providing half-life prolonging domain.

Linear representation of embodiments of regulatory domains of a precursor tri-specific antibody construct disclosed herein include but are not limited to (N-terminal to C-terminal) (1) CAP-L-protease cleavable domain-L, wherein the L may or may not be present;

(2) HSA-L-protease cleavable domain-L, wherein the L may or may not be present;

(3) CAP-L-non-cleavable domain-L, wherein the L may or may not be present;

(4) HSA-L-non-cleavable domain-L, wherein the L may or may not be present;

(5) Protease cleavable domain-L-CAP;

(6) Protease cleavable domain-L-HSA;

(7) Non-cleavable domain-L-CAP; and (8) Non-cleavable domain-L-HSA.

In some embodiments, a precursor tri-specific antibody construct disclosed herein comprises a precursor construct having an increased therapeutic window, wherein its restricted presence provides the ability to target a wide array of new targets or provide improved activities or a combination thereof, for example but not limited to, the ability to activate T-cells only in the cancer microenvironment and targeting cancer-specific TAAs depending on a cancer type and the specific TAAs that are uniquely expressed by this cancer type in conjunction with the proteases produced by this cancer type. In some embodiments, the precursor construct has the ability to activate T-cells only in the TME and targets a cancer specific TAA and a different TAA present in the TME.

As used herein, the "C-terminal" of a polypeptide and the like, e.g., carboxyl-terminus, carboxy-terminus, C-terminal tail, C-terminal end, or COOH-terminus) is the end of an amino acid chain (protein or polypeptide), terminated by a free carboxyl group (—COOH). When the protein is translated from messenger RNA, it is created from N-terminus to C-terminus. The convention for writing peptide sequences is to put the C-terminal end on the right and write the sequence from N- to C-terminus. In some embodiments, the C-terminal end of a polypeptide encompasses to the last amino acid residue of the polypeptide which donates its amine group to form a peptide bond with the carboxyl group of its adjacent amino acid residue.

As used herein, the "N-terminal" of a polypeptide and the like, e.g., amino-terminus, NH2-terminus, N-terminal end or amine-terminus) is the start of a protein or polypeptide referring to the free amine group (—$NH_2$) located at the end of a polypeptide. Normally the amine group is bonded to another carboxylic group in a protein to make it a chain, but since the end of a protein has only 1 out of 2 areas chained, the free amine group is referred to the N-terminus. As stated above, by convention, peptide sequences are written N-terminus to C-terminus, left to right in LTR languages. This correlates the translation direction to the text direction (because when a protein is translated from messenger RNA, it is created from N-terminus to C-terminus-amino acids are added to the carbonyl end). In some embodiments, the N-terminal end of a polypeptide encompasses the first amino acid of the polypeptide which donates its carboxyl group to form a peptide bond with the amine group of its adjacent amino acid residue.

A skilled artisan would appreciate that a linker component may encompass an amino acid peptide linking through one or more chemical bonds or indirect linking through one or more linkers. Any suitable chemical bonds can be used to make a direct link, including without limitation, covalent bonds such as peptide bond and disulfide bond, non-covalent bonds such as hydrogen bond, hydrophobic bond, ionic bond, and Van der Waals bond.

A "covalent bond" refers herein to a stable association between two atoms which share one or more electrons. Examples of the covalent bonds include, without limitation, a peptide bond and a disulfide bond. "Peptide bond" as used herein refers to the covalent bond formed between the carboxyl group of an amino acid and the amine group of the adjacent amino acid. "Disulfide bond" as used herein refers to a covalent bond formed between two sulfur atoms. A disulfide bond can be formed from oxidation of two thiol groups. In certain embodiments, the covalently link is direct link through a covalent bond. In certain embodiments, the covalently link is direct link through a peptide bond or a disulfide bond.

A "non-covalent bond" refers herein to an attractive interaction between two molecules or two chemical groups that does not involve sharing of electrons. Examples of non-covalent bonds include, without limitation, a hydrogen bond, a hydrophobic bond, an ionic bond, and a Van der Waals bond. A "hydrogen bond" refers herein to attractive force between a hydrogen atom of a first molecule/group and an electronegative atom of a second molecule/group. A "hydrophobic bond" refers herein to a force that causes hydrophobic or non-polar molecules/groups to aggregate or associate together in an aqueous environment. An "ionic bond" refers herein to an attraction between a positive ion and a negative ion. A "Van der Waals bond" refers herein to a non-specific attraction force between two adjacent molecules/groups which have momentary random fluctuations in the distribution of electrons. In certain embodiments, the covalently link is direct link through a non-covalent bond. In certain embodiments, the covalently link is direct link through a hydrogen bond, a hydrophobic bond, an ionic bond, or a Van der Waals bond.

A skilled artisan would appreciate that a protease cleavable domain described herein encompasses linker comprising a protease cleavage site. Thus, the terms "protease cleavable domain" and protease cleavable linker" may be used interchangeably herein having all the same meanings and qualities.

A skilled artisan would appreciate that the terms "tumor microenvironment", "cancer microenvironment", "TME", and "tumor milieu" may be used interchangeably having the same qualities and meanings and encompassing the microenvironment to tumor development. While the normal cellular microenvironment can inhibit malignant cell growth, the modifications that occur in the tumor microenvironment may synergistically support cell proliferation.

Tumors shape their microenvironment and support the development of both tumor cells and non-malignant cells. The tumor microenvironment affects angiogenesis by interfering with the signaling pathways required for cell recruitment and vascular construction. Endothelial progenitor cells (EPCs) that are recruited under hypoxic conditions for angiogenesis have been associated as well with metastasis. In some embodiments, TAA comprise cell surface antigens associated with angiogenesis. In some embodiments, a TAA is overexpressed by a cancer cell. In some embodiments, a TAA is expressed on an embryonic cell. In some embodiments, a TAA is expressed on an embryonic cell and on a cancer cell but has no or only minimal expression on normal adult cells. In some embodiments, a TAA is expressed on a solid tumor cell. In some embodiments, a TAA is expression on a non-solid cancerous cell. In some embodiments, a TAA is expressed on an angiogenic tissue cell.

In addition. proteins secreted by the tumor modify the microenvironment by contributing growth factors and proteases that degrade the extracellular matrix and affect cell motility and adhesion. Stromal cells secrete ECM proteins, cytokines, growth factors, proteases, protease inhibitors, and endoglycosidases such as heparanase. Matrix metalloproteinases (MMP) are important secreted proteins closely associated with cancer development. MMP are expressed at higher levels by tumor-associated epithelial cells than by normal epithelial cells. In some embodiments, the microenvironment of a tumor comprises increased protease activity compared with a non-tumor environment.

FIGS. 3A and 3B provide non-limiting examples of a precursor tri-specific antibody construct that may have an enhanced half-live in vivo in circulation and while present in a non-tumor environment. Further, the anti-CD3 third binding domain of the precursor tri-specific antibody construct is blocked and may not interact or bind with a target T-cell while the precursor construct is in the non-tumor environment. In some embodiments, as is shown by the scissors in FIG. 3A and just prior to T-cell activation in FIG. 3B, the cancer microenvironment provides protease cleavage of a precursor tri-specific antibody construct, which removes the half-life extending regulatory domain (HSA) and the CD3ε CAP regulatory domain, leading to the presence of an activated EGFR (2scFvs) x CD3ε antibody (FIG. 2E) and T-cell activation.

In some embodiments, a protease cleavable domain comprises a protease cleavable amino acid sequence (cleavable peptide/cleavable linker; CP) comprises a peptide cleavable by a serine protease, a cysteine protease, an aspartate protease, or a matrix metalloprotease (MMP) cleavable sequence. In some embodiments, a protease cleavable domain comprises a protease cleavable amino acid sequence (cleavable peptide/cleavable linker; CP) comprises a peptide, which is a substrate for cleavage by multiple difference proteases. In some embodiments, a protease cleavable domain comprises a protease cleavable amino acid sequence (cleavable peptide/cleavable linker; CP) comprises a peptide, which is a substrate for cleavage by a MMP2/MMP9 protease, or a urokinase-type plasminogen activator (uPA) protease, or a matriptase, or a legumain protease. In some embodiments, the serine protease, cysteine protease, aspartate protease, uPA protease, matriptase, legumain protease, or matrix metalloprotease (MMP) is expressed at higher levels in a tumor microenvironment. In some embodiments, the matrix metalloprotease is expressed at higher levels in a tumor microenvironment.

In some embodiments, the protease cleavable sequence is an MMP cleavable sequence. In some embodiments, the matrix metalloprotease cleavable sequence may be a matrix metalloprotease 1 (MMP-1), a matrix metalloprotease 2 (MMP-2), a matrix metalloprotease 9 (MMP-9), or a matrix metalloprotease 14 (MMP-14) cleavable sequence.

In some embodiments, the protease cleavable sequence is a uPA (urokinase-type plasminogen activator) cleavable sequence. In some embodiments, the protease cleavable sequence is a MT-SP1 (matripase) cleavable sequence.

In some embodiments, the protease cleavable sequence is an MMP, uPA, matriptase, and legumain cleavable sequence.

In some embodiments, the protease cleavable domain comprises an amino acid sequence 1 to 10 amino acids long. In some embodiments, the protease cleavable domain is 1 to 20 amino acids long.

In some embodiments, a protease cleavable domain comprises a protease substrate cleavage sequence, for example but not limited to, an MMP substrate cleavage sequence. A well-known peptide sequence of PLGLAG (SEQ ID NO: 9) in a substrate can be cleaved by most MMPs. Substrate sequences that can be cleaved by MMPs have been extensively studied. A protease substrate cleavage sequence refers to a peptide sequence that can be cleaved by protease treatment. An MMP substrate sequence refers to a peptide sequence that can be cleaved by incubation with an MMP. SEQ ID NO: 9 is a commonly used MMP substrate cleavage sequence (see e.g., Jiang, PNAS (2004) 101:17867-72; Olson, PNAS (2010) 107:4311-6). In another embodiment, the protease cleavage site is recognized by MMP-2, MMP-9, or a combination thereof. In yet another embodiment, the protease site comprises the sequence set forth as GPLGMLSQ (SEQ ID NO: 10), GPLGLWAQ (SEQ ID NO: 11), GPLGLAG (SEQ ID NO: 12), KKNPAELIGPVD (SEQ ID NO: 13), KKQPAANLVAPED (SEQ ID NO: 14), GPLGIAGQ (SEQ ID NO: 15), or PVGLIG (SEQ ID NO: 16). In some embodiments, the protease cleavage site comprises any protease cleavage site (protease cleavable peptide; CP) known in the art to be susceptible to proteases present in a tumor environment, for example by not limited to the protease cleavage sites disclosed in Eckhard, U, et al., (2016) Matrix Biol. Jan;49:37-60.

In some embodiments, a protease cleavable sequence comprising a uPA cleavable sequence comprises the sequence set forth as NSGRAV (SEQ ID NO: 17), SGRSA (SEQ ID NO: 18), LGGSGRSANAILE (SEQ ID NO: 19), SGRS (SEQ ID NO: 20), GGSGRSANK (SEQ ID NO: 21), LGGSGRSANAILEC (SEQ ID NO: 22), GGGRR (SEQ ID NO: 23), TGRGPS (SEQ ID NO: 24), LSGRSDNH (SEQ ID NO: 25), or PLTGRSGG (SEQ ID NO: 26).

In some embodiments, a protease cleavable sequence comprising a matripase cleavable sequence comprises the sequence set forth as QRRVVGG (SEQ ID NO: 27), QAR, AANL (SEQ ID NO: 29), PTNL (SEQ ID NO: 30), PTN, or SAN.

In some embodiments, a cleavable peptide is encoded by the nucleic acid sequence set forth in SEQ ID NO: 33: CCACTGGGCCTGGCCGGC.

In some embodiments, the amino acid sequence of a protease cleavable sequence that serves as a substrate for MMP2/9, uPA, matriptase, and legumain cleavable sequence is set forth as PLGLAGSGRSDNH (SEQ ID NO: 35). In some embodiments, all of the protease cleavable sequences comprised in a precursor construct comprise SEQ ID NO: 35. In some embodiments, at least one of the protease cleavable sequences comprised in a precursor construct comprise SEQ ID NO: 35. In some embodiments, at least 2 of the protease cleavable sequences comprised in a precursor construct comprise SEQ ID NO: 35. In some embodiments, at least 3 of the protease cleavable sequences comprised in a precursor construct comprise SEQ ID NO: 35.

In some embodiments, the sequence of the protease cleavable peptide component of regulatory domain one is the same as the protease cleavable peptide component of regulatory domain two. In some embodiments, the sequence of the protease cleavable peptide component of regulatory domain one is not the same as the protease cleavable peptide component of regulatory domain two. In some embodiments, the protease cleaving the cleavable peptide component of regulatory domain one is the same protease as is cleaving the protease cleavable peptide component of regulatory domain two. In some embodiments, the protease cleaving the cleavable peptide component of regulatory domain one is not the same protease as is cleaving the protease cleavable peptide component of regulatory domain two.

In some embodiments, the protease cleaving the first and second sub-regulatory domains is an MMP protease. In some embodiments, the protease cleaving the first and second sub-regulatory domains is a uPA protease. In some embodiments, the protease cleaving the first and second sub-regulatory domains is a matripase protease. In some embodiments, one of the first or second sub-regulatory domains is cleaved by an MMP protease, while the other regulatory domain is cleaved by a non-MMP protease. In some embodiments, one of the first or second sub-regulatory domains is cleaved by an MMP protease, while the other regulatory domain is cleaved by a uPA protease. In some embodiments, one of the first or second sub-regulatory domains is cleaved by an MMP protease, while the other regulatory domain is cleaved by a matripase protease. In some embodiments, one of the first or second sub-regulatory domains is cleaved by one MMP protease, while the other regulatory domain is cleaved by another MMP protease.

A stable linker or a protease non-cleavable linker refers to a linker peptide sequence that does not belong to the known protease substrate sequences and thus does not lead to significant cleavage product formation upon incubation with a protease.

In some embodiments, the cleavage substrate (or cleavage sequence) of the linker may include an amino acid sequence that can serve as a substrate for a protease, usually an extracellular protease. In other embodiments, the cleavage sequence comprises a cysteine-cysteine pair capable of forming a disulfide bond, which can be cleaved by action of a reducing agent. In other embodiments the cleavage sequence comprises a substrate capable of being cleaved upon photolysis.

The cleavage substrate is positioned within the protease cleavable domain such that when the cleavage substrate is cleaved by a cleaving agent (e.g., a cleavage substrate of a linker is cleaved by the protease and/or the cysteine-cysteine disulfide bond is disrupted via reduction by exposure to a reducing agent) or by light-induced photolysis, in the presence of a target, resulting in cleavage products having various functional properties as described herein. In some embodiments, cleavage products have decreased half-life. In some embodiments, cleavage product has the ability to activate T-cell (FIGS. 3A-3B).

The cleavage substrate of a cleavage domain may be selected based on a protease that is co-localized in the diseased tissue, or on the surface of the cell that expresses the target antigen of interest of a binding domain of a fusion moiety. A variety of different conditions are known in which a target of interest is co-localized with a protease, where the substrate of the protease is known in the art. In the example of cancer, the target tissue can be a cancerous tissue, particularly cancerous tissue of a solid tumor. There are reports in the literature of increased levels of proteases having known substrates in a number of cancers, e.g., solid tumors. See, e.g., [La Rocca et al, (2004) British J. of Cancer 90 (7): 1414-1421. Radisky ES, Front Biosci (Landmark Ed). 2015 Jun. 1; 20:1144-63; Miao C, et al., Oncotarget. 2017 May 9;8 (19): 32309-32321]. Non-limiting examples of disease include: all types of cancers (breast, lung, colorectal, prostate, head and neck, pancreatic, etc), rheumatoid arthritis, Crohn's disease, melanomas, SLE, cardiovascular damage, ischemia, etc. Furthermore, anti-angiogenic targets, such as VEGF, are known.

In some embodiments, where the TAA of the first or second binding domain is selected such that it is capable of binding a tumor antigen, a suitable cleavage substrate sequence for the linker will be one which comprises a peptide substrate that is cleavable by a protease that is present at the cancerous treatment site, that is the tumor microenvironment that is particularly present at elevated levels at the cancer treatment site as compared to non-cancerous tissues.

In some embodiments, the first or second, or both the first and second binding domain of a precursor construct disclosed herein can bind a TAA, e.g., EGFR and the cleavage substrate sequence can be a matrix metalloprotease (MMP) substrate, and thus is cleavable by an MMP. In other embodiments, a TAA comprises ROR1 and the cleavage substrate sequence can be a matripase (MT-SP1, TADG-15, epithin, ST14) substrate, and thus is cleavable by a matriptase. In other embodiments, the first or second, or both the first and second binding domain of a precursor construct can bind a target of interest and the cleavage substrate present in the cleavable domain can be, for example, legumain, plasmin, TMPRSS-3/4, MMP-9, MT1-MMP, cathepsin, caspase, human neutrophil elastase, beta-secretase, uPA, or PSA. In other embodiments, the cleavage domain is cleaved by other disease-specific proteases, in diseases other than cancer such as multiple sclerosis or rheumatoid arthritis.

In some embodiments, a precursor tri-specific antibody construct may bind to a TAA by way of the first or second, or both the first and the second binding domain, wherein the cleavable domain of the regulatory arm remains uncleaved and therefore the third binding domain of a precursor construct or a partially cleaved precursor construct may be specifically unavailable to a target CD3ε antigen due to the presence of the CAP component. In some embodiments, a precursor tri-specific antibody construct may bind to a TAA by way of the first or second, or both the first and the second binding domain, wherein the cleavable domain of the regulatory arm remains uncleaved, wherein the precursor construct or partially cleaved precursor construct has enhanced half-life due to a half-life prolonging domain (e.g., an HSA polypeptide sequence) and the third binding domain is available or partially available to a target CD3ε antigen. In some embodiments, a precursor tri-specific antibody construct may bind to a TAA by way of the first or second, or both the first and the second binding domain, wherein the cleavable domain of both regulatory arms remain uncleaved, wherein the precursor construct has enhanced half-life due to a half-life prolonging domain (e.g., an HSA polypeptide sequence) and the third binding domain remains specifically unavailable to a target CD3ε antigen due to the presence of the CAP component.

In some embodiments, there are linkers (L) between any of the component parts of the precursor tri-specific antibody construct (FIGS. 1 and 2A-2D). In some embodiments, the linkers of the precursor construct (e.g., the linkers between the VL and VH of the Fab and the regulatory domains) comprise cleavable domain linkers. In some embodiments, the ability to be cleaved is independently selected for each linker. In some embodiments, the ability to be cleaved by a protease is independently selected for each linker. In some embodiments, a linker is cleavable by a protease. In some embodiments, a linker is not cleavable by a protease. In some embodiments, the linker between the CH1 or CL of the Fab and the ScFv of the first binding domain comprises a non-cleavable linker. In some embodiments, the linker between the CH1 or CL of the Fab and the ScFv of the second binding domain comprises a non-cleavable linker.

A skilled artisan would appreciate that in some embodiments, a linker comprises a spacer between two active components or between two regions of an active component.

A skilled artisan would appreciate that the cleavable domain comprises a linear amino acid sequence comprising an enzyme cleavage site and may, in certain embodiments, be termed a "cleavable linker" or a "linker" or a "cleavable peptide" or a "CP", wherein linkers disclosed herein may be cleavable or non-cleavable.

In some embodiments, a linker is present C-terminal to the Constant Heavy chain (CH1) of the Fab fragment. In some embodiments, a linker is present C-terminal to the Constant Light chain (CL) of the Fab fragment. In some embodiments, the linker C-terminal to the CH1 is cleavable. In some embodiments, the linker C-terminal to the CH1 is non-cleavable. In some embodiments, the linker C-terminal to the CL is cleavable. In some embodiments, the linker C-terminal to the CL is non-cleavable.

In some embodiments, a linker is a single amino acid. In some embodiments, a cleavable linker comprises the amino acid sequence set forth in any of SEQ ID NOs: 9-32. In some embodiments, a cleavable linker is encoded by the nucleic acid sequence set forth in SEQ ID NO: 33. In some embodiments, a cleavable linker is encoded by the nucleic acid sequence set forth in SEQ ID NO: 35.

In some embodiments, a non-cleavable linker comprises the amino acid sequence set forth in SEQ ID NOs: 162. In some embodiments, a non-cleavable linker is encoded by the nucleic acid sequence set forth in SEQ ID NO: 163.

For specific cleavage by an enzyme protease, contact between the enzyme and the cleavage substrate is made. When the precursor construct comprising a first and a second binding domain binding to a TAA, a third binding domain binding to an extracellular epitope of CD3ε, and two regulatory domains comprising cleavable linkers is in the presence sufficient enzyme activity, the cleavable domains can be cleaved. Sufficient enzyme activity can refer to the ability of the enzyme to make contact with a protease cleavable domain having the cleavage site and effect cleavage. In some embodiments, an enzyme may be in the vicinity of the precursor construct but unable to cleave because of other cellular factors or protein modification of the enzyme.

In some embodiments, cleavable domain substrates can include but are not limited to substrates cleavable by one or more of the following enzymes or proteases: ADAM10; Caspase 8, Cathepsin S, MMP 8, ADAM12, Caspase 9, FAP, MMP 9, ADAM17, Caspase 10, Granzyme B, MMP 13, ADAMTS, Caspase 11, Guanidinobenzotase (GB), MMP 14, ADAMTS5. Caspase 12, Hepsin, MT-SP1, BACE, Caspase 13, Human Neutrophil Elastase Neprilysin (HNE), Caspases, Caspase 14, Legumain, NS3/4A, Caspase 1, Cathepsins, Matriptase 2, Plasmin, Caspase 2, Cathepsin A, Meprin, PSA, Caspase 3, Cathepsin B, MMP 1, PSMA, Caspase 4, Cathepsin D, MMP 2, TACE, Caspase 5, Cathepsin E, MMP 3, TMPRSS 3/4, Caspase 6, Cathepsin K, MMP 7, uPA, Caspase 7, Matripase (MT-SP1, TADG-15, epithin, ST14) and MT1-MMP.

In another embodiment, the cleavage substrate can involve a disulfide bond of a cysteine pair, which is thus cleavable by a reducing agent such as, for example, but not limited to a cellular reducing agent such as glutathione (GSH), thioredoxins, NADPH, flavins, ascorbate, and the like, which can be present in large amounts in tissue of or surrounding a solid tumor.

Other appropriate protease cleavage sites for use in the cleavable linkers herein are known in the art or may be identified using methods such as those described by Turk et al., 2001 Nature Biotechnology 19, 661-667.

In some embodiments, both the first binding domain, the second binding domain, and the third binding domain of the precursor tri-specific antibody constructs can bind to their respective human and non-chimpanzee primate target molecules. The first binding domain and or the second binding domain, thus, binds to a human cell surface tumor associated antigen (TAA) and to the corresponding homolog of the cell surface TAA in a non-chimpanzee primate. The identification and determination of homologs of human cell surface TAA in non-chimpanzee primates is well known to the person skilled in the art and can be carried out e.g. by sequence alignments. The third binding domain can bind to an antigen comprising a human CD3ε extracellular epitope, and can bind to the corresponding homolog of the CD3ε in a non-chimpanzee primate. In some embodiments, the first or second or third binding domains, or any combination thereof, also bind to their respective chimpanzee target molecules.

A skilled artisan would appreciate that in some embodiments, a cell surface tumor associated antigen (TAA) encompasses a molecule which is displayed on the surface of a cell. In some embodiments, the cell is a tumor cell. In some embodiments, the cell is a non-tumor cell present in the milieu of a tumor, for example but not limited to a cell present within vasculature tissue associated with a tumor or cancer.

A skilled artisan would appreciate that the terms "antigen" or "immunogen" encompass a peptide, protein, polypeptide which is immunogenic. In some embodiments, an antigen is capable of eliciting an immune response in a mammal, and therefore contains at least one and may contain multiple epitopes. An "antigen" molecule or a portion of a molecule is capable of being bound by a selective binding agent, such as an antigen-binding portion of a Fab fragment or an antigen-binding portion of an scFv fragment. Additionally, an "antigen" is capable of being used in an animal to produce antibodies capable of binding to an epitope of that antigen. In some embodiments, a CAP component comprises the portion of an antigen to which the second binding domain binds.

The term "epitope" includes any determinant, in certain embodiments, a polypeptide determinant, capable of specific binding to a TAA or an immunoglobulin or T-cell receptor. An epitope is a region of an antigen that is bound by an antibody or an antigen-binding fragment thereof. In some embodiments, a CAP component comprises the epitope to which the third binding domain binds.

In certain embodiments, epitope determinants include chemically active surface groupings of molecules such as amino acids, sugar side chains, phosphoryl or sulfonyl, and may in certain embodiments have specific three-dimensional structural characteristics, and/or specific charge characteristics. In certain embodiments, a precursor tri-specific antibody construct is said to specifically bind an antigen when it preferentially recognizes its target antigen in a complex mixture of proteins and/or macromolecules. A precursor tri-specific antibody construct is said to specifically bind an antigen when the equilibrium dissociation constant is ≤10-5, 10-6 or 10-7 M. In some embodiments, the equilibrium dissociation constant may be≤10-8 M or 10-9 M. In some further embodiments, the equilibrium dissociation constant may be≤10-10 M or 10-11 M. Antigens disclosed herein included but are not limited to TAA, CAP components, and immuno-effector molecules such as a human CD3 epsilon polypeptide.

In some embodiments, the tumor associated antigen (TAA) is a tumor antigen. In some embodiments, tumor antigens comprise those antigens are presented on tumor cells. In some embodiments, the tumor antigen is present on a cell of solid tumor. In some embodiments, the tumor antigen is a cancer antigen, present on a cell of a non-solid tumor.

In some embodiments, when the TAA is a tumor cell antigen, the tumor cell comprises a cell from a solid tumor. Solid tumors may be benign (not cancer), or malignant (cancer). Different types of solid tumors are named for the type of cells that form them. Examples of solid tumors are sarcomas, carcinomas, and lymphomas. In some embodiments, solid tumors are neoplasms (new growth of cells) or lesions (damage of anatomic structures or disturbance of physiological functions) formed by an abnormal growth of body tissue cells other than blood, bone marrow or lymphatic cells. In some embodiments, a solid tumor consists of an abnormal mass of cells which may stem from different tissue types such as liver, colon, breast, or lung, and which initially grows in the organ of its cellular origin. However, such cancers may spread to other organs through metastatic tumor growth in advanced stages of the disease.

In some embodiments, the solid tumor comprises a sarcoma or a carcinoma, a fibrosarcoma, a myxosarcoma, a liposarcoma, a chondrosarcoma, an osteogenic sarcoma, a chordoma, an angiosarcoma, an endotheliosarcoma, a lymphangiosarcoma, a lymphangioendotheliosarcoma, a synovioma, a mesothelioma, an Ewing's tumor, a leiomyosarcoma, a rhabdomyosarcoma, a colon carcinoma, a pancreatic cancer or tumor, a breast cancer or tumor, an ovarian cancer or tumor, a prostate cancer or tumor, a squamous cell carcinoma, a basal cell carcinoma, an adenocarcinoma, a sweat gland carcinoma, a sebaceous gland carcinoma, a papillary carcinoma, a papillary adenocarcinomas, a cystadenocarcinoma, a medullary carcinoma, a bronchogenic carcinoma, a renal cell carcinoma, a hepatoma, a bile duct carcinoma, a choriocarcinoma, a seminoma, an embryonal carcinoma, a Wilm's tumor, a cervical cancer or tumor, a uterine cancer or tumor, a testicular cancer or tumor, a lung carcinoma, a small cell lung carcinoma, a bladder carcinoma, an epithelial carcinoma, a glioma, an astrocytoma, a medulloblastoma, a craniopharyngioma, an ependymoma, a pinealoma, a hemangioblastoma, an acoustic neuroma, an oligodenroglioma, a schwannoma, a meningioma, a melanoma, a neuroblastoma, or a retinoblastoma. In some embodiments, the solid tumor comprises an Adrenocortical Tumor (Adenoma and Carcinoma), a Carcinoma, a Colorectal Carcinoma, a Desmoid Tumor, a Desmoplastic Small Round Cell Tumor, an Endocrine Tumor, an Ewing Sarcoma, a Germ Cell Tumor, a Hepatoblastoma a Hepatocellular Carcinoma, a Melanoma, a Neuroblastoma, an Osteosarcoma, a Retinoblastoma, a Rhabdomyosarcoma, a Soft Tissue Sarcoma Other Than Rhabdomyosarcoma, and a Wilms Tumor. In some embodiments, the solid tumor is a breast tumor. In another embodiment, the solid tumor is a prostate cancer. In another embodiment, the solid tumor is a colon cancer. In some embodiments, the tumor is a brain tumor. In another embodiment, the tumor is a pancreatic tumor. In another embodiment, the tumor is a colorectal tumor.

In some embodiments, the tumor cell comprises a cell from a non-solid tumor, that is a non-solid cancer. In some embodiments, a cancer may be a diffuse cancer, wherein the cancer is widely spread; not localized or confined. In some embodiments, a diffuse cancer may comprise a non-solid tumor. Examples of diffuse cancers include leukemias. Leukemias comprise a cancer that starts in blood-forming tissue, such as the bone marrow, and causes large numbers of abnormal blood cells to be produced and enter the bloodstream.

In some embodiments, a diffuse cancer comprises a B-cell malignancy. In some embodiments, the diffuse cancer comprises leukemia. In some embodiments, the cancer is lymphoma. In some embodiments, the lymphoma is large B-cell lymphoma.

In some embodiments, the diffuse cancer or tumor comprises a hematological tumor. In some embodiments, hematological tumors are cancer types affecting blood, bone marrow, and lymph nodes. Hematological tumors may derive from either of the two major blood cell lineages: myeloid and lymphoid cell lines. The myeloid cell line normally produces granulocytes, erythrocytes, thrombocytes, macrophages, and masT-cells, whereas the lymphoid cell line produces B, T, and plasma cells. Lymphomas (e.g. Hodgkin's Lymphoma), lymphocytic leukemias, and myeloma are derived from the lymphoid line, while acute and chronic myelogenous leukemia (AML, CML), myelodysplastic syndromes and myeloproliferative diseases are myeloid in origin.

In some embodiments, a non-solid (diffuse) cancer or tumor comprises a hematopoietic malignancy, a blood cell cancer, a leukemia, a myelodysplastic syndrome, a lymphoma, a multiple myeloma (a plasma cell myeloma), an acute lymphoblastic leukemia, an acute myelogenous leukemia, a chronic myelogenous leukemia, a Hodgkin lymphoma, a non-Hodgkin lymphoma, or plasma cell leukemia.

In some embodiments, the tumor or cancer comprises a metastasis of a tumor or cancer.

In some embodiments a cell surface TAA is located in or on the plasma membrane of the cell, such that at least part of this molecule remains accessible from outside the cell in tertiary form. In some embodiments, a cell surface TAA that is located in the plasma membrane is a transmembrane protein comprising, in its tertiary conformation, regions of hydrophilicity and hydrophobicity.

These antigens can be presented on the cell surface with an extracellular part which is often combined with a transmembrane and cytoplasmic part of the molecule. These antigens can sometimes be presented only by tumor cells and never by the normal ones. Tumor antigens can be exclusively expressed on tumor cells or might represent a tumor specific mutation compared to normal cells. In this case, they are called tumor-specific antigens. More common are antigens that are presented by tumor cells and normal cells. In some embodiments, TAA include antigens exclusively expressed on a tumor cell. In some embodiments, TAA include antigens expressed on both tumor and normal cells.

In some embodiments, TAA can be overexpressed on tumor cells compared to normal cells or are accessible for antibody binding in tumor cells due to the less compact structure of the tumor tissue compared to normal tissue.

In some embodiments, a first binding domain or a second binding domain or both, binding to a cell surface TAA comprises an amino acid sequence that binds to a human TAA. In some embodiments, an anti-scFv includes both a heavy chain variable region and a light chain variable region, wherein each region further comprises complementary-determining regions (CDR). In some embodiments, a first binding domain or a second binding domain or both, binding to a cell surface TAA comprises a linker between a scFv variable light chain (VH) region and a scFv variable heavy chain (VH) region. In some embodiments, a first binding domain or a second binding domain, binding to a cell surface TAA comprises a linker between a scFv fragment and the C-terminal of the CL region of the third binding domain. In some embodiments, a first binding domain or a second binding domain, binding to a cell surface TAA comprises a linker between a scFv fragment and the C-terminal of the CH1 region of the third binding domain. In some embodiments, a first binding domain binding to a cell surface TAA comprises a linker between a scFv fragment and the C-terminal of the CH1 region of the third binding domain, and a second binding domain binding to a cell surface TAA comprises a linker between a scFv fragment and the C-terminal of the CL region or the third binding domain. In some embodiments, a first binding domain binding to a cell surface TAA comprises a linker between a scFv fragment and the C-terminal of the CL region of the third binding domain, and a second binding domain binding to a cell surface TAA comprises a linker between a scFv fragment and the C-terminal of the CH1 region or the third binding domain.

FIGS. 2A-2F present embodiments, wherein the TAA is EGFR (first and second binding domains comprise an anti-EGFR scFv). A skilled artisan would appreciate that in other embodiments, the TAAs may be a TAA known in the art, for example but not limited to a TAA comprising a FcγRI, FcγRIIa FcγRIIb, FcγRIIIb, CD28, CD137, CTLA-4, FAS, fibroblast growth factor receptor 1 (FGFR1), FGFR2, FGFR3, FGFR4, glucocorticoid-induced TNFR-related (GITR) protein, lymphotoxin-beta receptor (LTβR), toll-like receptors (TLR), tumor necrosis factor-related apoptosis-inducing ligand-receptor 1 (TRAIL receptor 1) and TRAIL receptor 2, prostate-specific membrane antigen (PSMA) protein, prostate stem cell antigen (PSCA) protein, tumor-associated protein carbonic anhydrase IX (CAIX), epidermal growth factor receptor 1 (EGFR1), EGFRvIII, human epidermal growth factor receptor 2 (Her2/neu; Erb2), ErbB3 also known as HER3, Folate receptor, ephrin receptors, PDGFRa, ErbB-2, CD20, CD22, CD30, CD33, CD40, CD37, CD3ε, CD70, CD74, CD40), CD80, CD86, CD2, p53, cMet also known as tyrosine-protein kinase Met or hepatocyte growth factor receptor (HGFR), MAGE-A1, MAGE-A2, MAGE-A3, MAGE-A4, MAGE-A6, MAGE-A10, MAGE-A12, BAGE, DAM−6,-10, GAGE-1,-2,-8, GAGE-3,-4,-5,-6,-7B, NA88-A, NY-ESO-1, BRCA1, BRCA2, MART-1, MC1R, Gp100, PSA, PSM, PSMA, Tyrosinase, Wilms' tumor antigen (WT1), TRP-1, TRP-2, ART-4, CAMEL, Cyp-B, hTERT, hTRT, iCE, MUC1, MUC2, P-cadherin, Myostatin (GDF8), Cripto (TDGF1), MUC5AC, PRAME, P15, RU1, RU2, SART-1, SART-3, WT1, AFP, β-catenin/m, Caspase-8/m, CDK-4/m, ELF2M, GnT-V, G250, HSP70-2M, HST-2, KIAA0205, MUM−1, MUM−2, MUM−3, Myosin/m, RAGE, SART-2, TRP-2/INT2, 707-AP, Annexin II, CDC27/m, TPI/mbcr-abl, ETV6/AML, LDLR/FUT, Pml/RARa, TEL/AML1, CD28, CD137, CanAg, Mesothelin, DR5, PD-1, PDIL, IGF-1R, CXCR4, Neuropilin 1, Glypicans, EphA2, CD138, B7-H3, B7-H4, gpA33, GPC3, SSTR2, ROR1, 5T4, or a VEGF-R2. In some embodiments, a TAA comprises a PSMA, CD30, B7-H3, B7-H4, gpA33, HER2, P-cadherin, gp100, DR5, GPC3, SSTR2, Mesothelin, ROR1, 5T4, Folate receptor, or an EGFR. In some embodiments, a TAA comprises an EGFR. In some embodiments, a TAA comprises a ROR1. In some embodiments, a TAA comprises an PSMA. In some embodiments, a TAA comprises an 5T4.

Tri-specific antibodies can be designed to bind at least one tumor associated antigen (TAA), which in some embodiments comprises a tumor cell surface antigen, a T-cell antigen, and a second TAA, with the goal of the antibody being to bind and kill tumor cells more selectively over normal cells, and ultimately to increase the efficacy and safety over a monospecific reagent, wherein a tri-specific antibody comprises a binding domain binding at least one cell surface tumor associated antigen (TAA), a binding domain binding second TAA, and a binding domain binding an extracellular epitope of a T-cell. However, such tri-specific antibodies fail to regulate the order of binding and therefore, may bind a T-cell prior to or in the absence of binding a TAA, wherein cytotoxicity provided by the activated T-cell may actually cause harmful side effects by non-specifically causing non-tumor cell death. In some embodiments, a TAA comprises a human antigen.

In some embodiments, a TME antigen comprises a KIR, a LILR, or a TIGIT antigen.

In some embodiments, a first binding domain or a second binding domain, or both, binding to a cell surface TAA, binds to a polypeptide target, which in some embodiments is associated with a particular cancer or cancers or disease condition, for example but not limited to a TAA comprising FcγRI, FcγRIIa, FcγRIIb, FcγRIIIb, CD28, CD137, CTLA-4, FAS, fibroblast growth factor receptor 1 (FGFR1), FGFR2, FGFR3, FGFR4, glucocorticoid-induced TNFR-related (GITR) protein, lymphotoxin-beta receptor (LTβR), toll-like receptors (TLR), tumor necrosis factor-related apoptosis-inducing ligand-receptor 1 (TRAIL receptor 1; multiple malignancies including ovarian and colorectal carcinomas) and TRAIL receptor 2, prostate-specific membrane antigen (PSMA; prostate carcinoma) protein, prostate stem cell antigen (PSCA) protein (prostate adenocarcinoma), CA125 (multiple cancers including ovarian carcinoma), tumor-associated protein carbonic anhydrase IX (CAIX; multiple cancers including renal cell carcinoma), epidermal growth factor receptor 1 (EGFR1; epithelial malignancies), EGFR (non-small cell lung cancer, epithelial ovarian cancer, colorectal cancer, head & neck cancer, breast cancer, lung cancer, esophageal cancer), EGFRvIII, human epidermal growth factor receptor 2 (Her2/neu; Erb2; epithelial malignancies), ErbB3 also known as HER3 (epithelial malignancies), Folate receptor, ephrin receptors, PDGFRa (epithelial malignancies), ErbB-2, CD20 (B cells, autoimmune, allergic or malignant), CD22 (B cells, autoimmune or malignant), CD30 (B cell malignancies), CD33 (myeloid malignancies), CD40, CD37, CD3ε, CD70 (B cells, autoimmune, allergic or malignant), CD74 (B cells, autoimmune, allergic or malignant), CD40 (B cells, autoimmune, allergic or malignant); CD80 (B cells, autoimmune, allergic or malignant), CD86 (B cells, autoimmune, allergic or malignant), CD2 (T cell), p53, cMet also known as tyrosine-protein kinase Met or hepatocyte growth factor receptor (HGFR; Gastrointestinal tract and hepatic malignancies), MAGE-A1, MAGE-A2, MAGE-A3, MAGE-A4, MAGE-A6, MAGE-A10, MAGE-A12, BAGE, DAM−6,-10, GAGE-1,-2,-8, GAGE-3,-4,-5,-6,-7B, NA88-A, NY-ESO-1, BRCA1, BRCA2, MART-1, MC1R, Gp100, PSA, PSM, Tyrosinase, Wilms' tumor antigen (WT1), TRP-1, TRP-2, ART-4, CAMEL, Cyp-B, hTERT, hTRT, iCE, MUC1 (epithelial malignancies), MUC2, P-cadherin (Epithelial malignancies, including breast adenocarcinoma), Myostatin (GDF8) (many tumors including sarcoma and ovarian and pancreatic adenocarcinoma), Cripto (TDGF1) (Epithelial malignancies including colon, breast, lung, ovarian, and pancreatic cancers), ACVRLI/ALK1 (multiple malignancies including leukemias and lymphomas), MUC5AC (Epithelial malignancies, including breast adenocarcinoma), PRAME, P15, RU1, RU2, SART-1, SART-3, WT1, AFP, B-catenin/m, Caspase-8/m, CDK-4/m, ELF2M, GnT-V, G250, HSP70-2M, HST-2, KIAA0205, MUM−1, MUM−2, MUM−3, Myosin/m, RAGE, SART-2, TRP-2/INT2, 707-AP, Annexin II, CDC27/m, TPI/mbcr-abl, ETV6/AML, LDLR/FUT, Pml/RARa, TEL/AML1, CD28, CD137 (B cells or T cells, autoimmune, allergic or malignant), CanAg (tumors such as carcinomas of the colon and pancreas), Mesothelin (many tumors including mesothelioma and ovarian and pancreatic adenocarcinoma), DR5 (multiple malignancies including ovarian and colorectal carcinoma), PD-1 (B cells, autoimmune, allergic or malignant), PDIL (Multiple malignancies including epithelial adenocarcinoma), IGF-1R (Most malignancies including epithelial adenocarcinoma), CXCR4 (B cells or T cells, autoimmune, allergic or malignant), Neuropilin 1 (Epithelial malignancies, including lung cancer), Glypicans (multiple cancers including liver, brain and breast cancers), EphA2 (multiple cancers including neuroblastoma, melanoma, breast cancer, and small cell lung carcinoma), CD138 (Myeloma), B7-H3 (CSC, stroma, NSCLC, Bladder tumors, mesothelioma, melanoma), gpA33 (colorectal cancers), GPC3 (liver, lung, esophageal, gastric, head and neck cancers), SSTR2 (Neuroendocrine tumors, GIST), ROR1 (Hematological, pancreatic, ovarian, renal cell carcinoma, NSCLC, and triple negative breast cancer), 5T4 (mesothelioma, gastic, ovarian, renal cancer, cancer stem cells in NSCLC, head and neck cancer), or a VEGF-R2 (vasculature associated with the majority of malignancies including epithelial adenocarcinomas). Examples of the unwanted target cells or cancer cells associated with the TAA presented are included in italics in parenthesis.

In some embodiments, a TAA is selected from the group consisting of EGFR, ROR1, PSMA, and 5T4. In some embodiments, a first binding domain comprises an scFv that binds to a human EGFR (anti-hEGFR), or a human ROR1 (anti-ROR1), or a human PSMA (anti-PSMA), or a human 5T4 (anti-5T4).

In some embodiments, the TAA is EGFR. In some embodiments, a first binding domain comprises an scFv that binds to human EGFR (anti-hEGFR). In some embodiments, the amino acid sequence of an anti-hEGFR-scFv light chain variable region (VL) is set forth in SEQ ID NO: 34. In some embodiments, an anti-hEGFR scFv VL sequence comprises a homolog of SEQ ID NO: 34.

In some embodiments, the anti-hEGFR-scFv light chain variable region (VL) is encoded by the nucleic acid sequence set forth in SEQ ID NO: 36. In some embodiments, the anti-hEGFR-scFv light chain variable region (VL) is encoded by a homolog of the nucleic acid sequence set forth in SEQ ID NO: 36.

In some embodiments, the amino acid sequence of an anti-hEGFR-scFv heavy chain variable region (VH) set forth in SEQ ID NO: 37. In some embodiments, an anti-hEGFR scFv VH sequence comprises a homolog of SEQ ID NO: 37.

In some embodiments, the anti-hEGFR-scFv heavy chain variable region (VH) is encoded by the nucleic acid sequence set forth in SEQ ID NO: 38. In some embodiments, the anti-hEGFR-scFv heavy chain variable region (VH1) is encoded by a homolog of the nucleic acid sequence set forth in SEQ ID NO: 38.

In some embodiments, an anti-EGFR scFV comprises a linker between a VL and a VH region. In some embodiments, the linker between a VL and a VH region comprises any linker disclosed herein. In some embodiments, the amino acid sequence of a linker between a VL and VH region of an anti-EGFR scFV is set forth by SEQ ID NO: 39. In some embodiments, the linker between a VL and a VH region of an anti-EGFR scFV comprises a homolog of SEQ ID NO: 39. In some embodiments, a linker between a VL and VH region of an anti-EGFR scFV is encoded by the nucleic acid sequence set forth in SEQ ID NO:40. In some embodiments, a linker between a VL and VH region of an anti-EGFR scFV is encoded by a homolog by the nucleic acid sequence set forth in SEQ ID NO: 40.

In some embodiments, components of an anti-EGFR scFv comprises a VL-linker-VH order (N-terminal to C-terminal) (FIGS. 8A and 9A. In some embodiments, components of an anti-EGFR scFv comprises a VH-linker-VL order (N-terminal to C-terminal) (FIGS. 8B and 9B).

In some embodiments, an anti-EGFR scFV sequence including a linker sequence comprises the sequence SEQ ID NO: 41. In some embodiments, an anti-EGFR scFv including a linker sequence comprises a homolog of SEQ ID NO: 41.

In some embodiments, an anti-EGFR scFV sequence including a linker sequence comprises the sequence SEQ ID NO: 42. In some embodiments, an anti-EGFR scFv including a linker sequence comprises a homolog of SEQ ID NO: 42.

In some embodiments, the amino acid sequence of an anti-hROR1-scFv, or an anti-PSMA-scFv, or an anti-5T4-scFv light chain variable region are set forth in in Table 1 below:

TABLE 1

Amino acid Sequence of and Optimized Nucleotide Acid sequences encoding anti-hROR1-scFv, or an anti-PSMA-scFv, or an anti-5T4-scFv

| Antigen Binding (anti-antigen) | SEQ ID NO: |
|---|---|
| ROR1 (VL-VH) | 156 |
| ROR1 (VL-VH) | 157 |
| ROR1 (VH-VL) | 166 |
| ROR1 (VH-VL) | 167 |
| PSMA (VL-VH) | 168 |
| PSMA (VL-VH) | 169 |
| PSMA (VH-VL) | 170 |
| PSMA (VH-VL) | 171 |
| 5T4 (VL-VH) | 172 |
| 5T4 (VL-VH) | 173 |
| 5T4 (VH-VL) | 174 |
| 5T4 (VH-VL) | 175 |

In some embodiments, homologues comprise polypeptides which are at least 50%, at least 55%, at least 60%, at least 65%, at least 70%, at least 75%, at least 80%, at least 85%, at least 87%, at least 89%, at least 91%, at least 93%, at least 95%, at least 96%, at least 97%, at least 98%, or at least 99% homologous to the amino acid sequence of an anti-EGFR scFv. In some embodiments, homologues comprise polypeptides which are at least 50%, at least 55%, at least 60%, at least 65%, at least 70%, at least 75%, at least 80%, at least 85%, at least 87%, at least 89%, at least 91%, at least 93%, at least 95%, at least 96%, at least 97%, at least 98%, or at least 99% identical to an amino acid sequence of an anti-EGFR scFv, or any anti-ROR1 scFv, or an anti-PSMA scFv, or an anti-5T4 scFv.

In some embodiments, a nucleotide sequence encoding an anti-EGFR scFV including a linker sequence comprises the sequence SEQ ID NO: 43. In some embodiments, an anti-EGFR scFv including a linker sequence comprises a homolog of SEQ ID NO: 43.

In some embodiments, a nucleotide sequence encoding an anti-EGFR scFV including a linker sequence comprises the sequence SEQ ID NO: 44. In some embodiments, an anti-EGFR scFv including a linker sequence comprises a homolog of SEQ ID NO: 44.

In some embodiments, homologues comprise nucleotides which are at least 50%, at least 55%, at least 60%, at least 65%, at least 70%, at least 75%, at least 80%, at least 85%, at least 87%, at least 89%, at least 91%, at least 93%, at least 95%, at least 96%, at least 97%, at least 98%, or at least 99% homologous to the nucleic acid sequence of an anti-EGFR scFv,. In some embodiments, homologues comprise nucleotides which are at least 50%, at least 55%, at least 60%, at least 65%, at least 70%, at least 75%, at least 80%, at least 85%, at least 87%, at least 89%, at least 91%, at least 93%, at least 95%, at least 96%, at least 97%, at least 98%, or at least 99% identical to the nucleic acid sequence of an anti-EGFR scFv or any anti-ROR1 scFv, or an anti-PSMA scFv, or an anti-5T4 scFv.

In some embodiments, disclosed herein are homologues of an anti-hEGFR scFv VL (SEQ ID NO: 34 or SEQ ID NO: 35) or anti-hEGFR scFv VH (SEQ ID NO: 37) or an anti-hEGFR scFv (SEQ ID NO: 41) or an anti-hEGFR scFv (SEQ ID NO: 42), respectively, as determined using BlastP software of the National Center of Biotechnology Information (NCBI) using default parameters. In some embodiments, disclosed herein are homologues of nucleotide sequences encoding an anti-hEGFR scFv VL (SEQ ID NO: 36) or anti-hEGFR scFv VH (SEQ ID NO: 38) or an anti-hEGFR scFv (SEQ ID NO: 43) or an anti-hEGFR scFv (SEQ ID NO: 44), respectively, as determined using BlastP software of the National Center of Biotechnology Information (NCBI) using default parameters.

In some embodiments, disclosed herein are homologues of an anti-hROR1 scFv VL-VH (SEQ ID NO: 156) or an anti-hROR1 scFv VH-VL (SEQ ID NO: 169), as determined using BlastP software of the National Center of Biotechnology Information (NCBI) using default parameters. In some embodiments, disclosed herein are homologues of nucleotide sequences encoding an anti-hROR1 scFv VL-VH (SEQ ID NO: 157) or an anti-hROR1 scFv VH-VL (SEQ ID NO: 167), as determined using BlastP software of the National Center of Biotechnology Information (NCBI) using default parameters.

In some embodiments, disclosed herein are homologues of an anti-hPSMA scFv VL-VH (SEQ ID NO: 168) or an anti-hPSMA scFv VH-VL (SEQ ID NO: 170), as determined using BlastP software of the National Center of Biotechnology Information (NCBI) using default parameters. In some embodiments, disclosed herein are homologues of nucleotide sequences encoding an anti-hPSMA scFv VL-VH (SEQ ID NO: 169) or an anti-hPSMA scFv VH-VL (SEQ ID NO: 171), as determined using BlastP software of the National Center of Biotechnology Information (NCBI) using default parameters.

In some embodiments, disclosed herein are homologues of an anti-h5T4 scFv VL-VH (SEQ ID NO: 172) or an anti-h5T4 scFv VH-VL (SEQ ID NO: 174), as determined using BlastP software of the National Center of Biotechnology Information (NCBI) using default parameters. In some embodiments, disclosed herein are homologues of nucleotide sequences encoding an anti-h5T4 scFv VL-VH (SEQ ID NO: 173) or an anti-h5T4 scFv VH-VL (SEQ ID NO: 174), as determined using BlastP software of the National Center of Biotechnology Information (NCBI) using default parameters.

In some embodiments, homology also encompasses deletion, insertion, or substitution variants, including an amino acid substitution, thereof and biologically active polypeptide fragments thereof. In one embodiment, the variant comprises conservative substitutions, or deletions, insertions, or substitutions that do not significantly alter the three-dimensional structure of the polypeptide of interest, e.g., VL or VH region of the first binding domain, particularly in the areas of the CDR epitope binding regions. In some embodiments, the deletion, insertion, or substitution does not alter the function of interest of the anti-hEGFR VL or anti-hEGFR VH or an anti-EGFR ScFv, present in the first, or the second binding domain, or in both the first and the second binding domains of a precursor construct, which in some embodiment, is binding to an EGFR on a target tumor cell. In some embodiments, the deletion, insertion, or substitution does not alter the function of interest of an anti-ROR1 ScFv, or an anti-PSMA, or an anti-5T4 scFv present in the first, or the second binding domain, or in both the first and the second binding domains of a precursor construct, which in some embodiment, is binding to an ROR1, PSMA, or 5T4, respectively on a target tumor cell.

In some embodiments, a first or second binding domain, or both a first and second binding domain binding to a cell surface tumor associated antigen includes the sequence set forth in SEQ ID NO: 34, or a homolog thereof. In some embodiments, a first or second binding domain, or both a first and second binding domain binding to a cell surface tumor associated antigen includes the sequence set forth in SEQ ID NO: 37, or a homolog thereof.

In some embodiments, a first or second binding domain, or a first and second binding domain binding to a cell surface tumor associated antigen includes the sequence set forth in any of SEQ ID NO: 34, 37, 156, 166, 168, 170, 172, or 174 or a homolog thereof.

In some embodiments, a first or second binding domain, or a first and second binding domain binding to a cell surface tumor associated antigen includes the sequence set forth in SEQ ID NO: 41 or a homolog thereof. In some embodiments, a first or second binding domain, or a first and second binding domain binding to a cell surface tumor associated antigen includes the sequence set forth in SEQ ID NO: 42 or a homolog thereof.

In some embodiments, a first or second binding domain, or both a first and second binding domain binding to a cell surface tumor associated antigen and encoded by a nucleotide sequence including the sequences set forth in any of SEQ ID NO: 36, 38, 157, 167, 169, 171, 173, or 175, or a homolog thereof.

In some embodiments, a first or second binding domain, or a first and second binding domain binding to a cell surface tumor associated antigen is encoded by a nucleotide sequence that includes the sequence set forth in SEQ ID NO: 36 or a homolog thereof, and the sequence set forth in SEQ ID NO: 38 or a homolog thereof.

In some embodiments, a first or second binding domain, or a first and second binding domain binding to a cell surface tumor associated antigen in encoded by a nucleotide sequence that includes the sequence set forth in SEQ ID NO: 43 or a homolog thereof. In some embodiments, a first or second binding domain, or a first and second binding domain binding to a cell surface tumor associated antigen includes the sequence set forth in SEQ ID NO: 44 or a homolog thereof.

In some embodiments, the nucleotide sequences encoding a precursor tri-specific antibody construct polypeptide is optimized for mammalian transcription and translation. In some embodiments, the nucleotide sequences encoding a first binding domain or a second binding domain or both a first and a second binding domain of a precursor tri-specific antibody construct polypeptides is optimized for mammalian transcription and translation. In some embodiments, the nucleotide sequence of a VL or VH, or of both a VL and VH regions of a first binding domain or a second binding domain, or a first and a second binding domain are optimized for mammalian transcription and translation.

In another embodiment, the TAA provided herein is an angiogenic antigen which is expressed on both activated pericytes and pericytes in tumor angiogenic vasculature, which is associated with neovascularization in vivo. Angiogenic antigens are known in the art see for example WO2010/102140, which is incorporated by reference herein. For example, an angiogenic antigen may be selected from; Angiopoietin-1 (Ang1), Angiopoietin 3, Angiopoietin 4, Angiopoietin 6; Del-1; Fibroblast growth factors: acidic (aFGF) and basic (bFGF); Follistatin; Granulocyte colony-stimulating factor (G-CSF); Hepatocyte growth factor (HGF)/scatter factor (SF); Interleukin-8 (IL-8); Leptin; Midkine; Placental growth factor; Platelet-derived endothelial cell growth factor (PD-ECGF); Platelet-derived growth factor-BB (PDGF-BB); Pleiotrophin (PTN); Progranulin; Proliferin; survivin; Transforming growth factor-alpha (TGF-alpha); Transforming growth factor-beta (TGF-beta); Tumor necrosis factor-alpha (TNF-alpha); Vascular endothelial growth factor (VEGF)/vascular permeability factor (VPF).

As described above and throughout, in some embodiments the first binding domain or the second binding domain, or the first and a second binding domain (TAA binding domain) comprises a single chain variable fragment (scFv).

In some embodiments, the third binding domain (CD3ε extracellular epitope binding domain) comprises a Fab fragment. The specific structural order of components of a precursor tri-specific antibody construct, for example comprised in a polypeptide A and a polypeptide B, is described throughout in more detail.

In some embodiments, a precursor tri-specific antibody construct comprises at its core, an Fab fragment, which in some embodiments, comprises the third binding domain. As would be understood by the skilled person, a Fab fragment is the antigen-binding fragment of an antibody. The Fab is composed of one constant and one variable region of an immunoglobulin heavy and an immunoglobulin light chain. The heavy chain constant (CH1) and variable (VH) regions heterodimerize with the light chain variable (VL) and constant (CL) regions and are usually covalently linked by a disulfide bond between the heavy and light chain constant regions (see e.g., diagrams in FIGS. 1 and 2A-2B and 2F, and the amino acid sequences presented in FIGS. 8A, 9A, 10A, 11A, 45A-45B, 46, 47A-47B, and 48, wherein the cysteine residues that may form a disulfide bond (Cys-S—S-Cys bond) between polypeptides A and B of a precursor construct are indicated (highlighted in bold and underlined). The codons encoding these Cys residues are indicated in the nucleic acid sequences presented in FIGS. 8B, 9B, 10B, and 11B (highlighted in bold and underlined). Thus, a skilled artisan would appreciate that the term "Fab" with regard to an antibody generally encompasses that portion of the antibody consisting of a single light chain (both variable and constant regions) bound to the variable region and first constant region of a single heavy chain by a disulfide bond.

As would be recognized by the skilled person, a disulfide bond between the heavy and light chain is preferable, but not essential for function (Orcutt, et al. (2010), PEDS, 23:221-228). Thus, in certain embodiments the Fab fragment disclosed herein may not comprise a disulfide bond. In this regard, the heavy and light chains may be engineered in such a way so as to stably interact without the need for disulfide bond. For example, in certain embodiments, the heavy or light chain can be engineered to remove a cysteine residue and wherein the heavy and light chains still stably interact and function as a Fab. In some embodiments, mutations are made to facilitate stable interaction between the heavy and light chains. For example, a "knobs into holes" engineering strategy can be used to facilitate dimerization between the heavy and light chains of a Fab (see e.g., 1996 Protein Engineering, 9:617-621). Using this strategy, "knobs" are created by replacing small amino acid side chains at the interface between interacting domains with larger ones. Corresponding "holes" are made at the interface between interacting molecules by replacing large side chains with smaller ones. Thus, also contemplated for use herein are variant Fab fragments designed for a particular purpose, for example, amino acid changes in the constant domains of CH1 and or CL, and removal of a disulfide bond or addition of tags for purification.

In some embodiments, the configuration of the variable and constant regions within the Fab fragment may be different from what is found in a native Fab. In other words, in one embodiment, the orientation of the variable and constant regions may be VH-CL in one chain and in another VL-CH1 (Shaefer et al. (2011), PNAS, 108:111870-92). Such modified Fab fragments still function to bind their particular target antigen and are contemplated for use in the precursor construct disclosed herein. Thus, in this regard the variable regions and constant regions that make up the Fab are considered modular.

In certain embodiments, the Fab fragments of this disclosure are derived from monoclonal antibodies and may be derived from antibodies of any type, including IgA, IgM, IgD, IgG, IgE and subtypes thereof, such as IgG1, IgG2, IgG3, and IgG4. The light chain domains may be derived from the kappa or lambda chain. The Fab fragments for use herein may be made recombinantly.

As is well known in the art, an antibody is an immunoglobulin molecule capable of specific binding to a target, such as a carbohydrate, polynucleotide, lipid, polypeptide, etc., through at least one epitope recognition site, located in the variable region of the immunoglobulin molecule. A skilled artisan would appreciate that the term "antibody" encompasses not only intact polyclonal or monoclonal antibodies, but also humanized antibodies, chimeric antibodies, antibody fragments including antibody fragments lacking an Fc region, and any other modified configuration of the immunoglobulin molecule that comprises an antigen-binding site or fragment (epitope recognition site) of the required specificity, including scFv fragments and Fab fragments. In some embodiments, the precursor antibody constructs described herein lack an Fc region. The Fab fragment as disclosed herein, comprises an antigen-binding portion (third binding domain) comprised of an immunoglobulin heavy chain variable region and an immunoglobulin light chain variable region (VH and VL, respectively). Similarly, the scFv fragment described above (first or second binding domain), comprises an antigen-binding portion comprised of an immunoglobulin heavy chain variable region and an immunoglobulin light chain variable region (VH and VL, respectively). More specifically, the term "antigen-binding portion" as used herein refers to a polypeptide fragment that contains at least one CDR of an immunoglobulin heavy and/or light chains that binds to the target antigen of interest, such as the TAA of the first or second binding region, or a CD3 molecule of the third binding region. In this regard, an antigen-binding portion of the herein described precursor constructs may comprise 1, 2, 3, 4, 5, or all 6 CDRs of a VH and VL sequence of a parent antibody that binds to a target antigen of interest. In certain embodiments, the antigen-binding portion of the scFv fragment (first or second binding domain, or both first and second binding domains) of a precursor tri-specific antibody construct binds to a TAA, for example but not limited to a human EGFR. In certain embodiments, the antigen-binding portion of the Fab fragment of a precursor tri-specific antibody construct binds to CD3.

In certain embodiments, a specific VH and/or VL of the precursor tri-specific antibody construct described herein may be used to screen a library of the complementary variable region to identify VH/VL with desirable properties, such as increased affinity for a target antigen of interest. Such methods are described, for example, in Portolano et al., J. Immunol. (1993) 150:880-887; Clarkson et al., Nature (1991) 352:624-628.

Other methods may also be used to mix and match CDRs to identify Fab having desired binding activity (such as binding to CD3, or other target antigen of interest as described herein for other binding domains present in the precursor tri-specific antibody construct). For example: Klimka et al., British Journal of Cancer (2000) 83:252-260, describe a screening process using a mouse VL and a human VH library with CDR3 and FR4 retained from the mouse VH. After obtaining antibodies, the VH was screened against a human VL library to obtain antibodies that bound antigen. Beiboer et al., J. Mol. Biol. (2000) 296:833-849 describe a screening process using an entire mouse heavy chain and a human light chain library. After obtaining antibodies, one VL was combined with a human VH library with the CDR3 of the mouse retained. Antibodies capable of binding antigen were obtained. Rader et al., PNAS (1998) 95:8910-8915 describe a process similar to Beiboer et al above.

These just-described techniques are, in and of themselves, known as such in the art. The skilled person will, however, be able to use such techniques to obtain antigen-binding fragments of antibodies according to several embodiments of the disclosure described herein, using routine methodology in the art.

Also disclosed herein is a method for obtaining an antibody antigen binding domain specific for a target antigen (e.g., CD3 or any target antigen described elsewhere herein for targets of binding domains described herein), the method comprising providing by way of addition, deletion, substitution or insertion of one or more amino acids in the amino acid sequence of a VH domain set out herein a VH domain which is an amino acid sequence variant of the VH domain, optionally combining the VH domain thus provided with one or more VL domains, and testing the VH domain or VH/VL combination or combinations to identify a specific binding member or an antibody antigen binding domain specific for a target antigen of interest (e.g., CD3) and optionally with one or more desired properties. The VL domains may have an amino acid sequence which is substantially as set out herein. An analogous method may be employed in which one or more sequence variants of a VL domain disclosed herein are combined with one or more VH domains.

A skilled artisan would appreciate that an epitope that "specifically binds" or "preferentially binds" (used interchangeably herein) to an antibody or a polypeptide is a term well understood in the art, and methods to determine such specific or preferential binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody, or Fab or scFv thereof, "specifically binds" or "preferentially binds" to a target if it binds with greater affinity, avidity, more readily, and/or with greater duration than it binds to other substances. For example, an antibody that specifically or preferentially binds to a CD3 epitope is an antibody that binds one CD3 epitope with greater affinity, avidity, more readily, and/or with greater duration than it binds to other CD3 epitopes or non-CD3 epitopes. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

In certain embodiments, antigen-binding portions of the Fab fragment (third binding domain) as described herein include a heavy chain and a light chain CDR set, respectively interposed between a heavy chain and a light chain framework region (FR) set which provide support to the CDRs and define the spatial relationship of the CDRs relative to each other. As used herein, the term "CDR set" refers to the three hypervariable regions of a heavy or light chain V region. Proceeding from the N-terminus of a heavy or light chain, these regions are denoted as "CDR1," "CDR2," and "CDR3" respectively. An antigen-binding site, therefore, includes six CDRs, comprising the CDR set from each of a heavy and a light chain V region. A polypeptide comprising a single CDR, (e.g., a CDR1, CDR2 or CDR3) is referred to herein as a "molecular recognition unit." Crystallographic analysis of a number of antigen-antibody complexes has demonstrated that the amino acid residues of CDRs form extensive contact with bound antigen, wherein the most extensive antigen contact is with the heavy chain CDR3. Thus, the molecular recognition units are primarily responsible for the specificity of an antigen-binding site.

As used herein, the term "FR set" refers to the four flanking amino acid sequences which frame the CDRs of a CDR set of a heavy or light chain V region. Some FR residues may contact bound antigen; however, FRs are primarily responsible for folding the V region into the antigen-binding site, particularly the FR residues directly adjacent to the CDRs. Within FRs, certain amino residues and certain structural features are very highly conserved. In this regard, all V region sequences contain an internal disulfide loop of around 90 amino acid residues. When the V regions fold into a binding-site, the CDRs are displayed as projecting loop motifs which form an antigen-binding surface. It is generally recognized that there are conserved structural regions of FRs which influence the folded shape of the CDR loops into certain "canonical" structures-regardless of the precise CDR amino acid sequence. Further, certain FR residues are known to participate in non-covalent interdomain contacts which stabilize the interaction of the antibody heavy and light chains.

The structures and locations of immunoglobulin variable regions may be determined by reference to Kdbat, E. A. et al., Sequences of Proteins of Immunological Interest. 4th Edition. US Department of Health and Human Services. 1987, and updates thereof, now available on the Internet (79mmune.bme.nwu.edu).

A skilled artisan would recognize that the term "monoclonal antibody" encompasses a homogeneous antibody population wherein the monoclonal antibody is comprised of amino acids (naturally occurring and non-naturally occurring) that are involved in the selective binding of an epitope. Monoclonal antibodies are highly specific, being directed against a single epitope. The term "monoclonal antibody" encompasses not only intact monoclonal antibodies and full-length monoclonal antibodies, but also fragments thereof (such as Fab, Fab', F(ab') 2, Fv), single chain (ScFv), variants thereof, fusion proteins comprising an antigen-binding portion, humanized monoclonal antibodies, chimeric monoclonal antibodies, and any other modified configuration of the immunoglobulin molecule that comprises an antigen-binding fragment (epitope recognition site) of the required specificity and the ability to bind to an epitope. It is not intended to be limited as regards the source of the antibody or the manner in which it is made (e.g., by hybridoma, phage selection, recombinant expression, transgenic animals, etc.). The term includes whole immunoglobulins as well as the fragments etc. as described herein.

The proteolytic enzyme papain preferentially cleaves IgG molecules to yield several fragments, two of which (the F (ab) fragments) each comprise a covalent heterodimer that includes an intact antigen-binding site. The enzyme pepsin is able to cleave IgG molecules to provide several fragments, including the F(ab') 2 fragment which comprises both antigen-binding sites. An Fv fragment for use according to certain embodiments as disclosed herein, can be produced by preferential proteolytic cleavage of an IgM, and on rare occasions of an IgG or IgA immunoglobulin molecule. Fv fragments are, however, more commonly derived using recombinant techniques known in the art. The Fv fragment includes a non-covalent VH:: VL heterodimer including an antigen-binding site which retains much of the antigen recognition and binding capabilities of the native antibody molecule. Inbar et al. (1972) Proc. Nat. Acad. Sci. USA 69:2659-2662; Hochman et al. (1976) Biochem 15:2706-2710; and Ehrlich et al. (1980) Biochem 19:4091-4096.

In some embodiments of the present disclosure, the Fab fragment comprising a third binding domain binds to CD3. In some embodiments of the present disclosure, the Fab fragment comprising a third binding domain binds to CD3epsilon.

"T-cell receptor" (TCR) is a molecule found on the surface of T-cells that, along with CD3, is generally responsible for recognizing antigens bound to major histocompatibility complex (MHC) molecules. It consists of a disulfide-linked heterodimer of the highly variable (alpha) and (beta) chains in most T-cells. In other T-cells, an alternative receptor made up of variable Y and (delta) chains is expressed. Each chain of the TCR is a member of the immunoglobulin superfamily and possesses one N-terminal immunoglobulin variable region, one immunoglobulin constant region, a transmembrane region, and a short cytoplasmic tail at the C-terminal end (see, Abbas and Lichtman, Cellular and Molecular Immunology (5th Ed.), Editor: Saunders, Philadelphia, 2003; Janeway et ai, Immunobiology: The Immune System in Health and Disease, 4th Ed., Current Biology Publications, p 148, 149, and 172, 1999). TCR as used in the present disclosure may be from various animal species, including human, mouse, rat, or other mammals.

"Anti-TCR Fab" or "Anti-TCR precursor bispecific antibody construct", refers to a Fab or a precursor tri-specific antibody construct comprising an Fab that specifically binds to a TCR molecule or one of its individual chains (e.g., TCR (alpha), TCR (beta), TCRY or TCR (delta) chain). In certain embodiments, an anti-TCR Fab binds to a TCR (alpha), a TCR (beta), or both. A skilled person would appreciate that the term "Anti-TCR Fab", may in some embodiments encompass the third binding domain of a precursor tri-specific antibody construct described herein. In some embodiments, the term "Anti-TCR Fab" may encompass the precursor construct, wherein reference is being made to the binding attributes of the third binding domain.

"CD3" is known in the art as a multi-protein complex of six chains (see, Smith-Garvin et al., Annu Rev Immunol. 2009; 27:591-619). In mammals, the complex comprises a CD3 (gamma) chain, a CD3(delta) chain, two CD3(epsilon; ε) chains, and a homodimer of CD3 (zeta) chains. The CD3 (gamma), CD3 (delta), and CD3 (epsilon) chains are highly related cell surface proteins of the immunoglobulin superfamily containing a single immunoglobulin domain. The transmembrane regions of the CD3 (gamma), CD3 (delta), and CD3 (epsilon) chains are negatively charged, which is a characteristic that allows these chains to associate with the positively charged T-cell receptor chains. The intracellular tails of the CD3 (gamma), CD3 (delta), and CD3 (epsilon) chains each contain a single conserved motif known as an immunoreceptor tyrosine-based activation motif or ITAM, whereas each CD3 (zeta) chain has three. Without wishing to be bound by theory, it is believed the ITAMs are important for the signaling capacity of a TCR complex. CD3 as used in the present disclosure may be from various animal species, including human, mouse, rat, or other mammals.

"Anti-CD3 Fab" as used herein, refers to a Fab comprising a third binding domain that specifically binds to individual CD3 chains (e.g., CD3 (gamma) chain, CD3 (delta) chain, or CD3 (epsilon; ε) chain) or a complex formed from two or more individual CD3 chains (e.g., a complex of more than one CD3 (epsilon) chains, a complex of a CD3 (gamma) and CD3 (epsilon) chain, a complex of a CD3 (delta) and CD3 (epsilon) chain). In certain embodiments, an anti-CD3 Fab specifically binds to a CD3 (gamma), a CD3 (delta), or a CD3 (epsilon), or any combination thereof, and in certain embodiments, a CD3 (epsilon). In some embodiments, an anti-CD3 Fab binds to the N-terminus of CD3 epsilon. In some embodiments, an anti-CD3 Fab binds to an extracellular epitope of CD3 epsilon.

In some embodiments, the anti-CD3 Fab binds to an epitope comprised within amino acids 1-27 of CD3 epsilon. In some embodiments, the anti-CD3 Fab binds to amino acids 1-27 of CD3 epsilon. In some embodiments, the anti-CD3 Fab binds to amino acids 1-27 of a human CD3 epsilon. Amino acids 1-27 of CD3 epsilon are set forth in SEQ ID NO: 5.

A skilled person would appreciate that the term "Anti-CD3 Fab", may in some embodiments encompass the third binding domain of a precursor tri-specific antibody construct described herein. In some embodiments, the term "Anti-CD3 Fab" may encompass the precursor construct, wherein reference is being made to the binding attributes of the third binding domain.

In some embodiments, a third binding domain of a precursor construct comprises a Fab. In some embodiments, when referring to a third binding domain of a precursor construct the term "Fab" will be used, wherein the term encompasses a third bind domain of a precursor construct. In some embodiments, the term "Fab" may be used interchangeably with the phrase "third binding domain" having all the same qualities and meanings.

In some embodiments, a precursor tri-specific antibody construct comprises a third binding domain that binds to an extracellular epitope of CD3 epsilon. In some embodiments, a precursor tri-specific antibody construct comprises a third binding domain that binds to the N-terminus of CD3 epsilon. In some embodiments, a precursor tri-specific antibody construct comprises a third binding domain that binds to an epitope with amino acids 1-27 of CD3 epsilon. In some embodiments, the anti-CD3 Fab binds to amino acids 1-27 of CD3 epsilon. In some embodiments, the anti-CD3 Fab binds to amino acids 1-27 of a human CD3 epsilon. Amino acids 1-27 of CD3 epsilon are set forth in SEQ ID NO: 5.

"TCR complex," as used herein, refers to a complex formed by the association of CD3 with TCR. For example, a TCR complex can be composed of a CD3 (gamma) chain, a CD3 (delta) chain, two CD3 (epsilon) chains, a homodimer of CD3 (zeta) chains, a TCR (alpha) chain, and a TCR (beta) chain. Alternatively, a TCR complex can be composed of a CD3 (gamma) chain, a CD3 (delta) chain, two CD3 (epsilon) chains, a homodimer of CD3 (zeta) chains, a TCRY chain, and a TCR (delta) chain.

"A component of a TCR complex," as used herein, refers to a TCR chain (i.e., TCR (alpha), TCR (beta), TCRY or TCR (delta)), a CD3 chain (i.e., CD3 (gamma), CD3 (delta), CD3 (epsilon) or CD3 (zeta)), or a complex formed by two or more TCR chains or CD3 chains (e.g., a complex of TCR (alpha) and TCR (beta), a complex of TCRY and TCR (delta), a complex of CD3 (epsilon) and CD3 (delta), a complex of CD3 (gamma) and CD3 (epsilon), or a sub-TCR complex of TCR (alpha), TCR (beta), CD3 (gamma), CD3 (delta), and two CD3 (epsilon) chains).

By way of background, the TCR complex is generally responsible for initiating a T-cell response to antigen bound to MHC molecules. It is believed that binding of a peptide: MHC ligand to the TCR and a co-receptor (i.e., CD4 or CD8) brings together the TCR complex, the co-receptor, and CD45 tyrosine phosphatase. This allows CD45 to remove inhibitory phosphate groups and thereby activate Lck and Fyn protein kinases. Activation of these protein kinases leads to phosphorylation of the ITAM on the CD3 (zeta) chains, which in turn renders these chains capable of binding the cytosolic tyrosine kinase ZAP-70. The subsequent activation of bound ZAP-70 by phosphorylation triggers three signaling pathways, two of which are initiated by the phosphorylation and activation of PLC-(gamma), which then cleaves phosphatidylinositol phosphates (PIPs) into diacylglycerol (DAG) and inositol trisphosphate (IP3). Activation of protein kinase C by DAG leads to activation of the transcription factor NFKB. The sudden increase in intracellular free Ca2+ as a result of IP3 action activates a cytoplasmic phosphatase, calcineurin, which enables the transcription factor NFAT (nuclear factor of activated T-cells) to translocate form the cytoplasm to the nucleus. Full transcriptional activity of NFAT also requires a member of the AP-1 family of transcription factors; dimers of members of the Fos and Jun families of transcription regulators.

A third signaling pathway initiated by activated ZAP-70 is the activation of Ras and subsequent activation of a MAP kinase cascade. This culminates in the activation of Fos and hence of the AP-1 transcription factors. Together, NFKB, NFAT, and AP-1 act on the T-cell chromosomes, initiating new gene transcription that results in the differentiation, proliferation and effector actions of T-cells. See, Pitcher et al., 2003., TRENDS in Immunol. 24, 554-560; Smith-Garvin et al., Annu Rev Immunol. 2009; 27:591-619.

In certain embodiments, the Fab specifically binds to an individual human CD3 chain (e.g., human CD3 (gamma) chain, human CD3 (delta) chain, or human CD3 (epsilon) chain) or a combination of two or more of the individual human CD3 chains (e.g., a complex of human CD3 (gamma) and human CD3 (epsilon) or a complex of human CD3 (delta) and human CD3 (epsilon)). In certain embodiments, the Fab specifically binds to a human CD3 (epsilon) chain. In certain embodiments, the Fab specifically binds to an extracellular epitope of a human CD3 (epsilon) chain. In certain embodiments, the Fab specifically binds to an epitope within SEQ ID NO: 3.

In certain embodiments, the third binding domain specifically binds to an individual human CD3 chain (e.g., human CD3 (gamma) chain, human CD3 (delta) chain, or human CD3 (epsilon) chain) or a combination of two or more of the individual human CD3 chains (e.g., a complex of human CD3 (gamma) and human CD3 (epsilon) or a complex of human CD3 (delta) and human CD3 (epsilon)). In certain embodiments, the third binding domain specifically binds to a human CD3 (epsilon) chain. In certain embodiments, the third binding domain specifically binds to an extracellular epitope of a human CD3 (epsilon) chain. In certain embodiments, the third binding domain specifically binds to an epitope within SEQ ID NO: 3.

In certain other embodiments, a Fab of the present disclosure comprising a third binding domain specifically binds to TCR (alpha), TCR (beta), or a heterodimer formed from TCR (alpha) and TCR (beta). In certain embodiments, a Fab specifically binds to one or more of human TCR (alpha), human TCR (beta), or a heterodimer formed from human TCR (alpha) and human TCR (beta).

In certain embodiments, a Fab of the present disclosure comprising a third binding domain binds to a complex formed from one or more CD3 chains with one or more TCR chains, such as a complex formed from a CD3 (gamma) chain, a CD3 (delta) chain, a CD3 (epsilon) chain, a TCR (alpha) chain, or a TCR (beta) chain, or any combination thereof. In other embodiments, a Fab of the present disclosure binds to a complex formed from one CD3 (gamma) chain, one CD3 (delta) chain, two CD3 (epsilon) chains, one TCR (alpha) chain, and one TCR (beta) chain. In further embodiments, a Fab of the present disclosure binds to a complex formed from one or more human CD3 chains with one or more human TCR chains, such as a complex formed from a human CD3 (gamma) chain, a human CD3 (delta) chain, a human CD3 (epsilon), a human TCR (alpha) chain, or a human TCR (beta) chain, or any combination thereof. In certain embodiments, a Fab of the present disclosure binds to a complex formed from one human CD3 (gamma) chain, one human CD3 (delta) chain, two human CD3 (epsilon) chains, one human TCR (alpha) chain, and one human TCR (beta) chain.

Fabs of this disclosure can be generated as described herein or by a variety of methods known in the art (see, e.g., U.S. Pat. Nos. 6,291,161; 6,291,158). Sources of Fabs include monoclonal antibody nucleic acid sequences from various species (which can be formatted as antibodies, Fvs, scFvs or Fabs, such as in a phage library), including human, camelid (from camels, dromedaries, or llamas; Hamers-Casterman et al. (1993) Nature, 363:446 and Nguyen et al. (1998) J. Mol. Biol., 275:413), shark (Roux et al. (1998) Proc. Nat'l. Acad. Sci. (USA) 95:11804), fish (Nguyen et al. (2002) Immunogenetics, 54:39), rodent, avian, or ovine.

An anti-human CD3 antibody with cross reactivity to monkey CD3 is particularly desirable, such as the SP34 mouse monoclonal antibody, which binds specifically to human CD3 in denatured form (Western blot or dot blot) and in native form (on T-cells) (Pressano, S. The EMBO J. 4:337-344, 1985; Alarcon, B. EMBO J. 10:903-912, 1991). SP34 mouse monoclonal antibody also binds to CD3c singly transfected COS cells as well as CD3ε/γ or CD3.ε/δ double transfectants (Salmeron A. et al., J. Immunol. 147:3047-52, 1991). SP34 antibody also cross reacts non-human primates (Yoshino N. et al., Exp. Anim 49:97-110, 2000; Conrad M L. et al., Cytometry 71A: 925-33, 2007). In addition, SP34 activates T-cell when cross-linked (Yang et al., J. Immunol. 137:1097-1100, 1986). Cross-reactivity to monkey CD3 is important as this allows toxicity studies to be carried out in non-human primates using the clinical candidate directly, rather than in chimpanzee or using a surrogate molecule. Thus, toxicity studies using such cross-reactive anti-CD3 Fab in a precursor bispecific antibody construct of the present disclosure provide more relevant safety assessments.

Other illustrative anti-CD3 antibodies include the Cris-7 monoclonal antibody (Reinherz, E. L. et al. (eds.), Leukocyte typing II., Springer Verlag, New York, (1986)), BC3 monoclonal antibody (Anasetti et al. (1990) J. Exp. Med. 172:1691), OKT3 (Ortho multicenter Transplant Study Group (1985) N. Engl. J. Med. 313:337) and derivatives thereof such as OKT3 ala-ala (Herold et al. (2003) J. Clin. Invest. 11:409), visilizumab (Carpenter et al. (2002) Blood 99:2712), and 145-2C11 monoclonal antibody (Hirsch et al. (1988) J. Immunol. 140:3766). Further CD3 binding molecules contemplated for use herein include UCHT-1 (Beverley, P C and Callard, R. E. (1981) Eur. J. Immunol. 11:329-334) and CD3 binding molecules described in WO2004/106380; WO2010/037838; WO2008/119567; WO2007/042261; WO2010/0150918, which are incorporated herein in their entirety.

In some embodiments, the amino acid sequence of a third binding region comprising an anti-CD3 epsilon binding activity comprises any anti-CD3epsilon sequence known in the art. In some embodiments, the amino acid sequence of a third binding region comprising binding activity to an anti-CD3 epsilon or a derivative thereof or an antibody fragment thereof, comprises any anti-CD3epsilon sequence known in the art. Examples of known anti-CD3 epsilon amino acid sequences may be found for example but no limit to U.S. Pat. Nos. 9,822,180; 9,493,563; 9,587,021; 9,562,073; United States Published Application Nos: 2013/0129729; 2017/0247476; 2016/0194399; 2010/0150918; 2018/0112011; and WO2017/162587, which all included herein in their entirety.

An exemplary anti-TCR antibody is H57 monoclonal antibody (Lavasani et al. (2007) Scandinavian Journal of Immunology 65:39-47).

Antigen binding fragment sequences (e.g., heavy and light chain variable region sequences) for Fab fragments may be available in public databases or using traditional strategies for hybridoma development using a CD3 chain, TCR component, or other Fab binding target as an immunogen in convenient systems (e.g., mice, HuMAb Mouse.RTM., TC Mouse.TM., KM-Mouse.RTM., llamas, chicken, rats, hamsters, rabbits, etc.) can be used to develop Fabs for use herein. As would be understood by the skilled person, Fab fragments may be generated using various technologies known in the art, including antibody display technologies such as phage, yeast, ribosome and mRNA display technologies; B cell culture technology such as SLAM technology; or using high throughput gene sequencing technologies on B cells or plasma B cells isolated from an immunized animal subject or immunized human subject.

In some embodiments, a third binding domain (an Fab) disclosed herein, comprises humanized FR amino acid sequence and native sequence of a mouse monoclonal antibody for the CDR amino acid sequences. Examples of anti-CD3 epsilon amino acid sequences wherein the FR sequences have been humanized while the CDR amino acid sequences remain those of the SP34 mouse monoclonal antibody, are disclosed in International Application Publication No. WO 2007/042261, which is incorporated here in its entirety.

Illustrative third binding domains (for example but not limited to anti-CD3 epsilon Fabs) sequences comprised within a precursor bispecific antibody construct of the present disclosure include the VH, CH1, VL, and CL amino acid sequences, and the polynucleotides encoding them, as set forth in Tables 1 and 2 below, respectively. Amino acid sequences comprising a third binding domain include those set forth as: SEQ ID NOs: 46-72 and 114 (VH) and 75-103 and 116 (VL) including CDRs thereof, such as those set forth in SEQ ID NOs: 104-112. In some embodiments, third binding domains (e.g., Fabs) sequences comprised within a precursor tri-specific antibody construct of the present disclosure include the VH, CH1, VL, and CL amino acid sequences, as set forth in Table 2, or a homolog thereof. In some embodiments, homologs of SEQ ID NOs: 46-72 and 114, and 75-103 and 116, maintain their CDR regions, for example as set for the in SEQ ID NOs: 104-112.

TABLE 2

Amino Acid Sequences of Anti-CD3 VH, VL, HC, LC, and CDR, and Combinations Thereof.

| SEQ ID No | Description |
|---|---|
| 45 | Mouse monoclonal SP34(mu) variable heavy chain |
| 46 | Variable Heavy chain |
| 47 | Variable Heavy chain |
| 48 | Variable Heavy chain |
| 49 | Variable Heavy chain |
| 50 | Variable Heavy chain |
| 51 | Variable Heavy chain |
| 52 | Variable Heavy chain |
| 53 | Variable Heavy chain |
| 54 | Variable Heavy chain |
| 55 | Variable Heavy chain |
| 56 | Variable Heavy chain |
| 57 | Variable Heavy chain |
| 58 | Variable Heavy chain |
| 59 | Variable Heavy chain |
| 60 | Variable Heavy chain |
| 61 | Variable Heavy chain |
| 62 | Variable Heavy chain |
| 63 | Variable Heavy chain |
| 64 | Variable Heavy chain |
| 65 | Variable Heavy chain |
| 66 | Variable Heavy chain |
| 67 | Variable Heavy chain |
| 68 | Variable Heavy chain |
| 69 | Variable Heavy chain |
| 70 | Variable Heavy chain |
| 71 | Variable Heavy chain |
| 72 | Variable Heavy chain |
| 73 | Variable Light chain from mouse monoclonal antibody SP34VL(mu) |
| 74 | Variable Light chain and Constant Light Chain |
| 75 | Variable Light chain |
| 76 | Variable light chain |
| 77 | Variable Light chain |
| 78 | Variable Light chain |
| 79 | Variable Light chain |
| 80 | Variable Light chain |
| 81 | Variable Light chain |
| 82 | Variable Light chain |
| 83 | Variable Light chain |
| 84 | Variable Light chain |
| 85 | Variable Light chain |
| 86 | Variable Light chain |
| 87 | Variable Light chain |
| 88 | Variable Light chain |
| 89 | Variable Light chain |
| 90 | Variable Light chain |
| 91 | Variable Light chain |
| 92 | Variable Light chain |
| 93 | Variable Light chain |
| 94 | Variable Light chain |
| 95 | Variable Light chain |
| 96 | Variable Light chain |
| 97 | Variable Light chain |
| 98 | Variable Light chain |
| 99 | Variable Light chain |
| 100 | Variable Light chain |
| 101 | Variable Light chain |
| 102 | Variable Light chain |
| 103 | Variable Light chain |
| 104 | CDR1 of Heavy Chain (CDR-H1) |
| 105 | CDR2 of Heavy Chain (CDR-H2) |
| 106 | CDR3 of Heavy Chain (CDR-H3) |
| 107 | CDR1 of Light Chain (CDR-L1) |
| 108 | CDR1 of Light Chain (CDR-L1) |
| 109 | CDR1 of Light Chain (CDR-L1) |
| 110 | CDR2 of Light Chain (CDR-L2) |
| 111 | CDR3 of Light Chain (CDR-L3) |
| 112 | CDR3 of Light Chain (CDR-L3) |
| 113 | anti-CD3 Variable Heavy chain and heavy constant region 1 |
| 114 | anti-CD3 epsilon VH |

TABLE 2-continued

Amino Acid Sequences of Anti-CD3 VH, VL, HC, LC, and CDR, and Combinations Thereof.

| SEQ ID No | Description |
|---|---|
| 115 | anti-CD3 epsilon Constant Heavy Chain. |
| 116 | anti-CD3 epsilon VL |
| 117 | anti-CD3 epsilon Constant Light Chain. |

In some embodiments, a third binding domain binds a CD3 epsilon polypeptide. In some embodiments, a third binding domain binds an extracellular domain of a human CD3 epsilon polypeptide. In some embodiments, a third binding domain comprises an Fab fragment comprising a variable heavy chain region (VH) comprising a CDR-H1, a CDR-H2, and a CDR-H3, and a variable light chain region (VL) comprising a CDR-L1, a CDR-L2, and a CDR-L3, wherein the third binding domain binds an extracellular domain of a human CD3 epsilon polypeptide. In some embodiments, a third binding domain binds to an epitope within SEQ ID NO: 3. In some embodiments, a third binding domain binds SEQ ID NO: 5.

In some embodiments, the amino acid sequence of an anti-human CD3 epsilon CDR-H1 is set forth in SEQ ID NO: 104. In some embodiments, the amino acid sequence of an anti-human CD3 epsilon CDR-H2 is set forth in SEQ ID NO: 105. In some embodiments, the amino acid sequence of an anti-human CD3 epsilon CDR-H3 is set forth in SEQ ID NO: 106. In some embodiments, the amino acid sequence of an anti-human CD3 epsilon CDR-L1 is set forth in any one of SEQ ID NOs: 107-109. In some embodiments, the amino acid sequences of an anti-human CD3 3epsilon CDR-L1 is set forth in SEQ ID NO: 110. In some embodiments, the amino acid sequences of an anti-human CD3 3epsilon CDR-L1 is set forth in SEQ ID NO: 111-112.

In some embodiments, a third binding domain comprises an Fab fragment comprising a variable heavy chain region (VH) and a variable light chain region (VL) that binds an extracellular domain of a human CD3 epsilon polypeptide. In some embodiments, the amino acid sequence of VH and VL for an anti-human CD3 epsilon are selected from the amino acid sequences set forth in any of SEQ ID NO: 46-72 and 114 (VH), and 75-103 and 116 (VL). In some embodiments, the amino acid sequence of VH and VL for an anti-human CD3 epsilon comprises a homolog of sequences selected from the amino acid sequences set forth in any of SEQ ID NO: 46-72 and 114 (VH), and 75-103 and 116 (VL).

In some embodiments, the amino acid sequence of a VH for a human CD3 epsilon third binding domain (VH1) are selected from the amino acid sequences set forth in any of SEQ ID NOs: 75-103 and 116, or a homolog thereof. In some embodiments, the amino acid sequence of a VL for a human CD3 epsilon third binding domain (VL1) are selected from the amino acid sequences set forth in any of SEQ ID NOs: 75-103 and 116, or a homolog thereof.

In some embodiments, homologues comprise polypeptides which are at least 50%, at least 55%, at least 60%, at least 65%, at least 70%, at least 75%, at least 80%, at least 85%, at least 87%, at least 89%, at least 91%, at least 93%, at least 95%, at least 96%, at least 97%, at least 98%, or at least 99% homologous to the amino acid sequence of variable light or variable heavy chains of anti-CD3epsilon. In some embodiments, homologues comprise polypeptides which are at least 50%, at least 55%, at least 60%, at least 65%, at least 70%, at least 75%, at least 80%, at least 85%, at least 87%, at least 89%, at least 91%, at least 93%, at least 95%, at least 96%, at least 97%, at least 98%, or at least 99% identical to the amino acid sequence of variable light or variable heavy chains of anti-CD3epsilon. In some embodiments, homologues comprise polypeptides which are at least 50%, at least 55%, at least 60%, at least 65%, at least 70%, at least 75%, at least 80%, at least 85%, at least 87%, at least 89%, at least 91%, at least 93%, at least 95%, at least 96%, at least 97%, at least 98%, or at least 99% homologous to an anti-human CD3 epsilon VH or an anti-human CD3 epsilon VL, respectively, as determined using BlastP software of the National Center of Biotechnology Information (NCBI) using default parameters.

In some embodiments, homology also encompasses deletion, insertion, or substitution variants, including an amino acid substitution, thereof and biologically active polypeptide fragments thereof. In one embodiment, the variant comprises conservative substitutions, or deletions, insertions, or substitutions that do not significantly alter the three-dimensional structure of the polypeptide of interest, e.g., VL or VH region, particularly in the areas of the CDR epitope binding regions. In some embodiments, the deletion, insertion, or substitution does not alter the function of interest of the anti-human CD3 epsilon Fab, which in some embodiments, is binding to a CD3 epsilon sequence on a target T-cell.

In some embodiments, a third binding domain binding to a CD3 epsilon extracellular epitope VH1 includes the sequences set forth in SEQ ID NOs: 46-72 and 114, or a homolog thereof. In some embodiments, a second binding domain binding to a CD3 epsilon extracellular epitope VL1 includes the sequences set forth in SEQ ID NO: 75-103 and 116, or a homolog thereof. In some embodiments, a third binding domain binding to a CD3 epsilon extracellular epitope comprises a sequence selected from the sequences set forth in SEQ ID NOs: 46-72, 74, and 114 or a homolog thereof, and a sequence selected from the sequences set forth in SEQ ID NOs: 75-103, 113, 115, and 116, or a homolog thereof. In some embodiments, a third binding domain binding to a CD3 epsilon extracellular epitope comprises the sequence set forth in SEQ ID NO: 113 or a homolog thereof, and the sequence set forth in SEQ ID NO: 74 or a homolog thereof.

In some embodiments, the third binding domain VL region comprises amino acid sequences as set forth for CDR-L1 (selected from SEQ ID NO: 107-109), CDR-L2 (SEQ ID NO: 110), and CDR-L3 (selected from SEQ ID NOs: 111 and 112), and the third binding domain VH region comprises CDR-H1 (SEQ ID NO: 104), CDR-H2 (SEQ ID NO: 105), and CDR-H3 (SEQ ID NO: 106).

In some embodiments of a precursor tri-specific antibody construct, the VL region of the third binding domain comprises the amino acid sequence set forth in any of SEQ ID NO: 75-103 and 116, or an amino acid sequence having at least 80% homology thereto. In some embodiments, a VL region of the third binding comprising an amino acid sequence having at least 80% homology thereto, comprises framework sequences having at least 80% homology, wherein the CDR regions are “as is” in the selected amino acid sequence (SEQ ID NO: 107-112).

In some embodiments of a precursor tri-specific antibody construct, the VH region of the third binding comprises the amino acid sequence set forth in any of SEQ ID NO: 46-72 and 114, or an amino acid sequence having at least 80% homology thereto. In some embodiments, a VH region of the third binding comprising an amino acid sequence having at least 80% homology thereto, comprises framework sequences having at least 80% homology, wherein the CDR regions are "as is" in the selected amino acid sequence (SEQ ID NO: 104-106).

In some embodiments, a first binding domain comprises a humanized binding domain. In some embodiments, a second binding domain comprises a humanized binding domain. In some embodiments, a third binding domain comprises a humanized binding domain. In some embodiments, a first, or a second or a third binding domain, or any combination thereof, comprises a humanized binding domain.

As would be understood by the skilled person and as described herein, in some embodiments, a complete antibody comprises two heavy chains and two light chains Each heavy chain consists of a variable region and a first, second, and third constant region, while each light chain consists of a variable region and a constant region. Mammalian heavy chains are classified as α, δ, ε, γ, and μ, and mammalian light chains are classified as λ or κ. Immunoglobins comprising the α, δ, ε, γ, and μ, heavy chains are classified as immunoglobin (Ig) A, IgD, IgE, IgG, and IgM. The complete antibody forms a "Y" shape. The stem of the Y consists of the second and third constant regions (and for IgE and IgM, the fourth constant region) of two heavy chains bound together and disulfide bonds (inter-chain) are formed in the hinge. Heavy chains γ, α, and δ have a constant region composed of three tandem (in a line) Ig domains, and a hinge region for added flexibility; heavy chains μ and ε have a constant region composed of four immunoglobulin domains. The second and third constant regions are referred to as "CH2 domain" and "CH3 domain", respectively. Each arm of the Y includes the variable region and first constant region of a single heavy chain bound to the variable and constant regions of a single light chain. The variable regions of the light and heavy chains are responsible for antigen binding.

"Complementarity determining region" or "CDR" with regard to an antibody refers to a highly variable loop in the variable region of the heavy chain or the light chain of an antibody. CDRs can interact with the antigen conformation and largely determine binding to the antigen (although some framework regions are known to be involved in binding). The heavy chain variable region and the light chain variable region each contain 3 CDRs. The CDRs can be defined or identified by conventional methods, such as by sequence according to Kdbat et al (Wu, T T and Kdbat, E. A., J Exp Med. 132 (2): 211-50, (1970); Borden, P. and Kdbat E. A., PNAS, 84:2440-2443 (1987); Kdbat, E. A. et al, Sequences of proteins of immunological interest, Published by DIANE Publishing, 1992), or by structure according to Chothia et al (Choithia, C. and Lesk, A. M., J. Mol. Biol., 196 (4): 901-917 (1987), Choithia, C. et al, Nature, 342:877-883 (1989)).

"Heavy chain variable region" or "VH" with regard to an antibody refers to the fragment of the heavy chain that contains three CDRs interposed between flanking stretches known as framework regions, which are more highly conserved than the CDRs and form a scaffold to support the CDRs.

"Light chain variable region" or "VL" with regard to an antibody refers to the fragment of the light chain that contains three CDRs interposed between framework regions.

"Fv" with regard to an antibody refers to the smallest fragment of the antibody to bear the complete antigen binding site. An Fv fragment consists of the variable region of a single light chain bound to the variable region of a single heavy chain.

"Single-chain Fv antibody" or "scFv" with regard to an antibody refers to an engineered antibody consisting of a light chain variable region and a heavy chain variable region connected to one another directly or via a peptide linker sequence.

"Single domain camel antibody" or "camelid VHH" as used herein refers to the smallest known antigen-binding unit of a heavy chain antibody (Koch-Nolte, et al, FASEB J., 21:3490-3498 (2007)). A "heavy chain antibody" or a "camelid antibody" refers to an antibody that contains two VH domains and no light chains (Riechmann L. et al, J. Immunol. Methods 231:25-38 (1999); WO94/04678; WO94/25591; U.S. Pat. No. 6,005,079).

"Single domain antibody" or "dAb" refers to an antibody fragment that consists of the variable region of an antibody heavy chain (VH domain) or the variable region of an antibody light chain (VL domain) (Holt, L., et al, Trends in Biotechnology, 21 (11): 484-490).

The term "disulfide bond" as used herein refers to the binding of a heavy chain fragment and a light chain fragment through one or more disulfide bonds. The one or more disulfide bonds can be formed between the two fragments by linking the thiol groups in the two fragments. In certain embodiments, the one or more disulfide bonds can be formed between one or more cysteine residues in the heavy chain fragment and the light chain fragment, respectively.

A "variable region linking sequence" is an amino acid sequence that connects a heavy chain variable region to a light chain variable region and provides a linker function compatible with interaction of the two sub-binding domains so that the resulting polypeptide retains a specific binding affinity to the same target molecule as an antibody that comprises the same light and heavy chain variable regions. In certain embodiments, a hinge useful for linking a binding domain to an immunoglobulin CH2 or CH3 region polypeptide may be used as a variable region linking sequence.

In some embodiments, a third binding domain comprises a variable heavy chain (VH) region and a variable light chain (VL) region, wherein said first or second sub-regulatory domain is located N-terminally to said VL region or VH region of said third binding domain. In some embodiments, a third binding domain comprises a variable heavy chain (VH) region and a variable light chain (VL) region, wherein said first sub-regulatory domain is located N-terminally to said VL region of said third binding domain, and a second sub-regulatory domain is located N-terminally to said VH region of said third binding domain. In some embodiments, a third binding domain comprises a variable heavy chain (VH) region and a variable light chain (VL) region, wherein said first sub-regulatory domain is located N-terminally to said VH region of the third binding domain, and the second sub-regulatory domain is located N-terminally to said VL region of the third binding domain.

In some embodiments, a third binding domain comprises a constant heavy chain (CH1) region and a constant light chain (CL) region, wherein said first or second binding domain is located C-terminally to said CH1 region or CL region of said third binding domain. In some embodiments, a third binding domain comprises a constant heavy chain (CH1) region and a constant light chain (CL) region, wherein said first binding domain is located C-terminally to said CL region of said third binding domain, and a second binding domain is located C-terminally to said CH1 region of said third binding domain. In some embodiments, a third binding domain comprises a constant heavy chain (CH1) region and a constant light chain (CL) region, wherein said first binding domain is located C-terminally to said CH1 region of the third binding domain, and the second binding domain is located C-terminally to said CL region of the third binding domain. A skilled artisan would appreciate that the first and second sub-regulatory domains are located N-terminally to the VH and VL, wherein when a first sub-regulatory domain is located N-terminally to VH than the second sub-regulatory domain is located N-terminally to the VL, and vice-versa when the second sub-regulatory domain is located N-terminal to the VH of the third binding domain, the first sub-regulatory domain is located N-terminally to the VL of the third binding domain. Similarly, the skilled artisan would appreciate that the first and second binding domains are located C-terminally to the CH1 and CL domains of the third binding domain, wherein when the first binding domain is located C-terminally to the CH1 the second binding domain is location C-terminally to the CL, and vice-versa, when the second binding domain is located C-terminally to the CH1, the first binding domain is located C-terminally to the CL of the third binding domain.

An alternative source of binding domains may include sequences that encode random peptide libraries or sequences that encode an engineered diversity of amino acids in loop regions of alternative non-antibody scaffolds, such as fibrinogen domains (see, e.g., Weisel et al. (1985) Science 230:1388), Kunitz domains (see, e.g., U.S. Pat. No. 6,423, 498), lipocalin domains (see, e.g., WO 2006/095164), V-like domains (see, e.g., US Patent Application Publication No. 2007/0065431), C-type lectin domains (Zelensky and Gready (2005) FEBS J. 272:6179), or Fcab.TM. (see, e.g., PCT Patent Application Publication Nos. WO 2007/098934; WO 2006/072620), or the like.

As depicted in the FIGS. 1 and 2A-2F, scFv are particularly illustrative binding domains. A first or second binding domain, or both a first and second binding domain, which in some embodiments comprises an scFv fragment, may bind to any of a variety of target molecules, including but not limited to a FcγRI, FcγRIIa FcγRIIb, FcγRIIIb, CD28, CD137, CTLA-4, FAS, fibroblast growth factor receptor 1 (FGFR1), FGFR2, FGFR3, FGFR4, glucocorticoid-induced TNFR-related (GITR) protein, lymphotoxin-beta receptor (LTβR), toll-like receptors (TLR), tumor necrosis factor-related apoptosis-inducing ligand-receptor 1 (TRAIL receptor 1) and TRAIL receptor 2, prostate-specific membrane antigen (PSMA) protein, prostate stem cell antigen (PSCA) protein, tumor-associated protein carbonic anhydrase IX (CAIX), epidermal growth factor receptor 1 (EGFR1), EGFRvIII, human epidermal growth factor receptor 2 (Her2/neu; Erb2), ErbB3 also known as HER3, Folate receptor, ephrin receptors, PDGFRa, ErbB-2, CD20, CD22, CD30, CD33, CD40, CD37, CD3ε, CD70, CD74, CD40), CD80, CD86, CD2, p53, cMet also known as tyrosine-protein kinase Met or hepatocyte growth factor receptor (HGFR), MAGE-A1, MAGE-A2, MAGE-A3, MAGE-A4, MAGE-A6, MAGE-A10, MAGE-A12, BAGE, DAM-6,-10, GAGE-1,-2,-8, GAGE-3,-4,-5,-6,-7B, NA88-A, NY-ESO-1, BRCA1, BRCA2, MART-1, MC1R, Gp100, PSA, PSM, Tyrosinase, Wilms' tumor antigen (WT1), TRP-1, TRP-2, ART-4, CAMEL, Cyp-B, hTERT, hTRT, iCE, MUC1, MUC2, P-cadherin, Myostatin (GDF8), Cripto (TDGF1), MUC5AC, PRAME, P15, RU1, RU2, SART-1, SART-3, WT1, AFP, β-catenin/m, Caspase-8/m, CDK-4/m, ELF2M, GnT-V, G250, HSP70-2M, HST-2, KIAA0205, MUM−1, MUM−2, MUM−3, Myosin/m, RAGE, SART-2, TRP-2/INT2, 707-AP, Annexin II, CDC27/m, TPI/mbcr-abl, ETV6/AML, LDLR/FUT, Pml/RARa, TEL/AML1, CD28, CD137, CanAg, Mesothelin, DR5, PD-1, PD1L, IGF-1R, CXCR4, Neuropilin 1, Glypicans, EphA2, CD138, B7-H3, B7-H4, gpA33, GPC3, SSTR2, ROR1, 5T4, or a VEGF-R2. In some embodiments, a TAA comprises a PSMA, CD30, B7-H3, B7-H4, gpA33, HER2, P-cadherin, gp100, DR5, GPC3, SSTR2, Mesothelin, ROR1, 5T4, Folate receptor, or an EGFR. In some embodiments, a TAA is selected from the group consisting of a PSMA, an ROR1, a 5T4, and an EGFR. These and other tumor proteins or tumor associated proteins are known to the skilled artisan.

In certain embodiments, the first or second binding domain, or both the first and second binding domain specifically binds to an antigen target that is associated with a disease condition. The disease condition may include a physiological condition, a pathological condition and a cosmetic condition. Examples of illustrative conditions include, without limitation, cancer, inflammatory disorders, allograft transplantation, type I diabetes, type II diabetes, and multiple sclerosis.

In some embodiments, the specific structural components of a precursor tri-specific antibody construct comprise a first and second binding domain, for example but not limited to an scFv fragment, a third binding domain, for example but not limited to an Fab fragment, linker regions, and a first and second sub-regulatory domain, where said regulatory domains may each comprise a protease cleavable domain and an HSA polypeptide sequence or a protease cleavable domain and a CAP component, and linkers, or any combination thereof, as have been described herein detail.

In some embodiments, a precursor tri-specific antibody construct comprises two polypeptides. In some embodiments, these polypeptides may be identified based on the Heavy chain (HC) or Light chain (LC) components based of the third binding domain. In some embodiments, these polypeptides may be identified as polypeptide A and polypeptide B. In some embodiments, polypeptide A comprises a HC polypeptide and polypeptide B comprises a LC polypeptide. In other embodiments, polypeptide A comprises a LC polypeptide and polypeptide B comprises a HC polypeptide.

In some embodiments, a precursor tri-specific antibody construct described herein, comprises a third binding domain comprising a variable heavy chain (VH) region and a variable light chain (VL) region; wherein a first binding domain is located C-terminally to said CL or said CH1 region of the third binding domain; wherein when said first binding domain is located C-terminally to said CL region, said second binding domain is located C-terminally to said CH1 region, and when said first binding domain is located C-terminally to said CH1 region, said second binding domain is located C-terminally to said CL region. In some embodiments, a precursor tri-specific antibody construct described herein, comprises a third binding domain comprising a variable heavy chain (VH) region and a variable light chain (VL) region;

wherein said first and second binding domains are located as described above, and wherein said first sub-regulatory domain, comprising said HLP domain located N-terminally to said protease cleavage domain, is located N-terminally to said VH region or to said VL region of said third binding domain;

wherein (a) when said first sub-regulatory domain is located N-terminally to said VL region, said second sub-regulatory domain, comprising said CAP component located N-terminally to said protease cleavage domain, is located N-terminally to said VH region, and (b) when said first sub-regulatory domain is located N-terminally to said VH region, said second sub-regulatory domain comprising said CAP component located N-terminally to said protease cleavage domain, is located N-terminally to said VL region.

For clarity in the following schematic descriptions, the first and second anti-TAA binding sites will be represented by the term "TAA" and the anti-CD3 third binding site will be represented by the term "CD3".

In some embodiments, a precursor tri-specific antibody construct described herein, comprises two polypeptides, polypeptide A and polypeptide B, wherein polypeptide A comprises components having an order N-terminal to C-terminal: HLP domain, protease cleavage domain, CD3 third binding domain VH-CH1 region, first binding domain (VL-VH); and polypeptide B comprises components having an order N-terminal to C-terminal: CAP component, protease cleavage domain, CD3 third binding domain VL-CL region, second binding domain (VL-VH). In some embodiments, a precursor tri-specific antibody construct described herein comprises two polypeptides as follows (order is N-terminal to C-terminal):

Polypeptide A: HLP-L-CP-L-CD3VH-L-CD3CH1-L-TAA VL-L-TAA VH

Polypeptide B: CAP-L-CP-L-CD3VL-L-CD3CL-L-TAA VL-L-TAA VH, wherein "L" is a linker, which may or may not be present in each embodiment.

In some embodiments, a precursor tri-specific antibody construct described herein, comprises two polypeptides, polypeptide A and polypeptide B, wherein polypeptide A comprises components having an order N-terminal to C-terminal: HLP domain, protease cleavage domain, CD3 third binding domain VH-CH1 region, first binding domain (VH-VL); and polypeptide B comprises components having an order N-terminal to C-terminal: CAP component, protease cleavage domain, CD3 third binding domain VL-CL region, second binding domain (VL-VH). In some embodiments, a precursor tri-specific antibody construct described herein comprises two polypeptides as follows (order is N-terminal to C-terminal)

Polypeptide A: HLP-L-CP-L-CD3VH-L-CD3CH1-L-TAA VH-L-TAA VL

Polypeptide B: CAP-L-CP-L-CD3VL-L-CD3CL-L-TAA VL-L-TAA VH, wherein "L" is a linker, which may or may not be present in each embodiment (FIG. 1).

In some embodiments, a precursor tri-specific antibody construct described herein, comprises two polypeptides, polypeptide A and polypeptide B, wherein polypeptide A comprises components having an order N-terminal to C-terminal: HLP domain, protease cleavage domain, CD3 third binding domain VH-CH1 region, first binding domain (VH-VL); and polypeptide B comprises components having an order N-terminal to C-terminal: CAP component, protease cleavage domain, CD3 third binding domain VL-CL region, second binding domain (VH-VL). In some embodiments, a precursor tri-specific antibody construct described herein comprises two polypeptides as follows (order is N-terminal to C-terminal)

Polypeptide A: HLP-L-CP-L-CD3VH-L-CD3CH1-L-TAA VH-L-TAA VL

Polypeptide B: CAP-L-CP-L-CD3VL-L-CD3CL-L-TAA VH-L-TAA VL, wherein "L" is a linker, which may or may not be present in each embodiment.

In some embodiments, a precursor tri-specific antibody construct described herein, comprises two polypeptides, polypeptide A and polypeptide B, wherein polypeptide A comprises components having an order N-terminal to C-terminal: HLP domain, protease cleavage domain, CD3 third binding domain VH-CH1 region, first binding domain (VL-VH); and polypeptide B comprises components having an order N-terminal to C-terminal: CAP component, protease cleavage domain, CD3 third binding domain VL-CL region, second binding domain (VH-VL). In some embodiments, a precursor tri-specific antibody construct described herein comprises two polypeptides as follows (order is N-terminal to C-terminal)

Polypeptide A: HLP-L-CP-L-CD3VH-L-CD3CH1-L-TAA VL-L-TAA VH

Polypeptide B: CAP-L-CP-L-CD3VL-L-CD3CL-L-TAA VH-L-TAA VL, wherein "L" is a linker, which may or may not be present in each embodiment.

The above four constructs provide non-limiting examples of tri-specific precursor antibody constructs wherein the position of VL and VH within an scFv of a first or second binding region is alternated. A skilled artisan would appreciate these alternate positions would also be comprised in the following embodiments, where the scFv is represented as VL-VH in order to illustrate other alternative non-limiting combinations of components.

In some embodiments, a precursor tri-specific antibody construct described herein, comprises two polypeptides, polypeptide A and polypeptide B, wherein polypeptide A comprises components having an order N-terminal to C-terminal: CAP domain, protease cleavage domain, CD3 third binding domain VH-CH1 region, first binding domain (VL-VH); and polypeptide B comprises components having an order N-terminal to C-terminal: HLP component, protease cleavage domain, CD3 third binding domain VL-CL region, second binding domain (VL-VH). In some embodiments, a precursor tri-specific antibody construct described herein comprises two polypeptides as follows (order is N-terminal to C-terminal)

Polypeptide A: CAP-L-CP-L-CD3VH-L-CD3CH1-L-TAA VL-L-TAA VH

Polypeptide B: HLP-L-CP-L-CD3VL-L-CD3CL-L-TAA VL-L-TAA VH, wherein "L" is a linker, which may or may not be present in each embodiment.

The above construct provides a non-limiting example of a tri-specific precursor antibody construct wherein the position of the two regulatory domains is alternated. The skilled artisan would appreciate these alternate positions could also be comprised in other embodiments, where the regulatory domain positions is represented as HLP domain being a component of the HC and CAP being a component of the LC, and the scFv is represented as VL-VH, in order to illustrate other alternative non-limiting combinations of components.

In some embodiments, a precursor tri-specific antibody construct described herein, comprises two polypeptides, polypeptide A and polypeptide B, wherein polypeptide A comprises components having an order N-terminal to C-terminal: HLP domain, protease cleavage domain, CD3 third binding domain VL-CL region, first binding domain (VL-VH); and polypeptide B comprises components having an order N-terminal to C-terminal: CAP component, protease cleavage domain, CD3 third binding domain VH-CH1 region, second binding domain (VL-VH). In some embodiments, a precursor tri-specific antibody construct described herein comprises two polypeptides as follows (order is N-terminal to C-terminal)

Polypeptide A: HLP-L-CP-L-CD3VL-L-CD3CL-L-TAA VH-L-TAA VL

Polypeptide B: CAP-L-CP-L-CD3VH-L-CD3CH1-L-TAA VH-L-TAA VL, wherein “L” is a linker, which may or may not be present in each embodiment.

A skilled artisan would appreciate that the designations “Polypeptide A” and “Polypeptide B” are merely names indicating two heterologous polypeptide chains, and as such the names themselves may be interchanged or change, e.g., Polypeptide 1 and Polypeptide 2. Further, encompassed by this terminology are two structurally different polypeptide chains that together form a precursor tri-specific antibody construct, as described herein. Further, the skilled artisan would appreciate the modular nature of the precursor constructs described herein, wherein modules may be substituted one for another, wherein they provide similar or different activities. For example, but not limited to, an ScFv may have to order N-terminus to C-terminus VL-VH or VH-VL; or a regulatory domain may comprise a CAP component or a HLP domain.

The order of the components may be alternated as shown in the non-limiting examples above, wherein in some embodiments, the first or second sub-regulatory domains are components of either the HC or LC and may be positioned N-terminal to the third binding domain, and the first or second binding domains comprises scFv, wherein the components of the scFv (VL, L, and VH) are independently ordered VL-L-VH or VH-L-VL, are positioned C-terminal to the third binding domain, and are components of either the HC or LC, respectively.

A skilled artisan would appreciate that different regulatory domains may be included with a precursor construct depending on the desired functionality of the precursor construct. For example, a tri-specific precursor construct may comprise just a single regulatory domain, either an HLP domain or a CAP domain (See FIGS. 2C and 2D, respectively).

In certain embodiments, a first or second binding domain, or both a first and second binding domain, or a first or second sub-regulatory domain, or both a first and second sub-regulatory domain, or a combination thereof are linked directly to the respective termini of the VH-CH1 or VL-CL of the third binding domain, e.g., an Fab (i.e., with no additional amino acids added between). In other embodiments, the linking with the third binding domain, e.g., an Fab, comprises use of a linker as described above (with additional amino acids as described below). In some embodiments, it may be necessary to delete several amino acids (e.g., from 1-3 amino acids or from 1-10 amino acids; e.g., 1, 2, 3, 4, 5, 6, 7, 8, 9, or 10 amino acids) from the C-terminus of a given first or second binding domain or both, and/or a first or second sub-regulatory domain or both, depending on the third binding domain target and the surrounding space of the first and second binding domain targets on the cell surface (i.e., for example, accessibility of the CD3 epsilon target on the cell surface of a T-cell).

In other embodiments, it may be necessary to delete several amino acids (e.g., from 1-3 amino acids or from 1-10 amino acids; e.g., 1, 2, 3, 4, 5, 6, 7, 8, 9, or 10 amino acids) from the N-terminus of the heavy and/or light chain of the third binding domain. In yet further embodiments, it may be necessary to delete several amino acids (e.g., from 1-3 amino acids or from 1-10 amino acids; e.g., 1, 2, 3, 4, 5, 6, 7, 8, 9, or 10 amino acids) from the N-terminus of the first or second binding domains or both, and/or the C-terminus of the first or second sub-regulatory domains or both, and at the same time, to delete several amino acids (e.g., from 1-3 amino acids or from 1-10 amino acids; e.g., 1, 2, 3, 4, 5, 6, 7, 8, 9, or 10 amino acids) from the N-terminus and/or C-terminus of a third binding domain chain (VH-CH1 or VL-CL). The length and the sequence of the junction between a first or second binding domain, and/or a first or second sub-regulatory domain, and the third binding domain VH-CH1 and VL-CL chains can be the same or different.

The junction between the first or second binding domain or both, and/or the first or second sub-regulatory domain or both, and the third binding domain VH-CH1 and VL-CL chains may make use of a combination of deletions and linkers as needed. As would be understood by the skilled artisan, the junction between the third binding domain VH-CH1 and VL-CL chains and the first or second binding domain or both and/or the first or second sub-regulatory domain or both, can be adjusted accordingly and tested for desired functionality (e.g., binding affinity, T-cell activity) using methods known in the art and described herein.

As described herein, junctions between domain or between components within domains comprises linkers. In some embodiments, a linker is present between domains. In some embodiments, there is not a linker between domains. In some embodiments, a linker is present between components that comprise a domain. In some embodiments, there is not a linker between components that comprise a domain.

FIGS. 1 and 2A-2D, and 2F show graphically where linkers may exist in an embodiment of precursor tri-specific antibody constructs disclosed herein.

In some embodiments, the linker between a first or second binding domain or both and a third binding domain VH-CH1 or VL-CL is 1-10 amino acids long. In other embodiments, the linker between a first or second binding domain or both, and a third binding domain VH-CH1 or VL-CL is 1-20 or 20 amino acids long. In this regard, the linker may be 1, 2, 3, 4, 5, 6, 7, 8, 9, 10, 11, 12, 13, 14, 15, 16, 17, 18, 19 or 20 amino acids long. In further embodiments, the linker may be 21, 22, 23, 24, 25, 26, 27, 28, 29 or 30 amino acids long.

In some embodiments, the linker between a first or second sub-regulatory domain or both and a third binding domain VH-CH1 or VL-CL is 1-10 amino acids long. In other embodiments, the linker between a first or second sub-regulatory domain or both, and a third binding domain VH-CH1 or VL-CL is 1-20 or 20 amino acids long. In this regard, the linker may be 1, 2, 3, 4, 5, 6, 7, 8, 9, 10, 11, 12, 13, 14, 15, 16, 17, 18, 19 or 20 amino acids long. In further embodiments, the linker may be 21, 22, 23, 24, 25, 26, 27, 28, 29 or 30 amino acids long.

In some embodiments, the linker between components within a first or second binding domain or both is 1-10 amino acids long. In other embodiments, the linker between components within a first or second binding domain or both is 1-20 or 20 amino acids long. In this regard, the linker between components may be 1, 2, 3, 4, 5, 6, 7, 8, 9, 10, 11, 12, 13, 14, 15, 16, 17, 18, 19 or 20 amino acids long. In further embodiments, the linker between components may be 21, 22, 23, 24, 25, 26, 27, 28, 29 or 30 amino acids long.

In some embodiments, the linker between components within a first or second sub-regulatory domain or both is 1-10 amino acids long, wherein it should be understood that a linker between different components need not be the same length. In other embodiments, the linker between components within a first or second sub-regulatory domain or both is 1-20 or 20 amino acids long, wherein it should be understood that a linker between different components need not be the same length. In this regard, the linker between each set of components may be 1, 2, 3, 4, 5, 6, 7, 8, 9, 10, 11, 12, 13, 14, 15, 16, 17, 18, 19 or 20 amino acids long. In further embodiments, the linker between each set of components may be 21, 22, 23, 24, 25, 26, 27, 28, 29 or 30 amino acids long.

In some embodiments, there are linkers between components within an HC or LC Fab polypeptide components VH and CH1, and polypeptide components VL and CL, respectively. In some embodiments, a linker is 1-10 amino acids long, wherein it should be understood that a linker between different components need not be the same length. In other embodiments, the linker between components within a third binding domain is 1-20 or 20 amino acids long, wherein it should be understood that a linker between different components need not be the same length. In this regard, the linker between each set of components may be 1, 2, 3, 4, 5, 6, 7, 8, 9, 10, 11, 12, 13, 14, 15, 16, 17, 18, 19 or 20 amino acids long. In further embodiments, the linker between each set of components may be 21, 22, 23, 24, 25, 26, 27, 28, 29 or 30 amino acids long.

In certain embodiments, linkers suitable for use in the precursor constructs described herein are flexible linkers. Suitable linkers can be readily selected and can be of any of a suitable of different lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and may be 1, 2, 3, 4, 5, 6, or 7 amino acids.

In some embodiments, flexible linkers include glycine polymers (G) n, glycine-serine polymers (including, for example, (GS) n, (GSGGS) n (SEQ ID NO: 119) and (GGGS) n (SEQ ID NO: 120), where n is an integer of at least one), glycine-alanine polymers, alanine-serine polymers, and other flexible linkers known in the art. Glycine and glycine-serine polymers are relatively unstructured, and therefore may be able to serve as a neutral tether between components. Glycine accesses significantly more phi-psi space than even alanine and is much less restricted than residues with longer side chains (see Scheraga, Rev. Computational Chem. 11173-142 (1992)). In some embodiments, flexible linkers include, but are not limited to Gly-Gly-Ser-Gly (GGSG; SEQ ID NO: 121), Gly-Gly-Ser-Gly-Gly (GGSGG; SEQ ID NO: 122), Gly-Ser-Gly-Ser-Gly (GSGSG; SEQ ID NO: 123), Gly-Ser-Gly-Gly-Gly (GSGGG; SEQ ID NO: 124), Gly-Gly-Gly-Ser-Gly (GGGSG; SEQ ID NO: 125), Gly-Ser-Ser-Ser-Gly (GSSSG; SEQ ID NO: 126), and the like. The ordinarily skilled artisan will recognize that design of a precursor tri-specific antibody construct can include linkers that are all or partially flexible, such that the linker can include a flexible linker as well as one or more portions that confer less flexible structure to provide for a desired precursor tri-specific antibody construct structure.

In some embodiments, a flexible linker used in a precursor construct comprises any flexible linker known in the art. In some embodiments, a flexible linker comprises a flexible unstructured linker. Linkers known in the art have been describe at least in Chengcheng Liu, Ju Xin Chin, Dong-Yup Lee; SynLinker: an integrated system for designing linkers and synthetic fusion proteins, Bioinformatics, Volume 31, Issue 22, 15 Nov. 2015, Pages 3700-3702; Fusion protein linkers: property, design and functionality Chen X et al, Adv Drug Deliv Rev. 2013 October;65 (10): 1357-69; The Linker Data base provided by The Centre for Integrative Bioinformatics vrije Universiteit Amsterdam; and the CSD Linker Database provided by The Cambridge Crystallographic Data Centre.

In certain embodiments, the linker between the third binding domain and the first or second binding domain or both, or the first or second sub-regulatory domain or, or both binding and regulatory domains is a stable linker (not cleavable by protease, especially MMPs). In certain embodiments, the linker is a peptide linker.

In some embodiments, the linker between the third binding domain VH-CH1 or VL-CL chains and a first or second sub-regulatory domain or both, comprises a protease substrate cleavage sequence, for example, an MMP substrate cleavage sequence. In some embodiments, the linker between the third binding domain VH-CH1 or VL-CL chains and a first or second sub-regulatory domain or both, comprises a protease substrate cleavage sequence, for example, an MMP2/9, uPA, matriptase, and legumain substrate cleavage sequence. A peptide sequence of SEQ ID NO: 9 in a substrate can be cleaved by most MMPs. A peptide sequence of SEQ ID NO: 35 in a substrate can be cleaved by MMP2/9, uPA, matriptase, and legumain.

A protease substrate cleavage sequence refers to a peptide sequence that can be cleaved by protease treatment. An MMP substrate sequence refers to a peptide sequence that can be cleaved by incubation with a MMP. SEQ ID NO: 9 is a commonly used MMP substrate cleavage sequence (see e.g., Jiang, PNAS (2004) 101:17867-72; Olson, PNAS (2010) 107:4311-6). In another embodiment, the protease cleavage site is recognized by MMP-2, MMP-9 or a combination thereof. In yet another embodiment, the protease site comprises the sequence selected from the group consisting of (SEQ ID NO: 9, SEQ ID NO: 10, SEQ ID NO: 11, and SEQ ID NO: 35). In a further embodiment, the protease site comprises the sequence set forth in SEQ ID NO: 35.

In some embodiments, all of the protease sites comprise the same proteolytic sequence. In other embodiments, the protease sites of a precursor construct differ. Differences of the proteolytic sequences within a precursor construct may provide for additional regulation of function of the precursor or partially activated construct.

A stable linker or a protease non-cleavable linker refers to a linker peptide sequence that does not belong to the known protease substrate sequences and thus does not lead to significant cleavage product formation upon incubation with a protease.

In some embodiments, the cleavage substrate (or cleavage sequence or protease cleavage domain) of the linker may include an amino acid sequence that can serve as a substrate for a protease, usually an extracellular protease. In other embodiments, the cleavage sequence comprises a cysteine-cysteine pair capable of forming a disulfide bond, which can be cleaved by action of a reducing agent. In other embodiments the cleavage sequence comprises a substrate capable of being cleaved upon photolysis.

The cleavage substrate is positioned in the linker such that when the cleavage substrate is cleaved by a cleaving agent (e.g., a cleavage substrate of a linker is cleaved by the protease and/or the cysteine-cysteine disulfide bond is disrupted via reduction by exposure to a reducing agent) or by light-induced photolysis, in the presence of a target, resulting in cleavage products having various functional properties as described herein.

The cleavage substrate of a linker may be selected based on a protease that is co-localized in the diseased tissue, or on the surface of the cell that expresses the target antigen of interest of a binding domain of a fusion moiety. A variety of different conditions are known in which a target of interest is co-localized with a protease, where the substrate of the protease is known in the art. In the example of cancer, the target tissue can be a cancerous tissue, particularly cancerous tissue of a solid tumor. There are reports in the literature of increased levels of proteases having known substrates in a number of cancers, e.g., solid tumors. (See, e.g., La Rocca et al, (2004) British J. of Cancer 90 (7): 1414-1421). Non-limiting examples of disease include: all types of cancers (breast, lung, colorectal, prostate, head and neck, pancreatic, etc), rheumatoid arthritis, Crohn's disease, melanomas, SLE, cardiovascular damage, ischemia, etc. Furthermore, anti-angiogenic targets, such as VEGF, are known. As such, where the binding domains of a fusion moiety of the precursor tri-specific antibody construct of the present disclosure is selected such that it is capable of binding a TAA, a suitable cleavage substrate sequence for a protease cleavable linker will be one which comprises a peptide substrate that is cleavable by a protease that is present at the cancerous treatment site, particularly that is present at elevated levels at the cancer treatment site as compared to non-cancerous tissues.

In some embodiments, the first or second binding domain or both of a precursor tri-specific antibody construct can bind, e.g., Her2, and the cleavage substrate sequence can be a matrix metalloprotease (MMP) substrate, and thus is cleavable by an MMP. In other embodiments, the first or second binding domain or both of a fusion moiety in the precursor tri-specific antibody construct can bind a target of interest or two targets of interest, and the cleavage substrate present in the linker can be, for example, legumain, plasmin, TMPRSS-3/4, MMP-9, MT1-MMP, cathepsin, caspase, human neutrophil elastase, beta-secretase, uPA, or PSA. In other embodiments, the first or second binding domain or both of a fusion moiety in the precursor tri-specific antibody construct can bind a target of interest or two targets of interest, and the cleavage substrate present in the linker can be, for example, a combination of MMP2/9, legumain, uPA, and matriptase. In some embodiments, the first or second binding domain or both of a fusion moiety in the precursor tri-specific antibody construct can bind a target of interest or two targets of interest, and the cleavage substrate present in the linker comprises a combination of MMP2/9, legumain, uPA, and matriptase as set forth in SEQ ID NO: 35. In other embodiments, the cleave substrate is cleaved by other disease-specific proteases, in diseases other than cancer such as multiple sclerosis or rheumatoid arthritis.

The unmodified or uncleaved linker can allow for tethering the binding domains (first, second, or third, or a combination thereof) and regulatory domains (first or second, or both).

The linkers of the precursor tri-specific antibody construct (e.g., the linker between the CH1 or CL of the third binding domain and a first or second binding domain or both, and the linker between the VH or VL of the third binding domain and a first or second sub-regulatory domain or both, can comprise the same cleavage substrate or may comprise different cleavage substrates, e.g., the first linker may comprise a first cleavage substrate and the second linker may comprise a second cleavage substrate, etc. The cleavage substrates can be different substrates for the same enzyme (for example exhibiting different binding affinities to the enzyme), or different substrates for different enzymes, or one of the cleavage substrates can be an enzyme substrate and another of the cleavage substrate can be a photolysis substrate, or another cleavage substrate can be a substrate for reduction, or any combination thereof.

In some embodiments, some of the linkers may be non-cleavable while the others of the linkers are cleavable linker. For example, but not limited to the linkers between the Fab CH1 and CL and the first and second binding domain are non-cleavable, while the linkers between the Fab VH and VL and the first and second sub-regulatory domains are cleavable. A skilled artisan would appreciate that there are a limited number of combinations of the linkers, and in some embodiments, each linker may be cleavable or non-cleavable. Thus, in some embodiments, a linker between the third binding domain and a first or second sub-regulatory domain or both is cleavable while the linker between the third binding domain and the first or second binding domain or both is not cleavable.

For specific cleavage by an enzyme, contact between the enzyme and the cleavage substrate is made. When the precursor tri-specific antibody construct is present within a microenvironment comprising sufficient enzyme activity, the cleavage substrate can be cleaved. Sufficient enzyme activity can refer to the ability of the enzyme to make contact with the linker having the cleavage substrate and effect cleavage. It can readily be envisioned that an enzyme may be in the vicinity of the precursor tri-specific antibody construct but unable to cleave because of other cellular factors or protein modification of the enzyme.

In some embodiments, substrates can include but are not limited to substrates cleavable by one or more of the following enzymes or proteases: ADAM10; Caspase 8, Cathepsin S, MMP 8, ADAM12, Caspase 9, FAP, MMP 9, ADAM17, Caspase 10, Granzyme B, MMP-13, ADAMTS, Caspase 11, Guanidinobenzotase (GB), MMP 14, ADAMTS5. Caspase 12, Hepsin, MT-SP1, BACE, Caspase 13, Human Neutrophil Elastase Neprilysin (HNE), Caspases, Caspase 14, Legumain, NS3/4A, Caspase 1, Cathepsins, Matriptase 2, Plasmin, Caspase 2, Cathepsin A, Meprin, PSA, Caspase 3, Cathepsin B, MMP 1, PSMA, Caspase 4, Cathepsin D, MMP 2, TACE, Caspase 5, Cathepsin E, MMP 3, TMPRSS 3/4, Caspase 6, Cathepsin K, MMP 7, uPA, Caspase 7, Matripase (MT-SP1, TADG-15, epithin, ST14), and MT1-MMP.

In other embodiments, the cleavage substrate can involve a disulfide bond of a cysteine pair, which is thus cleavable by a reducing agent such as, for example, but not limited to a cellular reducing agent such as glutathione (GSH), thioredoxins, NADPH, flavins, ascorbate, and the like, which can be present in large amounts in tissue of or surrounding a solid tumor.

Other appropriate protease cleavage sites for use in the cleavable linkers herein are known in the art or may be identified using methods such as those described by Turk et al., 2001 Nature Biotechnology 19, 661-667.

In certain embodiments, the linker can be a peptide linker, a thiol residue-containing peptide linker, such as a cysteine residue, a polymer linker or a chemical linker. In certain embodiments, the precursor tri-specific antibody construct comprises a linker where one end of the linker is covalently linked to the N-terminal of a first or second binding domain or both fusion moiety, and the other end of the linker is covalently linked to the C-terminal of the CH1 or CL of the third binding domain.

In some embodiment, there is just one or a few amino acids between domains or components within domains. In certain embodiments, there may be one or a few amino acid residues between two domains of a precursor tri-specific antibody construct, such as between a binding domain and a linker polypeptide, such as amino acid residues resulting from construct design of the precursor construct (e.g., amino acid residues resulting from the use of a restriction enzyme site during the construction of a nucleic acid molecule encoding the polypeptide chains (polypeptide A and polypeptide B). As described herein, such amino acid residues may be referred to "junction amino acids" or "junction amino acid residues", or "peptide linkers".

In certain illustrative embodiments, a peptide linker is between 1 to 5 amino acids, between 5 to 10 amino acids, between 5 to 25 amino acids, between 5 to 50 amino acids, between 10 to 25 amino acids, between 10 to 50 amino acids, between 10 to 100 amino acids, or any intervening range of amino acids. In other illustrative embodiments, a peptide linker comprises about 1, 5, 10, 15, 20, 25, 30, 35, 40, 45, 50 or more amino acids in length.

Such junctional amino acids link any of the domains or components within domain of the precursor tri-specific antibody construct. In certain embodiments, the junctional amino acid(s) is a hinge, or a part of a hinge as defined herein. In certain embodiments, a variable region linking sequence useful for connecting a heavy chain variable region to a light chain variable region may be used as a peptide linker.

In one illustrative embodiment, peptide linker sequences contain, for example, Gly, Asn and Ser residues. Other near neutral amino acids, such as Thr and Ala, may also be included in the linker sequence.

Other amino acid sequences which may be usefully employed as linkers include those disclosed in Maratea et al., Gene 40:39 46 (1985); Murphy et al., Proc. Natl. Acad. Sci. USA 83:8258 8262 (1986); U.S. Pat. Nos. 4,935,233 and 4,751,180, incorporated herein in their entirety.

Other illustrative linkers may include, for example, Glu-Gly-Lys-Ser-Ser-Gly-Ser-Gly-Ser-Glu-Ser-Lys-Val-Asp (EGKSSGSGSESKVD; SEQ ID NO: 127) (Chaudhary et al., 1990, Proc. Natl. Acad. Sci. U.S.A. 87:1066-1070) and Lys-Glu-Ser-Gly-Ser-Val-Ser-Ser-Glu-Gln-Leu-Ala-Gln-Phe-Arg-Ser-Leu-Asp (KESGSVSSEQLAQFRSLD; SEQ ID NO: 128) (Bird et al., 1988, Science 242:423-426).

In some embodiments, linker sequences are not required when the HC and LC polypeptides (polypeptides A and B) have non-essential N-terminal amino acid regions that can be used to separate the functional domains and prevent steric interference. Coding sequences or domains of the precursor tri-specific antibody construct of the present disclosure can be fused directly without any junctional amino acids or by using a flexible polylinker composed, for example, of the pentamer Gly-Gly-Gly-Gly-Ser (GGGGS; SEQ ID NO: 129) repeated 1 to 3 times. Such a linker has been used in constructing single chain antibodies (scFv) by being inserted between VH and VL (Bird et al., 1988, Science 242:423-426; Huston et al., 1988, Proc. Natl. Acad. Sci. U.S.A. 85:5979-5883).

A peptide linker, in certain embodiments, is designed to enable the correct interaction between two beta-sheets forming the variable region of the single chain antibody. Any suitable linkers can be used to make an indirect link, such as without limitation, peptide linker, polymer linker, and chemical linker. In certain embodiments, the covalent link is an indirect link through a peptide linker.

A distinguishing characteristic of the precursor tri-specific antibody construct, as described herein, is that the precursor construct does not depend on steric hindrance to reduce or inhibit the binding affinity of the third binding domain. In the case of the precursor constructs described herein, reduction or inhibition of binding affinity is due to specific binding between a CAP component and a third binding domain of the precursor construct. On the contrary, the proteins described in US 2012/0321626 depend solely on three-dimensional structure for reduced specificity, wherein the polypeptides may or may not form such a three-dimensional structure, and thus they lack any specificity for the reduction or inhibition of binding to the antibody target of the second binding region. Further distinguishing characteristics in comparison with other multi- or tri-specific antibodies that include a mask, is that the reduction or inhibition of binding to a target of the third binding domain by precursor tri-specific antibody construct, may also be temporally controlled, wherein reduction or inhibition of binding to a target of the third binding domain may be maintained when the precursor construct is in circulation in vivo or within a non-tumor microenvironment. This may reduce negative side effects caused by the use of multi- or bi-specific antibodies lacking this temporal regulation.

In some embodiments, precursor tri-specific antibody constructs of the present disclosure comprise a Polypeptide A (HC polypeptide) comprising the amino acid sequences set forth in SEQ ID NO:130, or a homologue thereof; and a Polypeptide B (LC polypeptide) comprising the amino acid sequence set forth in SEQ ID NO: 131. In some embodiments, precursor tri-specific antibody constructs of the present disclosure comprise a Polypeptide A (HC polypeptide) comprising the amino acid sequences set forth in SEQ ID NO:132, or a homologue thereof; and a Polypeptide B (LC polypeptide) comprising the amino acid sequence set forth in SEQ ID NO: 133.

In some embodiments, precursor tri-specific antibody constructs of the present disclosure comprise a Polypeptide A (HC polypeptide) encoded by the nucleotide sequence set forth in SEQ ID NO: 142, or a homologue thereof; and comprise a Polypeptide B (LC polypeptide) encoded by the nucleotide sequence set forth in SEQ ID NO: 143. In some embodiments, precursor tri-specific antibody constructs of the present disclosure comprise a Polypeptide A (HC polypeptide) encoded by the nucleotide sequence set forth in SEQ ID NO: 144, or a homologue thereof; and comprise a Polypeptide B (LC polypeptide) encoded by the nucleotide sequence set forth in SEQ ID NO: 145.

Functionality of Precursor Tri-specific Antibody Constructs

In some embodiments, a precursor tri-specific antibody construct disclosed herein possesses many unique features and these features can be utilized to develop human therapeutics with desirable attributes in drug safety, efficacy and manufacturability. In some embodiments, the precursor tri-specific antibody constructs of this disclosure comprising a first and a second binding domain binding to cell surface tumor associated antigens (TAA), a third binding domain binding to an extracellular epitope of human CD3 epsilon, and two regulatory domains, possesses many unique features and these features can be utilized to develop human therapeutics with desirable attributes in drug safety, efficacy and manufacturability. These features have been described in detail above and will not necessarily be repeated herein. A skilled artisan would appreciate that the uses as described herein below, include use of the many embodiments of precursor tri-specific antibody constructs as described above.

As described herein, the property of a precursor construct comprising a regulatable extended half-life, a regulatory reduction of T-cell binding (reduction of T-cell activation), or a combination thereof, may be used advantageously in the precursor tri-specific antibody construct of the present disclosure to mask T-cell binding until the precursor tri-specific antibody construct are in an appropriate microenvironment (e.g., in the vicinity of a tumor). In some embodiments, a pharmaceutical composition comprises a precursor tri-specific antibody construct, as described herein, and a pharmaceutically acceptable carrier.

A skilled artisan would recognize that in some embodiments, the term "precursor tri-specific antibody construct" may be used interchangeably with the term "drug" having all the same meanings and qualities. In some embodiments, a drug comprising a precursor tri-specific antibody construct comprises a pharmaceutical composition.

In some embodiments, a precursor tri-specific antibody disclosed herein comprises a first and a second binding domain binding to a TAA a third binding domain binding to an extracellular epitope of human CD3ε, and two regulatory domains. A precursor tri-specific antibody comprising a first and a second binding domain binding to a TAA, a third binding domain binding to an extracellular epitope of human CD3ε, and two regulatory domains comprising for example, a cleavable half-life prolonging domain comprising a protease cleavable domain and a human serum albumin (HSA) polypeptide (a first sub-regulatory domain), and a cleavable masking domain comprising a protease cleavable domain and a CAP region (a second sub-regulatory domain), provides unique properties as described throughout.

The precursor tri-specific antibody construct of the present disclosure functions to enhance drug stability, specificity, selectivity, potency, and safety and the convenience of drug administration. In certain embodiments, the third binding domain, when expressed without the regulatory domain comprising said CAP region and fused to its N-terminus (VH or VL chain), is able to bind to its target antigen in soluble recombinant form (usually the extracellular domain of a receptor protein, e.g., a T-cell receptor component such as CD3) as well as on the cell surface. In certain embodiments, the third binding domain, when expressed with a regulatory domain fused to its N-terminus (VL or VH chain) and comprising a CAP region, and a first and a second binding domain fused to the C-terminus (CL or CH1 chains), has no binding or has reduced binding to its specific antigen presented on a T cell surface at pharmacological concentrations of the drug (concentration of the polypeptide in treated patients) compared with a third binding domain present in a construct lacking a regulatory domain comprising a CAP region. Lack of binding or greatly reduced binding to a T cell surface antigen in the absence of the target antigen binding by a third binding domain may be explained by the dramatically reduced affinity resulting from the specific blocking of the antigen binding site by a CAP component.

Lack of binding or greatly reduced binding to cell surface antigen, for example an antigen on a T-cell, in the absence of the TAA target antigen binding by a first or second binding domain or both, may be viewed as a desirable property for use of a precursor tri-specific antibody construct as a human therapeutic. It is important to note that lack of binding or significantly reduced binding of the precursor tri-specific antibody construct alone (in the absence of tumor target cells) to, e.g., T-cell can, 1) dramatically improve the undesirable systematic T-cell activation, therefore to dramatically improve the drug safety profile; 2) dramatically improve the feasibility of subcutaneous route of drug administration; and 3) dramatically increase the drug tolerability of high drug concentration in blood circulation. Further, the regulatable temporal regulation provided by a second regulatory domain comprising a half-life prolonging component (e.g., an HSA polypeptide) of a precursor construct may ensure the extended presence of the precursor construct in circulation until such time as the drug is present in the environment of TAA target cells (e.g., tumor target cell microenvironment).

It is important to note that T-cell binding by antibodies such as OKT3 or UCHT-1 via conformational epitopes may transduce partial signaling, leading either to unwanted T-cell activation (causing cytokine storm) or T-cell anergy (resulting in T-cells unable to kill tumor cells). Mu-1F3, hu-1F3 and its variants binding to a linear epitope of CD3 is conceivably less likely to induce T-cell signaling in the absence of cross linking of the CD3. This property may be advantageous for reducing systemic side effects that occur when using OKT3 and UCHT-1 like antibodies.

It is also important to note that once a regulatory domain comprising a CAP region or a portion thereof comprising the CAP region in a precursor tri-specific antibody construct is cleaved by protease, its function such that the specific binding inhibition at the third antigen-binding site (e.g., CD3 epsilon binding site) is removed so that it can then bind to its target with high affinity, particularly target antigens expressed on the cell surface. Therefore, following cleavage at the cleavage substrate sequence in a protease cleavable linker (thereby releasing a regulatory domain comprising a CAP region and releasing a regulatory domain comprising a HLP) the precursor tri-specific antibody construct is converted into a more potent cross linker between tumor and T-cells (FIGS. 3A and 3B). In some embodiments, the regulatory domain comprising the HLP is not cleaved, yet the precursor construct is converted into a more potent cross linker between tumor and T-cells.

Similarly, once a regulatory domain comprising a CAP region able to associated with a first or second binding region in a precursor tri-specific antibody construct is cleaved by protease, its function such that the specific binding inhibition at the first or second antigen-binding site is removed so that it can then bind to its target with high affinity.

Furthermore, it is important to note that once a TAA first or second binding domain or both, binds to its target antigen, the precursor tri-specific antibody construct molecules become highly concentrated on a tumor cell surface to create high avidity based binding toward the third binding domain target (e.g. CD3) on T-cells. Therefore, only in the presence of the TAA first or second binding domain or both is the third antigen-binding domain able to bind its target, for precursor tri-specific antibody construct to function as a cross-linker between tumor and T-cells.

The properties of the precursor tri-specific antibody construct of the present disclosure allow for relatively high dose of the precursor tri-specific antibody construct in circulation for an enhanced period of time, without unwanted side-effects (e.g., the precursor tri-specific antibody construct does not bind to the third binding domain target antigen (e.g., CD3) when in circulation. This also allows for reduced dosing frequency and promotes tissue penetration by diffusion driven by concentration gradient.

The properties of the precursor tri-specific antibody construct of the present disclosure also allow the potential for the subcutaneous administration, which can enhance access to the target. Further, although in certain embodiments the precursor tri-specific antibody construct are permissive for cross-linking without protease treatment, in certain embodiments, the binding activity and the tumor killing potency increase dramatically after protease treatment.

In one embodiment, the third binding domain antigen binding domain formed by VH and VL is stabilized by the CH1 and CL heterodimerizing domain, and is further stabilized by the disulfide bond, or other stabilizing interaction (e.g., knobs/hole interaction), between CH1 and CL.

In some embodiments, the third binding domain in the precursor tri-specific antibody construct is specifically blocked by the CAP regulatory domain at its N-terminus, such that binding to the third binding domain target antigen (especially when cell surface target antigens are concerned) is specifically reduced or inhibited in a statistically significant manner (i.e., relative to an appropriate control as will be known to those skilled in the art; e.g., as compared to the same third binding domain in a format without a regulatory domain comprising a CAP component, at its N-termini (either VH and VL)). In a further embodiment, the third binding domain in the precursor tri-specific antibody construct is specifically blocked so that binding to the desirable antigen (especially when cell surface target antigens are concerned) is reduced by at least 2 fold, 3 fold, 4 fold, 5 fold, 6 fold, 7 fold, 8 fold, 9 fold, 10 fold, 11 fold, 12 fold, 13 fold, 14 fold, 15 fold, 20 fold, 30 fold, or 100 fold, or 1000 fold, or 10,000 fold as compared to the same third binding domain in a format without a regulatory domain comprising a CAP component at its N-terminus (either VH and VL).

In certain embodiments, the affinity of the third binding domain (e.g., CD3 epsilon antigen-binding domain) in the precursor construct is below 500 nM. In further embodiments, the affinity of the third binding domain antigen binding of a precursor construct demonstrates no significant detectible binding as measured using FACS or other binding measurement method (e.g., cell binding ELISA) at concentration ranges of the therapeutics used in humans. In one embodiment, less than 1% of a population of target cells (e.g., CD3+ cells) will be bound by the third binding domain of a precursor construct at a therapeutic concentration (this is in the absence of a tumor cell microenvironment). In one embodiment, less than 5% population of the target cells will be bound by the precursor tri-specific antibody construct at a therapeutic concentration. In yet another embodiment, less than 10% population of the target cells will be bound by the precursor tri-specific antibody construct at a therapeutic concentration.

The elevated level of proteases, especially MMPs, present in tumor tissues (tumor microenvironment) will generate cleavage products at the MMP substrate cleavage site of a protease cleavable linker. Because the cleavage of the protease substrate sequence of a linker results in the release of a CAP component that may be bound at the third binding domain antigen-binding region, the binding to the third binding domain cell surface target will be fully restored or at least partially restored. The restored binding can be demonstrated using techniques of FACS, cell-based ELISA) or other cell binding techniques known to the skilled person.

A skilled artisan would appreciate that the term "dramatically reduced affinity" may encompass at least 30% reduction in the binding of the third binding domain antigen-binding domain, as compared to the binding in the absence of a CAP component of a regulatory domain present at the N-terminus of the third binding domain. The percentage of reduction can be, for example without limitation, 30%, about 40%, about 50%, about 60%, about 70%, about 80%, about 90%, or about 99% or greater. Methods for detecting binding are known to the skilled person and can be performed using FACS, cell binding ELISA or cell binding using radio-isotype labeled antibodies.

An embodiment of a third binding domain for use in the precursor tri-specific antibody construct of the present disclosure as described herein is an anti-CD3 epsilon domain. In this regard, the precursor tri-specific antibody construct functions such that, when the TAA first binding domain or second TAA binding domain or both first and second binding domains binds to a tumor associated antigen, the precursor construct is present within a tumor microenvironment comprising proteases, wherein the cleavable regulatory domains are cleaved releasing a CAP anti-CD3 epsilon binding component such that the third binding domain is now able to bind to CD3 epsilon of passing T-cells, thereby redirecting the T-cells and activating them to kill the tumor cell or tumor associate cell. (FIG. 3B) In another embodiment, an activated tri-specific antibody construct (also referred to herein as activated tri-specific antibody construct (FIG. 2E) where the third binding domain fragment binds to an immune effector molecule, such as CD3 epsilon) can exhibit an avidity effect when clustered on tumor cell surface via TAA (e.g., tumor antigen) binding by the TAA first or second binding domain or both. As such, the apparent binding to immune cells by the third binding domain can increase due to avidity. As such, an activated tri-specific antibody construct becomes capable of bridging immune and tumor cells thereby mediating anti-tumor activity. Additionally, an activated Tr-specific antibody construct may have improved tumor penetration compared with the precursor construct, due to decreased size.

In certain embodiments, a precursor tri-specific antibody construct is separately bound to a TAA or two TAAs, and not bound to a CD3 epsilon, and thus the T-cells will not be activated. In some embodiments, this lack of binding to a CD3 epsilon antigen may be a result of the TAA(s) present on a non-tumor cell. In some embodiments, this lack of binding to a CD3 epsilon antigen may be the results of the TAA(s) present on a cell in a non-tumor microenvironment. As such, the precursor construct bound to a TAA(s) in a non-tumor environment and in certain embodiments, can therefore not be activated (i.e., there will be no cleavage of the regulatable domain comprising the CAP or a portion thereof. This avoids significant side effects and tissue damage that may occur were the precursor construct to activate T-cells in a non-tumor cell environment. However, within a tumor microenvironment, when the CD3 and tumor surface antigen are simultaneously bound to the activated tri-specific antibody construct and when multiple copies of the bound complexes are anchored and clustered on tumor cell surface, the T-cells are activated in the vicinity of cancer cells bearing the tumor surface antigen, and therefore significantly enhance the tumor killing efficiency of T-cells locally and avoid the side effects due to cytokine storm.

In certain embodiments, the combination of a third binding domain antigen target being CD3 epsilon and a first or second binding domain antigen or both target being a cell surface tumor associated antigen comprised within a precursor construct, which is temporally regulated by a half-life enhancing regulatory domain and activity regulated by a CAP regulatory domain, the combination of which provide for enhanced tumor killing effects by T-cells once the precursor construct has been located to a tumor microenvironment. In certain embodiments, the combination of the third binding domain antigen target and the first or second binding domain antigen target or both can be FcγR and TAA, respectively, which combination can induce FcγR-expressing immune cells to kill tumor cells once the precursor construct has been located to a tumor microenvironment.

Thus, in some embodiments, the precursor tri-specific antibody construct of the present disclosure comprises a third binding domain that binds to the TCR or a component thereof, such as a CD3 polypeptide. As noted above, the precursor tri-specific antibody construct of the present disclosure does not bind to the third binding domain target antigen except following a linker cleavage event, wherein a CAP component is release or in the absence of a CAP component comprised within the precursor construct.

Thus, in certain embodiments, a precursor tri-specific antibody construct of the present disclosure does not activate T-cells in the absence of target antigen engagement at the third binding domain. A precursor tri-specific antibody construct "does not or minimally or nominally activates T-cells" if the precursor tri-specific antibody construct does not cause a statistically significant increase in the percentage of activated T-cells as compared to activation of T-cells in the presence of cells expressing TAA first or second binding domain target antigens (e.g., an appropriate tumor cell/cell line; tumor micro-environment), as measured in at least one in vitro or in vivo assay. Such assays are known in the art and include, without limitation, proliferation assays, CTL chromium release assays (see e.g., Lavie et al., (2000) International Immunology 12 (4): 479-486), ELISPOT assays, intracellular cytokine staining assays, and others as described, for example, in Current Protocols in Immunology, John Wiley & Sons, New York, N.Y. (2009). In certain embodiments, T-cell activation is measured using an in vitro primed T-cell activation assay.

In a related aspect, therefore, the present disclosure provides a method for detecting T-cell activation induced by an activated precursor tri-specific antibody construct that comprises a first or second binding domain or both that specifically binds to a TAA, a third binding domain that specifically binds to a TCR complex, and two sub-regulatory domains, wherein the precursor construct is activated in the presence of a tumor microenvironment. In some embodiments, activation of a precursor construct comprises cleavage of a both sub-regulatory domains. In some embodiments, activation of a precursor construct comprises cleavage of one regulatory domain. In some embodiments, activation of a precursor construct comprises cleavage of a complete regulatory domain comprising a CAP component. In some embodiments, activation of a precursor construct comprises cleavage of a portion of a regulatory domain, wherein the portion of the regulatory domain comprises a CAP component. In some embodiments, activation of a precursor construct comprises cleavage of a complete regulatory domain comprising a HLP component. In some embodiments, activation of a precursor construct comprises cleavage of a portion of a regulatory domain, wherein the portion of the regulatory domain comprises a HLP component. In some embodiments, activation of a precursor construct comprises cleavage of both regulatory domains, one comprising a CAP component and the other comprising an HSA component.

In some embodiments, a method for detecting T-cell activation comprises (a) providing antigen or mitogen-primed T-cells, (b) treating the primed T-cells of step (a) with the precursor tri-specific antibody construct that comprises a third binding domain that specifically binds to a TCR complex or a component thereof (following exposure to a tumor microenvironment and cleavage of a regulatory CAP domain or a portion thereof), and (c) detecting activation of the primed T-cells that have been treated in step (b).

The term "mitogen" as used herein refers to a chemical substance that induces mitosis in lymphocytes of different specificities or clonal origins. Exemplary mitogens that may be used to prime T-cells include phytohaemagglutinin (PHA), concanavalin A (ConA), lipopolysaccharide (LPS), pokeweed mitogen (PWM), and phorbol myristate acetate (PMA). Antigen-loaded beads or PBMC can also be used to prime T-cells.

In certain embodiments of methods for detecting T-cell activation provided herein, the precursor tri-specific antibody construct comprising a third binding domain that specifically binds to a TCR complex or a component thereof comprises a first and a second binding domain that bind to tumor associated antigens or both or wherein one binds to two sub-regulatory domains, wherein one provides enhanced half-life prolonging properties, and the second provide reduction in T-cell binding properties, reduction in T-cell activation properties, or any combination thereof. In certain embodiments, methods for detecting T-cell activation provided herein, are performed in tumor and non-tumor microenvironments.

T-cell activation may be detected by measuring the expression of activation markers known in the art, such as CD25, CD40 ligand, and CD69. Activated T-cells may also be detected by cell proliferation assays, such as CFSE labeling and thymidine uptake assays (Adams (1969) Exp. Cell Res. 56:55). T-cell effector function (e.g., cell killing) can be measured, for example, by chromium release assays or FACS based assays using fluorescent dyes (e.g. TP3). In a related aspect, T-cell activation and cytolytic activity can be measured by lytic synapse formation between T-cell and tumor cell. Effector molecules such as Granzymes and porforin can be detected in the cytolytic synapse.

In another related aspect, T-cell activation may be measured by cytokine release. A method for detecting cytokine release induced by a precursor tri-specific antibody construct that comprises a third binding domain that specifically binds to a TCR complex or a component thereof, may comprise: (a) providing primed T-cells, (b) treating the primed T-cells of step (a) with the precursor tri-specific antibody construct that comprises a third binding domain that specifically binds to a TCR complex or a component thereof, (c) incubating the precursor construct in a tumor microenvironment e.g., with tumor cells associated with the antigen target of the TAA first or second binding domain or both, and (d) detecting release of a cytokine from the primed T-cells that have been treated in step (b). In some embodiments, experiments are carried out in the presence or absence of appropriate cancer cells or cell lines expressing target tumor antigens bound by binding domains present in the first or second binding domain or both of the precursor tri-specific antibody construct (step c).

In certain embodiments of methods for detecting cytokine release provided herein, the precursor tri-specific antibody construct that comprises a third binding domain that specifically binds to a TCR complex or a component thereof is performed in the presence or absence of appropriate cancer cells or cell lines expressing target tumor antigens bound by binding domains present in the first or second binding domain or both of the precursor tri-specific antibody construct In certain embodiments, the precursor tri-specific antibody construct of the present disclosure does not induce a cytokine storm or does not induce a cytokine release sufficient to induce toxic side-effects. A precursor tri-specific antibody construct "does not induce a cytokine storm" (also referred to as "inducing an undetectable, nominal, or minimal cytokine release" or "does not induce or induces a minimally detectable cytokine release") if, in the absence of TAA target cells or appropriate linker cleavage agents (such as proteases), it does not cause a statistically significant increase in the amount of at least one cytokine including Interferon (IFNγ).; In certain embodiments at least two cytokines including IFNγ and TNFα or IL-6 and TNFα.; in one embodiment three cytokines including IL-6, IFNγ and TNFα; in another embodiment four cytokines including IL-2, IL-6, IFNγ, and TNFα; and in yet a further embodiment at least five cytokines including IL-2, IL-6, IL-10,, IFNγ, and TNFα; released from treated cells in the absence of TAA target cells (e.g., an appropriate cancer cell line) or appropriate linker cleavage agents, as compared to from treated cells in the presence of appropriate TAA target cells or linker cleavage agents, in at least one in vitro or in vivo assay known in the art or provided herein. Clinically, cytokine-release syndrome is characterized by fever, chills, rash, nausea, and sometimes dyspnea and tachycardia, which is in parallel with maximal release of certain cytokines, such as IFNγ, as well as IL-2, IL-6, and TNFα. Cytokines that may be tested for release in an in vitro assay or in vivo include G-CSF, GM-CSF, IL-2, IL-4, IL-5, IL-6, IL-10, IL-13, IL-17, IP-10, KC, MCP1, IFNγ, and TNFα; and in another embodiment include IL-2, IL-6, IL-10, IFNγ, and TNFα.

In further embodiments, a precursor tri-specific antibody construct of the present disclosure causes an increase in calcium flux in cells, such as T-cells. A precursor tri-specific antibody construct causes an "increase in calcium" if, when used to activate T-cells in the presence of an appropriate TAA target cell (e.g., cancer cell) or linker cleavage agents, it causes a statistically significant, rapid increase in calcium flux of the treated cells (within 300 seconds, or within 200 seconds, or within 100 seconds of treatment) as compared to cells treated in the absence of an appropriate TAA target cell or linker cleavage agents, as measured in an in vitro assay known in the art or provided herein.

In further embodiments, a precursor tri-specific antibody construct of the present disclosure induces phosphorylation of a molecule in the TCR signal transduction pathway. The "TCR signal transduction pathway" refers to the signal transduction pathway initiated via the binding of a peptide: MHC ligand to the TCR and its co-receptor (CD4 or CD8). A "molecule in the TCR signal transduction pathway" refers to a molecule that is directly involved in the TCR signal transduction pathway, such as a molecule whose phosphorylation state (e.g., whether the molecule is phosphorylated or not), whose binding affinity to another molecule, or whose enzymatic activity, has been changed in response to the signal from the binding of a peptide: MHC ligand to the TCR and its co-receptor. Exemplary molecules in the TCR signal transduction pathway include the TCR complex or its components (e.g., CD3 chains), ZAP-70, Fyn, Lck, phospholipase c-y, protein kinase C, transcription factor NF.kappa.B, phosphatase calcineurin, transcription factor NFAT, guanine nucleotide exchange factor (GEF), Ras, MAP kinase kinase kinase (MAPKKK), MAP kinase kinase (MAPKK), MAP kinase (ERK1/2), and Fos.

A precursor tri-specific antibody construct of this disclosure "induces phosphorylation of a molecule in the TCR signal transduction pathway" if it causes a statistically significant increase in phosphorylation of a molecule in the TCR signal transduction pathway (e.g., CD3 chains, ZAP-70, and ERK1/2) only in the presence of cells expressing TAA antigen (e.g., cancer cells expressing tumor antigens bound by a first binding domains, or when the TAA is present on a non-tumor cell, tumor cells expressing proteases able to cleave the protease cleavable domain of a regulatory domain are present) or linker cleavage agents, in an in vitro or in vivo assay or receptor signaling assays known in the art. Results from most receptor signaling assays known in the art are determined using immunohistochemical methods, such as western blots or fluorescence microscopy.

Similarly, an activated precursor tri-specific antibody construct of the present disclosure may induce killing of TAA target cell, such as tumor cells or vascular cells which support the growth and maintenance of tumor cells, by T-cells following exposure to a tumor cell microenvironment or exposure to a protease or proteases able to cleave the protease cleavable component of a regulatory domain(s). Such cell killing can be measured using a variety of assays known in the art, including chromium release assays.

The specificity and function of a precursor tri-specific antibody construct of the present disclosure may be tested by contacting the precursor tri-specific antibody construct with appropriate test sample and, in certain embodiments, treating the precursor tri-specific antibody construct with an appropriate protease which is thought to be specific for the cleavage recognition site in the linker and assaying for cleavage products. Proteases may be isolated, for example from cancer cells or they may be prepared recombinantly, for example following the procedures in Darket et al. (J. Biol. Chem. 254:2307-2312 (1988)). The cleavage products may be identified for example based on size, antigenicity or activity. The toxicity of the precursor tri-specific antibody construct may be investigated by subjecting the precursor tri-specific antibody construct and cleavage products thereof to in vitro cytotoxicity, proliferation, binding, or other appropriate assays known to the skilled person. Toxicity of the cleavage products may be determined using a ribosomal inactivation assay (Westby et al., Bioconjugate Chem. 3:377-382 (1992)). The effect of the cleavage products on protein synthesis may be measured in standardized assays of in vitro translation utilizing partially defined cell free systems composed for example of a reticulocyte lysate preparation as a source of ribosomes and various essential cofactors, such as mRNA template and amino acids. Use of radiolabeled amino acids in the mixture allows quantitation of incorporation of free amino acid precursors into trichloroacetic acid precipitable proteins. Rabbit reticulocyte lysates may be conveniently used (O'Hare, FEBS Lett. 273:200-204 (1990)).

The ability of an activated precursor tri-specific antibody construct as disclosed herein, to destroy cancer cells and/or activate T-cells may be readily tested in vitro using cancer cell lines, T-cell lines or isolated PBMC or T-cells. The effects of the precursor tri-specific antibody construct of the present disclosure may be determined, for example, by demonstrating by selective lysis of cancer cells. In addition, the protease specificity can be tested by comparing the inhibition of cellular proliferation using a precursor bispecific antibody construct of the present disclosure alone or in the presence of protease-specific inhibitors. Such protease inhibitors may include MMP-2/MMP-9 inhibitors GM1489, GM6001 and G1-I to GI-IV.

Toxicity may also be measured based on cell viability, for example the viability of normal and cancerous cell cultures exposed to the precursor tri-specific antibody construct may be compared. Cell viability may be assessed by known techniques, such as trypan blue exclusion assays. Toxicity may also be measured based on cell lysis, for example the lysis of normal and cancerous cell cultures exposed to the precursor bispecific antibody construct may be compared. Cell lysis may be assessed by known techniques, such as Chromium (Cr) release assays or dead cell indicator dyes (propidium Iodide, TO-PRO-3 Iodide).

Precursor Bispecific Antibody Construct Components

The present disclosure provides precursor tri-specific antibody construct polypeptides. As described in detail above, in some embodiments a precursor tri-specific antibody construct comprises two polypeptides: polypeptide A and polypeptide B. Illustrative polypeptides, and the polynucleotides encoding them, are provided in SEQ ID NOs: 131 (polypeptide sequence of polypeptide A), 132 (polypeptide sequence of polypeptide B), 143 (polynucleotide sequence encoding polypeptide A), and 144 (polynucleotide sequence encoding polypeptide B). In some embodiments, illustrative polypeptides and the polynucleotides encoding them, are provided in SEQ ID NOs: 133 (polypeptide sequence of polypeptide A), 134 (polypeptide sequence of polypeptide B), 145 (polynucleotide sequence encoding polypeptide A), and 146 (polynucleotide sequence encoding polypeptide B).

A skilled artisan would appreciate that terms "polypeptide" "protein" and "peptide" and "glycoprotein" are used interchangeably and encompass a polymer of amino acids not limited to any particular length. The term does not exclude modifications such as myristylation, sulfation, glycosylation, phosphorylation and addition or deletion of signal sequences. The terms "polypeptide" or "protein" may encompass one or more chains of amino acids, wherein each chain comprises amino acids covalently linked by peptide bonds, and wherein said polypeptide or protein can comprise a plurality of chains non-covalently and/or covalently linked together by peptide bonds, having the sequence of native proteins, that is, proteins produced by naturally-occurring and specifically non-recombinant cells, or genetically-engineered or recombinant cells, and comprise molecules having the amino acid sequence of the native protein, or molecules having deletions from, additions to, and/or substitutions of one or more amino acids of the native sequence. The terms "polypeptide" and "protein" may encompass a polypeptide A or a polypeptide B of a precursor tri-specific antibody construct and heterodimers thereof of the present disclosure, or sequences that have deletions from, additions to, and/or substitutions of one or more amino acid of a precursor bispecific antibody construct as disclosed herein. Thus, a "polypeptide" or a "protein" can comprise one (termed "a monomer") or a plurality (termed "a multimer") of amino acid chains.

The term "isolated protein" referred to herein encompasses a subject protein (1) is free of at least some other proteins with which it would typically be found in nature, (2) is essentially free of other proteins from the same source, e.g., from the same species, (3) is expressed by a cell from a different species, (4) has been separated from at least about 50 percent of polynucleotides, lipids, carbohydrates, or other materials with which it is associated in nature, (5) is not associated (by covalent or noncovalent interaction) with portions of a protein with which the "isolated protein" is associated in nature, (6) is operably associated (by covalent or noncovalent interaction) with a polypeptide with which it is not associated in nature, or (7) does not occur in nature. Such an isolated protein can be encoded by genomic DNA, cDNA, mRNA or other RNA, of may be of synthetic origin, or any combination thereof. In certain embodiments, the isolated protein is substantially free from proteins or polypeptides or other contaminants that are found in its natural environment that would interfere with its use (therapeutic, diagnostic, prophylactic, research or otherwise).

The term "polypeptide fragment" encompasses a polypeptide, which can be monomeric or multimeric, that has an amino-terminal deletion, a carboxyl-terminal deletion, and/or an internal deletion or substitution of a naturally-occurring or recombinantly-produced polypeptide. In certain embodiments, a polypeptide fragment can comprise an amino acid chain at least 5 to about 500 amino acids long. It will be appreciated that in certain embodiments, fragments are at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 150, 200, 250, 300, 350, 400, or 450 amino acids long. Particularly useful polypeptide fragments include functional domains, including antigen-binding domains or fragments of antibodies. In the case of an anti-CD3, or other antibody, useful fragments include, but are not limited to: a CDR region, especially a CDR3 region of the heavy or light chain; a variable region of a heavy or light chain; a portion of an antibody chain or just its variable region including two CDRs; and the like.

Polypeptides may comprise a signal (or leader) sequence at the N-terminal end of the protein, which co-translationally or post-translationally directs transfer of the protein. The polypeptide may also be fused in-frame or conjugated to a linker or other sequence for ease of synthesis, purification or identification of the polypeptide (e.g., poly-His), or to enhance binding of the polypeptide to a solid support.

Amino acid sequence modification(s) of the precursor tri-specific antibody constructs described herein are contemplated. For example, it may be desirable to improve the binding affinity and/or other biological properties of the precursor tri-specific antibody construct. For example, amino acid sequence variants of a linker sequence, or a binding domain, or a regulatory component(s) thereof may be prepared by introducing appropriate nucleotide changes into a polynucleotide that encodes the precursor tri-specific antibody construct polypeptides, or a domain thereof, or by peptide synthesis. Such modifications include, for example, deletions from, and/or insertions into and/or substitutions of, residues within the amino acid sequences of the precursor tri-specific antibody construct polypeptides. Any combination of deletion, insertion, and substitution may be made to arrive at the final precursor tri-specific antibody construct polypeptides, provided that the final construct possesses the desired characteristics, such as specific binding to a target antigen of interest by a first or second binding domain or both, or a third binding domain, or enhanced half-life by an HSA polypeptide comprised in a regulatory domain, or specific binding to a third binding domain by a regulatory domain comprising a CAP component, or protease cleavage by a protease cleavage domain(s) (linker). The amino acid changes also may alter post-translational processes of the precursor tri-specific antibody construct polypeptides, such as changing the number or position of glycosylation sites. Any of the variations and modifications described above for polypeptides as disclosed herein, may be included in precursor tri-specific antibody constructs presented herein.

The present disclosure provides variants of the precursor tri-specific antibody construct polypeptides disclosed herein. In certain embodiments, such variant precursor tri-specific antibody construct polypeptides comprise variant binding domains or fragments thereof, or antigen-binding fragments, or TAA binding fragments, or CDRs of binding domains, bind to a target of interest at least about 50%, at least about 70%, and in certain embodiments, at least about 90% as well as a given reference or wild-type sequence, including any such sequences specifically set forth herein. In further embodiments, such variants bind to a target antigen with greater affinity the reference or wild-type sequence set forth herein, for example, that bind quantitatively at least about 105%, 106%, 107%, 108%, 109%, or 110% as well as a reference sequence specifically set forth herein. In certain embodiments, such variant precursor tri-specific antibody construct polypeptides comprise variant regulatory domains or fragments thereof, or HSA components, or CAP components or fragments thereof, wherein said variant has at least about 50%, at least about 70%, and in certain embodiments, at least about 90% of the activity of a reference or wild-type regulatory domain or component, including any such sequences specifically set forth herein. In certain embodiments, the present disclosure provides variants of the precursor tri-specific antibody constructs or polypeptides thereof, disclosed herein where such variants comprise third binding domains that have been modified with regard to the disulfide bond between the VH and VL chains. As would be recognized by the skilled person, in certain embodiments the third binding domain, which in some embodiments comprises an Fab fragment, used in the precursor tri-specific antibody construct described herein may not comprise a disulfide bond. In this regard, the heavy and light chains may be engineered in such a way so as to stably interact without the need for disulfide bond. For example, in certain embodiments, the heavy or light chain can be engineered to remove a cysteine residue and wherein the heavy and light chains still stably interact and function as a binding domain e.g. a Fab fragment. In some embodiments, mutations are made to facilitate stable interaction between the heavy and light chains. For example, a "knobs into holes" engineering strategy can be used to facilitate dimerization between the heavy and light chains of a Fab second binding domain (see e.g., 1996 Protein Engineering, 9:617-621). Thus, also contemplated for use herein are variant amino acid sequences of the third binding domain (e.g., Fab fragments) designed for a particular purpose, for example, removal of a disulfide bond addition of tax for purification, etc.

In particular embodiments, a subject precursor tri-specific antibody construct polypeptide may have: an amino acid sequence that is at least 80% identical, at least 95% identical, at least 90%, at least 95% or at least 98% or 99% identical, to the precursor tri-specific antibody construct polypeptides described herein.

Determination of the three-dimensional structures of representative polypeptides may be made through routine methodologies such that substitution, addition, deletion or insertion of one or more amino acids with selected natural or non-natural amino acids can be virtually modeled for purposes of determining whether a so derived structural variant retains the space-filling properties of presently disclosed species. See, for instance, Donate et al., 1994 Prot. Sci. 3:2378; Bradley et al., Science 309:1868-1871 (2005); Schueler-Furman et al., Science 310:638 (2005); Dietz et al., Proc. Nat. Acad. Sci. USA 103:1244 (2006); Dodson et al., Nature 450:176 (2007); Qian et al., Nature 450:259 (2007); Raman et al. Science 327:1014-1018 (2010). Some additional non-limiting examples of computer algorithms that may be used for these and related embodiments, include VMD which is a molecular visualization program for displaying, animating, and analyzing large biomolecular systems using 3-D graphics and built-in scripting (see the website for the Theoretical and Computational Biophysics Group, University of Illinois at Urbana-Champagne, at ks.uiuc.edu/Research/vmd/). Many other computer programs are known in the art and available to the skilled person and which allow for determining atomic dimensions from space-filling models (van der Waals radii) of energy-minimized conformations; GRID, which seeks to determine regions of high affinity for different chemical groups, thereby enhancing binding, Monte Carlo searches, which calculate mathematical alignment, and CHARMM (Brooks et al. (1983) J. Comput. Chem. 4:187-217) and AMBER (Weiner et al (1981) J. Comput. Chem. 106:765), which assess force field calculations, and analysis (see also, Eisenfield et al. (1991) Am. J. Physiol. 261: C376-386; Lybrand (1991) J. Pharm. Belg. 46:49-54; Froimowitz (1990) Biotechniques 8:640-644; Burbam et al. (1990) Proteins 7:99-111; Pedersen (1985) Environ. Health Perspect. 61:185-190; and Kini et al. (1991) J. Biomol. Struct. Dyn. 9:475-488). A variety of appropriate computational computer programs are also commercially available, such as from Schrodinger (Munich, Germany).

Polynucleotides Encoding Precursor Bispecific Antibody Construct Components, Vectors, Host Cells, and Methods of Producing Precursor Bispecific Antibody Constructs The present disclosure further provides in certain embodiments an isolated nucleic acid encoding the polypeptide precursor tri-specific antibody construct as described herein. Illustrative polynucleotides and fragments thereof, are provided in Table 3 below. Nucleic acids include DNA and RNA. These and related embodiments may include polynucleotides encoding the precursor tri-specific antibody construct as described herein. The term "isolated polynucleotide" as used herein shall mean a polynucleotide of genomic, cDNA, or synthetic origin or some combination thereof, which by virtue of its origin the isolated polynucleotide (1) is not associated with all or a portion of a polynucleotide in which the isolated polynucleotide is found in nature, (2) is linked to a polynucleotide to which it is not linked in nature, or (3) does not occur in nature as part of a larger sequence.

A skilled artisan would appreciate that the terms "polynucleotide" and "nucleic acid sequence" may in some embodiments be used interchangeably having all the same meanings and qualities.

In some embodiments, isolated nucleic acid sequences encode a polypeptide A and a polypeptide B of a precursor tri-specific antibody construct as disclosed herein throughout in detail. In some embodiments, an isolated nucleic acid sequences encodes polypeptide A of a precursor tri-specific antibody construct, as described above in detail. In some embodiments, an isolated nucleic acid sequences encodes polypeptide B of a precursor tri-specific antibody construct, as described above in detail. In some embodiments, polypeptides A and B form a heterodimer comprising a precursor construct as described herein comprising (a) a first and a second binding domain binding to a cell surface tumor associated antigen (TAA binding domain), or a TAA; (b) a third binding domain binding to an extracellular epitope of human CD3ε (CD3 binding domain); and (c) two cleavable sub-regulatory domains one comprising a half-life prolonging domain, and the other comprising a CAP masking domain.

TABLE 3

Nucleotide Sequences of Encoding Anti-CD3 VH, VL, HC, LC, Anti-EGFR, Regulatory components, and Combinations thereof (See also nucleotide sequences in Example 1 below.)

| SEQ ID No | Description |
|---|---|
| 155 | Anti-CD3 epsilon VH-CH1 |
| 159 | Anti-CD3epsilon VL-CL |
| 36 | Anti-EGFR VL |
| 38 | Anti-EGFR VH |
| 43 | Anti-EGFR VL-L-VH |
| 44 | Anti-EGFR VH-L-VL |
| 8 | HSA |
| 164 | CAP |
| 33 | MMP Cleavable Sequence |

The term "operably linked" encompasses components to which the term is applied are in a relationship that allows them to carry out their inherent functions under suitable conditions. For example, a transcription control sequence "operably linked" to a protein coding sequence is ligated thereto so that expression of the protein coding sequence is achieved under conditions compatible with the transcriptional activity of the control sequences.

The term "control sequence" as used herein encompasses polynucleotide sequences that can affect expression, processing or intracellular localization of coding sequences to which they are ligated or operably linked. The nature of such control sequences may depend upon the host organism. In particular embodiments, transcription control sequences for prokaryotes may include a promoter, ribosomal binding site, and transcription termination sequence. In other particular embodiments, transcription control sequences for eukaryotes may include promoters comprising one or a plurality of recognition sites for transcription factors, transcription enhancer sequences, transcription termination sequences and polyadenylation sequences. In certain embodiments, "control sequences" can include leader sequences and/or fusion partner sequences.

The term "polynucleotide" as used herein encompasses single-stranded or double-stranded nucleic acid polymers. In certain embodiments, the nucleotides comprising the polynucleotide can be ribonucleotides or deoxyribonucleotides or a modified form of either type of nucleotide. Said modifications include base modifications such as bromouridine, ribose modifications such as arabinoside and 2',3'-dideoxyribose and internucleotide linkage modifications such as phosphorothioate, phosphorodithioate, phosphoroselenoate, phosphorodiselenoate, phosphoroanilothioate, phoshoraniladate and phosphoroamidate. The term "polynucleotide" specifically includes single and double stranded forms of DNA.

The term "naturally occurring nucleotides" includes deoxyribonucleotides and ribonucleotides. The term "modified nucleotides" includes nucleotides with modified or substituted sugar groups and the like. The term "oligonucleotide linkages" includes oligonucleotide linkages such as phosphorothioate, phosphorodithioate, phosphoroselenoate, phosphorodiselenoate, phosphoroanilothioate, phoshoraniladate, phosphoroamidate, and the like. See, e.g., LaPlanche et al., 1986, Nucl. Acids Res., 14:9081; Stec et al., 1984, J. Am. Chem. Soc., 106:6077; Stein et al., 1988, Nucl. Acids Res., 16:3209; Zon et al., 1991, Anti-Cancer Drug Design, 6:539; Zon et al., 1991, OLIGONUCLEOTIDES AND ANALOGUES: A PRACTICAL APPROACH, pp. 87-108 (F. Eckstein, Ed.), Oxford University Press, Oxford England; Stec et al., U.S. Pat. No. 5,151,510; Uhlmann and Peyman, 1990, Chemical Reviews, 90:543, the disclosures of which are hereby incorporated by reference for any purpose. An oligonucleotide can include a detectable label to enable detection of the oligonucleotide or hybridization thereof.

In other related embodiments, polynucleotide variants may have substantial identity to a polynucleotide sequence encoding a precursor tri-specific antibody construct, or domain thereof as described herein. For example, a polynucleotide may be a polynucleotide comprising at least 70% sequence identity, preferably at least 75%, 80%, 85%, 90%, 95%, 96%, 97%, 98%, or 99% or higher, sequence identity compared to a reference polynucleotide sequence such as a sequence encoding a precursor bispecific antibody construct or domain thereof described herein, using the methods described herein, (e.g., BLAST analysis using standard parameters, as described below). One skilled in this art will recognize that these values can be appropriately adjusted to determine corresponding identity of proteins encoded by two nucleotide sequences by taking into account codon degeneracy, amino acid similarity, reading frame positioning and the like.

Typically, polynucleotide variants will contain one or more substitutions, additions, deletions and/or insertions, preferably such that the binding affinity of a binding domain, or binding affinity of a first or second or a third binding domain, or function of the precursor tri-specific antibody construct polypeptide encoded by the variant polynucleotide is not substantially diminished relative to the unmodified reference protein encoded by a polynucleotide sequence specifically set forth herein.

In certain other related embodiments, polynucleotide fragments may comprise or consist essentially of various lengths of contiguous stretches of sequence identical to or complementary to a sequence encoding a precursor tri-specific antibody construct polypeptide or domain thereof as described herein. For example, polynucleotides are provided that comprise or consist essentially of at least about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 85, 90, 95, 100, 110, 120, 130, 140, 150, 200, 300, 400, 500 or 1000 or more contiguous nucleotides of a sequences the encodes a precursor tri-specific antibody construct polypeptide or domain thereof, such as a first binding domain or a second binding domain or a third binding domain or a first sub-regulatory domain or a second sub-regulatory domain, or components thereof, disclosed herein as well as all intermediate lengths there between. It will be readily understood that "intermediate lengths", in this context, means any length between the quoted values, such as 50, 51, 52, 53, etc.; 100, 101, 102, 103, etc.; 150, 151, 152, 153, etc.; including all integers through 200-500; 500-1,000, and the like. A polynucleotide sequence as described here may be extended at one or both ends by additional nucleotides not found in the native sequence. This additional sequence may consist of 1, 2, 3, 4, 5, 6, 7, 8, 9, 10, 11, 12, 13, 14, 15, 16, 17, 18, 19, or 20 nucleotides at either end of a polynucleotide encoding a precursor tri-specific antibody construct polypeptide or domain or component part thereof described herein or at both ends of a polynucleotide encoding a precursor tri-specific antibody construct polypeptide or domain or component part thereof described herein.

In another embodiment, polynucleotides are provided that are capable of hybridizing under moderate to high stringency conditions to a polynucleotide sequence encoding precursor tri-specific antibody construct polypeptide or domain or component part thereof, such as a first binding domain or a second binding domain or a third binding domain or a first sub-regulatory domain or a second sub-regulatory domain, or component parts thereof, as provided herein, or a fragment thereof, or a complementary sequence thereof. Hybridization techniques are well known in the art of molecular biology. For purposes of illustration, suitable moderately stringent conditions for testing the hybridization of a polynucleotide as provided herein with other polynucleotides include prewashing in a solution of 5×SSC, 0.5% SDS, 1.0 mM EDTA (pH 8.0); hybridizing at 50° C. . . . 60° C., 5×SSC, overnight; followed by washing twice at 65°. C. for 20 minutes with each of 2X, 0.5X and 0.2×SSC containing 0.1% SDS. One skilled in the art will understand that the stringency of hybridization can be readily manipulated, such as by altering the salt content of the hybridization solution and/or the temperature at which the hybridization is performed. For example, in another embodiment, suitable highly stringent hybridization conditions include those described above, with the exception that the temperature of hybridization is increased, e.g., to 60° C.-65° C. or 65° C.-70° C.

In certain embodiments, the polynucleotides described above, e.g., polynucleotide variants, fragments and hybridizing sequences, encode a precursor tri-specific antibody construct polypeptide or domain thereof or component part thereof, such as a first or a second binding domain or both, e.g., a scFv that binds to a human EGFR, or a third binding domain, e.g., a Fab fragment that binds CD3 epsilon, or a regulatory domain comprising an HSA polypeptide that extends half-life, or a regulatory domain comprising a CAP component that specifically binds to a third binding domain. In other embodiments, such polynucleotides encode precursor tri-specific antibody construct polypeptides or domains or components thereof that bind to CD3 and/or a tumor associated antigen at least about 50%, at least about 70%, and in certain embodiments, at least about 90% as well as a precursor tri-specific antibody construct polypeptide sequence specifically set forth herein. In other embodiments, such polynucleotides encode precursor tri-specific antibody construct polypeptides or domains or components thereof that extend the half-life of the precursor construct at least about 50%, at least about 70%, and in certain embodiments, at least about 90% as well as a precursor tri-specific antibody construct polypeptide sequence specifically set forth herein. In other embodiments, such polynucleotides encode precursor tri-specific antibody construct polypeptides or domains or components thereof that specifically bind to the third binding site of the precursor construct at least about 50%, at least about 70%, and in certain embodiments, at least about 90% as well as a precursor tri-specific antibody construct polypeptide sequence specifically set forth herein. In further embodiments, such polynucleotides encode a precursor tri-specific antibody construct polypeptide or domain thereof, that, e.g., bind to CD3 and/or a tumor associated antigen with greater affinity than the precursor tri-specific antibody construct polypeptide, or domain thereof, set forth herein, for example, that bind quantitatively at least about 105%, 106%, 107%, 108%, 109%, or 110% as well as a precursor tri-specific antibody construct polypeptide or domain thereof sequence specifically set forth herein.

As described elsewhere herein, determination of the three-dimensional structures of representative polypeptides (e.g., variant precursor tri-specific antibody construct and polypeptides thereof, as provided herein, for instance, a precursor tri-specific antibody construct having a first TAA binding domain and a second TAA binding domain, and a third CD3 epsilon binding domain as provided herein) may be made through routine methodologies such that substitution, addition, deletion or insertion of one or more amino acids with selected natural or non-natural amino acids can be virtually modeled for purposes of determining whether a so derived structural variant retains the space-filling properties of presently disclosed species. A variety of computer programs are known to the skilled artisan for determining appropriate amino acid substitutions (or appropriate polynucleotides encoding the amino acid sequence) within, for example, an antibody or antigen-binding fragment thereof, such that, for example, affinity is maintained, or better affinity is achieved.

The polynucleotides described herein, or fragments thereof, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, illustrative polynucleotide segments with total lengths of about 10,000, about 5000, about 3000, about 2,000, about 1,000, about 500, about 200, about 100, about 50 base pairs in length, and the like, (including all intermediate lengths) are contemplated to be useful.

When comparing polynucleotide sequences, two sequences are said to be "identical" if the sequence of nucleotides in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins--Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J., Unified Approach to Alignment and Phylogenes, pp. 626-645 (1990); Methods in Enzymology vol. 183, Academic Press, Inc., San Diego, Calif.; Higgins, D. G. and Sharp, P. M., CABIOS 5:151-153 (1989); Myers, E. W. and Muller W., CABIOS 4:11-17 (1988); Robinson, E. D., Comb. Theor 11:105 (1971); Santou, N. Nes, M., Mol. Biol. Evol. 4:406-425 (1987); Sneath, P. H. A. and Sokal, R. R., Numerical Taxonomy—the Principles and Practice of Numerical Taxonomy, Freeman Press, San Francisco, Calif. (1973); Wilbur, W. J. and Lipman, D. J., Proc. Natl. Acad., Sci. USA 80:726-730 (1983).

Alternatively, optimal alignment of sequences for comparison may be conducted by the local identity algorithm of Smith and Waterman, Add. APL. Math 2:482 (1981), by the identity alignment algorithm of Needleman and Wunsch, J. Mol. Biol. 48:443 (1970), by the search for similarity methods of Pearson and Lipman, Proc. Natl. Acad. Sci. USA 85:2444 (1988), by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One example of algorithms that are suitable for determining percent sequence identity and sequence similarity are the BLAST and BLAST 2.0 algorithms, which are described in Altschul et al., Nucl. Acids Res. 25:3389-3402 (1977), and Altschul et al., J. Mol. Biol. 215:403-410 (1990), respectively. BLAST and BLAST 2.0 can be used, for example with the parameters described herein, to determine percent sequence identity among two or more the polynucleotides. Software for performing BLAST analyses is publicly available through the National Center for Biotechnology Information. In one illustrative example, cumulative scores can be calculated using, for nucleotide sequences, the parameters M (reward score for a pair of matching residues; always >0) and N (penalty score for mismatching residues;

always <0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, and expectation (E) of 10, and the BLOSUM62 scoring matrix (see Henikoff and Henikoff, Proc. Natl. Acad. Sci. USA 89:10915 (1989)) alignments, (B) of 50, expectation (E) of 10, M=5, N=−4 and a comparison of both strands.

In certain embodiments, the "percentage of sequence identity" is determined by comparing two optimally aligned sequences over a window of comparison of at least 20 positions, wherein the portion of the polynucleotide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases occurs in both sequences to yield the number of matched positions, dividing the number of matched positions by the total number of positions in the reference sequence (i.e., the window size) and multiplying the results by 100 to yield the percentage of sequence identity.

It will be appreciated by those of ordinary skill in the art that, as a result of the degeneracy of the genetic code, there are many nucleotide sequences that encode a precursor bispecific antibody construct as described herein. Some of these polynucleotides bear minimal sequence identity to the nucleotide sequence of the native or original polynucleotide sequence that encode precursor tri-specific antibody construct polypeptides or domains or components thereof, for example forming a precursor bispecific antibody construct that binds to CD3 and or a tumor associated antigen. Nonetheless, polynucleotides that vary due to differences in codon usage are expressly contemplated by the present disclosure. In certain embodiments, sequences that have been codon-optimized for mammalian expression are specifically contemplated.

Therefore, in another embodiment as disclosed herein, a mutagenesis approach, such as site-specific mutagenesis, may be employed for the preparation of variants and/or derivatives of the precursor tri-specific antibody construct polypeptides described herein. By this approach, specific modifications in a polypeptide sequence can be made through mutagenesis of the underlying polynucleotides that encode them. These techniques provide a straightforward approach to prepare and test sequence variants, for example, incorporating one or more of the foregoing considerations, by introducing one or more nucleotide sequence changes into the polynucleotide.

Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Mutations may be employed in a selected polynucleotide sequence to improve, alter, decrease, modify, or otherwise change the properties of the polynucleotide itself, and/or alter the properties, activity, composition, stability, or primary sequence of the encoded polypeptide.

In certain embodiments, mutagenesis of the polynucleotide sequences that encode a precursor tri-specific antibody construct polypeptide or domain thereof or component part thereof, as disclosed herein, is contemplated in order to alter one or more properties of the encoded polypeptide/domain/component, such as the binding affinity of a first binding domain or a second binding domain or a third binding domain, or the function of a first or second sub-regulatory domain or component thereof. The techniques of site-specific mutagenesis are well-known in the art and are widely used to create variants of both polypeptides and polynucleotides. For example, site-specific mutagenesis is often used to alter a specific portion of a DNA molecule. In such embodiments, a primer comprising typically about 14 to about 25 nucleotides or so in length is employed, with about 5 to about 10 residues on both sides of the junction of the sequence being altered.

As will be appreciated by those of skill in the art, site-specific mutagenesis techniques have often employed a phage vector that exists in both a single stranded and double stranded form. Typical vectors useful in site-directed mutagenesis include vectors such as the M13 phage. These phages are readily commercially-available and their use is generally well-known to those skilled in the art. Double-stranded plasmids are also routinely employed in site directed mutagenesis that eliminates the step of transferring the gene of interest from a plasmid to a phage.

In general, site-directed mutagenesis in accordance herewith is performed by first obtaining a single-stranded vector or melting apart of two strands of a double-stranded vector that includes within its sequence a DNA sequence that encodes the desired peptide. An oligonucleotide primer bearing the desired mutated sequence is prepared, generally synthetically. This primer is then annealed with the single-stranded vector and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected which include recombinant vectors bearing the mutated sequence arrangement.

The preparation of sequence variants of the selected peptide-encoding DNA segments using site-directed mutagenesis provides a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents, such as hydroxylamine, to obtain sequence variants. Specific details regarding these methods and protocols are found in the teachings of Maloy et al., 1994; Segal, 1976; Prokop and Bajpai, 1991; Kuby, 1994; and Maniatis et al., 1982, each incorporated herein by reference, for that purpose.

As used herein, the term "oligonucleotide directed mutagenesis procedure" encompasses template-dependent processes and vector-mediated propagation which result in an increase in the concentration of a specific nucleic acid molecule relative to its initial concentration, or in an increase in the concentration of a detectable signal, such as amplification. As used herein, the term "oligonucleotide directed mutagenesis procedure" encompasses a process that involves the template-dependent extension of a primer molecule. The term "template dependent process" encompasses nucleic acid synthesis of an RNA or a DNA molecule wherein the sequence of the newly synthesized strand of nucleic acid is dictated by the well-known rules of complementary base pairing (see, for example, Watson, 1987). Typically, vector mediated methodologies involve the introduction of the nucleic acid fragment into a DNA or RNA vector, the clonal amplification of the vector, and the recovery of the amplified nucleic acid fragment. Examples of such methodologies are provided by U.S. Pat. No. 4,237,224, specifically incorporated herein by reference in its entirety.

In another approach for the production of polypeptide variants, recursive sequence recombination, as described in U.S. Pat. No. 5,837,458, may be employed. In this approach, iterative cycles of recombination and screening or selection are performed to "evolve" individual polynucleotide variants having, for example, increased binding affinity. Certain embodiments also provide constructs in the form of plasmids, vectors, transcription or expression cassettes which comprise at least one polynucleotide as described herein.

In certain embodiments, the isolated polynucleotide is inserted into a vector. The term "vector" as used herein encompasses a vehicle into which a polynucleotide encoding a protein may be covalently inserted so as to bring about the expression of that protein and/or the cloning of the polynucleotide. The isolated polynucleotide may be inserted into a vector using any suitable methods known in the art, for example, without limitation, the vector may be digested using appropriate restriction enzymes and then may be ligated with the isolated polynucleotide having matching restriction ends.

Examples of suitable vectors include, without limitation, plasmids, phagemids, cosmids, artificial chromosomes such as yeast artificial chromosome (YAC), bacterial artificial chromosome (BAC), or P1-derived artificial chromosome (PAC), bacteriophages such as lambda phage or M13 phage, and animal viruses. Examples of categories of animal viruses useful as vectors include, without limitation, retrovirus (including lentivirus), adenovirus, adeno-associated virus, herpesvirus (e.g., herpes simplex virus), poxvirus, baculovirus, papillomavirus, and papovavirus (e.g., SV40).

For expression of the polypeptide, the vector may be introduced into a host cell to allow expression of the polypeptide within the host cell. The expression vectors may contain a variety of elements for controlling expression, including without limitation, promoter sequences, transcription initiation sequences, enhancer sequences, selectable markers, and signal sequences. These elements may be selected as appropriate by a person of ordinary skill in the art. For example, the promoter sequences may be selected to promote the transcription of the polynucleotide in the vector. Suitable promoter sequences include, without limitation, T7 promoter, T3 promoter, SP6 promoter, beta-actin promoter, EFla promoter, CMV promoter, and SV40 promoter. Enhancer sequences may be selected to enhance the transcription of the polynucleotide. Selectable markers may be selected to allow selection of the host cells inserted with the vector from those not, for example, the selectable markers may be genes that confer antibiotic resistance. Signal sequences may be selected to allow the expressed polypeptide to be transported outside of the host cell.

A vector may also include materials to aid in its entry into the cell, including but not limited to a viral particle, a liposome, or a protein coating.

In some embodiments, an expression vector comprises an isolated nucleic acid sequence encoding a polypeptide of a precursor construct or encoding a domain within a polypeptide of the precursor construct or encoding a component part of a domain within a polypeptide of the precursor construct. Binding domains and the components thereof have been described in detail above.

In some embodiments, an expression vector comprises an isolated nucleic acid sequence encoding a polypeptide A. In some embodiments, an expression vector comprises an isolated nucleic acid sequence encoding a polypeptide B. In some embodiments, an expression vector comprises an isolated nucleic acid sequence encoding a part of a polypeptide A. In some embodiments, an expression vector comprises an isolated nucleic acid sequence encoding a part of a polypeptide B. In some embodiments, an expression vector comprises an isolated nucleic acid sequence encoding a first binding domain. In some embodiments, an expression vector comprises an isolated nucleic acid sequence encoding an scFv of a first binding domain. In some embodiments, an expression vector comprises an isolated nucleic acid sequence encoding an scFv of a second binding domain. In some embodiments, an expression vector comprises an isolated nucleic acid sequence encoding part of an scFv of a first binding domain. In some embodiments, an expression vector comprises an isolated nucleic acid sequence encoding part of an scFv of a second binding domain. In some embodiments, an expression vector comprises an isolated nucleic acid sequence encoding an EGFR binding domain. In some embodiments, an expression vector comprises an isolated nucleic acid sequence encoding an EGFR scFv binding domain. In some embodiments, an expression vector comprises an isolated nucleic acid sequence encoding a VH region of a CD3 epsilon binding domain. In some embodiments, an expression vector comprises an isolated nucleic acid sequence encoding a VL region of a CD3 epsilon binding domain. In some embodiments, an expression vector comprises an isolated nucleic acid sequence encoding a CAP regulatory domain. In some embodiments, an expression vector comprises an isolated nucleic acid sequence encoding an HSA regulatory domain. In some embodiments, an expression vector comprises an isolated nucleic acid sequence encoding a component part of a regulatory domain. In some embodiments, an expression vector comprises an isolated nucleic acid sequence encoding a CAP component of a regulatory domain. In some embodiments, an expression vector comprises an isolated nucleic acid sequence encoding an HSA component of a regulatory domain. In some embodiments, an expression vector comprises an isolated nucleic acid sequence encoding a CAP component of a regulatory domain, and a linker(s) including a protease cleavable linker. In some embodiments, an expression vector comprises an isolated nucleic acid sequence encoding an HSA component of a regulatory domain, and a linker(s) including a protease cleavable linker.

For cloning of the polynucleotide, the vector may be introduced into a host cell (an isolated host cell) to allow replication of the vector itself and thereby amplify the copies of the polynucleotide contained therein. The cloning vectors may contain sequence components generally include, without limitation, an origin of replication, promoter sequences, transcription initiation sequences, enhancer sequences, and selectable markers. These elements may be selected as appropriate by a person of ordinary skill in the art. For example, the origin of replication may be selected to promote autonomous replication of the vector in the host cell.

In certain embodiments, the present disclosure provides isolated host cells containing the vector provided herein. The host cells containing the vector may be useful in expression or cloning of the polynucleotide(s) contained in the vector.

Suitable host cells can include, without limitation, prokaryotic cells, fungal cells, yeast cells, or higher eukaryotic cells such as mammalian cells.

Suitable prokaryotic cells for this purpose include, without limitation, eubacteria, such as Gram-negative or Gram-positive organisms, for example, Enterobactehaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis, Pseudomonas* such as *P. aeruginosa*, and *Streptomyces*.

The expression of antibodies and antigen-binding fragments in prokaryotic cells such as *E. coli* is well established in the art. For a review, see for example Pluckthun, A. Bio/Technology 9:545-551 (1991). Expression in eukaryotic cells in culture is also available to those skilled in the art as an option for production of antibodies or antigen-binding fragments thereof, see recent reviews, for example Ref, M. E. (1993) Curr. Opinion Biotech. 4:573-576; Trill J. J. et al. (1995) Curr. Opinion Biotech 6:553-560.

Suitable fungal cells for this purpose include, without limitation, filamentous fungi and yeast. Illustrative examples of fungal cells include, *Saccharomyces cerevisiae*, common baker's yeast, *Schizosaccharomyces pombe, Kluyveromyces* hosts such as, eg., *K. lactis, K. fragilis* (ATCC 12,424), K. *bulgaricus* (ATCC 16,045), K. wickeramii (ATCC 24,178), *K. waltii* (ATCC 56,500), K. *drosophilarum* (ATCC 36,906), *K. thermotolerans*, and *K. marxianus; yarrowia* (EP 402, 226); *Pichia pastoris* (EP 183,070); *Candida; Trichoderma* reesia (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger.*

Higher eukaryotic cells, in particular, those derived from multicellular organisms can be used for expression of glycosylated polypeptide provided herein. Suitable higher eukaryotic cells include, without limitation, invertebrate cells and insect cells, and vertebrate cells. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruiffly), and *Bombyx mori* have been identified. A variety of viral strains for transfection are publicly available, e.g., the K-1 variant of *Autographa californica* NPV and the Bm-5 strain of *Bombyx mori* NPV, and such viruses may be used as the virus herein as described herein, particularly for transfection of *Spodoptera frugiperda* cells. Plant cell cultures of cotton, corn, potato, soybean, *petunia*, tomato, and tobacco can also be utilized as hosts. Examples of vertebrate cells include, mammalian host cell lines such as monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); mouse Sertoli cells (TM4, Mather, Biol. Reprod. 23:243-251 (1980)); monkey kidney cells (CV1 ATCC CCL 70); African green monkey kidney cells (VERO-76, ATCC CRK-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2).

The vector can be introduced to the host cell using any suitable methods known in the art, including, without limitation, DEAE-dextran mediated delivery, calcium phosphate precipitate method, cationic lipids mediated delivery, liposome mediated transfection, electroporation, microprojectile bombardment, receptor-mediated gene delivery, delivery mediated by polylysine, histone, chitosan, and peptides. Standard methods for transfection and transformation of cells for expression of a vector of interest are well known in the art.

In certain embodiments, the host cells comprise a first vector encoding a first polypeptide and a second vector encoding a second polypeptide. In certain embodiments, the first vector and the second vector may be the same or not the same. In certain embodiments, the first polypeptide and the second polypeptide may be the same or not the same.

In certain embodiments, the host cells comprise a first vector encoding a polypeptide A and a second vector encoding a polypeptide B. In certain embodiments, the first vector and the second vector may be the same or not the same. In certain embodiments, the polypeptide A and the polypeptide B may be encoded on the same vector.

In some embodiments, an isolated cell comprises an isolated nucleic acid sequence, as disclosed herein. In some embodiments, an isolated cell comprises two isolated nucleic acid sequences as disclosed herein, wherein one nucleic acid encodes polypeptide A and the other nucleic acid encodes polypeptide B. In some embodiments, an isolated cell comprises two expression vectors as disclosed herein, wherein one vector comprises a nucleic acid encoding polypeptide A and the other vector comprises a nucleic acid encoding polypeptide B.

In certain embodiments, the first vector and the second vector may or may not be introduced simultaneously. In certain embodiments, the first vector and the second vector may be introduced together into the host cell. In certain embodiments, the first vector may be introduced first into the host cell, and then the second vector may be introduced. In certain embodiments, the first vector may be introduced into the host cell which is then established into a stable cell line expressing the first polypeptide, and then the second vector may be introduced into the stable cell line.

In certain embodiments, the host cells comprise a vector encoding for a first polypeptide and a second polypeptide.

In certain embodiments, the present disclosure provides methods of expressing the polypeptide provided herein, comprising culturing the host cell containing the vector under conditions in which the inserted polynucleotide in the vector is expressed.

Suitable conditions for expression of the polynucleotide may include, without limitation, suitable medium, suitable density of host cells in the culture medium, presence of necessary nutrients, presence of supplemental factors, suitable temperatures and humidity, and absence of microorganism contaminants. A person with ordinary skill in the art can select the suitable conditions as appropriate for the purpose of the expression.

In some embodiments, a method of producing a precursor tri-specific antibody construct comprising (a) a first binding domain binding to a cell surface tumor associated antigen (TAA binding domain); (b) a second binding domain binding to a cell surface tumor associated antigen (TAA binding domain); (c) a third binding domain binding to an extracellular epitope of human CD3ε (CD3 binding domain); (d) a CAP regulatory domain; and (e) an HSA regulatory domain, comprises steps of culturing a cell or cells comprising a nucleic acid sequence encoding polypeptide A and polypeptide B of the precursor tri-specific antibody construct, wherein said precursor tri-specific antibody construct polypeptides are expressed and isolated, and wherein said isolated polypeptides A and B form a heterodimer. As disclosed herein in detail, the isolated nucleic acid sequences encoding polypeptides A and B may be comprised within vectors, wherein the same vector or different vectors are used. In some embodiments, each polypeptide may be expressed from a different host cell, wherein dimerization occurs following isolation or purification of the component polypeptides A and B. In some embodiments, polypeptides A and B may be expressed from a same host cell, wherein dimerization occurs in culture or following isolation or purification of the component polypeptides A and B.

In certain embodiments, the polypeptide expressed in the host cell can form a dimer and thus produce a precursor tri-specific antibody construct dimer, for example a heterodimer comprising a polypeptide A and a polypeptide B. In certain embodiments, where the host cells express a first polynucleotide and a second polynucleotide, the first polynucleotide (A) and the second polynucleotide (B) can form a polypeptide complex which is a heterodimer.

In certain embodiments, the polypeptide complex may be formed inside the host cell. For example, the heterodimer may be formed inside the host cell with the aid of relevant enzymes and/or cofactors. In certain embodiments, the polypeptide complex may be secreted out of the cell. In certain embodiments, the first polypeptide (A) and the second polypeptide (B) may be secreted out of the host cell and form a heterodimer outside of the host cell.

In certain embodiments, the first polypeptide and the second polypeptide may be separately expressed and allowed to dimerize under suitable conditions. For example, the first polypeptide (A) and the second polypeptide (B) may be combined in a suitable buffer and allow the first protein monomer (A) and the second protein monomer (B) to dimerize through appropriate interactions such as hydrophobic interactions. For another example, the first polypeptide (A) and the second polypeptide (B) may be combined in a suitable buffer containing an enzyme and/or a cofactor which can promote the dimerization of the first polypeptide (A) and the second polypeptide (B). For another example, the first polypeptide (A) and the second polypeptide (A) may be combined in a suitable vehicle and allow them to react with each other in the presence of a suitable reagent and/or catalyst.

In certain embodiments, the first polypeptide (A) and the second polypeptide (B) may be generated by DNA synthesis and PCR. In certain embodiments, the generated sequences may be subcloned into an expression vector. In certain embodiments, the generated sequences may be subcloned into two expression vectors. In certain embodiments, said expression vector is a plasmid. In certain embodiments, said plasmid is pTT5-based plasmid.

In certain embodiments, transient expression is performed by co-transfecting the expression vector encoding the first polypeptide (A) and the second polypeptide (B) or by transfecting an expression vector encoding both into a suitable cell. A skilled artisan would appreciate that there are a number of transfection methods and protocols that can be used for this purpose. In certain embodiments, transfection or co-transfection is executed using the PEI method. In certain embodiments, 1L of CHO cells at approximately $2.3\times10^6$/ml in a 3L shake flask is used as the host. Transfection is initiated by adding a mixture of 2 mg of total DNA and 4 mg PEI in 100 ml OptiMEM medium (Invitrogen) to the cells and gentle mixing. Cells are then cultured in an incubator shaker at 120 rpm, 37° C., and 8% CO2, for 8-10 days. Feeding with peptone and glucose is carried out 24 h later and every 2-3 days thereafter depending on the cell density and viability. The cell culture is terminated on day 8-10 when cell viability reduces to <70%. The conditioned medium is then harvested for protein purification.

The expressed polypeptides (A) and (B) and/or the polypeptide complex can be collected using any suitable methods. The polypeptides (A) and (B) and/or the polypeptide complex can be expressed intracellularly, in the periplasmic space or be secreted outside of the cell into the medium. If the polypeptides (A) and (B) and/or the polypeptide complex is expressed intracellularly, the host cells containing the polypeptides (A) and (B) and/or the polypeptide complex may be lysed and polypeptide and/or the polypeptide complex may be isolated from the lysate by removing the unwanted debris by centrifugation or ultrafiltration. If the polypeptides (A) and (B) and/or the polypeptide complex is secreted into periplasmic space of *E. coli*, the cell paste may be thawed in the presence of agents such as sodium acetate (pH 3.5), EDTA, and phenylmethylsulfonylfluoride (PMSF) over about 30 min, and cell debris can be removed by centrifugation (Carter et al., BioTechnology 10:163-167 (1992)). If the polypeptides (A) and (B) and/or the polypeptide complex is secreted into the medium, the supernatant of the cell culture may be collected and concentrated using a commercially available protein concentration filter, for example, an Amincon or Millipore Pellicon ultrafiltration unit. A protease inhibitor and/or an antibiotic may be included in the collection and concentration steps to inhibit protein degradation and/or growth of contaminated microorganisms.

The expressed polypeptides (A) and (B) and/or the polypeptide complex can be further purified by a suitable method, such as without limitation, affinity chromatography, hydroxylapatite chromatography, size exclusion chromatography, gel electrophoresis, dialysis, ion exchange fractionation on an ion-exchange column, ethanol precipitation, reverse phase HPLC, chromatography on silica, chromatography on heparin sepharose, chromatography on an anion or cation exchange resin (such as a polyaspartic acid column), chromatofocusing, SDS-PAGE, and ammonium sulfate precipitation (see, for review, Bonner, P. L., Protein purification, published by Taylor & Francis, 2007; Janson, J. C., et al, Protein purification: principles, high resolution methods and applications, published by Wiley-VCH, 1998).

In certain embodiments, the polypeptides (A) and (B) and/or polypeptide dimer complexes can be purified by affinity chromatography. In certain embodiments, protein A chromatography or protein A/G (fusion protein of protein A and protein G) chromatography can be useful for purification of polypeptides and/or polypeptide complexes comprising a component derived from antibody CH2 domain and/or CH3 domain (Lindmark et al., J. Immunol. Meth. 62:1-13 (1983)); Zettlit, K. A., Antibody Engineering, Part V, 531-535, 2010). In certain embodiments, a precursor tri-specific antibody construct disclosed herein does not bind to protein A. In certain embodiments, protein G chromatography can be useful for purification of polypeptides and/or polypeptide complexes comprising IgGγ3 heavy chain (Guss et al., EMBO J. 5:1567 1575 (1986)). In certain embodiments, protein L chromatography can be useful for purification of polypeptides and/or polypeptide complexes comprising K light chain (Sudhir, P., Antigen engineering protocols, Chapter 26, published by Humana Press, 1995; Nilson, B. H. K. et al, J. Biol. Chem., 267, 2234-2239 (1992)). The matrix to which the affinity ligand is attached is most often agarose, but other matrices are available. Mechanically stable matrices such as controlled pore glass or poly(styrenedivinyl) benzene allow for faster flow rates and shorter processing times than can be achieved with agarose. Where the antibody comprises a CH3 domain, the Bakerbond ABX resin (J. T. Baker, Phillipsburg, N.J.) is useful for purification.

Following any preliminary purification step(s), the mixture comprising the precursor tri-specific antibody construct and contaminants may be subjected to low pH hydrophobic interaction chromatography using an elution buffer at a pH between about 2.5-4.5, preferably performed at low salt concentrations (e.g., from about 0-0.25M salt).

In certain embodiments, the polypeptides (A) and (B) and/or polypeptide dimer complexes can be purified by affinity chromatography and size exclusion chromatography (SEC). A skilled artisan would appreciate that there are a number of methods and protocols suitable for this purpose. In certain embodiments, protein purification by affinity chromatography and SEC is performed using an AKTA pure instrument (GE Lifesciences). In certain embodiments, affinity capture of the precursor bispecific antibody is achieved by passing the harvested supernatants over a column of CaptureSelect™ CH1-XL Affinity Matrix (Thermo Scientific). After washing column with PBS, the protein is eluted with 0.1M Glycine, pH 2.5, and immediately neutralized with 1/6 volume of 1M Tris-HCl, pH 8.0. The affinity purified protein is then concentrated to 5-10 mg/ml using Amicon 30 kD concentrator (Merck Millipore) and subjected to SEC purification on a Superdex200 column (GE Lifesciences) equilibrated with PBS. Protein fractions are then collected and analyzed using SDS-PAGE and HPLC-SEC.

Methods of Use of Precursor Tri-specific Antibody Constructs

In some embodiments, described herein are compositions comprising the precursor tri-specific antibody construct as described herein and administration of such composition in a variety of therapeutic settings.

Administration of the precursor tri-specific antibody constructs described herein, in pure form or in an appropriate pharmaceutical composition, can be carried out via any of the accepted modes of administration of agents for serving similar utilities. The pharmaceutical compositions can be prepared by combining a precursor tri-specific antibody construct or a precursor tri-specific antibody construct-containing composition with an appropriate physiologically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. In addition, other pharmaceutically active ingredients (including other anti-cancer agents as described elsewhere herein) and/or suitable excipients such as salts, buffers and stabilizers may, but need not, be present within the composition. Administration may be achieved by a variety of different routes, including oral, parenteral, nasal, intravenous, intradermal, subcutaneous or topical. In some embodiments, modes of administration depend upon the nature of the condition to be treated or prevented. An amount that, following administration, reduces, inhibits, prevents or delays the progression and/or metastasis of a cancer is considered effective. A skilled artisan would appreciate that the term "physiologically acceptable carrier, diluent or excipient", may in some embodiments be used interchangeably with the term "pharmaceutically acceptable carrier" having all the same means and qualities.

In some embodiments, a pharmaceutical composition described herein comprises a nucleotide sequence encoding a precursor tri-specific antibody construct. In some embodiments, a nucleotide sequence encoding a precursor construct disclosed herein, comprises a single linear nucleotide sequence. In some embodiments, a nucleotide sequence encoding a precursor construct disclosed herein, comprises two nucleotide sequences. In some embodiments, a nucleotide sequence encoding a precursor construct disclosed herein, comprises two nucleotide sequences present on the same vector. In some embodiments, a nucleotide sequence encoding a precursor construct disclosed herein, comprises two nucleotide sequences present on different vectors.

In some embodiments, the nucleotide sequence encodes polypeptide A and polypeptide B. In some embodiments, the same nucleotide sequence encodes polypeptide A and polypeptide B. In some embodiments, different nucleotide sequences encode polypeptide A and polypeptide B. In some embodiments, one nucleotide sequence encodes polypeptide A and another nucleotide sequence encodes polypeptide B. In some embodiments, one nucleotide sequence encodes polypeptide A and another nucleotide sequence encodes polypeptide B having a protease cleavage sequence between them, thus allowing polypeptide A and polypeptide B to hetero-dimerize, as described in Duperret EK et al., Cancer Res, October 4 (doi: 10.1158/0008-5472.CAN-18-1429) In some embodiments, a method of treating, preventing, inhibiting the growth of, delaying disease progression, reducing the tumor load, or reducing the incidence of a cancer or a tumor in a subject, or any combination thereof, comprises a step of administering a pharmaceutical composition comprising a precursor tri-specific antibody construct comprising (a) a first binding domain binding to a cell surface tumor associated antigen (TAA binding domain); (b) a second binding domain binding to a cell surface tumor associated antigen (TAA binding domain),; (c) a third binding domain binding to an extracellular epitope of human CD3ε (CD3 binding domain); (d) a CAP regulatory domain; and (e) an HSA regulatory domain; to a subject in need, wherein the method treats, prevents, inhibits the growth of, delays the disease progression, reduces the tumor load, or reduces the incidence of the cancer or a tumor in said subject, or reduces the minimal residual disease, increases remission, increases remission duration, reduces tumor relapse rate, prevents metastasis of said tumor or said cancer, or reduces the rate of metastasis of said tumor or said cancer, or any combination thereof, compared with a subject not administered said pharmaceutical composition.

In some embodiments, a method of treating, preventing, inhibiting the growth of, delaying disease progression, reducing the tumor load, or reducing the incidence of a cancer or a tumor in a subject, or any combination thereof, comprises a step of administering a pharmaceutical composition comprising a nucleotide sequence encoding a precursor bispecific antibody construct comprising (a) a first binding domain binding to a cell surface tumor associated antigen (TAA binding domain); (b) a second binding domain binding to a cell surface tumor associated antigen (TAA binding domain); (c) a third binding domain binding to an extracellular epitope of human CD3ε (CD3 binding domain); (d) a CAP regulatory domain; and (e) an HSA regulatory domain to a subject in need, wherein the method treats, prevents, inhibits the growth of, delays the disease progression, reduces the tumor load, or reduces the incidence of the cancer or a tumor in said subject, or reduces the minimal residual disease, increases remission, increases remission duration, reduces tumor relapse rate, prevents metastasis of said tumor or said cancer, or reduces the rate of metastasis of said tumor or said cancer, or any combination thereof, compared with a subject not administered said pharmaceutical composition.

A skilled artisan would appreciate that the term “treating” and grammatical forms thereof, may in some embodiments encompass both therapeutic treatment and prophylactic or preventative measures with respect to a tumor or cancer as described herein, wherein the object is to prevent or lessen the targeted tumor or cancer as described herein. Thus, in some embodiments of methods disclosed herein, treating may include directly affecting or curing, suppressing, inhibiting, preventing, reducing the severity of, delaying the onset of, reducing symptoms associated with the disease, disorder or condition, or a combination thereof; for example, when said disease or disorder comprises a cancer or tumor. Thus, in some embodiments, “treating” encompasses preventing, delaying progression, inhibiting the growth of, delaying disease progression, reducing tumor load, reducing the incidence of, expediting remission, inducing remission, augmenting remission, speeding recovery, increasing efficacy of or decreasing resistance to alternative therapeutics, or a combination thereof. In some embodiments, “preventing” encompasses delaying the onset of symptoms, preventing relapse to a disease, decreasing the number or frequency of relapse episodes, increasing latency between symptomatic episodes, or a combination thereof. In some embodiments, “suppressing” or “inhibiting”, encompass reducing the severity of symptoms, reducing the severity of an acute episode, reducing the number of symptoms, reducing the incidence of disease-related symptoms, reducing the latency of symptoms, ameliorating symptoms, reducing secondary symptoms, reducing secondary infections, prolonging patient survival, or a combination thereof.

In some embodiments, the size of a cancer or tumor is reduced. In some embodiments, the growth rate of a cancer or tumor is reduced. In some embodiments, the size or the growth rate or a combination thereof, of a cancer or tumor is reduced. In some embodiments, the survival of the subject in need is increased. In some embodiments, the size or the growth rate or a combination thereof, of a cancer or tumor is reduced, or wherein the survival of the subject in need is increased or a combination thereof.

In some embodiments, the subject in need is a human subject. In some embodiments, the subject in need is a human child. In some embodiments, the subject in need is an adult human. In some embodiments, the subject in need is a human infant.

In certain embodiments, the amount administered is sufficient to result in tumor regression, as indicated by a statistically significant decrease in the amount of viable tumor, for example, at least a 50% decrease in tumor mass, or by altered (e.g., decreased with statistical significance) scan dimensions. In other embodiments, the amount administered is sufficient to result in clinically relevant reduction in disease symptoms as would be known to the skilled clinician.

The precise dosage and duration of treatment is a function of the disease being treated and may be determined empirically using known testing protocols or by testing the compositions in model systems known in the art and extrapolating therefrom. Controlled clinical trials may also be performed. Dosages may also vary with the severity of the condition to be alleviated. A pharmaceutical composition is generally formulated and administered to exert a therapeutically useful effect while minimizing undesirable side effects. The composition may be administered one time or may be divided into a number of smaller doses to be administered at intervals of time. For any particular subject, specific dosage regimens may be adjusted over time according to the individual need.

The precursor tri-specific antibody construct-containing compositions may be administered alone or in combination with other known cancer treatments, such as radiation therapy, chemotherapy, transplantation, immunotherapy, hormone therapy, photodynamic therapy, etc. In some embodiments, compositions comprising nucleotide sequences encoding a precursor bispecific antibody construct, may be administered alone or in combination with other known cancer treatments, such as radiation therapy, chemotherapy, transplantation, immunotherapy, hormone therapy, photodynamic therapy, etc. The compositions may also be administered in combination with antibiotics.

Typical routes of administering these and related pharmaceutical compositions thus include, without limitation, oral, topical, transdermal, inhalation, parenteral, sublingual, buccal, rectal, vaginal, and intranasal. The term parenteral as used herein includes subcutaneous injections, intravenous, intramuscular, intrasternal injection or infusion techniques. Pharmaceutical compositions according to certain embodiments as described herein, are formulated so as to allow the active ingredients contained therein to be bioavailable upon administration of the composition to a patient. Compositions that will be administered to a subject or patient may take the form of one or more dosage units, where for example, a tablet may be a single dosage unit, and a container of a herein described precursor tri-specific antibody construct in aerosol form may hold a plurality of dosage units. Actual methods of preparing such dosage forms are known, or will be apparent, to those skilled in this art; for example, see Remington: The Science and Practice of Pharmacy, 20th Edition (Philadelphia College of Pharmacy and Science, 2000). The composition to be administered will, in any event, contain a therapeutically effective amount of a precursor bispecific antibody construct of the present disclosure, for treatment of a disease or condition of interest in accordance with teachings herein.

A pharmaceutical composition may be in the form of a solid or liquid. In one embodiment, the pharmaceutically acceptable carrier(s) are particulate, so that the compositions are, for example, in tablet or powder form. The pharmaceutically acceptable carrier(s) may be liquid, with the compositions being, for example, an oral oil, injectable liquid or an aerosol, which is useful in, for example, inhalatory administration. When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like. Such a solid composition will typically contain one or more inert diluents or edible pharmaceutically acceptable carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent. When the pharmaceutical composition is in the form of a capsule, for example, a gelatin capsule, it may contain, in addition to materials of the above type, a liquid pharmaceutically acceptable carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition intended for either parenteral or oral administration should contain an amount of a precursor tri-specific antibody construct as herein disclosed such that a suitable dosage will be obtained. Typically, this amount is at least 0.01% of the precursor bispecific antibody construct in the composition. When intended for oral administration, this amount may be varied to be between 0.1 and about 70% of the weight of the composition. Certain oral pharmaceutical compositions contain between about 4% and about 75% of the precursor bispecific antibody construct. In certain embodiments, pharmaceutical compositions and preparations according to the embodiments described herein, are prepared so that a parenteral dosage unit contains between 0.01 to 10% by weight of the precursor tri-specific antibody construct prior to dilution.

The pharmaceutical composition may be intended for topical administration, in which case the pharmaceutically acceptable carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. The pharmaceutical composition may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule. The pharmaceutical composition in solid or liquid form may include an agent that binds to the antibody as disclosed herein, and thereby assists in the delivery of the compound. Suitable agents that may act in this capacity include other monoclonal or polyclonal antibodies, one or more proteins or a liposome. The pharmaceutical composition may consist essentially of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols may be delivered in single phase, bi-phasic, or tri-phasic systems in order to deliver the active ingredient(s). Delivery of the aerosol includes the necessary container, activators, valves, subcontainers, and the like, which together may form a kit. One of ordinary skill in the art, without undue experimentation may determine preferred aerosols.

The pharmaceutical compositions may be prepared by methodology well known in the pharmaceutical art. For example, a pharmaceutical composition intended to be administered by injection can be prepared by combining a composition that comprises a precursor tri-specific antibody construct as described herein and optionally, one or more of salts, buffers and/or stabilizers, with sterile, distilled water so as to form a solution. A surfactant may be added to facilitate the formation of a homogeneous solution or suspension. Surfactants are compounds that non-covalently interact with the precursor bispecific antibody construct composition so as to facilitate dissolution or homogeneous suspension of the precursor bispecific antibody construct in the aqueous delivery system.

The compositions may be administered in a therapeutically effective amount, which will vary depending upon a variety of factors including the activity of the specific compound (e.g., precursor bispecific antibody construct) employed; the metabolic stability and length of action of the compound; the age, body weight, general health, sex, and diet of the patient; the mode and time of administration; the rate of excretion; the drug combination; the severity of the particular disorder or condition; and the subject undergoing therapy. Generally, a therapeutically effective daily dose is (for a 70 kg mammal) from about 0.001 mg/kg (i.e., 0.07 mg) to about 100 mg/kg (i.e., 7.0 g); preferably a therapeutically effective dose is (for a 70 kg mammal) from about 0.01 mg/kg (i.e., 0.7 mg) to about 50 mg/kg (i.e., 3.5 g); more preferably a therapeutically effective dose is (for a 70 kg mammal) from about 1 mg/kg (i.e., 70 mg) to about 25 mg/kg (i.e., 1.75 g).

Compositions comprising the precursor tri-specific antibody construct of the present disclosure or comprising a nucleotide sequence encoding the precursor tri-specific antibody construct may also be administered simultaneously with, prior to, or after administration of one or more other therapeutic agents. Such combination therapy may include administration of a single pharmaceutical dosage formulation which contains a compound as disclosed herein, and one or more additional active agents, as well as administration of compositions comprising precursor tri-specific antibody construct as disclosed herein, and each active agent in its own separate pharmaceutical dosage formulation. For example, a precursor tri-specific antibody construct or comprising a nucleotide sequence encoding the precursor tri-specific antibody construct, as described herein, and the other active agent can be administered to the patient together in a single oral dosage composition such as a tablet or capsule, or each agent administered in separate oral dosage formulations. Similarly, a precursor tri-specific antibody construct or comprising a nucleotide sequence encoding the precursor tri-specific antibody construct, as described herein, and the other active agent can be administered to the patient together in a single parenteral dosage composition such as in a saline solution or other physiologically acceptable solution, or each agent administered in separate parenteral dosage formulations. Where separate dosage formulations are used, the compositions comprising precursor tri-specific antibody construct or comprising a nucleotide sequence encoding the precursor tri-specific antibody construct, and one or more additional active agents can be administered at essentially the same time, i.e., concurrently, or at separately staggered times, i.e., sequentially and in any order; combination therapy is understood to include all these regimens.

Thus, in certain embodiments, also contemplated is the administration of precursor tri-specific antibody construct compositions of this disclosure or comprising a nucleotide sequence encoding the precursor tri-specific antibody construct, in combination with one or more other therapeutic agents. Such therapeutic agents may be accepted in the art as a standard treatment for a particular disease state as described herein, such as cancer, inflammatory disorders, allograft transplantation, type I diabetes, and multiple sclerosis. Exemplary therapeutic agents contemplated include cytokines, growth factors, steroids, NSAIDs, DMARDs, anti-inflammatories, chemotherapeutics, radiotherapeutics, or other active and ancillary agents.

In certain embodiments, the precursor tri-specific antibody construct or comprising a nucleotide sequence encoding the precursor tri-specific antibody construct, disclosed herein may be administered in conjunction with any number of chemotherapeutic agents. Examples of chemotherapeutic agents include alkylating agents such as thiotepa and cyclophosphamide (CYTOXAN.TM.); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK.RTM.; razoxane; sizofuran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL.RTM., Bristol-Myers Squibb Oncology, Princeton, N.J.) and doxetaxel (TAXOTERE.RTM., Rhne-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylomithine (DMFO); retinoic acid derivatives such as Targretin.TM. (bexarotene), Panretin.TM. (alitretinoin); ONTAK.TM. (denileukin diftitox); esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4 (5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

A variety of other therapeutic agents may be used in conjunction with the precursor tri-specific antibody construct described herein. In one embodiment, the precursor tri-specific antibody construct or comprising a nucleotide sequence encoding the precursor tri-specific antibody construct, is administered with an anti-inflammatory agent. Anti-inflammatory agents or drugs include, but are not limited to, steroids and glucocorticoids (including betamethasone, budesonide, dexamethasone, hydrocortisone acetate, hydrocortisone, hydrocortisone, methylprednisolone, prednisolone, prednisone, triamcinolone), nonsteroidal anti-inflammatory drugs (NSAIDS) including aspirin, ibuprofen, naproxen, methotrexate, sulfasalazine, leflunomide, anti-TNF medications, cyclophosphamide and mycophenolate.

The compositions comprising herein described precursor tri-specific antibody construct or comprising a nucleotide sequence encoding the precursor tri-specific antibody construct may be administered to an individual afflicted with a disease as described herein, including, but not limited to cancer and autoimmune and inflammatory diseases. For in vivo use for the treatment of human disease, the precursor tri-specific antibody construct or comprising a nucleotide sequence encoding the precursor tri-specific antibody construct described herein are generally incorporated into a pharmaceutical composition prior to administration. A pharmaceutical composition comprises one or more of the precursor tri-specific antibody construct or comprising a nucleotide sequence encoding the precursor tri-specific antibody construct described herein in combination with a pharmaceutically acceptable carrier or excipient as described elsewhere herein. To prepare a pharmaceutical composition, an effective amount of one or more of the precursor tri-specific antibody constructs or comprising a nucleotide sequence encoding the precursor tri-specific antibody construct is mixed with any pharmaceutically acceptable carrier(s) or excipient known to those skilled in the art to be suitable for the particular mode of administration.

A pharmaceutically acceptable carrier may be liquid, semi-liquid or solid. Solutions or suspensions used for parenteral, intradermal, subcutaneous or topical application may include, for example, a sterile diluent (such as water), saline solution, fixed oil, polyethylene glycol, glycerin, propylene glycol or other synthetic solvent; antimicrobial agents (such as benzyl alcohol and methyl parabens, phenols or cresols, mercurials, chlorobutanol, methyl and propyl p-hydroxybenzoic acid esters, thimerosal, benzalkonium chloride and benzethonium chloride); antioxidants (such as ascorbic acid and sodium bisulfite; methionine, sodium thiosulfate, platinum, catalase, citric acid, cysteine, thioglycerol, thioglycolic acid, thiosorbitol, butylated hydroxyanisol, butylated hydroxytoluene, and/or propyl gallate) and chelating agents (such as ethylenediaminetetraacetic acid (EDTA)); buffers (such as acetates, citrates and phosphates). If administered intravenously, suitable pharmaceutically acceptable carriers include physiological saline or phosphate buffered saline (PBS), and solutions containing thickening and solubilizing agents, such as glucose, polyethylene glycol, polypropylene glycol and mixtures thereof.

The compositions comprising precursor tri-specific antibody construct as described herein may be prepared with pharmaceutically acceptable carriers that protect the precursor tri-specific antibody construct against rapid elimination from the body, such as time release formulations or coatings. Such pharmaceutically acceptable carriers include controlled release formulations, such as, but not limited to, implants and microencapsulated delivery systems, and biodegradable, biocompatible polymers, such as ethylene vinyl acetate, polyanhydrides, polyglycolic acid, polyorthoesters, polylactic acid and others known to those of ordinary skill in the art.

The present precursor tri-specific antibody construct are useful for the treatment of a variety of cancers or tumors. In some embodiments, the cancer or tumor comprises a solid tumor. In some embodiments, the cancer or tumor comprises a non-solid tumor. In some embodiments, the cancer or tumor comprises a metastasis of a cancer or tumor.

For example, some embodiments of a method for the treatment of a cancer are directed to cancers including, but not limited to, melanoma, non-Hodgkin's lymphoma, Hodgkin's disease, leukemia, plasmocytoma, sarcoma, glioma, thymoma, breast cancer, prostate cancer, colo-rectal cancer, kidney cancer, renal cell carcinoma, uterine cancer, pancreatic cancer, esophageal cancer, brain cancer, lung cancer, ovarian cancer, cervical cancer, testicular cancer, gastric cancer, esophageal cancer, multiple myeloma, hepatoma, acute lymphoblastic leukemia (ALL), acute myelogenous leukemia (AML), chronic myelogenous leukemia (CML), and chronic lymphocytic leukemia (CLL), or other cancers, by administering to a cancer patient a therapeutically effective amount of a herein disclosed precursor bispecific antibody construct or a nucleotide sequence encoding the precursor tri-specific antibody construct.

Solid tumors may be benign (not cancer), or malignant (cancer). Different types of solid tumors are named for the type of cells that form them. Examples of solid tumors for which treatment may be provided include sarcomas, carcinomas, and lymphomas. In some embodiments, solid tumors for which treatment may be provided include neoplasms (new growth of cells) or lesions (damage of anatomic structures or disturbance of physiological functions) formed by an abnormal growth of body tissue cells other than blood, bone marrow or lymphatic cells. In some embodiments, a solid tumor for which treatment may be provided consists of an abnormal mass of cells which may stem from different tissue types such as liver, colon, breast, or lung, and which initially grows in the organ of its cellular origin. However, such cancers may spread to other organs through metastatic tumor growth in advanced stages of the disease.

In some embodiments of a method for treatment of a cancer or tumor, the solid tumor or cancer comprises a sarcoma or a carcinoma, adrenocortical tumor (adenoma and carcinoma), a fibrosarcoma, a myxo-sarcoma, a liposarcoma, a chondrosarcoma, an osteogenic sarcoma, a chordoma, an angiosarcoma, an endothelio a sarcoma, a lymphangiosarcoma, lymphangioendothelio sarcoma, a synovioma, a mesothelioma, an Ewing's tumor, a leiomyosarcoma, a rhabdomyosarcoma, a colon carcinoma, a pancreatic cancer or tumor, a breast cancer or tumor, an ovarian cancer or tumor, a prostate cancer or tumor, a squamous cell carcinoma, a squamous cell carcinoma of the lung, a basal cell carcinoma, an adenocarcinoma, a sweat gland carcinoma, a sebaceous gland carcinoma, a papillary carcinoma, a papillary adenocarcinomas, a cystadenocarcinoma, a medullary carcinoma, a bronchogenic carcinoma, a renal cell carcinoma, a hepatoma, a bile duct carcinoma, a choriocarcinoma, a seminoma, an embryonal carcinoma, a colorectal carcinoma, a desmoid tumor, a desmoplastic small round cell tumor, an endocrine tumor, a germ cell tumor, a hepatoblastoma, a hepatocellular carcinoma, a melanoma, a neuroblastoma, an osteosarcoma, a retinoblastoma, a rhabdomyosarcoma, a soft tissue sarcoma other than rhabdomyosarcoma, a Wilms, Tumor, a cervical cancer or tumor, a uterine cancer or tumor, a testicular cancer or tumor, a lung carcinoma, a small cell lung carcinoma, an anal cancer, a glioblastoma, an epithelial tumor of the head and neck, a bladder carcinoma, an epithelial carcinoma, a glioma, an astrocytoma, a medulloblastoma, a craniopharyngioma, an ependymoma, a pinealoma, a hemangioblastoma, an acoustic neuroma, an oligodenroglioma, a schwannoma, a meningioma, a melanoma, a neuroblastoma, or a retinoblastoma.

In some embodiments of a method for treatment of a cancer or tumor, the tumor or cancer comprises a non-solid tumor, that is a non-solid cancer. In some embodiments, methods for treatment of a cancer or tumor may be for a diffuse cancer, wherein the cancer is widely spread; not localized or confined. In some embodiments, a diffuse cancer may comprise a non-solid tumor. Examples of diffuse cancers include leukemias. Leukemias comprise a cancer that starts in blood-forming tissue, such as the bone marrow, and causes large numbers of abnormal blood cells to be produced and enter the bloodstream.

In some embodiments of a method for treatment of a cancer or tumor, the diffuse cancer comprises a B-cell malignancy. In some embodiments, the diffuse cancer comprises leukemia. In some embodiments, the cancer is lymphoma. In some embodiments, the lymphoma is large B-cell lymphoma.

In some embodiments of a method for treatment of a cancer or tumor, the diffuse cancer or tumor comprises a hematological tumor. In some embodiments, hematological tumors are cancer types affecting blood, bone marrow, and lymph nodes. Hematological tumors may derive from either of the two major blood cell lineages: myeloid and lymphoid cell lines. The myeloid cell line normally produces granulocytes, erythrocytes, thrombocytes, macrophages, and masT-cells, whereas the lymphoid cell line produces B, T, and plasma cells. Lymphomas (e.g. Hodgkin's Lymphoma), lymphocytic leukemias, and myeloma are derived from the lymphoid line, while acute and chronic myelogenous leukemia (AML, CML), myelodysplastic syndromes and myeloproliferative diseases are myeloid in origin.

In some embodiments of a method for treatment of a cancer or tumor, the non-solid (diffuse) cancer or tumor comprises a hematopoietic malignancy, a blood cell cancer, a leukemia, a myelodysplastic syndrome, a lymphoma, a multiple myeloma (a plasma cell myeloma), an acute lymphoblastic leukemia, an acute myelogenous leukemia, a chronic myelogenous leukemia, a Hodgkin lymphoma, a non-Hodgkin lymphoma, or plasma cell leukemia.

An amount that, following administration, inhibits, prevents reduces the incidence of, reduces the tumor load, or delays the growth, progression and/or metastasis of a cancer in a statistically significant manner (i.e., relative to an appropriate control as will be known to those skilled in the art) is considered effective.

Another embodiment provides a method for preventing metastasis of a cancer including, but not limited to a solid or non-solid tumor or cancer as disclosed above, by administering to a cancer patient a therapeutically effective amount of a herein disclosed precursor tri-specific antibody construct or a nucleotide sequence encoding the precursor bispecific antibody construct (e.g., an amount that, following administration, inhibits, prevents or delays metastasis of a cancer in a statistically significant manner, i.e., relative to an appropriate control as will be known to those skilled in the art).

Another embodiment provides a method for preventing a cancer including, but not limited to a solid or non-solid tumor or cancer as disclosed above, by administering to a cancer patient a therapeutically effective amount of a herein disclosed precursor tri-specific antibody construct or a nucleotide sequence encoding the precursor bispecific antibody construct.

Another embodiment provides a method for treating, inhibiting the progression of a tumor or cancer including but not limited to a solid or non-solid tumor or cancer as disclosed above, by administering to a patient afflicted by one or more of these diseases a therapeutically effective amount of a herein disclosed precursor bispecific antibody construct or a nucleotide sequence encoding the precursor tri-specific antibody construct.

In one embodiment, the present disclosure provides a method for directing T cell activation, comprising administering to a patient in need thereof an effective amount of a precursor tri-specific antibody construct that comprises a CD3 binding domain, as described herein, that is able to specifically binds TCRα, TCRβ, CD3γ, CD3ε, CD3ε, or a combination thereof, and a TAA first or a second binding domain or both, that specifically binds a TAA target, for instance, a tumor-specific antigen (e.g., EGFR) or other antigens of choice at a site or cell where T-cell activation is desired,, wherein in some embodiments, a first or second binding domain binds a CAP regulatory domain and an HSA regulatory domain, as described above.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

EXAMPLES

Example 1: Production of Precursor and Active Tri-Specific Antibody Constructs Objective The objective of this study was to produce functional Tri-Specific (active) and Precursor Tri-Specific antibody constructs.

Methods

Gene Synthesis and Plasmid Construction

The coding sequences for heavy chain (HC polypeptide) and light chain (LC polypeptide) of the antibody constructs (Precursor and Activated Tribody Antibody constructs) were generated by DNA synthesis and PCR, and were subsequently subcloned into pTT5-based plasmids (NRC Biotechnology Research Institute) for protein expression in mammalian cell systems. Gene sequences in the expression vectors were confirmed by DNA sequencing. The designation of polypeptides representing the heavy chain polypeptide (HC polypeptide) and the light chain polypeptide (LC polypeptide) is based on the Fab component of the constructs.

Six different EGFR antibody constructs were generated as follows.

Construct 1:

Tri-Specific variable light chain-variable heavy chain (VLVH), comprising an anti-CD3ε (Fab portion) and two anti-EGFR variable light (VL) and variable heavy (VH) single-chain variable fragment (scFv) chains, ordered in a N'-XXX-XXX-XXX-C' manner. The HC polypeptide is ordered N'-linker-(anti-CD3ε VH1-linker-CH1)-linker-(anti-EGFR VL2-linker-VH2)-linker-C'. The amino acid sequence of the HC polypeptide is SEQ ID NO:138 (FIG. 4A). The nucleotide sequence encoding the HC polypeptide of construct 1 is set forth in SEQ ID NO: 150 and FIG. 4B.

The Light Chain (LC) polypeptide is ordered N'-linker-(anti-CD3ε VL1-linker-CL)-linker-(anti-EGFR VL3-linker-VH3)-linker-C'. The amino acid sequence of the LC polypeptide of Construct 1 is SEQ ID NO: 139 (FIG. 5A). The nucleotide sequence encoding the LC polypeptide of Construct 1 is SEQ ID NO: 151 (FIG. 5B).

Construct 2:

Tri-Specific variable heavy chain-variable light chain (VHVL), comprising an anti-CD3ε (Fab portion) and two anti-EGFR VH and VL single-chain variable fragment (scFv) chains, ordered in a N'-XXX-XXX-XXX-C' manner.

The HC polypeptide chain of Construct 2 is ordered N'-linker-(anti-CD3ε VH1-linker-CH1)-linker-(anti-EGFR VH2-linker-VL2)-linker-C'. The amino acid sequence of the HC polypeptide chain of Construct 2 is SEQ ID NO: 140 (FIG. 6A). The nucleotide sequence encoding the HC polypeptide heavy chain of Construct 2 is SEQ ID NO: 152 (FIG. 6B).

The LC polypeptide chain of Construct 2 is ordered N'-linker-(anti-CD3ε VL1-linker-CL)-linker-(anti-EGFR VH3-linker-VL3)-linker-C'. The amino acid sequence of the LC polypeptide chain of Construct 2 is SEQ ID NO: 141

(FIG. 7A). The nucleotide sequence of the LC polypeptide chain of Construct 2 is SEQ ID NO: 153 (FIG. 7B).

Construct 3:

Precursor Tri-Specific-Variable Light-Variable Heavy (VLVH), comprising an anti-CD3ε (Fab portion), two anti-EGFR VL and VH single-chain variable fragment (scFv) chains, and two sub-regulatory domains linked by MMP9/2 cleavable sequences, ordered in a N'-XXX-XXX-XXX-C' manner.

The HC polypeptide chain of Construct 3 is ordered N' human serum albumin (HSA)-linker-protease cleavage peptide (MMP2/9)-linker-(anti-CD3ε VH1-linker-CH1)-linker-(anti-EGFR VL3-linker-VH3)-linker-C'. The amino acid sequence of the HC polypeptide chain of Construct 3 is SEQ ID NO:130 (FIG. 8A). The nucleotide sequence encoding the HC polypeptide of Construct 3 is SEQ ID NO:142 (FIG. 8B).

The LC polypeptide chain of Construct 3 is ordered N' CAP-linker-protease cleavage peptide (MMP2/9)-linker-(anti-CD3ε VL1-linker-CL1)-linker-(anti-EGFR VL2-linker-VH2)-linker-C'. The amino acid sequence of the LC polypeptide chain of Construct 3 is SEQ ID NO: 131 (FIG. 9A). The nucleotide sequence of LC of Construct 3 is SEQ ID NO:143 (FIG. 9B).

Construct 4

Precursor Tri-Specific-Construct Variable Heavy Variable Light (VHVL), comprising an anti-CD3ε (Fab portion), two anti-EGFR VL and VH single-chain variable fragment (scFv) chains, and two sub-regulatory domains linked by MMP9/2 cleavable sequences, ordered in a N'-XXX-XXX-XXX-C' manner.

The HC polypeptide of Construct 4 is ordered N'-human serum albumin (HSA)-linker-protease cleavable peptide MMP2/9-linker-VH1-linker-CH1-linker-VH3-linker-VL3-linker. The amino acid sequence of the HC polypeptide chain of Construct 4 is SEQ ID NO:132 (FIG. 10A).

The nucleotide sequence of the HC polypeptide of Construct 4 is SEQ ID NO:144 (FIG. 10B).

The LC polypeptide of Construct 4 is ordered N'-CAP-linker-protease cleavable peptide MMP2/9-linker-VL1-linker-CL-linker-VH2-linker-VL2-linker. The amino acid sequence of the LC polypeptide chain of Construct 4 is SEQ ID NO:133 (FIG. 11A).

The nucleotide sequence of the LC polypeptide chain of Construct 4 is SEQ ID NO:145 (FIG. 11B).

Construct 5

Precursor Tri-Specific-Non-Cleavable (NC) Variable Light Variable Heavy (VLVH), comprising an anti-CD3ε (Fab portion), two anti-EGFR VL and VH single-chain variable fragment (scFv) chains, and two sub-regulatory domains, without including a MMP9/2 cleavable sequence, ordered in a N'-XXX-XXX-XXX-C' manner.

The HC polypeptide of Construct 5 is ordered N'-human serum albumin (HSA)-linker-VH1-linker-CH1-linker-VL3-linker-VH3-linker. The amino acid sequence of the HC polypeptide chain of Construct 5 is SEQ ID NO:134 (FIG. 12A).

The nucleotide sequence of the HC polypeptide of Construct 5 is SEQ ID NO:146 (FIG. 12B).

The LC polypeptide of Construct 5 is ordered N'-CAP-linker-VL1-linker-CL-linker-VL2-linker-VH2-linker. The amino acid sequence of the LC polypeptide chain of Construct 5 is SEQ ID NO:135 (FIG. 13A).

The nucleotide sequence of the LC polypeptide chain of Construct 5 is SEQ ID NO:147 (FIG. 13B).

Construct 6

Precursor Tri-Specific-Non-Cleavable (NC) Variable Heavy Variable Light (VHVL), comprising an anti-CD3ε (Fab portion), two anti-EGFR VL and VH single-chain variable fragment (scFv) chains, and two sub-regulatory domains, without including a MMP9/2 cleavable sequences, ordered in a N'-XXX-XXX-XXX-C' manner.

The HC polypeptide of Construct 6 is ordered N'-human serum albumin (HSA)-linker-VH1-linker-CH1-linker-VH3-linker-VL3-linker. The amino acid sequence of the HC polypeptide chain of Construct 6 is SEQ ID NO:136 (FIG. 14A).

The nucleotide sequence encoding the HC polypeptide of Construct 6 is SEQ ID NO:148 (FIG. 14B).

The LC polypeptide of Construct 6 is ordered N'-CAP-linker-VL1-linker-CL-linker-VH2-linker-VL2-linker. The amino acid sequence of the LC polypeptide chain of Construct 6 is SEQ ID NO:137 (FIG. 15A).

The nucleotide sequence encoding the LC polypeptide of Construct 6 is SEQ ID NO:149 (FIG. 15B).

Constructs of FIG. 2F, Targeting EGFR or 5T4

The HC polypeptide of a construct of FIG. 2F is ordered N-terminal to C-terminal CAP, linker, human serum albumin, protease cleavage sequence, VH1/CH1 of anti-CD3e Fab, V, VH (EGFR or 5T4 scFv). The two marked cysteine residues (double underline), may participate in disulfide double bonds. The amino acid sequence of the HC polypeptide chain of a construct of FIG. 2F wherein the scFv target EGFR are set forth in SEQ ID NO: 28 and 31 (FIGS. 45A and 45B). The amino acid sequence of the HC polypeptide chain of a construct of FIG. 2F wherein the scFv target 5T4 are set forth in SEQ ID NO: 118 and 176 (FIGS. 47A and 47B).

The LC polypeptide of a construct of FIG. 2F is ordered N-terminal to C-terminal order as follows: Linker, VL1-CL of anti-CD3e Fab, VL, and VH, (EGFR or 5T4 scFv). The two marked cysteine residues (double underline), may participate in disulfide double bonds. The amino acid sequence of the LC polypeptide chain of a construct of FIG. 2F wherein the scFv target is EGFR is set forth in SEQ ID NO: 32 (FIG. 46). The amino acid sequence of the LC polypeptide chain of a construct of FIG. 2F wherein the scFv target is 5T4 is set forth in SEQ ID NO: 177 (FIG. 48).

Expression of Antibody Constructs

Transient expression of the antibody constructs was performed by co-transfection of paired heavy chain (HC) and light chain (LC) polypeptide constructs into CHO cells using the polyethylenimine (PEI) method. Briefly, 1L of CHO cells at approximately $2.3\times10^{6}$/ml in a 3L shake flask was used as host. Transfection was initiated by adding a mixture of 2 mg of total DNA and 4 mg PEI in 100 ml OptiMEM medium (Invitrogen) to the cells and gentle mixing it. Cells were then cultured in an incubator shaker at 120 rpm, 37° C., and 8% CO2, for 8-10 days. Feeding with peptone and glucose was carried out 24 h later and every 2-3 days thereafter depending on the cell density and viability. The cell culture was terminated on day 8-10 when cell viability reduced to <70%. The conditioned medium was harvested for protein purification.

Purification of Antibody Constructs

Protein purification by affinity chromatography and size-exclusion (SEC) was performed using an AKTA pure instrument (GE Lifesciences). Affinity capture of the antibodies was achieved by passing the harvested supernatants over a column of CaptureSelect™ CH1-XL Affinity Matrix (Thermo Scientific). After washing column with PBS, the protein was eluted with 0.1M Glycine, pH 2.5, and immediately neutralized with 1/6 volume of 1M Tris-HCl, pH 8.0.

The affinity purified protein was then concentrated to 5-10 mg/ml using Amicon 30 kD concentrator (Merck Millipore) and subjected to SEC purification on a Superdex200 column (GE Lifesciences) equilibrated with PBS. Protein fractions were collected and analyzed using SDS-PAGE and HPLC-SEC.

SEC-HPLC Analysis of Precursor Tri-Specific Antibody Constructs

Analytical SEC-HPLC was performed using a TSK G3000SWXL column (Tosoh Instruments), Shimadzu LC-10 HPLC instrument (Shimadzu Corp.), and common conditions for IgG, i.e. mobile phase buffer, PBS; flow rate, 1 ml/min; running cycle, 30 min; protein sample concentration 1 mg/ml diluted in PBS; and 20 μl/injection/run.

Results

Confirmation of Precursor Tri-Specific and Tri-Specific Molecular Weight by SDS-PAGE Reduced and non-reduced SDS-PAGE of all the Tri-Specific and Precursor Tri-Specific constructs confirmed their expected molecular weights. The predicted molecular weight of the Tri-Specific construct is 100,112 Da, the Fd moiety having a molecular weight of 51,105 DA, and the AC moiety having a molecular weight of 49,029 Da. SDS-PAGE confirmed that the produced Tri-body constructs were pure, as they migrated according to their predicted molecular weights, both in their reduced and non-reduced forms (FIG. 16). The predicted molecular weight of the Precursor Tri-Specific construct is 170,390 Da, the Fd having a molecular weight of 117,649 Da, and the AC fusion having a molecular weight of 52,762 Da. The SDS-PAGE confirmed that the produced Precursor Tri-Bodies were pure, as they migrate according to the predicted molecular weights, both in their reduced and non-reduced forms (FIG. 16).

Figure 17A:
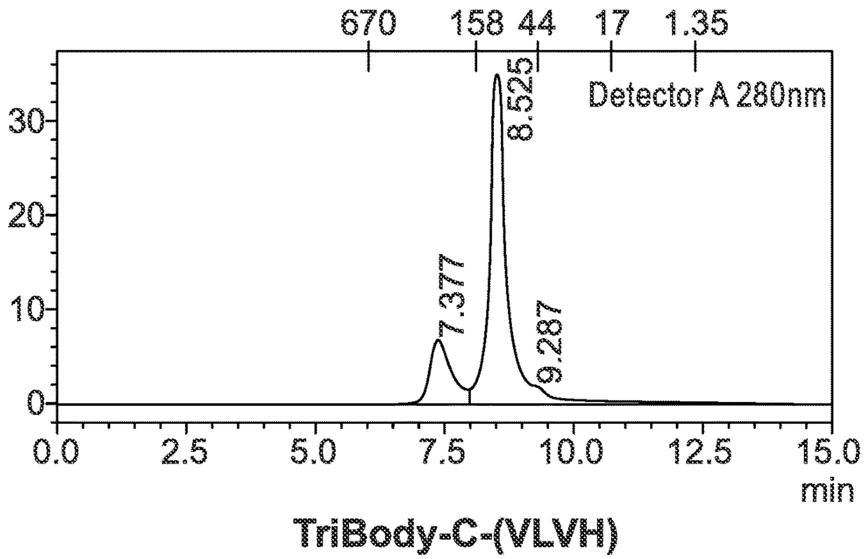
Figure 17B:
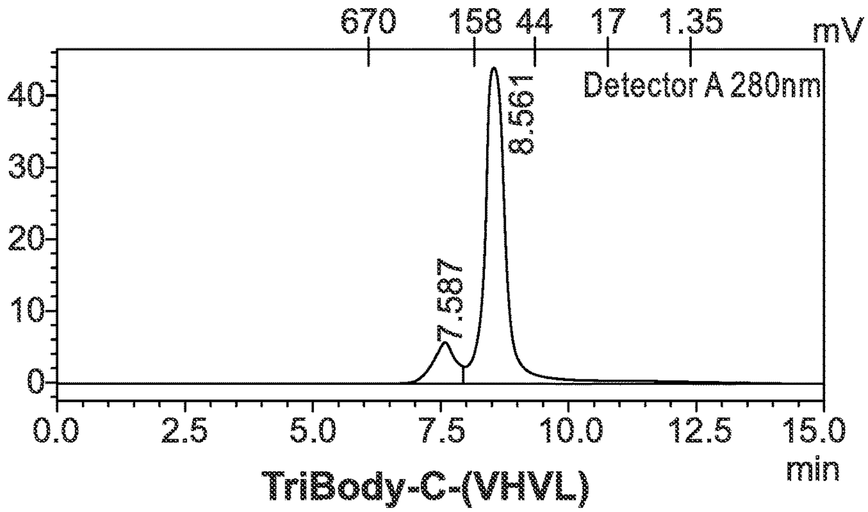
Figure 17C:
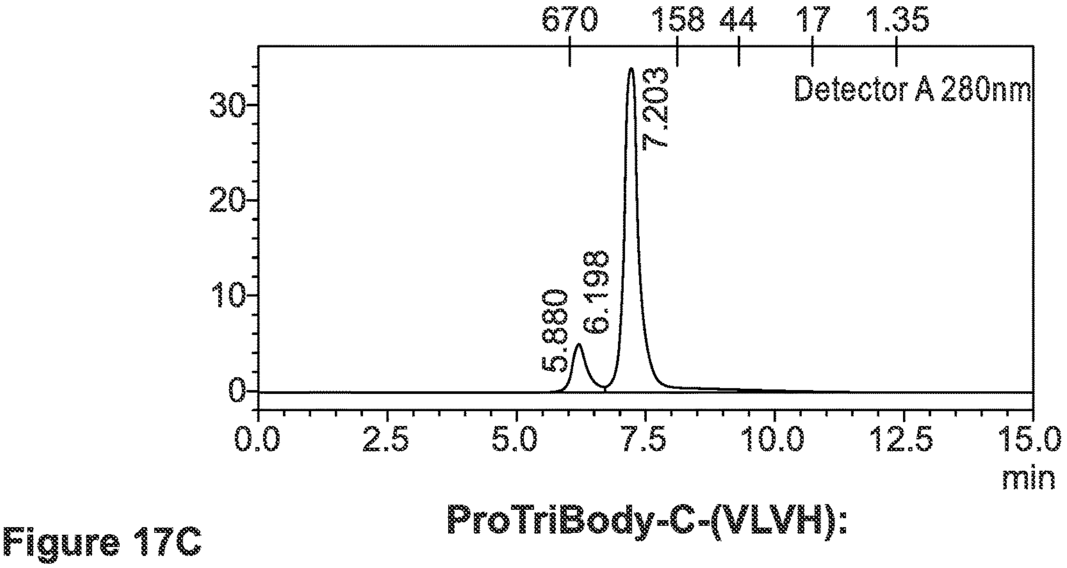
Figure 17D:
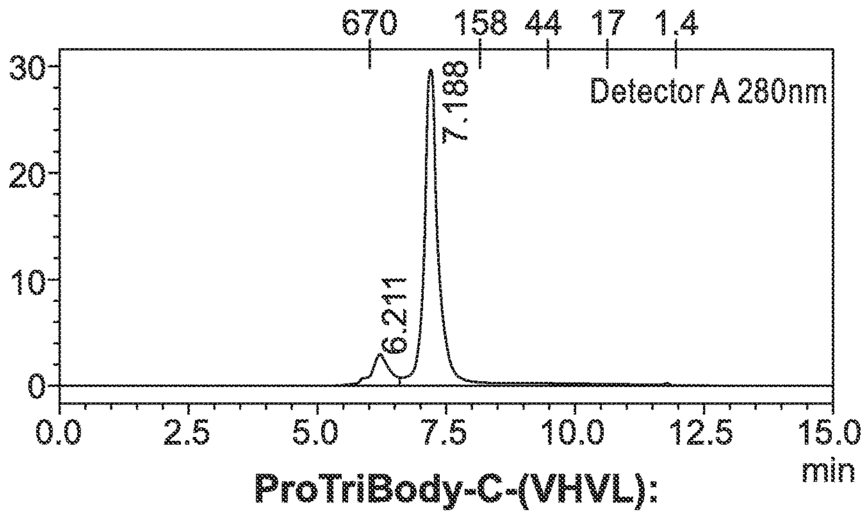
Figure 17E:
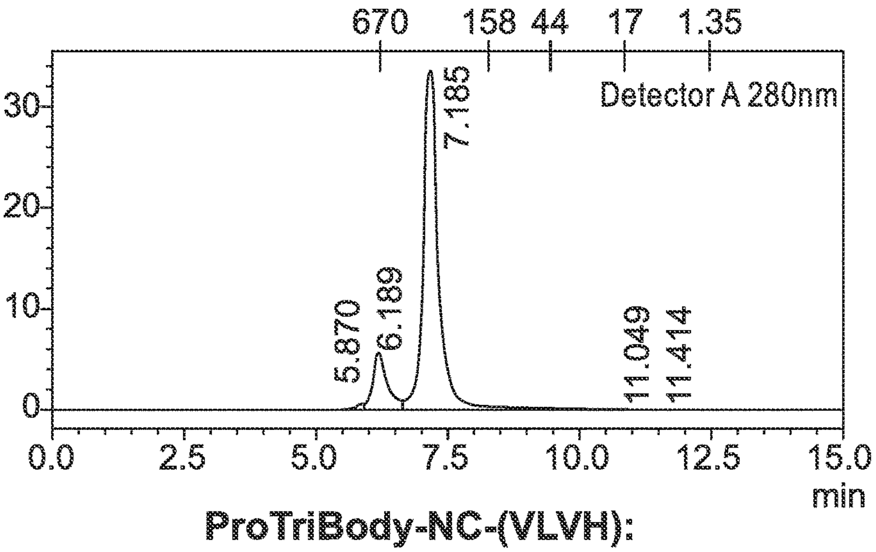
Figure 17F:
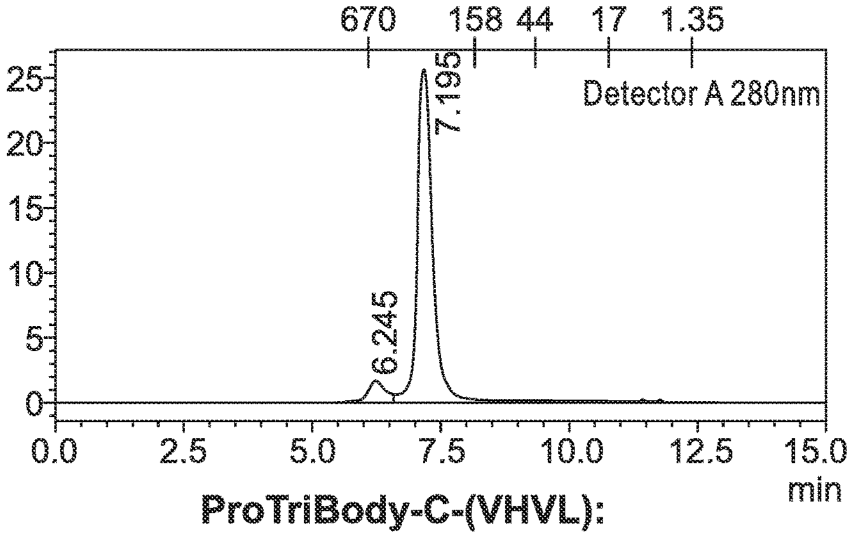

Confirmation of Precursor Tri-Specific and Tri-Specific Molecular Weight by Analytical HPLC-Size Exclusion Chromatography Analytical HPLC-size exclusion chromatography showed that all Tri-Specific constructs migrated as monomers and according to their predicted molecular weight of 100,112 Da (FIGS. 17A and 17B). Similarly, all Precursor Tri-Specific constructs migrated as monomers and according to their predicted molecular weight of 170,390 Da (FIGS. 17C, 17D, 17E, and 17F).

Example 2: Binding of Tri-Specific and Precursor Tri-Specific Constructs to EGFR and CD3e Antigens Objective The objective of these experiments was to determine the EGFR and CD3e binding affinity of Tri-Specific and Precursor Tri-Specific constructs.

Methods

ELIsA Detection of Tri-Specific and Precursor Tri-Specific Antigen Binding

The EGFR antigens hEGFR-Fc (Cat #344-ER-050, Biotechne) and rhesus EGFR-Fc (Cat #EGR-C5252, Acro Biosystems)) were diluted to a 0.05 ug/ml concentration in PBS. Human CD3epsilon (hCD3epsilon-His (Cat #10977-H08S, Sino Biological) and cynomolgus CD3epsilon (Cat #CDE-C5226, Acro Biosystems)) were diluted to a 0.01 ug/ml concentration in PBS. ELISA plate (Cat #9018, Corning) wells were filled with 100 μl of antigen suspension. Plates were incubated overnight at 4° C. Wells were blocked with 250 μl 1% BSA in PBST for 1 hr at 37° C. and then washed four times with PBST. All washes were done using Biotek (Elx 405). All construct antibodies were diluted to 15 μg/ml and prepared with 3-fold serial dilutions (12 points, including 0 μg/ml). 100 μl/well of diluted antibody construct solution was added to plate and incubated for 1 hr at 37° C. Plates were washed four times with PBST, then 100 μl/well of anti-human kappa light chain-HRP antibody (1:10000) was added and incubated for 0.5 hr at 37° C. Wells were washed 4 times with PBST, then 100 μl/well of TMB substrate was added and plates were incubated at RT for 5 min. 100 μl/well of 1.0 N HCl was added to terminate the reaction. Plates were read using ELISA plate reader at 450 nm wavelength (SpectraMax M5e). Data Analysis was performed using Graphpad Prism 5 software by using nonlinear regression (curve fit): log (agonist) vs. response, agonist is antibody concentration (nM) and response is OD value.

Results

Binding of Tri-Specific and Precursor Tri-Specific Antibodies to Human EGFR Antigen The binding of the VLVH and VHVL forms of Tri-Specific and Precursor Tri-Specific antibodies to human EGFR was tested by ELISA using EGFR extracellular fusion antigen (hEGFR-Fc). Tri-Specific and Precursor Tri-Specific constructs were found to bind the extracellular domain of hEGFR with similar affinities (FIG. 18A). Furthermore, no differences in hEGFR binding affinities were found between the VLVH and the VHVL forms of the constructs (FIG. 18A).

Binding of Tri-Specific and Precursor Tri-Specific Antibodies to rhesus EGFR Antigen The binding of the VLVH and VHVL forms of Tri-Specific and Precursor Tri-Specific antibodies to rhesus EGFR was tested by ELISA using EGFR extracellular fusion antigen (rhesus EGFR-Fc). Tri-Specific and Precursor Tri-Specific constructs were found to bind the extracellular domain of rhesus EGFR with similar affinities (FIG. 18B). Furthermore, no differences in rhesus EGFR binding affinities were found between the VLVH and the VHVL forms of the constructs (FIG. 18B). Furthermore, the binding affinities of all Tri-Specific and Precursor Tri-Specific constructs was similar to human and rhesus EGFR.

Binding of Tri-Specific and Precursor Tri-Specific Antibodies to human CD3epsilon Antigen The binding of the VLVH and VHVL forms of Tri-Specific and Precursor Tri-Specific antibodies to human CD3epsilon was tested by ELISA using CD3epsilon extracellular fusion antigen (human CD3epsilon-His). Tri-Specific constructs bound to human CD3epsilon at sub-nanomolar concentrations, while cleaved (C) and non-cleaved (NC) Precursor Tri-Specific constructs bound to human CD3epsilon at a much higher half maximal effective concentration (EC50). This suggests hindrance of the CD3epsilon cap to human CD3epsilon antigen (FIG. 7A). Furthermore, no differences in human CD3epsilon binding affinities were found between the VLVH and the VHVL forms of the constructs (FIG. 19A).

Binding of Tri-Specific and Precursor Tri-Specific Antibodies to cynomolgus CD3epsilon Antigen The binding of the VLVH and VHVL forms of Tri-Specific and Precursor Tri-Specific antibodies to cynomolgus CD3epsilon was tested by ELISA using CD3epsilon extracellular fusion antigen (cynoCD3epsilon-His). Tri-Specific constructs bound to cynoCD3epsilon at sub-nanomolar concentrations, while cleaved (C) and non-cleaved (NC) Precursor Tri-Specific constructs bound to cynoCD3epsilon at a much higher half maximal effective concentration (EC50). This suggests hindrance of the CD3epsilon cap to cynoCD3epsilon antigen (FIG. 7B). Furthermore, no differences in human CD3epsilon binding affinities were found between the VLVH and the VHVL forms of the constructs (FIG. 19B). Furthermore, the binding affinities of all Tri-Specific and Precursor Tri-Specific constructs was similar to human and cynomolgus CD3epsilon.

Example 3: Digestion of Tri-Specific and Precursor Tri-Specific Antibody Constructs by MMP9

Objective

The objective of this study was to confirm digestion of Precursor Tri-Specific antibody constructs by MMP9.

Methods

In Vitro MMP9 Cleavage

First, rhMMP9 (911-MP, bio-techne) was activated by adding APMA (#A9563, Sigma) in assay buffer (50 mM Tris, 10 mM CaCl2, 150 mM NaCl, 0.05% Brij®35 (w/v), pH 7.5 (TCNB)) at a final concentration of 100 ug/ml rhMMP9 in 1 mM APMA, and incubated at 37° C. for 24 hours. Activated rhMMP9 was then incubated with Precursor Tri-Specific and Tri-Specific antibodies (rhMMP9 1 ug/ml; antibodies 266.7 ug/ml) in assay buffer at RT overnight. The mixture was used for ELISA binding assays, FACS binding assays, and SDS-PAGE.

Results

Tri-Specific and Precursor Tri-Specific constructs were incubated with MMP9 and the cleavage products were analyzed by SDS-PAGE in non-reduced conditions. Incubation with MMP9 had no apparent activity on the Tri-Specific construct, as this construct does not have MMP9 cleavage sequences. Therefore, SDS-PAGE of the Tri-Specific construct showed the molecular weight of the full molecule, which is 100,112 Da (FIG. 20).

Precursor Tri-Specific-C is a Precursor Tri-Specific construct having MMP9 cleavage sequences both at the C-terminal end of the half-life extending moiety human serum albumin (HSA), and at the C-terminal end of the CD3epsilon CAP masking moiety. Incubation of Precursor Tri-Specific-C construct with MMP9 resulted in two bands, the heaviest containing the cleaved Tri-Specific moiety, and the lightest containing the half-life extending moiety HSA (FIG. 20).

The Precursor Tri-Specific-NC is a Precursor Tri-Specific construct lacking MMP9 cleavage sequences. Therefore, it should not be cleaved by MMP9. Incubation with MMP9 had no effect on Precursor Tri-Specific-NC single band at the expected molecular weight of 170,390 Da.

Example 4: Binding of Cleaved and non-Cleaved Precursor Tri-Specific Constructs to human CD3ε Antigen Objective The objective of this study was to study the effect of MMP9 cleavage to the binding of Precursor Tri-Specific constructs to a human CD3ε antigen.

Methods

MMP9 was used as described in Example 3. ELISA assays were performed as described in Example 2.

Results

The binding of Precursor Tri-Specific-C(VHVL) and Precursor Tri-Specific-NC (VHVL) constructs to human CD3epsilon was tested by ELISA using human CD3epsilon extracellular fusion antigen (human CD3epsilon-His). Binding to CD3epsilon was assessed in constructs cleaved by MMP9 and in constructs not cleaved by MMP9.

The non-cleaved Precursor Tri-Specific-C construct did not bind human CD3epsilon, while the MMP9 cleaved Precursor Tri-Specific-C construct bound human CD3epsilon at sub-nanomolar concentrations (FIG. 21A). The Precursor Tri-Specific-NC construct did not bind CD3epsilon either before or after incubation with MMP9 (FIG. 21B).

This data suggests that hindrance by the CAP and HSA results in very little binding of Precursor Tri-Specific-C to human CD3epsilon. Once Precursor Tri-Specific-C is cleaved by MMP9, the EC50 binding of Precursor Tri-Specific-C to human CD3epsilon is markedly improved towards nanomolar binding affinity. Precursor Tri-Specific-NC lacks MMP9 cleavage sequence and thus did not bind human CD3epsilon even after incubation with MMP9.

Example 5: Binding of Cleaved and Non-Cleaved Precursor Tri-Specific Constructs to Cynomolgus CD3ε Antigen Objective The objective of this study was to study the effect of MMP9 cleavage to the binding of Precursor Tri-Specific constructs to a cynomolgus CD3ε antigen.

Methods

MMP9 was used as described in Example 3. ELISA assays were performed as described in Example 2.

Results

The binding of Precursor Tri-Specific-C(VHVL) and Precursor Tri-Specific-NC (VHVL) constructs to cynomolgus CD3epsilon was tested by ELISA method using cynomolgus CD3epsilon extracellular fusion antigen (cynoCD3epsilon-His). Binding to CD3epsilon was assessed in constructs cleaved by MMP9 and in constructs not cleaved by MMP9.

The non-cleaved Precursor Tri-Specific-C construct did not bind cynoCD3epsilon-His, while the MMP9 cleaved Precursor Tri-Specific-C construct bound cynoCD3epsilon-His at sub-nanomolar concentrations (FIG. 22A). The Precursor Tri-Specific-NC construct did not bind cynoCD3epsilon-His either before or after incubation with MMP9 (FIGS. 22B).

This data suggests that hindrance by the CAP and HSA results in very little binding of Precursor Tri-Specific-C to cynomolgus CD3epsilon. Once Precursor Tri-Specific-C is cleaved by MMP9, the EC50 binding of Precursor Tri-Specific-C to cynomolgus CD3epsilon is markedly improved towards nanomolar binding affinity. Precursor Tri-Specific-NC lacks MMP9 cleavage sequence and thus did not bind cynomolgus CD3epsilon even after incubation with MMP9.

Example 6: Binding of Cleaved Tri-Specific and Precursor Tri-Specific Constructs to human or cyno CD3ε Antigen Objective The objective of this study was to compare the CD3ε binding affinity of cleaved Precursor Tri-Specific and Tri-Specific constructs.

Methods

MMP9 was used as described in Example 3. ELISA assays were performed as described in Example 2.

Results

The binding of Precursor Tri-Specific-C(VHVL) and Precursor Tri-Specific-NC (VHVL), and Tri-Specific (VHVL) constructs to human CD3epsilon was tested by ELISA using human CD3epsilon extracellular fusion antigen (human CD3epsilon-His). Binding to CD3epsilon was assessed in constructs cleaved by MMP9 and in constructs not cleaved by MMP9. Similar analysis was performed with cyno CD3 epsilon.

The non-cleaved Precursor Tri-Specific-C construct did not bind human CD3epsilon-His, while the MMP9 cleaved Precursor Tri-Specific-C construct bound human CD3epsilon-His at sub-nanomolar concentrations, similarly to the Tri-Specific construct (FIG. 23). The Precursor Tri-Specific-NC construct did not bind cynoCD3epsilon-His either before or after incubation with MMP9 (FIG. 23). Similarly, the non-cleaved Precursor Tri-Specific-C construct did not bind cyno CD3epsilon-His, while the MMP9 cleaved Precursor Tri-Specific-C construct bound cyno CD3epsilon-His at sub-nanomolar concentrations, similarly to the Tri-Specific construct (FIG. 24). The Precursor Tri-Specific-NC construct did not bind cynoCD3epsilon-His either before or after incubation with MMP9 (FIG. 24).

This data suggests that hindrance by the CAP and HSA results in very little binding of Precursor Tri-Specific-C to human or cynomolgus CD3epsilon. Once Precursor Tri-Specific-C is cleaved by MMP9, the EC50 binding of Precursor Tri-Specific-C to human or cynomolgus CD3epsilon is markedly improved to nanomolar binding affinity. Precursor Tri-Specific-NC lacks MMP9 cleavage sequence and thus did not bind human or cynomolgus CD3epsilon even after incubation with MMP9.

Example 7: Binding of Cleaved Tri-Specific and Precursor Tri-Specific Constructs to Human CD3ε Expressing Cells Objective The objective of this study was to determine binding of the antibody constructs to cells expressing human CD3ε antigen.

Methods

FACs Analysis of Antibody Construct Binding to Cancer Cells

Cells were digested with TrypLE Express Enzyme (Cat #12604-013, Life technologies). Harvested cells were centrifuged at 1000 rpm for 5 min and supernatant discarded. Cells were suspended at a concentration of $2\times10^6$ cells/ml in FACS buffer (2% FBS in PBS) and 100 μl/well of cell suspension added to plates (Cat #3799, Corning). Plates were centrifuged at 2000 rpm for 5 min, and the supernatant discarded. Cells were resuspended in 100 μl/well primary antibody (anti-hCD3, Cat #A05-001, produced by CP; anti-hEGFR, Cat #10001-MM08, Sino Biological) at final concentrations (2 ug/ml, 1 ug/ml and 0 μg/ml) and incubated for 30 min at 4° C. Plates were centrifuged at 2000 rpm, 4° C. for 5 min and supernatant discarded. Afterwards, cells were washed 3 times with 170 μl FACS buffer. Cells were re-suspended at 100 μl/well with secondary antibody (anti-Mouse IgG (H+L)-Alexa Fluor 488, Cat #A-21202, ThermoFisher) at a final concentration of 2 ug/ml and incubated for 30 min at 4° C. in dark. Plates were centrifuged at 2000 rpm, 4° C. for 5 min and supernatant discarded. Cells were then washed 3 times with FACS buffer and sample were analyzed with FACS.

Results

The binding of Tri-Specific (VHVL), Precursor Tri-Specific-C(VHVL), and Precursor Tri-Specific-NC (VHVL) human-CD3e expressing Jurkat cells was detected by FACS.

Precursor Tri-Specific-C and Precursor Tri-Specific-NC constructs did not bind to Jurkat cells, while the Tri-Specific construct bound Jurkat cells at nanomolar concentrations (FIG. 25).

This data suggests that hindrance by the CAP and HSA result in very little binding of uncleaved Precursor Tri-Specific constructs to cells expressing CD3e. Contrarily, in the Tri-Specific construct lacking HSA and CAP hindrance CD3e is markedly improved to nanomolar binding affinities.

Example 8: Production of Precursor and Active Tri-Specific Antibody Constructs (anti-ROR1, anti-PSMA, and anti-5T4)

Objective

The objective of this study was to produce functional Tri-Specific (active) and Precursor Tri-Specific antibody constructs that would bind either an ROR1 antigen, a PSMA antigen, or a 5T4 antigen.

Methods

Gene synthesis and plasmid construction, expression of antibody constructs, purification of antibody constructs, and SEC-HPLC analysis of antibody constructs was performed as in Example 1, except the nucleotide sequences of the $1^{st}$ and $2^{nd}$ binding domains used in the antibody constructs where those presented in Table 1 above for the anti-ROR1, anti-PSMA antigen, or anti-5T4 antigen, respectfully. Similarly, the amino acid sequences of the constructs are similar to those of Constructs 1-6 of Example 1 except for the $1^{st}$ and $2^{nd}$ binding domains, wherein the amino acid sequences are those presented in Table 1 above for the anti-ROR1, anti-PSMA antigen, or anti-5T4 binding sites generated, respectfully. Constructs produced are listed in Table 4.

TABLE 4

Tribody and ProTribody ROR1, PSMA, and 5T4 Constructs Produced.

| Construct # | Description |
|---|---|
| 7 | Tri-Specific variable light chain-variable heavy chain (ROR1; VLVH) comprising an anti-CD3ε (Fab portion) and two anti-ROR1 variable light (VL) and variable heavy (VH) single-chain variable fragment (scFv) chains, ordered in a N'-XXX-XXX-XXX-C' manner. The HC polypeptide is ordered N'-linker-(anti-CD3ε VH1-linker-CH1)-linker-(anti-ROR1 VL2-linker-VH2)-linker-C'. The Light Chain (LC) polypeptide is ordered N'-linker-(anti-CD3ε VL1-linker-CL)-linker-(anti-ROR1 VL3-linker-VH3)-linker-C'. ROR1 VL-VH amino acid sequence is shown in FIG. 26A (SEQ ID NO: 156), which is encoded by the nucleotide sequence shown in FIG. 26B (SEQ ID NO: 157). |
| 8 | Tri-Specific variable heavy chain-variable light chain (VHVL), comprising an anti-CD3ε (Fab portion) and two anti-ROR1 VH and VL single-chain variable fragment (scFv) chains, ordered in a N'-XXX-XXX-XXX-C' manner. The HC polypeptide chain is ordered N'-linker-(anti-CD3ε VH1-linker-CH1)-linker-(anti-ROR1 VH2-linker-VL2)-linker-C'. |

TABLE 4-continued

| Tribody and ProTribody ROR1, PSMA, and 5T4 Constructs Produced. | |
|---|---|
| Construct # | Description |
| | The LC polypeptide chain is ordered N'-linker-(anti-CD3ε VL1-linker-CL)-linker-(anti-ROR1 VH3-linker-VL3)-linker-C'. ROR1 VH-VL amino acid sequence is shown in FIG. 27A (SEQ ID NO: 166), which is encoded by the nucleotide sequence shown in FIG. 27B (SEQ ID NO: 167). |
| 9 | Precursor Tri-Specific-Variable Light-Variable Heavy (VLVH), comprising an anti-CD3ε (Fab portion), two anti-ROR1 VL and VH single-chain variable fragment (scFv) chains, and two regulatory domains linked by MMP9/2 cleavable sequences, ordered in a N'-XXX-XXX-XXX-C' manner. The HC polypeptide chain is ordered N' human serum albumin (HSA)-linker-protease cleavage peptide (MMP2/9)-linker-(anti-CD3ε VH1-linker-CH1)-linker-(anti-ROR1 VL3-linker-VH3)-linker-C'. The LC polypeptide chain is ordered N' CAP-linker-protease cleavage peptide (MMP2/9)-linker-(anti-CD3ε VL1-linker-CL1)-linker-(anti-ROR1 VL2-linker-VH2)-linker-C'. ROR1 VL-VH amino acid sequence is shown in FIG. 26A (SEQ ID NO: 156), which is encoded by the nucleotide sequence shown in FIG. 26B (SEQ ID NO: 157). |
| 10 | Precursor Tri-Specific-Construct Variable Heavy Variable Light (VHVL), comprising an anti-CD3ε (Fab portion), two anti-ROR1 VL and VH single-chain variable fragment (scFv) chains, and two regulatory domains linked by MMP9/2 cleavable sequences, ordered in a N'-XXX-XXX-XXX-C' manner. The HC polypeptide is ordered N'-human serum albumin (HSA)-linker-protease cleavable peptide MMP2/9-linker-VH1-linker-CH1-linker-VH3-linker-VL3-linker. The LC polypeptide is ordered N'-CAP-linker-protease cleavable peptide MMP2/9-linker-VL1-linker-CL-linker-VH2-linker-VL2-linker. ROR1 VH-VL amino acid sequence is shown in FIG. 27A (SEQ ID NO: 166), which is encoded by the nucleotide sequence shown in FIG. 27B (SEQ ID NO: 167). |
| 11 | Precursor Tri-Specific-Non-Cleavable (NC) Variable Light Variable Heavy (VLVH), comprising an anti-CD3ε (Fab portion), two anti-ROR1 VL and VH single-chain variable fragment (scFv) chains, and two regulatory domains, without including a MMP9/2 cleavable sequence, ordered in a N'-XXX-XXX-XXX-C' manner. The HC polypeptide is ordered N'-human serum albumin (HSA)-linker-VH1-linker-CH1-linker-VL3-linker-VH3-linker. The LC polypeptide is ordered N'-CAP-linker-VL1-linker-CL-linker-VL2-linker-VH2-linker. ROR1 VL-VH amino acid sequence is shown in FIG. 26A (SEQ ID NO: 156), which is encoded by the nucleotide sequence shown in FIG. 26B (SEQ ID NO: 157). |
| 12 | Precursor Tri-Specific-Non-Cleavable (NC) Variable Heavy Variable Light (VHVL), comprising an anti-CD3ε (Fab portion), two anti-ROR1 VL and VH single-chain variable fragment (scFv) chains, and two regulatory domains, without including a MMP9/2 cleavable sequences, ordered in a N'-XXX-XXX-XXX-C' manner. The HC polypeptide is ordered N'-human serum albumin (HSA)-linker-VH1-linker-CH1-linker-VH3-linker-VL3-linker. The LC polypeptide is ordered N'-CAP-linker-VL1-linker-CL-linker-VH2-linker-VL2-linker. ROR1 VH-VL amino acid sequence is shown in FIG. 27A (SEQ ID NO: 166), which is encoded by the nucleotide sequence shown in FIG. 27B (SEQ ID NO: 167). |
| 13 | Tri-Specific variable light chain-variable heavy chain (5T4; VLVH) comprising an anti-CD3ε (Fab portion) and two anti-5T4 variable light (VL) and variable heavy (VH) single-chain variable fragment (scFv) chains, ordered in a N'-XXX-XXX-XXX-C' manner. The HC polypeptide is ordered N'-linker-(anti-CD3ε VH1-linker-CH1)-linker-(anti-5T4 VL2-linker-VH2)-linker-C'. The Light Chain (LC) polypeptide is ordered N'-linker-(anti-CD3ε VL1-linker-CL)-linker-(anti-5T4 VL3-linker-VH3)-linker-C'. 5T4 VL-VH amino acid sequence is shown in FIG. 30A (SEQ ID NO: 172), which is encoded by the nucleotide sequence shown in FIG. 30B (SEQ ID NO: 173). |
| 14 | Tri-Specific variable heavy chain-variable light chain (VHVL), comprising an anti-CD3ε (Fab portion) and two anti-5T4 VH and VL single-chain variable fragment (scFv) chains, ordered in a N'-XXX-XXX-XXX-C' manner. The HC polypeptide chain is ordered N'-linker-(anti-CD3ε VH1-linker-CH1)-linker-(anti-5T4 VH2-linker-VL2)-linker-C'. The LC polypeptide chain is ordered N'-linker-(anti-CD3ε VL1-linker-CL)-linker-(anti-5T4 VH3-linker-VL3)-linker-C'. 5T4 VH-VL amino acid sequence is shown in FIG. 31A (SEQ ID NO: 174), which is encoded by the nucleotide sequence shown in FIG. 31B (SEQ ID NO: 175). |
| 15 | Precursor Tri-Specific-Variable Light-Variable Heavy (VLVH), comprising an anti-CD3ε (Fab portion), two anti-5T4 VL and VH single-chain variable fragment (scFv) chains, and two regulatory domains linked by MMP9/2 cleavable sequences, ordered in a N'-XXX-XXX-XXX-C' manner. The HC polypeptide chain is ordered N' human serum albumin (HSA)-linker-protease cleavage peptide (MMP2/9)-linker-(anti-CD3ε VH1-linker-CH1)-linker-(anti-5T4 VL3-linker-VH3)-linker-C'. The LC polypeptide chain is ordered N' CAP-linker-protease cleavage peptide (MMP2/9)-linker-(anti-CD3ε VL1-linker-CL1)-linker-(anti-5T4 VL2- |

TABLE 4-continued

| Tribody and ProTribody ROR1, PSMA, and 5T4 Constructs Produced. | |
|---|---|
| Construct # | Description |
| | linker-VH2)-linker-C'. 5T4 VL-VH amino acid sequence is shown in FIG. 30A (SEQ ID NO: 172), which is encoded by the nucleotide sequence shown in FIG. 30B (SEQ ID NO: 173). |
| 16 | Precursor Tri-Specific-Construct Variable Heavy Variable Light (VHVL), comprising an anti-CD3ε (Fab portion), two anti-5T4 VL and VH single-chain variable fragment (scFv) chains, and two regulatory domains linked by MMP9/2 cleavable sequences, ordered in a N'-XXX-XXX-XXX-C' manner. The HC polypeptide is ordered N'-human serum albumin (HSA)-linker-protease cleavable peptide MMP2/9-linker-VH1-linker-CH1-linker-VH3-linker-VL3-linker. The LC polypeptide is ordered N'-CAP-linker-protease cleavable peptide MMP2/9-linker-VL1-linker-CL-linker-VH2-linker-VL2-linker. 5T4 VH-VL amino acid sequence is shown in FIG. 31A (SEQ ID NO: 174), which is encoded by the nucleotide sequence shown in FIG. 31B (SEQ ID NO: 175). |
| 17 | Precursor Tri-Specific-Non-Cleavable (NC) Variable Light Variable Heavy (VLVH), comprising an anti-CD3ε (Fab portion), two anti-5T4 VL and VH single-chain variable fragment (scFv) chains, and two regulatory domains, without including a MMP9/2 cleavable sequence, ordered in a N'-XXX-XXX-XXX-C' manner. The HC polypeptide is ordered N'-human serum albumin (HSA)-linker-VH1-linker-CH1-linker-VL3-linker-VH3-linker. The LC polypeptide is ordered N'-CAP-linker-VL1-linker-CL-linker-VL2-linker-VH2-linker. 5T4 VL-VH amino acid sequence is shown in FIG. 30A (SEQ ID NO: 172), which is encoded by the nucleotide sequence shown in FIG. 30B (SEQ ID NO: 173). |
| 18 | Precursor Tri-Specific-Non-Cleavable (NC) Variable Heavy Variable Light (VHVL), comprising an anti-CD3ε (Fab portion), two anti-5T4 VL and VH single-chain variable fragment (scFv) chains, and two regulatory domains, without including a MMP9/2 cleavable sequences, ordered in a N'-XXX-XXX-XXX-C' manner. The HC polypeptide is ordered N'-human serum albumin (HSA)-linker-VH1-linker-CH1-linker-VH3-linker-VL3-linker. The LC polypeptide is ordered N'-CAP-linker-VL1-linker-CL-linker-VH2-linker-VL2-linker. 5T4 VH-VL amino acid sequence is shown in FIG. 31A (SEQ ID NO: 174), which is encoded by the nucleotide sequence shown in FIG. 31B (SEQ ID NO: 175). |
| 19 | Tri-Specific variable light chain-variable heavy chain (PSMA; VLVH) comprising an anti-CD3ε (Fab portion) and two anti-PSMA variable light (VL) and variable heavy (VH) single-chain variable fragment (scFv) chains, ordered in a N'-XXX-XXX-XXX-C' manner. The HC polypeptide is ordered N'-linker-(anti-CD3ε VH1-linker-CH1)-linker-(anti-PSMA VL2-linker-VH2)-linker-C'. The Light Chain (LC) polypeptide is ordered N'-linker-(anti-CD3ε VL1-linker-CL)-linker-(anti-PSMA VL3-linker-VH3)-linker-C'. PSMA VL-VH amino acid sequence is shown in FIG. 28A (SEQ ID NO: 168), which is encoded by the nucleotide sequence shown in FIG. 28B (SEQ ID NO: 169). |
| 20 | Tri-Specific variable heavy chain-variable light chain (VHVL), comprising an anti-CD3ε (Fab portion) and two anti-PSMA VH and VL single-chain variable fragment (scFv) chains, ordered in a N'-XXX-XXX-XXX-C' manner. The HC polypeptide chain is ordered N'-linker-(anti-CD3ε VH1-linker-CH1)-linker-(anti-PSMA VH2-linker-VL2)-linker-C'. The LC polypeptide chain is ordered N'-linker-(anti-CD3ε VL1-linker-CL)-linker-(anti-PSMA VH3-linker-VL3)-linker-C'. PSMA VH-VL amino acid sequence is shown in FIG. 29A (SEQ ID NO: 170), which is encoded by the nucleotide sequence shown in FIG. 29B (SEQ ID NO: 171). |
| 21 | Precursor Tri-Specific-Variable Light-Variable Heavy (VLVH), comprising an anti-CD3ε (Fab portion), two anti-PSMA VL and VH single-chain variable fragment (scFv) chains, and two regulatory domains linked by MMP9/2 cleavable sequences, ordered in a N'-XXX-XXX-XXX-C' manner. The HC polypeptide chain is ordered N' human serum albumin (HSA)-linker-protease cleavage peptide (MMP2/9)-linker-(anti-CD3ε VH1-linker-CH1)-linker-(anti-PSMA VL3-linker-VH3)-linker-C'. The LC polypeptide chain is ordered N' CAP-linker-protease cleavage peptide (MMP2/9)-linker-(anti-CD3ε VL1-linker-CL1)-linker-(anti-PSMA VL2-linker-VH2)-linker-C'. PSMA VL-VH amino acid sequence is shown in FIG. 28A (SEQ ID NO: 168), which is encoded by the nucleotide sequence shown in FIG. 28B (SEQ ID NO: 169). |
| 22 | Precursor Tri-Specific-Construct Variable Heavy Variable Light (VHVL), comprising an anti-CD3ε (Fab portion), two anti-PSMA VL and VH single-chain variable fragment (scFv) chains, and two regulatory domains linked by MMP9/2 cleavable sequences, ordered in a N'-XXX-XXX-XXX-C' manner. The HC polypeptide is ordered N'-human serum albumin (HSA)-linker-protease cleavable peptide MMP2/9-linker-VH1-linker-CH1-linker-VH3-linker-VL3-linker. The LC polypeptide is ordered N'-CAP-linker-protease cleavable peptide MMP2/9-linker-VL1-linker-CL-linker-VH2-linker-VL2-linker. PSMA VH-VL amino acid sequence is |

TABLE 4-continued

| Tribody and ProTribody ROR1, PSMA, and 5T4 Constructs Produced. | |
|---|---|
| Construct # | Description |
| | shown in FIG. 29A (SEQ ID NO: 170), which is encoded by the nucleotide sequence shown in FIG. 29B (SEQ ID NO: 171). |
| 23 | Precursor Tri-Specific-Non-Cleavable (NC) Variable Light Variable Heavy (VLVH), comprising an anti-CD3ε (Fab portion), two anti-PSMA VL and VH single-chain variable fragment (scFv) chains, and two regulatory domains, without including a MMP9/2 cleavable sequence, ordered in a N'-XXX-XXX-XXX-C' manner. The HC polypeptide is ordered N'-human serum albumin (HSA)-linker-VH1-linker-CH1-linker-VL3-linker-VH3-linker. The LC polypeptide is ordered N'-CAP-linker-VL1-linker-CL-linker-VL2-linker-VH2-linker. PSMA VL-VH amino acid sequence is shown in FIG. 28A (SEQ ID NO: 168), which is encoded by the nucleotide sequence shown in FIG. 28B (SEQ ID NO: 169). |
| 24 | Precursor Tri-Specific-Non-Cleavable (NC) Variable Heavy Variable Light (VHVL), comprising an anti-CD3ε (Fab portion), two anti-PSMA VL and VH single-chain variable fragment (scFv) chains, and two regulatory domains, without including a MMP9/2 cleavable sequences, ordered in a N'-XXX-XXX-XXX-C' manner. The HC polypeptide is ordered N'-human serum albumin (HSA)-linker-VH1-linker-CH1-linker-VH3-linker-VL3-linker. The LC polypeptide is ordered N'-CAP-linker-VL1-linker-CL-linker-VH2-linker-VL2-linker. PSMA VH-VL amino acid sequence is shown in FIG. 29A (SEQ ID NO: 170), which is encoded by the nucleotide sequence shown in FIG. 29B (SEQ ID NO: 171). |

Results: While all of the above constructs have been produced, included herein is a sampling of the data showing molecular weights and purity of the different constructs. Similar results were found for the constructs not shown. FIGS. 34A-34C show the molecular weight and purity of Construct 7 (Tribody-ROR1 (VL-VH). FIGS. 34D-34F show the molecular weight and purity of Construct 11 (Pro-TriBody-NC-ROR1 (VL-VH). FIGS. 35A-35C show the molecular weight and purity of Construct 19 (Tribody-5T4 (VL-VH). FIGS. 35D-35F show the molecular weight and purity of Construct 21 (Pro-TriBody-C-5T4 (VL-VH). FIGS. 35G-35I show the molecular weight and purity of Construct 23 (Pro-TriBody-NC-5T4 (VL-VH).

Example 9: In Vitro and In Vivo Characterization of EGFR Precursor TriSpecific Constructs Objective The objective of this study was to further characterize, in vitro and in vivo, the properties of the EGFR precursor and active Tri-Specific antibody constructs.

Methods

Constructs: As described above in Example 1.

FACS Analysis: As described above in Example 7.

In vitro MMP9 cleavage: rhMMP9 (911-MP, bio-techne) was activated by adding APMA (#A9563, Sigma) in Assay buffer (50 mM Tris, 10 mM CaCl2, 150 mM NaCl, 0.05% Brij35 (w/v), pH 7.5 (TCNB)) with the final concentration (rhMMP9 100 ug/ml; APMA 1 mM), incubated at 37° C. for 24 hours. Activated rhMMP9 was incubated with TriBody precursor and activated antibody constructs (rhMMP9 1 ug/ml; antibody 266.7 ug/ml) in Assay buffer at RT overnight. The mixture was used for ELISA binding assays, FACS binding assays, and SDS-PAGE.

Pharmacokinetic analysis in mice: Male C57BL/6 mice were injected intravenously (IV) with TriBody-EGFR (VHVL; construct 2), ProTriBody-C-EGFR (VHVL; construct 4) and ProTriBody-NC-EGFR (VHVL; construct 6) at two doses of IV-2 mg/kg, IV-0.5 mg/kg. Sampling at Day 0: pre-dose, 10 min, 1, 2, 4, 8 hr and Day 1, 2, 4, 7, 10 and 14; (12 time points, semi-serial bleeding for serum generation). Analysis was performed that huEGFR-ECD-Fc was used as the capturing reagent and anti-Fab antibody as the detecting reagent.

Results

FIG. 32 clearly shows that in the absence of protease cleavage by MMP9, little to no binding to the surface EGFR of Jurkat cells by Precursor Tri-Specific Antibody constructs is observed (upward facing triangles-Protribody with cleavable regulatory arms no MMP9 added [construct 4], diamonds-ProTribody with non-cleavable regulatory arms no MMP9 added [construct 6], large circles-ProTribody with non-cleavable regulatory arms [construct 6] with MMP9 added). The Jurkat cell binding of the Pro-Tribody construct 4 cleaved by MMP9, while significantly greater than in the absence of MMP9, does not quite reach the level of binding observed in with the construct lacking regulatory domains. As this experiment was performed in a closed system, it is possible that the cleaved CAP regulatory domain remains in equilibrium with the activated construct and therefore may still partially bind to the anti-CD3ε, thus partially hindering the binding to the antigen on the cells. The binding of the Activated Tribody construct 2 (small circles/squares) is not affected by the presence or absence of the MMP9 protease.

The in vivo pharmacokinetic data presented in FIGS. 33A-33B clearly shows the increased half-life of precursor constructs comprising a regulatory HSA domain compared with antibody constructs lacking such a regulatory HSA domain. The half-life results of construct 1 (FIG. 33A), lacking regulatory domains (Tribody EGFR (VL-VH) are: IV-0.5 mg/kg=$T_{1/2}$ day 0.201 and IV-2.0 mg/kg=$T_{1/2}$ day 0.286. While the half-life results of ProTribody constructs with cleavable (construct 3; FIG. 33B) arms (ProTribody-C EGFR (VL-VH)) are: Construct 3: IV-0.5 mg/kg=$T_{1/2}$ day 0.595 and IV-2.0 mg/kg=$T_{1/2}$ day 0.651; and Construct 5: IV-0.5 mg/kg=$T_{1/2}$ day 0.713 and IV-2.0 mg/kg=$T_{1/2}$ day 0.604.

Thus, a ProTribody construct with cleavable a half-life prolonging and CAP masking regulatory domains may remain in the body longer until reaching a target tumor micro-environment, wherein the regulatory arms may be cleaved. Then upon cleavage of the HSA cleavable regulatory domain within a tumor micro-environment, the Tribody construct would have a decreased half-life. This regulated half-time for the precursor constructs described herein, provides the advantage that the antibody remains in circulation until it reaches its target destination, e.g., tumor micro-environment wherein cleavable regulatory arms are cleaved, and then upon providing a therapeutic function (activating a T-cell) is removed from circulation.

Example 10: Binding of Cleaved and Non-Cleaved Precursor 5T4 Tri-Specific Constructs to Human CD3ε Antigen Objective The objective of this study was to study the effect of MMP9 cleavage to the binding of Precursor 5T4 Tri-Specific constructs to a human CD3ε antigen.

Methods

MMP9 was used as described in Example 3. ELISA assays were performed as described in Example 2.

Results

FIG. 36 shows that the absence or presence of regulatory arms (cleavable or non-cleavable) only minimally affected binding of TriSpecific and ProTriSpecific constructs to human CD3ε Antigen (5T4-Tribody circles, construct 13 (VL-VH); Cleavable 5T4-PTTribody-C, construct 15 (VL-VH); and Non-Cleavable 5T4-PTTribody-NC, construct 17 (VL-VH).

Structural and size differences of the constructs used were observed by SDS-PAGE. Inclusion of MMP9 protease with the different constructs showed that only the Pro-Tribody-5T4-C (VL-VH) construct 15 was affected by the protease inclusion, wherein the regulatory arms were cleaved from the construct (FIG. 37).

The affect of binding to human CD3ε antigen in the presence (+MMP9) or the absence (-MMP9) of the MMP9 protease is shown in FIG. 38. The binding curve results of FIG. 38, as indicated by the upper arrow, shows nearly equivalent binding between activated 5T4 tribody construct 13, with (square) or without MMP9 (small circle), and Precursor 5T4 tribody construct 15 that has been incubated in the presence of MMP9 (downward facing triangle). This is in contrast with the results of FIG. 38 indicated by the lower arrow, which shows minimal binding to CD3ε antigen by construct 15 in the absence of MMP9 (upward facing triangle), and construct 17 in the presence or absence of MMP9 (diamonds, and large circle respectively).

Example 11: Follow-Up Analysis of 5T4 and EGFR Tri-Specific Constructs to Human CD3ε Antigen Objective: To further analyze the 5T4 Tri-Specific Precursor constructs, as described in Example 10.

Results:

FIG. 39 presents FACS Binding of TriBody-5T4, ProTriBody-5T4-C and ProTriBody-5T4-NC to Jurkat Cells (Human CD3e) in the presence and absence of MMP9 protease.

As can be seen in FIG. 39, ProTriBody-C and ProTriBody-NC antibodies did not bind to Jurkat Cells in the absence of MMP9 cleavage, while TriBody bound with low nM affinities. In the presence of MMP9, ProTriBody-C was found to bing the CD3e on the Jurkat cells, while ProTriBody-NC did not bind to the jurkat cells. The data suggests that hindrance by the CAP and HSA of the precursor structures resulted in very little binding towards Jurkat cells, expressing human CD3epsilon. Once the HSA and CAP hindrance of the CD3epsilon is absent (Tribody, either absent or cleaved by MMP9, the binding EC50 towards human CD3epsilon is markedly improved towards low-nM biding affinities.

FIGS. 40 show ELISA Binding studies. FIG. 40 shows ELISA binding studies of TriBody and Precursor TriBody Antibody Constructs Towards human 5T4 Antigen. TriBody and Precursor TriBody antibodies, were tested for their binding to 5T4 extracellular fusion antigen (5T4-Fc) using an ELISA method.

As can be seen in FIG. 40, all TriBody and Precursor TriBody forms bound the extracellular domain of h5T4 with similar affinities.

FIG. 41 presents FACS binding data of 5T4 binding Tribody and precursor Tribody antibody constructs to CHO cells expressing human 5T4. MFI (mean fluorescent intensity) provides a relative scale of antibody binding.

The results of FIG. 41 show that all TriBody and precursor TriBody forms bind to CHO-h5T4 with similar affinities.

FIG. 42 presents FACS binding data of 5T4 binding Tribody and precursor Tribody antibody constructs to MCF7 breast cancer cell line, known to highly express human 5T4. MFI (mean fluorescent intensity) provides a relative scale of antibody binding.

The results presented in FIG. 42 show that all TriBody and Precursor TriBody forms bound to MCF7 with similar affinities.

The results shown in FIGS. 43 and 44 were obtained as follows: Briefly, human PBMCs were purchased from ALLCELLS. CD3+ T cells were negatively selected and purified from human PBMCs by magnetic activated cell sorting using the CD3+ T Cell Isolation Kit (StemCell). Purified T cells acts as effector cells and human cell lines MCF-7 and NCI-H226 as target cells. The cytolytic activity was tested in an LDH release assay. Briefly, target cells (T) were co-incubated with effector cells (E) in 96-well U-bottomed plates at an E:T ratio of 10:1 in duplicates of 10000 target cells/well. To test the cytolytic activity, 5T4-Tribody and 5T4-ProTriBody-NC were added at serial dilutions to wells. After incubation for 24 hr at 37° C. and 5% $CO_2$, supernatants were collected, treated with reagents in the CytoTox 96 Non-radioactive cytotoxicity assay kit (Promega, G1780) according to manufacturer's manual. Readout was the absorbance at 490 nm or 492 nm (Molecular Devices). The percentage of specific lysis was calculated as: % Cytotoxicity=(Experimental-E only-T only)/(T max-T only)×100. Maximum release was determined through lysis in the presence of lysis buffer supplies with the kit.

The results shown in FIGS. 43 and 44 show that the presence of a cleavable regulatory domain slightly increases cytotoxicity of the construct compared with a construct comprising a non-cleavable linker.

What is claimed is:

1. A precursor tri-specific antibody construct, comprising:

(a) a first binding domain that binds to a tumor associated antigen (TAA), wherein the TAA is Trophoblast glycoprotein (TPGB) (5T4);

(b) a second binding domain that binds to the TAA 5T4;

(c) a third binding domain that binds to an extracellular epitope of human CD3ε, wherein the first binding domain and the second binding domain are each located C-terminal to the third binding domain; and (d) a regulatory domain located N-terminal to the third binding domain, said regulatory domain comprising:

(i) a protease cleavage domain comprising a protease-cleavable amino acid sequence cleavable by a serine protease, a cysteine protease, an aspartate protease, a matrix metalloprotease (MMP), or a combination substrate cleaved by one or more of MMP2/9, urokinase-type plasminogen activator (uPA), matriptase and legumain, or any combination thereof;

(ii) a half-life prolonging (HLP) domain comprising a human serum albumin (HSA) polypeptide; and (iii) a Cap component comprising an amino acid sequence of the extracellular epitope of human CD3ε that reduces the ability of the third binding domain to bind the extracellular epitope of human CD3ε, wherein the first binding domain and the second binding domain, each comprises a single chain variable fragment (scFv), and the third binding domain comprises a Fab antigen binding fragment;

wherein the first binding domain and/or the second binding domain comprises a single chain variable fragment (scFv) comprising the amino acid sequence selected from the group consisting of SEQ ID NOs: 172 and 174;

wherein the third binding domain comprises a Fab antigen binding fragment comprising a VH and VL comprising amino acid sequences set forth in SEQ ID NOs: 114 and 116, respectively; and wherein the Cap comprises the amino acid sequence set forth in SEQ ID NO: 5.

2. A nucleic acid construct comprising one or more nucleic acid sequences that encode the precursor tri-specific antibody construct of claim 1.

3. An expression vector comprising the nucleic acid construct of claim 2.

4. An isolated host cell comprising the expression vector of claim 3.

5. A pharmaceutical composition comprising the precursor tri-specific antibody construct of claim 1 and a pharmaceutically acceptable carrier.

6. A method of treating, inhibiting the growth of, delaying disease progression of a cancer or a tumor, or any combination thereof, in a subject in need of such treatment, comprising a step of administering to the subject the pharmaceutical composition of claim 5, wherein the method treats, inhibits the growth of, delays the disease progression, or reduces the tumor load in the subject.

7. The method of claim 6, wherein the cancer or tumor comprises a solid tumor or non-solid tumor, or wherein the cancer or tumor comprises a metastasis of a cancer or tumor.

* * * * *